(12) United States Patent
Yamamoto et al.

(10) Patent No.: US 11,851,449 B2
(45) Date of Patent: *Dec. 26, 2023

(54) HETEROCYCLIC AMIDE COMPOUNDS HAVING AN RORVT INHIBITORY ACTION

(71) Applicant: TAKEDA PHARMACEUTICAL COMPANY LIMITED, Osaka (JP)

(72) Inventors: Satoshi Yamamoto, Fujisawa (JP); Junya Shirai, Fujisawa (JP); Mitsunori Kono, Fujisawa (JP); Yoshihide Tomata, San Diego, CA (US); Ayumu Sato, Fujisawa (JP); Atsuko Ochida, Fujisawa (JP); Yoshiyuki Fukase, New York, NY (US); Shoji Fukumoto, Kobe (JP); Tsuneo Oda, Fujisawa (JP); Hidekazu Tokuhara, Fujisawa (JP); Naoki Ishii, Fujisawa (JP); Yusuke Sasaki, Fujisawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 148 days.

This patent is subject to a terminal disclaimer.

(21) Appl. No.: 17/316,185

(22) Filed: May 10, 2021

(65) Prior Publication Data

US 2021/0277030 A1 Sep. 9, 2021

Related U.S. Application Data

(60) Continuation of application No. 16/576,293, filed on Sep. 19, 2019, now Pat. No. 11,053,262, which is a (Continued)

(30) Foreign Application Priority Data

Jul. 3, 2013 (JP) ................................. 2013-140213

(51) Int. Cl.
*C07F 7/08* (2006.01)
*C07D 205/04* (2006.01)
(Continued)

(52) U.S. Cl.
CPC .............. *C07F 7/0812* (2013.01); *A61P 1/04* (2018.01); *A61P 17/06* (2018.01); *A61P 19/02* (2018.01); *A61P 25/00* (2018.01); *A61P 29/00* (2018.01); *A61P 43/00* (2018.01); *C07C 237/22* (2013.01); *C07D 205/04* (2013.01); *C07D 207/12* (2013.01); *C07D 207/26* (2013.01); *C07D 209/18* (2013.01); *C07D 211/62* (2013.01); *C07D 213/64* (2013.01); *C07D 231/12* (2013.01); *C07D 231/56* (2013.01); *C07D 233/72* (2013.01); *C07D 237/14* (2013.01); *C07D 239/36* (2013.01); *C07D 239/54* (2013.01); *C07D 261/08* (2013.01); *C07D 261/12* (2013.01); *C07D 271/10* (2013.01); *C07D 295/14* (2013.01); *C07D 309/06* (2013.01); *C07D 309/08* (2013.01); *C07D 333/38* (2013.01); *C07D 403/06* (2013.01);
(Continued)

(58) Field of Classification Search
CPC .. C07C 237/22; C07D 205/04; C07D 207/12; C07D 207/26; C07D 209/18; C07D 211/62; C07D 213/64; C07D 231/12; C07D 231/56; C07D 233/72; C07D 237/14; C07D 239/36; C07D 239/54; C07D 261/08; C07D 261/12; C07D 271/10; C07D 295/14; C07D 309/06; C07D 309/08; C07D 333/38; C07D 403/06; C07D 405/12; C07D 413/12; C07D 487/04; C07F 7/081; C07F 7/0812; C07F 7/10; C07F 7/30; C07K 5/06078; C07K 5/081; A61P 17/06; A61P 19/02; A61P 1/04; A61P 25/00; A61P 29/00; A61P 43/00

See application file for complete search history.

(56) References Cited

U.S. PATENT DOCUMENTS 6,037,472 A 3/2000 Castelhano et al.
6,066,649 A 5/2000 Podzuweit
(Continued)

FOREIGN PATENT DOCUMENTS

EP 1341035 9/2003
EP 2873669 5/2015
(Continued)

OTHER PUBLICATIONS

Nakamura, I. et al. Transition-Metal-Catalyzed Reactions in Heterocyclic Synthesis. Chem. Rev. 2004, vol. 104, p. 2127.*
(Continued)

*Primary Examiner* — Savitha M Rao
(74) *Attorney, Agent, or Firm* — Casimir Jones, S.C.; Anne M. Reynolds

(57) ABSTRACT

The present invention relates to compound (I) or a salt thereof which has a RORγt inhibitory action. In the formula (I), each symbol is as defined in the specification.

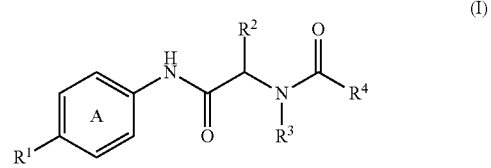

11 Claims, No Drawings

Specification includes a Sequence Listing.

Related U.S. Application Data division of application No. 14/902,388, filed as application No. PCT/JP2014/067649 on Jul. 2, 2014, now Pat. No. 10,472,376.

(51) Int. Cl.

| | | |
|---|---|---|
| C07D 207/12 | (2006.01) | |
| C07K 5/065 | (2006.01) | |
| C07D 239/36 | (2006.01) | |
| C07D 213/64 | (2006.01) | |
| C07D 309/06 | (2006.01) | |
| C07D 333/38 | (2006.01) | |
| C07F 7/10 | (2006.01) | |
| C07D 403/06 | (2006.01) | |
| C07D 271/10 | (2006.01) | |
| C07C 237/22 | (2006.01) | |
| C07D 295/14 | (2006.01) | |
| C07D 207/26 | (2006.01) | |
| C07D 413/12 | (2006.01) | |
| C07F 7/30 | (2006.01) | |
| C07D 233/72 | (2006.01) | |
| C07D 309/08 | (2006.01) | |
| C07D 231/56 | (2006.01) | |
| C07D 261/08 | (2006.01) | |
| C07D 209/18 | (2006.01) | |
| C07D 405/12 | (2006.01) | |
| C07D 261/12 | (2006.01) | |
| C07D 239/54 | (2006.01) | |
| C07D 211/62 | (2006.01) | |
| C07D 237/14 | (2006.01) | |
| C07D 231/12 | (2006.01) | |
| C07D 487/04 | (2006.01) | |
| A61P 43/00 | (2006.01) | |
| A61P 29/00 | (2006.01) | |
| A61P 25/00 | (2006.01) | |
| A61P 19/02 | (2006.01) | |
| A61P 17/06 | (2006.01) | |
| A61P 1/04 | (2006.01) | |
| C07K 5/087 | (2006.01) | |

(52) U.S. Cl.
CPC ......... *C07D 405/12* (2013.01); *C07D 413/12* (2013.01); *C07D 487/04* (2013.01); *C07F 7/081* (2013.01); *C07F 7/10* (2013.01); *C07F 7/30* (2013.01); *C07K 5/06078* (2013.01); *C07K 5/0812* (2013.01)

(56) References Cited

U.S. PATENT DOCUMENTS

| | | | |
|---|---|---|---|
| 6,245,746 | B1 | 6/2001 | Chamberland et al. |
| 7,135,498 | B1 | 11/2006 | Chopp |
| 9,187,453 | B2 | 11/2015 | Tsukamoto |
| 2002/0032203 | A1 | 3/2002 | Swope |
| 2002/0119978 | A1 | 8/2002 | Swope |
| 2002/0132754 | A1 | 9/2002 | Boss |
| 2002/0155173 | A1 | 10/2002 | Chopp |
| 2002/0198377 | A1 | 12/2002 | Niewohner et al. |
| 2004/0127538 | A1 | 7/2004 | Oinuma |
| 2005/0143388 | A1 | 6/2005 | Chopp |
| 2005/0282880 | A1 | 12/2005 | Oinuma |
| 2006/0106037 | A1 | 5/2006 | Baer |
| 2006/0128695 | A1 | 6/2006 | Bourguignon |
| 2006/0135557 | A1 | 6/2006 | Nan et al. |
| 2006/0148802 | A1 | 7/2006 | Niewohner et al. |
| 2007/0135457 | A1 | 6/2007 | Beyer |
| 2007/0299079 | A1 | 12/2007 | Norbert et al. |
| 2008/0027064 | A1 | 1/2008 | Hofgen et al. |
| 2008/0280907 | A1 | 11/2008 | Schmidt et al. |
| 2008/0312225 | A1 | 12/2008 | Schmidt et al. |
| 2009/0163552 | A1 | 6/2009 | Benson et al. |
| 2009/0203691 | A1 | 8/2009 | Oinuma |
| 2009/0239874 | A1 | 9/2009 | Hofgen et al. |
| 2010/0035882 | A1 | 2/2010 | Ellinghaus |
| 2010/0063063 | A1 | 3/2010 | Benbow et al. |
| 2010/0120762 | A1 | 5/2010 | Stange |
| 2010/0120763 | A1 | 5/2010 | Stange |
| 2010/0150839 | A1 | 6/2010 | Kelleher |
| 2011/0071168 | A1 | 3/2011 | Chopp |
| 2011/0136803 | A1 | 6/2011 | Schmidt et al. |
| 2011/0144153 | A1 | 6/2011 | Nozawa |
| 2012/0009152 | A1 | 1/2012 | Chopp |
| 2012/0136012 | A1 | 5/2012 | Breslin et al. |
| 2012/0136064 | A1 | 5/2012 | Nixon |
| 2012/0252780 | A1 | 10/2012 | Ng |
| 2013/0115194 | A1 | 5/2013 | Long et al. |
| 2013/0115404 | A1 | 5/2013 | Goehlich |
| 2014/0088080 | A1 | 3/2014 | Koga |
| 2015/0105373 | A1 | 4/2015 | Mikami et al. |
| 2015/0158863 | A1 | 6/2015 | Nakamura |
| 2016/0229814 | A1 | 8/2016 | Yamamoto et al. |
| 2020/0010487 | A1 | 1/2020 | Yamamoto et al. |

FOREIGN PATENT DOCUMENTS

| | | |
|---|---|---|
| FR | 2860793 | 4/2005 |
| GB | 2404658 | 2/2005 |
| JP | H06145169 | 5/1994 |
| JP | H09221423 | 8/1997 |
| JP | H11292877 | 10/1999 |
| JP | 2001512137 | 8/2001 |
| JP | 2004525098 | 8/2004 |
| JP | 2005145840 | 6/2005 |
| JP | 2006519243 | 8/2006 |
| JP | 2007513996 | 5/2007 |
| JP | 2008526716 | 7/2008 |
| JP | 2008526717 | 7/2008 |
| JP | 2009538853 | 11/2009 |
| WO | WO 92/01938 | 2/1992 |
| WO | WO 99/06435 | 2/1999 |
| WO | WO 99/37667 | 7/1999 |
| WO | WO 00/23091 | 4/2000 |
| WO | WO 00/32575 | 6/2000 |
| WO | WO 01/09125 | 2/2001 |
| WO | WO 01/44228 | 6/2001 |
| WO | WO 01/44266 | 6/2001 |
| WO | WO 01/55106 | 8/2001 |
| WO | WO 02/50078 | 6/2002 |
| WO | WO 2004/037784 | 5/2004 |
| WO | WO 2004/044234 | 5/2004 |
| WO | WO 2004/056823 | 7/2004 |
| WO | WO 2004/060872 | 7/2004 |
| WO | WO 2004/108892 | 12/2004 |
| WO | WO 2005/035534 | 4/2005 |
| WO | WO 2005/037839 | 4/2005 |
| WO | WO 2005/058892 | 6/2005 |
| WO | WO 2005/120497 | 12/2005 |
| WO | WO 2006/015159 | 2/2006 |
| WO | WO 2006/064286 | 6/2006 |
| WO | WO 2009/095324 | 8/2006 |
| WO | WO 2006/128129 | 11/2006 |
| WO | WO 2006/128172 | 11/2006 |
| WO | WO 2007/020521 | 2/2007 |
| WO | WO 2007/125405 | 11/2007 |
| WO | WO 2007/137819 | 12/2007 |
| WO | WO 2007/146230 | 12/2007 |
| WO | WO 2008/016659 | 2/2008 |
| WO | WO 2008/043461 | 4/2008 |
| WO | WO 2008/044700 | 4/2008 |
| WO | WO 2008/085302 | 7/2008 |
| WO | WO 2008/121602 | 10/2008 |
| WO | WO 2009/019508 | 2/2009 |
| WO | WO 2009/026276 | 2/2009 |
| WO | WO 2009/138338 | 11/2009 |
| WO | WO 2010/013161 | 2/2010 |
| WO | WO 2010/054253 | 5/2010 |
| WO | WO 2010/054260 | 5/2010 |
| WO | WO 2010/090290 | 8/2010 |

(56) References Cited

FOREIGN PATENT DOCUMENTS

| WO | WO 2010/097410 | 9/2010 |
|---|---|---|
| WO | WO 2010/142752 | 12/2010 |
| WO | WO 2011/022213 | 2/2011 |
| WO | WO 2011/044157 | 4/2011 |
| WO | WO 2011/059839 | 5/2011 |
| WO | WO 2012/042541 | 4/2012 |
| WO | WO 2012/051036 | 4/2012 |
| WO | WO 2012/087861 | 6/2012 |
| WO | WO 2012/100734 | 8/2012 |
| WO | WO 2012/165399 | 12/2012 |
| WO | WO 2012/178124 | 12/2012 |
| WO | WO 2013/018695 | 2/2013 |
| WO | WO 2013/019682 | 2/2013 |
| WO | WO 2013/042782 | 3/2013 |
| WO | WO 2013/055984 | 4/2013 |
| WO | WO 2013/100027 | 7/2013 |
| WO | WO 2013/146963 | 10/2013 |
| WO | WO 2013/161913 | 10/2013 |
| WO | WO 2014/142255 | 9/2014 |
| WO | WO 2015/002230 | 1/2015 |
| WO | WO 2015/002231 | 1/2015 |
| WO | WO 2015/012328 | 1/2015 |
| WO | WO 2015/016206 | 2/2015 |

OTHER PUBLICATIONS

Akdis M et al. "Interleukins from 1 to 37 and interferon-γ: Receptors functions and roles in diseases" Journal of Allergy and Clinical Immunology 2011 127 3701-721.e70.
Anderson, "The process of structure-based drug design." Chem Biol. Sep. 2003;10(9):787-97.
Banerjee B. et al. "Second-generation DBFOX ligands for the synthesis of beta-substituted alpha-amino acids via enantioselective radical conjugate additions" J. Org. Chem. (2008) 73:8973-8978.
Beavo J.A. et al. "Stimulation of adenosine 3'5'-monophosphate hydrolysis by guanosine 3'5'-monophosphate" J. Biol. Chem. (1971) 246(12):3841-3846.
Bender A.T. et al. "Differentiation of human monocytes in vitro with granulocyte-macrophage colony-stimulating factor and macrophage colony-stimulating factor produces distinct changes in cGMP phosphodiesterase expression" Cell. Signalling (2004) 16:365-374.
Benton H.P. "Cytokines and their receptors" Curr Opin Cell Biol. 1991 3(2):171-5.
Blanco P. et al. "Dendritic cells and cytokines in human inflammatory and autoimmune diseases" Cytokine Growth Factor Rev. Feb. 2008 19(1):41-52.
Boess F.G. et al. "Inhibition of phosphodiesterase 2 increases neuronal CGMP synaptic plasticity and memory performance" Neuropharmacology (2004) 47:1081-1092.
CAS Registry No. 1217709-83-5 (2010).
CAS Registry No. 1217860-74-6 (2010).
CAS Registry No. 1277664-46-6 (2011).
CAS Registry No. 1286063-95-3 (2011).
CAS Registry No. 1316015-84-5 (2011).
CAS Registry No. 1323005-31-7 (2011).
CAS Registry No. 1323260-38-3 (2011).
CAS Registry No. 1427736-73-9 (2013).
CAS Registry No. 956728-16-8 (2007).
CAS Registry No. 957036-06-5 (2007).
Chemical Abstracts 1422576-26-8 Imidazo[12-a]pyridine-2-carboxamide N-[2-methoxy-1-(2-pyridinyl)ethyl]-6-methyl-(2016) ChemBridge Corporation.
Chemical Abstracts 1422628-80-5 "Imidazo[12-a]pyridine-6-carboxamide N-[1-(35- dichlorophenyl)-2-hydroxyethyl]-" (2013) ChemBridge Corporation.
Chen Y. et al. "Design Synthesis and Biological Evaluation of Isoquinoline-1 3 4-trione Derivatives as Potent Caspase-3 Inhibitors" Journal of Medicinal Chemistry 2006 vol. 49 No. 5 p. 1613-1623.

Chi W. et al. "Upregulated IL-23 and IL-17 in Behçet patients with active uveitis" Invest Opthalmol Vis Sci. 2008 49(7):3058-64.
Domek-Lopacinska K.U. et al. "Cyclic GMP and nitric oxide synthase in aging and Alzheimer's disease" Mol. Neurobiol. (2010) 41:129-137.
Dorwald F.Z. Side Reactions in Organic Synthesis. A Guide to Successful Synthesis Design (2005) Wiley-VCH Weinheim 6 pages.
Du J. et al. "Isoquinoline-1 3 4-trione Derivates Inactivate Caspase-3 by Generation of Reactive Oxygen Species" Journal of Biological Chemistry 2008 vol. 283 No. 44 p. 30205-30215.
European Patent Office Extended Search Report for Application No. 14819944.1 dated Jan. 4, 2017.
European Patent Office Supplementary Search Report for Application No. 14762328.4 dated Nov. 3, 2016.
Fauber, B. P et al., "Modulators of the Nuclear Receptor Retinoic Acid Receptor-Related Orphan Receptor-γ (RORγ or RORc)," Journal of Medicinal Chemistry, 2014, vol. 57, No. 14, pp. 5871-5892.
Ghoreschi K. et al. "Selective and therapeutic inhibition of kinases: to be or not to be?" Nat Immunol. Apr. 2009 10(4):356-360.
Harada S. et al. "Inclusion Compounds of Lankacidin-Group Antibiotics with Cyclodextrins" The Journal of Antibiotics 1985 vol. 38 No. 7 pp. 877-885.
Houslay M.D. et al. "cAMP-specific phosphodiesterase-4 enzymes in the cardiovascular system—A molecular toolbox for generating compartmentalized cAMP signaling"Cir. Red. (2007) 100:950-966.
Imramovsky A. et al. "Synthetic Route for the Preperation of 2-Hydroxy-N-[1-(2-hydroxyphenylamino)-1-oxoalkan-2-yl] benzamides" J. Comb. Chem. 2010 12 414-416.
International Search Report for Application No. PCT/JP2014/056721 dated May 27, 2014.
International Search Report for Application No. PCT/JP2014/067649 dated Sep. 30, 2014.
International Search Report for Application No. PCT/JP2014/067650 dated Aug. 19, 2014.
International Search Report for Application No. PCT/JP2014/069494 dated Sep. 24, 2014.
International Search Report for Application No. PCT/JP2014/069907 dated Aug. 26, 2014.
Jaeger R. et al. "Activation of PDE2 and PDE5 by specific GAF ligands: delayed activation of PDE5" British J. Pharmacol. (2010) 161:1645-1660.
Jiang Z. et al. "IL-23R gene congers susceptibility to Behcet's disease in a Chinese Han population" Ann Rheum Dis 2010 69(7):1325-8.
Jones G. H. "Inhibitors of cyclic AMP phosphodiesterase. 1. Analogues of Cilostamide and Anagrelide" Journal of Medicinal Chemistry 1987 vol. 30 No. 2 p. 295-303.
Jordan V.C. "Tamoxifen: a most unlikely pioneering medicine" Nature Rev. Drug Disc. (2003) 2:205-213.
Juilfs D.M. et al. "Cyclic GMP as substrate and regulator of cyclic nucleotide phosphodiesterases (PDEs)" in Rev. Physiol. Biochem. Pharmacol. (1999) 135:67-104.
Klimkowski V.J. et al. "D-phenylglycinol-derived non-covalent factor Xa inhibitors: effect of non-peptidic S4 linkage elements on affinity and anticoagulant activity" Biorg. Med. Chem. Lett (2007) 17:5801-5805.
Lakics V. et al. "Quantitative comparison of phosphodiesterase mRNA distribution in human brain and peripheral tissues" Neuropharmacology (2010) 59:367-374.
Martinez S.E. et al. "The two GAF domains in phosphodiesterase 2A have distinct roles in dimerization and in cGMP binding" Proc. Natl. Acad. Sci. (2002) 99(20):13260-13265.
Martins T.J. et al. "Purification and characterization of a cyclic GMP-stimulated cyclic nucleotide phosphodiesterase from Bovine Tissues" J. Biol. Chem. (1982) 257(4):1973-1979.
Masood A. et al. "Anxiolytic effects of phosphodiesterase-2 inhibitors associates with increased cGMP signaling" J. Pharmacology and Exp. Ther. (2009) 331(2):690-699.
Masood A. et al. "Reversal of oxidative stress-induced anxiety by inhibition of phosphodiesterase-2 in mice" J. Pharm. Exp. Thera. (2008) 326(2):369-379.

(56) References Cited

OTHER PUBLICATIONS

Menniti F.S. et al. "Phosphodiesterases in the CNS: targets for drug development" Nature Rev. Drug Discov. (2006) 5:660-670.
Minegishi Y. et al. "Molecular mechanisms of the immunological abnormalities in hyper-IgE syndrome" New York Academy of Science 2011 1246:34-40.
Nakamura & Yamamoto, "Transition-metal-catalyzed reactions in heterocyclic synthesis." Chem Rev. May 2004; 104(5):2127-98.
Pfefferkorn J.A. et al. "Pyridones as glucokinase activators: Identification of a unique metabolic liability of the 4-sulfonyl-2-pyridone heterocycle" Bioorganic & Medicinal Chemistry Letters 19 2009 3247-3252.
Rodefer J.S. et al. "Selective phosphodiesterase inhibitors improve performance on the ED/ID cognitive task in rats" Neuropharmacology (2012) 62:1182-1190.
Russell T.R. et al. "Separate phosphodiesterases for the hydrolysis of cyclic adenosine 3'5'-monophosphate and cyclic guanosine 3'5'-monophosphate in rat liver" J. Biol. Chem. (1973) 248(4):1334-1340.
Shen H.C. et al. "Discovery of pyrazolopyrimidines as the first class of allosteric agonists for the high affinity nicotinic acid receptor GPR109A" Bioorg. Med. Chem. Lett. (2008) 18:4948-4951.
Sheridan J. "The Most Common Chemical Replacements in Drug-Like Compounds" Chem Inf. Comput. Sci. 2002 42 103-108.
Stephenson D.T. et al. "Immunohistochemical localization of phosphodiesterase 2A in multiple mammalian species" J. Histochem. Cytochem. (2009) 57(10):933-949.
Strobl B. et al. "Tyrosine kinase 2 (TYK2) in cytokine signalling and host immunity" Front Biosci 2011 16:3214-32.
Tenor H. et al. "2. Analysis of PDE isoenzyme profiles in cells and tissues by pharmacological methods" in Phosphodiesterase Inhibitors (1996) Academic Press Limited pp. 21-40.
Thiel, "Structure-aided drug design's next generation." Nature Biotechnology vol. 22, pp. 513-519 (2004).
Toguchi H. et al. "Gastro-Intestinal Absorption of Ethyl 2-Chloro-3-[4-(2-methyl-2-phenylpropyloxy)phenyl]propionate from Different Dosage Forms in Rats and Dogs" Chemical and Pharmaceutical Bulletin 1990 vol. 38 No. 10 pp. 2792-2796.
United States Patent Office Action for U.S. Appl. No. 14/909,427 dated Oct. 20, 2016.
Venuti M.C. et al. "Inhibitors of cyclic AMP phosphodiesterase. 4. Synthesis and evaluation of potential prodrugs of lixazinone (N-cyclohexyl-N-methyl-4-[(1 2 3 5-tetrahydro-2-oxoimidazo [21-b] quinazolin-7-yl)oxy] butyramide RS-82856)" Journal of Medicinal Chemistry 1988 vol. 31 No. 11 p. 2145-2152.
Wong J.C. et al. "Application of p21 and klf2 reporter gene assays to indentify selective histone deacetylase inhibitors for cancer therapy" Bioorganic & Medicinal Chemistry Letters 2011 21(1) 110-116.
Wong J.C. et al. "Pharmacokinetic Optimization of Class-Selective Histone Deacetylase Inhibitors and Identification of Associated Candidate Predictive Biomarkers of Hepatocellular Carcinoma Tumor Response" Journal of Medicinal Chemistry 2012 55(20) 8903-8925.
Written Opinion for Application No. PCT/JP2014/056721 dated May 27, 2014.
Written Opinion for Application No. PCT/JP2014/067649 dated Sep. 30, 2014.
Written Opinion for Application No. PCT/JP2014/067650 dated Aug. 19, 2014.
Written Opinion for Application No. PCT/JP2014/069494 dated Sep. 24, 2014.
Written Opinion for Application No. PCT/JP2014/069907 dated Aug. 26, 2014.
Wu A.Y. et al. "Molecular determinants for cyclic nucleotide binding to the regulatory domains of phosphodiesterase 2A" J. Biol. Chem. (2004) 279(36):37928-37938.
Yamagata K. et al. "Synthesis of 1-acyl-2-oxo-3-pyrrolidinecarbonitriles by the reaction of 2-acylamino-45-dihydro-3-furancarbonitriles with sodium iodide" Journal of Heterocyclic Chemistry 2005 vol. 42 Issue 4 pp. 542-549.
Yamamoto T. et al. "Purification and characterization of cyclic GMP-stimulated cyclic nucleotide phosphodiesterase from calf liver. Effects of divalent cations on activity" J. Biol. Chem. (1983) 258(20):12526-12533.
Afzali et al. "The role of T helper 17 (Th17) and regulatory T cells (Treg) in human organ transplantation and autoimmune disease" *Clin. Exp. Immunol.* 2007; 148(1): 32-46.
Cosmi et al. "Th17cells: new players in asthma pathogenesis" *Allergy* 2011; 66(8): 989-998.
Monteleone et al. "Th17-related cytokines: new players in the control of chronic intestinal inflammation" *BMC Med.* 2011, 9:122.
Pernis, "Th17 cells in rheumatoid arthritis and systemic lupus erythematosus" *J. Intern. Med.* 2009; 265(6): 644-652.
Petro, "Regulatory role of resveratrol on Th17 in autoimmune disease" *Int. Immunopharmacol.* 2011; 11(3): 310-318.
Prescribing information for COSENTYX, an FDA-approved human interleukin-17A antagonist (Jan. 2016).
Sanchez-Muñoz et al., "Role of cytokines in inflammatory bowel disease." *World J. Gastroenterol.* 2008; 14(27): 4280-4288.
Sarra et al. "IL-23IL-17 Axis in IBD." *Inflamm. Bowel Dis.* 2010; 16(10): 1808-1813.
Sugita et al. "Inhibition of Th17 differentiation by anti-TNF alpha therapy in uveitis patients with Behçet's disease" *Arthritis Res. Ther.* 2012, 14(3): R99.

\* cited by examiner

SEQUENCE LISTING

```
<160> NUMBER OF SEQ ID NOS: 1

<210> SEQ ID NO 1
<211> LENGTH: 20
<212> TYPE: PRT
<213> ORGANISM: Artificial Sequence
<220> FEATURE:
<223> OTHER INFORMATION: SRC-1 peptide

<400> SEQUENCE: 1

Cys Leu Thr Ala Arg His Lys Ile Leu His Arg Leu Leu Gln Glu Gly
1               5                   10                  15

Ser Pro Ser Asp
            20
```

HETEROCYCLIC AMIDE COMPOUNDS HAVING AN RORVT INHIBITORY ACTION

CROSS-REFERENCE TO RELATED APPLICATIONS

This is a continuation of U.S. application Ser. No. 16/576,293, filed on Sep. 29, 2019, which is a divisional of U.S. application Ser. No. 14/902,388, filed on Dec. 31, 2015, now U.S. Pat. No. 10,472,376, issued on Nov. 12, 2019, which is a U.S. national stage entry of International Patent Application No. PCT/JP2014/067649, filed on Jul. 2, 2014, which claims priority to Japanese Patent Application No. 2013-140213, filed on Jul. 3, 2013, the entire contents of all of which are fully incorporated herein by reference.

SEQUENCE LISTING

The text of the computer readable sequence listing filed herewith, titled "36015-303_Sequence_Listing_ST25", created May 10, 2021, having a file size of 698 bytes, is hereby incorporated by reference in its entirety.

TECHNICAL FIELD

The present invention relates to a heterocyclic compound having an RORγt inhibitory action, a medicament containing the compound, and the like.

BACKGROUND OF THE INVENTION

Th17 cell and inflammatory cytokine (IL-17A, IL-17F, etc.) produced thereby cause a decrease in QOL as a severe etiology cell and factor accompanying enhancement of a systemic new immune response, in various autoimmune disease such as inflammatory bowel disease (IBD), rheumatoid arthritis, multiple sclerosis or psoriasis. However, the existing therapeutic drugs show only limited effects, and therefore, the earliest possible development of a novel therapeutic drug has been desired.

Involvement of T cells, inter alia, Th17 cell and inflammatory cytokines (IL-17A, IL-17F, etc.) produced thereby, in the pathology of these immune disease has been drawing attention in recent years.

Moreover, it has been recently clarified that a Retinoid-related Orphan Receptor (ROR) γt, which is one of the orphan nuclear receptors, plays an important role in the differentiation of Th17 cells and production of IL-17A/IL-17F. That is, it has been reported that RORγt is mainly expressed in Th17 cells and functions as a transcription factor of IL-17A and IL-17F, as well as a master regulator of Th17 cell differentiation.

Therefore, a medicament that inhibits the action of RORγt is expected to show a treatment effect on various immune disease by suppressing differentiation and activation of Th17 cells.

Non-Patent Document 1 discloses the following compound as an amide compound.

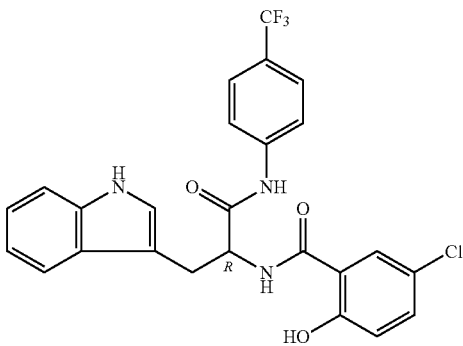

Patent Document 1 discloses a compound represented by the formula:

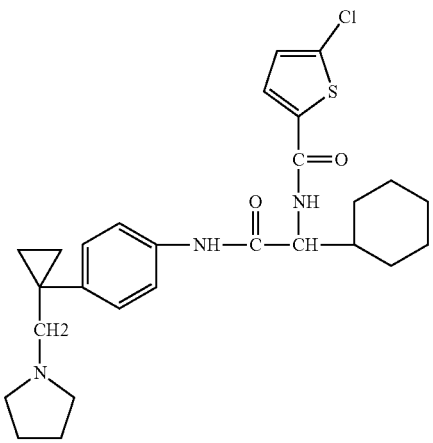 [SMILES: O=C(NC(C(=O)Nc1ccc(C2(CN3CCCC3)CC2)cc1)C1CCCCC1)c1ccc(Cl)s1]

which is a compound having a Xa factor inhibitory action, and is useful for the treatment of thromboembolism.

Patent Document 2 discloses a compound represented by the general formula:

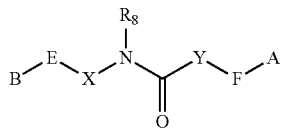

wherein

E and F are independently a saturated or unsaturated non-cyclic hydrocarbon group having 1, 2, 3, 4 or 5 carbon atoms;

X and Y are independently methylene or the like;

$R_8$ is hydrogen or the like; and

A and B are the same or different and each is selected from

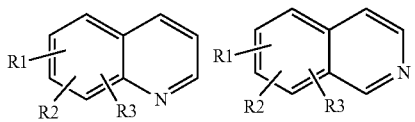

-continued

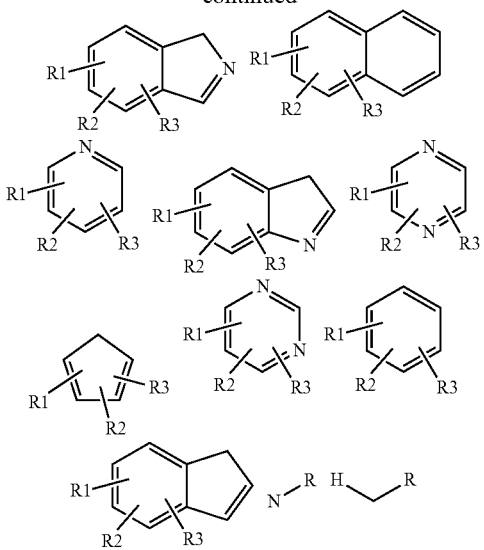

wherein R1, R2 and R3 are the same or different and each is selected from hydrogen, halogen, an alkyl group having 1 to 5 carbon atoms, and the like,
which is a melanocortin receptor agonist or antagonist, and is useful for the treatment of inflammation and the like.

Patent Document 3 discloses a compound represented by the formula:

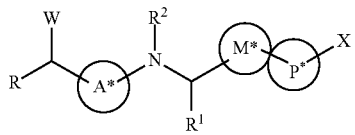

wherein
M* is $(CH_2)_n$, (n=0, 1 or 2);
P* is C=O, CONH, $CO_2$, —$CH_2$— or the like;
A* is carbonyl(C=O) or the like;
R is selected from H, alkyl ($C_1$-$C_4$) and the like;
$R^1$ is selected from H, alkyl ($C_1$-$C_4$) and the like;
$R^2$ is selected from H, alkyl ($C_1$-$C_4$) and the like;
W is selected from (alpha-aminoacyl)amide, aminoalkyl, amino and the like; and
X is selected from aryl ($C_6$-$C_{10}$), mono-substituted aryl ($C_6$-$C_{10}$) and the like,
which is an efflux pump inhibitor, and is useful for the treatment of bacterial infection.

Patent Document 4 discloses, as a fused heterocyclic compound, a compound represented by the formula:

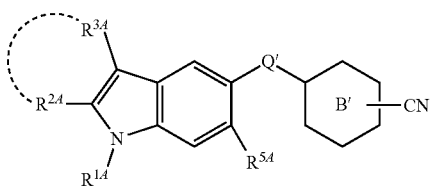

wherein
$R^{1A}$ is an optionally substituted hydrocarbon group or an optionally substituted hydrocarbon-oxy group, $R^{2A}$ and $R^{3A}$ are each independently a hydrogen atom, an optionally substituted hydrocarbon group or the like, or $R^{2A}$ and $R^{3A}$ in combination optionally form, together with the carbon atoms which they are bonded to, an optionally substituted hydrocarbon ring,
$R^{5A}$ is a hydrogen atom or a halogen atom,
Q' is

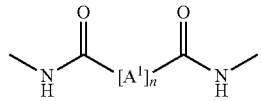

wherein
[$A^1$] are the same or different and each is a methylene group optionally substituted by $C_{1-6}$ alkyl group(s) optionally substituted by hydroxy group(s) and the like, wherein the two substituents bonded to the single carbon atom are optionally combined to each other to form a hydrocarbon ring, and
n is an integer of 1 to 5, or the like, and
Ring B' is a benzene ring optionally further having substituent(s), or the like,
which has a RORγt inhibitory action, and is useful for the treatment of inflammatory bowel disease (IBD) and the like.

Patent Document 5 discloses a compound represented by the formula:

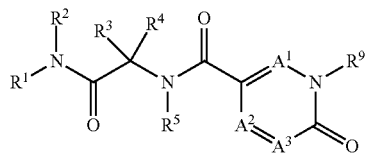

wherein
$A^1$ is $CR^{A1}$ wherein $R^{A1}$ is a hydrogen atom or a substituent, or a nitrogen atom,
$A^2$ is $CR^{A2}$ wherein $R^{A2}$ is a hydrogen atom or a substituent, or a nitrogen atom,
$A^3$ is $CR^{A3}$ wherein $R^{A3}$ is a hydrogen atom or a substituent, or a nitrogen atom, or,
provided that when $A^2$ is $CR^{A2}$ wherein $R^{A2}$ is a substituent, and
$A^3$ is $CR^{A3}$ wherein $R^{A3}$ is a substituent, then $R^{A2}$ and $R^{A3}$ in combination optionally form, together with the carbon atoms which they are bonded to, a carbocycle or a heterocycle,
$R^1$ is an optionally substituted carbocyclic group or the like,
$R^2$ is a hydrogen atom or a substituent,
one of $R^3$ or $R^4$ is an optionally substituted carbocyclic group, an optionally substituted aromatic nitrogen-containing heterocyclic group or an optionally substituted fused non-aromatic heterocyclic group, and the other is a hydrogen atom or a substituent,
$R^5$ is a hydrogen atom or a substituent, and
$R^9$ is a hydrogen atom or a hydroxy group, provided that when $R^9$ is a hydroxy group, then $A^1$, $A^2$ and $A^3$ are $CR^{A1}$, $CR^{A2}$ and $CR^{A3}$, respectively.

Patent Document 6 discloses a compound represented by the formula:

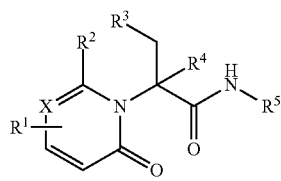

wherein

X is carbon or nitrogen, $R^1$ is —$CF_2R^a$, wherein $R^a$ is H, F or $C_{1-6}$ alkyl, $R^2$ is H, halo, $CF_3$, a $C_{1-6}$ alkyl or $C_{1-3}$ alkoxy, $R^3$ is a chemical moiety selected from the group consisting of $C_{3-6}$ cycloalkyl, 5- to 6-membered heterocycle, 5- to 6-membered heteroaryl and phenyl, wherein the heterocycle and heteroaryl each independently contains 1 to 3 heteroatoms selected from N, O and S, and the moiety is each independently optionally substituted by 1 to 3 substituents selected from halo, $C_{1-6}$ alkyl, $C_{1-6}$ alkoxy, $CF_3$ and cyano, $R^4$ is H or $C_{1-6}$ alkyl, and $R^5$ is a chemical moiety selected from the group consisting of 5- to 6-membered heteroaryl and quinolinyl, wherein the heteroaryl each independently contains 1 to 3 heteroatoms selected from N, O and S, and the moiety is each independently optionally substituted by 1 to 3 of $R^6$ substituents selected from $C_{1-6}$ alkyl, $CF_3$, cyano, $C_{1-6}$ alkoxy, halo, amino, $C_{1-3}$ alkylamino, di-$C_{1-3}$ alkylamino, —$CH_2P(O)(OR^7)(OR^8)$, —$C(O)OR^7$, —$CH_2C(O)OR^7$ and aryl $C_{1-6}$ alkyl, and $R^7$ and $R^8$ are each independently H or $C_{1-6}$ alkyl, and the aryl of the arylalkyl is each independently optionally substituted by 1 to 3 substituents selected from $C_{1-6}$ alkyl, $CF_3$, cyano, $C_{1-6}$ alkoxy, halo, carboxy, amino, $C_{1-3}$ alkylamino and di-$C_{1-3}$ alkylamino, which is useful for the treatment of glucokinase activation-related diseases.

Non-Patent Document 2 discloses the following compound.

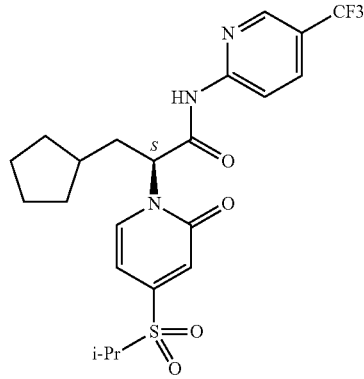

Patent Document 7 discloses a compound represented by the formula:

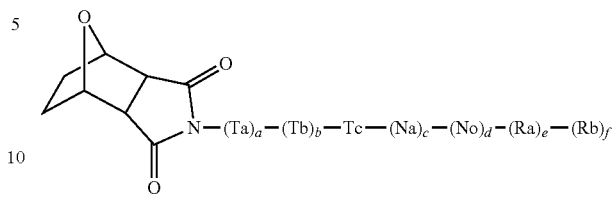

wherein each symbol is as defined in the document, which is useful for the treatment or prophylaxis of cancer, cell signaling pathway-related diseases and microorganism infection-related diseases.

Patent Document 8 discloses a compound represented by the formula:

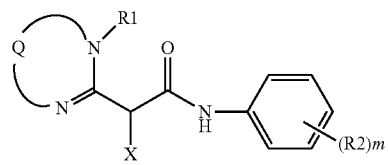

wherein

Q is a group represented by —C(—R11)=C(—R12)-$SO_2$— wherein R11 and R12 are bonded to each other to form a 5- to 7-membered ring together with —C=C—, or each independently a hydrogen atom or a substituent, R1 is a substituent, R2 is a substituent, m is an integer of 0 to 5, when m is 2 or more, then plural R2 are the same or different, or they are optionally bonded to each other to form a ring, and X is a group capable of being leaved by coupling reaction with an oxidized product of a developing agent.

Patent Document 9 discloses a compound represented by the formula:

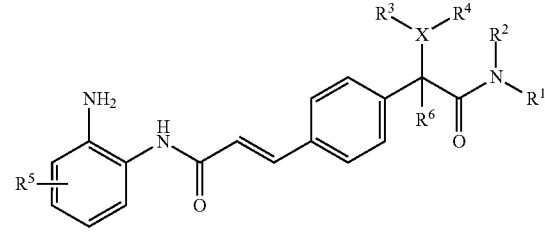

wherein $R^1$, $R^2$, $R^3$ and $R^4$ are independently selected from hydrogen; $C_{1-3}$ alkyl; 3- to 8-membered monocyclic or bicyclic cycloalkyl; 3- to 8-membered monocyclic or bicyclic heterocycle wherein one, two or three carbon atoms are replaced by heteroatom(s) selected from oxygen, nitrogen and sulfur; 6- to 10-membered monocyclic or bicyclic aryl; or 5- to 10-membered monocyclic or bicyclic heteroaryl wherein one, two, three or four carbon atoms are optionally replaced by nitrogen, oxygen or sulfur; the all of groups are optionally unsubstituted or substituted by 1 or plural substituents;

X is —N— or —O—;

$R^5$ is —H or —F;

$R^6$ is —H or —$CH_3$; or when X is —N—, and R³ and R⁴ in combination form a 4- to 6-membered heterocycle together with the nitrogen atom they are bonded to, then one additional carbon atom may be replaced by nitrogen, oxygen or sulfur, which is useful for the treatment of cancer.

The following compounds are registered Chemical Abstracts.

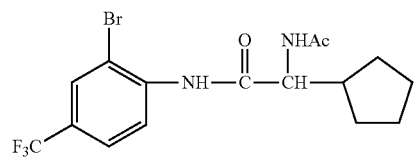 [SMILES: CC(=O)NC(C(=O)Nc1ccc(C(F)(F)F)cc1Br)C1CCCC1]

CAS Registry Number: 1427736-73-9

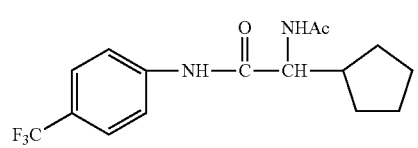 [SMILES: CC(=O)NC(C(=O)Nc1ccc(C(F)(F)F)cc1)C1CCCC1]

CAS Registry Number: 1323260-38-3

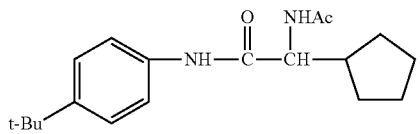 [SMILES: CC(=O)NC(C(=O)Nc1ccc(C(C)(C)C)cc1)C1CCCC1]

CAS Registry Number: 1323005-31-7

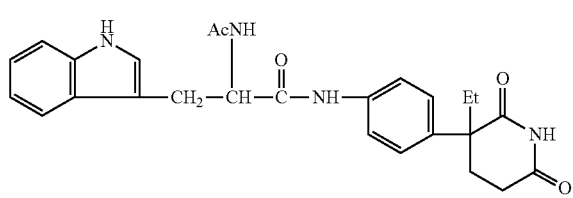

CAS Registry Number: 1316015-84-5

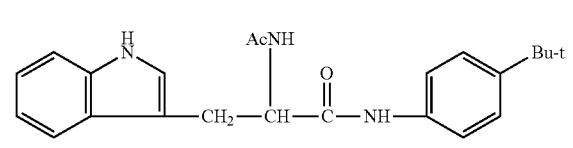

CAS Registry Number: 1286063-95-3

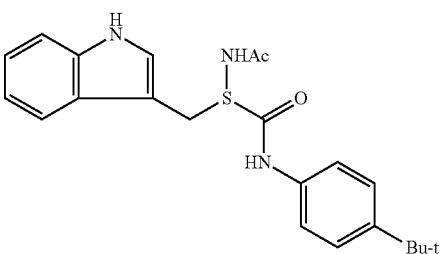

CAS Registry Number: 1277664-46-6

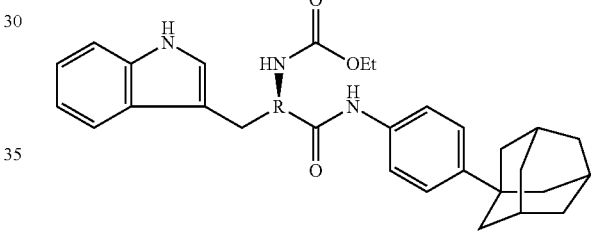

CAS Registry Number: 1217860-74-6

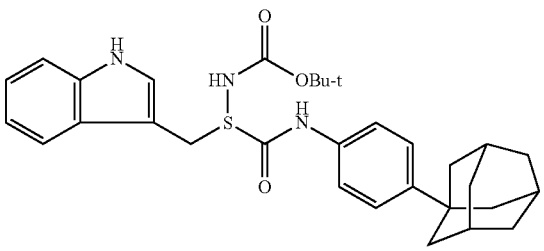

CAS Registry Number: 1217709-83-5

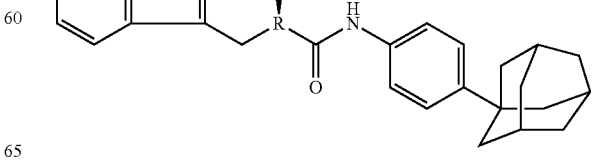

CAS Registry Number: 957036-06-5

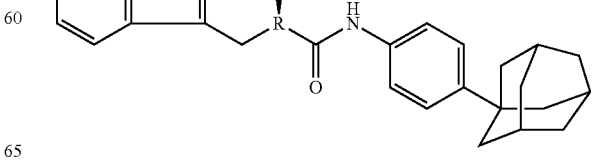

CAS Registry Number: 956728-16-8

DOCUMENT LIST

Patent Document

[Patent Document 1] WO 2004/108892
[Patent Document 2] WO 2001/055106
[Patent Document 3] WO 99/37667
[Patent Document 4] WO 2013/042782
[Patent Document 5] WO 2013/100027
[Patent Document 6] WO 2010/013161
[Patent Document 7] FR 2860793
[Patent Document 8] EP 1341035
[Patent Document 9] WO 2009/095324

Non-Patent Document

[Non-Patent Document 1] Journal of Combinatorial Chemistry (2010), 12(4), 414-416
[Non-Patent Document 2] Bioorganic & Medicinal Chemistry Letters (2009), 19(12), 3247-3252

SUMMARY OF THE INVENTION

Problems to be Solved by the Invention

The present invention aims to provide a compound having a superior RORγt inhibitory action, and is useful as an agent for the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis, systemic lupus erythematosus (SLE) and the like.

Means of Solving the Problems

The present inventors have found that a compound represented by the following formula (I) or a salt thereof has a superior RORγt inhibitory action based on the specific chemical structure thereof and affords superior efficacy as an agent for the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis, systemic lupus erythematosus (SLE) and the like. The present inventors have conducted intensive studies based on the finding and completed the present invention.

Accordingly, the present invention relates to the followings.

[1] A compound represented by the following formula (I):

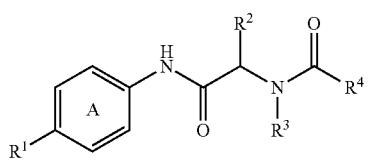

wherein
Ring A is an optionally further substituted 6-membered aromatic ring,
$R^1$ is
  (1) a group represented by the formula: $-Q(R^{1a})(R^{1b})(R^{1c})$
  wherein
    Q is a carbon atom, a silicon atom or a germanium atom, and
    $R^{1a}$, $R^{1b}$ and $R^{1c}$ are each independently a substituent, or
    $R^{1a}$ and $R^{1b}$ in combination optionally form, together with the adjacent Q, an optionally substituted ring,
  (2) a neopentyl group, or
  (3) a trimethylsilylmethyl group,
$R^2$ is
  (1) a group represented by the formula:

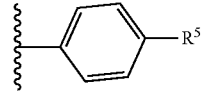

wherein
$R^5$ is an optionally substituted alkyl group or an optionally substituted alkoxy group, and
the benzene ring in the formula optionally has additional substituent (s) besides $R^5$,
  (2) an optionally substituted bicyclic fused heterocyclic group, or
  (3) a group represented by the formula: $-L-Z^1$
wherein
L is a bond or $CH_2$, and $Z^1$ is an optionally substituted non-aromatic ring group,
$R^3$ is a hydrogen atom or a substituent, and
$R^4$ is a substituent (provided that
  (1) a group represented by the formula:

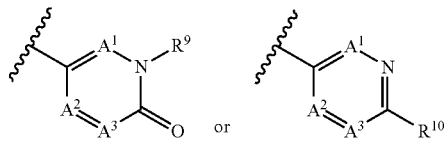

wherein
$A^1$ is $CR^{A1}$ wherein $R^{A1}$ is a hydrogen atom or a substituent, or a nitrogen atom,
$A^2$ is $CR^{A2}$ wherein $R^{A2}$ is a hydrogen atom or a substituent, or a nitrogen atom,
  $A^3$ is $CR^{A3}$ wherein $R^{A3}$ is a hydrogen atom or a substituent, or a nitrogen atom, or
  when $A^2$ is $CR^{A2}$ wherein $R^{A2}$ is a substituent, and $A^3$ is $CR^{A3}$ wherein $R^{A3}$ is a substituent, then $R^{A2}$ and $R^{A3}$ in combination optionally form, together with the carbon atoms that they are bonded to, a hydrocarbon ring or a heterocycle,
  $R^9$ is a hydrogen atom or a hydroxy group, and when $R^9$ is a hydroxy group, then $A^1$, $A^2$ and $A^3$ are $CR^{A1}$, $CR^{A2}$ and $CR^{A3}$, respectively, and
  $R^{10}$ is a hydroxy group or an optionally substituted $C_{1-6}$ alkoxy group, and
  (2) an optionally substituted $C_{1-6}$ alkoxy group are excluded), or
when $R^3$ is a substituent, then $R^3$ and $R^4$ in combination optionally form, together with the nitrogen atom adjacent to $R^3$ and the carbon atom adjacent to $R^4$, an optionally substituted ring (provided that (1) a cyclic group represented by the formula:

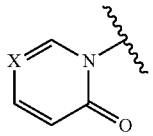

wherein X is CH or a nitrogen atom, which is optionally further substituted, and
(2) a cyclic group represented by the formula:

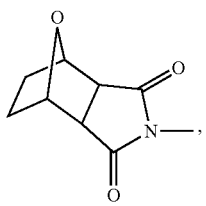

are excluded), and
the substituents that the ring optionally has optionally form a spiro ring,
provided that
5-chloro-N-[1-cyclohexyl-2-oxo-2-[[4-[1-(1-pyrrolidinylmethyl)cyclopropyl]phenyl]amino]ethyl]-2-thiophenecarboxamide,
α-(acetylamino)-N-[4-(trifluoromethyl)phenyl]-cyclopentaneacetamide,
α-(acetylamino)-N-[4-(1,1-dimethylethyl)phenyl]-cyclopentaneacetamide,
α-(acetylamino)-N-[2-bromo-4-(trifluoromethyl)phenyl]-cyclopentaneacetamide, and
N-(4-tert-butyl-2-((5-ethyl-2-(2-ethyl-4,4-dimethylpentyl)-7,7-dimethyloctyl)oxy)phenyl)-2-(5,5-dimethyl-2,4-dioxo-1,3-oxazolidin-3-yl)-2-(2-octadecyl-1,1-dioxido-2H-1,2,4-benzthiadiazin-3-yl)acetamide
are excluded,
or a salt thereof (hereinafter sometimes to be referred to as compound (I)).
[2] The compound or salt of the above-mentioned [1], wherein the substituent that Ring A optionally further has is a fluorine atom or a chlorine atom.
[3] The compound or salt of the above-mentioned [1], wherein $R^1$ is a tert-butyl group, a neopentyl group or a trimethylsilyl group.
[4] The compound or salt of the above-mentioned [1], wherein $R^2$ is
(1) a group represented by the formula:

wherein $R^5$ is an alkoxy group or an alkoxyalkyl group,
(2) a tetrahydro-2H-pyran-4-yl group,
(3) a 4,4-difluorocyclohexyl group,
(4) a 1-methyl-1H-indazol-5-yl group, or
(5) a 2,3-dihydro-1-benzofuran-5-yl group.
[5] The compound or salt of the above-mentioned [1], wherein $R^3$ is a hydrogen atom or a methyl group.

[6] The compound or salt of the above-mentioned [1], wherein $R^4$ is (1) an optionally substituted 5-membered heterocyclic group, (2) an optionally substituted 6-membered non-aromatic heterocyclic group, (3) an optionally substituted 4-membered non-aromatic heterocyclic group, (4) an optionally substituted $C_{3-4}$ cycloalkyl group, or (5) an optionally substituted $C_{1-4}$ alkyl group.
[7] (3S)—N-((1R)-2-((4-tert-Butyl-3-fluorophenyl)amino)-1-(4,4-difluorocyclohexyl)-2-oxoethyl)-5-oxopyrrolidine-3-carboxamide or a salt thereof.
[8] N-((1R)-2-((3,5-Difluoro-4-(trimethylsilyl)phenyl)amino)-1-(4-methoxyphenyl)-2-oxoethyl)-3-hydroxy-N-methyl-1,2-oxazole-5-carboxamide or a salt thereof.
[9] (2R)—N-(4-tert-Butyl-3,5-difluorophenyl)-2-(((3-hydroxy-1,2-oxazol-5-yl)acetyl)amino)-2-(1-methyl-1H-indazol-5-yl)acetamide or a salt thereof.
[10] A medicament comprising the compound or salt of claim 1.
[11] A medicament comprising a compound represented by the following formula (I'):

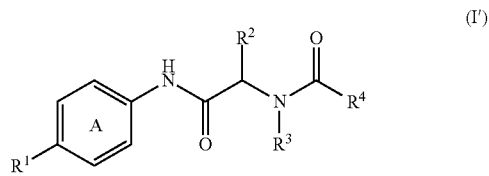

wherein
Ring A is an optionally further substituted 6-membered aromatic ring,
$R^1$ is
(1) a group represented by the formula: $-Q(R^{1a})(R^{1b})(R^{1c})$
wherein
Q is a carbon atom, a silicon atom or a germanium atom, and
$R^{1a}$, $R^{1b}$ and $R^{1c}$ are each independently a substituent, or
$R^{1a}$ and $R^{1b}$ in combination optionally form, together with the adjacent Q, an optionally substituted ring,
(2) a neopentyl group, or
(3) a trimethylsilylmethyl group,
$R^2$ is
(1) a group represented by the formula:

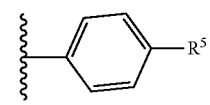

wherein
$R^5$ is an optionally substituted alkyl group or an optionally substituted alkoxy group, and
the benzene ring in the formula optionally has additional substituent(s) besides $R^7$,
(2) an optionally substituted bicyclic fused heterocyclic group, or
(3) a group represented by the formula: $-L-Z^1$
wherein
L is a bond or $CH_2$, and
$Z^1$ is an optionally substituted non-aromatic ring group, $R^3$ is a hydrogen atom or a substituent, and
$R^4$ is a substituent (provided that
(1) a group represented by the formula:

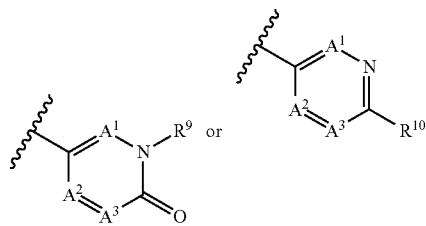

wherein
$A^1$ is $CR^{A1}$ wherein $R^{A1}$ is a hydrogen atom or a substituent, or a nitrogen atom,
$A^2$ is $CR^{A2}$ wherein $R^{A2}$ is a hydrogen atom or a substituent, or a nitrogen atom,
$A^3$ is $CR^{A3}$ wherein $R^{A3}$ is a hydrogen atom or a substituent, or a nitrogen atom, or
when $A^2$ is $CR^{A2}$ wherein $R^{A2}$ is a substituent, and $A^3$ is $CR^{A3}$ wherein $R^{A3}$ is a substituent, then $R^{A2}$ and $R^{A3}$ in combination optionally form, together with the carbon atoms that they are bonded to, a hydrocarbon ring or a heterocycle,
$R^9$ is a hydrogen atom or a hydroxy group, and when $R^9$ is a hydroxy group, then $A^1$, $A^2$ and $A^3$ are $CR^{A1}$, $CR^{A2}$ and $CR^{A}$, respectively, and
$R^{10}$ is a hydroxy group or an optionally substituted $C_{1-6}$ alkoxy group, and
(2) an optionally substituted $C_{1-6}$ alkoxy group are excluded), or
when $R^3$ is a substituent, then $R^3$ and $R^4$ in combination optionally form, together with the nitrogen atom adjacent to R and the carbon atom adjacent to $R^4$, an optionally substituted ring, and the substituents that the ring optionally has optionally form a spiro ring,
or a salt thereof (hereinafter sometimes to be referred to as compound (I')), which is a RORγt inhibitor.

[12] A medicament comprising a compound represented by the following formula (I'):

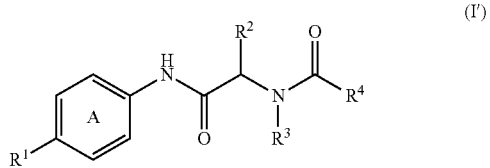

wherein
Ring A is an optionally further substituted 6-membered aromatic ring,
$R^1$ is
(1) a group represented by the formula: -Q($R^{1a}$)($R^{1b}$)($R^{1c}$) wherein
Q is a carbon atom, a silicon atom or a germanium atom, and
$R^{1a}$, $R^{1b}$ and $R^{1c}$ are each independently a substituent, or $R^{1a}$ and $R^{1b}$ in combination optionally form, together with the adjacent Q, an optionally substituted ring,
(2) a neopentyl group, or
(3) a trimethylsilylmethyl group, $R^2$ is
(1) a group represented by the formula:

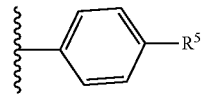

wherein
$R^5$ is an optionally substituted alkyl group or an optionally substituted alkoxy group, and
the benzene ring in the formula optionally has additional substituent(s) besides $R^5$,
(2) an optionally substituted bicyclic fused heterocyclic group, or
(3) a group represented by the formula: -L-$Z^1$
wherein
L is a bond or $CH_2$, and
$Z^1$ is an optionally substituted non-aromatic ring group,
$R^3$ is a hydrogen atom or a substituent, and
$R^4$ is a substituent (provided that
(1) a group represented by the formula:

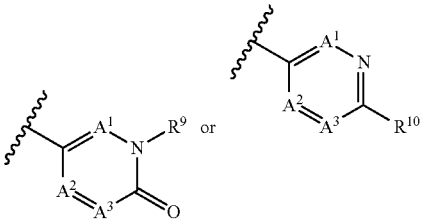

wherein
$A^1$ is $CR^{A1}$ wherein $R^{A1}$ is a hydrogen atom or a substituent, or a nitrogen atom,
$A^2$ is $CR^{A2}$ wherein $R^{A2}$ is a hydrogen atom or a substituent, or a nitrogen atom,
$A^3$ is $CR^{A3}$ wherein $R^{A3}$ is a hydrogen atom or a substituent, or a nitrogen atom, or
when $A^2$ is $CR^{A2}$ wherein $R^{A2}$ is a substituent, and $A^3$ is $CR^{A3}$ wherein $R^{A3}$ is a substituent, then $R^{A2}$ and $R^{A3}$ in combination optionally form, together with the carbon atoms that they are bonded to, a hydrocarbon ring or a heterocycle,
$R^9$ is a hydrogen atom or a hydroxy group, and when $R^9$ is a hydroxy group, then $A^1$, $A^2$ and $A^3$ are $CR^{A1}$, $CR^{A2}$ and $CR^{A}$, respectively, and
$R^{10}$ is a hydroxy group or an optionally substituted $C_{1-6}$ alkoxy group, and
(2) an optionally substituted $C_{1-6}$ alkoxy group are excluded), or
when $R^3$ is a substituent, then $R^3$ and $R^4$ in combination optionally form, together with the nitrogen atom adjacent to $R^3$ and the carbon atom adjacent to $R^4$, an optionally substituted ring, and the substituents that the ring optionally has optionally form a spiro ring,
or a salt thereof, which is an agent for the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis or systemic lupus erythematosus (SLE).

[13] A method of inhibiting RORγt, which comprises administering an effective amount of a compound represented by the following formula (I'):

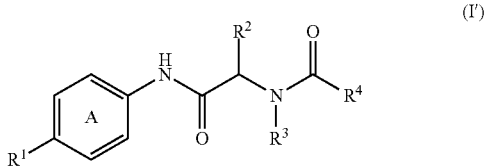

(I')

wherein
Ring A is an optionally further substituted 6-membered aromatic ring,
$R^1$ is
(1) a group represented by the formula: $-Q(R^{1a})(R^{1b})(R^{1c})$
wherein
Q is a carbon atom, a silicon atom or a germanium atom, and
$R^{1a}$, $R^{1b}$ and $R^{1c}$ are each independently a substituent, or $R^{1a}$ and $R^{1b}$ in combination optionally form, together with the adjacent Q, an optionally substituted ring,
(2) a neopentyl group, or
(3) a trimethylsilylmethyl group,
$R^1$ is
(1) a group represented by the formula:

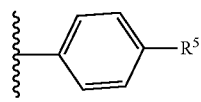

wherein
$R^5$ is an optionally substituted alkyl group or an optionally substituted alkoxy group, and
the benzene ring in the formula optionally has additional substituent(s) besides $R^5$,
(2) an optionally substituted bicyclic fused heterocyclic group, or
(3) a group represented by the formula: $-L-Z^1$
wherein
L is a bond or $CH_2$, and
$Z^1$ is an optionally substituted non-aromatic ring group,
$R^3$ is a hydrogen atom or a substituent, and
$R^4$ is a substituent (provided that
(1) a group represented by the formula:

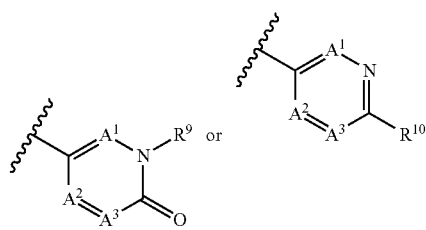

wherein
$A^1$ is $CR^{A1}$ wherein $R^{A1}$ is a hydrogen atom or a substituent, or a nitrogen atom,
$A^2$ is $CR^{A2}$ wherein $R^{A2}$ is a hydrogen atom or a substituent, or a nitrogen atom,
$A^3$ is $CR^{A3}$ wherein $R^{A3}$ is a hydrogen atom or a substituent, or a nitrogen atom, or
when $A^2$ is $CR^{A2}$ wherein $R^{A2}$ is a substituent, and $A^3$ is $CR^{A3}$ wherein $R^{A3}$ is a substituent, then $R^{A2}$ and $R^{A3}$ in combination optionally form, together with the carbon atoms that they are bonded to, a hydrocarbon ring or a heterocycle,
$R^9$ is a hydrogen atom or a hydroxy group, and when $R^9$ is a hydroxy group, then $A^1$, $A^2$ and $A^3$ are $CR^{A1}$, $CR^{A2}$ and $CR^{A3}$, respectively, and
$R^{10}$ is a hydroxy group or an optionally substituted $C_{1-6}$ alkoxy group, and
(2) an optionally substituted $C_{1-6}$ alkoxy group are excluded), or
when $R^3$ is a substituent, then $R^3$ and $R^4$ in combination optionally form, together with the nitrogen atom adjacent to $R^3$ and the carbon atom adjacent to $R^4$, an optionally substituted ring, and the substituents that the ring optionally has optionally form a spiro ring, or a salt thereof to a mammal.

[14] A method for the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis or systemic lupus erythematosus (SLE), which comprises administering an effective amount of a compound represented by the following formula (I'):

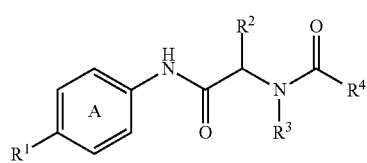

(I')

wherein
Ring A is an optionally further substituted 6-membered aromatic ring,
$R^1$ is
(1) a group represented by the formula: $-Q(R^{1a})(R^{1b})(R^{1c})$
wherein
Q is a carbon atom, a silicon atom or a germanium atom, and
$R^{1a}$, $R^{1b}$ and $R^{1c}$ are each independently a substituent, or
$R^{1a}$ and $R^{1b}$ in combination optionally form, together with the adjacent Q, an optionally substituted ring,
(2) a neopentyl group, or
(3) a trimethylsilylmethyl group,
$R^2$ is
(1) a group represented by the formula:

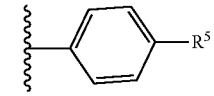

wherein
$R^5$ is an optionally substituted alkyl group or an optionally substituted alkoxy group, and the benzene ring in the formula optionally has additional substituent (s) besides $R^5$,
(2) an optionally substituted bicyclic fused heterocyclic group, or
(3) a group represented by the formula: $-L-Z^1$ wherein
L is a bond or $CH_2$, and
$Z^1$ is an optionally substituted non-aromatic ring group, $R^3$ is a hydrogen atom or a substituent, and
$R^4$ is a substituent (provided that
(1) a group represented by the formula:

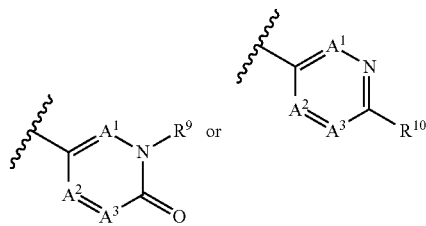

wherein
$A^1$ is $CR^{41}$ wherein $R^{41}$ is a hydrogen atom or a substituent, or a nitrogen atom,
$A^2$ is $CR^{42}$ wherein $R^{42}$ is a hydrogen atom or a substituent, or a nitrogen atom,
$A^3$ is $CR^{43}$ wherein $R^{43}$ is a hydrogen atom or a substituent, or a nitrogen atom, or
when $A^2$ is $CR^{42}$ wherein $R^{42}$ is a substituent, and $A^3$ is $CR^{43}$ wherein $R^{43}$ is a substituent, then $R^{42}$ and $R^{43}$ in combination optionally form, together with the carbon atoms that they are bonded to, a hydrocarbon ring or a heterocycle,
$R^9$ is a hydrogen atom or a hydroxy group, and when $R^9$ is a hydroxy group, then $A^1$, $A^2$ and $A^3$ are $CR^{41}$, $CR^{42}$ and $CR^4$, respectively, and
$R^{10}$ is a hydroxy group or an optionally substituted $C_{1-6}$ alkoxy group, and
(2) an optionally substituted $C_{1-6}$ alkoxy group are excluded), or
when $R^3$ is a substituent, then $R^3$ and $R^4$ in combination optionally form, together with the nitrogen atom adjacent to $R^3$ and the carbon atom adjacent to $R^4$, an optionally substituted ring, and the substituents that the ring optionally has optionally form a spiro ring,
or a salt thereof to a mammal.

[15] Use of a compound represented by the following formula (I'):

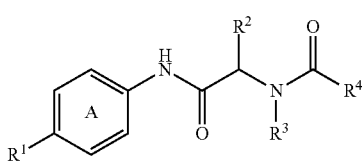

wherein
Ring A is an optionally further substituted 6-membered aromatic ring,
$R^1$ is
(1) a group represented by the formula: $-Q(R^{1a})(R^{1b})(R^{1c})$
wherein
Q is a carbon atom, a silicon atom or a germanium atom, and
$R^{1a}$, $R^{1b}$ and $R^{1c}$ are each independently a substituent, or
$R^{1a}$ and $R^{1b}$ in combination optionally form, together with the adjacent Q, an optionally substituted ring,
(2) a neopentyl group, or
(3) a trimethylsilylmethyl group, $R^2$ is
(1) a group represented by the formula:

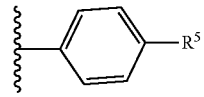

wherein
$R^5$ is an optionally substituted alkyl group or an optionally substituted alkoxy group, and
the benzene ring in the formula optionally has additional substituent(s) besides $R^5$,
(2) an optionally substituted bicyclic fused heterocyclic group, or
(3) a group represented by the formula: $-L-Z^1$
wherein
L is a bond or $CH_2$, and
$Z^1$ is an optionally substituted non-aromatic ring group,
$R^3$ is a hydrogen atom or a substituent, and
$R^4$ is a substituent (provided that
(1) a group represented by the formula:

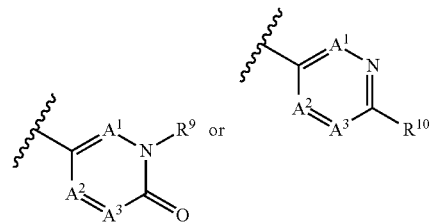

wherein
$A^1$ is $CR^{41}$ wherein $R^{41}$ is a hydrogen atom or a substituent, or a nitrogen atom,
$A^2$ is $CR^{42}$ wherein $R^{42}$ is a hydrogen atom or a substituent, or a nitrogen atom,
$A^3$ is $CR^{43}$ wherein $R^{43}$ is a hydrogen atom or a substituent, or a nitrogen atom, or
when $A^2$ is $CR^{42}$ wherein $R^{42}$ is a substituent, and $A^3$ is $CR^{43}$ wherein $R^{43}$ is a substituent, then $R^{42}$ and $R^{43}$ in combination optionally form, together with the carbon atoms that they are bonded to, a hydrocarbon ring or a heterocycle,
$R^9$ is a hydrogen atom or a hydroxy group, and when $R^9$ is a hydroxy group, then $A^1$, $A^2$ and $A^3$ are $CR^{41}$, $CR^{42}$ and $CR^4$, respectively, and
$R^{10}$ is a hydroxy group or an optionally substituted $C_{1-6}$ alkoxy group, and
(2) an optionally substituted $C_{1-6}$ alkoxy group are excluded), or
when $R^3$ is a substituent, then $R^3$ and $R^4$ in combination optionally form, together with the nitrogen atom adjacent to $R^3$ and the carbon atom adjacent to $R^4$, an optionally substituted ring, and the substituents that the ring optionally has optionally form a spiro ring,
or a salt thereof, for the production of an agent for the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis or systemic lupus erythematosus (SLE).

[16] A compound represented by the following formula (I'):

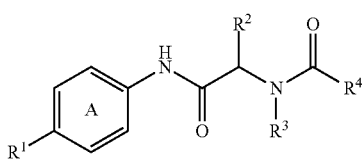

wherein
Ring A is an optionally further substituted 6-membered aromatic ring,
$R^1$ is
  (1) a group represented by the formula: $-Q(R^{1a})(R^{1b})(R^{1c})$
    wherein
    Q is a carbon atom, a silicon atom or a germanium atom, and
    $R^{1a}$, $R^{1b}$ and $R^{1c}$ are each independently a substituent, or
    $R^{1a}$ and $R^{1b}$ in combination optionally form, together with the adjacent Q, an optionally substituted ring,
  (2) a neopentyl group, or
  (3) a trimethylsilylmethyl group,
$R^2$ is
  (1) a group represented by the formula:

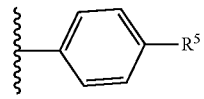

wherein
    $R^5$ is an optionally substituted alkyl group or an optionally substituted alkoxy group, and
    the benzene ring in the formula optionally has additional substituent(s) besides $R^5$,
  (2) an optionally substituted bicyclic fused heterocyclic group, or
  (3) a group represented by the formula: $-L-Z^1$
    wherein
    L is a bond or $CH_2$, and
    $Z^1$ is an optionally substituted non-aromatic ring group,
$R^3$ is a hydrogen atom or a substituent, and
$R^4$ is a substituent (provided that
  (1) a group represented by the formula:

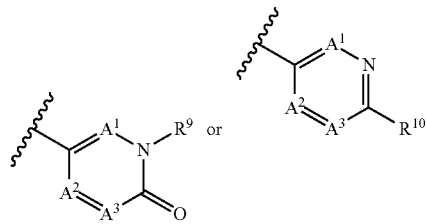

wherein
    $A^1$ is $CR^{A1}$ wherein $R^{A1}$ is a hydrogen atom or a substituent, or a nitrogen atom,
    $A^2$ is $CR^{A2}$ wherein $R^{A2}$ is a hydrogen atom or a substituent, or a nitrogen atom,
    $A^3$ is $CR^{A3}$ wherein $R^{A3}$ is a hydrogen atom or a substituent, or a nitrogen atom, or when $A^2$ is $CR^{A2}$ wherein $R^{A2}$ is a substituent, and $A^3$ is $CR^{A3}$ wherein $R^{A3}$ is a substituent, then $R^{A2}$ and $R^{A3}$ in combination optionally form, together with the carbon atoms that they are bonded to, a hydrocarbon ring or a heterocycle,
$R^9$ is a hydrogen atom or a hydroxy group, and when $R^9$ is a hydroxy group, then $A^1$, $A^2$ and $A^3$ are $CR^{A1}$, $CR^{A2}$ and $CR^{A3}$, respectively, and
$R^{10}$ is a hydroxy group or an optionally substituted $C_{1-6}$ alkoxy group, and
  (2) an optionally substituted $C_{1-6}$ alkoxy group are excluded), or
when $R^3$ is a substituent, then $R^3$ and $R^4$ in combination optionally form, together with the nitrogen atom adjacent to $R^3$ and the carbon atom adjacent to $R^4$, an optionally substituted ring, and the substituents that the ring optionally has optionally form a spiro ring,
or a salt thereof, for use in the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis or systemic lupus erythematosus (SLE).

[1'] A compound represented by the formula (I"):

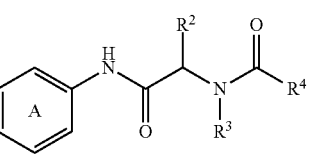

wherein
Ring A is an optionally further substituted 6-membered aromatic ring,
$R^1$ is
  (1) a group represented by the formula: $-Q(R^{1a})(R^{1b})(R^{1c})$
    wherein
    Q is a carbon atom, a silicon atom or a germanium atom, and
    $R^{1a}$, $R^{1b}$ and $R^{1c}$ are each independently a substituent, or
    $R^{1a}$ and $R^{1b}$ in combination optionally form, together with the adjacent Q, an optionally substituted ring,
  (2) a neopentyl group, or
  (3) a trimethylsilylmethyl group,
$R^1$ is
  (1) a group represented by the formula:

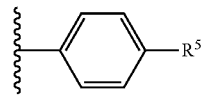

wherein
    $R^5$ is an optionally substituted alkyl group or an optionally substituted alkoxy group, and
    the benzene ring in the formula optionally has additional substituent(s) besides $R^5$,
  (2) an optionally substituted bicyclic fused heterocyclic group, or
  (3) a group represented by the formula: $-L-Z^1$
    wherein
    L is a bond or $CH_2$, and
    $Z^1$ is an optionally substituted non-aromatic ring group, $R^3$ is a hydrogen atom or a substituent, and
$R^4$ is a substituent (provided that a group represented by the formula:

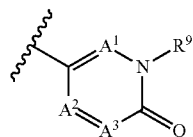

wherein
$A^1$ is $CR^{A1}$ wherein $R^{A1}$ is a hydrogen atom or a substituent, or a nitrogen atom,
$A^2$ is $CR^{A2}$ wherein $R^{A2}$ is a hydrogen atom or a substituent, or a nitrogen atom,
$A^3$ is $CR^{A3}$ wherein $R^{A3}$ is a hydrogen atom or a substituent, or a nitrogen atom, or
when $A^2$ is $CR^{A2}$ wherein $R^{A2}$ is a substituent, and $A^3$ is $CR^{A3}$ wherein $R^{A3}$ is a substituent, then $R^{A2}$ and $R^{A3}$ in combination optionally form, together with the carbon atoms that they are bonded to, a hydrocarbon ring or a heterocycle, and
$R^9$ is a hydrogen atom or a hydroxy group, and when $R^9$ is a hydroxy group, then $A^1$, $A^2$ and $A^3$ are $CR^{A1}$, $CR^{A2}$ and $CR^A$, respectively,
is excluded), or
when $R^3$ is a substituent, then $R^3$ and $R^4$ in combination optionally form, together with the nitrogen atom adjacent to $R^3$ and the carbon atom adjacent to $R^4$, an optionally substituted ring,
provided that
5-chloro-N-[1-cyclohexyl-2-oxo-2-[[4-[1-(1-pyrrolidinylmethyl)cyclopropyl]phenyl]amino]ethyl]-2-thiophenecarboxamide,
α-(acetylamino)-N-[4-(trifluoromethyl)phenyl]-cyclopentaneacetamide,
α-(acetylamino)-N-[4-(1,1-dimethylethyl)phenyl]-cyclopentaneacetamide, and
α-(acetylamino)-N-[2-bromo-4-(trifluoromethyl)phenyl]-cyclopentaneacetamide are excluded,
or a salt thereof (hereinafter sometimes to be referred to as compound (I")).
[2'] A compound represented by the formula (I"):

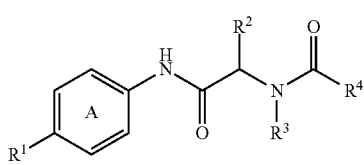

(I")

wherein
Ring A is an optionally further substituted 6-membered aromatic ring,
$R^1$ is a group represented by the formula: $-Q(R^{1a})(R^{1b})(R^{1c})$
wherein
Q is a carbon atom or a silicon atom, and
$R^{1a}$, $R^{1b}$ and $R^{1c}$ are each independently a substituent, or $R^{1a}$ and $R^{1b}$ in combination optionally form, together with the adjacent Q, an optionally substituted ring, or a neopentyl group, $R^2$ is
(1) a group represented by the formula:

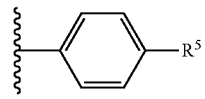

wherein
$R^5$ is an optionally substituted alkyl group or an optionally substituted alkoxy group, and the benzene ring in the formula optionally has additional substituent (s) besides $R^5$,
(2) an optionally substituted bicyclic fused heterocyclic group, or
(3) a group represented by the formula: $-L-Z^1$
wherein
L is a bond or $CH_2$, and
$Z^1$ is an optionally substituted non-aromatic ring group,
$R^3$ is a hydrogen atom or a substituent, and
$R^4$ is a substituent (provided that a group represented by the formula:

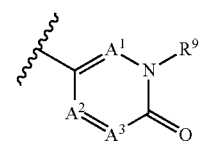

wherein
$A^1$ is $CR^{A1}$ wherein $R^{A1}$ is a hydrogen atom or a substituent, or a nitrogen atom,
$A^2$ is $CR^{A2}$ wherein $R^{A2}$ is a hydrogen atom or a substituent, or a nitrogen atom,
$A^3$ is $CR^{A3}$ wherein $R^{A3}$ is a hydrogen atom or a substituent, or a nitrogen atom, or
when $A^2$ is $CR^{A2}$ wherein $R^{A2}$ is a substituent, and $A^3$ is $CR^{A3}$ wherein $R^{A3}$ is a substituent, then $R^{A2}$ and $R^{A3}$ in combination optionally form, together with the carbon atoms that they are bonded to, a hydrocarbon ring or a heterocycle, and
$R^9$ is a hydrogen atom or a hydroxy group, and when $R^9$ is a hydroxy group, then $A^1$, $A^2$ and $A^3$ are $CR^{A1}$, $CR^{A2}$ and $CR^A$, respectively,
is excluded), or provided that
5-chloro-N-[1-cyclohexyl-2-oxo-2-[[4-[1-(1-pyrrolidinylmethyl)cyclopropyl]phenyl]amino]ethyl]-2-thiophenecarboxamide or a salt thereof,
α-(acetylamino)-N-[4-(trifluoromethyl)phenyl]-cyclopentaneacetamide or a salt thereof,
α-(acetylamino)-N-[4-(1,1-dimethylethyl)phenyl]-cyclopentaneacetamide or a salt thereof, and
α-(acetylamino)-N-[2-bromo-4-(trifluoromethyl)phenyl]-cyclopentaneacetamide or a salt thereof,
are excluded,
or a salt thereof.
[3'] A medicament comprising the compound or salt of the above-mentioned [1'] or [2'].
[4'] The medicament of the above-mentioned [3'], which is a RORγt inhibitor.
[5'] The medicament of the above-mentioned [3'], which is an agent for the prophylaxis or treatment of inflammatory bowel disease (IBD), ulcerative colitis (UC), Crohn's disease (CD), rheumatoid arthritis, multiple sclerosis or psoriasis.

Effect of the Invention

The compound of the present invention has a superior RORγt inhibitory action, and is useful as an agent for the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis, systemic lupus erythematosus (SLE) and the like.

DETAILED DESCRIPTION OF THE INVENTION

The present invention is explained in detail in the following.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, a halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, a halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, a halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, a halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, a halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, a halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent Group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-16}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl) an amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),

(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent Group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent Group A".

Preferable examples of the optionally substituted amino group include an amino group, a mono- or di-(optionally halogenated $C_{1-6}$ alkyl) an amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) an amino group (e.g., methylcarbamoylamino), a (mono- or di-$C_{7-16}$ aralkyl-carbamoyl) an amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$ alkyl-carbonyl) an amino group (e.g., N-acetyl-N-methylamino) and a ($C_{1-6}$ alkyl) ($C_{6-14}$ aryl-carbonyl) an amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{5-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent Group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent Group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent Group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-15}$ aralkyl group, each of which optionally has 1 to 3 substituents selected from Substituent Group A".

Preferable examples of the optionally substituted silyl group include a tri-$C_{1-6}$ alkylsilyl group (e.g., trimethylsilyl, tert-butyl(dimethyl)silyl).

In the present specification, examples of the "$C_{1-6}$ alkylene group" include —$CH_2$—, —$(CH_2)_2$—, —$(CH_2)_3$—, —$(CH_2)_4$—, —$(CH_2)_5$—, —$(CH_2)_6$—, —$CH(CH_3)$—, —$C(CH_3)_2$—, —$CH(C_2H_5)$—, —$CH(C_3H_7)$—, —$CH(CH(CH_3)_2)$—, —$(CH(CH_3))_2$—, —$CH_2$—$CH(CH_3)$—, —$CH(CH_3)$—$CH_2$—, —$CH_2$—$CH_2$—$C(CH_3)_2$—, —$C(CH_3)_2$—$CH_2$—$CH_2$—, —$CH_2$—$CH_2$—$CH_2$—$C(CH_3)_2$— and —$C(CH_3)_2$—$CH_2$—$CH_2$—$CH_2$—.

In the present specification, examples of the "$C_{2-6}$ alkenylene group" include —CH=CH—, —$CH_2$—CH=CH—, —CH=CH—$CH_2$—, —$C(CH_3)_2$—CH=CH—, —CH=CH—$C(CH_3)_2$—, —$CH_2$—CH=CH—$CH_2$—, —$CH_2$—$CH_2$—CH=CH—, —CH=CH—$CH_2$—$CH_2$—, —CH=CH—CH=CH—, —CH=CH—$CH_2$—$CH_2$—$CH_2$— and —$CH_2$—$CH_2$—$CH_2$—CH=CH—.

In the present specification, examples of the "$C_{2-6}$ alkynylene group" include —C≡C—, —$CH_2$—C≡C—, —C≡C—$CH_2$—, —$C(CH_3)_2$—C≡C—, —C≡C—$C(CH_3)_2$—, —$CH_2$—C≡C—$CH_2$—, —$CH_2$—$CH_2$—C≡C—, —C≡C—$CH_2$—$CH_2$—, —C≡C—C≡C—, —C≡C—$CH_2$—$CH_2$—$CH_2$— and —$CH_2$—$CH_2$—$CH_2$—C≡C—.

The definition of each symbol in the formulas (I), (I') and (I") is explained in detail in the following.

Ring A is an optionally further substituted 6-membered aromatic ring.

Examples of the "6-membered aromatic ring" of the "optionally further substituted 6-membered aromatic ring" represented by Ring A include a benzene ring, a pyridine ring, a pyridazine ring, a pyrimidine ring, a pyrazine ring and a triazine ring. Among them, a benzene ring is preferable.

The "6-membered aromatic ring" is optionally further substituted, for example, by substituent(s) selected from the above-mentioned Substituent Group A. The number of the substituents is, for example, 1 to 3. When the number of the substituents is 2 or more, the respective substituents may be the same or different.

Examples of the substituent that the "6-membered aromatic ring" optionally further has are preferably (1) a halogen atom (e.g., a fluorine atom, a chlorine atom) and (2) a cyano group; more preferably a halogen atom; further more preferably a fluorine atom and a chlorine atom; particularly preferably a fluorine atom.

Ring A is preferably a 6-membered aromatic ring (preferably a benzene ring) optionally further substituted by 1 to 3 substituents selected from (1) a halogen atom (e.g., a fluorine atom, a chlorine atom), and (2) a cyano group.

Ring A is more preferably a benzene ring optionally further substituted by 1 to 3 substituents selected from
(1) a halogen atom (e.g., a fluorine atom, a chlorine atom), and
(2) a cyano group.

Ring A is further more preferably a benzene ring optionally further substituted by 1 to 3 halogen atoms (e.g., a fluorine atom).

$R^1$ is
(1) a group represented by the formula: $-Q(R^{1a})(R^{1b})(R^{1c})$
wherein
Q is a carbon atom, a silicon atom or a germanium atom, and
$R^{1a}$, $R^{1b}$ and $R^{1c}$ are each independently a substituent, or
$R^{1a}$ and $R^{1b}$ in combination optionally form, together with the adjacent Q, an optionally substituted ring,
(2) a neopentyl group, or
(3) a trimethylsilylmethyl group.

Examples of the "optionally substituted ring" formed by $R^{1a}$ and $R^{1b}$ in combination together with the adjacent Q include a $C_{3-10}$ cycloalkane ring, a $C_{3-10}$ cycloalkene ring and a non-aromatic heterocycle, each of which is optionally substituted by substituent(s) selected from the above-mentioned Substituent Group A.

Examples of the "$C_{3-10}$ cycloalkane ring" exemplified as the "optionally substituted ring" formed by $R^{1a}$ and $R^{1b}$ in combination together with the adjacent Q include a ring corresponding to the above-mentioned "$C_{3-10}$ cycloalkyl group".

Examples of the "$C_{3-10}$ cycloalkene ring" exemplified as the "optionally substituted ring" formed by $R^{1a}$ and $R^{1b}$ in combination together with the adjacent Q include a ring corresponding to the above-mentioned "$C_{3-10}$ cycloalkenyl group".

Examples of the "non-aromatic heterocycle" exemplified as the "optionally substituted ring" formed by $R^{1a}$ and $R^{1b}$ in combination together with the adjacent Q include a ring corresponding to the above-mentioned "non-aromatic heterocyclic group".

The number of the substituents in the "optionally substituted ring" is, for example, 1 to 3. When the number of the substituents is 2 or more, the respective substituents may be the same or different.

$R^{1a}$, $R^{1b}$ and $R^{1c}$ in the formula: $-Q(R^{1a})(R^{1b})(R^{1c})$ are each preferably neither a cyclic group, nor a group substituted by cyclic group(s).

Examples of the "cyclic group" in $R^{1a}$, $R^{1b}$ and $R^{1c}$ include the above-mentioned "$C_{3-10}$ cycloalkyl group", "$C_{3-10}$ cycloalkenyl group", "$C_{6-14}$ aryl group" and "heterocyclic group".

$R^1$ is preferably
(1) a group represented by the formula: $-Q(R^{1a})(R^{1b})(R^{1c})$
wherein
Q is a carbon atom, a silicon atom or a germanium atom, and
$R^{1a}$, $R^{1b}$ and $R^{1c}$ are each independently
(a) a $C_{1-6}$ alkyl group (e.g., methyl, ethyl) optionally substituted by 1 to 3 halogen atoms (e.g., a fluorine atom),
(b) a hydroxy group,
(c) a $C_{6-14}$ aryl group (e.g., phenyl),
(d) a $C_{3-10}$ cycloalkyl group (e.g., cyclopropyl),
(e) a cyano group,
(f) a carbamoyl group optionally mono- or di-substituted by $C_{3-10}$ cycloalkyl group(s) (e.g., cyclopropyl), or
(g) a 3- to 8-membered monocyclic non-aromatic heterocyclylcarbonyl group (e.g., pyrrolidinylcarbonyl), or
$R^{1a}$ and $R^{1b}$ in combination form, together with the adjacent Q, a $C_{1-10}$ cycloalkane ring (e.g., cyclopentane),
(2) a neopentyl group, or
(3) a trimethylsilylmethyl group.

In another embodiment, $R^1$ is preferably
(1) a group represented by the formula: $-Q(R^{1a})(R^{1b})(R^{1c})$
wherein
Q is a carbon atom, a silicon atom or a germanium atom, and
$R^{1a}$, $R^{1b}$ and $R^{1c}$ are each independently
(a) a $C_{1-6}$ alkyl group (e.g., methyl, ethyl) optionally substituted by 1 to 3 substituents selected from
(i) a halogen atom (e.g., a fluorine atom), and
(ii) a $C_{1-6}$ alkoxy group (e.g., methoxy),
(b) a hydroxy group,
(c) a $C_{6-14}$ aryl group (e.g., phenyl),
(d) a $C_{3-10}$ cycloalkyl group (e.g., cyclopropyl),
(e) a cyano group,
(f) a carbamoyl group optionally mono- or di-substituted by $C_{3-10}$ cycloalkyl group(s) (e.g., cyclopropyl), or
(g) a 3- to 8-membered monocyclic non-aromatic heterocyclylcarbonyl group (e.g., pyrrolidinylcarbonyl), or
$R^{1a}$ and $R^{1b}$ in combination form, together with the adjacent Q, a $C_{3-10}$ cycloalkane ring (e.g., cyclopentane),
(2) a neopentyl group, or
(3) a trimethylsilylmethyl group.

In another embodiment, $R^1$ is preferably
(1) a group represented by the formula: $-Q(R^{1a})(R^{1b})(R^{1c})$
wherein
Q is a carbon atom, a silicon atom or a germanium atom, and
$R^{1a}$, $R^{1b}$ and $R^{1c}$ are each independently
(a) a $C_{1-6}$ alkyl group (e.g., methyl, ethyl) optionally substituted by 1 to 3 halogen atoms (e.g., a fluorine atom),
(b) a hydroxy group, or
(c) a cyano group,
(2) a neopentyl group, or
(3) a trimethylsilylmethyl group.

In another embodiment, $R^1$ is preferably
(1) a group represented by the formula: $-Q(R^{1a})(R^{1b})(R^{1c})$
wherein
Q is a carbon atom, a silicon atom or a germanium atom, and
$R^{1a}$, $R^{1b}$ and $R^{1c}$ are each independently
(a) a $C_{1-6}$ alkyl group (e.g., methyl, ethyl) optionally substituted by 1 to 3 substituents selected from
(i) a halogen atom (e.g., a fluorine atom), and
(ii) a $C_{1-6}$ alkoxy group (e.g., methoxy),
(b) a hydroxy group, or
(c) a cyano group,
(2) a neopentyl group, or
(3) a trimethylsilylmethyl group.

$R^1$ is more preferably
(1) a group represented by the formula: $-Q(R^{1a})(R^{1b})(R^{1c})$
wherein
Q is a carbon atom or a silicon atom, and
$R^{1a}$, $R^{1b}$ and $R^{1c}$ are each independently a $C_{1-6}$ alkyl group (e.g., methyl), or
(2) a neopentyl group.

$R^1$ is further more preferably a group represented by the formula: $-Q(R^{1a})(R^{1b})(R^{1c})$ wherein Q is a carbon atom or a silicon atom, and $R^{1a}$, $R^{1b}$ and $R^{1c}$ are each independently a $C_{1-6}$ alkyl group (e.g., methyl).

In another embodiment, $R^1$ is preferably
(1) a tert-butyl group,
(2) a neopentyl group,
(3) a trimethylsilyl group,
(4) a 1,1,1,3,3,3-hexafluoro-2-hydroxypropan-2-yl group,
(5) a dimethylphenylsilyl group,
(6) a trimethylsilylmethyl group,
(7) a trimethylgermyl group,
(8) a cyclopropyldimethylsilyl group,
(9) a cyclopropyldimethylgermyl group,
(10) an ethyldimethylsilyl group,
(11) a 1-cyanocyclopentyl group,
(12) a 1-(cyclopropylamino)-2-methyl-1-oxopropan-2-yl group,
(13) a 2-methyl-1-oxo-1-(pyrrolidin-1-yl)propan-2-yl group, or
(14) a 1-methoxy-2-methylpropan-2-yl group.

$R^1$ is more preferably
(1) a tert-butyl group,
(2) a neopentyl group, or
(3) a trimethylsilyl group.

$R^1$ is further more preferably
(1) a tert-butyl group, or
(2) a trimethylsilyl group.

$R^2$ is (1) a group represented by the formula:

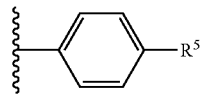

wherein $R^5$ is an optionally substituted alkyl group or an optionally substituted alkoxy group, and the benzene ring in the formula optionally has additional substituent(s) besides $R^5$, (2) an optionally substituted bicyclic fused heterocyclic group, or (3) a group represented by the formula: $-L-Z^1$ wherein L is a bond or $CH_2$, and $Z^1$ is an optionally substituted non-aromatic ring group.

Examples of the "optionally substituted alkyl group" represented by $R^5$ include a $C_{1-6}$ alkyl group optionally having 1 to 3 substituents selected from Substituent Group A.

Examples of the "optionally substituted alkoxy group" represented by $R^5$ include a $C_{1-6}$ alkoxy group optionally having 1 to 3 substituents selected from Substituent Group A.

Examples of the "bicyclic fused heterocyclic group" of the "optionally substituted bicyclic fused heterocyclic group" represented by $R^5$ include bicyclic groups from among the above-mentioned 8- to 14-membered fused polycyclic aromatic heterocyclic group and 9- to 14-membered fused polycyclic non-aromatic heterocyclic group.

The "bicyclic fused heterocyclic group" is optionally substituted, for example, by substituent(s) selected from Substituent Group A. The number of the substituents is, for example, 1 to 3. When the number of the substituents is 2 or more, the respective substituents may be the same or different.

Examples of the "optionally substituted non-aromatic ring group" represented by $Z^1$ include a $C_{3-10}$ cycloalkyl group, a $C_{3-10}$ cycloalkenyl group and a non-aromatic heterocyclic group, each of which optionally has 1 to 3 substituents selected from Substituent Group A.

$R^2$ is preferably (1) a group represented by the formula:

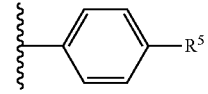

wherein $R^5$ is (A) a $C_{1-6}$ alkyl group (e.g., methyl, ethyl, isopropyl) optionally substituted by 1 to 3 substituents selected from
  (a) a $C_{1-6}$ alkoxy group (e.g., methoxy, ethoxy, propoxy) optionally substituted by 1 to 3 substituents selected from
    (i) a halogen atom (e.g., a fluorine atom), and
    (ii) a $C_{1-6}$ alkoxy group (e.g., methoxy), and
  (b) a hydroxy group, or (B) a $C_{1-6}$ alkoxy group (e.g., methoxy, ethoxy, propoxy) optionally substituted by 1 to 3 $C_{1-6}$ alkoxy groups (e.g., methoxy), and the benzene ring in the formula optionally has, besides $R^5$, additional 1 to 3 substituents selected from
  (A) a $C_{1-6}$ alkyl group (e.g., methyl), and
  (B) a $C_{1-6}$ alkoxy group (e.g., methoxy), (2) a bicyclic fused heterocyclic group (e.g., dihydrobenzofuryl (2,3-dihydrobenzofuryl), indazolyl (1H-indazolyl, 2H-indazolyl), indolyl, indolinyl) optionally substituted by 1 to 3 $C_{1-6}$ alkyl groups (e.g., methyl), or (3) a group represented by the formula $-L-Z^1$:

wherein

L is a bond; and $Z^1$ is (A) a $C_{3-10}$ cycloalkyl group (e.g., cyclohexyl) optionally substituted by 1 to 3 substituents selected from
  (a) a halogen atom (e.g., a fluorine atom), and
  (b) a hydroxy group, or (B) a 3- to 8-membered monocyclic non-aromatic heterocyclic group (e.g., tetrahydropyranyl, piperidyl, 1,1-dioxidotetrahydrothiopyranyl) optionally substituted by $C_{1-6}$ alkyl group(s) (e.g., ethyl) optionally substituted by 1 to 3 halogen atoms (e.g., a fluorine atom).

$R^2$ is more preferably (1) a group represented by the formula:

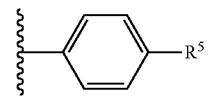

wherein $R^5$ is (A) a $C_{1-6}$ alkyl group (e.g., methyl) optionally substituted by 1 to 3 $C_{1-6}$ alkoxy groups (e.g., methoxy), or (B) a $C_{1-6}$ alkoxy group (e.g., methoxy), (2) a bicyclic fused heterocyclic group (e.g., dihydrobenzofuryl (2,3-dihydrobenzofuryl), indazolyl (1H-indazolyl)) optionally substituted by 1 to 3 $C_{1-6}$ alkyl groups (e.g., methyl), or
(3) a group represented by the formula -L-$Z^1$:
  wherein
  L is a bond; and
  $Z^1$ is
  (A) a $C_{3-10}$ cycloalkyl group (e.g., cyclohexyl) optionally substituted by 1 to 3 halogen atoms (e.g., a fluorine atom), or
  (B) a 3- to 8-membered monocyclic non-aromatic heterocyclic group (e.g., tetrahydropyranyl).
$R^2$ is further more preferably
(1) a group represented by the formula:

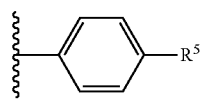

wherein
  $R^5$ is $C_{1-6}$ alkoxy group (e.g., methoxy),
(2) a bicyclic fused heterocyclic group (e.g., indazolyl (1H-indazolyl)) optionally substituted by 1 to 3 $C_{1-6}$ alkyl groups (e.g., methyl), or
(3) a group represented by the formula -L-$Z^1$:
  wherein
  L is a bond; and
  $Z^1$ is a $C_{3-10}$ cycloalkyl group (e.g., cyclohexyl) optionally substituted by 1 to 3 halogen atoms (e.g., a fluorine atom).
In another embodiment, $R^2$ is preferably
(1) a group represented by the formula:

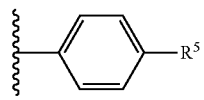

wherein
  $R^5$ is
  (A) an alkoxy group (e.g., methoxy, ethoxy, propoxy) optionally substituted by 1 to 3 alkoxy groups (e.g., methoxy),
  (B) an alkyl group (e.g., methyl, ethyl, isopropyl) optionally substituted by hydroxy group(s), or
  (C) an alkoxyalkyl group (e.g., methoxymethyl, ethoxymethyl, propoxymethyl, 1-methoxyethyl) optionally substituted by 1 to 3 substituents selected from
    (i) a halogen atom (e.g., a fluorine atom), and
    (ii) an alkoxy group (e.g., methoxy), and the benzene ring in the formula optionally has, besides $R^5$, additional 1 to 3 substituents selected from
    (A) alkyl group (e.g., methyl), and
    (B) an alkoxy group (e.g., methoxy),
(2) a tetrahydro-2H-pyran-4-yl group,
(3) a 4,4-difluorocyclohexyl group,
(4) a 1-methyl-1H-indazol-5-yl group,
(5) a 2,3-dihydro-1-benzofuran-5-yl group,
(6) a 1-(2,2,2-trifluoroethyl)piperidin-4-yl group,
(7) a 1,1-dioxidotetrahydro-2H-thiopyran-4-yl group,
(8) a 4,4-difluoro-1-hydroxycyclohexyl group,
(9) a 1-methylindol-5-yl group,
(10) a 1-methyl-2,3-dihydroindol-5-yl group, or
(11) a 2-methyl-2H-indazol-5-yl group.
$R^2$ is more preferably
(1) a group represented by the formula:

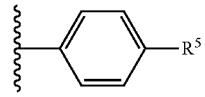

wherein
  $R^5$ is an alkoxy group (e.g., methoxy) or an alkoxyalkyl group (e.g., methoxymethyl),
(2) a tetrahydro-2H-pyran-4-yl group
(3) a 4,4-difluorocyclohexyl group
(4) a 1-methylindazol-5-yl group, or
(5) a 2,3-dihydro-1-benzofuran-5-yl group.
$R^1$ is further more preferably
(1) a group represented by the formula:

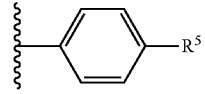

wherein
  $R^5$ is an alkoxy group (e.g., methoxy)),
(2) a 4,4-difluorocyclohexyl group, or
(3) a 1-methylindazol-5-yl group.
Examples of the above-mentioned "alkyl group" include a $C_{1-6}$ alkyl group. Examples of the above-mentioned "alkoxy group" include a $C_{1-6}$ alkoxy group. Examples of the above-mentioned "alkoxyalkyl group" include a $C_{1-6}$ alkyl group substituted by 1 or 2 $C_{1-6}$ alkoxy groups. Specific examples thereof include methoxymethyl, ethoxymethyl, propoxymethyl, isopropoxymethyl, 1-methoxyethyl, 1-ethoxyethyl, 1-propoxyethyl, 1-isopropoxyethyl, 2-methoxyethyl, 2-ethoxyethyl, 2-propoxyethyl, 2-isopropoxyethyl and the like.
$R^3$ is a hydrogen atom or a substituent, and
$R^4$ is a substituent (provided that a group represented by the formula:

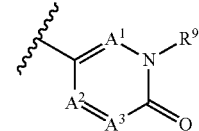

wherein
  $A^1$ is $CR^{A1}$ wherein $R^{A1}$ is a hydrogen atom or a substituent, or a nitrogen atom,
  $A^2$ is $CR^{A2}$ wherein $R^{A2}$ is a hydrogen atom or a substituent, or a nitrogen atom,
  $A^3$ is $CR^{A3}$ wherein $R^{A3}$ is a hydrogen atom or a substituent, or a nitrogen atom, or
  when $A^2$ is $CR^{A2}$ wherein $R^{A2}$ is a substituent, and $A^3$ is $CR^{A3}$ wherein $R^{A3}$ is a substituent, then $R^{A2}$ and $R^{A3}$ in combination optionally form, together with the carbon atoms that they are bonded to, a hydrocarbon ring or a heterocycle, and
  $R^9$ is a hydrogen atom or a hydroxy group, and when $R^9$ is a hydroxy group, then $A^1$, $A^2$ and $A^3$ are $CR^{A1}$, $CR^{A2}$ and $CR^A$, respectively, is excluded), or
when R³ is a substituent, then R⁵ and R⁴ in combination optionally form, together with the nitrogen atom adjacent to R³ and the carbon atom adjacent to R⁴, an optionally substituted ring.

In another embodiment,
R³ is a hydrogen atom or a substituent, and
R⁴ is a substituent (provided that
(1) a group represented by the formula:

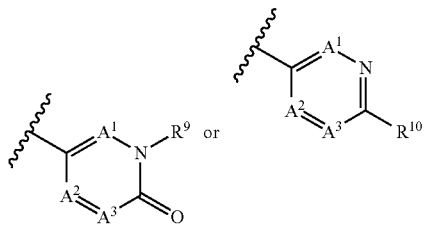

wherein
A¹ is $CR^{A1}$ wherein $R^{A1}$ is a hydrogen atom or a substituent, or a nitrogen atom,
A² is $CR^{A2}$ wherein $R^{A2}$ is a hydrogen atom or a substituent, or a nitrogen atom,
A³ is $CR^{A3}$ wherein $R^{A3}$ is a hydrogen atom or a substituent, or a nitrogen atom, or
when A² is $CR^{A2}$ wherein $R^{A2}$ is a substituent, and A³ is $CR^{A3}$ wherein $R^{A3}$ is a substituent, then $R^{A2}$ and $R^{A3}$ in combination optionally form, together with the carbon atoms that they are bonded to, a hydrocarbon ring or a heterocycle,
R⁹ is a hydrogen atom or a hydroxy group, and when R⁹ is a hydroxy group, then A¹, A² and A³ are $CR^{A1}$, $CR^{A2}$ and $CR^{A3}$, respectively, and
R¹⁰ is a hydroxy group or an optionally substituted $C_{1-6}$ alkoxy group, and
(2) an optionally substituted $C_{1-6}$ alkoxy group are excluded), or when R³ is a substituent, then R⁵ and R⁴ in combination optionally form, together with the nitrogen atom adjacent to R³ and the carbon atom adjacent to R⁴, an optionally substituted ring (provided that
(1) a cyclic group represented by the formula:

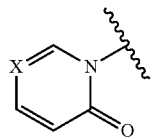

wherein X is CH or a nitrogen atom, which is optionally further substituted, and
(2) a cyclic group represented by the formula:

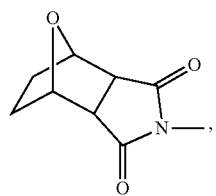

are excluded), and
the substituents that the ring optionally has optionally form a spiro ring.

In yet another embodiment,
R³ is a hydrogen atom or a substituent, and
R⁴ is a substituent (provided that
(1) a group represented by the formula:

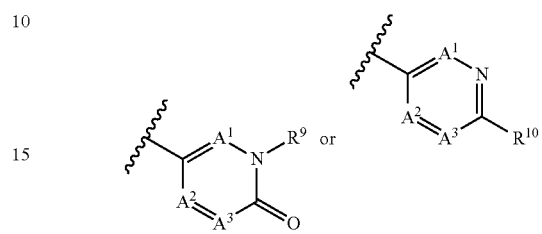

wherein
A¹ is $CR^{A1}$ wherein $R^{A1}$ is a hydrogen atom or a substituent, or a nitrogen atom,
A² is $CR^{A2}$ wherein $R^{A2}$ is a hydrogen atom or a substituent, or a nitrogen atom,
A³ is $CR^{A3}$ wherein $R^{A3}$ is a hydrogen atom or a substituent, or a nitrogen atom, or
when A² is $CR^{A2}$ wherein $R^{A2}$ is a substituent, and A³ is $CR^{A3}$ wherein $R^{A3}$ is a substituent, then $R^{A2}$ and $R^{A3}$ in combination optionally form, together with the carbon atoms that they are bonded to, a hydrocarbon ring or a heterocycle,
R⁹ is a hydrogen atom or a hydroxy group, and when R⁹ is a hydroxy group, then A¹, A² and A³ are $CR^{A1}$, $CR^{A2}$ and $CR^{A3}$, respectively, and
R¹⁰ is a hydroxy group or an optionally substituted $C_{1-6}$ alkoxy group, and
(2) an optionally substituted $C_{1-6}$ alkoxy group are excluded), or when R³ is a substituent, then R⁵ and R⁴ in combination optionally form, together with the nitrogen atom adjacent to R³ and the carbon atom adjacent to R⁴, an optionally substituted ring, and the substituents that the ring optionally has optionally form a spiro ring.

Examples of the "substituent" represented by the above-mentioned $R^{A1}$, $R^{A2}$ or $R^{A3}$ include Substituent Group AA selected from the followings, respectively, regardless of the above-mentioned description.

[Substituent Group AA]
(1) a halogen atom;
(2) a nitro group;
(3) a cyano group;
(4) a carboxy group;
(5) an optionally substituted $C_{1-12}$ alkyl group;
(6) an optionally substituted $C_{2-12}$ alkenyl group;
(7) an optionally substituted $C_{2-12}$ alkynyl group;
(8) an optionally substituted $C_{3-12}$ cycloalkyl group;
(9) an optionally substituted $C_{6-14}$ aryl group;
(10) an optionally substituted $C_{7-16}$ aralkyl group;
(11) an optionally substituted $C_{6-14}$ aryl-$C_{2-12}$ alkenyl group;
(12) an optionally substituted heterocyclic group;
(13) a hydroxy group;
(14) an optionally substituted $C_{1-12}$ alkoxy group;
(15) an optionally substituted $C_{3-12}$ cycloalkyloxy group;
(16) an optionally substituted $C_{6-14}$ aryloxy group;
(17) an optionally substituted $C_{7-16}$ aralkyloxy group;
(18) an optionally substituted $C_{1-12}$ alkyl-carbonyloxy group;

(19) an optionally substituted $C_{1-12}$ alkoxy-carbonyloxy group;
(20) an optionally substituted mono-$C_{1-12}$ alkyl-carbamoyloxy group;
(21) an optionally substituted di-$C_{1-12}$ alkyl-carbamoyloxy group;
(22) an optionally substituted $C_{6-14}$ aryl-carbonyloxy group;
(23) an optionally substituted mono- or di-$C_{6-14}$ aryl-carbamoyloxy group;
(24) an optionally substituted heterocyclyl-oxy group;
(25) an optionally substituted $C_{1-12}$ alkylsulfonyloxy group;
(26) a pentafluorosulfanyl group;
(27) an optionally substituted $C_{1-12}$ alkylsulfanyl group;
(28) an optionally substituted $C_{3-10}$ cycloalkylsulfanyl group;
(29) an optionally substituted $C_{6-14}$ arylsulfanyl group;
(30) an optionally substituted $C_{7-16}$ aralkylsulfanyl group;
(31) an optionally substituted heterocyclyl-sulfanyl group;
(32) a formyl group;
(33) an optionally substituted $C_{1-12}$ alkyl-carbonyl group;
(34) an optionally substituted $C_{3-12}$ cycloalkyl-carbonyl group;
(35) an optionally substituted $C_{5-14}$ aryl-carbonyl group;
(36) an optionally substituted $C_{7-16}$ aralkyl-carbonyl group;
(37) an optionally substituted heterocyclyl-carbonyl group;
(38) an optionally substituted $C_{1-12}$ alkylsulfonyl group;
(39) an optionally substituted $C_{3-12}$ cycloalkylsulfonyl group;
(40) an optionally substituted $C_{6-14}$ arylsulfonyl group;
(41) an optionally substituted $C_{7-16}$ aralkylsulfonyl group;
(42) an optionally substituted heterocyclyl-sulfonyl group;
(43) an optionally substituted $C_{1-12}$ alkylsulfinyl group;
(44) an optionally substituted $C_{3-12}$ cycloalkylsulfinyl group;
(45) an optionally substituted $C_{6-14}$ arylsulfinyl group;
(46) an optionally substituted $C_{7-15}$ aralkylsulfinyl group;
(47) an optionally substituted heterocyclyl-sulfinyl group;
(48) a sulfo group;
(49) an optionally substituted sulfamoyl group;
(50) an optionally substituted sulfinamoyl group;
(51) an optionally substituted sulfenamoyl group;
(52) an optionally substituted thiocarbamoyl group;
(53) an optionally substituted carbamoyl group
[e.g.,
a carbamoyl group,
an optionally substituted mono- or di-$C_{1-12}$ alkyl-carbamoyl group,
an optionally substituted mono- or di-$C_{1-12}$ cycloalkyl-carbamoyl group,
an optionally substituted mono- or di-$C_{6-14}$ aryl-carbamoyl group,
an optionally substituted mono- or di-heterocyclyl-carbamoyl group
and the like];
(54) an optionally substituted amino group
[e.g.,
an amino group,
an optionally substituted mono- or di-$C_{1-12}$ alkyl-amino group,
an optionally substituted mono- or di-$C_{3-12}$ cycloalkyl-amino group,
an optionally substituted mono- or di-$C_{6-14}$ aryl-amino group,
an optionally substituted mono- or di-$C_{7-16}$ aralkyl-amino group,
an optionally substituted mono- or di-heterocyclyl-amino group,
an optionally substituted mono- or di-$C_{6-14}$ aryl-carbonylamino group,
a formylamino group,
an optionally substituted mono- or di-($C_{1-12}$ alkyl-carbonyl) amino group,
an optionally substituted mono- or di-($C_{3-12}$ cycloalkyl-carbonyl)amino group,
an optionally substituted mono- or di-(heterocyclyl-carbonyl)amino group,
an optionally substituted mono- or di-($C_{1-12}$ alkoxy-carbonyl)amino group,
an optionally substituted mono- or di-($C_{3-10}$ cycloalkoxy-carbonyl)amino group,
an optionally substituted mono- or di-(heterocyclyl-oxycarbonyl)amino group,
an optionally substituted mono- or di-($C_{1-12}$ alkylsulfonyl) amino group,
an optionally substituted mono- or di-($C_{3-12}$ cycloalkylsulfonyl)amino group,
an optionally substituted mono- or di-($C_{6-14}$ arylsulfonyl) amino group,
an optionally substituted heterocyclyl-sulfonylamino group
and the like];
(55) an optionally substituted $C_{1-12}$ alkoxy-carbonyl group;
(56) an optionally substituted $C_{5-14}$ aryloxy-carbonyl group;
(57) an optionally substituted $C_{7-16}$ aralkyloxy-carbonyl group;
(58) an optionally substituted heterocyclyloxy-carbonyl group;
(59) an optionally substituted tri-$C_{1-12}$ alkylsilyl group;
(60) an optionally substituted ($C_{3-12}$ cycloalkyl)di($C_{1-12}$ alkyl)silyl group;
(61) an optionally substituted ($C_{6-14}$ aryl)di($C_{1-12}$ alkyl)silyl group;
(62) an optionally substituted ($C_{1-12}$ alkyl)di($C_{6-14}$ aryl)silyl group;
(63) an optionally substituted tri-$C_{1-12}$ alkylgermyl group;
(64) an optionally substituted ($C_{3-10}$ cycloalkyl)di($C_{1-12}$ alkyl)germyl group;
(65) an optionally substituted ($C_{6-14}$ aryl)di($C_{1-12}$ alkyl) germyl group;
(66) an optionally substituted ($C_{1-12}$ alkyl)di($C_{6-14}$ aryl) germyl group;
(67) an oxo group
and the like.
Examples of the substituent of
the "optionally substituted $C_{1-12}$ alkyl group",
"optionally substituted $C_{2-12}$ alkenyl group",
"optionally substituted $C_{2-12}$ alkynyl group",
"optionally substituted $C_{1-12}$ alkoxy group",
"optionally substituted $C_{1-12}$ alkyl-carbonyloxy group",
"optionally substituted $C_{1-12}$ alkoxy-carbonyloxy group",
"optionally substituted mono- or di-$C_{1-12}$ alkyl-carbamoyl group",
"optionally substituted mono-$C_{1-12}$ alkyl-carbamoyloxy group",
"optionally substituted di-$C_{1-12}$ alkyl-carbamoyloxy group",
"optionally substituted $C_{1-12}$ alkylsulfonyloxy group",
"optionally substituted $C_{1-12}$ alkylsulfanyl group",
"optionally substituted $C_{1-12}$ alkyl-carbonyl group",
"optionally substituted $C_{1-12}$ alkylsulfonyl group",
"optionally substituted $C_{1-12}$ alkylsulfinyl group",
"optionally substituted sulfamoyl group",
"optionally substituted sulfinamoyl group",
"optionally substituted sulfenamoyl group",
"optionally substituted thiocarbamoyl group", "optionally substituted mono- or di-$C_{1-12}$ alkyl-carbamoyl group",
"optionally substituted mono- or di-$C_{1-12}$ alkyl-amino group",
"optionally substituted mono- or di-($C_{1-12}$ alkyl-carbonyl) amino group",
"optionally substituted mono- or di-($C_{1-12}$ alkoxy-carbonyl)amino group",
"optionally substituted mono- or di-($C_{1-12}$ alkylsulfonyl) amino group",
"optionally substituted $C_{1-12}$ alkoxy-carbonyl group",
"optionally substituted tri-$C_{1-12}$ alkylsilyl group", and
"optionally substituted tri-$C_{1-12}$ alkylgermyl group" in Substituent Group AA include substituents selected from the following Substituent Group BB. The number of the substituents is 1 to substitutable maximum number, preferably 1 to 7, more preferably 1 to 3.

Examples of the substituent of
the "optionally substituted $C_{3-12}$ cycloalkyl group",
"optionally substituted $C_{6-14}$ aryl group",
"optionally substituted $C_{7-16}$ aralkyl group",
"optionally substituted $C_{6-14}$ aryl-$C_{2-12}$ alkenyl group",
"optionally substituted heterocyclic group",
"optionally substituted $C_{3-12}$ cycloalkyloxy group",
"optionally substituted $C_{6-14}$ aryloxy group",
"optionally substituted $C_{7-16}$ aralkyloxy group",
"optionally substituted heterocyclyl-oxy group",
"optionally substituted $C_{6-14}$ aryl-carbonyloxy group",
"optionally substituted mono- or di-$C_{3-12}$ cycloalkyl-carbamoyl group",
"optionally substituted mono- or di-$C_{6-14}$ aryl-carbamoyl group",
"optionally substituted mono- or di-heterocyclyl-carbamoyl group",
"optionally substituted mono- or di-$C_{6-14}$ aryl-carbamoyloxy group",
"optionally substituted $C_{3-12}$ cycloalkylsulfanyl group",
"optionally substituted $C_{6-14}$ arylsulfanyl group",
"optionally substituted $C_{7-16}$ aralkylsulfanyl group",
"optionally substituted heterocyclyl-sulfanyl group",
"optionally substituted $C_{3-12}$ cycloalkyl-carbonyl group",
"optionally substituted $C_{6-14}$ aryl-carbonyl group",
"optionally substituted $C_{7-16}$ aralkyl-carbonyl group",
"optionally substituted heterocyclyl-carbonyl group",
"optionally substituted $C_{3-12}$ cycloalkylsulfonyl group",
"optionally substituted $C_{6-14}$ arylsulfonyl group",
"optionally substituted heterocyclyl-sulfonyl group",
"optionally substituted $C_{3-10}$ cycloalkylsulfinyl group",
"optionally substituted $C_{6-14}$ arylsulfinyl group",
"optionally substituted $C_{7-16}$ aralkylsulfinyl group",
"optionally substituted heterocyclyl-sulfinyl group",
"optionally substituted mono- or di-$C_{3-10}$ cycloalkyl-amino group",
"optionally substituted mono- or di-$C_{6-14}$ aryl-amino group",
"optionally substituted mono- or di-$C_{7-16}$ aralkyl-amino group",
"optionally substituted mono- or di-heterocyclyl-amino group",
"optionally substituted mono- or di-$C_{6-14}$ aryl-carbonylamino group",
"optionally substituted mono- or di-($C_{3-12}$ cycloalkyl-carbonyl)amino group",
"optionally substituted mono- or di-(heterocyclyl-carbonyl)amino group",
"optionally substituted mono- or di-($C_{3-12}$ cycloalkoxy-carbonyl)amino group",
"optionally substituted mono- or di-(heterocyclyl-oxycarbonyl)amino group",
"optionally substituted mono- or di-($C_{3-12}$ cycloalkylsulfonyl)amino group",
"optionally substituted mono- or di-($C_{6-14}$ arylsulfonyl) amino group",
"optionally substituted heterocyclyl-sulfonylamino group",
"optionally substituted $C_{6-14}$ aryloxy-carbonyl group",
"optionally substituted $C_{7-16}$ aralkyloxy-carbonyl group",
"optionally substituted heterocyclyloxy-carbonyl group",
"optionally substituted ($C_{3-12}$ cycloalkyl)di($C_{1-12}$ alkyl) silyl group",
"optionally substituted ($C_{6-14}$ aryl)di($C_{1-12}$ alkyl)silyl group",
"optionally substituted ($C_{1-12}$ alkyl)di($C_{6-14}$ aryl) silyl group",
"optionally substituted ($C_{3-12}$ cycloalkyl)di($C_{1-12}$ alkyl) germyl group",
"optionally substituted ($C_{6-14}$ aryl)di($C_{1-12}$ alkyl)germyl group", and
"optionally substituted ($C_{1-12}$ alkyl)di($C_{6-14}$ aryl)germyl group" in Substituent Group AA include substituents selected from the following Substituent Group BB and Substituent Group BB'. The number of the substituents is 1 to substitutable maximum number, more preferably 1 to 3, further more preferably 1.

In the present specification, Substituent Group BB consists of
(a) a halogen atom;
(b) a hydroxy group;
(c) a nitro group;
(d) a cyano group;
(e) an optionally substituted $C_{6-14}$ aryl group (the $C_{6-14}$ aryl group is optionally substituted by 1 to 5 (preferably 1 to 3, more preferably 1) substituents selected from a halogen atom, a hydroxy group, a cyano group, an amino group, a $C_{1-12}$ alkyl group optionally substituted by 1 to 3 halogen atoms, a mono- or di-$C_{1-12}$ alkyl-amino group, a mono- or di-$C_{6-14}$ aryl-amino group, a mono- or di-$C_{7-16}$ aralkyl-amino group, a $C_{3-12}$ cycloalkyl group, a $C_{1-12}$ alkoxy group, a formyl group, a $C_{1-12}$ alkyl-carbonyl group, a $C_{3-12}$ cycloalkyl-carbonyl group, a $C_{6-14}$ aryl-carbonyl group, a $C_{7-16}$ aralkyl-carbonyl group, a $C_{1-12}$ alkoxy-carbonyl group, a $C_{6-14}$ aryloxy-carbonyl group, a $C_{7-16}$ aralkyloxy-carbonyl group, a $C_{1-12}$ alkylsulfanyl group, a $C_{1-12}$ alkylsulfinyl group, a $C_{1-12}$ alkylsulfonyl group, a carbamoyl group, a thiocarbamoyl group, a mono- or di-$C_{1-12}$ alkyl-carbamoyl group, a mono- or di-$C_{6-14}$ aryl-carbamoyl group and the like);
(f) an optionally substituted $C_{6-14}$ aryloxy group (the $C_{6-4}$ aryloxy group is optionally substituted by 1 to 5 (preferably 1 to 3, more preferably 1) substituents selected from a halogen atom, a hydroxy group, a cyano group, an amino group, a $C_{1-12}$ alkyl group optionally substituted by 1 to 3 halogen atoms, a mono- or di-$C_{1-12}$ alkyl-amino group, a mono- or di-$C_{6-14}$ aryl-amino group, a mono- or di-$C_{7-16}$ aralkyl-amino group, a $C_{3-12}$ cycloalkyl group, a $C_{1-12}$ alkoxy group, a formyl group, a $C_{1-12}$ alkyl-carbonyl group, a $C_{3-12}$ cycloalkyl-carbonyl group, a $C_{6-14}$ aryl-carbonyl group, a $C_{7-16}$ aralkyl-carbonyl group, a $C_{1-12}$ alkoxy-carbonyl group, a $C_{6-14}$ aryloxy-carbonyl group, a $C_{7-16}$ aralkyloxy-carbonyl group, a $C_{1-12}$ alkylsulfanyl group, a $C_{1-12}$ alkylsulfinyl group, a $C_{1-12}$ alkylsulfonyl group, a carbamoyl group, a thiocarbamoyl group, a mono- or di-$C_{1-12}$ alkyl-carbamoyl group, a mono- or di-$C_{6-14}$ aryl-carbamoyl group and the like);
(g) an optionally substituted $C_{7-16}$ aralkyloxy group (the $C_{7-16}$ aralkyloxy group is optionally substituted by 1 to 5 (preferably 1 to 3, more preferably 1) substituents selected from a halogen atom, a hydroxy group, a cyano group, an amino group, a $C_{1-12}$ alkyl group optionally substituted by 1 to 3 halogen atoms, a mono- or di-$C_{1-12}$ alkyl-amino group, a mono- or di-$C_{6-14}$ aryl-amino group, a mono- or di-$C_{7-16}$ aralkyl-amino group, a $C_{3-12}$ cycloalkyl group, a $C_{1-12}$ alkoxy group, a formyl group, a $C_{1-12}$ alkyl-carbonyl group, a $C_{3-12}$ cycloalkyl-carbonyl group, a $C_{6-14}$ aryl-carbonyl group, a $C_{7-16}$ aralkyl-carbonyl group, a $C_{1-12}$ alkoxy-carbonyl group, a $C_{6-14}$ aryloxy-carbonyl group, a $C_{7-16}$ aralkyloxy-carbonyl group, a $C_{1-12}$ alkylsulfanyl group, a $C_{1-12}$ alkylsulfinyl group, a $C_{1-12}$ alkylsulfonyl group, a carbamoyl group, a thiocarbamoyl group, a mono- or di-$C_{1-12}$ alkyl-carbamoyl group, a mono- or di-$C_{6-14}$ aryl-carbamoyl group and the like);
(h) an optionally substituted 3- to 14-membered heterocyclic group containing 1 to 5 heteroatoms selected from a nitrogen atom, a sulfur atom and an oxygen atom (the heterocyclic group is optionally substituted by 1 to 5 (preferably 1 to 3, more preferably 1) substituents selected from a halogen atom, a hydroxy group, a cyano group, an amino group, a $C_{1-12}$ alkyl group optionally substituted by 1 to 3 halogen atoms, a mono- or di-$C_{1-12}$ alkyl-amino group, a mono- or di-$C_{6-14}$ aryl-amino group, a mono- or di-$C_{7-16}$ aralkyl-amino group, a $C_{3-12}$ cycloalkyl group, a $C_{1-12}$ alkoxy group, a formyl group, a $C_{1-12}$ alkyl-carbonyl group, a $C_{3-10}$ cycloalkyl-carbonyl group, a $C_{6-14}$ aryl-carbonyl group, a $C_{7-16}$ aralkyl-carbonyl group, a $C_{1-12}$ alkoxy-carbonyl group, a $C_{6-14}$ aryloxy-carbonyl group, a $C_{7-16}$ aralkyloxy-carbonyl group, a $C_{1-12}$ alkylsulfanyl group, a $C_{1-12}$ alkylsulfinyl group, a $C_{1-12}$ alkylsulfonyl group, a carbamoyl group, a thiocarbamoyl group, a mono- or di-$C_{1-12}$ alkyl-carbamoyl group, a mono- or di-$C_{6-14}$ aryl-carbamoyl group and the like);
(i) an optionally substituted amino group {for example, an amino group optionally mono- or di-substituted by substituent(s) selected from the group consisting of a $C_{1-12}$ alkyl group, a $C_{2-12}$ alkenyl group, a $C_{6-14}$ aryl group, a $C_{7-16}$ aralkyl group, a heterocyclic group and a heterocyclyl-$C_{1-12}$ alkyl group [the $C_{1-12}$ alkyl group, $C_{2-12}$ alkenyl group, $C_{6-14}$ aryl group, $C_{7-16}$ aralkyl group, heterocyclic group and heterocyclyl-$C_{1-12}$ alkyl group are each optionally substituted by 1 to 5 (preferably 1 to 3, more preferably 1) substituents selected from a halogen atom, a hydroxy group, a cyano group, an amino group, a $C_{1-12}$ alkyl group optionally substituted by 1 to 3 halogen atoms (provided that the "$C_{1-6}$ alkyl group optionally substituted by 1 to 3 halogen atoms" is not a substituent for the $C_{1-12}$ alkyl group and $C_{2-12}$ alkenyl group), a mono- or di-$C_{1-12}$ alkyl-amino group, a mono- or di-$C_{6-14}$ aryl-amino group, a mono- or di-$C_{7-16}$ aralkyl-amino group, a $C_{3-12}$ cycloalkyl group, a $C_{1-12}$ alkoxy group, a formyl group, a $C_{1-12}$ alkyl-carbonyl group, a $C_{3-12}$ cycloalkyl-carbonyl group, a $C_{6-14}$ aryl-carbonyl group, a $C_{7-16}$ aralkyl-carbonyl group, a $C_{1-12}$ alkoxy-carbonyl group, a $C_{3-12}$ cycloalkyloxy-carbonyl group, a $C_{6-14}$ aryloxy-carbonyl group, a $C_{7-16}$ aralkyloxy-carbonyl group, a $C_{1-12}$ alkylsulfanyl group, a $C_{3-12}$ cycloalkylsulfanyl group, a $C_{1-12}$ alkylsulfinyl group, a $C_{3-12}$ cycloalkylsulfinyl group, a $C_{1-12}$ alkylsulfonyl group, a $C_{3-12}$ cycloalkylsulfonyl group, a carbamoyl group, a thiocarbamoyl group, a mono- or di-$C_{1-12}$ alkyl-carbamoyl group, a mono- or di-$C_{6-14}$ aryl-carbamoyl group and the like]};
(j) a $C_{3-12}$ cycloalkyl group;
(k) an optionally substituted $C_{1-12}$ alkoxy group (the $C_{1-12}$ alkoxy group is optionally substituted by 1 to 5 (preferably 1 to 3, more preferably 1) substituents selected from a halogen atom, a hydroxy group, an amino group, a mono- or di-$C_{1-12}$ alkyl-amino group, a mono- or di-$C_{6-14}$ aryl-amino group, a $C_{3-10}$ cycloalkyl group, a $C_{1-12}$ alkoxy group, a formyl group, a $C_{1-12}$ alkyl-carbonyl group, a $C_{3-10}$ cycloalkyl-carbonyl group, a $C_{6-14}$ aryl-carbonyl group, a $C_{7-16}$ aralkyl-carbonyl group, a $C_{1-12}$ alkoxy-carbonyl group, a $C_{6-14}$ aryloxy-carbonyl group, a $C_{7-16}$ aralkyloxy-carbonyl group, a $C_{1-12}$ alkylsulfanyl group, a $C_{1-12}$ alkylsulfinyl group, a $C_{1-12}$ alkylsulfonyl group, a carbamoyl group, a thiocarbamoyl group, a mono- or di-$C_{1-12}$ alkyl-carbamoyl group, a mono- or di-$C_{6-14}$ aryl-carbamoyl group, a tri-$C_{1-12}$ alkylsilyl group (e.g., trimethylsilyl) and the like);
(l) a formyl group;
(m) a $C_{1-12}$ alkyl-carbonyl group (e.g., acetyl);
(n) a $C_{3-12}$ cycloalkyl-carbonyl group;
(o) a $C_{6-14}$ aryl-carbonyl group;
(p) a $C_{7-16}$ aralkyl-carbonyl group;
(q) a $C_{1-12}$ alkoxy-carbonyl group;
(r) a $C_{6-14}$ aryloxy-carbonyl group;
(s) a $C_{7-16}$ aralkyloxy-carbonyl group;
(t) a $C_{1-12}$ alkylsulfanyl group;
(u) a $C_{1-12}$ alkylsulfinyl group;
(v) a $C_{1-12}$ alkylsulfonyl group;
(w) a carbamoyl group;
(x) a thiocarbamoyl group;
(y) a mono- or di-$C_{1-12}$ alkyl-carbamoyl group (e.g., methylcarbamoyl, ethylcarbamoyl, dimethylcarbamoyl, diethylcarbamoyl, ethylmethylcarbamoyl etc.);
(z) a mono- or di-$C_{6-14}$ aryl-carbamoyl group (e.g., phenylcarbamoyl, 1-naphthylcarbamoyl, 2-naphthylcarbamoyl etc.);
(aa) a mono- or di-(5- to 7-membered heterocycle containing 1 to 4 heteroatoms selected from a nitrogen atom, a sulfur atom and an oxygen atom)-carbamoyl group (e.g., 2-pyridylcarbamoyl, 3-pyridylcarbamoyl, 4-pyridylcarbamoyl, 2-thienylcarbamoyl, 3-thienylcarbamoyl etc.);
(ab) a tri-$C_{1-12}$ alkylsilyl group (e.g., trimethylsilyl);
(ac) a ($C_{3-10}$ cycloalkyl)di($C_{1-12}$ alkyl)silyl group;
(ad) a ($C_{6-14}$ aryl)di($C_{1-12}$ alkyl) silyl group;
(ae) a ($C_{1-12}$ alkyl)di($C_{6-14}$ aryl) silyl group;
(af) a tri-$C_{1-12}$ alkylgermyl group;
(ag) a ($C_{3-12}$ cycloalkyl)di($C_{1-12}$ alkyl)germyl group;
(ah) a ($C_{6-14}$ aryl)di($C_{1-12}$ alkyl) germyl group; and
(ai) a ($C_{1-12}$ alkyl)di($C_{6-14}$ aryl) germyl group.
In the present specification, Substituent Group BB' consists of
(a) an optionally substituted $C_{1-12}$ alkyl group (the $C_{1-12}$ alkyl group is optionally substituted by 1 to 5 (preferably 1 to 3, more preferably 1) substituents selected from a halogen atom, a hydroxy group, a cyano group, an amino group, a mono- or di-$C_{1-12}$ alkyl-amino group, a mono- or di-$C_{6-14}$ aryl-amino group, a mono- or di-$C_{7-16}$ aralkyl-amino group, a $C_{3-12}$ cycloalkyl group, a $C_{1-12}$ alkoxy group, a formyl group, a $C_{1-12}$ alkyl-carbonyl group, a $C_{3-12}$ cycloalkyl-carbonyl group, a $C_{6-14}$ aryl-carbonyl group, a $C_{7-16}$ aralkyl-carbonyl group, a $C_{1-12}$ alkoxy-carbonyl group, a $C_{6-14}$ aryloxy-carbonyl group, a $C_{7-16}$ aralkyloxy-carbonyl group, a $C_{1-12}$ alkylsulfanyl group, a $C_{1-12}$ alkylsulfinyl group, a $C_{1-12}$ alkylsulfonyl group, a carbamoyl group, a thiocarbamoyl group, a mono- or di-$C_{1-12}$ alkyl-carbamoyl group, a mono- or di-$C_{6-14}$ aryl-carbamoyl group and the like);

(b) an optionally substituted $C_{2-12}$ alkenyl group (the $C_{2-12}$ alkenyl group is optionally substituted by 1 to 5 (preferably 1 to 3, more preferably 1) substituents selected from a halogen atom, a hydroxy group, a cyano group, an amino group, a mono- or di-$C_{1-12}$ alkyl-amino group, a mono- or di-$C_{6-14}$ aryl-amino group, a mono- or di-$C_{7-16}$ aralkyl-amino group, a $C_{3-12}$ cycloalkyl group, a $C_{1-12}$ alkoxy group, a formyl group, a $C_{1-12}$ alkyl-carbonyl group, a $C_{3-12}$ cycloalkyl-carbonyl group, a $C_{6-14}$ aryl-carbonyl group, a $C_{7-16}$ aralkyl-carbonyl group, a $C_{1-12}$ alkoxy-carbonyl group, a $C_{6-14}$ aryloxy-carbonyl group, a $C_{7-16}$ aralkyloxy-carbonyl group, a $C_{1-12}$ alkylsulfanyl group, a $C_{1-12}$ alkylsulfinyl group, a $C_{1-12}$ alkylsulfonyl group, a carbamoyl group, a thiocarbamoyl group, a mono- or di-$C_{1-12}$ alkyl-carbamoyl group, a mono- or di-$C_{6-14}$ aryl-carbamoyl group and the like); and (c) an optionally substituted $C_{2-12}$ alkynyl group (the $C_{2-12}$ alkynyl group is optionally substituted by 1 to 5 (preferably 1 to 3, more preferably 1) substituents selected from a halogen atom, a hydroxy group, a cyano group, an amino group, a mono- or di-$C_{1-12}$ alkyl-amino group, a mono- or di-$C_{C-14}$ aryl-amino group, a mono- or di-$C_{7-16}$ aralkyl-amino group, a $C_{3-12}$ cycloalkyl group, a $C_{1-12}$ alkoxy group, a formyl group, a $C_{1-12}$ alkyl-carbonyl group, a $C_{3-12}$ cycloalkyl-carbonyl group, a $C_{6-14}$ aryl-carbonyl group, a $C_{7-16}$ aralkyl-carbonyl group, a $C_{1-12}$ alkoxy-carbonyl group, a $C_{6-14}$ aryloxy-carbonyl group, a $C_{7-16}$ aralkyloxy-carbonyl group, a $C_{1-12}$ alkylsulfanyl group, a $C_{1-12}$ alkylsulfinyl group, a $C_{1-12}$ alkylsulfonyl group, a carbamoyl group, a thiocarbamoyl group, a mono- or di-$C_{1-12}$ alkyl-carbamoyl group, a mono- or di-$C_{6-14}$ aryl-carbamoyl group and the like).

The above-mentioned "Substituent Group AA", "Substituent Group BB" and "Substituent Group BB'" each corresponds to the "Substituent Group A", "Substituent Group B" and "Substituent Group B'" described in WO 2013/100027, and the term of each substituent is as defined in WO 2013/100027.

Examples of the "hydrocarbon ring" formed by $R^{42}$ and $R^{43}$ in combination together with the carbon atoms that they are bonded to include rings corresponding to the above-mentioned "$C_{3-10}$ cycloalkyl group", "$C_{3-10}$ cycloalkenyl group" and "$C_{6-14}$ aryl group".

Examples of the "heterocycle" formed by $R^{42}$ and $R^{43}$ in combination together with the carbon atoms that they are bonded to include a ring corresponding to the above-mentioned "heterocyclic group".

Examples of the "$C_{1-6}$alkoxy group" of the "optionally substituted $C_{1-6}$alkoxy group" represented by $R^{10}$ and the "(2) an optionally substituted $C_{1-6}$ alkoxy group" excluded from $R^4$ is optionally substituted, for example, by substituent(s) selected from the above-mentioned Substituent Group A.

The number of the substituents for the "$C_{1-6}$ alkoxy group" is, for example, 1 to 3. When the number of the substituents is 2 or more, the respective substituents may be the same or different.

The "heterocyclic group" of the "optionally substituted heterocyclic group" exemplified as the "substituent" represented by $R^4$ encompasses an aromatic heterocyclic group, a non-aromatic heterocyclic group and a 7- to 10-membered bridged heterocyclic group, as well as a 5- to 14-membered spiro heterocyclic group such as 2-oxa-6-azaspiro[3.5]nonyl, 2-oxa-6-azaspiro[3.4]octyl and the like.

The "ring" of the "optionally substituted ring" form by $R^3$ and $R^4$ in combination together with the nitrogen atom adjacent to $R^3$ and the carbon atom adjacent to $R^4$ means a non-aromatic heterocycle contains at least one nitrogen atom wherein the carbon atom adjacent to the nitrogen atom is substituted by an oxo group. Examples thereof include pyrrolidin-2-one, piperidin-2-one, morpholin-3-one and the like.

The ring is optionally fused with a hydrocarbon ring (e.g., a $C_{3-10}$ cycloalkane such as cyclopropane, cyclobutane, cyclopentane, cyclohexane and the like, a benzene ring) or a heterocycle (e.g., an aromatic heterocycle such as a pyridine ring and the like, a non-aromatic heterocycle such as pyrrolidine, piperidine and the like). Examples thereof include isoindolin-1-one, isoquinoline-1(2H)one, 3,4-dihydroisoquinoline-1(2H)one and the like.

The ring optionally forms a spiro ring with a hydrocarbon ring (e.g., a $C_{3-10}$ cycloalkane such as cyclopropane, cyclobutane, cyclopentane, cyclohexane and the like, a benzene ring) or a heterocycle (e.g., a non-aromatic heterocycle such as pyrrolidine, piperidine and the like). Examples thereof include 2,7-diazaspiro[4.4]nonane-1,8-dione and the like.

The "ring" of the "optionally substituted ring" form by $R^3$ and $R^4$ in combination together with the nitrogen atom adjacent to $R^3$ and the carbon atom adjacent to $R^4$ is optionally substituted, for example, by substituent(s) selected from the above-mentioned Substituent Group A The number of the substituents of the "optionally substituted ring" is, for example, 1 to 3. When the number of the substituents is 2 or more, the respective substituents may be the same or different.

The "substituent" represented by $R^3$ is preferably an optionally substituted hydrocarbon group.

The "substituent" represented by $R^4$ is preferably an optionally substituted hydrocarbon group, an optionally substituted heterocyclic group, an acyl group, an optionally substituted amino group, or an optionally substituted hydroxy group.

Examples of the "optionally substituted hydrocarbon group" exemplified as the "substituent" represented by $R^4$ include a hydrocarbon group optionally having substituent(s) selected from the following Substituent Group B, regardless of the above-mentioned description.

[Substituent Group B]

(A) Substituent Group A wherein

"(9) a 5- to 14-membered aromatic heterocyclyloxy group" is replaced by "(9) a 5- to 14-membered aromatic heterocyclyloxy group optionally substituted by $C_{1-6}$ alkyl group(s)", "(21) a 5- to 14-membered aromatic heterocyclic group" is replaced by "(21) a 5- to 14-membered aromatic heterocyclic group optionally substituted by substituent(s) selected from (a) a $C_{1-6}$ alkyl group optionally substituted by substituent(s) selected from a halogen atom and a $C_{6-14}$ aryl group, (b) a hydroxy group and (c) a $C_{1-6}$alkoxy group optionally substituted by $C_{6-14}$ aryl group(s)", and "(22) a 3- to 14-membered non-aromatic heterocyclic group" is replaced by "(22) a 3- to 14-membered non-aromatic heterocyclic group optionally substituted by substituent(s) selected from (a) an oxo group, (b) a $C_{1-12}$ alkyl group, (c) a hydroxy group and (d) a cyano group", and (B) an imino group optionally substituted by a hydroxy group.

The number of the substituents of the above-mentioned "optionally substituted hydrocarbon group" is, for example, 1 to 5, preferably 1 to 3. When the number of the substituents is 2 or more, the respective substituents may be the same or different.

Examples of the "optionally substituted heterocyclic group" exemplified as the "substituent" represented by $R^4$ include a heterocyclic group optionally having substituent(s) selected from the following Substituent Group C, regardless of the above-mentioned description.

[Substituent Group C]

(A) Substituent Group A wherein
"(6) an optionally halogenated $C_{1-6}$ alkoxy group" is replaced by
"(6) a $C_{1-6}$ alkoxy group optionally substituted by substituent(s) selected from (a) a halogen atom and (b) a $C_{6-14}$ aryl group", and
"(57) an optionally halogenated $C_{1-6}$ alkyl group" is replaced by
"(57) a $C_{1-6}$ alkyl group optionally substituted by substituent(s) selected from (a) a halogen atom and (b) a hydroxy group", and
(B) a $C_{1-6}$ alkylidene group optionally substituted by 5- or 6-membered monocyclic aromatic heterocyclic group(s) optionally substituted by substituent(s) selected from (a) a $C_{1-6}$ alkyl group, and (b) a halogenated boryl group.

The number of the substituents of the above-mentioned "optionally substituted heterocyclic group" is, for example, 1 to 5, preferably 1 to 3. When the number of the substituents is 2 or more, the respective substituents may be the same or different.

Examples of the "$C_{1-6}$ alkylidene group" in the "substituent" represented by $R^4$ include methylidene (=CH$_2$), ethylidene (=CH—CH$_3$), propylidene (=CH—CH$_2$—CH$_3$), buthylidene (=CH—CH$_2$—CH$_2$—CH$_3$) and the like.

$R^3$ is preferably
(1) a hydrogen atom, or
(2) a $C_{1-6}$ alkyl group (e.g., methyl, ethyl) optionally substituted by 1 to 3 cyano groups.

$R^3$ is more preferably
(1) a hydrogen atom, or
(2) a $C_{1-6}$ alkyl group (e.g., methyl).

In another embodiment, $R^3$ is preferably a hydrogen atom, a methyl group, an ethyl group or a 2-cyanoethyl group.

$R^3$ is more preferably a hydrogen atom or a methyl group.

$R^4$ is preferably
(1) a $C_{1-6}$ alkyl group (e.g., methyl, ethyl, propyl, isopropyl, butyl, isobutyl, tert-butyl) optionally substituted by 1 to 7 substituents selected from
 (a) a 3- to 8-membered monocyclic non-aromatic heterocyclic group (e.g., dihydropyrimidinyl (1,6-dihydropyrimidinyl), dihydropyridyl (1,2-dihydropyridyl, 1,4-dihydropyridyl), tetrahydropyrimidinyl (1,2,3,4-tetrahydropyrimidinyl), dihydropyridazinyl (1,4-dihydropyridazinyl, 2,3-dihydropyridazinyl), imidazolidinyl, tetrahydropyranyl, morpholinyl, piperidyl, dihydrooxadiazolyl (4,5-dihydro-1,2,4-oxadiazolyl), pyrrolidinyl, tetrahydrofuryl, piperazinyl, thiazolidinyl, oxazolidinyl, azetidinyl) optionally substituted by 1 to 3 substituents selected from
  (i) an oxo group,
  (ii) a $C_{1-6}$ alkyl group (e.g., methyl),
  (iii) a hydroxy group, and
  (iv) a cyano group,
 (b) a 5- or 6-membered monocyclic aromatic heterocyclic group (e.g., oxadiazolyl (1,3,4-oxadiazolyl), isoxazolyl, pyrazolyl, pyridyl, imidazolyl (1H-imidazolyl), thienyl, tetrazolyl (1H-tetrazolyl)) optionally substituted by 1 to 3 substituents selected from
  (i) a $C_{1-6}$ alkyl group (e.g., methyl, ethyl) optionally substituted by 1 to 3 substituents selected from a halogen atom (e.g., a fluorine atom) and a $C_{6-14}$ aryl group (e.g., phenyl),
  (ii) a hydroxy group, and
  (iii) a $C_{1-6}$ alkoxy group (e.g., methoxy) optionally substituted by 1 to 3 $C_{6-14}$ aryl groups (e.g., phenyl),
 (c) a 8- to 14-membered fused polycyclic (preferably bi- or tri-cyclic) aromatic heterocyclic group (e.g., indazolyl (1H-indazolyl), benzisoxazolyl (benzo[d]isoxazolyl), benzimidazolyl (1H-benzimidazolyl)),
 (d) a 9- to 14-membered fused polycyclic (preferably bi- or tri-cyclic) non-aromatic heterocyclic group (e.g., dihydrobenzoxazolyl(2,3-dihydrobenzoxazolyl)) optionally substituted by 1 to 3 oxo groups,
 (e) a halogen atom (e.g., a fluorine atom),
 (f) a hydroxy group,
 (g) a cyano group,
 (h) a carboxy group,
 (i) a carbamoyl group,
 (j) a $C_{1-6}$ alkylsulfonyl group (e.g., methylsulfonyl),
 (k) a $C_{3-10}$ cycloalkyl group (e.g., cyclopentyl) optionally substituted by 1 to 3 substituents selected from
  (i) a hydroxy group, and
  (ii) a cyano group,
 (l) an amino group optionally mono- or di-substituted by substituent(s) selected from
  (i) a $C_{1-6}$ alkyl group (e.g., methyl),
  (ii) a $C_{1-6}$ alkyl-carbonyl group (e.g., acetyl), and
  (iii) a $C_{1-6}$ alkoxy-carbonyl group (e.g., tert-butoxycarbonyl),
 (m) an imino group optionally substituted by a hydroxy group, and
 (n) a 5- or 6-membered monocyclic aromatic heterocyclyloxy group (e.g., pyrazolyloxy) optionally substituted by 1 to 3 $C_{1-6}$ alkyl groups (e.g., methyl),
(2) a 3- to 8-membered monocyclic non-aromatic heterocyclic group (e.g., pyrrolidinyl, oxazolidinyl, azetidinyl, piperidyl, tetrahydropyranyl, tetrahydrothiopyranyl, 1,1-dioxidotetrahydrothiopyranyl, 1-oxidotetrahydrothiopyranyl, imidazolidinyl, tetrahydrofuryl, 1,1-dioxidotetrahydrothienyl, morpholinyl, dihydrooxazolyl (2,3-dihydrooxazolyl), dihydrothiazolyl (2,3-dihydrothiazolyl), piperazinyl, dihydrooxadiazolyl (4,5-dihydro-1,2,4-oxadiazolyl)) optionally substituted by 1 to 3 substituents selected from
 (a) an oxo group,
 (b) a hydroxy group,
 (c) a cyano group,
 (d) a halogen atom (e.g., a fluorine atom),
 (e) a $C_{1-6}$ alkyl group (e.g., methyl) optionally substituted by 1 to 3 hydroxy groups,
 (f) a $C_{1-6}$ alkoxy group (e.g., methoxy) optionally substituted by 1 to 3 $C_{6-14}$ aryl groups (e.g., phenyl), and
 (g) a $C_{1-6}$ alkyl-carbonyl group (e.g., acetyl),
(3) a 5- or 6-membered monocyclic aromatic heterocyclic group (e.g., isoxazolyl, furyl, pyridyl, imidazolyl (1H-imidazolyl), pyrazolyl, thienyl, triazolyl (1,2,4-triazolyl), oxazolyl, thiazolyl, oxadiazolyl (1,3,4-oxadiazolyl)) optionally substituted by 1 to 3 substituents selected from
 (a) a hydroxy group,
 (b) a cyano group, (c) a carboxy group,
(d) a halogen atom (e.g., a fluorine atom, a bromine atom),
(e) a $C_{1-6}$ alkyl group (e.g., methyl) optionally substituted by 1 to 3 hydroxy groups,
(f) a $C_{1-6}$ alkoxy group (e.g., methoxy),
(g) a $C_{1-6}$ alkoxy-carbonyl group (e.g., methoxycarbonyl), and
(h) an amino group optionally mono- or di-substituted by $C_{1-6}$ alkyl-carbonyl group(s) (e.g., acetyl),
(4) a $C_{3-10}$ cycloalkyl group (e.g., cyclopropyl, cyclobutyl, cyclopentyl, cyclohexyl) optionally substituted by 1 to 3 substituents selected from
    (a) a halogen atom (e.g., a fluorine atom),
    (b) a hydroxy group,
    (c) an oxo group,
    (d) a cyano group,
    (e) a carboxy group, and
    (f) a $C_{1-6}$ alkyl group (e.g., methyl) optionally substituted by 1 to 3 hydroxy groups,
(5) a $C_{2-6}$ alkenyl group (e.g., allyl) optionally substituted by 1 to 3 substituents selected from
    (a) a carbamoyl group, and
    (b) a hydroxy group,
(6) a $C_{6-14}$ aryl group (e.g., phenyl) optionally substituted by 1 to 3 hydroxy groups,
(7) a 9- to 14-membered fused polycyclic (preferably bi- or tri-cyclic) non-aromatic heterocyclic group (e.g., indolinyl, dihydrobenzoxadinyl (2,3-dihydro-1,4-benzoxadinyl), tetrahydroquinolyl (e.g., 1,2,3,4-tetrahydroquinolyl)) optionally substituted by 1 to 3 oxo groups,
(8) a 8- to 14-membered fused polycyclic (preferably bi- or tri-cyclic) aromatic heterocyclic group (e.g., pyrrolopyridyl (pyrrolo[2,3-b]pyridyl), pyrazolopyridyl (1H-pyrazolo[3,4-b]pyridyl)),
(9) a $C_{1-6}$ alkoxy-carbonyl group (e.g., ethoxycarbonyl),
(10) a 5- to 14-membered spiro heterocyclic group (e.g., 2-oxa-6-azaspiro[3.5]nonyl, 2-oxa-6-azaspiro[3.4]octyl),
(11) a 3- to 8-membered monocyclic non-aromatic heterocyclyloxy group (e.g., oxetanyloxy),
(12) a $C_{1-6}$alkoxy group (e.g., methoxy, ethoxy) optionally substituted by 1 to 3 substituents selected from
    (a) a $C_{6-14}$ aryl group (e.g., phenyl), and
    (b) a 3- to 8-membered monocyclic non-aromatic heterocyclic group (e.g., oxetanyl), or
(13) an amino group optionally mono- or di-substituted by substituent(s) selected from
    (a) a $C_{1-6}$ alkyl group (e.g., ethyl, isobutyl) optionally substituted by 1 to 3 hydroxy groups, and
    (b) a 5- or 6-membered monocyclic aromatic heterocyclic group (e.g., pyridazinyl).

In one embodiment, $R^4$ is not a methyl group substituted by substituent(s) selected from
(1) an amino group,
(2) a mono-substituted amino group (e.g., a mono-$C_{1-6}$ alkylamino group, a mono-$C_{6-14}$ arylamino group, a $C_{7-16}$ aralkylamino group, a 5- to 14-membered aromatic heterocyclylamino group, a $C_{7-16}$ aralkylamino group, a formylamino group, a $C_{1-6}$ alkyl-carbonylamino group, a $C_{6-14}$ aryl-carbonylamino group, a $C_{1-6}$ alkoxy-carbonylamino group, a $C_{7-16}$ aralkyloxycarbonylamino group, a $C_{1-6}$ alkylsulfonylamino group, a $C_{6-14}$ arylsulfonylamino group optionally substituted by $C_{1-6}$ alkyl group(s)),
(3) a di-substituted amino group (e.g., a di-$C_{1-6}$ alkylamino group, a di-$C_{6-14}$ arylamino group, a ($C_{1-6}$ alkyl) ($C_{1-6}$ alkyl-carbonyl) amino group),
(4) an azaheterocyclic group (e.g., a group containing at least one nitrogen atom as a ring constituting atom, from among a 5- to 14-membered aromatic heterocyclic group and a 3- to 14-membered non-aromatic heterocyclic group),
(5) a hydroxy group,
(6) a $C_{1-6}$ alkoxy group, and
(7) a $C_{1-6}$ alkylsulfanyl group.

In another embodiment, $R^4$ is preferably
(1) a $C_{1-6}$ alkyl group (e.g., methyl, ethyl, propyl, isopropyl, butyl, isobutyl, tert-butyl) optionally substituted by 1 to 7 substituents selected from
    (a) a 3- to 8-membered monocyclic oxygen-containing non-aromatic heterocyclic group (e.g., tetrahydropyranyl, tetrahydrofuryl),
    (b) a 5- or 6-membered monocyclic sulfur-containing aromatic heterocyclic group (e.g., thienyl),
    (c) a halogen atom (e.g., a fluorine atom),
    (d) a cyano group,
    (e) a carboxy group,
    (f) a carbamoyl group,
    (g) a $C_{1-6}$ alkylsulfonyl group (e.g., methylsulfonyl),
    (h) a $C_{3-10}$ cycloalkyl group (e.g., cyclopentyl) optionally substituted by 1 to 3 substituents selected from
        (i) a hydroxy group, and
        (ii) a cyano group,
    (i) an imino group optionally substituted by a hydroxy group, and
    (j) a 5- or 6-membered monocyclic aromatic heterocyclyloxy group (e.g., pyrazolyloxy) optionally substituted by 1 to 3 $C_{1-6}$ alkyl groups (e.g., methyl),
(2) a 3- to 8-membered monocyclic non-aromatic heterocyclic group (e.g., pyrrolidinyl, oxazolidinyl, azetidinyl, piperidyl, tetrahydropyranyl, tetrahydrothiopyranyl, 1,1-dioxidotetrahydrothiopyranyl, 1-oxidotetrahydrothiopyranyl, imidazolidinyl, tetrahydrofuryl, 1,1-dioxidotetrahydrothienyl, morpholinyl, dihydrooxazolyl (2,3-dihydrooxazolyl), dihydrothiazolyl (2,3-dihydrothiazolyl), piperazinyl, dihydrooxadiazolyl (4,5-dihydro-1,2,4-oxadiazolyl)) optionally substituted by 1 to 3 substituents selected from
    (a) an oxo group,
    (b) a hydroxy group,
    (c) a cyano group,
    (d) a halogen atom (e.g., a fluorine atom),
    (e) a $C_{1-6}$ alkyl group (e.g., methyl) optionally substituted by 1 to 3 hydroxy groups,
    (f) a $C_{1-6}$ alkoxy group (e.g., methoxy) optionally substituted by 1 to 3 $C_{6-14}$ aryl groups (e.g., phenyl), and
    (g) a $C_{1-6}$ alkyl-carbonyl group (e.g., acetyl),
(3) a 5- or 6-membered monocyclic aromatic heterocyclic group (e.g., isoxazolyl, furyl, pyridyl, imidazolyl (1H-imidazolyl), pyrazolyl, thienyl, triazolyl (1,2,4-triazolyl), oxazolyl, thiazolyl, oxadiazolyl (1,3,4-oxadiazolyl)) optionally substituted by 1 to 3 substituents selected from
    (a) a hydroxy group,
    (b) a cyano group,
    (c) a carboxy group,
    (d) a halogen atom (e.g., a fluorine atom, a bromine atom),
    (e) a $C_{1-6}$ alkyl group (e.g., methyl) optionally substituted by 1 to 3 hydroxy groups,
    (f) a $C_{1-6}$ alkoxy group (e.g., methoxy),
    (g) a $C_{1-6}$alkoxy-carbonyl group (e.g., methoxycarbonyl), and
    (h) an amino group optionally mono- or di-substituted by $C_{1-6}$ alkyl-carbonyl group(s) (e.g., acetyl), (4) a $C_{3-10}$ cycloalkyl group (e.g., cyclopropyl, cyclobutyl, cyclopentyl, cyclohexyl) optionally substituted by 1 to 3 substituents selected from
  (a) a halogen atom (e.g., a fluorine atom),
  (b) a hydroxy group,
  (c) an oxo group,
  (d) a cyano group,
  (e) a carboxy group, and
  (f) a $C_{1-6}$ alkyl group (e.g., methyl) optionally substituted by 1 to 3 hydroxy groups,
(5) a $C_{2-6}$ alkenyl group (e.g., allyl) optionally substituted by 1 to 3 substituents selected from
  (a) a carbamoyl group, and
  (b) a hydroxy group,
(6) a $C_{6-14}$ aryl group (e.g., phenyl) optionally substituted by 1 to 3 hydroxy groups,
(7) a 9- to 14-membered fused polycyclic (preferably bi- or tri-cyclic) non-aromatic heterocyclic group (e.g., indolinyl, dihydrobenzoxadinyl (2,3-dihydro-1,4-benzoxadinyl), tetrahydroquinolyl (e.g., 1,2,3,4-tetrahydroquinolyl)) optionally substituted by 1 to 3 oxo groups,
(8) a 8- to 14-membered fused polycyclic (preferably bi- or tri-cyclic) aromatic heterocyclic group (e.g., pyrrolopyridyl (pyrrolo[2,3-b]pyridyl), pyrazolopyridyl (1H-pyrazolo[3,4-b]pyridyl)),
(9) a $C_{1-6}$ alkoxy-carbonyl group (e.g., ethoxycarbonyl),
(10) a 5- to 14-membered spiro heterocyclic group (e.g., 2-oxa-6-azaspiro[3.5]nonyl, 2-oxa-6-azaspiro[3.4]octyl),
(11) a 3- to 8-membered monocyclic non-aromatic heterocyclyloxy group (e.g., oxetanyloxy),
(12) a $C_{1-6}$ alkoxy group (e.g., methoxy, ethoxy) optionally substituted by 1 to 3 substituents selected from
  (a) a $C_{6-14}$ aryl group (e.g., phenyl), and
  (b) a 3- to 8-membered monocyclic non-aromatic heterocyclic group (e.g., oxetanyl), or
(13) an amino group optionally mono- or di-substituted by substituent(s) selected from
  (a) a $C_{1-6}$ alkyl group (e.g., ethyl, isobutyl) optionally substituted by 1 to 3 hydroxy groups, and
  (b) a 5- or 6-membered monocyclic aromatic heterocyclic group (e.g., pyridazinyl).

Examples of the "3- to 8-membered monocyclic oxygen-containing non-aromatic heterocyclic group" that the "$C_{1-6}$ alkyl group", which is exemplified as the "substituent" represented by $R^4$, has include a non-aromatic heterocyclic group containing at least one oxygen atom as a ring constituting atom and not containing a nitrogen atom as a ring constituting atom, from among the above-mentioned "3- to 8-membered monocyclic non-aromatic heterocyclic group".

Examples of the "sulfur-containing heterocyclic group" that the "$C_{1-6}$ alkyl group", which is exemplified as the "substituent" represented by $R^4$, has include a heterocyclic group containing at least one sulfur atom as a ring constituting atom and not containing a nitrogen atom as a ring constituting atom, from among the above-mentioned "heterocyclic group".

In one embodiment, when $R^4$ is an optionally substituted methyl group, then $R^4$ is preferably a methyl group having substituent(s). In another embodiment, $R^4$ is preferably not a methyl group.

In another embodiment, when $R^4$ is a cyclic group (e.g., a $C_{6-14}$ aryl group, a $C_{3-10}$ cycloalkyl group, a $C_{3-10}$ cycloalkenyl group or a heterocyclic group), then $R^4$ is preferably not a 6-membered nitrogen-containing heterocyclic group having an oxo group at the p-position.

In another embodiment, $R^4$ is preferably
(1) a $C_{1-6}$ alkyl group (e.g., methyl, ethyl, propyl, isopropyl, butyl, isobutyl, tert-butyl) optionally substituted by 1 to 7 substituents selected from
  (a) a 3- to 8-membered monocyclic non-aromatic heterocyclic group (e.g., dihydropyrimidinyl (1,6-dihydropyrimidinyl), dihydropyridyl (1,2-dihydropyridyl, 1,4-dihydropyridyl), tetrahydropyrimidinyl (1,2,3,4-tetrahydropyrimidinyl), dihydropyridazinyl (1,4-dihydropyridazinyl, 2,3-dihydropyridazinyl), imidazolidinyl, tetrahydropyranyl, morpholinyl, piperidyl, dihydrooxadiazolyl (4,5-dihydro-1,2,4-oxadiazolyl), pyrrolidinyl, tetrahydrofuryl, piperazinyl, thiazolidinyl, oxazolidinyl, azetidinyl) optionally substituted by 1 to 3 substituents selected from
    (i) an oxo group,
    (ii) a $C_{1-6}$ alkyl group (e.g., methyl),
    (iii) a hydroxy group, and
    (iv) a cyano group,
  (b) a 5- or 6-membered monocyclic aromatic heterocyclic group (e.g., oxadiazolyl (1,3,4-oxadiazolyl), isoxazolyl, pyrazolyl, pyridyl, imidazolyl (1H-imidazolyl), thienyl, tetrazolyl (1H-tetrazolyl)) optionally substituted by 1 to 3 substituents selected from
    (i) a $C_{1-6}$ alkyl group (e.g., methyl, ethyl) optionally substituted by 1 to 3 substituents selected from a halogen atom (e.g., a fluorine atom) and a $C_{6-14}$ aryl group (e.g., phenyl),
    (ii) a hydroxy group, and
    (iii) a $C_{1-6}$ alkoxy group (e.g., methoxy) optionally substituted by 1 to 3 $C_{6-14}$ aryl groups (e.g., phenyl),
  (c) a 8- to 14-membered fused polycyclic (preferably bi- or tri-cyclic) aromatic heterocyclic group (e.g., indazolyl (1H-indazolyl), benzisoxazolyl (benzo[d]isoxazolyl), benzimidazolyl (1H-benzimidazolyl)),
  (d) a 9- to 14-membered fused polycyclic (preferably bi- or tri-cyclic) non-aromatic heterocyclic group (e.g., dihydrobenzoxazolyl(2,3-dihydrobenzoxazolyl)) optionally substituted by 1 to 3 oxo groups,
  (e) a halogen atom (e.g., a fluorine atom),
  (f) a hydroxy group,
  (g) a cyano group,
  (h) a carboxy group,
  (i) a carbamoyl group,
  (j) a $C_{1-6}$ alkylsulfonyl group (e.g., methylsulfonyl),
  (k) a $C_{3-10}$ cycloalkyl group (e.g., cyclopentyl) optionally substituted by 1 to 3 substituents selected from
    (i) a hydroxy group, and
    (ii) a cyano group,
  (l) an amino group optionally mono- or di-substituted by substituent(s) selected from
    (i) a $C_{1-6}$ alkyl group (e.g., methyl),
    (ii) a $C_{1-6}$ alkyl-carbonyl group (e.g., acetyl), and
    (iii) a $C_{1-6}$alkoxy-carbonyl group (e.g., tert-butoxycarbonyl),
  (m) an imino group optionally substituted by a hydroxy group, and
  (n) a 5- or 6-membered monocyclic aromatic heterocyclyloxy group (e.g., pyrazolyloxy) optionally substituted by 1 to 3 $C_{1-6}$ alkyl groups (e.g., methyl),
(2) a 3- to 8-membered monocyclic non-aromatic heterocyclic group (e.g., pyrrolidinyl, oxazolidinyl, azetidinyl, piperidyl, tetrahydropyranyl, tetrahydrothiopyranyl, 1,1-dioxidotetrahydrothiopyranyl, 1-oxidotetrahydrothiopyranyl, imidazolidinyl, tetrahydrofuryl, 1,1-dioxidotetrahydrothienyl, morpholinyl, dihydrooxazolyl (2,3-dihydrooxazolyl), dihydrothiazolyl (2,3-dihydrothiazolyl), piperazinyl, dihydrooxadiazolyl (4,5- dihydro-1,2,4-oxadiazolyl), pyrrolyl (2H-pyrrolyl)) optionally substituted by 1 to 3 substituents selected from
(a) an oxo group,
(b) a hydroxy group,
(c) a cyano group,
(d) a halogen atom (e.g., a fluorine atom),
(e) a $C_{1-6}$ alkyl group (e.g., methyl) optionally substituted by 1 to 3 hydroxy groups,
(f) a $C_{1-6}$ alkoxy group (e.g., methoxy) optionally substituted by 1 to 3 $C_{6-14}$ aryl groups (e.g., phenyl),
(g) a $C_{1-6}$ alkyl-carbonyl group (e.g., acetyl), and
(h) a $C_{1-6}$ alkylidene group (e.g., methylidene (=$CH_2$)) optionally substituted by 5- or 6-membered monocyclic aromatic heterocyclic group(s) (e.g., pyrrolyl (1H-pyrrolyl)) optionally substituted by 1 to 3 substituents selected from
(i) a $C_{1-6}$ alkyl group (e.g., methyl), and
(ii) a halogenated boryl group (e.g., difluoroboryl),
(3) a 5- or 6-membered monocyclic aromatic heterocyclic group (e.g., isoxazolyl, furyl, pyridyl, imidazolyl (1H-imidazolyl), pyrazolyl, thienyl, triazolyl (1,2,4-triazolyl), oxazolyl, thiazolyl, oxadiazolyl (1,3,4-oxadiazolyl)) optionally substituted by 1 to 3 substituents selected from
(a) a hydroxy group,
(b) a cyano group,
(c) a carboxy group,
(d) a halogen atom (e.g., a fluorine atom, a bromine atom),
(e) a $C_{1-6}$ alkyl group (e.g., methyl) optionally substituted by 1 to 3 hydroxy groups,
(f) a $C_{1-6}$ alkoxy group (e.g., methoxy),
(g) a $C_{1-6}$ alkoxy-carbonyl group (e.g., methoxycarbonyl), and
(h) an amino group optionally mono- or di-substituted by $C_{1-6}$ alkyl-carbonyl group(s) (e.g., acetyl),
(4) a $C_{3-10}$ cycloalkyl group (e.g., cyclopropyl, cyclobutyl, cyclopentyl, cyclohexyl) optionally substituted by 1 to 3 substituents selected from
(a) a halogen atom (e.g., a fluorine atom),
(b) a hydroxy group,
(c) an oxo group,
(d) a cyano group,
(e) a carboxy group, and
(f) a $C_{1-6}$ alkyl group (e.g., methyl) optionally substituted by 1 to 3 hydroxy groups,
(5) a $C_{2-6}$ alkenyl group (e.g., allyl) optionally substituted by 1 to 3 substituents selected from
(a) a carbamoyl group, and
(b) a hydroxy group,
(6) a $C_{6-14}$ aryl group (e.g., phenyl) optionally substituted by 1 to 3 hydroxy groups,
(7) a 9- to 14-membered fused polycyclic (preferably bi- or tri-cyclic) non-aromatic heterocyclic group (e.g., indolinyl, dihydrobenzoxadinyl (2,3-dihydro-1,4-benzoxadinyl), tetrahydroquinolyl (e.g., 1,2,3,4-tetrahydroquinolyl)) optionally substituted by 1 to 3 oxo groups,
(8) a 8- to 14-membered fused polycyclic (preferably bi- or tri-cyclic) aromatic heterocyclic group (e.g., pyrrolopyridyl (pyrrolo[2,3-b]pyridyl), pyrazolopyridyl (1H-pyrazolo[3,4-b]pyridyl)),
(9) a $C_{1-6}$ alkoxy-carbonyl group (e.g., ethoxycarbonyl),
(10) a 5- to 14-membered spiro heterocyclic group (e.g., 2-oxa-6-azaspiro[3.5]nonyl, 2-oxa-6-azaspiro[3.4]octyl),
(11) a 3- to 8-membered monocyclic non-aromatic heterocyclyloxy group (e.g., oxetanyloxy), or
(12) an amino group optionally mono- or di-substituted by substituent(s) selected from (a) a $C_{1-6}$ alkyl group (e.g., ethyl, isobutyl) optionally substituted by 1 to 3 hydroxy groups, and
(b) a 5- or 6-membered monocyclic aromatic heterocyclic group (e.g., pyridazinyl).
$R^4$ is more preferably
(1) a $C_{1-6}$ alkyl group (e.g., methyl, ethyl, propyl, isobutyl) optionally substituted by 1 to 7 substituents selected from
(a) a 3- to 8-membered monocyclic non-aromatic heterocyclic group (e.g., dihydropyrimidinyl (1,6-dihydropyrimidinyl), dihydropyridyl (1,2-dihydropyridyl, 1,4-dihydropyridyl), dihydropyridazinyl (1,4-dihydropyridazinyl, 2,3-dihydropyridazinyl), imidazolidinyl, tetrahydropyranyl, morpholinyl, piperidyl, tetrahydropyrimidinyl (1,2,3,4-tetrahydropyrimidinyl)) optionally substituted by 1 to 3 substituents selected from
(i) an oxo group, and
(ii) a $C_{1-6}$ alkyl group (e.g., methyl),
(b) a 5- or 6-membered monocyclic aromatic heterocyclic group (e.g., oxadiazolyl (1,3,4-oxadiazolyl), isoxazolyl, pyrazolyl) optionally substituted by 1 to 3 substituents selected from
(i) a $C_{1-6}$ alkyl group (e.g., methyl), and
(ii) a hydroxy group,
(c) a 8- to 14-membered fused polycyclic (preferably bi- or tri-cyclic) aromatic heterocyclic group (e.g., indazolyl (1H-indazolyl), benzimidazolyl (1H-benzimidazolyl)),
(d) a halogen atom (e.g., a fluorine atom),
(e) a hydroxy group,
(f) a cyano group,
(g) a carboxy group,
(h) a $C_{1-6}$ alkylsulfonyl group (e.g., methylsulfonyl), and
(i) an amino group optionally mono- or di-substituted by $C_{1-6}$ alkyl-carbonyl group(s) (e.g., acetyl),
(2) a 3- to 8-membered monocyclic non-aromatic heterocyclic group (e.g., pyrrolidinyl, oxazolidinyl, azetidinyl, piperidyl, tetrahydropyranyl) optionally substituted by 1 to 3 substituents selected from
(a) an oxo group,
(b) a hydroxy group,
(c) a halogen atom (e.g., a fluorine atom), and
(d) a $C_{1-6}$ alkyl-carbonyl group (e.g., acetyl),
(3) a 5- or 6-membered monocyclic aromatic heterocyclic group (e.g., isoxazolyl) optionally substituted by 1 to 3 hydroxy groups,
(4) a $C_{3-10}$ cycloalkyl group (e.g., cyclopropyl, cyclobutyl) optionally substituted by 1 to 3 halogen atoms (e.g., a fluorine atom), or
(5) an amino group optionally mono- or di-substituted by $C_{1-6}$ alkyl group(s) (e.g., ethyl).
$R^4$ is further more preferably
(1) a $C_{1-6}$ alkyl group (e.g., methyl) optionally substituted by 5- or 6-membered monocyclic aromatic heterocyclic group(s) (e.g., isoxazolyl) optionally substituted by 1 to 3 hydroxy groups,
(2) a 3- to 8-membered monocyclic non-aromatic heterocyclic group (e.g., pyrrolidinyl) optionally substituted by 1 to 3 oxo groups, or
(3) a 5- or 6-membered monocyclic aromatic heterocyclic group (e.g., isoxazolyl) optionally substituted by 1 to 3 hydroxy groups.
In another embodiment, $R^4$ is preferably
(1) an optionally substituted 5-membered heterocyclic group,
(2) an optionally substituted 6-membered non-aromatic heterocyclic group, (3) an optionally substituted 4-membered non-aromatic heterocyclic group,
(4) an optionally substituted $C_{3-4}$ cycloalkyl group, or
(5) an optionally substituted $C_{1-6}$ alkyl group.

Examples of the "5-membered heterocyclic group" of the "optionally substituted 5-membered heterocyclic group" represented by $R^4$ include a 5-membered group, from among the above-mentioned "heterocyclic group". The "5-membered heterocyclic group" is optionally substituted, for example, by substituent(s) selected from the above-mentioned Substituent Group C. The number of the substituents is, for example, 1 to 3. When the number of the substituents is 2 or more, the respective substituents may be the same or different.

Examples of the "6-membered non-aromatic heterocyclic group" of the "optionally substituted 6-membered non-aromatic heterocyclic group" represented by $R^4$ include a 6-membered group, from among the above-mentioned "3- to 8-membered monocyclic non-aromatic heterocyclic group". The "6-membered non-aromatic heterocyclic group" is optionally further substituted, for example, by substituent(s) selected from the above-mentioned Substituent Group C. The number of the substituents is, for example, 1 to 3. When the number of the substituents is 2 or more, the respective substituents may be the same or different.

Examples of the "4-membered non-aromatic heterocyclic group" of the "optionally substituted 4-membered non-aromatic heterocyclic group" represented by $R^4$ include a 4-membered group, from among the above-mentioned "3- to 8-membered monocyclic non-aromatic heterocyclic group". The "4-membered non-aromatic heterocyclic group" is optionally further substituted, for example, by substituent(s) selected from the above-mentioned Substituent Group C. The number of the substituents is, for example, 1 to 3. When the number of the substituents is 2 or more, the respective substituents may be the same or different.

Examples of the "$C_{3-4}$ cycloalkyl group" of the "optionally substituted $C_{3-4}$ cycloalkyl group" represented by $R^4$ include cyclopropyl and cyclobutyl. The "$C_{3-4}$ cycloalkyl group" is optionally further substituted, for example, by substituent(s) selected from the above-mentioned Substituent Group A. The number of the substituents is, for example, 1 to 3. When the number of the substituents is 2 or more, the respective substituents may be the same or different.

Examples of the "$C_{1-4}$ alkyl group" of the "optionally substituted $C_{1-4}$ alkyl group" represented by $R^4$ include methyl, ethyl, propyl, isopropyl, butyl, isobutyl, sec-butyl and tert-butyl. The "$C_{1-4}$ alkyl group" is optionally further substituted, for example, by substituent(s) selected from the above-mentioned Substituent Group B. The number of the substituents is, for example, 1 to 3. When the number of the substituents is 2 or more, the respective substituents may be the same or different.

$R^4$ is more preferably
(1) a 5-membered heterocyclic group (e.g., isoxazolyl, pyrrolidinyl, oxazolidinyl) optionally substituted by 1 to 3 substituents selected from
  (a) a hydroxy group,
  (b) an oxo group, and
  (c) a halogen atom (e.g., a fluorine atom),
(2) a 6-membered non-aromatic heterocyclic group (e.g., piperidyl, tetrahydropyranyl) optionally substituted by 1 to 3 $C_{1-6}$ alkyl-carbonyl groups,
(3) a 4-membered non-aromatic heterocyclic group (e.g., azetidinyl) optionally substituted by 1 to 3 hydroxy groups,
(4) a $C_{3-4}$ cycloalkyl group optionally substituted by 1 to 3 halogen atoms (e.g., a fluorine atom), or
(5) a $C_{1-4}$ alkyl group (e.g., methyl, ethyl, propyl, isobutyl) optionally substituted by 1 to 7 substituents selected from
  (a) a 3- to 8-membered monocyclic non-aromatic heterocyclic group (e.g., dihydropyrimidinyl (1,6-dihydropyrimidinyl), dihydropyridyl (1,2-dihydropyridyl, 1,4-dihydropyridyl), dihydropyridazinyl (1,4-dihydropyridazinyl, 2,3-dihydropyridazinyl), imidazolidinyl, tetrahydropyranyl, morpholinyl, piperidyl) optionally substituted by 1 to 3 substituents selected from
    (i) an oxo group, and
    (ii) a $C_{1-6}$ alkyl group (e.g., methyl),
  (b) a 5- or 6-membered monocyclic aromatic heterocyclic group (e.g., oxadiazolyl (1,3,4-oxadiazolyl), isoxazolyl, pyrazolyl) optionally substituted by 1 to 3 substituents selected from
    (i) a $C_{1-6}$ alkyl group (e.g., methyl), and
    (ii) a hydroxy group,
  (c) a 8- to 14-membered fused polycyclic (preferably bi- or tri-cyclic) aromatic heterocyclic group (e.g., indazolyl (1H-indazolyl), benzimidazolyl (1H-benzimidazolyl)),
  (d) a halogen atom (e.g., a fluorine atom),
  (e) a hydroxy group,
  (f) a cyano group,
  (g) a carboxy group,
  (h) a $C_{1-6}$ alkylsulfonyl group (e.g., methylsulfonyl), and
  (i) an amino group optionally mono- or di-substituted by $C_{1-6}$ alkyl-carbonyl group(s) (e.g., acetyl).

$R^4$ is further more preferably
(1) a 5-membered heterocyclic group (e.g., isoxazolyl, pyrrolidinyl) optionally substituted by 1 to 3 substituents selected from
  (a) a hydroxy group, and
  (b) an oxo group, or
(2) a $C_{1-4}$ alkyl group (e.g., methyl) optionally substituted by 5- or 6-membered monocyclic aromatic heterocyclic group(s) (e.g., isoxazolyl) optionally substituted by 1 to 3 hydroxy groups.

In another embodiment, $R^4$ is preferably
(1) a $C_{1-6}$ alkyl group (e.g., methyl, ethyl, propyl, isopropyl, butyl, isobutyl, tert-butyl) optionally substituted by 1 to 7 substituents selected from
  (a) a 3- to 8-membered monocyclic oxygen-containing non-aromatic heterocyclic group (e.g., tetrahydropyranyl, tetrahydrofuryl),
  (b) a 5- or 6-membered monocyclic sulfur-containing aromatic heterocyclic group (e.g., thienyl),
  (c) a halogen atom (e.g., a fluorine atom),
  (d) a cyano group,
  (e) a carboxy group,
  (f) a carbamoyl group,
  (g) a $C_{1-6}$ alkylsulfonyl group (e.g., methylsulfonyl),
  (h) a $C_{3-10}$ cycloalkyl group (e.g., cyclopentyl) optionally substituted by 1 to 3 substituents selected from
    (i) a hydroxy group, and
    (ii) a cyano group,
  (i) an imino group optionally substituted by a hydroxy group, and
  (j) a 5- or 6-membered monocyclic aromatic heterocyclyloxy group (e.g., pyrazolyloxy) optionally substituted by 1 to 3 $C_{1-6}$ alkyl groups (e.g., methyl),
(2) a 3- to 8-membered monocyclic non-aromatic heterocyclic group (e.g., pyrrolidinyl, oxazolidinyl, azetidinyl, piperidyl, tetrahydropyranyl, tetrahydrothiopyranyl, 1,1- dioxidotetrahydrothiopyranyl, 1-oxidotetrahydrothiopyranyl, imidazolidinyl, tetrahydrofuryl, 1,1-dioxidotetrahydrothienyl, morpholinyl, dihydrooxazolyl (2,3-dihydrooxazolyl), dihydrothiazolyl (2,3-dihydrothiazolyl), piperazinyl, dihydrooxadiazolyl (4,5-dihydro-1,2,4-oxadiazolyl), pyrrolyl (2H-pyrrolyl)) optionally substituted by 1 to 3 substituents selected from
(a) an oxo group,
(b) a hydroxy group,
(c) a cyano group,
(d) a halogen atom (e.g., a fluorine atom),
(e) a $C_{1-6}$ alkyl group (e.g., methyl) optionally substituted by 1 to 3 hydroxy groups,
(f) a $C_{1-6}$ alkoxy group (e.g., methoxy) optionally substituted by 1 to 3 $C_{6-14}$ aryl groups (e.g., phenyl),
(g) a $C_{1-6}$ alkyl-carbonyl group (e.g., acetyl), and
(h) a $C_{1-6}$ alkylidene group (e.g., methylidene (=$CH_2$)) optionally substituted by 5- or 6-membered monocyclic aromatic heterocyclic group(s) (e.g., pyrrolyl (1H-pyrrolyl)) optionally substituted by 1 to 3 substituents selected from
 (i) a $C_{1-6}$ alkyl group (e.g., methyl), and
 (ii) a halogenated boryl group (e.g., difluoroboryl),
(3) a 5- or 6-membered monocyclic aromatic heterocyclic group (e.g., isoxazolyl, furyl, pyridyl, imidazolyl (1H-imidazolyl), pyrazolyl, thienyl, triazolyl (1,2,4-triazolyl), oxazolyl, thiazolyl, oxadiazolyl (1,3,4-oxadiazolyl)) optionally substituted by 1 to 3 substituents selected from
(a) a hydroxy group,
(b) a cyano group,
(c) a carboxy group,
(d) a halogen atom (e.g., a fluorine atom, a bromine atom),
(e) a $C_{1-6}$ alkyl group (e.g., methyl) optionally substituted by 1 to 3 hydroxy groups,
(f) a $C_{1-6}$ alkoxy group (e.g., methoxy),
(g) a $C_{1-6}$ alkoxy-carbonyl group (e.g., methoxycarbonyl), and
(h) an amino group optionally mono- or di-substituted by $C_{1-6}$ alkyl-carbonyl group(s) (e.g., acetyl),
(4) a $C_{3-10}$ cycloalkyl group (e.g., cyclopropyl, cyclobutyl, cyclopentyl, cyclohexyl) optionally substituted by 1 to 3 substituents selected from
(a) a halogen atom (e.g., a fluorine atom),
(b) a hydroxy group,
(c) an oxo group,
(d) a cyano group,
(e) a carboxy group, and
(f) a $C_{1-6}$ alkyl group (e.g., methyl) optionally substituted by 1 to 3 hydroxy groups,
(5) a $C_{2-6}$ alkenyl group (e.g., allyl) optionally substituted by 1 to 3 substituents selected from
(a) a carbamoyl group, and
(b) a hydroxy group,
(6) a $C_{6-14}$ aryl group (e.g., phenyl) optionally substituted by 1 to 3 hydroxy groups,
(7) a 9- to 14-membered fused polycyclic (preferably bi- or tri-cyclic) non-aromatic heterocyclic group (e.g., indolinyl, dihydrobenzoxadinyl (2,3-dihydro-1,4-benzoxadinyl), tetrahydroquinolyl (e.g., 1,2,3,4-tetrahydroquinolyl)) optionally substituted by 1 to 3 oxo groups,
(8) a 8- to 14-membered fused polycyclic (preferably bi- or tri-cyclic) aromatic heterocyclic group (e.g., pyrrolopyridyl (pyrrolo[2,3-b]pyridyl), pyrazolopyridyl (1H-pyrazolo[3,4-b]pyridyl)),
(9) a $C_{1-6}$ alkoxy-carbonyl group (e.g., ethoxycarbonyl),
(10) a 5- to 14-membered spiro heterocyclic group (e.g., 2-oxa-6-azaspiro[3.5]nonyl, 2-oxa-6-azaspiro[3.4]octyl),
(11) a 3- to 8-membered monocyclic non-aromatic heterocyclyloxy group (e.g., oxetanyloxy), or
(12) an amino group optionally mono- or di-substituted by substituent(s) selected from
 (a) a $C_{1-6}$ alkyl group (e.g., ethyl, isobutyl) optionally substituted by 1 to 3 hydroxy groups, and
 (b) a 5- or 6-membered monocyclic aromatic heterocyclic group (e.g., pyridazinyl).

$R^4$ is more preferably
(1) a $C_{1-6}$ alkyl group (e.g., methyl, ethyl, propyl, isobutyl) optionally substituted by 1 to 7 substituents selected from
(a) a 3- to 8-membered monocyclic oxygen-containing non-aromatic heterocyclic group (e.g., tetrahydropyranyl),
(b) a halogen atom (e.g., a fluorine atom),
(c) a cyano group,
(d) a carboxy group, and
(e) a $C_{1-6}$ alkylsulfonyl group (e.g., methylsulfonyl),
(2) a 3- to 8-membered monocyclic non-aromatic heterocyclic group (e.g., pyrrolidinyl, oxazolidinyl, azetidinyl, piperidyl, tetrahydropyranyl) optionally substituted by 1 to 3 substituents selected from
(a) an oxo group,
(b) a hydroxy group,
(c) a halogen atom (e.g., a fluorine atom), and
(d) a $C_{1-6}$ alkyl-carbonyl group (e.g., acetyl),
(3) a 5- or 6-membered monocyclic aromatic heterocyclic group (e.g., isoxazolyl) optionally substituted by 1 to 3 hydroxy groups,
(4) a $C_{3-10}$ cycloalkyl group (e.g., cyclopropyl, cyclobutyl) optionally substituted by 1 to 3 halogen atoms (e.g., a fluorine atom), or
(5) an amino group optionally mono- or di-substituted by $C_{1-6}$ alkyl group(s) (e.g., ethyl).

$R^4$ is further more preferably
(1) a 3- to 8-membered monocyclic non-aromatic heterocyclic group (e.g., pyrrolidinyl) optionally substituted by 1 to 3 oxo groups, or
(2) a 5- or 6-membered monocyclic aromatic heterocyclic group (e.g., isoxazolyl) optionally substituted by 1 to 3 hydroxy groups.

Or When $R^3$ is a substituent, then preferably $R^3$ and $R^4$ in combination optionally form, together with the nitrogen atom adjacent to $R^3$ and the carbon atom adjacent to $R^4$, a 3- to 14-membered non-aromatic heterocycle (containing a spiro ring) (e.g., pyrrolidine, 2,7-diazaspiro[4.4]nonane) substituted by one oxo group and optionally further substituted by 1 to 3 oxo groups.

In one embodiment, preferably $R^3$ and $R^4$ in combination do not form a ring, together with the nitrogen atom adjacent to R and the carbon atom adjacent to $R^4$.

Preferable examples of the ring, group, substituent and the like explained in the present specification are more preferably used in combination.

Preferable examples of compounds (I), (I') and (I") include the following compounds.

Provided that, in preferable compounds (I) or (I'), α-(acetylamino)-N-[4-(1,1-dimethylethyl)phenyl]-cyclopentaneacetamide is excluded from the compound, and a group represented by the formula:

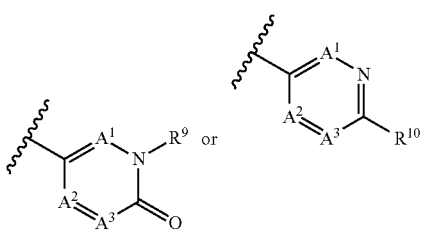 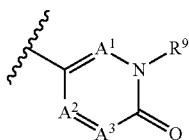

wherein
A$^1$ is CR$^{A1}$ wherein R$^{A1}$ is a hydrogen atom or a substituent, or a nitrogen atom,
A$^2$ is CR$^{A2}$ wherein R$^{A2}$ is a hydrogen atom or a substituent, or a nitrogen atom,
A$^3$ is CR$^{A3}$ wherein R$^{A3}$ is a hydrogen atom or a substituent, or a nitrogen atom, or
when A$^2$ is CR$^{A2}$ wherein R$^{A2}$ is a substituent, and A$^3$ is CR$^{A3}$ wherein R$^{A3}$ is a substituent, then R$^{A2}$ and R$^{A3}$ in combination optionally form, together with the carbon atoms that they are bonded to, a hydrocarbon ring or a heterocycle,
R$^9$ is a hydrogen atom or a hydroxy group, and when R$^9$ is a hydroxy group, then A$^1$, A$^2$ and A$^3$ are CR$^{A1}$, CR$^{A2}$ and CR$^{A4}$, respectively, and
R$^{10}$ is a hydroxy group or an optionally substituted C$_{1-6}$ alkoxy group,
is excluded from R$^4$, and
moreover, in preferable compounds (I), in addition to the above-mentioned exclusions,
(1) a cyclic group represented by the formula:

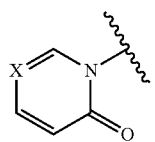

wherein X is CH or a nitrogen atom, which is optionally further substituted, and
(2) a cyclic group represented by the formula:

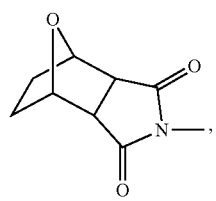

are excluded from the ring formed by R$^3$ and R$^4$ in combination together with the nitrogen atom adjacent to R$^3$ and the carbon atom adjacent to R$^4$.

In preferable compound (I''), α-(acetylamino)-N-[4-(1,1-dimethylethyl)phenyl]-cyclopentaneacetamide is excluded from the compound, and a group represented by the formula:

wherein
A$^1$ is CR$^{A1}$ wherein R$^{A1}$ is a hydrogen atom or a substituent, or a nitrogen atom,
A$^2$ is CR$^{A2}$ wherein R$^{A2}$ is a hydrogen atom or a substituent, or a nitrogen atom,
A$^3$ is CR$^{A3}$ wherein R$^{A3}$ is a hydrogen atom or a substituent, or a nitrogen atom, or
when A$^2$ is CR$^{A2}$ wherein R$^{A2}$ is a substituent, and A$^3$ is CR$^{A3}$ wherein R$^{A3}$ is a substituent, then R$^{A2}$ and R$^{A3}$ in combination optionally form, together with the carbon atoms that they are bonded to, a hydrocarbon ring or a heterocycle, and
R$^9$ is a hydrogen atom or a hydroxy group, and when R$^9$ is a hydroxy group, then A$^1$, A$^2$ and A$^3$ are CR$^{A1}$, CR$^{A2}$ and CR$^{A4}$, respectively,
is excluded from R$^4$.

[Compound A-1]
A compound wherein
Ring A is a 6-membered aromatic ring (preferably a benzene ring) optionally further substituted by 1 to 3 substituents selected from
(1) a halogen atom (e.g., a fluorine atom, a chlorine atom), and
(2) a cyano group;
R$^1$ is
(1) a group represented by the formula: -Q(R$^{1a}$)(R$^{1b}$)(R$^{1c}$)
wherein
Q is a carbon atom, a silicon atom or a germanium atom, and
R$^{1a}$, R$^{1b}$ and R$^{1c}$ are each independently
(a) a C$_{1-6}$ alkyl group (e.g., methyl, ethyl) optionally substituted by 1 to 3 substituents selected from
(i) a halogen atom (e.g., a fluorine atom), and
(ii) a C$_{1-6}$ alkoxy group (e.g., methoxy),
(b) a hydroxy group,
(c) a C$_{6-14}$ aryl group (e.g., phenyl),
(d) a C$_{3-10}$ cycloalkyl group (e.g., cyclopropyl),
(e) a cyano group,
(f) a carbamoyl group optionally mono- or di-substituted by C$_{3-10}$ cycloalkyl group(s) (e.g., cyclopropyl), or
(g) a 3- to 8-membered monocyclic non-aromatic heterocyclylcarbonyl group (e.g., pyrrolidinylcarbonyl), or
R$^{1a}$ and R$^{1b}$ in combination form, together with the adjacent Q a C$_{3-10}$ cycloalkane ring (e.g., cyclopentane),
(2) a neopentyl group, or
(3) a trimethylsilylmethyl group;
R$^2$ is
(1) a group represented by the formula:

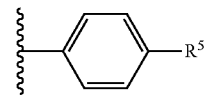

wherein
R⁵ is
(A) a $C_{1-6}$ alkyl group (e.g., methyl, ethyl, isopropyl) optionally substituted by 1 to 3 substituents selected from
  (a) a $C_{1-6}$ alkoxy group (e.g., methoxy, ethoxy, propoxy) optionally substituted by 1 to 3 substituents selected from
    (i) a halogen atom (e.g., a fluorine atom), and
    (ii) a $C_{1-6}$ alkoxy group (e.g., methoxy), and
  (b) a hydroxy group, or
(B) a $C_{1-6}$ alkoxy group (e.g., methoxy, ethoxy, propoxy) optionally substituted by 1 to 3 $C_{1-6}$ alkoxy groups (e.g., methoxy), and
the benzene ring in the formula optionally has, besides R⁵, additional 1 to 3 substituents selected from
  (A) a $C_{1-6}$ alkyl group (e.g., methyl), and
  (B) a $C_{1-6}$ alkoxy group (e.g., methoxy),
(2) a bicyclic fused heterocyclic group (e.g., dihydrobenzofuryl (2,3-dihydrobenzofuryl), indazolyl (1H-indazolyl, 2H-indazolyl), indolyl, indolinyl) optionally substituted by 1 to 3 $C_{1-6}$ alkyl groups (e.g., methyl), or
(3) a group represented by the formula -L-Z¹:
wherein
L is a bond; and
Z¹ is
(A) a $C_{3-10}$ cycloalkyl group (e.g., cyclohexyl) optionally substituted by 1 to 3 substituents selected from
  (a) a halogen atom (e.g., a fluorine atom), and
  (b) a hydroxy group, or
(B) a 3- to 8-membered monocyclic non-aromatic heterocyclic group (e.g., tetrahydropyranyl, piperidyl, 1,1-dioxidotetrahydrothiopyranyl) optionally substituted by $C_{1-6}$ alkyl group(s) (e.g., ethyl) optionally substituted by 1 to 3 halogen atoms (e.g., a fluorine atom);
R³ is
(1) a hydrogen atom, or
(2) a $C_{1-6}$ alkyl group (e.g., methyl, ethyl) optionally substituted by 1 to 3 cyano groups; and
R⁴ is
(1) a $C_{1-6}$ alkyl group (e.g., methyl, ethyl, propyl, isopropyl, butyl, isobutyl, tert-butyl) optionally substituted by 1 to 7 substituents selected from
  (a) a 3- to 8-membered monocyclic non-aromatic heterocyclic group (e.g., dihydropyrimidinyl (1,6-dihydropyrimidinyl), dihydropyridyl (1,2-dihydropyridyl, 1,4-dihydropyridyl), tetrahydropyrimidinyl (1,2,3,4-tetrahydropyrimidinyl), dihydropyridazinyl (1,4-dihydropyridazinyl, 2,3-dihydropyridazinyl), imidazolidinyl, tetrahydropyranyl, morpholinyl, piperidyl, dihydrooxadiazolyl (4,5-dihydro-1,2,4-oxadiazolyl), pyrrolidinyl, tetrahydrofuryl, piperazinyl, thiazolidinyl, oxazolidinyl, azetidinyl) optionally substituted by 1 to 3 substituents selected from
    (i) an oxo group,
    (ii) a $C_{1-6}$ alkyl group (e.g., methyl),
    (iii) a hydroxy group, and
    (iv) a cyano group,
  (b) a 5- or 6-membered monocyclic aromatic heterocyclic group (e.g., oxadiazolyl (1,3,4-oxadiazolyl), isoxazolyl, pyrazolyl, pyridyl, imidazolyl (1H-imidazolyl), thienyl, tetrazolyl (1H-tetrazolyl)) optionally substituted by 1 to 3 substituents selected from
    (i) a $C_{1-6}$ alkyl group (e.g., methyl, ethyl) optionally substituted by 1 to 3 substituents selected from a halogen atom (e.g., a fluorine atom) and a $C_{6-14}$ aryl group (e.g., phenyl),
    (ii) a hydroxy group, and
    (iii) a $C_{1-6}$ alkoxy group (e.g., methoxy) optionally substituted by 1 to 3 $C_{6-14}$ aryl groups (e.g., phenyl),
  (c) a 8- to 14-membered fused polycyclic (preferably bi- or tri-cyclic) aromatic heterocyclic group (e.g., indazolyl (1H-indazolyl), benzisoxazolyl (benzo[d]isoxazolyl), benzimidazolyl (1H-benzimidazolyl)),
  (d) a 9- to 14-membered fused polycyclic (preferably bi- or tri-cyclic) non-aromatic heterocyclic group (e.g., dihydrobenzoxazolyl(2,3-dihydrobenzoxazolyl)) optionally substituted by 1 to 3 oxo groups,
  (e) a halogen atom (e.g., a fluorine atom),
  (f) a hydroxy group,
  (g) a cyano group,
  (h) a carboxy group,
  (i) a carbamoyl group,
  (j) a $C_{1-6}$ alkylsulfonyl group (e.g., methylsulfonyl),
  (k) a $C_{3-10}$ cycloalkyl group (e.g., cyclopentyl) optionally substituted by 1 to 3 substituents selected from
    (i) a hydroxy group, and
    (ii) a cyano group,
  (l) an amino group optionally mono- or di-substituted by substituent(s) selected from
    (i) a $C_{1-6}$ alkyl group (e.g., methyl),
    (ii) a $C_{1-6}$ alkyl-carbonyl group (e.g., acetyl), and
    (iii) a $C_{1-6}$ alkoxy-carbonyl group (e.g., tert-butoxycarbonyl),
  (m) an imino group optionally substituted by a hydroxy group, and
  (n) a 5- or 6-membered monocyclic aromatic heterocyclyloxy group (e.g., pyrazolyloxy) optionally substituted by 1 to 3 $C_{1-6}$ alkyl groups (e.g., methyl),
(2) a 3- to 8-membered monocyclic non-aromatic heterocyclic group (e.g., pyrrolidinyl, oxazolidinyl, azetidinyl, piperidyl, tetrahydropyranyl, tetrahydrothiopyranyl, 1,1-dioxidotetrahydrothiopyranyl, 1-oxidotetrahydrothiopyranyl, imidazolidinyl, tetrahydrofuryl, 1,1-dioxidotetrahydrothienyl, morpholinyl, dihydrooxazolyl (2,3-dihydrooxazolyl), dihydrothiazolyl (2,3-dihydrothiazolyl), piperazinyl, dihydrooxadiazolyl (4,5-dihydro-1,2,4-oxadiazolyl), pyrrolyl (2H-pyrrolyl)) optionally substituted by 1 to 3 substituents selected from
  (a) an oxo group,
  (b) a hydroxy group,
  (c) a cyano group,
  (d) a halogen atom (e.g., a fluorine atom),
  (e) a $C_{1-6}$ alkyl group (e.g., methyl) optionally substituted by 1 to 3 hydroxy groups,
  (f) a $C_{1-6}$ alkoxy group (e.g., methoxy) optionally substituted by 1 to 3 $C_{6-14}$ aryl groups (e.g., phenyl),
  (g) a $C_{1-6}$ alkyl-carbonyl group (e.g., acetyl), and
  (h) a $C_{1-6}$ alkylidene group (e.g., methylidene ($=CH_2$)) optionally substituted by 5- or 6-membered monocyclic aromatic heterocyclic group(s) (e.g., pyrrolyl (1H-pyrrolyl)) optionally substituted by 1 to 3 substituents selected from
    (i) a $C_{1-6}$ alkyl group (e.g., methyl), and
    (ii) a halogenated boryl group (e.g., difluoroboryl),
(3) a 5- or 6-membered monocyclic aromatic heterocyclic group (e.g., isoxazolyl, furyl, pyridyl, imidazolyl (1H-imidazolyl), pyrazolyl, thienyl, triazolyl (1,2,4-triazolyl), oxazolyl, thiazolyl, oxadiazolyl (1,3,4-oxadiazolyl)) optionally substituted by 1 to 3 substituents selected from
  (a) a hydroxy group,
  (b) a cyano group,
  (c) a carboxy group,
  (d) a halogen atom (e.g., a fluorine atom, a bromine atom), (e) a $C_{1-6}$ alkyl group (e.g., methyl) optionally substituted by 1 to 3 hydroxy groups,
(f) a $C_{1-6}$ alkoxy group (e.g., methoxy),
(g) a $C_{1-6}$ alkoxy-carbonyl group (e.g., methoxycarbonyl), and
(h) an amino group optionally mono- or di-substituted by $C_{1-6}$ alkyl-carbonyl group(s) (e.g., acetyl),
(4) a $C_{3-10}$ cycloalkyl group (e.g., cyclopropyl, cyclobutyl, cyclopentyl, cyclohexyl) optionally substituted by 1 to 3 substituents selected from
(a) a halogen atom (e.g., a fluorine atom),
(b) a hydroxy group,
(c) an oxo group,
(d) a cyano group,
(e) a carboxy group, and
(f) a $C_{1-6}$ alkyl group (e.g., methyl) optionally substituted by 1 to 3 hydroxy groups,
(5) a $C_{2-6}$ alkenyl group (e.g., allyl) optionally substituted by 1 to 3 substituents selected from
(a) a carbamoyl group, and
(b) a hydroxy group,
(6) a $C_{6-14}$ aryl group (e.g., phenyl) optionally substituted by 1 to 3 hydroxy groups,
(7) a 9- to 14-membered fused polycyclic (preferably bi- or tri-cyclic) non-aromatic heterocyclic group (e.g., indolinyl, dihydrobenzoxadinyl (2,3-dihydro-1,4-benzoxadinyl), tetrahydroquinolyl (e.g., 1,2,3,4-tetrahydroquinolyl)) optionally substituted by 1 to 3 oxo groups,
(8) a 8- to 14-membered fused polycyclic (preferably bi- or tri-cyclic) aromatic heterocyclic group (e.g., pyrrolopyridyl (pyrrolo[2,3-b]pyridyl), pyrazolopyridyl (1H-pyrazolo[3,4-b]pyridyl)),
(9) a $C_{1-12}$ alkoxy-carbonyl group (e.g., ethoxycarbonyl),
(10) a 5- to 14-membered spiro heterocyclic group (e.g., 2-oxa-6-azaspiro[3.5]nonyl, 2-oxa-6-azaspiro[3.4]octyl),
(11) a 3- to 8-membered monocyclic non-aromatic heterocyclyloxy group (e.g., oxetanyloxy), or
(12) an amino group optionally mono- or di-substituted by substituent(s) selected from
(a) a $C_{1-6}$ alkyl group (e.g., ethyl, isobutyl) optionally substituted by 1 to 3 hydroxy groups, and
(b) a 5- or 6-membered monocyclic aromatic heterocyclic group (e.g., pyridazinyl); or
when $R^3$ is a substituent, $R^3$ and $R^4$ in combination form, together with the nitrogen atom adjacent to $R^3$ and the carbon atom adjacent to $R^4$, a 3- to 14-membered non-aromatic heterocycle (containing a spiro ring) (e.g., pyrrolidine, 2,7-diazaspiro[4.4]nonane) substituted by one oxo group and optionally further substituted by 1 to 3 oxo groups, or a salt thereof.
[Compound A-2]
A compound wherein
Ring A is a 6-membered aromatic ring (preferably a benzene ring) optionally further substituted by 1 to 3 substituents selected from
(1) a halogen atom (e.g., a fluorine atom, a chlorine atom), and
(2) a cyano group;
$R^1$ is
(1) a group represented by the formula: $-Q(R^{1a})(R^{1b})(R^{1c})$ wherein
Q is a carbon atom, a silicon atom or a germanium atom, and
$R^{1a}$, $R^{1b}$ and $R^{1c}$ are each independently
(a) a $C_{1-6}$ alkyl group (e.g., methyl, ethyl) optionally substituted by 1 to 3 substituents selected from
(i) a halogen atom (e.g., a fluorine atom), and
(ii) a $C_{1-6}$ alkoxy group (e.g., methoxy),
(b) a hydroxy group,
(c) a $C_{6-14}$ aryl group (e.g., phenyl),
(d) a $C_{3-10}$ cycloalkyl group (e.g., cyclopropyl),
(e) a cyano group,
(f) a carbamoyl group optionally mono- or di-substituted by $C_{3-10}$ cycloalkyl group(s) (e.g., cyclopropyl), or
(g) a 3- to 8-membered monocyclic non-aromatic heterocyclylcarbonyl group (e.g., pyrrolidinylcarbonyl), or $R^{1a}$ and $R^{1b}$ in combination form, together with the adjacent Q, a $C_{3-10}$ cycloalkane ring (e.g., cyclopentane),
(2) a neopentyl group, or
(3) a trimethylsilylmethyl group;
$R^2$ is
(1) a group represented by the formula:

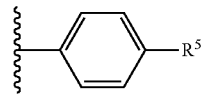

wherein
$R^5$ is
(A) a $C_{1-6}$ alkyl group (e.g., methyl, ethyl, isopropyl) optionally substituted by 1 to 3 substituents selected from
(a) a $C_{1-6}$ alkoxy group (e.g., methoxy, ethoxy, propoxy) optionally substituted by 1 to 3 substituents selected from
(i) a halogen atom (e.g., a fluorine atom), and
(ii) a $C_{1-6}$ alkoxy group (e.g., methoxy), and
(b) a hydroxy group, or
(B) a $C_{1-6}$ alkoxy group (e.g., methoxy, ethoxy, propoxy) optionally substituted by 1 to 3 $C_{1-6}$ alkoxy groups (e.g., methoxy), and
the benzene ring in the formula optionally has, besides $R^5$, additional 1 to 3 substituents selected from
(A) a $C_{1-6}$ alkyl group (e.g., methyl), and
(B) a $C_{1-6}$ alkoxy group (e.g., methoxy),
(2) a bicyclic fused heterocyclic group (e.g., dihydrobenzofuryl (2,3-dihydrobenzofuryl), indazolyl (1H-indazolyl, 2H-indazolyl), indolyl, indolinyl) optionally substituted by 1 to 3 $C_{1-6}$ alkyl groups (e.g., methyl), or
(3) a group represented by the formula -L-$Z^1$:
wherein
L is a bond; and
$Z^1$ is
(A) a $C_{3-10}$ cycloalkyl group (e.g., cyclohexyl) optionally substituted by 1 to 3 substituents selected from
(a) a halogen atom (e.g., a fluorine atom), and
(b) a hydroxy group, or
(B) a 3- to 8-membered monocyclic non-aromatic heterocyclic group (e.g., tetrahydropyranyl, piperidyl, 1,1-dioxidotetrahydrothiopyranyl) optionally substituted by $C_{1-6}$ alkyl group(s) (e.g., ethyl) optionally substituted by 1 to 3 halogen atoms (e.g., a fluorine atom);
$R^3$ is
(1) a hydrogen atom, or
(2) a $C_{1-6}$ alkyl group (e.g., methyl, ethyl) optionally substituted by 1 to 3 cyano groups; and
$R^4$ is
(1) a $C_{1-6}$ alkyl group (e.g., methyl, ethyl, propyl, isopropyl, butyl, isobutyl, tert-butyl) optionally substituted by 1 to 7 substituents selected from (a) a 3- to 8-membered monocyclic oxygen-containing non-aromatic heterocyclic group (e.g., tetrahydropyranyl, tetrahydrofuryl),
(b) a 5- or 6-membered monocyclic sulfur-containing aromatic heterocyclic group (e.g., thienyl),
(c) a halogen atom (e.g., a fluorine atom),
(d) a cyano group,
(e) a carboxy group,
(f) a carbamoyl group,
(g) a $C_{1-6}$ alkylsulfonyl group (e.g., methylsulfonyl),
(h) a $C_{3-10}$ cycloalkyl group (e.g., cyclopentyl) optionally substituted by 1 to 3 substituents selected from
  (i) a hydroxy group, and
  (ii) a cyano group,
(i) an imino group optionally substituted by a hydroxy group, and
(j) a 5- or 6-membered monocyclic aromatic heterocycyloxy group (e.g., pyrazolyloxy) optionally substituted by 1 to 3 $C_{1-6}$ alkyl groups (e.g., methyl),
(2) a 3- to 8-membered monocyclic non-aromatic heterocyclic group (e.g., pyrrolidinyl, oxazolidinyl, azetidinyl, piperidyl, tetrahydropyranyl, tetrahydrothiopyranyl, 1,1-dioxidotetrahydrothiopyranyl, 1-oxidotetrahydrothiopyranyl, imidazolidinyl, tetrahydrofuryl, 1,1-dioxidotetrahydrothienyl, morpholinyl, dihydrooxazolyl (2,3-dihydrooxazolyl), dihydrothiazolyl (2,3-dihydrothiazolyl), piperazinyl, dihydrooxadiazolyl (4,5-dihydro-1,2,4-oxadiazolyl), pyrrolyl (2H-pyrrolyl)) optionally substituted by 1 to 3 substituents selected from
(a) an oxo group,
(b) a hydroxy group,
(c) a cyano group,
(d) a halogen atom (e.g., a fluorine atom),
(e) a $C_{1-6}$ alkyl group (e.g., methyl) optionally substituted by 1 to 3 hydroxy groups,
(f) a $C_{1-6}$ alkoxy group (e.g., methoxy) optionally substituted by 1 to 3 $C_{6-14}$ aryl groups (e.g., phenyl),
(g) a $C_{1-6}$ alkyl-carbonyl group (e.g., acetyl), and
(h) a $C_{1-6}$ alkylidene group (e.g., methylidene (=CH$_2$)) optionally substituted by 5- or 6-membered monocyclic aromatic heterocyclic group(s) (e.g., pyrrolyl (1H-pyrrolyl)) optionally substituted by 1 to 3 substituents selected from
  (i) a $C_{1-6}$ alkyl group (e.g., methyl), and
  (ii) a halogenated boryl group (e.g., difluoroboryl),
(3) a 5- or 6-membered monocyclic aromatic heterocyclic group (e.g., isoxazolyl, furyl, pyridyl, imidazolyl (1H-imidazolyl), pyrazolyl, thienyl, triazolyl (1,2,4-triazolyl), oxazolyl, thiazolyl, oxadiazolyl (1,3,4-oxadiazolyl)) optionally substituted by 1 to 3 substituents selected from
(a) a hydroxy group,
(b) a cyano group,
(c) a carboxy group,
(d) a halogen atom (e.g., a fluorine atom, a bromine atom),
(e) a $C_{1-6}$ alkyl group (e.g., methyl) optionally substituted by 1 to 3 hydroxy groups,
(f) a $C_{1-6}$ alkoxy group (e.g., methoxy),
(g) a $C_{1-6}$ alkoxy-carbonyl group (e.g., methoxycarbonyl), and
(h) an amino group optionally mono- or di-substituted by $C_{1-6}$ alkyl-carbonyl group(s) (e.g., acetyl),
(4) a $C_{3-10}$ cycloalkyl group (e.g., cyclopropyl, cyclobutyl, cyclopentyl, cyclohexyl) optionally substituted by 1 to 3 substituents selected from
(a) a halogen atom (e.g., a fluorine atom),
(b) a hydroxy group,
(c) an oxo group,
(d) a cyano group,
(e) a carboxy group, and
(f) a $C_{1-6}$ alkyl group (e.g., methyl) optionally substituted by 1 to 3 hydroxy groups,
(5) a $C_{2-6}$ alkenyl group (e.g., allyl) optionally substituted by 1 to 3 substituents selected from
(a) a carbamoyl group, and
(b) a hydroxy group,
(6) a $C_{6-14}$ aryl group (e.g., phenyl) optionally substituted by 1 to 3 hydroxy groups,
(7) a 9- to 14-membered fused polycyclic (preferably bi- or tri-cyclic) non-aromatic heterocyclic group (e.g., indolinyl, dihydrobenzoxadinyl (2,3-dihydro-1,4-benzoxadinyl), tetrahydroquinolyl (e.g., 1,2,3,4-tetrahydroquinolyl)) optionally substituted by 1 to 3 oxo groups,
(8) a 8- to 14-membered fused polycyclic (preferably bi- or tri-cyclic) aromatic heterocyclic group (e.g., pyrrolopyridyl (pyrrolo[2,3-b]pyridyl), pyrazolopyridyl (1H-pyrazolo[3,4-b]pyridyl)),
(9) a $C_{1-12}$ alkoxy-carbonyl group (e.g., ethoxycarbonyl),
(10) a 5- to 14-membered spiro heterocyclic group (e.g., 2-oxa-6-azaspiro[3.5]nonyl, 2-oxa-6-azaspiro[3.4]octyl),
(11) a 3- to 8-membered monocyclic non-aromatic heterocyclyloxy group (e.g., oxetanyloxy), or
(12) an amino group optionally mono- or di-substituted by substituent(s) selected from
(a) a $C_{1-6}$ alkyl group (e.g., ethyl, isobutyl) optionally substituted by 1 to 3 hydroxy groups, and
(b) a 5- or 6-membered monocyclic aromatic heterocyclic group (e.g., pyridazinyl); or
when $R^3$ is a substituent, $R^3$ and $R^4$ in combination form, together with the nitrogen atom adjacent to $R^3$ and the carbon atom adjacent to $R^4$, a 3- to 14-membered non-aromatic heterocycle (containing a spiro ring) (e.g., pyrrolidine, 2,7-diazaspiro[4.4]nonane) substituted by one oxo group and optionally further substituted by 1 to 3 oxo groups, or a salt thereof.

[Compound A-3]

A compound wherein

Ring A is a 6-membered aromatic ring (preferably a benzene ring) optionally further substituted by 1 to 3 substituents selected from
(1) a halogen atom (e.g., a fluorine atom, a chlorine atom), and
(2) a cyano group;

$R^1$ is
(1) a group represented by the formula: $-Q(R^{1a})(R^{1b})(R^{1c})$ wherein
Q is a carbon atom, a silicon atom or a germanium atom, and
$R^{1a}$, $R^{1b}$ and $R^{1c}$ are each independently
(a) a $C_{1-6}$ alkyl group (e.g., methyl, ethyl) optionally substituted by 1 to 3 substituents selected from
  (i) a halogen atom (e.g., a fluorine atom), and
  (ii) a $C_{1-6}$ alkoxy group (e.g., methoxy),
(b) a hydroxy group,
(c) a $C_{6-14}$ aryl group (e.g., phenyl),
(d) a $C_{3-10}$ cycloalkyl group (e.g., cyclopropyl),
(e) a cyano group,
(f) a carbamoyl group optionally mono- or di-substituted by $C_{3-10}$ cycloalkyl group(s) (e.g., cyclopropyl), or
(g) a 3- to 8-membered monocyclic non-aromatic heterocyclylcarbonyl group (e.g., pyrrolidinylcarbonyl), or
$R^{1a}$ and $R^{1b}$ in combination form, together with the adjacent Q, a $C_{3-10}$ cycloalkane ring (e.g., cyclopentane), (2) a neopentyl group, or
(3) a trimethylsilylmethyl group;
R² is
(1) a group represented by the formula:

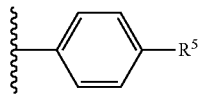

wherein
R⁵ is
(A) a C$_{1-6}$ alkyl group (e.g., methyl, ethyl, isopropyl) optionally substituted by 1 to 3 substituents selected from
  (a) a C$_{1-6}$ alkoxy group (e.g., methoxy, ethoxy, propoxy) optionally substituted by 1 to 3 substituents selected from
    (i) a halogen atom (e.g., a fluorine atom), and
    (ii) a C$_{1-6}$ alkoxy group (e.g., methoxy), and
  (b) a hydroxy group, or
(B) a C$_{1-6}$ alkoxy group (e.g., methoxy, ethoxy, propoxy) optionally substituted by 1 to 3 C$_{1-6}$ alkoxy groups (e.g., methoxy), and the benzene ring in the formula optionally has, besides R⁵, additional 1 to 3 substituents selected from
  (A) a C$_{1-6}$ alkyl group (e.g., methyl), and
  (B) a C$_{1-6}$ alkoxy group (e.g., methoxy),
(2) a bicyclic fused heterocyclic group (e.g., dihydrobenzofuryl (2,3-dihydrobenzofuryl), indazolyl (1H-indazolyl, 2H-indazolyl), indolyl, indolinyl) optionally substituted by 1 to 3 C$_{1-6}$ alkyl groups (e.g., methyl), or
(3) a group represented by the formula -L-Z¹:
  wherein
  L is a bond; and
  Z¹ is
  (A) a C$_{3-10}$ cycloalkyl group (e.g., cyclohexyl) optionally substituted by 1 to 3 substituents selected from
    (a) a halogen atom (e.g., a fluorine atom), and
    (b) a hydroxy group, or
  (B) a 3- to 8-membered monocyclic non-aromatic heterocyclic group (e.g., tetrahydropyranyl, piperidyl, 1,1-dioxidotetrahydrothiopyranyl) optionally substituted by C$_{1-6}$ alkyl group(s) (e.g., ethyl) optionally substituted by 1 to 3 halogen atoms (e.g., a fluorine atom);
R³ is
(1) a hydrogen atom, or
(2) a C$_{1-6}$ alkyl group (e.g., methyl, ethyl) optionally substituted by 1 to 3 cyano groups; and
R⁴ is
(1) a C$_{1-6}$ alkyl group (e.g., methyl, ethyl, propyl, isopropyl, butyl, isobutyl, tert-butyl) optionally substituted by 1 to 7 substituents selected from
  (a) a 3- to 8-membered monocyclic non-aromatic heterocyclic group (e.g., dihydropyrimidinyl (1,6-dihydropyrimidinyl), dihydropyridyl (1,2-dihydropyridyl, 1,4-dihydropyridyl), tetrahydropyrimidinyl (1,2,3,4-tetrahydropyrimidinyl), dihydropyridazinyl (1,4-dihydropyridazinyl, 2,3-dihydropyridazinyl), imidazolidinyl, tetrahydropyranyl, morpholinyl, piperidyl, dihydrooxadiazolyl (4,5-dihydro-1,2,4-oxadiazolyl), pyrrolidinyl, tetrahydrofuryl, piperazinyl, thiazolidinyl, oxazolidinyl, azetidinyl) optionally substituted by 1 to 3 substituents selected from
    (i) an oxo group,
    (ii) a C$_{1-6}$ alkyl group (e.g., methyl),
    (iii) a hydroxy group, and
    (iv) a cyano group,
  (b) a 5- or 6-membered monocyclic aromatic heterocyclic group (e.g., oxadiazolyl (1,3,4-oxadiazolyl), isoxazolyl, pyrazolyl, pyridyl, imidazolyl (1H-imidazolyl), thienyl, tetrazolyl (1H-tetrazolyl)) optionally substituted by 1 to 3 substituents selected from
    (i) a C$_{1-6}$ alkyl group (e.g., methyl, ethyl) optionally substituted by 1 to 3 substituents selected from a halogen atom (e.g., a fluorine atom) and a C$_{6-14}$ aryl group (e.g., phenyl),
    (ii) a hydroxy group, and
    (iii) a C$_{1-6}$ alkoxy group (e.g., methoxy) optionally substituted by 1 to 3 C$_{6-14}$ aryl groups (e.g., phenyl),
  (c) a 8- to 14-membered fused polycyclic (preferably bi- or tri-cyclic) aromatic heterocyclic group (e.g., indazolyl (1H-indazolyl), benzisoxazolyl (benzo[d]isoxazolyl), benzimidazolyl (1H-benzimidazolyl)),
  (d) a 9- to 14-membered fused polycyclic (preferably bi- or tri-cyclic) non-aromatic heterocyclic group (e.g., dihydrobenzoxazolyl(2,3-dihydrobenzoxazolyl)) optionally substituted by 1 to 3 oxo groups,
  (e) a halogen atom (e.g., a fluorine atom),
  (f) a hydroxy group,
  (g) a cyano group,
  (h) a carboxy group,
  (i) a carbamoyl group,
  (j) a C$_{1-6}$ alkylsulfonyl group (e.g., methylsulfonyl),
  (k) a C$_{3-10}$ cycloalkyl group (e.g., cyclopentyl) optionally substituted by 1 to 3 substituents selected from
    (i) a hydroxy group, and
    (ii) a cyano group,
  (l) an amino group optionally mono- or di-substituted by substituent(s) selected from
    (i) a C$_{1-6}$ alkyl group (e.g., methyl),
    (ii) a C$_{1-6}$ alkyl-carbonyl group (e.g., acetyl), and
    (iii) a C$_{1-6}$ alkoxy-carbonyl group (e.g., tert-butoxycarbonyl),
  (m) an imino group optionally substituted by a hydroxy group, and
  (n) a 5- or 6-membered monocyclic aromatic heterocylyloxy group (e.g., pyrazolyloxy) optionally substituted by 1 to 3 C$_{1-6}$ alkyl groups (e.g., methyl),
(2) a 3- to 8-membered monocyclic non-aromatic heterocyclic group (e.g., pyrrolidinyl, oxazolidinyl, azetidinyl, piperidyl, tetrahydropyranyl, tetrahydrothiopyranyl, 1,1-dioxidotetrahydrothiopyranyl, 1-oxidotetrahydrothiopyranyl, imidazolidinyl, tetrahydrofuryl, 1,1-dioxidotetrahydrothienyl, morpholinyl, dihydrooxazolyl (2,3-dihydrooxazolyl), dihydrothiazolyl (2,3-dihydrothiazolyl), piperazinyl, dihydrooxadiazolyl (4,5-dihydro-1,2,4-oxadiazolyl), pyrrolyl (2H-pyrrolyl)) optionally substituted by 1 to 3 substituents selected from
  (a) an oxo group,
  (b) a hydroxy group,
  (c) a cyano group,
  (d) a halogen atom (e.g., a fluorine atom),
  (e) a C$_{1-6}$ alkyl group (e.g., methyl) optionally substituted by 1 to 3 hydroxy groups,
  (f) a C$_{1-6}$ alkoxy group (e.g., methoxy) optionally substituted by 1 to 3 C$_{6-14}$ aryl groups (e.g., phenyl),
  (g) a C$_{1-6}$ alkyl-carbonyl group (e.g., acetyl), and
  (h) a C$_{1-6}$ alkylidene group (e.g., methylidene (=CH$_2$)) optionally substituted by 5- or 6-membered monocyclic aromatic heterocyclic group(s) (e.g., pyrrolyl (1H-pyrrolyl)) optionally substituted by 1 to 3 substituents selected from (i) a $C_{1-6}$ alkyl group (e.g., methyl), and
(ii) a halogenated boryl group (e.g., difluoroboryl),
(3) a 5- or 6-membered monocyclic aromatic heterocyclic group (e.g., isoxazolyl, furyl, pyridyl, imidazolyl (1H-imidazolyl), pyrazolyl, thienyl, triazolyl (1,2,4-triazolyl), oxazolyl, thiazolyl, oxadiazolyl (1,3,4-oxadiazolyl)) optionally substituted by 1 to 3 substituents selected from
(a) a hydroxy group,
(b) a cyano group,
(c) a carboxy group,
(d) a halogen atom (e.g., a fluorine atom, a bromine atom),
(e) a $C_{1-6}$ alkyl group (e.g., methyl) optionally substituted by 1 to 3 hydroxy groups,
(f) a $C_{1-6}$ alkoxy group (e.g., methoxy),
(g) a $C_{1-6}$ alkoxy-carbonyl group (e.g., methoxycarbonyl), and
(h) an amino group optionally mono- or di-substituted by $C_{1-6}$ alkyl-carbonyl group(s) (e.g., acetyl),
(4) a $C_{3-10}$ cycloalkyl group (e.g., cyclopropyl, cyclobutyl, cyclopentyl, cyclohexyl) optionally substituted by 1 to 3 substituents selected from
(a) a halogen atom (e.g., a fluorine atom),
(b) a hydroxy group,
(c) an oxo group,
(d) a cyano group,
(e) a carboxy group, and
(f) a $C_{1-6}$ alkyl group (e.g., methyl) optionally substituted by 1 to 3 hydroxy groups,
(5) a $C_{2-6}$ alkenyl group (e.g., allyl) optionally substituted by 1 to 3 substituents selected from
(a) a carbamoyl group, and
(b) a hydroxy group,
(6) a $C_{6-14}$ aryl group (e.g., phenyl) optionally substituted by 1 to 3 hydroxy groups,
(7) a 9- to 14-membered fused polycyclic (preferably bi- or tri-cyclic) non-aromatic heterocyclic group (e.g., indolinyl, dihydrobenzoxadinyl (2,3-dihydro-1,4-benzoxadinyl), tetrahydroquinolyl (e.g., 1,2,3,4-tetrahydroquinolyl)) optionally substituted by 1 to 3 oxo groups,
(8) a 8- to 14-membered fused polycyclic (preferably bi- or tri-cyclic) aromatic heterocyclic group (e.g., pyrrolopyridyl (pyrrolo[2,3-b]pyridyl), pyrazolopyridyl (1H-pyrazolo[3,4-b]pyridyl)),
(9) a $C_{1-12}$ alkoxy-carbonyl group (e.g., ethoxycarbonyl),
(10) a 5- to 14-membered spiro heterocyclic group (e.g., 2-oxa-6-azaspiro[3.5]nonyl, 2-oxa-6-azaspiro[3.4]octyl),
(11) a 3- to 8-membered monocyclic non-aromatic heterocyclyloxy group (e.g., oxetanyloxy), or
(12) an amino group optionally mono- or di-substituted by substituent(s) selected from
(a) a $C_{1-6}$ alkyl group (e.g., ethyl, isobutyl) optionally substituted by 1 to 3 hydroxy groups, and
(b) a 5- or 6-membered monocyclic aromatic heterocyclic group (e.g., pyridazinyl),
or a salt thereof.

[Compound A-4]

A compound wherein

Ring A is a 6-membered aromatic ring (preferably a benzene ring) optionally further substituted by 1 to 3 substituents selected from
(1) a halogen atom (e.g., a fluorine atom, a chlorine atom), and
(2) a cyano group;

$R^1$ is
(1) a group represented by the formula: $-Q(R^{1a})(R^{1b})(R^{1c})$
wherein
Q is a carbon atom, a silicon atom or a germanium atom, and
$R^{1a}$, $R^{1b}$ and $R^{1c}$ are each independently
(a) a $C_{1-6}$ alkyl group (e.g., methyl, ethyl) optionally substituted by 1 to 3 substituents selected from
(i) a halogen atom (e.g., a fluorine atom), and
(ii) a $C_{1-6}$ alkoxy group (e.g., methoxy),
(b) a hydroxy group, or
(c) a cyano group,
(2) a neopentyl group, or
(3) a trimethylsilylmethyl group;

$R^2$ is
(1) a group represented by the formula:

wherein
$R^5$ is
(A) a $C_{1-6}$ alkyl group (e.g., methyl, ethyl, isopropyl) optionally substituted by 1 to 3 substituents selected from
(a) a $C_{1-6}$ alkoxy group (e.g., methoxy, ethoxy, propoxy) optionally substituted by 1 to 3 substituents selected from
(i) a halogen atom (e.g., a fluorine atom), and
(ii) a $C_{1-6}$ alkoxy group (e.g., methoxy), and
(b) a hydroxy group, or
(B) a $C_{1-6}$ alkoxy group (e.g., methoxy, ethoxy, propoxy) optionally substituted by 1 to 3 $C_{1-6}$ alkoxy groups (e.g., methoxy), and
the benzene ring in the formula optionally has, besides $R^5$, additional 1 to 3 substituents selected from
(A) a $C_{1-6}$ alkyl group (e.g., methyl), and
(B) a $C_{1-6}$ alkoxy group (e.g., methoxy),
(2) a bicyclic fused heterocyclic group (e.g., dihydrobenzofuryl (2,3-dihydrobenzofuryl), indazolyl (1H-indazolyl, 2H-indazolyl), indolyl, indolinyl) optionally substituted by 1 to 3 $C_{1-6}$ alkyl groups (e.g., methyl), or
(3) a group represented by the formula $-L-Z^1$:
wherein
L is a bond; and
$Z^1$ is
(A) a $C_{3-10}$ cycloalkyl group (e.g., cyclohexyl) optionally substituted by 1 to 3 substituents selected from
(a) a halogen atom (e.g., a fluorine atom), and
(b) a hydroxy group, or
(B) a 3- to 8-membered monocyclic non-aromatic heterocyclic group (e.g., tetrahydropyranyl, piperidyl, 1,1-dioxidotetrahydrothiopyranyl) optionally substituted by $C_{1-6}$ alkyl group(s) (e.g., ethyl) optionally substituted by 1 to 3 halogen atoms (e.g., a fluorine atom);

$R^3$ is
(1) a hydrogen atom, or
(2) a $C_{1-6}$ alkyl group (e.g., methyl, ethyl) optionally substituted by 1 to 3 cyano groups; and $R^4$ is
(1) a $C_{1-6}$ alkyl group (e.g., methyl, ethyl, propyl, isopropyl, butyl, isobutyl, tert-butyl) optionally substituted by 1 to 7 substituents selected from
(a) a 3- to 8-membered monocyclic non-aromatic heterocyclic group (e.g., dihydropyrimidinyl (1,6-dihydropyrimidinyl), dihydropyridyl (1,2-dihydropyridyl, 1,4-dihydropyridyl), tetrahydropyrimidinyl (1,2,3,4- tetrahydropyrimidinyl), dihydropyridazinyl (1,4-dihydropyridazinyl, 2,3-dihydropyridazinyl), imidazolidinyl, tetrahydropyranyl, morpholinyl, piperidyl, dihydrooxadiazolyl (4,5-dihydro-1,2,4-oxadiazolyl), pyrrolidinyl, tetrahydrofuryl, piperazinyl, thiazolidinyl, oxazolidinyl, azetidinyl) optionally substituted by 1 to 3 substituents selected from
  (i) an oxo group,
  (ii) a $C_{1-6}$ alkyl group (e.g., methyl),
  (iii) a hydroxy group, and
  (iv) a cyano group,
(b) a 5- or 6-membered monocyclic aromatic heterocyclic group (e.g., oxadiazolyl (1,3,4-oxadiazolyl), isoxazolyl, pyrazolyl, pyridyl, imidazolyl (1H-imidazolyl), thienyl, tetrazolyl (1H-tetrazolyl)) optionally substituted by 1 to 3 substituents selected from
  (i) a $C_{1-6}$ alkyl group (e.g., methyl, ethyl) optionally substituted by 1 to 3 substituents selected from a halogen atom (e.g., a fluorine atom) and a $C_{6-14}$ aryl group (e.g., phenyl),
  (ii) a hydroxy group, and
  (iii) a $C_{1-6}$ alkoxy group (e.g., methoxy) optionally substituted by 1 to 3 $C_{6-14}$ aryl groups (e.g., phenyl),
(c) a 8- to 14-membered fused polycyclic (preferably bi- or tri-cyclic) aromatic heterocyclic group (e.g., indazolyl (1H-indazolyl), benzisoxazolyl (benzo[d]isoxazolyl), benzimidazolyl (1H-benzimidazolyl)),
(d) a 9- to 14-membered fused polycyclic (preferably bi- or tri-cyclic) non-aromatic heterocyclic group (e.g., dihydrobenzoxazolyl(2,3-dihydrobenzoxazolyl)) optionally substituted by 1 to 3 oxo groups,
(e) a halogen atom (e.g., a fluorine atom),
(f) a hydroxy group,
(g) a cyano group,
(h) a carboxy group,
(i) a carbamoyl group,
(j) a $C_{1-6}$ alkylsulfonyl group (e.g., methylsulfonyl),
(k) a $C_{3-10}$ cycloalkyl group (e.g., cyclopentyl) optionally substituted by 1 to 3 substituents selected from
  (i) a hydroxy group, and
  (ii) a cyano group,
(l) an amino group optionally mono- or di-substituted by substituent(s) selected from
  (i) a $C_{1-6}$ alkyl group (e.g., methyl),
  (ii) a $C_{1-6}$ alkyl-carbonyl group (e.g., acetyl), and
  (iii) a $C_{1-6}$ alkoxy-carbonyl group (e.g., tert-butoxycarbonyl),
(m) an imino group optionally substituted by a hydroxy group, and
(n) a 5- or 6-membered monocyclic aromatic heterocyclyloxy group (e.g., pyrazolyloxy) optionally substituted by 1 to 3 $C_{1-6}$ alkyl groups (e.g., methyl),
(2) a 3- to 8-membered monocyclic non-aromatic heterocyclic group (e.g., pyrrolidinyl, oxazolidinyl, azetidinyl, piperidyl, tetrahydropyranyl, tetrahydrothiopyranyl, 1,1-dioxidotetrahydrothiopyranyl, 1-oxidotetrahydrothiopyranyl, imidazolidinyl, tetrahydrofuryl, 1,1-dioxidotetrahydrothienyl, morpholinyl, dihydrooxazolyl (2,3-dihydrooxazolyl), dihydrothiazolyl (2,3-dihydrothiazolyl), piperazinyl, dihydrooxadiazolyl (4,5-dihydro-1,2,4-oxadiazolyl), pyrrolyl (2H-pyrrolyl)) optionally substituted by 1 to 3 substituents selected from
  (a) an oxo group,
  (b) a hydroxy group,
  (c) a cyano group,
  (d) a halogen atom (e.g., a fluorine atom),
  (e) a $C_{1-6}$ alkyl group (e.g., methyl) optionally substituted by 1 to 3 hydroxy groups,
  (f) a $C_{1-6}$ alkoxy group (e.g., methoxy) optionally substituted by 1 to 3 $C_{6-14}$ aryl groups (e.g., phenyl),
  (g) a $C_{1-6}$ alkyl-carbonyl group (e.g., acetyl), and
  (h) a $C_{1-4}$ alkylidene group (e.g., methylidene (=$CH_2$)) optionally substituted by 5- or 6-membered monocyclic aromatic heterocyclic group(s) (e.g., pyrrolyl (1H-pyrrolyl)) optionally substituted by 1 to 3 substituents selected from
    (i) a $C_{1-6}$ alkyl group (e.g., methyl), and
    (ii) a halogenated boryl group (e.g., difluoroboryl),
(3) a 5- or 6-membered monocyclic aromatic heterocyclic group (e.g., isoxazolyl, furyl, pyridyl, imidazolyl (1H-imidazolyl), pyrazolyl, thienyl, triazolyl (1,2,4-triazolyl), oxazolyl, thiazolyl, oxadiazolyl (1,3,4-oxadiazolyl)) optionally substituted by 1 to 3 substituents selected from
  (a) a hydroxy group,
  (b) a cyano group,
  (c) a carboxy group,
  (d) a halogen atom (e.g., a fluorine atom, a bromine atom),
  (e) a $C_{1-4}$ alkyl group (e.g., methyl) optionally substituted by 1 to 3 hydroxy groups,
  (f) a $C_{1-6}$ alkoxy group (e.g., methoxy),
  (g) a $C_{1-6}$ alkoxy-carbonyl group (e.g., methoxycarbonyl), and
  (h) an amino group optionally mono- or di-substituted by $C_{1-6}$ alkyl-carbonyl group(s) (e.g., acetyl),
(4) a $C_{3-10}$ cycloalkyl group (e.g., cyclopropyl, cyclobutyl, cyclopentyl, cyclohexyl) optionally substituted by 1 to 3 substituents selected from
  (a) a halogen atom (e.g., a fluorine atom),
  (b) a hydroxy group,
  (c) an oxo group,
  (d) a cyano group,
  (e) a carboxy group, and
  (f) a $C_{1-6}$ alkyl group (e.g., methyl) optionally substituted by 1 to 3 hydroxy groups,
(5) a $C_{2-6}$ alkenyl group (e.g., allyl) optionally substituted by 1 to 3 substituents selected from
  (a) a carbamoyl group, and
  (b) a hydroxy group,
(6) a $C_{6-14}$ aryl group (e.g., phenyl) optionally substituted by 1 to 3 hydroxy groups,
(7) a 9- to 14-membered fused polycyclic (preferably bi- or tri-cyclic) non-aromatic heterocyclic group (e.g., indolinyl, dihydrobenzoxadinyl (2,3-dihydro-1,4-benzoxadinyl), tetrahydroquinolyl (e.g., 1,2,3,4-tetrahydroquinolyl)) so optionally substituted by 1 to 3 oxo groups,
(8) a 8- to 14-membered fused polycyclic (preferably bi- or tri-cyclic) aromatic heterocyclic group (e.g., pyrrolopyridyl (pyrrolo[2,3-b]pyridyl), pyrazolopyridyl (1H-pyrazolo[3,4-b]pyridyl)),
(9) a $C_{1-6}$ alkoxy-carbonyl group (e.g., ethoxycarbonyl),
(10) a 5- to 14-membered spiro heterocyclic group (e.g., 2-oxa-6-azaspiro[3.5]nonyl, 2-oxa-6-azaspiro[3.4]octyl),
(11) a 3- to 8-membered monocyclic non-aromatic heterocyclyloxy group (e.g., oxetanyloxy), or
(12) an amino group optionally mono- or di-substituted by substituent(s) selected from
  (a) a $C_{1-6}$ alkyl group (e.g., ethyl, isobutyl) optionally substituted by 1 to 3 hydroxy groups, and
  (b) a 5- or 6-membered monocyclic aromatic heterocyclic group (e.g., pyridazinyl); or
when $R^3$ is a substituent, $R^3$ and $R^4$ in combination form, together with the nitrogen atom adjacent to $R^3$ and the carbon atom adjacent to $R^4$, a 3- to 14-membered non-aromatic heterocycle (containing a spiro ring) (e.g., pyrrolidine, 2,7-diazaspiro[4.4]nonane) substituted by one oxo group and optionally further substituted by 1 to 3 oxo groups, or a salt thereof.

[Compound A-5]

A compound wherein

Ring A is a 6-membered aromatic ring (preferably a benzene ring) optionally further substituted by 1 to 3 substituents selected from
(1) a halogen atom (e.g., a fluorine atom, a chlorine atom), and
(2) a cyano group;

$R^1$ is
(1) a group represented by the formula: $-Q(R^{1a})(R^{1b})(R^{1c})$
wherein
Q is a carbon atom, a silicon atom or a germanium atom, and
$R^{1a}$, $R^{1b}$ and $R^{1c}$ are each independently
(a) a $C_{1-6}$ alkyl group (e.g., methyl, ethyl) optionally substituted by 1 to 3 halogen atoms (e.g., a fluorine atom),
(b) a hydroxy group,
(c) a $C_{6-14}$ aryl group (e.g., phenyl),
(d) a $C_{3-10}$ cycloalkyl group (e.g., cyclopropyl),
(e) a cyano group,
(f) a carbamoyl group optionally mono- or di-substituted by $C_{3-10}$ cycloalkyl group(s) (e.g., cyclopropyl), or
(g) a 3- to 8-membered monocyclic non-aromatic heterocyclylcarbonyl group (e.g., pyrrolidinylcarbonyl), or
$R^{1a}$ and $R^{1b}$ in combination form, together with the adjacent Q, a $C_{3-10}$ cycloalkane ring (e.g., cyclopentane),
(2) a neopentyl group, or
(3) a trimethylsilylmethyl group;

$R^2$ is
(1) a group represented by the formula:

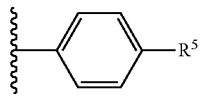

wherein
$R^5$ is
(A) a $C_{1-6}$ alkyl group (e.g., methyl, ethyl, isopropyl) optionally substituted by 1 to 3 substituents selected from
(a) a $C_{1-6}$ alkoxy group (e.g., methoxy, ethoxy, propoxy) optionally substituted by 1 to 3 substituents selected from
(i) a halogen atom (e.g., a fluorine atom), and
(ii) a $C_{1-6}$ alkoxy group (e.g., methoxy), and
(b) a hydroxy group, or
(B) a $C_{1-6}$ alkoxy group (e.g., methoxy, ethoxy, propoxy) optionally substituted by 1 to 3 $C_{1-6}$ alkoxy groups (e.g., methoxy), and
the benzene ring in the formula optionally has, besides $R^5$, additional 1 to 3 substituents selected from
(A) a $C_{1-6}$ alkyl group (e.g., methyl), and
(B) a $C_{1-6}$ alkoxy group (e.g., methoxy),
(2) a bicyclic fused heterocyclic group (e.g., dihydrobenzofuryl (2,3-dihydrobenzofuryl), indazolyl (1H-indazolyl, 2H-indazolyl), indolyl, indolinyl) optionally substituted by 1 to 3 $C_{1-6}$ alkyl groups (e.g., methyl), or
(3) a group represented by the formula $-L-Z^1$:
wherein
L is a bond; and
$Z^1$ is
(A) a $C_{3-10}$ cycloalkyl group (e.g., cyclohexyl) optionally substituted by 1 to 3 substituents selected from
(a) a halogen atom (e.g., a fluorine atom), and
(b) a hydroxy group, or
(B) a 3- to 8-membered monocyclic non-aromatic heterocyclic group (e.g., tetrahydropyranyl, piperidyl, 1,1-dioxidotetrahydrothiopyranyl) optionally substituted by $C_{1-6}$ alkyl group(s) (e.g., ethyl) optionally substituted by 1 to 3 halogen atoms (e.g., a fluorine atom);

$R^3$ is
(1) a hydrogen atom, or
(2) a $C_{1-6}$ alkyl group (e.g., methyl, ethyl) optionally substituted by 1 to 3 cyano groups; and $R^4$ is
(1) a $C_{1-6}$ alkyl group (e.g., methyl, ethyl, propyl, isopropyl, butyl, isobutyl, tert-butyl) optionally substituted by 1 to 7 substituents selected from
(a) a 3- to 8-membered monocyclic non-aromatic heterocyclic group (e.g., dihydropyrimidinyl (1,6-dihydropyrimidinyl), dihydropyridyl (1,2-dihydropyridyl, 1,4-dihydropyridyl), tetrahydropyrimidinyl (1,2,3,4-tetrahydropyrimidinyl), dihydropyridazinyl (1,4-dihydropyridazinyl, 2,3-dihydropyridazinyl), imidazolidinyl, tetrahydropyranyl, morpholinyl, piperidyl, dihydrooxadiazolyl (4,5-dihydro-1,2,4-oxadiazolyl), pyrrolidinyl, tetrahydrofuryl, piperazinyl, thiazolidinyl, oxazolidinyl, azetidinyl) optionally substituted by 1 to 3 substituents selected from
(i) an oxo group,
(ii) a $C_{1-6}$ alkyl group (e.g., methyl),
(iii) a hydroxy group, and
(iv) a cyano group,
(b) a 5- or 6-membered monocyclic aromatic heterocyclic group (e.g., oxadiazolyl (1,3,4-oxadiazolyl), isoxazolyl, pyrazolyl, pyridyl, imidazolyl (1H-imidazolyl), thienyl, tetrazolyl (1H-tetrazolyl)) optionally substituted by 1 to 3 substituents selected from
(i) a $C_{1-6}$ alkyl group (e.g., methyl, ethyl) optionally substituted by 1 to 3 substituents selected from a halogen atom (e.g., a fluorine atom) and a $C_{6-14}$ aryl group (e.g., phenyl),
(ii) a hydroxy group, and
(iii) a $C_{1-6}$ alkoxy group (e.g., methoxy) optionally substituted by 1 to 3 $C_{6-14}$ aryl groups (e.g., phenyl),
(c) a 8- to 14-membered fused polycyclic (preferably bi- or tri-cyclic) aromatic heterocyclic group (e.g., indazolyl (1H-indazolyl), benzisoxazolyl (benzo[d]isoxazolyl), benzimidazolyl (1H-benzimidazolyl)),
(d) a 9- to 14-membered fused polycyclic (preferably bi- or tri-cyclic) non-aromatic heterocyclic group (e.g., dihydrobenzoxazolyl(2,3-dihydrobenzoxazolyl)) optionally substituted by 1 to 3 oxo groups,
(e) a halogen atom (e.g., a fluorine atom),
(f) a hydroxy group,
(g) a cyano group,
(h) a carboxy group,
(i) a carbamoyl group,
(j) a $C_{1-6}$ alkylsulfonyl group (e.g., methylsulfonyl),
(k) a $C_{3-10}$ cycloalkyl group (e.g., cyclopentyl) optionally substituted by 1 to 3 substituents selected from
(i) a hydroxy group, and
(ii) a cyano group,
(l) an amino group optionally mono- or di-substituted by substituent(s) selected from
(i) a $C_{1-6}$ alkyl group (e.g., methyl), (ii) a $C_{1-6}$ alkyl-carbonyl group (e.g., acetyl), and
(iii) a $C_{1-6}$ alkoxy-carbonyl group (e.g., tert-butoxycarbonyl),
(m) an imino group optionally substituted by a hydroxy group, and
(n) a 5- or 6-membered monocyclic aromatic heterocyclyloxy group (e.g., pyrazolyloxy) optionally substituted by 1 to 3 $C_{1-6}$ alkyl groups (e.g., methyl),
(2) a 3- to 8-membered monocyclic non-aromatic heterocyclic group (e.g., pyrrolidinyl, oxazolidinyl, azetidinyl, piperidyl, tetrahydropyranyl, tetrahydrothiopyranyl, 1,1-dioxidotetrahydrothiopyranyl, 1-oxidotetrahydrothiopyranyl, imidazolidinyl, tetrahydrofuryl, 1,1-dioxidotetrahydrothienyl, morpholinyl, dihydrooxazolyl (2,3-dihydrooxazolyl), dihydrothiazolyl (2,3-dihydrothiazolyl), piperazinyl, dihydrooxadiazolyl (4,5-dihydro-1,2,4-oxadiazolyl)) optionally substituted by 1 to 3 substituents selected from
(a) an oxo group,
(b) a hydroxy group,
(c) a cyano group,
(d) a halogen atom (e.g., a fluorine atom),
(e) a $C_{1-6}$ alkyl group (e.g., methyl) optionally substituted by 1 to 3 hydroxy groups,
(f) a $C_{1-6}$ alkoxy group (e.g., methoxy) optionally substituted by 1 to 3 $C_{6-14}$ aryl groups (e.g., phenyl), and
(g) a $C_{1-6}$ alkyl-carbonyl group (e.g., acetyl),
(3) a 5- or 6-membered monocyclic aromatic heterocyclic group (e.g., isoxazolyl, furyl, pyridyl, imidazolyl (1H-imidazolyl), pyrazolyl, thienyl, triazolyl (1,2,4-triazolyl), oxazolyl, thiazolyl, oxadiazolyl (1,3,4-oxadiazolyl)) optionally substituted by 1 to 3 substituents selected from
(a) a hydroxy group,
(b) a cyano group,
(c) a carboxy group,
(d) a halogen atom (e.g., a fluorine atom, a bromine atom),
(e) a $C_{1-6}$ alkyl group (e.g., methyl) optionally substituted by 1 to 3 hydroxy groups,
(f) a $C_{1-6}$ alkoxy group (e.g., methoxy),
(g) a $C_{1-6}$ alkoxy-carbonyl group (e.g., methoxycarbonyl), and
(h) an amino group optionally mono- or di-substituted by $C_{1-6}$ alkyl-carbonyl group(s) (e.g., acetyl),
(4) a $C_{3-10}$ cycloalkyl group (e.g., cyclopropyl, cyclobutyl, cyclopentyl, cyclohexyl) optionally substituted by 1 to 3 substituents selected from
(a) a halogen atom (e.g., a fluorine atom),
(b) a hydroxy group,
(c) an oxo group,
(d) a cyano group,
(e) a carboxy group, and
(f) a $C_{1-6}$ alkyl group (e.g., methyl) optionally substituted by 1 to 3 hydroxy groups,
(5) a $C_{2-6}$ alkenyl group (e.g., allyl) optionally substituted by 1 to 3 substituents selected from
(a) a carbamoyl group, and
(b) a hydroxy group,
(6) a $C_{6-14}$ aryl group (e.g., phenyl) optionally substituted by 1 to 3 hydroxy groups,
(7) a 9- to 14-membered fused polycyclic (preferably bi- or tri-cyclic) non-aromatic heterocyclic group (e.g., indolinyl, dihydrobenzoxadinyl (2,3-dihydro-1,4-benzoxadinyl), tetrahydroquinolyl (e.g., 1,2,3,4-tetrahydroquinolyl)) optionally substituted by 1 to 3 oxo groups, (8) a 8- to 14-membered fused polycyclic (preferably bi- or tri-cyclic) aromatic heterocyclic group (e.g., pyrrolopyridyl (pyrrolo[2,3-b]pyridyl), pyrazolopyridyl (1H-pyrazolo[3,4-b]pyridyl)),
(9) a $C_{1-6}$ alkoxy-carbonyl group (e.g., ethoxycarbonyl),
(10) a 5- to 14-membered spiro heterocyclic group (e.g., 2-oxa-6-azaspiro[3.5]nonyl, 2-oxa-6-azaspiro[3.4]octyl),
(11) a 3- to 8-membered monocyclic non-aromatic heterocyclyloxy group (e.g., oxetanyloxy),
(12) a $C_{1-4}$ alkoxy group (e.g., methoxy, ethoxy) optionally substituted by 1 to 3 substituents selected from
(a) a $C_{6-14}$ aryl group (e.g., phenyl), and
(b) a 3- to 8-membered monocyclic non-aromatic heterocyclic group (e.g., oxetanyl), or
(13) an amino group optionally mono- or di-substituted by substituent(s) selected from
(a) a $C_{1-6}$ alkyl group (e.g., ethyl, isobutyl) optionally substituted by 1 to 3 hydroxy groups, and
(b) a 5- or 6-membered monocyclic aromatic heterocyclic group (e.g., pyridazinyl), or
when $R^3$ is a substituent, $R^3$ and $R^4$ in combination form, together with the nitrogen atom adjacent to $R^3$ and the carbon atom adjacent to $R^4$, a 3- to 14-membered non-aromatic heterocycle (e.g., pyrrolidine, 2,7-diazaspiro[4.4]nonane) substituted by one oxo group and optionally further substituted by 1 to 3 oxo groups,
or a salt thereof.
[Compound B-1]
A compound wherein
Ring A is a benzene ring optionally further substituted by 1 to 3 substituents selected from
(1) a halogen atom (e.g., a fluorine atom, a chlorine atom), and
(2) a cyano group;
$R^1$ is
(1) a group represented by the formula: -Q($R^{1a}$)($R^{1b}$)($R^{1c}$) wherein
Q is a carbon atom or a silicon atom, and
$R^{1a}$, $R^{1b}$ and $R^{1c}$ are each independently a $C_{1-6}$ alkyl group (e.g., methyl), or
(2) a neopentyl group;
$R^1$ is
(1) a group represented by the formula:

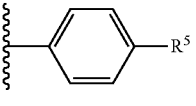

wherein
$R^5$ is
(A) a $C_{1-6}$ alkyl group (e.g., methyl) optionally substituted by 1 to 3 $C_{1-6}$ alkoxy groups (e.g., methoxy), or
(B) a $C_{1-6}$ alkoxy group (e.g., methoxy),
(2) a bicyclic fused heterocyclic group (e.g., dihydrobenzofuryl (2,3-dihydrobenzofuryl), indazolyl (1H-indazolyl)) optionally substituted by 1 to 3 $C_{1-6}$ alkyl groups (e.g., methyl), or
(3) a group represented by the formula -L-$Z^1$:
wherein
L is a bond; and
$Z^1$ is
(A) a $C_{3-10}$ cycloalkyl group (e.g., cyclohexyl) optionally substituted by 1 to 3 halogen atoms (e.g., a fluorine atom), or (B) a 3- to 8-membered monocyclic non-aromatic heterocyclic group (e.g., tetrahydropyranyl);
$R^3$ is
(1) a hydrogen atom, or
(2) a $C_{1-6}$ alkyl group (e.g., methyl); and
$R^4$ is
(1) a $C_{1-6}$ alkyl group (e.g., methyl, ethyl, propyl, isobutyl) optionally substituted by 1 to 7 substituents selected from
  (a) a 3- to 8-membered monocyclic non-aromatic heterocyclic group (e.g., dihydropyrimidinyl (1,6-dihydropyrimidinyl), dihydropyridyl (1,2-dihydropyridyl, 1,4-dihydropyridyl), dihydropyridazinyl (1,4-dihydropyridazinyl, 2,3-dihydropyridazinyl), imidazolidinyl, tetrahydropyranyl, morpholinyl, piperidyl, tetrahydropyrimidinyl (1,2,3,4-tetrahydropyrimidinyl)) optionally substituted by 1 to 3 substituents selected from
    (i) an oxo group, and
    (ii) a $C_{1-6}$ alkyl group (e.g., methyl),
  (b) a 5- or 6-membered monocyclic aromatic heterocyclic group (e.g., oxadiazolyl (1,3,4-oxadiazolyl), isoxazolyl, pyrazolyl) optionally substituted by 1 to 3 substituents selected from
    (i) a $C_{1-6}$ alkyl group (e.g., methyl), and
    (ii) a hydroxy group,
  (c) a 8- to 14-membered fused polycyclic (preferably bi- or tri-cyclic) aromatic heterocyclic group (e.g., indazolyl (1H-indazolyl), benzimidazolyl (1H-benzimidazolyl)),
  (d) a halogen atom (e.g., a fluorine atom),
  (e) a hydroxy group,
  (f) a cyano group,
  (g) a carboxy group,
  (h) a $C_{1-6}$ alkylsulfonyl group (e.g., methylsulfonyl), and
  (i) an amino group optionally mono- or di-substituted by $C_{1-6}$ alkyl-carbonyl group(s) (e.g., acetyl),
(2) a 3- to 8-membered monocyclic non-aromatic heterocyclic group (e.g., pyrrolidinyl, oxazolidinyl, azetidinyl, piperidyl, tetrahydropyranyl) optionally substituted by 1 to 3 substituents selected from
  (a) an oxo group,
  (b) a hydroxy group,
  (c) a halogen atom (e.g., a fluorine atom), and
  (d) a $C_{1-6}$ alkyl-carbonyl group (e.g., acetyl),
(3) a 5- or 6-membered monocyclic aromatic heterocyclic group (e.g., isoxazolyl) optionally substituted by 1 to 3 hydroxy groups,
(4) a $C_{3-10}$ cycloalkyl group (e.g., cyclopropyl, cyclobutyl) optionally substituted by 1 to 3 halogen atoms (e.g., a fluorine atom), or
(5) an amino group optionally mono- or di-substituted by $C_{1-6}$ alkyl group(s) (e.g., ethyl),
or a salt thereof.
[Compound B-2]
A compound wherein
Ring A is a benzene ring optionally further substituted by 1 to 3 substituents selected from
  (1) a halogen atom (e.g., a fluorine atom, a chlorine atom), and
  (2) a cyano group;
$R^1$ is
(1) a group represented by the formula: $-Q(R^{1a})(R^{1b})(R^{1c})$ wherein
Q is a carbon atom or a silicon atom, and
$R^{1a}$, $R^{1b}$ and $R^{1c}$ are each independently a $C_{1-6}$ alkyl group (e.g., methyl), or
(2) a neopentyl group;
$R^2$ is
(1) a group represented by the formula:

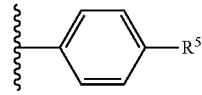

wherein
$R^3$ is
  (A) a $C_{1-6}$ alkyl group (e.g., methyl) optionally substituted by 1 to 3 $C_{1-6}$ alkoxy groups (e.g., methoxy), or
  (B) a $C_{1-6}$ alkoxy group (e.g., methoxy),
(2) a bicyclic fused heterocyclic group (e.g., dihydrobenzofuryl (2,3-dihydrobenzofuryl), indazolyl (1H-indazolyl)) optionally substituted by 1 to 3 $C_{1-6}$ alkyl groups (e.g., methyl), or
(3) a group represented by the formula $-L-Z^1$:
wherein
L is a bond; and
$Z^1$ is
  (A) a $C_{3-10}$ cycloalkyl group (e.g., cyclohexyl) optionally substituted by 1 to 3 halogen atoms (e.g., a fluorine atom), or
  (B) a 3- to 8-membered monocyclic non-aromatic heterocyclic group (e.g., tetrahydropyranyl);
$R^3$ is
(1) a hydrogen atom, or
(2) a $C_{1-6}$ alkyl group (e.g., methyl); and
$R^4$ is
(1) a $C_{1-6}$ alkyl group (e.g., methyl, ethyl, propyl, isobutyl) optionally substituted by 1 to 7 substituents selected from
  (a) a 3- to 8-membered monocyclic oxygen-containing non-aromatic heterocyclic group (e.g., tetrahydropyranyl),
  (b) a halogen atom (e.g., a fluorine atom),
  (c) a cyano group,
  (d) a carboxy group, and
  (e) a $C_{1-6}$ alkylsulfonyl group (e.g., methylsulfonyl),
(2) a 3- to 8-membered monocyclic non-aromatic heterocyclic group (e.g., pyrrolidinyl, oxazolidinyl, azetidinyl, piperidyl, tetrahydropyranyl) optionally substituted by 1 to 3 substituents selected from
  (a) an oxo group,
  (b) a hydroxy group,
  (c) a halogen atom (e.g., a fluorine atom), and
  (d) a $C_{1-6}$ alkyl-carbonyl group (e.g., acetyl),
(3) a 5- or 6-membered monocyclic aromatic heterocyclic group (e.g., isoxazolyl) optionally substituted by 1 to 3 hydroxy groups,
(4) a $C_{3-10}$ cycloalkyl group (e.g., cyclopropyl, cyclobutyl) optionally substituted by 1 to 3 halogen atoms (e.g., a fluorine atom), or
(5) an amino group optionally mono- or di-substituted by $C_{1-6}$ alkyl group(s) (e.g., ethyl),
or a salt thereof.
[Compound B-3]
A compound wherein
Ring A is a benzene ring optionally further substituted by 1 to 3 substituents selected from
  (1) a halogen atom (e.g., a fluorine atom, a chlorine atom), and
  (2) a cyano group;

R¹ is
(1) a group represented by the formula: -Q(R¹ᵃ)(R¹ᵇ)(R¹ᶜ)
wherein
Q is a carbon atom or a silicon atom, and
R¹ᵃ, R¹ᵇ and R¹ᶜ are each independently a $C_{1-6}$ alkyl group (e.g., methyl), or
(2) a neopentyl group;
R² is
(1) a group represented by the formula:

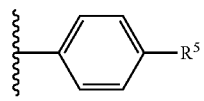

wherein
R⁵ is
(A) a $C_{1-6}$ alkyl group (e.g., methyl) optionally substituted by 1 to 3 $C_{1-6}$ alkoxy groups (e.g., methoxy), or
(B) a $C_{1-6}$ alkoxy group (e.g., methoxy),
(2) a bicyclic fused heterocyclic group (e.g., dihydrobenzofuryl (2,3-dihydrobenzofuryl), indazolyl (1H-indazolyl)) optionally substituted by 1 to 3 $C_{1-6}$ alkyl groups (e.g., methyl), or
(3) a group represented by the formula -L-Z¹:
wherein
L is a bond; and
Z¹ is
(A) a $C_{3-10}$ cycloalkyl group (e.g., cyclohexyl) optionally substituted by 1 to 3 halogen atoms (e.g., a fluorine atom), or
(B) a 3- to 8-membered monocyclic non-aromatic heterocyclic group (e.g., tetrahydropyranyl);
R³ is
(1) a hydrogen atom, or
(2) a $C_{1-6}$ alkyl group (e.g., methyl); and
R⁴ is
(1) a $C_{1-12}$ alkyl group (e.g., methyl, ethyl, propyl, isobutyl) optionally substituted by 1 to 7 substituents selected from
  (a) a 3- to 8-membered monocyclic non-aromatic heterocyclic group not containing a nitrogen atom as a ring constituting atom (e.g., tetrahydropyranyl) optionally substituted by 1 to 3 substituents selected from
    (i) an oxo group, and
    (ii) a $C_{1-6}$ alkyl group (e.g., methyl),
  (b) a halogen atom (e.g., a fluorine atom),
  (c) a cyano group,
  (d) a carboxy group, and
  (e) a $C_{1-6}$ alkylsulfonyl group (e.g., methylsulfonyl),
(2) a 3- to 8-membered monocyclic non-aromatic heterocyclic group (e.g., pyrrolidinyl, oxazolidinyl, azetidinyl, piperidyl, tetrahydropyranyl) optionally substituted by 1 to 3 substituents selected from
  (a) an oxo group,
  (b) a hydroxy group,
  (c) a halogen atom (e.g., a fluorine atom), and
  (d) a $C_{1-6}$ alkyl-carbonyl group (e.g., acetyl),
(3) a 5- or 6-membered monocyclic aromatic heterocyclic group (e.g., isoxazolyl) optionally substituted by 1 to 3 hydroxy groups,
(4) a $C_{3-10}$ cycloalkyl group (e.g., cyclopropyl, cyclobutyl) optionally substituted by 1 to 3 halogen atoms (e.g., a fluorine atom), or
(5) an amino group optionally mono- or di-substituted by $C_{1-6}$ alkyl group(s) (e.g., ethyl),
or a salt thereof.

[Compound C-1]
A compound wherein
Ring A is a benzene ring optionally further substituted by 1 to 3 halogen atoms (e.g., a fluorine atom);
R¹ is a group represented by the formula: -Q(R¹ᵃ)(R¹ᵇ)(R¹ᶜ)
wherein
Q is a carbon atom or a silicon atom, and
R¹ᵃ, R¹ᵇ and R¹ᶜ are each independently a $C_{1-6}$ alkyl group (e.g., methyl);
R² is
(1) a group represented by the formula:

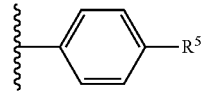

wherein
R⁵ is $C_{1-6}$ alkoxy group (e.g., methoxy),
(2) a bicyclic fused heterocyclic group (e.g., indazolyl (1H-indazolyl)) optionally substituted by 1 to 3 $C_{1-6}$ alkyl groups (e.g., methyl), or
(3) a group represented by the formula -L-Z¹:
wherein
L is a bond; and
Z¹ is a $C_{3-10}$ cycloalkyl group (e.g., cyclohexyl) optionally substituted by 1 to 3 halogen atoms (e.g., a fluorine atom);
R³ is
(1) a hydrogen atom, or
(2) a $C_{1-6}$ alkyl group (e.g., methyl); and
R⁴ is
(1) a $C_{1-6}$ alkyl group (e.g., methyl) optionally substituted by 5- or 6-membered monocyclic aromatic heterocyclic group(s) (e.g., isoxazolyl) optionally substituted by 1 to 3 hydroxy groups,
(2) a 3- to 8-membered monocyclic non-aromatic heterocyclic group (e.g., pyrrolidinyl) optionally substituted by 1 to 3 oxo groups, or
(3) a 5- or 6-membered monocyclic aromatic heterocyclic group (e.g., isoxazolyl) optionally substituted by 1 to 3 hydroxy groups,
or a salt thereof.

[Compound C-2]
A compound wherein
Ring A is a benzene ring optionally further substituted by 1 to 3 halogen atoms (e.g., a fluorine atom);
R¹ is a group represented by the formula: -Q(R¹ᵃ)(R¹ᵇ)(R¹ᶜ)
wherein
Q is a carbon atom or a silicon atom, and
R¹ᵃ, R¹ᵇ and R¹ᶜ are each independently a $C_{1-6}$ alkyl group (e.g., methyl);
R² is
(1) a group represented by the formula:

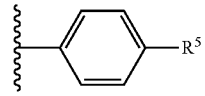

wherein
R⁵ is $C_{1-6}$ alkoxy group (e.g., methoxy),
(2) a bicyclic fused heterocyclic group (e.g., indazolyl (1H-indazolyl)) optionally substituted by 1 to 3 $C_{1-6}$ alkyl groups (e.g., methyl), or (3) a group represented by the formula -L-Z$^1$:
   wherein
   L is a bond; and
   Z$^1$ is a C$_{3-10}$ cycloalkyl group (e.g., cyclohexyl) optionally substituted by 1 to 3 halogen atoms (e.g., a fluorine atom);
R$^3$ is
(1) a hydrogen atom, or
(2) a C$_{1-6}$ alkyl group (e.g., methyl); and
R$^4$ is
(1) a 3- to 8-membered monocyclic non-aromatic heterocyclic group (e.g., pyrrolidinyl) optionally substituted by 1 to 3 oxo groups, or
(2) a 5- or 6-membered monocyclic aromatic heterocyclic group (e.g., isoxazolyl) optionally substituted by 1 to 3 hydroxy groups,
or a salt thereof.
[Compound D-1]
(3S)—N-((1R)-2-((4-tert-butyl-3-fluorophenyl)amino)-1-(4,4-difluorocyclohexyl)-2-oxoethyl)-5-oxopyrrolidine-3-carboxamide or a salt thereof.
[Compound D-2]
N-((1R)-2-((3,5-difluoro-4-(trimethylsilyl)phenyl)amino)-1-(4-methoxyphenyl)-2-oxoethyl)-3-hydroxy-N-methyl-1,2-oxazole-5-carboxamide or a salt thereof.
[Compound D-3]
(2R)—N-(4-tert-butyl-3,5-difluorophenyl)-2-(((3-hydroxy-1,2-oxazol-5-yl)acetyl)amino)-2-(1-methyl-1H-indazol-5-yl)acetamide or a salt thereof.

Specific Examples of the above-mentioned compound (I), compound (I') and compound (I") include the compounds of Examples 1 to 126, 128 to 154, 156 to 214, 216 to 253, 255 to 382, 384 to 402, 406, 407, 409 to 419 and 421 to 427.

Examples of salts of compound (I), compound (I') and compound (I") include metal salts, ammonium salts, salts with organic base, salts with inorganic acid, salts with organic acid, salts with basic or acidic amino acids, and the like. Preferable examples of the metal salt include alkaline metal salts such as sodium salt, potassium salt and the like; alkaline earth metal salts such as calcium salt, magnesium salt, barium salt and the like; aluminum salts, and the like. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salt with basic amino acid include salts with arginine, lysine, ornithine and the like. Preferable examples of the salt with acidic amino acid include salt with aspartic acid, glutamic acid and the like.

Among them, pharmaceutically acceptable salts are preferable. For example, if the compound has an acidic functional group therein, examples of the salt include inorganic salts such as alkaline metal salts (e.g., sodium salt, potassium salt and the like), alkaline earth metal salts (e.g., calcium salt, magnesium salt, barium salt and the like) and the like; ammonium salt, and the like. If the compound has a basic functional group therein, examples of the salt thereof include salts with inorganic acids such as hydrochloric acid, hydrobromic acid, nitric acid, sulfuric acid, phosphoric acid and the like, and salts with organic acids such as acetic acid, phthalic acid, fumaric acid, oxalic acid, tartaric acid, maleic acid, citric acid, succinic acid, methanesulfonic acid, p-toluenesulfonic acid and the like.

Next, The production methods of compound (I), compound (I') and compound (I") of the present invention are explained.

The intermediates produced in the following production methods may be isolated and purified according to methods such as column chromatography, recrystallization, distillation and the like, or may be directly used without isolation for the next step.

Compound (I), compound (I') and compound (I") of the present invention can be produced according to the following Method A. Compound (I), compound (I') and compound (I") wherein R$^3$ and R$^4$ in combination form, together with the nitrogen atom adjacent to R$^3$ and the carbon atom adjacent to R$^4$, an optionally substituted ring can be produced according to Step 3.

[Method A]

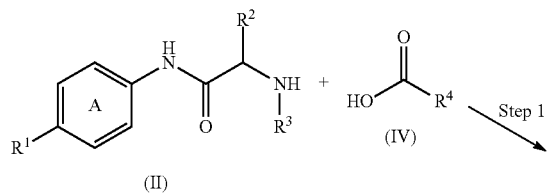

(II)         (IV)         Step 1

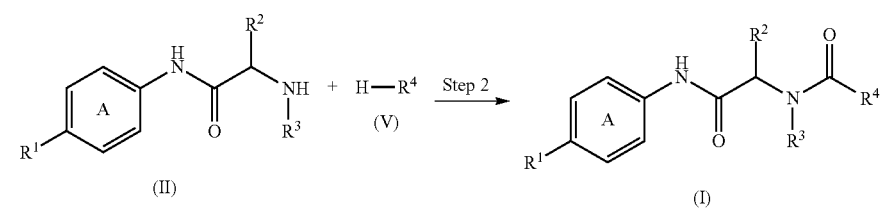

(II)         (V)         Step 2         (I)

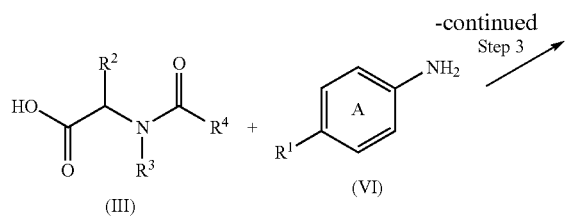

wherein each symbol is as defined above.
(Step 1)

This step is a step of subjecting compound (II) or a salt thereof to an acylation reaction to convert compound (II) or a salt thereof into compound (I), compound (I') or compound (I").

In the acylation reaction, compound (I), compound (I') or compound (I") can be produced by reacting compound (II) or a salt thereof with a compound represented by the formula:

(IV)

wherein symbol is as defined above (hereinafter to be referred to as compound (IV)) or a salt thereof.

Compound (IV) or a salt thereof may be a commercially available product, or can also be produced according to a method known per se or a method analogous thereto.

The acylation reaction can be carried out according to a method known per se, for example, the method described in Jikken Kagaku Kouza, 4th Edition, 1991, vol. 22, organic synthesis IV (the Chemical Society of Japan ed.) and the like, or a method analogous thereto. Examples of the method include a method using a condensing agent, a method via a reactive derivative, and the like.

Examples of the condensing agent to be used for the "method using a condensing agent" include (dimethylamino)-N,N-dimethyl(3H-[1,2,3]triazolo[4,5-b]pyridin-3-yloxy)methaneiminium hexafluorophosphorate (HATU), 1-[(1-(cyano-2-ethoxy-2-oxoethylideneaminooxy)-dimethylamino-morpholino)]carbenium hexafluorophosphorate (COMU), 2,4,6-tripropyl-1,3,5,2,4,6-trioxatriphosphorinane-2,4,6-trioxide (T3P), dicyclohexylcarbodiimide (DCC), diisopropylcarbodiimide (DIC), N-ethyl-N'-3-dimethylaminopropylcarbodiimide and a hydrochloride thereof (WSC, WSC.HCl, EDCI), benzotriazol-1-yl-tris(dimethylamino)phosphonium hexafluorophosphorate (BOP), diphenylphosphorylazide(DPPA) and the like. They can be used alone or in combination with an additive (e.g., N-hydroxysuccinimide, 1-hydroxybenzotriazole or 3-hydroxy-4-oxo-3,4-dihydro-1,2,3-benzotriazine, etc.). The amount of the condensing agent to be used is about 1 to 10 mol equivalent, preferably about 1 to 2 mol equivalent, per 1 mol of compound (II). The amount of the additive to be used is about 1 to 10 mol equivalent, preferably about 1 to 2 mol equivalent, per 1 mol of compound (II).

The above-mentioned reaction is generally carried out in a solvent that does not adversely influence the reaction, and a base may be added for the progress of the reaction. Examples of the solvent include hydrocarbons (benzene, toluene etc.), ethers (diethyl ether, dioxane, tetrahydrofuran etc.), esters (ethyl acetate etc.), halogenated hydrocarbons (chloroform, dichloromethane etc.), amides (N,N-dimethylformamide etc.), aromatic amines (pyridine etc.), water and the like, and they may be mixed as appropriate. Examples of the base include alkali metal hydroxides (sodium hydroxide, potassium hydroxide etc.), hydrogencarbonates (sodium hydrogencarbonate, potassium hydrogencarbonate etc.), carbonates (sodium carbonate, potassium carbonate etc.), acetates (sodium acetate etc.), tertiary amines (trimethylamine, triethylamine, N-methylmorpholine, diisopropylethylamine etc.), aromatic amines (pyridine, picoline, N,N-dimethylaniline, 4-dimethylaminopyridine etc.) and the like. The amount of the base to be used is generally about 1 to 100 mol equivalent, preferably about 1 to 5 mol equivalent, per 1 mol of compound (II). The reaction temperature is generally about −80 to 150° C., preferably about 0 to 50° C., and the reaction time is generally about 0.5 to 48 hr, preferably 0.5 to 16 hr.

Examples of the reactive derivative to be used for the "method via a reactive derivative" include a compound represented by the formula:

(IVa)

wherein LG is a leaving group, and the other symbols are as defined above (hereinafter to be referred to as compound (IVa)) or a salt thereof (e.g., acid halides, anhydrides, mixed anhydrides, activated esters etc.) and the like.

Examples of the leaving group represented by LG include halogen atoms (a chlorine atom, a bromine atom, an iodine atom etc.), substituted sulfonyloxy groups ($C_{1-6}$ alkylsulfonyloxy groups such as methanesulfonyloxy, ethanesulfonyloxy and the like; $C_{6-14}$ arylsulfonyloxy groups such as benzenesulfonyloxy, p-toluenesulfonyloxy and the like; $C_{7-16}$ aralkylsulfonyloxy groups such as benzylsulfonyloxy group and the like, etc.), acyloxy groups (acetoxy, benzoyloxy etc.), oxy groups substituted by a heterocyclic group or an aryl group (2,5-dioxo-1-pyrrolidinyl, benzotriazolyl, quinolyl, 4-nitrophenyl etc.), heterocyclic groups (imidazolyl etc.) and the like.

The conversion of compound (IV) into the reactive derivative (compound (IVa)) can be carried out according to a method known per se. For example, the conversion into the acid halide can be carried out by employing a method using an acid halide (e.g., thionyl chloride, oxalyl chloride, etc.), a method using a halide of phosphorus and phosphoric acid (e.g., phosphorus trichloride, phosphorus pentachloride, etc.), and the like. The method using a reactive derivative is generally carried out in a solvent that does not adversely influence the reaction, which varies depending on the kind of compound (IVa), and a base may be added for the progress of the reaction. The kind and amount of the solvent and base to be used for the reaction, the reaction temperature and the reaction time are the same as in the above-mentioned "method using a condensing agent".

(Step 2)

This step is a step of subjecting compound (II) or a salt thereof to an ureation reaction to convert compound (II) or a salt thereof into compound (I), compound (I') or compound (I").

In the ureation reaction, compound (I), compound (I') or compound (I") can be produced by reacting compound (II) or a salt thereof with the reactive intermediate (obtained by reacting a compound represented by the formula:

wherein symbol is as defined above (hereinafter to be referred to as compound (V)) or a salt thereof with a carbonylating agent), or by reacting the reactive intermediate (obtained by reacting compound (II) or a salt thereof with a carbonylating agent) with compound (V) or a salt thereof.

Compound (V) may be a commercially available product, or can also be produced according to a method known per se or a method analogous thereto.

Examples of the carbonylating agent to be used in this step include triphosgene, 4-nitrophenyl chloroformate or carbonyldiimidazole and the like. The amount of the carbonylating agent to be used is about 1 to 10 mol equivalent, preferably about 1 to 2 mol equivalent, per 1 mol of compound (II).

The above-mentioned reaction is generally carried out in a solvent that does not adversely influence the reaction, and a base may be added for the progress of the reaction. Examples of the solvent include hydrocarbons (benzene, toluene etc.), ethers (diethyl ether, dioxane, tetrahydrofuran etc.), esters (ethyl acetate etc.), halogenated hydrocarbons (chloroform, dichloromethane etc.), amides (N,N-dimethylformamide etc.) and the like, and they may be mixed as appropriate. Examples of the base include alkali metal hydroxides (sodium hydroxide, potassium hydroxide etc.), hydrogencarbonates (sodium hydrogencarbonate, potassium hydrogencarbonate etc.), carbonates (sodium carbonate, potassium carbonate etc.), acetates (sodium acetate etc.), tertiary amines (trimethylamine, triethylamine, N-methylmorpholine etc.), aromatic amines (pyridine, picoline, N,N-dimethylaniline etc.) and the like. The amount of the base to be used is generally about 1 to 100 mol equivalent, preferably about 1 to 5 mol equivalent, per 1 mol of compound (II). The reaction temperature is generally about −80 to 150° C., preferably about 0 to 50° C., and the reaction time is generally about 0.5 to 100 hr, preferably about 0.5 to 60 hr.

The reactive intermediate obtained by the reaction of compound (V) or a salt thereof with a carbonylating agent may be reacted with compound (II) or a salt thereof after isolation.

The reactive intermediate obtained by the reaction of compound (II) or a salt thereof with a carbonylating agent may be reacted with compound (V) or a salt thereof after isolation.

(Step 3)

This step is a step of reacting compound (III) or a salt thereof with a compound represented by the formula:

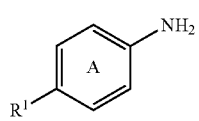

wherein each symbol is as defined above (hereinafter to be referred to as compound (VI)) or a salt thereof in the presence of a condensing agent to produce compound (I), compound (I') or compound (I").

Compound (VI) or a salt thereof may be a commercially available product, or can also be produced according to a method known per se, a method analogous thereto, or the below-mentioned method.

This step can be performed in the same manner as in the method described in Step 1 of Method A.

The raw materials used in Method A can be produced according to the following Methods B-I.

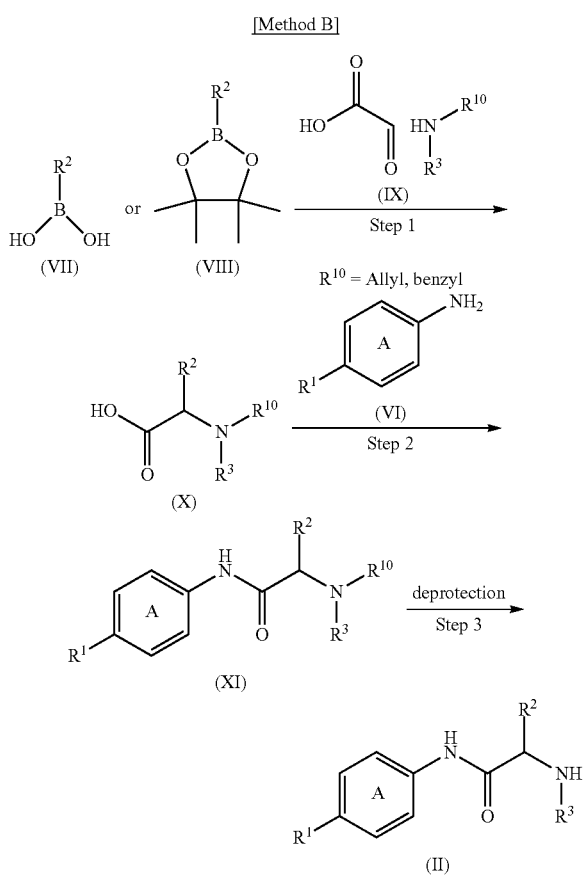

wherein $R^{16}$ is an allyl group or a benzyl group, and the other symbols are as defined above.

(Step 1)

This step is a step of reacting compound (VII) or a salt thereof or compound (VIII) or a salt thereof with glyoxylic acid and compound (IX) or a salt thereof to produce compound (X) or a salt thereof.

The compounds used for this reaction may be a commercially available product, or can also be produced according to a method known per se or a method analogous thereto.

The amount of the glyoxylic acid to be used is generally about 1 to 10 mol equivalent, preferably about 1 to 2 mol equivalent, per 1 mol of compound (VII) or compound (VIII).

The amount of compound (IX) to be used is generally about 1 to 10 mol equivalent, preferably about 1 to 2 mol equivalent, per 1 mol of compound (VII) or compound (VIII).

The above-mentioned reaction is generally carried out in a solvent that does not adversely influence the reaction. Examples of the solvent include nitriles (acetonitrile etc.), hydrocarbons (benzene, toluene etc.), ethers (diethyl ether, dioxane, tetrahydrofuran etc.), esters (ethyl acetate etc.), halogenated hydrocarbons (chloroform, dichloromethane etc.), amides (N,N-dimethylformamide etc.) and the like, and they may be mixed as appropriate. The reaction temperature is generally about −80 to 150° C., preferably about 0 to 10° C., and the reaction time is generally about 0.5 to 100 hr, preferably about 0.5 to 60 hr.
(Step 2)

This step is a step of reacting compound (X) or a salt thereof with compound (VI) or a salt thereof in the presence of a condensing agent to produce compound (XI) or a salt thereof.

This step can be performed in the same manner as in the method described in Step 1 of Method A.
(Step 3)

This step is a step of subjecting compound (XI) or a salt thereof to a deallylation reaction or a debenzylation reaction to produce compound (II) or a salt thereof.

The deallylation reaction is carried out by reacting compound (XI) or a salt thereof with thiosalicylic acid in the presence of $Pd_2(dba)_3$ and 1,4-bis(diphenylphosphino)butane, in a solvent that does not adversely influence the reaction, or by reacting compound (XI) or a salt thereof with 1,3-dimethylbarbituric acid in the presence of $Pd(PPh_3)_4$, in a solvent that does not adversely influence the reaction.

The amount of the $Pd_2(dba)_3$ to be used is generally about 0.01 to 1 mol equivalent, preferably about 0.05 to 0.2 mol equivalent, per 1 mol of compound (XI).

The amount of the 1,4-bis(diphenylphosphino)butane to be used is about 1 to 2 mol equivalent per 1 mol of $Pd_2(dba)_3$.

The amount of the $Pd(PPh_3)_4$ to be used is generally about 0.01 to 1 mol equivalent, preferably about 0.05 to 0.2 mol equivalent, per 1 mol of compound (XI).

The amount of the thiosalicylic acid or 1,3-dimethylbarbituric acid to be used is generally about 1 to 5 mol equivalent, preferably about 1 to 1.5 mol equivalent, per 1 mol of compound (XI).

Examples of the solvent that does not adversely influence the reaction include ethers (diethyl ether, dioxane, tetrahydrofuran etc.), nitriles (acetonitrile etc.), hydrocarbons (benzene, toluene etc.), esters (ethyl acetate etc.), halogenated hydrocarbons (chloroform, dichloromethane etc.), amides (N,N-dimethylformamide etc.) and the like, and they may be mixed as appropriate. The reaction temperature is generally about 0 to 150° C., preferably about 10 to 30° C., and the reaction time is generally about 0.5 to 100 hr, preferably about 0.5 to 60 hr.

The debenzylation reaction can be carried out in the presence of a palladium catalyst (e.g., palladium on carbon, palladium hydroxide, palladium oxide), in a solvent that does not adversely influence the reaction, under hydrogen atmosphere.

The amount of the palladium catalyst to be used is generally about 0.01 to 1 mol equivalent, preferably about 0.05 to 0.2 mol equivalent, per 1 mol of compound (XI).

Examples of the solvent that does not adversely influence the reaction include alcohols (methanol, ethanol, propanol, 2-propanol etc.), ethers (diethyl ether, dioxane, tetrahydrofuran etc.), nitriles (acetonitrile etc.), hydrocarbons (benzene, toluene etc.), esters (ethyl acetate etc.) and the like, and they may be mixed as appropriate. The hydrogen pressure for the reaction is generally about 1 to 50 atm, preferably about 1 to 10 atm. The reaction temperature is generally about 0 to 150° C., preferably about 10 to 30° C., and the reaction time is generally about 0.5 to 100 hr, preferably about 0.5 to 60 hr.

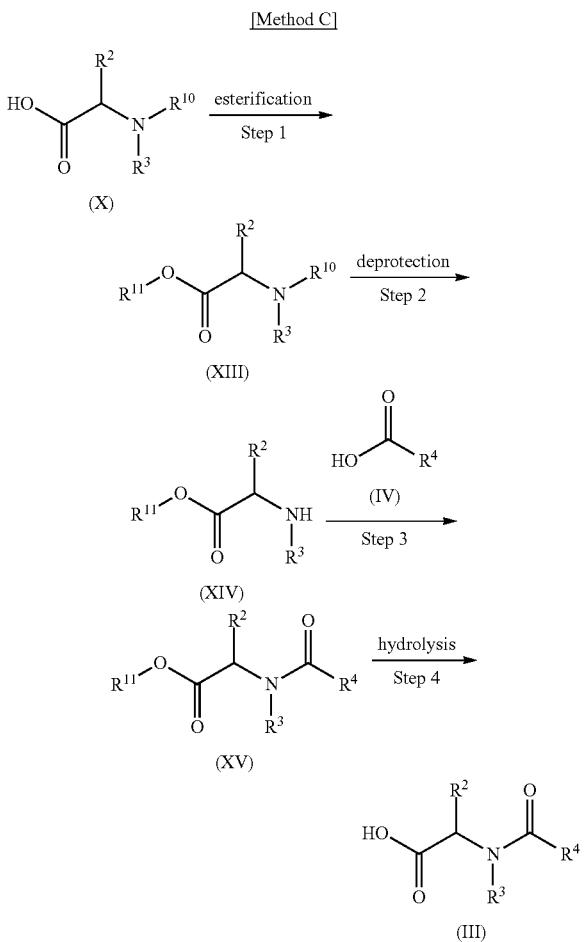

[Method C]

wherein $R^{11}$ is a hydrocarbon group optionally having substituent(s), and the other symbols are as defined above.
(Step 1) Hydrolysis This step is a step of subjecting compound (X) or a salt thereof to esterification to produce compound (XIII) or a salt thereof.

This reaction is a step of subjecting compound (X) or a salt thereof to a dehydration reaction with a compound represented by the formula:

$$R^{11}\text{—OH} \qquad (XII)$$

wherein symbol is as defined above (hereinafter to be referred to as compound (XII)) or a salt thereof in the presence of a acid catalyst to produce compound (XIII) or a salt thereof, or a step of subjecting compound (X) or a salt thereof to an alkylation reaction with a compound represented by the formula:

$$R^{11}\text{-LG} \qquad (XIIa)$$

wherein each symbol is as defined above (hereinafter to be referred to as compound (XIIa)) or a salt thereof in the presence of a base to produce compound (XIII) or a salt thereof.

Compound (XII) and compound (XIIa) may be a commercially available product, or can also be produced according to a method known per se or a method analogous thereto.

Examples of the acid catalyst used for the reaction of compound (X) or a salt thereof with compound (XII) include mineral acids (hydrochloric acid, sulfuric acid etc.), organic sulfonic acids (methanesulfonic acid, p-toluenesulfonic acid etc.), Lewis acids (boron fluoride etherate etc.), thionyl chloride and the like. While the amount of the acid catalyst to be used varies depending on the kind of the solvent and the other reaction condition, it is generally about 0.0001 to 10 mol equivalent, preferably about 0.01 to 0.1 mol equivalent, per 1 mol of compound (X).

The amount of compound (XII) to be used is generally about 1 to 1000 mol equivalent, preferably about 10 to 100 mol equivalent, per 1 mol of compound (X).

This step is carried out in a solvent that does not adversely influence the reaction. Examples of the solvent that does not adversely influence the reaction include aromatic hydrocarbons (benzene, toluene, xylene etc.), aliphatic hydrocarbons (hexane, heptane etc.), halogenated hydrocarbons (dichloromethane, chloroform etc.), ethers (diethyl ether, diisopropyl ether, t-butyl methyl ether, tetrahydrofuran, dioxane, dimethoxyethane etc.), nitriles (acetonitrile etc.), esters (ethyl acetate etc.) and the like. Compound (XII) may be used as a solvent.

The reaction temperature is, for example, within about 0 to 200° C., preferably about 25 to 100° C. While the reaction time varies depending on the kind of compound (X) or a salt thereof, the reaction temperature and the like, it is, for example, about 0.5 to 100 hr, preferably about 0.5 to 24 hr.

Examples of the base used for the reaction of compound (X) or a salt thereof with compound (XIIa) include inorganic bases (alkali metal hydrides such as sodium hydride, lithium hydride and the like, alkali metal hydroxides such as lithium hydroxide, sodium hydroxide, potassium hydroxide and the like, alkali metal hydrogencarbonates such as sodium hydrogencarbonate, potassium hydrogencarbonate and the like, alkali metal carbonates such lithium carbonate, sodium carbonate, potassium carbonate, cesium carbonate and the like, and the like. While the amount of the base to be used varies depending on the kind of the solvent and the other reaction condition, it is generally about 1 to 10 mol equivalent, preferably about 1 to 5 mol equivalent, per 1 mol of compound (X).

The amount of compound (XIIa) to be used is generally about 1 to 10 mol equivalent, preferably about 1 to 3 mol equivalent, per 1 mol of compound (X).

This step is carried out in a solvent that does not adversely influence the reaction. Examples of the solvent that does not adversely influence the reaction include aromatic hydrocarbons (benzene, toluene, xylene etc.), aliphatic hydrocarbons (hexane, heptane etc.), halogenated hydrocarbons (dichloromethane, chloroform etc.), ethers (diethyl ether, diisopropyl ether, t-butyl methyl ether, tetrahydrofuran, dioxane, dimethoxyethane etc.), nitriles (acetonitrile etc.), esters (ethyl acetate etc.), amides (dimethylformamide etc.), sulfoxides (dimethyl sulfoxide etc.) and the like. These solvent may be used in a mixture of two or more kinds thereof in an appropriate ratio.

The reaction temperature is, for example, within about 0 to 200° C., preferably about 25 to 100° C. While the reaction time varies depending on the kind of compound (X) or a salt thereof, the reaction temperature and the like, it is, for example, about 0.5 to 100 hr, preferably about 0.5 to 24 hr. when $R^{11}$ is a methyl group, trimethylsilyldiazomethane may be used instead of compound (XIIa). The amount of the trimethylsilyldiazomethane to be used is generally about 1 to 10 mol equivalent, preferably about 1 to 3 mol equivalent, per 1 mol of compound (X).

This reaction is carried out in a solvent that does not adversely influence the reaction. Examples of the solvent that does not adversely influence the reaction include aromatic hydrocarbons (benzene, toluene, xylene etc.), aliphatic hydrocarbons (hexane, heptane etc.), halogenated hydrocarbons (dichloromethane, chloroform etc.), ethers (diethyl ether, diisopropyl ether, t-butyl methyl ether, tetrahydrofuran, dioxane, dimethoxyethane etc.), nitriles (acetonitrile etc.), esters (ethyl acetate etc.), amides (dimethylformamide etc.), sulfoxides (dimethyl sulfoxide etc.) and the like. These solvent may be used in a mixture of two or more kinds thereof in an appropriate ratio.

The reaction temperature is, for example, within about 0 to 50° C., preferably about 0 to 30° C. While the reaction time varies depending on the kind of compound (X) or a salt thereof, the reaction temperature and the like, it is, for example, about 0.5 to 100 hr, preferably about 0.5 to 24 hr.

(Step 2)

This step is a step of subjecting compound (XIII) or a salt thereof to a deallylation reaction or a debenzylation reaction to produce compound (XIV) or a salt thereof.

This step can be performed in the same manner as in the method described in Step 3 of Method B.

(Step 3)

This step is a step of reacting compound (XIV) or a salt thereof with compound (IV) or a salt thereof in the presence of a condensing agent to produce compound (XV) or a salt thereof.

This step can be performed in the same manner as in the method described in Step 1 of Method A.

(Step 4)

This step is a step of subjecting compound (XV) or a salt thereof to hydrolysis to convert compound (XV) or a salt thereof into compound (III) or a salt thereof. This reaction can be carried out according to a method known per se, generally carried out in the presence of an acid or a base, in a solvent that does not adversely influence the reaction if necessary.

Examples of the acid include mineral acids (hydrochloric acid, hydrobromic acid, sulfuric acid etc.), carboxylic acids (acetic acid, trifluoroacetic acid, trichloroacetic acid etc.), sulfonic acids (methanesulfonic acid, p-toluenesulfonic acid etc.), Lewis acids (aluminium chloride, tin chloride, zinc bromide etc.) and the like. These solvent may be used in a mixture of two or more kinds thereof if necessary. While the amount of the acid to be used varies depending on the kind of the solvent and the other reaction condition, it is generally about 0.1 mol equivalent or more per 1 mol of compound (XV). The acid may be used as a solvent.

Examples of the base include inorganic bases (alkali metal hydroxides such as lithium hydroxide, sodium hydroxide, potassium hydroxide and the like, alkali metal hydrogencarbonates such as sodium hydrogencarbonate, potassium hydrogencarbonate and the like, alkali metal carbonates such as sodium carbonate, potassium carbonate and the like, alkoxides such as sodium methoxide, sodium ethoxide and the like, etc.) and organic bases (amines such as trimethylamine, triethylamine, diisopropylethylamine and the like, cyclic amines such as pyridine, 4-dimethylaminopyridine and the like, etc.) and the like. Among them, sodium hydroxide is preferable. While the amount of the base to be used varies depending on the kind of the solvent and the other reaction condition, it is generally about 0.1 to 10 mol equivalent, preferably about 1 to 5 mol equivalent, per 1 mol of compound (XV).

Examples of the solvent that does not adversely influence the reaction include alcohols (methanol, ethanol, propanol, 2-propanol, butanol, isobutanol, t-butanol etc.), hydrocarbons (benzene, toluene, xylene, hexane, heptane etc.), halogenated hydrocarbons (dichloromethane, chloroform etc.), ethers (diethyl ether, diisopropyl ether, t-butyl methyl ether, tetrahydrofuran, dioxane, dimethoxyethane etc.), nitriles (acetonitrile etc.), carboxylic acids (acetic acid etc.), amides (dimethylformamide, dimethylacetamide etc.), sulfoxides (dimethyl sulfoxide etc.), water and the like. Among them, ethanol, tetrahydrofuran and water are preferable. These solvent may be used in a mixture of two or more kinds thereof in an appropriate ratio.

The reaction temperature is, for example, within about −50 to 200° C., preferably about 0 to 100° C. While the reaction time varies depending on the kind of compound (XV) or a salt thereof, the reaction temperature and the like, it is, for example, about 0.5 to 100 hr, preferably about 0.5 to 24 hr.

When, in compound (I), compound (I') or compound (I"), $Z^1$ is a tetrahydropyran-4-yl group, L is a bond, and $R^3$ is a hydrogen atom, the raw material in Method A can be produce according to Method D.

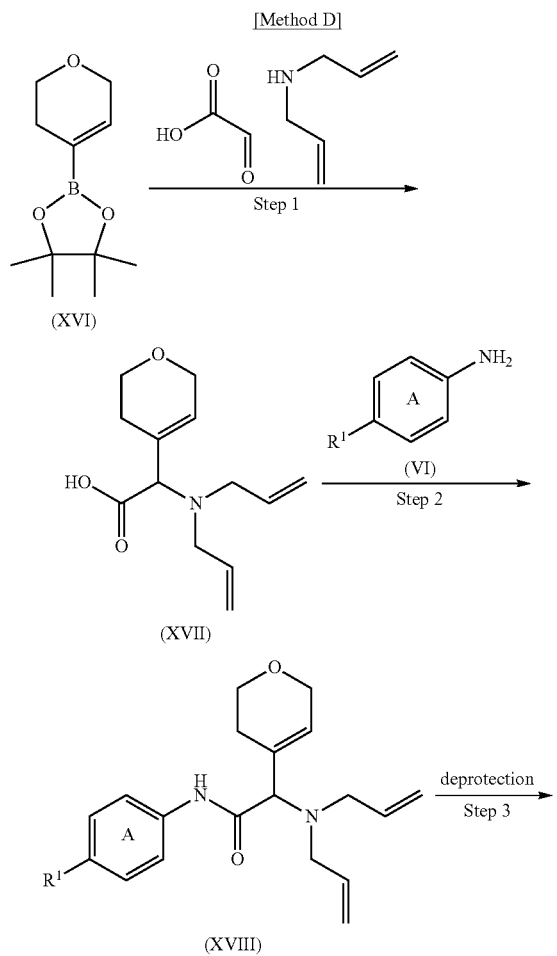

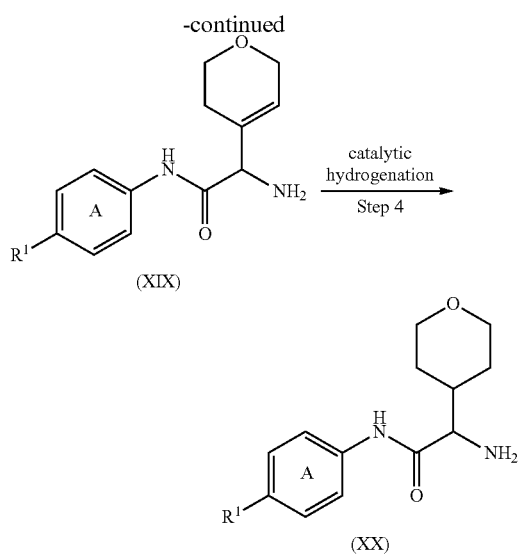

wherein each symbol is as defined above.

(Step 1)

This step is a step of reacting compound (XVI) with glyoxylic acid and diallylamine to produce compound (XVII) or a salt thereof.

The compounds used for this reaction may be a commercially available product.

This step can be performed in the same manner as in the method described in Step 1 of Method B.

(Step 2)

This step is a step of reacting compound (XVII) or a salt thereof with compound (VI) or a salt thereof in the presence of a condensing agent to produce compound (XVIII) or a salt thereof.

This step can be performed in the same manner as in the method described in Step 1 of Method A.

(Step 3)

This step is a step of subjecting compound (XVIII) or a salt thereof to a deallylation reaction to produce compound (XIX) or a salt thereof.

This step can be performed in the same manner as in the method described in Step 3 of Method B.

(Step 4)

This step is a step of subjecting compound (XIX) or a salt thereof to a catalytic hydrogenation reaction to produce compound (XX) or a salt thereof.

The catalytic hydrogenation reaction can be carried out in the presence of a catalyst under hydrogen atmosphere. Examples of the catalyst include palladiums such as palladium on carbon, palladium hydroxide carbon, palladium oxide and the like; nickels such as Raney nickel catalyst and the like; platinums such as platinum oxide, platinum on carbon and the like; rhodiums such as rhodium on carbon and the like, and the like. The amount of the catalyst to be used is generally about 0.001 to 1 mol, preferably about 0.01 to 0.5 mol, per 1 mol of compound (XIX).

The catalytic hydrogenation reaction is generally carried out in a solvent inert to the reaction. Examples of the solvent include alcohols such as methanol, ethanol, propanol, butanol and the like; hydrocarbons such as benzene, toluene, xylene and the like; halogenated hydrocarbons such as dichloromethane, chloroform and the like; ethers such as diethyl ether, dioxane, tetrahydrofuran and the like; esters such as ethyl acetate and the like; amides such as N,N- dimethylformamide and the like; carboxylic acids such as acetic acid and the like; water and mixtures thereof.

The hydrogen pressure for the reaction is generally about 1 to 50 atm, preferably about 1 to 10 atm. The reaction temperature is generally about 0° C. to 150° C., preferably about 20° C. to 100° C., and the reaction time is generally about 5 min to about 72 hr, preferably about 0.5 hr to about 40 hr.

When, in compound (I), compound (I') or compound (I"), $Z^1$ is a tetrahydropyran-4-yl group, L is a bond, and $R^3$ is a substituent, the raw material in Method A can be produce according to Method E.

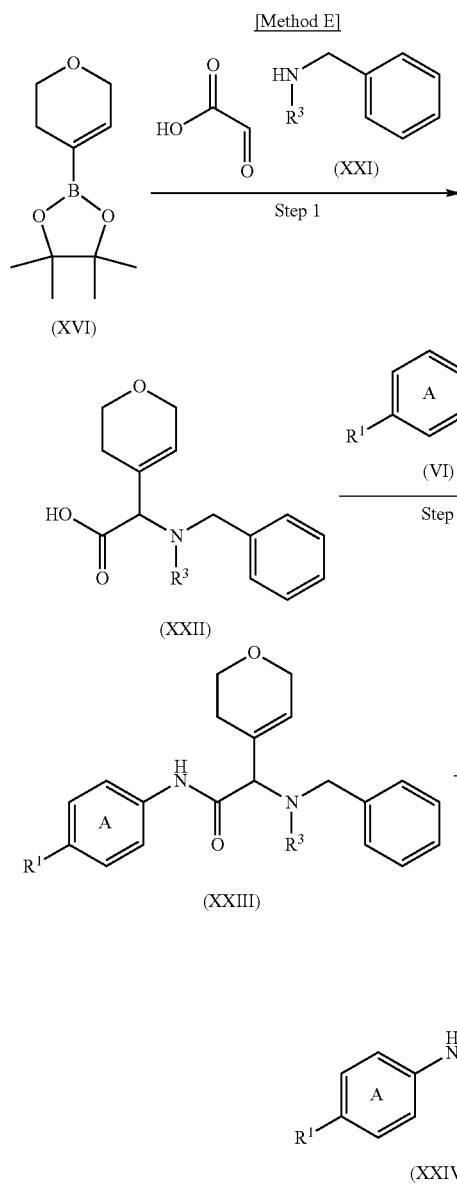

wherein each symbol is as defined above.

(Step 1)

This step is a step of reacting compound (XVI) with glyoxylic acid and compound (XXI) or a salt thereof to produce compound (XXII) or a salt thereof.

The compounds used for this reaction may be a commercially available product, or can also be produced according to a method known per se or a method analogous thereto.

This step can be performed in the same manner as in the method described in Step 1 of Method B.

(Step 2)

This step is a step of reacting compound (XXII) or a salt thereof with compound (VI) or a salt thereof in the presence of a condensing agent to produce compound (XXIII) or a salt thereof.

This step can be performed in the same manner as in the method described in Step 1 of Method A.

(Step 3)

This step is a step of subjecting compound (XXIII) or a salt thereof to a debenzylation reaction and a catalytic reduction reaction to produce compound (XXIV) or a salt thereof.

This step can be performed in the same manner as in the method described in Step 3 of Method B.

When, in compound (I), compound (I') or compound (I"), $Z^1$ is a tetrahydropyran-4-yl group, L is a bond, and $R^3$ is a hydrogen atom, the raw material in Method A can be produce according to Method F.

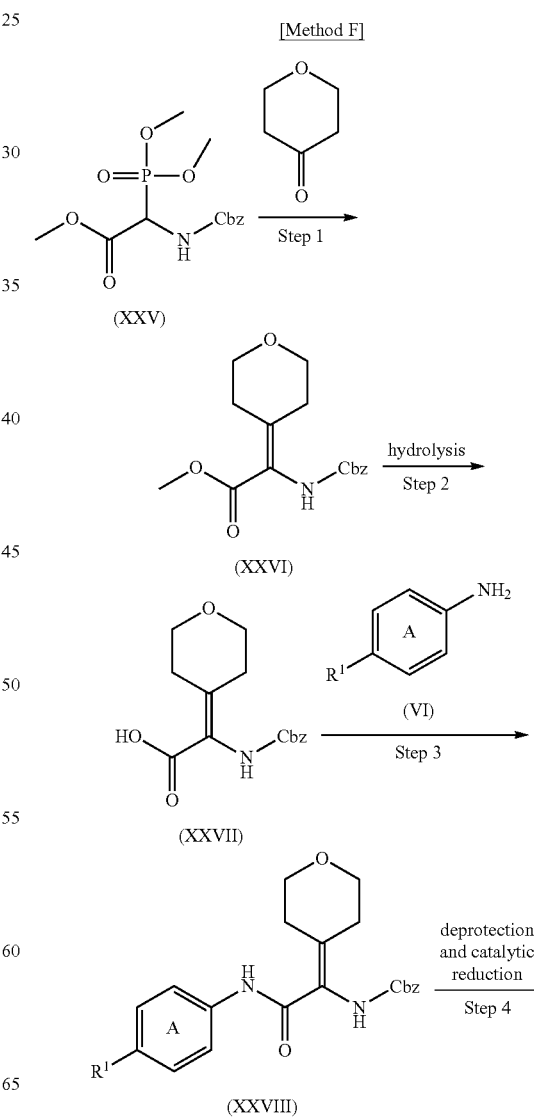

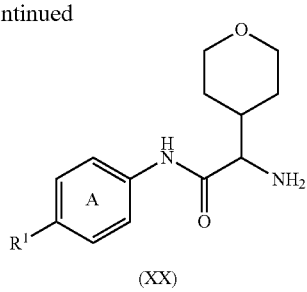

(XX)

wherein Cbz is a carbobenzoxy group, and the other symbols are as defined above.

(Step 1)

This step is a step of reacting compound (XXV) with dihydro-2H-pyran-4(3H)-one in the presence of a base, in a solvent that does not adversely influence this reaction to produce compound (XXVI) or a salt thereof.

The compounds used for this reaction may be a commercially available product.

Examples of the base to be used for this reaction include organic bases (amines such as 1,8-diazabicyclo[5.4.0]undec-7-ene, triethylamine, diisopropylethylamine and the like), inorganic bases (alkali metal hydrides such as sodium hydride, lithium hydride and the like) and the like. Among them, 1,8-diazabicyclo[5.4.0]undec-7-ene is preferable. While the amount of the base to be used varies depending on the kind of the solvent and the other reaction condition, it is generally about 1 to 10 mol equivalent, preferably about 1 to 5 mol equivalent, per 1 mol of compound (XXV).

Examples of the solvent that does not adversely influence the reaction include aromatic hydrocarbons (benzene, toluene, xylene etc.), aliphatic hydrocarbons (hexane, heptane etc.), halogenated hydrocarbons (dichloromethane, chloroform etc.), ethers (diethyl ether, diisopropyl ether, t-butyl methyl ether, tetrahydrofuran, dioxane, dimethoxyethane etc.), nitriles (acetonitrile etc.), esters (ethyl acetate etc.), amides (dimethylformamide etc.), sulfoxides (dimethyl sulfoxide etc.) and the like. These solvent may be used in a mixture of two or more kinds thereof in an appropriate ratio.

The amount of the dihydro-2H-pyran-4(3H)-one to be used is about 1 to 10 mol equivalent, preferably about 1 to 2 mol equivalent, per 1 mol of compound (XXV).

The reaction temperature is, for example, within about −10 to 100° C., and the reaction time is about 0.5 to 100 hr, preferably about 0.5 to 24 hr.

(Step 2)

This step is a step of subjecting compound (XXVI) or a salt thereof to hydrolysis to convert compound (XXVI) or a salt thereof into compound (XXVII) or a salt thereof.

This step can be performed in the same manner as in the method described in Step 4 of Method C.

(Step 3)

This step is a step of reacting compound (XXVII) or a salt thereof with compound (VI) or a salt thereof in the presence of a condensing agent to produce compound (XXVIII) or a salt thereof.

This step can be performed in the same manner as in the method described in Step 1 of Method A.

(Step 4)

This step is a step of subjecting compound (XXVIII) or a salt thereof to a deprotection reaction and a catalytic reduction reaction to produce compound (XX) or a salt thereof.

This step can be performed in the same manner as in the method described in Step 3 of Method B.

When, in compound (I), compound (I') or compound (I''), $Z^1$ is a 4,4-difluorocyclohexan-1-yl group, L is a bond, and $R^2$ is a hydrogen atom, the raw material in Method A can be produce according to Method G.

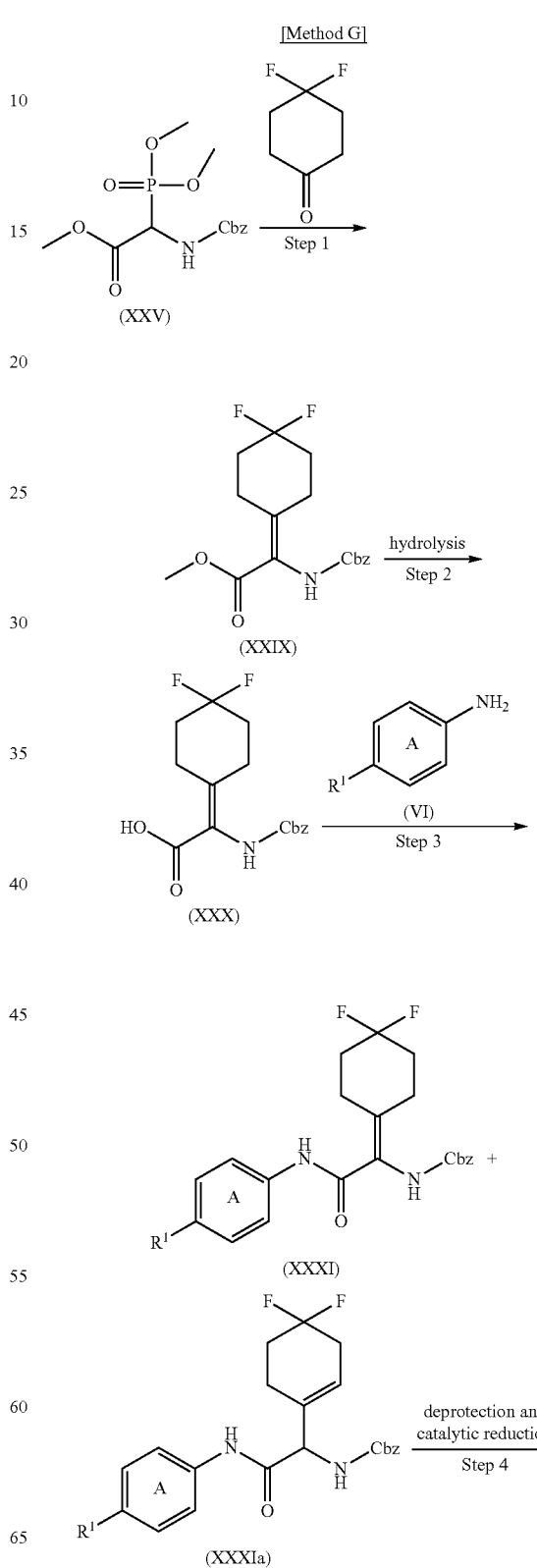

-continued

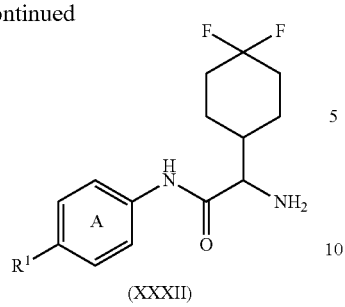

(XXXII)

wherein each symbol is as defined above.

(Step 1)

This step is a step of reacting compound (XXV) with 4,4-difluorocyclohexanone in the presence of a base to produce compound (XXIX) or a salt thereof.

This step can be performed in the same manner as in the method described in Step 1 of Method F.

(Step 2)

This step is a step of subjecting compound (XXIX) or a salt thereof to hydrolysis to convert compound (XXIX) or a salt thereof into compound (XXX) or a salt thereof.

This step can be performed in the same manner as in the method described in Step 4 of Method C.

(Step 3)

This step is a step of reacting compound (XXX) or a salt thereof with compound (VI) or a salt thereof in the presence of a condensing agent to produce compound (XXXI) and compound (XXXIa) or salts thereof.

This step can be performed in the same manner as in the method described in Step 1 of Method A.

(Step 4)

This step is a step of subjecting compound (XXXI) and compound (XXXIa) or salts thereof to a deprotection reaction and a catalytic reduction reaction to produce compound (XXXII) or a salt thereof.

This step can be performed in the same manner as in the method described in Step 3 of Method B.

When, in compound (I), compound (I') or compound (I"), $Z^1$ is an optionally substituted non-aromatic ring group, L is $CH_2$, and $R^3$ is optionally substituted $C_{1-6}$ alkyl group, the raw material in Method A can be produce according to Method H.

[Method H]

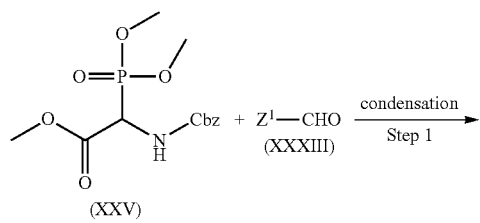

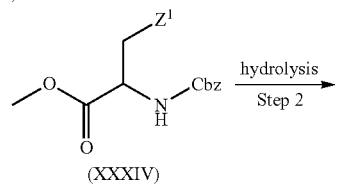

-continued

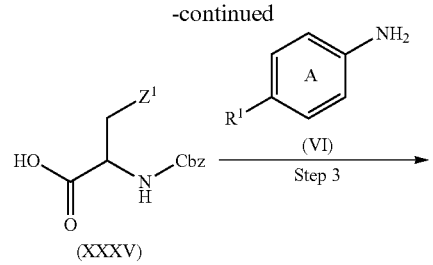

(XXXV)

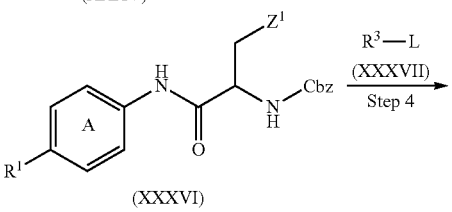

(XXXVI)

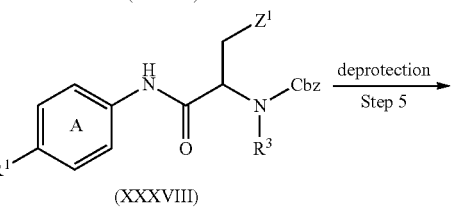

(XXXVIII)

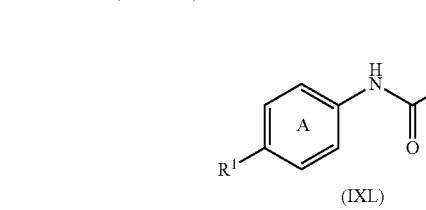

(IXL)

wherein each symbol is as defined above.

(Step 1)

This step is a step of reacting compound (XXV) with compound (XXXIII) or a salt thereof in the presence of a base to produce compound (XXXIV) or a salt thereof.

This step can be performed in the same manner as in the method described in Step 1 of Method F.

(Step 2)

This step is a step of subjecting compound (XXXIV) or a salt thereof to hydrolysis to convert compound (XXXIV) or a salt thereof into compound (XXXV) or a salt thereof.

This step can be performed in the same manner as in the method described in Step 4 of Method C.

(Step 3)

This step is a step of reacting compound (XXXV) or a salt thereof with compound (VI) or a salt thereof in the presence of a condensing agent to produce compound (XXXVI) or a salt thereof.

This step can be performed in the same manner as in the method described in Step 1 of Method A.

(Step 4)

This step is a step of subjecting compound (XXXVI) or a salt thereof to an alkylation reaction with a compound represented by the formula:

$R^3$-L   (XXXVII)

wherein each symbol is as defined above (hereinafter to be referred to as compound (XXXVII)) or a salt thereof, in the presence of a base, to produce compound (XXXVIII) or a salt thereof.

Compound (XXXVII) may be a commercially available product, or can also be produced according to a method known per se or a method analogous thereto.

Examples of the base to be used for this reaction include inorganic bases (alkali metal hydrides such as sodium hydride, lithium hydride and the like, alkali metal hydroxides such as lithium hydroxide, sodium hydroxide, potassium hydroxide and the like, alkali metal hydrogencarbonates such as sodium hydrogencarbonate, potassium hydrogencarbonate and the like, alkali metal carbonates such as lithium carbonate, sodium carbonate, potassium carbonate, cesium carbonate and the like) and the like. While the amount of the base to be used varies depending on the kind of the solvent and the other reaction condition, it is generally about 1 to 10 mol equivalent, preferably about 1 to 5 mol equivalent, per 1 mol of compound (XXXVI).

The amount of compound (XXXVII) to be used is generally about 1 to 10 mol equivalent, preferably about 1 to 3 mol equivalent, per 1 mol of compound (XXXVI).

This step is carried out in a solvent that does not adversely influence the reaction. Examples of the solvent that does not adversely influence the reaction include aromatic hydrocarbons (benzene, toluene, xylene etc.), aliphatic hydrocarbons (hexane, heptane etc.), halogenated hydrocarbons (dichloromethane, chloroform etc.), ethers (diethyl ether, diisopropyl ether, t-butyl methyl ether, tetrahydrofuran, dioxane, dimethoxyethane etc.), nitriles (acetonitrile etc.), esters (ethyl acetate etc.), amides (dimethylformamide etc.), sulfoxides (dimethyl sulfoxide etc.) and the like. These solvent may be used in a mixture of two or more kinds thereof in an appropriate ratio.

The reaction temperature is, for example, within about −75 to 200° C., preferably about −10 to 30° C. While the reaction time varies depending on the kind of compound (XXXVII) or a salt thereof, the reaction temperature and the like, it is, for example, about 0.5 to 100 hr, preferably about 0.5 to 24 hr.

(Step 5)

This step is a step of subjecting compound (XXXVIII) or a salt thereof to a deprotection reaction to produce compound (IXL) or a salt thereof.

This step can be performed in the same manner as in the method described in Step 3 of Method B.

When compound (VI) is a compound represented by the formula:

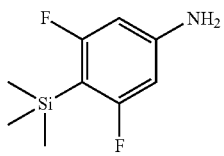

(hereinafter to be referred to as compound (XL)) or a salt thereof, the compound can be produced according to Method I.

[Method I]

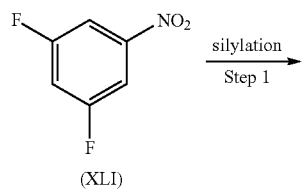

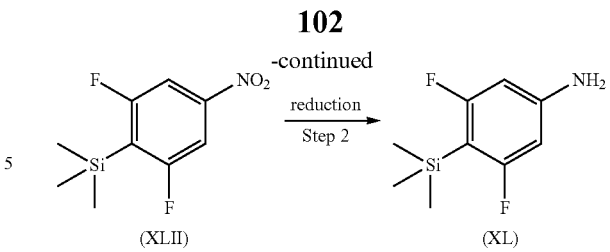

(Step 1)

This step is a step of reacting compound (XLI) with a silylating agent in the absence or presence of a transition metal catalyst to produce compound (XLII).

Compound (XLI) may be a commercially available product.

Examples of the transition metal catalyst to be used for this reaction include palladium catalysts (palladium acetate, palladium chloride, tetrakistriphenylphosphine palladium, tris(dibenzylideneacetone)dipalladium(0) etc.), nickel catalysts (nickel chloride etc.) and the like. Where necessary, a ligand (triphenylphosphine, tri-t-butylphosphine, S-Phos, BINAP, 2'-(di-tert-butylphosphino)-N, N-dimethyl-[1,1'-biphenyl]-2-amine etc.) and a base (e.g., organic amines (trimethylamine, triethylamine, diisopropylamine, N-methylmorpholine, 1,8-diazabicyclo[5,4,0]undec-7-ene, pyridine, N,N-dimethylaniline etc.), alkali metal salts (sodium hydrogencarbonate, potassium hydrogencarbonate, sodium carbonate, potassium carbonate, cesium carbonate, sodium phosphate, potassium phosphate, sodium hydroxide, potassium hydroxide, lithium acetate etc.), metal hydrides (potassium hydride, sodium hydride etc.), alkali metal alkoxides (sodium methoxide, sodium ethoxide, sodium-t-butoxide, potassium-t-butoxide etc.), alkali disilazides (lithium disilazide, sodium disilazide, potassium disilazide etc.)) may be added, or a metal oxide (copper oxide, silver oxide, etc.) and the like may be used as a co-catalyst. The amount of the catalyst to be used is about 0.0001 to 1 mol equivalent, preferably about 0.01 to 0.5 mol equivalent, per 1 mol of compound (XLI). The amount of the ligand to be used is about 0.0001 to 4 mol equivalent, preferably about 0.01 to 2 mol equivalent, per 1 mol of compound (XLI). The amount of the base to be used is about 1 to 10 mol equivalent, preferably about 1 to 2 mol equivalent, per 1 mol of compound (XLI). The amount of the co-catalyst to be used is about 0.0001 to 4 mol equivalent, preferably about 0.01 to 2 mol equivalent, per 1 mol of compound (XLI).

The solvent to be used is not particularly limited as long as it does not adversely influence the reaction, and examples thereof include hydrocarbons (benzene, toluene, xylene etc.), halogenated hydrocarbons (chloroform, 1,2-dichloroethane etc.), nitriles (acetonitrile etc.), ethers (dimethoxyethane, tetrahydrofuran), alcohols (methanol, ethanol etc.), aprotic polar solvents (dimethylformamide, dimethyl sulfoxide, hexamethylphosphoroamide etc.), water and mixtures thereof. The reaction temperature is generally about −100 to 200° C., preferably about −80 to 150° C., and the reaction time is generally about 0.5 to 48 hr, preferably about 0.5 to 24 hr. The reaction may be carried out under microwave irradiation, if necessary.

Examples of the silylating agent include 1,1,1,2,2,2-hexamethyldisilane and chlorotrimethylsilane.

(Step 2)

This step is a step of subjecting compound (XLII) to a reduction reaction using a transition metal catalyst to produce compound (XL).

Examples of the transition metal catalyst to be used for this reaction include palladiums (palladium on carbon, palladium hydroxide, palladium oxide etc.), nickels (Raney nickel etc.), platinums (platinum oxide, platinum on carbon etc.), rhodiums (rhodium acetate, rhodium on carbon etc.) and the like. The amount of the transition metal catalyst to be used is, for example, about 0.001 to 1 equivalent, preferably about 0.01 to 0.5 equivalent, per 1 mol of compound (XLII). The catalytic hydrogenation reaction is generally carried out in a solvent inert to the reaction. Examples of the solvent include alcohols (methanol, ethanol, propanol, butanol etc.), hydrocarbons (benzene, toluene, xylene etc.), halogenated hydrocarbons (dichloromethane, chloroform etc.), ethers (diethyl ether, dioxane, tetrahydrofuran etc.), esters (ethyl acetate etc.), amides (N,N-dimethylformamide etc.), carboxylic acids (acetic acid etc.), water and mixtures thereof. The hydrogen pressure for the reaction is generally about 1 to 500 atm, preferably about 1 to 100 atm. The reaction temperature is generally about 0 to 150° C., preferably about 20 to 100° C., and the reaction time is generally about 5 min to 72 hr, preferably about 0.5 to 40 hr.

When compound (VI) is a compound represented by the formula:

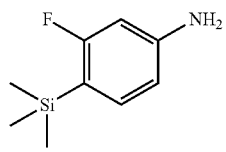

(hereinafter to be referred to as compound (XLIII)) or a salt thereof, the compound can be produced according to Method J.

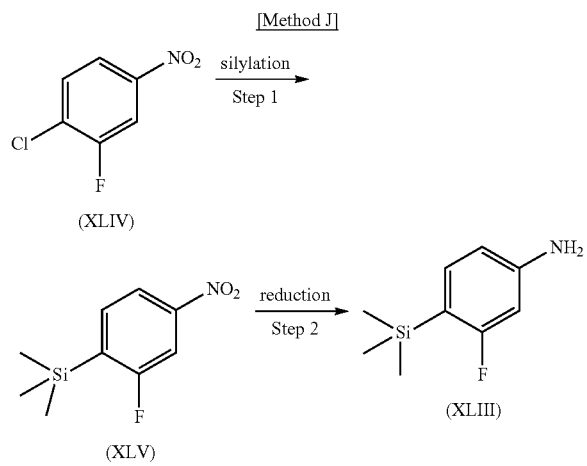

(Step 1)

This step is a step of reacting compound (XLIV) with a silylating agent in the presence of a transition metal catalyst to produce compound (XLV).

Compound (XLIV) may be a commercially available product.

This step can be performed in the same manner as in the method described in Step 1 of Method I.

(Step 2)

This step is a step of subjecting compound (XLV) to a reduction reaction using a transition metal catalyst to produce compound (XLIII).

This step is can be performed in the same manner as in the method described in Step 2 of Method I, or by a reduction reaction using a metal (e.g., iron).

When compound (VI) is a compound represented by the formula:

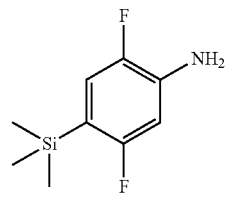

(hereinafter to be referred to as compound (XLVI)) or a salt thereof, the compound can be produced according to Method K.

[Method K]

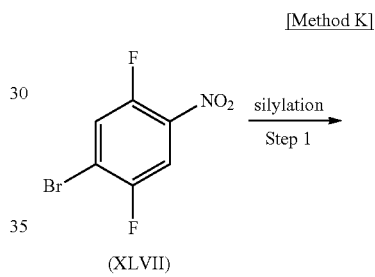

(Step 1)

This step is a step of reacting compound (XLVII) with a silylating agent in the presence of a transition metal catalyst to produce compound (XLVIII).

Compound (XLVII) may be a commercially available product.

This step can be performed in the same manner as in the method described in Step 1 of Method I.

(Step 2)

This step is a step of subjecting compound (XLVIII) to a reduction reaction using a transition metal catalyst to produce compound (XLVI).

This step can be performed in the same manner as in the method described in Step 2 of Method I.

When compound (VI) is a compound represented by the formula:

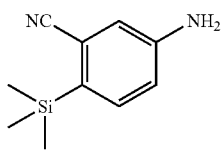

(hereinafter to be referred to as compound (XLIX)) or a salt thereof, the compound can be produced according to Method L.

[Method L]

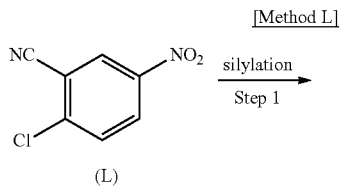

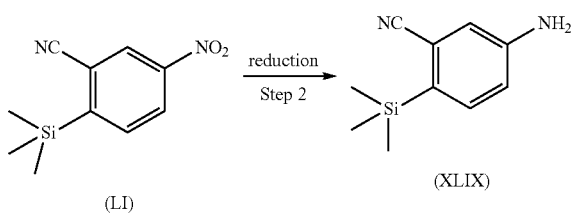

(Step 1)

This step is a step of reacting compound (L) with a silylating agent in the presence of a transition metal catalyst to produce compound (LI).

Compound (L) may be a commercially available product.

This step can be performed in the same manner as in the method described in Step 1 of Method I.

(Step 2)

This step is a step of subjecting compound (LI) to a reduction reaction using a transition metal catalyst to produce compound (XLIX).

This step can be performed in the same manner as in the method described in Step 2 of Method I.

When compound (VI) is a compound represented by the formula:

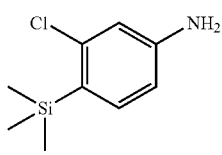

(hereinafter to be referred to as compound (LII)) or a salt thereof, the compound can be produced according to Method M.

[Method M]

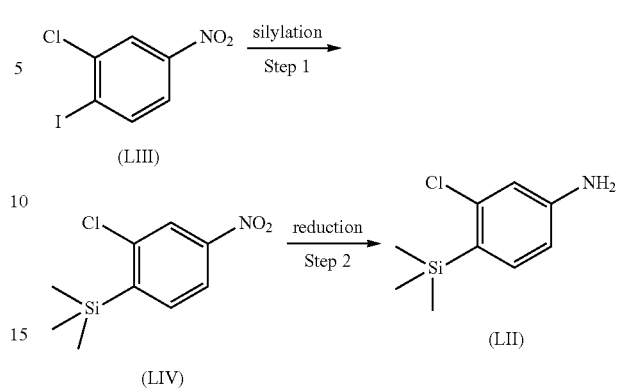

(Step 1)

This step is a step of reacting compound (LIII) with a silylating agent in the presence of an organic lithium reagent to produce compound (LIV).

Compound (LIII) may be a commercially available product.

Examples of the organic lithium reagent to be used include n-butyllithium, phenyllithium and the like.

While the amount of the organic lithium reagent to be used varies depending on the kind of the solvent and the other reaction condition, it is generally about 1 to 10 mol equivalent, preferably about 1 to 5 mol equivalent, per 1 mol of compound (LIII).

Examples of the silylating agent include 1,1,1,2,2,2-hexamethyldisilane and chlorotrimethylsilane.

This step is generally carried out in a solvent that does not adversely influence the reaction. Examples of the solvent include hydrocarbons (benzene, toluene etc.), ethers (diethyl ether, dioxane, tetrahydrofuran etc.) and the like, and they may be mixed as appropriate. Among them, tetrahydrofuran is preferable.

The reaction temperature is generally about −200 to 40° C., preferably about −80 to 5° C., and the reaction time is generally about 0.0001 to 12 hr, preferably about 0.0001 to 1 hr.

(Step 2)

This step is a step of subjecting compound (LIV) to a reduction reaction using a transition metal catalyst to produce compound (LII).

This step can be performed in the same manner as in the method described in Step 2 of Method I.

When compound (VI) is a compound represented by the formula:

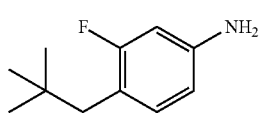

(hereinafter to be referred to as compound (LV)) or a salt thereof, the compound can be produced according to Method N.

[Method N]

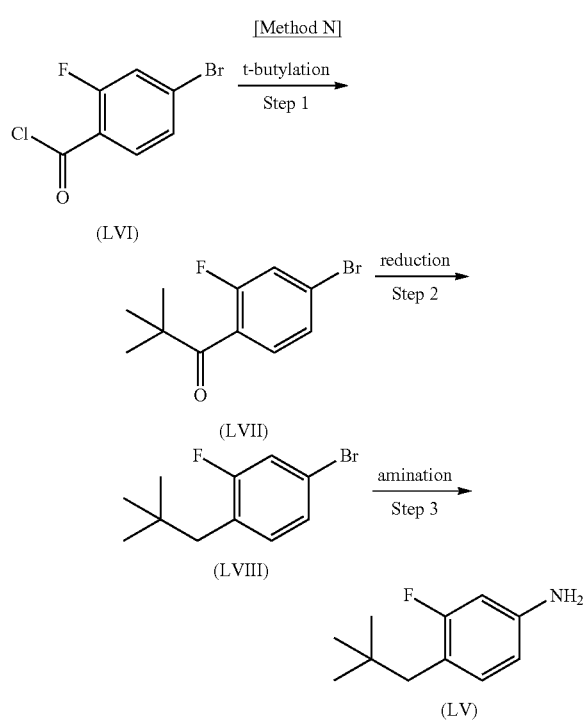

This step is a step of reacting compound (LVI) with t-butylmagnesium chloride or t-butylmagnesium bromide in the presence of copper cyanide and lithium chloride to produce compound (LVII).

Compound (LVI) may be a commercially available product.

The amount of the copper cyanide to be used is about 1 to 10 mol equivalent, preferably about 1 to 2 mol equivalent, per 1 mol of compound (LVI).

The amount of the lithium chloride to be used is about 1 to 10 mol equivalent, preferably about 1 to 5 mol equivalent, per 1 mol of compound (LVI).

The amount of the t-butylmagnesium chloride or t-butylmagnesium bromide to be used is about 1 to 5 mol equivalent, preferably about 1 to 2 mol equivalent, per 1 mol of compound (LVI).

This step is generally carried out in a solvent that does not adversely influence the reaction. Examples of the solvent include hydrocarbons (benzene, toluene etc.), ethers (diethyl ether, dioxane, tetrahydrofuran etc.) and the like, and they may be mixed as appropriate. Among them, tetrahydrofuran is preferable.

The reaction temperature is generally about −200 to 40° C., preferably about −80 to 5° C., and the reaction time is generally about 0.1 to 12 hr, preferably about 0.1 to 1 hr.
(Step 2)

This step is a step of subjecting compound (LVII) to a reduction reaction using triethylsilane and trifluoroacetic acid to produce compound (LVIII).

The amount of the triethylsilane to be used is about 1 to 10 mol equivalent, preferably about 1 to 2 mol equivalent, per 1 mol of compound (LVII).

The amount of the trifluoroacetic acid to be used is about 1 to 10 mol equivalent, preferably about 1 to 5 mol equivalent, per 1 mol of compound (LVII). Trifluoroacetic acid can be used as a solvent.

The reaction temperature is generally about −20 to 100° C., preferably about 0 to 30° C., and the reaction time is generally about 1 to 100 hr, preferably about 1 to 72 hr.
(Step 3)

This step is a step of reacting compound (LVIII) with an aminating agent in the presence of a transition metal catalyst and a base, and then treating the resulting compound with hydroxylamine hydrochloride and sodium acetate to produce compound (LV).

The kinds and amounts of the transition metal catalyst and base to be used are the same as in Step 1 of Method I.

Preferable examples of the aminating agent to be used include diphenylmethanimine. The amount of the aminating agent to be used is about 1 to 5 mol equivalent, preferably about 1 to 2 mol equivalent, per 1 mol of compound (LVII).

The kind of the solvent to be used for the reaction with an aminating agent, and the reaction temperature are the same as in Step 1 of Method I.

The amounts of the hydroxylamine hydrochloride and sodium acetate to be used are about 1 to 5 mol equivalent, preferably about 1 to 2 mol equivalent, per 1 mol of compound (LVII), respectively.

Preferable examples of the solvent to be used for the treatment with hydroxylamine hydrochloride and sodium acetate include methanol. The reaction temperature is about −20 to 100° C., preferably about 0 to 30° C., and the reaction time is generally about 1 to 100 hr, preferably about 1 to 72 hr.

When the object product is obtained in a free form by the above-mentioned reaction, it may be converted to a salt by a conventional method. When it is obtained as a salt, it can also be converted to a free form or other salt by a conventional method. The thus-obtained compound (I), compound (I') or compound (I") can be isolated and purified from the reaction solution by a known means, for example, phase transfer, concentration, solvent extraction, fractionation, crystallization, recrystallization, chromatography and the like.

When compound (I), compound (I') or compound (I") contains an isomer such as a tautomer, an optical isomer, a stereoisomer, a regioisomer, a rotamer and the like, any isomer and a mixture thereof are also encompassed in the compound of the present invention. Furthermore, when compound (I), compound (I') or compound (I") has an optical isomer, an optical isomer resolved from this compound is also encompassed in compound (I), compound (I') or compound (I").

Compound (I), compound (I') or compound (I") may be a crystal. Even if compound (I), compound (I') or compound (I") is in a single crystal form or mixed crystal form, it can be provided as compound (I), compound (I') or compound (I").

Compound (I), compound (I') or compound (I") may be a pharmaceutically acceptable co-crystal or co-crystal salt. Here, the co-crystal or co-crystal salt means a crystalline substance consisting of two or more particular substances which are solids at room temperature, each of which has different physical properties (e.g., structure, melting point, heat of melting, hygroscopicity, solubility, stability etc.). The cocrystal and cocrystal salt can be produced by cocrystallization known per se.

Compound (I), compound (I') or compound (I") may be a solvate (e.g., a hydrate) or a nonsolvate (e.g., non-hydrate, etc.). Any of them can be provided as compound (I), compound (I') or compound (I").

Any of the above compounds may be labeled or substituted with an isotope (e.g., $^2$H, $^3$H, $^{11}$C, $^{14}$C, $^{18}$F, $^{35}$S, or $^{125}$I)

and provided as compound (I), compound (I') or compound (I"). Compound (I), compound (I') or compound (I") labeled or substituted with an isotope can be used, for example, as a tracer (PET tracer) used for positron emission tomography (PET), and is useful in the field such as medical diagnosis and the like.

The prodrug of compound (I), compound (I') or compound (I") means a compound which can be converted into compound (I), compound (I') or compound (I") by reaction with an enzyme, gastric acid, or the like under physiological conditions in the living body. In other words, it means a compound which can be converted into compound (I), compound (I') or compound (I") by enzymatic oxidation, reduction, hydrolysis or the like, or a compound which can be converted into compound (I), compound (I') or compound (I") by hydrolysis with gastric acid or the like. Examples of the prodrug of compound (I), compound (I') or compound (I") include a compound in which amino of compound (I), compound (I') or compound (I") is acylated, alkylated, or phosphorylated (e.g., the amino of compound (I), compound (I') or compound (I") is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, or tert-butylated); a compound in which hydroxyl of compound (I), compound (I') or compound (I") is acylated, alkylated, phosphorylated, or borated (e.g., hydroxyl of compound (I), compound (I') or compound (I") is acetylated, palmitoylated, propanoylated, pivaloylated, succinylated, fumarylated, alanylated, or dimethylaminomethylcarbonylated); a compound in which carboxy of compound (I), compound (I') or compound (I") is esterified or amidated (e.g., a compound in which carboxy of compound (I), compound (I') or compound (I") is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl)methyl esterified, cyclohexyloxycarbonylethyl esterified, or methylamidated). These compounds can be produced from compound (I), compound (I') or compound (I") by a method known per se.

The prodrug of compound (I), compound (I') or compound (I") may be a compound that converts to compound (I), compound (I') or compound (I") under physiological conditions as described in Development of Pharmaceutical Products, vol. 7, Molecule Design, 163-198, Hirokawa Shoten (1990).

Since compound (I), compound (I') and compound (I") and a prodrug thereof [hereinafter sometimes to be abbreviated as the compound of the present invention] show superior RORγt inhibitory activity, they are also useful as safe medicaments based on such action.

For example, the medicament of the present invention containing the compound of the present invention can be used for a mammal (e.g., mouse, rat, hamster, rabbit, cat, dog, bovine, sheep, monkey, human etc.) as a prophylactic or therapeutic agent for RORγt associated diseases, Th17 cell associated diseases and IL-17A or IL-17F associated diseases, more specifically, the diseases described in (1)-(4) below.

(1) inflammatory diseases (e.g., rheumatoid arthritis, acute pancreatitis, chronic pancreatitis, asthma, bronchial asthma, adult respiratory distress syndrome, chronic obstructive pulmonary disease (COPD), inflammatory bone disease, inflammatory pulmonary disease, inflammatory bowel disease, celiac disease, hepatitis, systemic inflammatory response syndrome (SIRS), postoperative or posttraumatic inflammation, pneumonia, nephritis, meningitis, cystitis, pharyngolaryngitis, gastric mucosal injury, spondylitis, arthritis, dermatitis, chronic pneumonia, bronchitis, pulmonary infarction, silicosis, pulmonary sarcoidosis, uveitis etc.), (2) autoimmune diseases (e.g., rheumatoid arthritis, ankylosing spondylitis, psoriasis, multiple sclerosis (MS), polymyositis, dermatomyositis (DM), polyarteritis *nodosa* (PN), mixed connective tissue disease (MCTD), Sjogren's syndrome, systemic lupus erythematosus (SLE), scleroderma, *profundus* lupus erythematosus, chronic thyroiditis, Graves' disease, autoimmune gastritis, type I and type II diabetes, autoimmune hemolytic anemia, autoimmune neutropenia, thrombocytopenia, atopic dermatitis, chronic active hepatitis, myasthenia gravis, inflammatory bowel disease (IBD), ulcerative colitis (UC), Crohn's disease, graft versus host disease, Addison's disease, abnormal immunoresponse, arthritis, dermatitis, radiodermatitis etc.), (3) bone or joint degenerative diseases (e.g., rheumatoid arthritis, osteoporosis, osteoarthritis etc.), (4) neoplastic diseases [e.g., malignant tumor, angiogenesis glaucoma, infantile hemangioma, multiple myeloma, acute myeloblastic leukemia, chronic sarcoma, multiple myeloma, chronic myelogenous leukemia, metastasis melanoma, Kaposi's sarcoma, vascular proliferation, cachexia, metastasis of the breast cancer, cancer (e.g., colorectal cancer (e.g., familial colorectal cancer, hereditary nonpolyposis colorectal cancer, gastrointestinal stromal tumor and the like), lung cancer (e.g., non-small cell lung cancer, small cell lung cancer, malignant mesothelioma and the like), mesothelioma, pancreatic cancer (e.g., pancreatic duct cancer and the like), gastric cancer (e.g., papillary adenocarcinoma, mucinous adenocarcinoma, adenosquamous carcinoma and the like), breast cancer (e.g., invasive ductal carcinoma, ductal carcinoma in situ, inflammatory breast cancer and the like), ovarian cancer (e.g., ovarian epithelial carcinoma, extragonadal germ cell tumor, ovarian germ cell tumor, ovarian low malignant potential tumor and the like), prostate cancer (e.g., hormone-dependent prostate cancer, non-hormone dependent prostate cancer and the like), liver cancer (e.g., primary liver cancer, extrahepatic bile duct cancer and the like), thyroid cancer (e.g., medullary thyroid carcinoma and the like), kidney cancer (e.g., renal cell carcinoma, transitional cell carcinoma in kidney and urinary duct and the like), uterine cancer, endometrial cancer, brain tumor (e.g., pineal astrocytoma, pilocytic astrocytoma, diffuse astrocytoma, anaplastic astrocytoma and the like), melanoma (melanoma), sarcoma, urinary bladder cancer, hematologic cancer and the like including multiple myeloma, hypophyseal adenoma, glioma, acoustic neurinoma, retinoblastoma, head and neck cancer, pharyngeal cancer, laryngeal cancer, cancer of the tongue, thymoma, esophagus cancer, duodenal cancer, colorectal cancer, rectal cancer, hepatoma, pancreatic endocrine tumor, cancer of the bile duct, gallbladder cancer, penile cancer, urinary duct cancer, testis tumor, vulvar cancer, cervix cancer, endometrial cancer, uterus sarcoma, cholionic disease, vaginal cancer, skin cancer, fungoid mycosis, basal cell tumor, soft tissue sarcoma, malignant lymphoma, Hodgkin's disease, myelodysplastic syndrome, acute lymphocytic leukemia, chronic lymphocytic leukemia, adult T cell leukemia, chronic bone marrow proliferative disease, pancreatic endocrine tumor, fibrous histiocytoma, leiomyosarcoma, rhabdomyosarcoma, cancer of unknown primary).

The medicament of the present invention can be preferably used as an agent for the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis, systemic lupus erythematosus (SLE) and the like.

In another embodiment, the medicament of the present invention can be preferably used as an agent for the prophylaxis or treatment of autoimmune disease, inflammatory disease, bone or articular disease, or neoplastic disease, particularly preferably psoriasis, inflammatory bowel disease (IBD), ulcerative colitis (UC), Crohn's disease (CD), rheumatoid arthritis, multiple sclerosis, uveitis, asthma, ankylopoietic spondylarthritis, systemic lupus erythematosus (SLE), chronic obstructive pulmonary diseases, ovarian cancer, non small cell lung cancer, breast cancer, stomach cancer, head and neck cancer, prostate cancer or endometrial cancer.

Here, the above-mentioned "prophylaxis" of a disease means, for example, administration of a medicament containing the compound of the present invention to patients who are expected to have a high risk of the onset due to some factor relating to the disease but have not developed the disease or patients who have developed the disease but do not have a subjective symptom, or administration of a medicament containing the compound of the present invention to patients who are feared to show recurrence of the disease after treatment of the disease.

The medicament of the present invention shows superior pharmacokinetics (e.g., a half-life of the drug in plasma), low toxicity (e.g., HERG inhibition, CYP inhibition, CYP induction), and decreased drug interaction. The compound of the present invention can be directly used as a medicament, or as the medicament of the present invention by producing a pharmaceutical composition by mixing with a pharmaceutically acceptable carrier by a means known per se and generally used in a production method of pharmaceutical preparations. The medicament of the present invention can be orally or parenterally administered safely to mammals (e.g., humans, monkeys, cows, horses, pigs, mice, rats, hamsters, rabbits, cats, dogs, sheep and goats).

A medicament containing the compound of the present invention can be safely administered solely or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

The content of the compound of the present invention in the medicament of the present invention is about 0.01 to 100% by weight of the entire medicament. While the dose varies depending on the subject of administration, administration route, disease and the like, for example, for oral administration to an adult inflammatory bowel disease (IBD) patient (body weight about 60 kg), it is about 0.1 mg/kg body weight to 30 mg/kg body weight, preferably about 1 mg/kg body weight to 20 mg/kg body weight as an active ingredient (compound (I), compound (I') or compound (I")) for one day, which is administered once to several times, preferably once or two to three times.

The pharmaceutically acceptable carrier, which may be used for the production of the medicament of the present invention, may be exemplified by various organic or inorganic carrier materials that are conventionally used as preparation materials, for example, excipient, lubricant, binding agent and disintegrant for solid preparations; or solvent, solubilizing agent, suspending agent, isotonic agent, buffering agent, soothing agent and the like for liquid preparations. Furthermore, when necessary, ordinary additives such as preservative, antioxidant, colorant, sweetening agent, adsorbing agent, wetting agent and the like can be also used as appropriate in an appropriate amount.

Examples of the excipient include lactose, white sugar, D-mannitol, starch, corn starch, crystalline cellulose, light anhydrous silicic acid and the like.

Examples of the lubricant include magnesium stearate, calcium stearate, talc, colloidal silica and the like.

Examples of the binding agent include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, carboxymethylstarch sodium, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffering agent include buffer solutions such as phosphates, acetates, carbonates, citrates and the like.

Examples of the soothing agent include benzyl alcohol and the like.

Examples of the preservative include parahydroxybenzoates, chlorobutanol, benzyl alcohol, phenylethyl alcohol, dehydroacetic acid, sorbic acid and the like.

Examples of the antioxidant include sulfites, ascorbic acid, α-tocopherol and the like.

For the prophylaxis or treatment of various diseases, the compound of the present invention can also be used together with other medicaments. In the following, a medicament to be used when the compound of the present invention is used together with other drug is referred to as "the combination agent of the present invention".

For example, when the compound of the present invention is used as an RORγt inhibitor, Th17 cell inhibitor, IL-17A or IL-17F inhibitor, it can be used in combination with the following drugs.

(1) Non-Steroidal Anti-Inflammatory Drug (NSAIDs)
(i) Classical NSAIDs
alcofenac, aceclofenac, sulindac, tolmetin, etodolac, fenoprofen, thiaprofenic acid, meclofenamic acid, meloxicam, tenoxicam, lornoxicam, nabumeton, acetaminophen, phenacetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, piroxicam, epirizole, tiaramide hydrochloride, zaltoprofen, gabexate mesylate, camostat mesylate, ulinastatin, colchicine, probenecid, sulfinpyrazone, benzbromarone, allopurinol, sodium aurothiomalate, hyaluronate sodium, sodium salicylate, morphine hydrochloride, salicylic acid, atropine, scopolamine, morphine, pethidine, levorphanol, oxymorphone or a salt thereof and the like.

(ii) Cyclooxygenase Inhibitor (COX-1 Selective Inhibitor, COX-2 Selective Inhibitor and the Like)
salicylic acid derivatives (e.g., celecoxib, aspirin), etoricoxib, valdecoxib, diclofenac, indomethacin, loxoprofen and the like.

(iii) Nitric Oxide-Releasing NSAIDs (2) Disease-Modifying Anti-Rheumatic Drugs (DMARDs)
(i) Gold Preparation
auranofin and the like.
(ii) penicillamine
D-penicillamine.
(iii) Aminosalicylic Acid Preparation
sulfasalazine, mesalazine, olsalazine, balsalazide.
(iv) Antimalarial Drug
chloroquine and the like.
(v) pyrimidine synthesis inhibitor
leflunomide and the like.
(vi) tacrolimus (3) Anti-Cytokine Drug
(I) Protein Drug
(i) TNF Inhibitor
etanercept, infliximab, adalimumab, certolizumab pegol, golimumab, PASSTNF-α, soluble TNF-α receptor, TNF-α binding protein, anti-TNF-α antibody and the like.
(ii) Interleukin-1 Inhibitor
anakinra (interleukin-1 receptor antagonist), soluble interleukin-1 receptor and the like.
(iii) Interleukin-6 Inhibitor
tocilizumab (anti-interleukin-6 receptor antibody), anti-interleukin-6 antibody and the like.
(iv) Interleukin-10 Drug
interleukin-10 and the like.
(v) Interleukin-12/23 Inhibitor
ustekinumab, briakinumab (anti-interleukin-12/23 antibody) and the like.
(vi) B Cell Activation Inhibitor
rituxan, benrista and the like.
(vii) Co-Stimulatory Molecules Related Protein Drug
abatacept and the like.
(II) Non-Protein Drug
(i) MAPK Inhibitor
BMS-582949 and the like.
(ii) Gene Modulator
inhibitor of molecule involved in signal transduction, such as NF-κ, NF-κB, IKK-1, IKK-2, AP-1 and the like, and the like.
(iii) Cytokine Production Inhibitor
iguratimod, tetomilast and the like.
(iv) TNF-α converting enzyme inhibitor
(v) interleukin-1β converting enzyme inhibitor
belnacasan and the like.
(vi) Interleukin-6 Antagonist
HMPL-004 and the like.
(vii) Interleukin-8 Inhibitor
IL-8 antagonist, CXCR1 & CXCR2 antagonist, reparixin and the like.
(viii) Chemokine Antagonist
CCR9 antagonist (vercirnon (vercirnon sodium), CCX025, N-{4-chloro-2-[(1-oxidepyridin-4-yl)carbonyl]phenyl}-4-(propan-2-yloxy)benzenesulfonamide), MCP-1 antagonist and the like.
(ix) Interleukin-2 Receptor Antagonist
denileukin, diftitox and the like.
(x) therapeutic vaccines
TNF-α vaccine and the like.
(xi) Gene Therapy Drug
gene therapy drugs aiming at promoting the expression of gene having an anti-inflammatory action such as interleukin-4, interleukin-10, soluble interleukin-1 receptor, soluble TNF-α receptor and the like.
(xii) Antisense Compound
ISIS 104838 and the like.

(4) Integrin Inhibitor
natalizumab, vedolizumab, AJM300, TRK-170, E-6007 and the like.

(5) Immunomodulator (Immunosuppressant)
methotrexate, cyclophosphamide, MX-68, atiprimod dihydrochloride, abatacept, CKD-461, rimexolone, cyclosporine, tacrolimus, gusperimus, azathiopurine, anti-lymphocyte serum, freeze-dried sulfonated normal immunoglobulin, erythropoietin, colony stimulating factor, interleukin, interferon and the like.

(6) Proteasome Inhibitor
velcade and the like.

(7) JAK Inhibitor
tofacitinib and the like.

(8) Steroid
dexamethasone, hexestrol, methimazole, betamethasone, triamcinolone, triamcinolone acetonide, fluocinonide, fluocinolone acetonide, predonisolone, methylpredonisolone, cortisone acetate, hydrocortisone, fluorometholone, beclomethasone dipropionate, estriol and the like.

(9) Angiotensin Converting Enzyme Inhibitor
enalapril, captopril, ramipril, lisinopril, cilazapril, perindopril and the like.

(10) Angiotensin II Receptor Antagonist
candesartan cilexetil, valsartan, irbesartan, olmesartan, eprosartan and the like.

(11) Diuretic Drug
hydrochlorothiazide, spironolactone, furosemide, indapamide, bendrofluazide, cyclopenthiazide and the like.

(12) Cardiotonic Drug
digoxin, dobutamine and the like.

(13) β Receptor Antagonist
carvedilol, metoprolol, atenolol and the like.

(14) Ca Sensitizer
caldaret hydrate and the like.

(15) Ca Channel Antagonist
nifedipine, diltiazem, verapamil and the like.

(16) Anti-Platelet Drug, Anticoagulator
heparin, aspirin, warfarin and the like.

(17) HMG-CoA Reductase Inhibitor
atorvastatin, simvastatin and the like.

(18) Contraceptive (i) Sex Hormone or Derivatives Thereof
    gestagen or a derivative thereof (progesterone, 17α-hydroxy progesterone, medroxyprogesterone, medroxyprogesterone acetate, norethisterone, norethisterone enanthate, norethindrone, norethindrone acetate, norethynodrel, levonorgestrel, norgestrel, ethynodiol diacetate, desogestrel, norgestimate, gestodene, progestin, etonogestrel, drospirenone, dienogest, trimegestone, nestorone, chlormadinone acetate, mifepristone, nomegestrol acetate, tosagestin, TX-525, ethinylestradiol/TX525) or a combination agent of a gestagen or a derivative thereof and an estrogen or a derivative thereof (estradiol, estradiol benzoate, estradiol cypionate, estradiol dipropionate, estradiol enanthate, estradiol hexahydrobenzoate, estradiol phenylpropionate, estradiol undecanoate, estradiol valerate, estrone, ethinylestradiol, mestranol) and the like.
(ii) Antiestrogen
    ormeloxifene, mifepristone, Org-33628 and the like.
(iii) Spermatocide
    ushercell and the like.
(19) Others
(i) T Cell Inhibitors
(ii) Inosine Monophosphate Dehydrogenase (IMPDH) Inhibitor
    mycophenolate mofetil and the like.
(iii) Adhesion Molecule Inhibitor
    alicaforsen sodium, selectin inhibitor, ELAM-1 inhibitor, VCAM-1 inhibitor, ICAM-1 inhibitor and the like.
(iv) Thalidomide
(v) Cathepsin Inhibitor
(vi) Matrix Metalloprotease (MMPs) Inhibitor
    V-85546 and the like.
(vii) Glucose-6-Phosphate Dehydrogenase Inhibitor
(viii) Dihydroorotate Dehydrogenase (DHODH) Inhibitor
(ix) Phosphodiesterase IV (PDE IV) Inhibitor
    roflumilast, apremilast, CG-1088 and the like.
(x) Phospholipase $A_2$ Inhibitor
(xi) iNOS Inhibitor
    VAS-203 and the like.
(xii) Microtubule Stimulating Drug
    paclitaxel and the like.
(xiii) Microtuble Inhibitor
    reumacon and the like.
(xiv) MHC Class II Antagonist
(xv) Prostacyclin Agonist
    iloprost and the like.
(xvi) CD4 Antagonist
    zanolimumab and the like.
(xvii) CD23 Antagonist
(xviii) LTB4 Receptor Antagonist
    DW-1350 and the like.
(xix) 5-Lipoxygenase Inhibitor
    zileuton and the like.
(xx) Cholinesterase Inhibitor
    galanthamine and the like.
(xxi) Tyrosine Kinase Inhibitor
    Tyk2 inhibitor (WO2010/142752) and the like.
(xxii) Cathepsin B Inhibitor
(xxiii) Adenosine Deaminase Inhibitor
    pentostatin and the like.
(xxiv) Osteogenesis Stimulator
(xxv) Dipeptidylpeptidase Inhibitor
(xxvi) Collagen Agonist
(xxvii) Capsaicin Cream
(xxviii) Hyaluronic Acid Derivative
    synvisc (hylan G-F 20), orthovisc and the like.
(xxix) Glucosamine Sulfate
(xxx) amiprilose
(xxxi) CD-20 inhibitor
    rituximab, ibritumomab, tositumomab, ofatumumab and the like.
(xxxii) BAFF Inhibitor
    belimumab, tabalumab, atacicept, blisibimod and the like.
(xxxiii) CD52 Inhibitor
    alemtuzumab and the like.

Other concomitant drugs besides the above-mentioned include for example, antibacterial agent, antifungal agent, antiprotozoal agent, antibiotic, antitussive and expectorant drug, sedative, anesthetic, antiulcer drug, antiarrhythmic agent, hypotensive diuretic drug, anticoagulant, tranquilizer, antipsychotic, antitumor drug, hypolipidemic drug, muscle relaxant, antiepileptic drug, antidepressant, antiallergic drug, cardiac stimulants, therapeutic drug for arrhythmia, vasodilator, vasoconstrictor, therapeutic drug for diabetes, antinarcotic, vitamin, vitamin derivative, antiasthmatic, therapeutic agent for pollakisuria/anischuria, therapeutic agent for atopic dermatitis, therapeutic agent for allergic rhinitis, hypertensor, endotoxin-antagonist or -antibody, signal transduction inhibitor, inhibitor of inflammatory mediator activity, antibody to inhibit inflammatory mediator activity, inhibitor of anti-inflammatory mediator activity, antibody to inhibit anti-inflammatory mediator activity and the like. Specific examples thereof include the following.
(1) Antibacterial Agent
(i) Sulfa Drug
    sulfamethizole, sulfisoxazole, sulfamonomethoxine, salazosulfapyridine, silver sulfadiazine and the like.
(ii) Quinolone Antibacterial Agent
    nalidixic acid, pipemidic acid trihydrate, enoxacin, norfloxacin, ofloxacin, tosufloxacin tosylate, ciprofloxacin hydrochloride, lomefloxacin hydrochloride, sparfloxacin, fleroxacin and the like.
(iii) Antiphthisic
    isoniazid, ethambutol (ethambutol hydrochloride), p-aminosalicylic acid (calcium p-aminosalicylate), pyrazinamide, ethionamide, protionamide, rifampicin, streptomycin sulfate, kanamycin sulfate, cycloserine and the like.
(iv) Antiacidfast Bacterium Drug
    diaphenylsulfone, rifampicin and the like.
(v) Antiviral Drug
    idoxuridine, acyclovir, vidarabine, gancyclovir and the like.
(vi) anti-HIV agent
    zidovudine, didanosine, zalcitabine, indinavir sulfate ethanolate, ritonavir and the like.
(vii) Antispirochetele
(viii) Antibiotic
    tetracycline hydrochloride, ampicillin, piperacillin, gentamicin, dibekacin, kanendomycin, lividomycin, tobramycin, amikacin, fradiomycin, sisomicin, tetracycline, oxytetracycline, rolitetracycline, doxycycline, ampicillin, piperacillin, ticarcillin, cephalothin, cephapirin, cephaloridine, cefaclor, cephalexin, cefroxadine, cefadroxil, cefamandole, cefotoam, cefuroxime, cefotiam, cefotiam hexetil, cefuroxime axetil, cefdinir, cefditoren pivoxil, ceftazidime, cefpiramide, cefsulodin, cefmenoxime, cefpodoxime proxetil, cefpirome, cefozopran, cefepime, cefsulodin, cefmenoxime, cefmetazole, cefminox, cefoxitin, cefbuperazone, latamoxef, flomoxef, cefazolin, cefotaxime, cefoperazone, ceftizoxime, moxalactam, thienamycin, sulfazecin, aztreonam or a salt a salt thereof, griseofulvin, lankacidin-group [Journal of Antibiotics (J. Antibiotics), 38, 877-885 (1985)], azole compound [2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3(2H,4H)-1,2,4-triazolone, fluconazole, itraconazole and the like] and the like.

(2) Antifungal Agent (i) polyethylene antibiotic (e.g., amphotericin B, nystatin, trichomycin)

(ii) griseofulvin, pyrrolnitrin and the like (iii) cytosine metabolism antagonist (e.g., flucytosine)

(iv) imidazole derivative (e.g., econazole, clotrimazole, miconazole nitrate, bifonazole, croconazole)

(v) triazole derivative (e.g., fluconazole, itraconazole)

(vi) thiocarbamic acid derivative (e.g., trinaphthol) and the like.

(3) Antiprotozoal Agent metronidazole, tinidazole, diethylcarbamazine citrate, quinine hydrochloride, quinine sulfate and the like.

(4) Antitussive and Expectorant Drug ephedrine hydrochloride, noscapine hydrochloride, codeine phosphate, dihydrocodeine phosphate, isoproterenol hydrochloride, ephedrine hydrochloride, methylephedrine hydrochloride, noscapine hydrochloride, alloclamide, chlophedianol, picoperidamine, cloperastine, protokylol, isoproterenol, salbutamol, terbutaline oxymetebanol, morphine hydrochloride, dextromethorfan hydrobromide, oxycodone hydrochloride, dimemorphan phosphate, tipepidine hibenzate, pentoxyverine citrate, clofedanol hydrochloride, benzonatate, guaifenesin, bromhexine hydrochloride, ambroxol hydrochloride, acetylcysteine, ethyl cysteine hydrochloride, carbocysteine and the like.

(5) Sedative chlorpromazine hydrochloride, atropine sulfate, phenobarbital, barbital, amobarbital, pentobarbital, thiopental sodium, thiamylal sodium, nitrazepam, estazolam, flurazepam, haloxazolam, triazolam, flunitrazepam, bromovalerylurea, chloral hydrate, triclofos sodium and the like.

(6) Anesthetic (6-1) Local Anesthetic cocaine hydrochloride, procaine hydrochloride, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine and the like. (6-2) general anesthetic (i) inhalation anesthetic (e.g., ether, halothane, nitrous oxide, isoflurane, enflurane), (ii) intravenous anesthetic (e.g., ketamine hydrochloride, droperidol, thiopental sodium, thiamylal sodium, pentobarbital) and the like.

(7) Antiulcer Drug histidine hydrochloride, lansoprazole, metoclopramide, pirenzepine, cimetidine, ranitidine, famotidine, urogastrone, oxethazaine, proglumide, omeprazole, sucralfate, sulpiride, cetraxate, gefarnate, aldioxa, teprenone, prostaglandin and the like.

(8) Antiarrhythmic Agent (i) sodium channel blocker (e.g., quinidine, procainamide, disopyramide, ajmaline, lidocaine, mexiletine, phenytoin), (ii) β-blocker (e.g., propranolol, alprenolol, bufetolol hydrochloride, oxprenolol, atenolol, acebutolol, metoprolol, bisoprolol, pindolol, carteolol, arotinolol hydrochloride), (iii) potassium channel blocker (e.g., amiodarone), (iv) calcium channel blocker (e.g., verapamil, diltiazem) and the like.

(9) Hypotensive Diuretic Drug hexamethonium bromide, clonidine hydrochloride, hydrochlorothiazide, trichlormethiazide, furosemide, ethacrynic acid, bumetanide, mefruside, azosemide, spironolactone, potassium canrenoate, triamterene, amiloride, acetazolamide, D-mannitol, isosorbide, aminophylline and the like.

(10) Anticoagulant heparin sodium, sodium citrate, activated protein C, tissue factor pathway inhibitor, antithrombin III, dalteparin sodium, warfarin potassium, argatroban, gabexate, sodium citrate, ozagrel sodium, ethyl icosapentate, beraprost sodium, alprostadil, ticlopidine hydrochloride, pentoxifylline, dipyridamole, tisokinase, urokinase, streptokinase and the like.

(11) Tranquilizer diazepam, lorazepam, oxazepam, chlordiazepoxide, medazepam, oxazolam, cloxazolam, clotiazepam, bromazepam, etizolam, fludiazepam, hydroxyzine and the like.

(12) Antipsychotic chlorpromazine hydrochloride, prochlorperazine, trifluoperazine, thioridazine hydrochloride, perphenazine maleate, fluphenazine enanthate, prochlorperazine maleate, levomepromazine maleate, promethazine hydrochloride, haloperidol, bromperidol, spiperone, reserpine, clocapramine hydrochloride, sulpiride, zotepine and the like.

(13) Antitumor Drug

6-O—(N-chloroacetylcarbamoyl)fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, bleomycin hydrochloride, peplomycin sulfate, vincristine sulfate, vinblastine sulfate, irinotecan hydrochloride, cyclophosphamide, melphalan, busulfan, thiotepa, procarbazine hydrochloride, cisplatin, azathioprine, mercaptopurine, tegafur, carmofur, cytarabine, methyltestosterone, testosterone propionate, testosterone enanthate, mepitiostane, fosfestrol, chlormadinone acetate, leuprorelin acetate, buserelin acetate and the like.

(14) Hypolipidemic Drug clofibrate, ethyl 2-chloro-3-[4-(2-methyl-2-phenylpropoxy)phenyl]propionate [Chemical and Pharmaceutical Bulletin (Chem. Pharm. Bull), 38, 2792-2796 (1990)], pravastatin, simvastatin, probucol, bezafibrate, clinofibrate, nicomol, cholestyramine, dextran sulfate sodium and the like.

(15) Muscle Relaxant pridinol, tubocurarine, pancuronium, tolperisone hydrochloride, chlorphenesin carbamate, baclofen, chlormezanone, mephenesin, chlorzoxazone, eperisone, tizanidine and the like.

(16) Antiepileptic Drug phenytoin, ethosuximide, acetazolamide, chlordiazepoxide, trimethadione, carbamazepine, phenobarbital, primidone, sulthiame, sodium valproate, clonazepam, diazepam, nitrazepam and the like.

(17) Antidepressant imipramine, clomipramine, noxiptiline, phenelzine, amitriptyline hydrochloride, nortriptyline hydrochloride, amoxapine, mianserin hydrochloride, maprotiline hydrochloride, sulpiride, fluvoxamine maleate, trazodone hydrochloride and the like.

(18) Antiallergic Drug diphenhydramine, chlorpheniramine, tripelennamine, metodilamine, clemizole, diphenylpyraline, methoxyphenamine, sodium cromoglicate, tranilast, repirinast, amlexanox, ibudilast, ketotifen, terfenadine, mequitazine, azelastine hydrochloride, epinastine, ozagrel hydrochloride, pranlukast hydrate, seratrodast and the like.

(19) Cardiac Stimulants trans-n-oxocamphor, terephyllol, aminophylline, etilefrine, dopamine, dobutamine, denopamine, aminophylline, vesnarinone, amrinone, pimobendan, ubidecarenone, digitoxin, digoxin, methyldigoxin, lanatoside C, G-strophanthin and the like.

(20) Vasodilator oxyfedrine, diltiazem, tolazoline, hexobendine, bamethan, clonidine, methyldopa, guanabenz and the like.

(21) Vasoconstrictor dopamine, dobutamine denopamine and the like.

(22) Hypotensive Diuretic hexamethonium bromide, pentolinium, mecamylamine, ecarazine, clonidine, diltiazem, nifedipine and the like.

(23) Therapeutic Drug for Diabetes tolbutamide, chlorpropamide, acetohexamide, glibenclamide, tolazamide, acarbose, epalrestat, troglitazone, glucagon, glymidine, glipizide, phenformin, buformin, metformin and the like.

(24) Antinarcotic levallorphan, nalorphine, naloxone or a salt thereof and the like.

(25) Liposoluble Vitamins (i) vitamin A: vitamin $A_1$, vitamin $A_2$ and retinol palmitate (ii) vitamin D: vitamin $D_1$, $D_2$, $D_3$, $D_4$ and $D_5$ (iii) vitamin E: α-tocopherol, β-tocopherol, γ-tocopherol, δ-tocopherol, dl-α-tocopherol nicotinate (iv) vitamin K: vitamin $K_1$, $K_2$, $K_3$ and $K_4$ (v) folic acid (vitamin M) and the like.

(26) Vitamin Derivative various derivatives of vitamins, for example, vitamin $D_3$ derivatives such as 5,6-trans-cholecalciferol, 2,5-hydroxycholecalciferol, 1-α-hydroxycholecalciferol, calcipotriol and the like, vitamin $D_2$ derivatives such as 5,6-transergocalciferol and the like, and the like.

(27) Antiasthmatic isoprenaline hydrochloride, salbutamol sulfate, procaterol hydrochloride, terbutaline sulfate, trimetoquinol hydrochloride, tulobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglicate, tranilast, repirinast, amlexanox, ibudilast, ketotifen, terfenadine, mequitazine, azelastine, epinastine, ozagrel hydrochloride, pranlkast hydrate, seratrodast, dexamethasone, prednisolone, hydrocortisone, hydrocortisone sodium succinate, beclometasone dipropionate, ciclesonide and the like.

(28) Therapeutic Agent for Pollakisuria/Anischuria flavoxate hydrochloride and the like.

(29) Therapeutic Agent for Atopic Dermatitis sodium cromoglicate and the like.

(30) Therapeutic Agent for Allergic Rhinitis sodium cromoglicate, chlorpheniramine maleate, alimemazine tartrate, clemastine fumarate, homochlorcyclizine hydrochloride, fexofenadine, mequitazine, ketotifen fumarate, cetirizine hydrochloride, oxatomide, azelastine, ebastine, epinastine hydrochloride, loratadine and the like.

(31) Hypertensor dopamine, dobutamine, denopamine, digitoxin, digoxin, methyldigoxin, lanatoside C, G-strophanthin and the like.

(32) Others hydroxycam, diacerein, megestrol acetate, nicergoline, prostaglandins and the like.

For combined use, the administration time of the compound of the present invention and the concomitant drug is not restricted, and the compound of the present invention or the concomitant drug can be administered to an administration subject simultaneously, or may be administered at different times. The dosage of the concomitant drug may be determined according to the dose clinically used, and can be appropriately selected depending on an administration subject, administration route, disease, combination and the like.

The administration form of the combined use is not particularly limited, and the compound of the present invention and a concomitant drug only need to be combined on administration. Examples of such administration mode include the following:

(1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The mixing ratio of the compound of the present invention and a concomitant drug in the combination agent of the present invention can be appropriately selected based on the subject of administration, administration route, disease and the like.

For example, while the content of the compound of the present invention in the combination agent of the present invention varies depending on the preparation form, it is generally about 0.01-100 wt %, preferably about 0.1-50 wt %, more preferably about 0.5-20 wt %, of the whole preparation.

The content of the concomitant drug in the combination agent of the present invention varies depending on the preparation form, and generally about 0.01 to 100% by weight, preferably about 0.1 to 50% by weight, further preferably about 0.5 to 20% by weight, of the entire preparation.

While the content of the additive such as a carrier and the like in the combination agent of the present invention varies depending on the form of a preparation, it is generally about 1 to 99.99% by weight, preferably about 10 to 90% by weight, based on the preparation.

When the compound of the present invention and the concomitant drug are separately prepared, the same content may be adopted.

The dose varies depending on the kind of the compound of the present invention, administration route, symptom, age of patients and the like. For example, for oral administration to patients (body weight about 60 kg) with inflammatory bowel disease (IBD), about 0.1 mg/kg body weight—about 30 mg/kg body weight, preferably about 1 mg/kg body weight-20 mg/kg body weight, of compound (I), compound (I') or compound (I") can be administered once to several portions per day.

The dose of the medicament of the present invention as a sustained-release preparation varies depending on the kind and content of compound (I), compound (I') or compound (I"), dosage form, period of sustained drug release, subject animal of administration (e.g., mammals such as mouse, rat, hamster, guinea pig, rabbit, cat, dog, bovine, horse, swine, sheep, monkey, human and the like), and administration object. For example, for application by parenteral administration, about 0.1 to about 100 mg of compound (I), compound (I') or compound (I") needs to be released from the administered preparation per 1 week.

Any amount of the concomitant drug can be adopted as long as the side effects do not cause a problem. The daily dosage in terms of the concomitant drug varies depending on the severity, age, sex, body weight, sensitivity difference of the subject, administration period, interval, and nature, pharmacology, kind of the pharmaceutical preparation, kind of effective ingredient, and the like, and not particularly restricted, and the amount of a drug is, in the case of oral administration for example, generally about 0.001 to 2000 mg, preferably about 0.01 to 500 mg, further preferably about 0.1 to 100 mg, per 1 kg of a mammal and this is generally administered once to 4-times divided in a day.

When the combination agent of the present invention is administered, the compound of the present invention and the concomitant drug can be administered simultaneously, or may be administered in a staggered manner. When administered at a time interval, the interval varies depending on the effective ingredient, dosage form and administration method, and, for example, when the concomitant drug is administered first, a method in which the compound of the present invention is administered within time range of from 1 minute to 3 days, preferably from 10 minutes to 1 day, more preferably from 15 minutes to 1 hour, after administration of the concomitant drug is an example. When the compound of the present invention is administered first, a method in which the concomitant drug is administered within time range of from 1 minute to 1 day, preferably from 10 minutes to 6 hours, more preferably from 15 minutes to 1 hour after administration of the compound of the present invention is an example.

EXAMPLES

The present invention is explained in more detail in the following by referring to Examples, Formulation Examples and Experimental Examples, which are not to be construed as limitative and may be modified without departing from the scope of the invention.

Unless particularly specified, the elution in column chromatography in the Examples was performed under observation by TLC (Thin Layer Chromatography). For TLC observation, 60F254 manufactured by Merck was used as a TLC plate, and the solvent used as an elution solvent for column chromatography was used as a developing solvent. For detection, a UV detector was adopted. In silica gel column chromatography, NH means use of aminopropylsilane-bonded silica gel, and Diol means use of 3-(2,3-dihydroxypropoxy)propylsilane-bonded silica gel. In preparative HPLC (high performance liquid chromatography), C18 means use of octadecyl-bonded silica gel. The ratios of elution solvents are volume mixing ratios, unless otherwise specified. The room temperature generally means a temperature about 10° C. to 35° C. For drying extracts, sodium sulfate or magnesium sulfate was used.

In the chemical structure formulas described in Examples, the wavy line bonded to the asymmetric carbon

means one stereochemical structure which is not determined, and the solid line means a mixture of two stereochemical structure.

The abbreviations in the present specification or the Examples mean as follows.

LC: liquid chromatography
MS: mass analysis spectrum
API: atmospheric pressure ionization method
M: molecular weight of the compound
NMR: nuclear magnetic resonance spectrum
Hz: hertz
J: coupling constant
m: multiplet
q: quartet
t: triplet
d: doublet
s: singlet
dt: double triplet
sxt: sextet
brs: broad singlet
ADDP: 1,1'-(azodicarbonyl)dipiperidine
BINAP: 2,2'-bis(diphenylphosphino)-1,1'-binaphthyl
Boc: tert-butyloxycarbonyl group
Boc$_2$O: di-tert-butyl carbonate
CDI: carbonyldiimidazole
COMU: 1-[(1-(cyano-2-ethoxy-2-oxoethylideneaminooxy)-dimethylamino-morpholino)]carbenium hexafluorophosphate
DBU: 1,8-diazabicyclo[5.4.0]undec-7-ene
DIEA: diisopropylethylamine
DMA: dimethylacetamide
DMAP: 4-dimethylaminopyridine
DMF: N,N-dimethylformamide
DMSO: dimethyl sulfoxide
DPPA: diphenylphosphoryl azide
EtOH: ethanol
HATU: 2-(1H-7-azabenzotriazol-1-yl)-1,1,3,3-tetramethyluronium hexafluorophosphorate
HMDS: 1,1,1,2,2,2-hexamethyldisilane
HOBt: 1H-benzo[d][1,2,3]triazol-1-ol hydrate
IPE: diisopropyl ether
MeOH: methanol
N: normal concentration
NaHMDS: sodium bis(trimethylsilyl)amide
n-BuLi: 1.6M n-butyllithium/hexane solution
NMP: N-methyl-2-pyrrolidone
Pd(PPh$_3$)$_4$: tetrakis(triphenylphosphine)palladium(0)
Pd$_2$(dba)$_3$: tris(dibenzylideneacetone)dipalladium(0)
t-: tert-
T3P: 1.6M 2,4,6-tripropyl-1,3,5,2,4,6-trioxatriphosphorinane-2,4,6-trioxide/ethyl acetate solution or DMF solution
TEA: triethylamine
TFA: trifluoroacetic acid
THF: tetrahydrofuran
TMSCl: trimethylsilyl chloride, trimethylsilane chloride
WSC: N$^1$-((ethylimino)methylene)-N$^3$,N$^3$-dimethylpropane-1,3-diamine hydrochloride
XANTPHOS: 4,5-bis(diphenylphosphino)-9,9-dimethylxanthene

Example 1

N-(3,5-difluoro-4-(trimethylsilyl)phenyl)-2-(((6-oxopyrimidin-1(6H)-yl)acetyl)amino)-2-(tetrahydro-2H-pyran-4-yl)acetamide (Step 1)

To a solution of 1,3-difluoro-5-nitrobenzene (3 g, 18.86 mmol) in THF (60 mL) was added trimethylsilyl chloride (7.23 mL, 56.57 mmol) at −78° C. under nitrogen atmosphere. To the reaction solution was added sodium hexamethyldisilazide (19.85 mL, 37.71 mmol), and the mixture was kept at −75° C. or lower. The reaction solution was stirred for 1 hr, and water and ethyl acetate were added thereto. The organic layer was separated, and the aqueous layer was extracted with ethyl acetate. The organic layer was dried over magnesium sulfate, and the solvent was evaporated under reduced pressure. The obtained residue was purified by silica gel column chromatography (solvent; hexane) to give (2,6-difluoro-4-nitrophenyl)trimethylsilane (3.51 g, 15.18 mmol, 80%) as a colorless oil.

$^1$H NMR (300 MHz, CDCl$_3$): δ 0.42 (9H, s), 7.61-7.71 (2H, m).

(Step 2)

A solution of (2,6-difluoro-4-nitrophenyl)trimethylsilane (3.5 g, 15.13 mmol) and 10% palladium on carbon (350 mg, 0.16 mmol, 50% wet) in MeOH (70 mL) was stirred at room temperature for 5 hr under hydrogen atmosphere (1 atm). The catalyst was removed by filtration, and the filtrate was concentrated under reduced pressure. The obtained residue was purified by silica gel column chromatography (solvent; ethyl acetate/hexane) to give 3,5-difluoro-4-(trimethylsilyl)aniline (2.50 g, 12.42 mmol, 82%) as a pale yellow oil.

$^1$H NMR (300 MHz, CDCl$_3$): δ 0.30 (9H, s), 3.88 (2H, brs), 5.99-6.16 (2H, m).

(Step 3)

A solution of 2-(3,6-dihydro-2H-pyran-4-yl)-4,4,5,5-tetramethyl-1,3,2-dioxaborolane (3 g, 14.28 mmol), 2-oxoacetic acid hydrate (1.315 g, 14.28 mmol) and diallylamine (1.779 mL, 14.28 mmol) in acetonitrile (20 mL) was stirred overnight at room temperature. The reaction mixture was concentrated under reduced pressure, and the precipitate was washed with a mixed solvent of ethyl acetate/hexane to give 2-(diallylamino)-2-(3,6-dihydro-2H-pyran-4-yl)acetic acid (1.47 g, 6.19 mmol, 43.4%) as a pale yellow solid.

$^1$H NMR (300 MHz, DMSO-d$_6$): δ 1.87-2.04 (1H, m), 2.07-2.23 (1H, m), 3.10 (2H, dd, J=14.5, 7.0 Hz), 3.26 (2H, brs), 3.56-3.74 (2H, m), 3.84 (1H, brs), 4.06 (2H, brs), 5.01-5.29 (4H, m), 5.68 (1H, brs), 5.71-5.86 (2H, m).

(Step 4)

To a solution of 3,5-difluoro-4-(trimethylsilyl)aniline (0.933 g, 4.64 mmol), 2-(diallylamino)-2-(3,6-dihydro-2H-pyran-4-yl)acetic acid (1.0 g, 4.21 mmol), DMAP (0.566 g, 4.64 mmol) and DIEA (3.68 mL, 21.07 mmol) in ethyl acetate (30 mL) was added T3P (3.72 mL, 6.32 mmol) at room temperature, and the mixture was stirred at 80° C. for 2 hr. To the reaction mixture were added water and ethyl acetate, and the organic layer was separated. The organic layer was dried over sodium sulfate, and the solvent was evaporated under reduced pressure. The obtained residue was purified by silica gel column chromatography (solvent gradient; 3→70% ethyl acetate/hexane) to give 2-(diallylamino)-N-(3,5-difluoro-4-(trimethylsilyl)phenyl)-2-(3,6-dihydro-2H-pyran-4-yl)acetamide (650 mg, 1.546 mmol, 36.7%) as a white solid.

$^1$H NMR (300 MHz, CDCl$_3$): δ 0.34 (9H, t, J=1.3 Hz), 2.01-2.30 (2H, m), 3.11 (2H, dd, J=4.5, 6.6 Hz), 3.31 (2H, dd, J=14.7, 5.7 Hz), 3.68-3.84 (2H, m), 3.88 (1H, s), 4.22 (2H, q, J=2.6 Hz), 5.16-5.33 (4H, m), 5.72-5.93 (3H, m), 6.99-7.13 (2H, m), 9.10 (1H, s).

(Step 5)

A solution of 2-(diallylamino)-N-(3,5-difluoro-4-(trimethylsilyl)phenyl)-2-(3,6-dihydro-2H-pyran-4-yl)acetamide (650 mg, 1.55 mmol), Pd(PPh$_3$)$_4$ (53.6 mg, 0.05 mmol) and 1,3-dimethylbarbituric acid (507 mg, 3.25 mmol) in THF (20 mL) was stirred overnight at room temperature. The reaction mixture was concentrated under reduced pressure, and the obtained residue was purified by silica gel column chromatography (solvent gradient; 3% ethyl acetate/hexane→10% MeOH/ethyl acetate) to give 2-amino-N-(3,5-difluoro-4-(trimethylsilyl)phenyl)-2-(3,6-dihydro-2H-pyran-4-yl)acetamide (540 mg, 1.586 mmol, 103%) as a yellow oil.

$^1$H NMR (300 MHz, CDCl$_3$): δ 0.34 (9H, t, J=1.5 Hz), 1.73 (2H, brs), 2.07-2.16 (1H, m), 2.18-2.39 (1H, m), 3.71-3.86 (2H, m), 4.02 (1H, s), 4.11-4.25 (2H, m), 5.85 (1H, d, J=0.8 Hz), 7.01-7.16 (2H, m), 9.33 (1H, brs).

(Step 6)

A solution of 2-amino-N-(3,5-difluoro-4-(trimethylsilyl)phenyl)-2-(3,6-dihydro-2H-pyran-4-yl)acetamide (540 mg, 1.59 mmol) and 10% palladium on carbon (300 mg, 2.82 mmol) in MeOH (20 mL) was stirred at room temperature for 2 days under hydrogen atmosphere (1 atm). The catalyst was removed by filtration, and the filtrate was concentrated under reduced pressure. The obtained residue was purified by silica gel column chromatography (NH, solvent gradient; 0→10% MeOH/ethyl acetate) to give 2-amino-N-(3,5-difluoro-4-(trimethylsilyl)phenyl)-2-(tetrahydro-2H-pyran-4-yl)acetamide (525 mg, 1.533 mmol, 97%) as a colorless oil.

$^1$H NMR (300 MHz, CDCl$_3$): δ 0.26-0.41 (9H, m), 1.34-1.45 (2H, m), 1.46-1.68 (4H, m), 2.23-2.41 (1H, m), 3.28-3.54 (3H, m), 3.90-4.07 (2H, m), 7.05-7.18 (2H, m), 9.64 (1H, brs).

(Step 7)

A solution of 2-amino-N-(3,5-difluoro-4-(trimethylsilyl)phenyl)-2-(tetrahydro-2H-pyran-4-yl)acetamide (40 mg, 0.12 mmol), HATU (48.9 mg, 0.13 mmol), DIEA (0.022 ML, 0.13 mmol) and 2-(6-oxopyrimidin-1(6H)-yl)acetic acid (19.80 mg, 0.13 mmol) in DMF (4 mL) was stirred at room temperature for 1.5 hr. To the reaction mixture were added water and ethyl acetate, and the organic layer was separated. The organic layer was dried over magnesium sulfate, and the solvent was evaporated under reduced pressure. The obtained residue was purified by silica gel column chromatography (solvent gradient; 0→8% MeOH/ethyl acetate) to give the title compound (36 mg, 0.075 mmol, 64.4%) as white crystals.

MS(API): Calculated 478.6, Found 477.1 (M−H).

$^1$H NMR (300 MHz, DMSO-d$_6$): δ 0.31 (9H, t, J=0.9 Hz), 1.26-1.32 (1H, m), 1.32-1.46 (2H, m), 1.61 (1H, d, J=12.5 Hz), 1.77-2.03 (1H, m), 3.18-3.31 (2H, m), 3.86 (2H, t, J=10.6 Hz), 4.37 (1H, t, J=8.1 Hz), 4.58-4.82 (2H, m), 6.39 (1H, dd, J=6.8, 0.8 Hz), 7.25 (2H, d, J=9.8 Hz), 7.91 (1H, d, J=6.8 Hz), 8.37 (1H, s), 8.73 (1H, d, J=8.3 Hz), 10.59 (1H, s).

Example 2

N-(3,5-difluoro-4-(trimethylsilyl)phenyl)-2-(((5-methyl-1,3,4-oxadiazol-2-yl)acetyl)amino)-2-(tetrahydro-2H-pyran-4-yl)acetamide (Step 1)
To a solution of ethyl 2-(5-methyl-1,3,4-oxadiazol-2-yl)acetate (279 mg, 1.64 mmol) in a mixed solvent of water (2 mL) and THF (1 mL) was added lithium hydroxide monohydrate (68.9 mg, 1.64 mmol), and the mixture was stirred at room temperature for 1 hr. The reaction mixture was concentrated under reduced pressure, and the residue was subjected to azeotropy with toluene to give lithium 2-(5-methyl-1,3,4-oxadiazol-2-yl)acetate (250 mg, 1.689 mmol, 103%) as a white solid.

$^1$H NMR (300 MHz, DMSO-$d_6$): δ 2.41 (3H, s), 3.35 (2H, s).

(Step 2)
A solution of 2-amino-N-(3,5-difluoro-4-(trimethylsilyl)phenyl)-2-(tetrahydro-2H-pyran-4-yl)acetamide (48 mg, 0.14 mmol), HATU (58.6 mg, 0.15 mmol), DIEA (0.027 mL, 0.15 mmol) and lithium 2-(5-methyl-1,3,4-oxadiazol-2-yl)acetate (22.83 mg, 0.15 mmol) in DMF (4 mL) was stirred at room temperature for 1.5 hr. To the reaction mixture were added water and ethyl acetate, and the organic layer was separated. The organic layer was dried over magnesium sulfate, and the solvent was evaporated under reduced pressure. The obtained residue was purified by silica gel column chromatography (solvent gradient; 0→10% MeOH/ethyl acetate) to give the title compound (40 mg, 0.086 mmol, 61.2%) as white crystals.

MS(API): Calculated 466.6, Found 465.1 (M−H).

$^1$H NMR (300 MHz, DMSO-$d_6$): δ 0.31 (9H, t, J=1.3 Hz), 1.17-1.33 (1H, m), 1.33-1.45 (2H, m), 1.50-1.69 (1H, m), 1.84-2.02 (1H, m), 2.46 (3H, s), 3.19-3.30 (2H, m), 3.77-3.91 (2H, m), 3.94 (2H, d, J=2.6 Hz), 4.33 (1H, t, J=8.1 Hz), 7.25 (2H, d, J=9.8 Hz), 8.70 (1H, d, J=8.3 Hz), 10.61 (1H, s).

Example 3

N-((1R)-2-((3,5-difluoro-4-(trimethylsilyl)phenyl)amino)-2-oxo-1-(tetrahydro-2H-pyran-4-yl)ethyl)-3-hydroxy-1,2-oxazole-5-carboxamide A solution of 2-amino-N-(3,5-difluoro-4-(trimethylsilyl)phenyl)-2-(tetrahydro-2H-pyran-4-yl)acetamide (100 mg, 0.29 mmol), COMU (138 mg, 0.32 mmol), DIEA (0.056 mL, 0.32 mmol) and 3-hydroxy-1,2-oxazole-5-carboxylic acid (41.5 mg, 0.32 mmol) in DMF (2 mL) was stirred at room temperature for 2 hr. To the reaction mixture were added water and ethyl acetate, and the organic layer was separated. The organic layer was dried over magnesium sulfate, and the solvent was evaporated under reduced pressure. The obtained residue was purified by silica gel column chromatography (solvent gradient; 0→10% MeOH/ethyl acetate) to give N-(2-((3,5-difluoro-4-(trimethylsilyl)phenyl)amino)-2-oxo-1-(tetrahydro-2H-pyran-4-yl)ethyl)-3-hydroxy-1,2-oxazole-5-carboxamide (107.5 mg, 0.237 mmol, 81%) as white crystals.

The obtained compound (107 mg) was subjected to optical resolution using chiral column chromatography. The preparative fraction having a longer retention time was concentrated to give the title compound (46 mg, 99.4% ee) as a white solid.

MS(API): Calculated 453.5, Found 451.9 (M−H).

$^1$H NMR (300 MHz, DMSO-$d_6$): δ 0.20-0.39 (9H, m), 1.21-1.32 (1H, m), 1.34-1.48 (2H, m), 1.68 (1H, d, J=11.3 Hz), 2.04-2.21 (1H, m), 3.16-3.29 (2H, m), 3.73-3.95 (2H, m), 4.37 (1H, t, J=8.5 Hz), 6.73 (1H, s), 7.25 (2H, d, J=9.8 Hz), 9.02 (1H, d, J=7.9 Hz), 10.68 (1H, s), 11.76 (1H, brs).

purification condition using chiral column chromatography
column: CHIRALPAK AD(ILAK001) 50 mmID×500 mmL
solvent: hexane/EtOH/acetic acid=70/30/0.1
flow rate: 80 mL/min
temperature: 30° C.
detection method: UV 220 nm

Example 4

N-(1-(4,4-difluorocyclohexyl)-2-((3-fluoro-4-(trimethylsilyl)phenyl)amino)-2-oxoethyl)-3-hydroxy-1,2-oxazole-5-carboxamide (Step 1)
A solution of 1-chloro-2-fluoro-4-nitrobenzene (2.63 g, 15 mmol), HMDS (8.12 g, 55.50 mmol) and Pd(PPh$_3$)$_4$ (0.433 g, 0.38 mmol) in xylene (6.5 mL) was stirred at 200° C. for 1 hr under microwave irradiation. To the reaction mixture was added ethyl acetate (about 150 mL), and the insoluble substance was removed by filtration. The filtrate was concentrated under reduced pressure, and the obtained residue was purified by silica gel column chromatography (NH, solvent gradient; 2-5% ethyl acetate/hexane) to give (2-fluoro-4-nitrophenyl)trimethylsilane (3.22 g, 15.10 mmol, 101) as a yellow oil.

$^1$H NMR (300 MHz, CDCl$_3$): δ0.36 (9H, d, J=1.1 Hz), 7.57 (1H, dd, J=8.1, 5.5 Hz), 7.82 (1H, dd, J=8.1, 2.1 Hz), 7.99 (1H, dd, J=8.1, 2.1 Hz).

(Step 2)
A solution of (2-fluoro-4-nitrophenyl)trimethylsilane (3.22 g, 15.10 mmol) and 10% palladium-carbon (1.0 g, 0.47 mmol) in MeOH (65 mL) was stirred at room temperature for 3.5 hr under hydrogen atmosphere (1 atm). The catalyst was removed by filtration, and the filtrate was concentrated under reduced pressure. The obtained residue was purified by silica gel column chromatography (solvent gradient; 2→15% MeOH/ethyl acetate) to give 3-fluoro-4-(trimethylsilyl)aniline (1.89 g, 10.31 mmol, 68.3%) as a colorless oil.

$^1$H NMR (300 MHz, CDCl$_3$): δ0.26 (9H, d, J=0.8 Hz), 3.79 (2H, brs), 6.31 (1H, dd, J=10.6, 2.3 Hz), 6.44 (1H, dd, J=7.9, 1.9 Hz), 7.13 (1H, dd, J=7.9, 6.8 Hz).

(Step 3)
To a solution of methyl 2-(((benzyloxy)carbonyl)amino)-2-(dimethoxyphosphoryl)acetate (2.470 g, 7.46 mmol) in acetonitrile (25 mL) was added DBU (1.113 mL, 7.46 mmol) at room temperature, and the mixture was stirred for 30 min. To the reaction mixture was added a solution of 4,4-difluorocyclohexanone (1 g, 7.46 mmol) in acetonitrile (5 mL) at room temperature, and the mixture was stirred overnight. To the reaction mixture were added water and ethyl acetate, and the organic layer was separated. The organic layer was dried over magnesium sulfate, and the solvent was evaporated under reduced pressure. The obtained residue was crystallized from ethyl acetate/hexane to give methyl 2-(((benzyloxy)carbonyl)amino)-2-(4,4-difluorocyclohexylidene)acetate (2.13 g, 6.28 mmol, 84%) as a colorless solid.

$^1$H NMR (300 MHz, CDCl$_3$): δ1.88-2.17 (4H, m), 2.32-2.57 (2H, m), 2.92 (2H, d, J=6.4 Hz), 3.68-3.86 (3H, m), 5.14 (2H, s), 6.04 (1H, brs), 7.30-7.47 (5H, m).

(Step 4)

To a solution of methyl 2-(((benzyloxy)carbonyl)amino)-2-(4,4-difluorocyclohexylidene)acetate (1 g, 2.95 mmol) in a mixed solvent of THF (10 mL) and MeOH (10.00 mL) was added 1N aqueous sodium hydroxide solution (4.42 mL, 4.42 mmol) at room temperature, and the mixture was stirred overnight. The reaction mixture was concentrated under reduced pressure. To the obtained residue were added water and 1N hydrochloric acid. The precipitate was collected by filtration, and washed with water and hexane to give 2-(((benzyloxy)carbonyl)amino)-2-(4,4-difluorocyclohexylidene)acetic acid (790 mg, 2.428 mmol, 82%) as a pale yellow solid.

$^1$H NMR (300 MHz, DMSO-$d_6$): δ 1.67-2.12 (4H, m), 2.27-2.41 (2H, m), 2.60-2.80 (2H, m), 5.06 (2H, s), 7.07-7.54 (5H, m), 8.94 (1H, s), 12.69 (1H, brs).

(Step 5)

To a solution of 3-fluoro-4-(trimethylsilyl)aniline (225 mg, 1.23 mmol), 2-(((benzyloxy)carbonyl)amino)-2-(4,4-difluorocyclohexylidene)acetic acid (400 mg, 1.23 mmol), DIEA (1.074 mL, 6.15 mmol) and DMAP (165 mg, 1.35 mmol) in ethyl acetate (25 mL) was added T3P (0.723 mL, 1.23 mmol) at room temperature, and the mixture was stirred at 70° C. for 2 hr. To the reaction mixture were added water and ethyl acetate, and the organic layer was separated. The organic layer was dried over sodium sulfate, and the solvent was evaporated under reduced pressure. The obtained residue was purified by silica gel column chromatography (solvent gradient; 3→50% ethyl acetate/hexane) to give a mixture (420 mg) of benzyl (1-(4,4-difluorocyclohexylidene)-2-((3-fluoro-4-(trimethylsilyl)phenyl)amino)-2-oxoethyl)carbamate and benzyl (1-(4,4-difluorocyclohex-1-en-1-yl)-2-((3-fluoro-4-(trimethylsilyl)phenyl)amino)-2-oxoethyl)carbamate. The mixture was directly used in the next step.

(Step 6)

To a solution of a mixture (420 mg) of benzyl (1-(4,4-difluorocyclohexylidene)-2-((3-fluoro-4-(trimethylsilyl)phenyl)amino)-2-oxoethyl)carbamate and benzyl (1-(4,4-difluorocyclohex-1-en-1-yl)-2-((3-fluoro-4-(trimethylsilyl)phenyl)amino)-2-oxoethyl)carbamate in MeOH (25 mL) was added 10% palladium-carbon (91 mg, 0.043 mmol, 50% wet). The mixture was stirred at room temperature for 5 hr under hydrogen atmosphere (1 atm). The catalyst was removed by filtration, and the filtrate was concentrated under reduced pressure. The obtained residue was purified by silica gel column chromatography (NH, solvent gradient; 50→100% ethyl acetate/hexane) to give 2-amino-2-(4,4-difluorocyclohexyl)-N-(3-fluoro-4-(trimethylsilyl)phenyl)acetamide (278 mg, 0.776 mmol, 91%) as a colorless oil.

$^1$H NMR (300 MHz, CDCl$_3$): δ0.26-0.32 (9H, m), 1.36-1.49 (1H, m), 1.59-1.96 (5H, m), 2.05-2.30 (3H, m), 3.46 (1H, d, J=3.4 Hz), 7.20 (1H, dd, J=7.9, 1.9 Hz), 7.28-7.36 (1H, m), 7.48 (1H, dd, J=10.4, 1.7 Hz), 9.60 (1H, brs). (NH$_2$ proton was not observed.)

(Step 7)

A solution of 2-amino-2-(4,4-difluorocyclohexyl)-N-(3-fluoro-4-(trimethylsilyl)phenyl)acetamide (40 mg, 0.11 mmol), DIEA (0.021 mL, 0.12 mmol), 3-hydroxy-1,2-oxazole-5-carboxylic acid (15.84 mg, 0.12 mmol) and COMU (52.6 mg, 0.12 mmol) in DMF (2 mL) was stirred overnight at room temperature. To the reaction mixture were added water and ethyl acetate, and the organic layer was separated. The organic layer was dried over magnesium sulfate, and the solvent was evaporated under reduced pressure. The obtained residue was purified by silica gel column chromatography (solvent gradient; 30-100% ethyl acetate/hexane) to give the title compound (23 mg, 0.049 mmol, 43.9%) as white crystals.

MS(API): Calculated 469.5, Found 468.1 (M−H).

$^1$H NMR (300 MHz, DMSO-$d_6$): δ0.16-0.35 (9H, m), 1.19-1.51 (2H, m), 1.55-1.94 (4H, m), 1.94-2.14 (3H, m), 4.45 (1H, t, J=8.3 Hz), 6.73 (1H, s), 7.25-7.44 (2H, m), 7.53 (1H, d, J=9.8 Hz), 9.02 (1H, d, J=8.3 Hz), 10.51 (1H, s), 11.74 (1H, brs).

Example 5

(3S)—N-(1-(4,4-difluorocyclohexyl)-2-((3-fluoro-4-(trimethylsilyl)phenyl)amino)-2-oxoethyl)-5-oxopyrrolidine-3-carboxamide (Mixture of Two Diastereomers)

(Step 1)

A solution of (S)-1-(4-methoxyphenyl)ethanamine (30 g, 198.41 mmol) and 2-methylenesuccinic acid (25.8 g, 198.41 mmol) in NMP (150 mL) was stirred at 130° C. for 4 hr. To the reaction mixture was added water (400 mL), the mixture was cooled, and the precipitate was collected by filtration to give 1-((S)-1-(4-methoxyphenyl)ethyl)-5-oxopyrrolidine-3-carboxylic acid (46.7 g, 177 mmol, 89%) as a white solid.

(Step 2)

A solution of 1-((S)-1-(4-methoxyphenyl)ethyl)-5-oxopyrrolidine-3-carboxylic acid (38.5 g, 146.23 mmol), benzyl bromide (19.13 mL, 160.85 mmol) and cesium carbonate (52.4 g, 160.85 mmol) in DMF (160 mL) was stirred at room temperature for 45 min. To the reaction mixture were added water and ethyl acetate, and the organic layer was separated. The organic layer was dried over magnesium sulfate, and the solvent was evaporated under reduced pressure. The obtained residue was purified by silica gel column chromatography (solvent gradient; 45→100% ethyl acetate/hexane) to give benzyl (S)-1-((S)-1-(4-methoxyphenyl)ethyl)-5-oxopyrrolidine-3-carboxylate (22.7 g, 64.2 mmol, 44%) and benzyl (R)-1-((S)-1-(4-methoxyphenyl)ethyl)-5-oxopyrrolidine-3-carboxylate (20.46 g, 57.9 mmol, 40%).

Benzyl (S)-1-((S)-1-(4-methoxyphenyl)ethyl)-5-oxopyrrolidine-3-carboxylate $^1$H NMR (300 MHz, CDCl$_3$): δ1.47 (3H, d, J=7.2 Hz), 2.59-2.83 (2H, m), 3.03-3.23 (2H, m), 3.47-3.57 (1H, m), 3.79 (3H, s), 5.14 (2H, s), 5.44 (1H, q, J=7.1 Hz), 6.82-6.89 (2H, m), 7.17-7.24 (2H, m), 7.29-7.43 (5H, m).

Benzyl (R)-1-((S)-1-(4-methoxyphenyl)ethyl)-5-oxopyrrolidine-3-carboxylate $^1$H NMR (300 MHz, CDCl$_3$): δ1.49 (3H, d, J=7.2 Hz), 2.59-2.82 (2H, m), 3.11-3.30 (2H, m), 3.45-3.58 (1H, m), 3.79 (3H, s), 5.07 (2H, d, J=0.8 Hz), 5.44 (1H, q, J=6.9 Hz), 6.80-6.87 (2H, m), 7.15-7.22 (2H, m), 7.22-7.29 (2H, m), 7.30-7.39 (3H, m).

(Step 3)

A solution of benzyl (S)-1-((S)-1-(4-methoxyphenyl)ethyl)-5-oxopyrrolidine-3-carboxylate (22.7 g, 64.23 mmol) and 10% palladium-carbon (2 g, 0.94 mmol, 50% wet) in ethyl acetate (100 mL) was stirred at room temperature for 2 hr under hydrogen atmosphere (1 atm). The catalyst was removed by filtration, and the filtrate was concentrated under reduced pressure to give (S)-1-((S)-1-(4-methoxyphenyl)ethyl)-5-oxopyrrolidine-3-carboxylic acid (14.4 g, 54.7 mmol, 85%) as a white solid.

¹H NMR (300 MHz, CDCl₃): δ1.51 (3H, d, J=7.2 Hz), 2.65-2.85 (2H, m), 3.06-3.16 (1H, m), 3.16-3.26 (1H, m), 3.57 (1H, dd, J=9.4, 5.7 Hz), 3.80 (3H, s), 5.45 (1H, q, J=7.2 Hz), 6.87 (2H, d, J=8.7 Hz), 7.19-7.25 (2H, m).
(Step 4)
A solution of (S)-1-((S)-1-(4-methoxyphenyl)ethyl)-5-oxopyrrolidine-3-carboxylic acid (14.4 g, 54.69 mmol) in TFA (80 mL) was stirred at 80° C. for 4 hr. TFA was removed by subjecting the mixture to azeotropy with toluene to give (S)-5-oxopyrrolidine-3-carboxylic acid (6.78 g, 52.5 mmol, 96%) as a white solid.
¹H NMR (300 MHz, DMSO-d₆): δ2.22-2.42 (2H, m), 3.15-3.37 (2H, m), 3.37-3.50 (1H, m), 7.62 (1H, brs), 12.55 (1H, s).
(Step 5)
A solution of 2-amino-2-(4,4-difluorocyclohexyl)-N-(3-fluoro-4-(trimethylsilyl)phenyl)acetamide (40 mg, 0.11 mmol), COMU (52.6 mg, 0.12 mmol), DIEA (0.021 mL, 0.12 mmol) and (S)-5-oxopyrrolidine-3-carboxylic acid (15.85 mg, 0.12 mmol) in DMF (2 mL) was stirred overnight at room temperature. The precipitate was collected by filtration, and purified by silica gel column chromatography (solvent gradient; 30% ethyl acetate/hexane-15% MeOH/ethyl acetate) to give the title compound (26 mg, 0.055 mmol, 49.6%) as a white powder.
MS(API): Calculated 469.6, Found 468.1 (M−H).
¹H NMR (300 MHz, DMSO-d₆): δ0.16-0.35 (9H, m), 1.25-1.47 (2H, m, J=6.0 Hz), 1.53-1.90 (5H, m), 1.94-2.11 (2H, m), 2.20-2.34 (2H, m), 3.06-3.54 (3H, m), 4.24-4.49 (1H, m), 7.24-7.41 (2H, m), 7.45-7.60 (2H, m), 8.25-8.44 (1H, m), 10.44 (1H, s).

Example 6

N-(2-((3,5-difluoro-4-(trimethylsilyl)phenyl)amino)-2-oxo-1-(tetrahydro-2H-pyran-4-yl)ethyl)-3-hydroxy-N-methyl-1,2-oxazole-5-carboxamide (Step 1)
To 0.5M (4-(bis(trimethylsilyl)amino)phenyl)magnesium chloride THF solution (100 mL, 50.00 mmol) was added TMSCl (7.03 mL, 55.00 mmol) at room temperature, and the mixture was stirred for 30 min. To the reaction solution was added 0.1N hydrochloric acid under ice-cooling, the mixture was stirred for 10 min, and saturated aqueous sodium hydrogencarbonate solution and ethyl acetate were added thereto. The organic layer was separated, and dried over magnesium sulfate, and the solvent was evaporated under reduced pressure. The obtained residue was purified by silica gel column chromatography (solvent gradient; 5-30% ethyl acetate/hexane) to give 4-(trimethylsilyl)aniline (6.51 g, 39.4 mmol, 79%) as a yellow oil.
¹H NMR (300 MHz, DMSO-d₆): δ0.09-0.19 (9H, m), 5.14 (2H, s), 6.49-6.60 (2H, m), 7.09-7.19 (2H, m).
(Step 2)
A solution of 2-(3,6-dihydro-2H-pyran-4-yl)-4,4,5,5-tetramethyl-1,3,2-dioxaborolane (1.5 g, 7.14 mmol), glyoxylic acid monohydrate (0.657 g, 7.14 mmol) and N-methylbenzylamine (0.917 mL, 7.14 mmol) in acetonitrile (15 mL) was stirred overnight at room temperature. The reaction solution was concentrated under reduced pressure to give 2-(benzyl(methyl)amino)-2-(3,6-dihydro-2H-pyran-4-yl)acetic acid (810.2 mg, 3.10 mmol, 43.4%) as a pale yellow solid.
¹H NMR (300 MHz, DMSO-d₆): δ1.90-2.32 (5H, m), 3.60 (2H, s), 3.63-3.73 (3H, m), 4.00-4.14 (2H, m), 5.79 (1H, brs), 7.10-7.50 (5H, m).
(Step 3)
To a solution of 2-(benzyl(methyl)amino)-2-(3,6-dihydro-2H-pyran-4-yl)acetic acid (800 mg, 3.06 mmol), DIEA (2.423 mL, 13.91 mmol), 3,5-difluoro-4-(trimethylsilyl)aniline (560 mg, 2.78 mmol) and DMAP (357 mg, 2.92 mmol) in ethyl acetate (20 mL) was added T3P (2.61 mL, 4.17 mmol) at room temperature, and the mixture was stirred at 80° C. for 5 hr. To the reaction mixture were added water and ethyl acetate, and the organic layer was separated. The organic layer was dried over magnesium sulfate, and the solvent was evaporated under reduced pressure. The obtained residue was purified by silica gel column chromatography (solvent gradient; 0→20% ethyl acetate/hexane) to give 2-(benzyl(methyl)amino)-N-(3,5-difluoro-4-(trimethylsilyl)phenyl)-2-(3,6-dihydro-2H-pyran-4-yl)acetamide (1.00 g, 2.249 mmol, 81%) as a yellow oil.
¹H NMR (300 MHz, CDCl₃): δ0.34 (9H, t, J=1.3 Hz), 2.17 (2H, s), 2.22 (3H, s), 3.48-3.66 (3H, m), 3.69-3.88 (2H, m), 4.18-4.26 (2H, m), 5.91 (1H, s), 7.03-7.12 (2H, m), 7.28-7.43 (5H, m), 9.09 (1H, s).
(Step 4)
A solution of 2-(benzyl(methyl)amino)-N-(3,5-difluoro-4-(trimethylsilyl)phenyl)-2-(3,6-dihydro-2H-pyran-4-yl)acetamide (1.0 g, 2.25 mmol) and 10% palladium-carbon (100 mg, 0.047 mmol, 50% wet) in MeOH (20 mL) was stirred at room temperature for 5 hr under hydrogen atmosphere (1 atm). The catalyst was removed by filtration, and the filtrate was concentrated under reduced pressure. The obtained residue was purified by silica gel column chromatography (NH, solvent; ethyl acetate/hexane) to give N-(3,5-difluoro-4-(trimethylsilyl)phenyl)-2-(methylamino)-2-(tetrahydro-2H-pyran-4-yl)acetamide (759.5 mg, 2.131 mmol, 95%) as a yellow oil.
¹H NMR (300 MHz, CDCl₃): δ0.34 (9H, t, J=1.3 Hz), 1.35-1.54 (3H, m), 1.59-1.65 (1H, m), 2.00-2.13 (1H, m), 2.17 (1H, s), 2.46 (3H, s), 2.92 (1H, d, J=4.9 Hz), 3.27-3.45 (2H, m), 3.87-4.09 (2H, m), 7.06-7.20 (2H, m), 9.40 (1H, brs).
(Step 5)
To a solution of N-(3,5-difluoro-4-(trimethylsilyl)phenyl)-2-(methylamino)-2-(tetrahydro-2H-pyran-4-yl)acetamide (755 mg, 2.12 mmol), DIEA (0.724 mL, 4.24 mmol) and 3-hydroxy-1,2-oxazole-5-carboxylic acid (328 mg, 2.54 mmol) in DMF (15 mL) was added COMU (1088 mg, 2.54 mmol) at 0° C., and the mixture was stirred at room temperature for 5 hr. To the reaction mixture were added water and ethyl acetate, and the organic layer was separated. The organic layer was dried over magnesium sulfate, and the solvent was evaporated under reduced pressure. The obtained residue was purified by silica gel column chromatography (solvent gradient; 0-50% ethyl acetate/hexane) to give the title compound (740.7 mg, 1.584 mmol, 74.8%) as a colorless amorphous solid.
MS(API): Calculated 467.5, Found 466.0 (M−H).
¹H NMR (300 MHz, DMSO-d₆): δ0.31 (9H, s), 1.09-1.62 (4H, m), 2.16-2.37 (1H, m), 3.06-3.22 (3H, m), 3.26-3.43 (2H, m), 3.77-3.93 (2H, m), 4.88 (1H, d, J=10.6 Hz), 6.36-6.63 (1H, m), 7.19-7.36 (2H, m), 10.27-10.82 (1H, m), 11.72 (1H, s).

Example 7

(3S)—N-((1R)-2-((4-tert-butyl-3-fluorophenyl)amino)-1-(4,4-difluorocyclohexyl)-2-oxoethyl)-5-oxopyrrolidine-3-carboxamide (Step 1)

A solution of 2-amino-N-(4-(tert-butyl)-3-fluorophenyl)-2-(4,4-difluorocyclohexyl)acetamide (1.11 g, 3.24 mmol), Boc$_2$O (0.849 g, 3.89 mmol) and TEA (0.683 mL, 4.86 mmol) in THF (10 mL) was stirred overnight at room temperature. To the reaction mixture were added aqueous sodium hydrogencarbonate solution and ethyl acetate, and the organic layer was separated. The organic layer was dried over magnesium sulfate, and the solvent was evaporated under reduced pressure. The obtained residue was purified by silica gel column chromatography (solvent gradient; 1→30% ethyl acetate/hexane) to give tert-butyl (2-((4-(tert-butyl)-3-fluorophenyl)amino)-1-(4,4-difluorocyclohexyl)-2-oxoethyl)carbamate (1.35 g, 3.05 mmol, 94%) as a white solid.

$^1$H NMR (300 MHz, CDCl$_3$): δ1.35 (9H, s), 1.38-1.53 (11H, m), 1.61-2.02 (5H, m), 2.06-2.23 (2H, m, J=4.2 Hz), 4.05 (1H, d, J=8.7 Hz), 5.15 (1H, d, J=8.3 Hz), 7.05 (1H, dd, J=8.3, 2.3 Hz), 7.16-7.24 (1H, m), 7.39 (1H, dd, J=14.0, 2.3 Hz), 8.12 (1H, brs).

(Step 2)

tert-Butyl (2-((4-(tert-butyl)-3-fluorophenyl)amino)-1-(4,4-difluorocyclohexyl)-2-oxoethyl)carbamate (1.35 g) was subjected to optical resolution using chiral column chromatography. The preparative fraction having a shorter retention time was concentrated to give tert-butyl ((1S)-2-((4-(tert-butyl)-3-fluorophenyl)amino)-1-(4,4-difluorocyclohexyl)-2-oxoethyl)carbamate (shorter retention time) (601 mg, >99.9% ee). The preparative fraction having a longer retention time was concentrated to give tert-butyl ((1R)-2-((4-(tert-butyl)-3-fluorophenyl)amino)-1-(4,4-difluorocyclohexyl)-2-oxoethyl)carbamate (longer retention time) (553 mg, >99.9% ee).

purification condition using chiral column chromatography
column: CHIRALPAK AD(JG001)50 mmID×500 mmL
solvent: hexane/2-propanol=700/300
flow rate: 80 mL/min
temperature: 30° C.
detection method: UV 220 nm (Step 3)

To a solution of tert-butyl ((1R)-2-((4-(tert-butyl)-3-fluorophenyl)amino)-1-(4,4-difluorocyclohexyl)-2-oxoethyl)carbamate (553 mg, 1.25 mmol) in ethyl acetate (4 mL) was added 4M hydrogen chloride/ethyl acetate (5 mL), and the mixture was stirred at room temperature for 2 days. The reaction mixture was concentrated under reduced pressure, and the precipitate was washed with a mixed solvent of ethyl acetate/hexane to give (2R)-2-amino-N-(4-(tert-butyl)-3-fluorophenyl)-2-(4,4-difluorocyclohexyl)acetamide hydrochloride (461 mg, 1.217 mmol, 97%) as a white solid.

$^1$H NMR (300 MHz, DMSO-d$_6$): δ1.27-1.38 (10H, m), 1.40-1.57 (1H, m), 1.62-1.77 (2H, m), 1.79-1.91 (2H, m), 1.94-2.13 (3H, m), 3.85 (1H, d, J=6.4 Hz), 7.20-7.38 (2H, m), 7.52 (1H, dd, J=14.9, 1.7 Hz), 8.35 (3H, brs), 10.81 (1H, s).

(Step 4)

A solution of (2R)-2-amino-N-(4-(tert-butyl)-3-fluorophenyl)-2-(4,4-difluorocyclohexyl)acetamide hydrochloride (60 mg, 0.16 mmol), DIEA (45.0 mg, 0.35 mmol), (S)-5-oxopyrrolidine-3-carboxylic acid (24.54 mg, 0.19 mmol) and HATU (72.3 mg, 0.19 mmol) in DMF (2 mL) was stirred at room temperature for 2 hr. To the reaction mixture was added water, and the precipitate was collected by filtration, and washed with water to give the title compound (16.00 mg, 0.035 mmol, 22.28%) as a white solid.

MS(API): Calculated 453.5, Found 452.1 (M−H).

$^1$H NMR (300 MHz, DMSO-d$_6$): δ1.19-1.43 (11H, m), 1.54-1.64 (1H, m), 1.68-1.88 (4H, m), 1.93-2.09 (2H, m), 2.27 (2H, d, J=8.5 Hz), 3.18 (1H, dd, J=9.1, 6.1 Hz), 3.26-3.37 (1H, m), 3.38-3.51 (1H, m), 4.40 (1H, t, J=8.3 Hz), 7.17-7.32 (2H, m), 7.46-7.60 (2H, m), 8.37 (1H, d, J=8.5 Hz), 10.34 (1H, s).

Example 8

N-((1R)-2-((4-tert-butyl-3-fluorophenyl)amino)-1-(4,4-difluorocyclohexyl)-2-oxoethyl)-2-oxo-1,3-oxazolidine-5-carboxamide (mixture of two diastereomers)

A solution of (2R)-2-amino-N-(4-(tert-butyl)-3-fluorophenyl)-2-(4,4-difluorocyclohexyl)acetamide hydrochloride (41 mg, 0.11 mmol), DIEA (0.040 mL, 0.23 mmol), 2-oxooxazolidine-5-carboxylic acid (15.60 mg, 0.12 mmol) and HATU (45.3 mg, 0.12 mmol) in DMF (2 mL) was stirred at room temperature for 2 hr. To the reaction mixture was added water, and the precipitate was collected by filtration, and washed with water to give the title compound (44 mg, 0.097 mmol, 891) as a white solid.

MS(API): Calculated 455.5, Found 454.1 (M−H).

$^1$H NMR (300 MHz, DMSO-d$_6$): δ1.15-1.44 (11H, m), 1.56-1.94 (5H, m), 2.06 (2H, brs), 3.23-3.43 (1H, m), 3.70 (1H, t, J=9.1 Hz), 4.27-4.52 (1H, m), 5.05 (1H, dt, J=9.3, 5.9 Hz), 7.10-7.35 (2H, m), 7.52 (1H, d, J=15.1 Hz), 7.71 (1H, s), 8.35-8.54 (1H, m), 10.39 (1H, d, J=6.8 Hz).

Example 9

N-((1R)-2-((4-tert-butyl-3-chlorophenyl)amino)-2-oxo-1-(tetrahydro-2H-pyran-4-yl)ethyl)-3,3,3-trifluoropropanamide (Step 1)

To a solution of methyl 2-(((benzyloxy)carbonyl)amino)-2-(dimethoxyphosphoryl)acetate (10 g, 30.19 mmol) in acetonitrile (50 mL) was added DBU (4.51 mL, 30.19 mmol) at room temperature, and the mixture was stirred for 30 min. Then, a solution of dihydro-2H-pyran-4(3H)-one (3.02 g, 30.19 mmol) in acetonitrile (5 mL) was added thereto, and the mixture was stirred overnight at room temperature. To the reaction mixture were added water and ethyl acetate, and the organic layer was separated. The organic layer was washed with saturated brine, and dried over magnesium sulfate, and the solvent was evaporated under reduced pressure to give methyl 2-(((benzyloxy)carbonyl)amino)-2-(dihydro-2H-pyran-4(3H)-ylidene)acetate (9.17 g, 30.0 mmol, 99%) as a pale yellow oil. $^1$H NMR (300 MHz, CDCl$_3$): δ2.37-2.55 (2H, m), 2.93 (2H, t, J=4.9 Hz), 3.67-4.02 (7H, m), 5.14 (2H, s), 5.98 (1H, brs), 7.32-7.41 (5H, m).

(Step 2)

A solution of methyl 2-(((benzyloxy)carbonyl)amino)-2-(dihydro-2H-pyran-4(3H)-ylidene)acetate (9.17 g, 30.03 mmol) and 10% palladium-carbon (0.1 g, 0.047 mmol, 50% wet) in MeOH (200 mL) was stirred at room temperature for 2 days under hydrogen atmosphere (1 atm). The catalyst was removed by filtration, and the filtrate was concentrated under reduced pressure to give methyl 2-amino-2-(tetrahydro-2H-pyran-4-yl)acetate as an orange oil. This compound was used in the next step without purification.
(Step 3)

To a solution of methyl 2-amino-2-(tetrahydro-2H-pyran-4-yl)acetate (5.28 g, 30.48 mmol) in THF (100 mL) were added a solution of Boc₂O (8.40 mL, 36.58 mmol) in THF (50 mL) and TEA (6.37 mL, 45.72 mmol), and the mixture was stirred at room temperature for 5 hr. To the reaction mixture were added water and ethyl acetate, and the organic layer was separated. The organic layer was dried over magnesium sulfate, and the solvent was evaporated under reduced pressure. The obtained residue was purified by silica gel column chromatography (solvent gradient; 5→100% ethyl acetate/hexane) to give methyl 2-((tert-butoxycarbonyl)amino)-2-(tetrahydro-2H-pyran-4-yl)acetate (4.77 g, 17.45 mmol, 57.3%) as a colorless oil. $^1$H NMR (300 MHz, CDCl₃): δ1.41-1.55 (13H, m), 1.92-2.03 (1H, m), 3.25-3.43 (2H, m), 3.73 (3H, brs), 3.91-4.04 (2H, m), 4.28 (1H, dd, J=8.9, 5.5 Hz), 5.08 (1H, d, J=9.1 Hz).
(Step 4)

To a solution of methyl 2-((tert-butoxycarbonyl)amino)-2-(tetrahydro-2H-pyran-4-yl)acetate (4.77 g, 17.45 mmol) in a mixed solvent of THF (10 mL) and water (4 mL) was added lithium hydroxide monohydrate (1.099 g, 26.18 mmol), and the mixture was stirred overnight at room temperature. THF was evaporated under reduced pressure, 1N hydrochloric acid was added thereto, and the mixture was extracted with ethyl acetate. The organic layer was dried over magnesium sulfate, and the solvent was evaporated under reduced pressure to give 2-((tert-butoxycarbonyl)amino)-2-(tetrahydro-2H-pyran-4-yl)acetic acid (3.07 g, 11.84 mmol, 67.8-) as a white solid. $^1$H NMR (300 MHz, CDCl₃): δ1.45 (9H, s), 1.48-1.68 (4H, m), 1.92-2.21 (1H, m), 3.27-3.50 (2H, m), 4.02 (2H, d, J=11.0 Hz), 4.29 (1H, brs), 5.14 (1H, d, J=8.3 Hz).
(COOH group D hydrogen was not observed.)
(Step 5)

Sulfuric acid (600 g, 6117.55 mmol) was cooled to 0° C. or lower, and 2-(tert-butyl)aniline (75.24 g, 504.18 mmol) was slowly added thereto while the mixture was kept at 10° C. or lower. The mixture was stirred at 0° C. for 40 min, and potassium nitrate (61.2 g, 605.01 mmol) was slowly added thereto while the mixture was kept at 5° C. or lower. The mixture was stirred at 0° C. for 30 min, the reaction mixture was poured into ice water (3000 mL), and the mixture was extracted with ethyl acetate/THF (3:1, v/v) (×3). The organic layer was separated, and dried over magnesium sulfate, and the solvent was evaporated under reduced pressure to give 2-(tert-butyl)-5-nitroaniline (78.95 g, 406 mmol, 81%) as a yellow solid. $^1$H NMR (300 MHz, CDCl₃): δ1.44 (9H, s), 4.12 (2H, brs), 7.34 (1H, d, J=8.7 Hz), 7.46 (1H, d, J=2.3 Hz), 7.54 (1H, dd).
(Step 6)

2-(tert-Butyl)-5-nitroaniline (8.95 g, 46.08 mmol) was suspended in conc. hydrochloric acid (50 mL) at 0° C., and a solution of sodium nitrite (3.50 g, 50.69 mmol) in water (20 mL) was slowly added thereto while the mixture was kept at 0-5° C. The reaction mixture was added to a solution of copper(I) chloride (5.02 g, 50.69 mmol) in conc. hydrochloric acid (50 mL) at 0° C., and the mixture was vigorously stirred. The reaction mixture was stirred at 70° C. for 30 min, and poured into water (500 mL). The mixture was extracted with ethyl acetate, the organic layer was dried over magnesium sulfate, and the solvent was evaporated under reduced pressure to give 1-(tert-butyl)-2-chloro-4-nitrobenzene (8.57 g, 40.1 mmol, 87%) as a yellow powder.

$^1$H NMR (300 MHz, CDCl₃): δ1.52 (9H, s), 7.60 (1H, d, J=8.7 Hz), 8.04 (1H, dd, J=8.9, 2.5 Hz), 8.22 (1H, d, J=2.3 Hz).
(Step 7)

To a solution of 1-(tert-butyl)-2-chloro-4-nitrobenzene (8.57 g, 40.11 mmol) and nickel(II) bromide (0.438 g, 2.01 mmol) in a mixed solvent of MeOH (170 mL) and THF (170 mL) was added sodium borohydride (4.55 g, 120.33 mmol) at 0° C., and the mixture was stirred at 0° C. for 20 min, and then at room temperature for 40 min. To the reaction mixture was added aqueous sodium hydrogencarbonate solution, and the mixture was extracted with ethyl acetate (×3). The organic layer was dried over magnesium sulfate, and the solvent was evaporated under reduced pressure. The obtained residue was purified by silica gel column chromatography (solvent gradient; 4-20% ethyl acetate/hexane) to give 4-(tert-butyl)-3-chloroaniline (7.30 g, 39.7 mmol, 995) as a colorless oil.

$^1$H NMR (300 MHz, CDCl₃): δ1.43 (9H, s), 3.58 (2H, brs), 6.51 (1H, dd, J=8.7, 2.6 Hz), 6.71 (1H, d, J=2.6 Hz), 7.18 (1H, d, J=8.7 Hz).
(Step 8)

To a solution of 2-((tert-butoxycarbonyl)amino)-2-(tetrahydro-2H-pyran-4-yl)acetic acid (1.55 g, 5.98 mmol), 4-(tert-butyl)-3-chloroaniline (1.098 g, 5.98 mmol), DMAP (0.803 g, 6.58 mmol) and DIEA (5.22 mL, 29.89 mmol) in ethyl acetate (20 mL) was added T3P (5.27 mL, 8.97 mmol) at room temperature. The reaction mixture was stirred overnight at 60° C., water and ethyl acetate were added thereto, and the organic layer was separated. The organic layer was dried over magnesium sulfate, and the solvent was evaporated under reduced pressure to give tert-butyl (2-((4-(tert-butyl)-3-chlorophenyl)amino)-2-oxo-1-(tetrahydro-2H-pyran-4-yl)ethyl)carbamate (2.23 g, 5.25 mmol, 88%) as a white solid.

$^1$H NMR (300 MHz, CDCl₃): δ1.41-1.51 (19H, m), 1.59-1.72 (2H, m), 2.08-2.25 (1H, m), 3.39 (2H, t, J=11.7 Hz), 3.90-4.07 (3H, m), 5.07 (1H, d, J=7.9 Hz), 7.29-7.41 (3H, m), 7.56-7.63 (1H, m), 7.95 (1H, brs).
(Step 9)

tert-Butyl ((1R)-2-((4-(tert-butyl)-3-chlorophenyl)amino)-2-oxo-1-(tetrahydro-2H-pyran-4-yl)ethyl)carbamate (2.23 g) was subjected to optical resolution using chiral column chromatography. The preparative fraction having a longer retention time was concentrated to give tert-butyl ((1R)-2-((4-(tert-butyl)-3-chlorophenyl)amino)-2-oxo-1-(tetrahydro-2H-pyran-4-yl)ethyl)carbamate (longer retention time) (1.0 g, >99.9% ee) as a white solid.
purification condition using chiral column chromatography
column: CHIRALPAK IA(QK001)50 mmID×500 mmL
solvent: hexane/EtOH=800/200
flow rate: 60 mL/min
temperature: 30° C.
detection method: UV 220 nm
(Step 10)

To a solution of tert-butyl ((1R)-2-((4-(tert-butyl)-3-chlorophenyl)amino)-2-oxo-1-(tetrahydro-2H-pyran-4-yl)ethyl)carbamate (1.0 g, 2.35 mmol) in ethyl acetate (10 mL) was added 4M hydrogen chloride/ethyl acetate (5 mL), and the mixture was stirred overnight at room temperature. The precipitate was washed with ethyl acetate/hexane to give (2R)-2-amino-N-(4-(tert-butyl)-3-chlorophenyl)-2-(tetrahydro-2H-pyran-4-yl)acetamide hydrochloride (770 mg, 2.131 mmol, 91%) as a white solid.
(Step 11)

A solution of (2R)-2-amino-N-(4-(tert-butyl)-3-chlorophenyl)-2-(tetrahydro-2H-pyran-4-yl)acetamide hydrochloride (50 mg, 0.14 mmol), DIEA (0.058 mL, 0.33 mmol), 3,3,3-trifluoropropanoic acid (0.013 mL, 0.15 mmol) and HATU (57.9 mg, 0.15 mmol) in DMF (2 mL) was stirred overnight at room temperature. To the reaction mixture was added water, and the precipitate was collected by filtration, and washed with water to give the title compound (60.0 mg, 0.138 mmol, 100%) as a white solid.

MS(API): Calculated 434.9, Found 433.0 (M−H).

$^1$H NMR (300 MHz, DMSO-$d_6$): δ1.14-1.46 (12H, m), 1.56 (1H, d, J=12.1 Hz), 1.82-2.01 (1H, m), 3.17-3.28 (2H, m), 3.34-3.51 (2H, m), 3.77-3.93 (2H, m), 4.38 (1H, t, J=8.3 Hz), 7.41 (2H, s), 7.77 (1H, s), 8.59 (1H, d, J=8.7 Hz), 10.37 (1H, s).

Example 10

N-((1R)-2-((4-tert-butyl-3-chlorophenyl)amino)-2-oxo-1-(tetrahydro-2H-pyran-4-yl)ethyl)-3,3,3-trifluoro-2-hydroxypropanamide (Single Optical Isomer, Shorter Retention Time)

Example 11

N-((1R)-2-((4-tert-butyl-3-chlorophenyl)amino)-2-oxo-1-(tetrahydro-2H-pyran-4-yl)ethyl)-3,3,3-trifluoro-2-hydroxypropanamide (Single Optical Isomer, Longer Retention Time)

A solution of (2R)-2-amino-N-(4-(tert-butyl)-3-chlorophenyl)-2-(tetrahydro-2H-pyran-4-yl)acetamide hydrochloride obtained in Step 10 of Example 9 (52 mg, 0.14 mmol), DIEA (0.060 mL, 0.35 mmol), 3,3,3-trifluoro-2-hydroxypropanoic acid (0.016 mL, 0.16 mmol) and HATU (60.2 mg, 0.16 mmol) in DMF (2 mL) was stirred overnight at room temperature. To the reaction mixture was added water, and the mixture was extracted with ethyl acetate. The organic layer was dried over magnesium sulfate, and the solvent was evaporated under reduced pressure. The obtained residue was purified by silica gel column chromatography (solvent gradient; 30→70% ethyl acetate/hexane) to give the title compound (17 mg, 0.038 mmol, 26.2%) of Example 10 from the preparative fraction having a shorter retention time, and the title compound (15 mg, 0.033 mmol, 23.1%) of Example 11 from the preparative fraction having a longer retention time.

The title compound of Example 10

MS(API): Calculated 450.9, Found 448.9 (M−H).

$^1$H NMR (300 MHz, DMSO-$d_6$): δ1.15-1.45 (12H, m), 1.47-1.58 (1H, m), 1.86-2.07 (1H, m), 3.14-3.27 (2H, m), 3.76-3.91 (2H, m), 4.43 (1H, t, J=8.1 Hz), 4.67 (1H, t, J=7.6 Hz), 7.33 (1H, d, J=6.8 Hz), 7.41 (2H, s), 7.76 (1H, s), 8.12 (1H, d, J=9.1 Hz), 10.41 (1H, s).

The title compound of Example 11

MS(API): Calculated 450.9, Found 448.9 (M−H).

$^1$H NMR (300 MHz, DMSO-$d_6$): δ1.15-1.46 (12H, m), 1.55 (1H, d, J=12.5 Hz), 1.82-2.09 (1H, m), 3.17-3.26 (2H, m), 3.78-3.94 (2H, m), 4.40 (1H, t, J=8.3 Hz), 4.71 (1H, t, J=7.9 Hz), 7.06 (1H, d, J=7.2 Hz), 7.41 (2H, s), 7.76 (1H, s), 8.34 (1H, d, J=9.8 Hz), 10.40 (1H, s).

Example 12

3-hydroxy-N-(1-(4-methoxyphenyl)-2-oxo-2-((4-(trimethylsilyl)phenyl)amino)ethyl)-N-methyl-1,2-oxazole-5-carboxamide (Step 1)

A solution of (4-methoxyphenyl)boronic acid (9.42 g, 62.01 mmol), glyoxylic acid monohydrate (5.71 g, 62.01 mmol) and N-methylallylamine (5.95 mL, 62.01 mmol) in acetonitrile (120 mL) was stirred at 60° C. for 2.5 hr. To the reaction mixture was added ethyl acetate, and the precipitate was removed by filtration. The filtrate was concentrated under reduced pressure, and the obtained residue was purified by silica gel column chromatography (Diol, solvent gradient; 0→20% MeOH/ethyl acetate) to give 2-(allyl(methyl)amino)-2-(4-methoxyphenyl)acetic acid (4.91 g, 20.87 mmol, 33.71) as white crystals.

$^1$H NMR (300 MHz, DMSO-$d_6$): δ2.20 (3H, s), 3.03-3.21 (2H, m), 3.75 (3H, s), 4.11 (1H, s), 5.14-5.28 (2H, m), 5.73-5.92 (1H, m), 6.87-6.97 (2H, m), 7.26-7.37 (2H, m).

(Step 2)

A solution of 2-(allyl(methyl)amino)-2-(4-methoxyphenyl)acetic acid (2.8 g, 11.90 mmol), 4-(trimethylsilyl)aniline (2.066 g, 12.50 mmol), DIEA (4.16 mL, 23.80 mmol) and HATU (5.43 g, 14.28 mmol) in DMF (50 mL) was stirred overnight at room temperature. To the reaction mixture were added water and ethyl acetate, and the organic layer was separated. The organic layer was washed with water, and dried over magnesium sulfate, and the solvent was evaporated under reduced pressure. The obtained residue was purified by silica gel column chromatography (solvent gradient; 0→30% ethyl acetate/hexane) to give 2-(allyl(methyl)amino)-2-(4-methoxyphenyl)-N-(4-(trimethylsilyl)phenyl) acetamide (2.82 g, 7.37 mmol, 61.9%) as a white solid.

$^1$H NMR (300 MHz, CDCl$_3$): δ0.25 (9H, s), 2.20 (3H, s), 2.95-3.14 (2H, m), 3.79 (3H, s), 4.10 (1H, s), 5.15-5.30 (2H, m), 5.78-5.98 (1H, m), 6.81-6.94 (2H, m), 7.18-7.31 (2H, m), 7.44-7.52 (2H, m), 7.54-7.62 (2H, m), 9.25 (1H, s).

(Step 3)

To a solution of 2-(allyl(methyl)amino)-2-(4-methoxyphenyl)-N-(4-(trimethylsilyl)phenyl)acetamide (2.82 g, 7.37 mmol) and 1,3-dimethylbarbituric acid (1.266 g, 8.11 mmol) in THF (50 mL) was added Pd(PPh$_3$)$_4$(0.170 g, 0.15 mmol), and the mixture was stirred at room temperature for 3 hr under nitrogen atmosphere. The reaction mixture was concentrated under reduced pressure, and the obtained residue was purified by silica gel column chromatography (NH, solvent gradient; 5→25% ethyl acetate/hexane) to give an oil. This oil was treated with 1N hydrochloric acid, and crystallized from EtOH/IPE to give 2-(4-methoxyphenyl)-2-(methylamino)-N-(4-(trimethylsilyl)phenyl)acetamide hydrochloride (1.840 g, 4.86 mmol, 65.9%) as a white solid.

$^1$H NMR (300 MHz, DMSO-$d_6$): δ0.21 (9H, s), 2.45 (3H, s), 3.77 (3H, s), 5.00 (1H, s), 6.97-7.10 (2H, m), 7.40-7.64 (6H, m), 9.44 (2H, brs), 10.83 (1H, s).

(Step 4)

A solution of 2-(4-methoxyphenyl)-2-(methylamino)-N-(4-(trimethylsilyl)phenyl)acetamide hydrochloride (100 mg, 0.29 mmol), 3-hydroxy-1,2-oxazole-5-carboxylic acid (45.2 mg, 0.35 mmol), DIEA (0.102 mL, 0.58 mmol) and HATU (133 mg, 0.35 mmol) in DMF (2.0 mL) was stirred overnight at room temperature. To the reaction mixture were added water and ethyl acetate, and the organic layer was separated. The organic layer was washed with water, and dried over magnesium sulfate, and the solvent was evaporated under reduced pressure. The obtained residue was purified by silica gel column chromatography (solvent; ethyl acetate), and crystallized from ethyl acetate/hexane to give the title compound (84.8 mg, 0.187 mmol, 64.0%) as white crystals.

MS(API): Calculated 453.6, Found 452.0 (M−H).

$^1$H NMR (300 MHz, DMSO-d$_6$): δ0.22 (9H, s), 2.88 (3H, s), 3.76 (3H, s), 6.18 (1H, s), 6.54 (1H, s), 7.00 (2H, d, J=8.7 Hz), 7.15-7.33 (2H, m), 7.40-7.51 (2H, m), 7.52-7.68 (2H, m), 10.37 (1H, s), 11.32-12.19 (1H, m).

Example 13

N-(1-(4-methoxyphenyl)-2-oxo-2-((4-(trimethylsilyl) phenyl)amino)ethyl)-5-oxopyrrolidine-3-carboxamide (Mixture of Four Optical Isomers)

(Step 1)

A solution of (4-methoxyphenyl)boronic acid (50 g, 329.04 mmol), diallylamine (32.0 g, 329.04 mmol) and glyoxylic acid monohydrate (30.3 g, 329.04 mmol) in acetonitrile (300 mL) was stirred at 80° C. for 2 hr. The precipitate was suspended overnight in ethyl acetate (1000 mL) at room temperature, and collected by filtration to give 2-(diallylamino)-2-(4-methoxyphenyl)acetic acid (96 g, 366 mmol, 111%) as white crystals.

$^1$H NMR (300 MHz, CDCl$_3$): δ3.34 (2H, dd, J=14.0, 7.2 Hz), 3.65 (2H, dd, J=14.0, 6.4 Hz), 3.80 (3H, s), 4.63 (1H, s), 5.21-5.47 (4H, m), 5.80-6.03 (2H, m), 6.88 (2H, d, J=8.7 Hz), 7.40 (2H, d, J=8.7 Hz)

(Step 2)

A solution of 2-(diallylamino)-2-(4-methoxyphenyl)acetic acid (200 mg, 0.77 mmol), HATU (349 mg, 0.92 mmol), 4-(trimethylsilyl)aniline (152 mg, 0.92 mmol) and TEA (0.127 mL, 0.92 mmol) in DMF (2 mL) was stirred overnight at room temperature. To the reaction mixture were added water and ethyl acetate, and the organic layer was separated. The organic layer was washed with water and brine, and dried over magnesium sulfate, and the solvent was evaporated under reduced pressure to give 2-(diallylamino)-2-(4-methoxyphenyl)-N-(4-(trimethylsilyl)phenyl) acetamide (313 mg, 0.766 mmol, 100%) as an orange oil. This compound was used in the next step without purification.

(Step 3)

A solution of 2-(diallylamino)-2-(4-methoxyphenyl)-N-(4-(trimethylsilyl)phenyl)acetamide (313 mg, 0.77 mmol), Pd(PPh$_3$)$_4$ (35.4 mg, 0.03 mmol) and 1,3-dimethylbarbituric acid (263 mg, 1.69 mmol) in THF (20 mL) was stirred overnight at room temperature under nitrogen atmosphere. The reaction mixture was concentrated under reduced pressure, and the obtained residue was purified by silica gel column chromatography (NH, solvent gradient; 1→50% ethyl acetate/hexane) to give 2-amino-2-(4-methoxyphenyl)-N-(4-(trimethylsilyl)phenyl)acetamide (100 mg, 0.304 mmol, 39.7%) as a colorless oil.

$^1$H NMR (300 MHz, CDCl$_3$): δ0.24 (9H, s), 3.79 (3H, s), 4.60 (1H, s), 6.84-6.92 (2H, m), 7.32-7.39 (2H, m), 7.45-7.49 (2H, m), 7.56-7.61 (2H, m), 9.32 (1H, brs).

(Step 4)

A solution of 2-amino-2-(4-methoxyphenyl)-N-(4-(trimethylsilyl)phenyl)acetamide (100 mg, 0.30 mmol), HATU (139 mg, 0.37 mmol), 5-oxopyrrolidine-3-carboxylic acid (47.2 mg, 0.37 mmol) and DIEA (0.064 mL, 0.37 mmol) in DMF (3 mL) was stirred overnight at room temperature. To the reaction mixture were added water and ethyl acetate, and the organic layer was separated. The organic layer was dried over sodium sulfate, and the solvent was evaporated under reduced pressure. The obtained residue was purified by silica gel column chromatography (NH, solvent gradient; 1-60% ethyl acetate/hexane) to give the title compound (70 mg, 0.159 mmol, 52.3%) as a white solid.

MS(API): Calculated 439.6, Found 438.2 (M−H).

$^1$H NMR (300 MHz, DMSO-d$_6$): δ0.20 (9H, s), 2.19-2.35 (2H, m), 3.09-3.27 (1H, m), 3.34-3.52 (2H, m), 3.73 (3H, s), 5.44-5.64 (1H, m), 6.84-7.00 (2H, m), 7.31-7.46 (4H, m), 7.48-7.62 (3H, m), 8.63-8.82 (1H, m), 10.22-10.36 (1H, m).

Example 14

3-hydroxy-N-((1R)-1-(4-methoxyphenyl)-2-oxo-2-((4-(trimethylsilyl)phenyl)amino)ethyl)-N-methyl-1,2-oxazole-5-carboxamide 3-Hydroxy-N-(1-(4-methoxyphenyl)-2-oxo-2-((4-(trimethylsilyl)phenyl)amino)ethyl)-N-methyl-1,2-oxazole-5-carboxamide (15.8 g) was subjected to optical resolution using chiral column chromatography. The preparative fraction having a shorter retention time was concentrated to give the title compound (6.95 g) as a white solid.

MS(API): Calculated 453.6, Found 452.0 (M−H).

$[\alpha]_D^{25}$−171.9 (c 0.1930, MeOH)

purification condition using chiral column chromatography
column: CHIRALPAK AD(IL001)50 mmID×500 mmL
solvent: EtOH/acetic acid=1000/1
flow rate: 80 mL/min
temperature: 30° C.
detection method: UV 220 nm Example 15

N-(2-((3-fluoro-4-(trimethylsilyl)phenyl)amino)-1-(4-methoxyphenyl)-2-oxoethyl)-3-hydroxy-N-methyl-1,2-oxazole-5-carboxamide A solution of 2-(3-hydroxy-N-methyl-1,2-oxazole-5-carboxamide)-2-(4-methoxyphenyl)acetic acid (100 mg, 0.33 mmol), 3-fluoro-4-(trimethylsilyl)aniline (65.8 mg, 0.36 mmol), DIEA (0.114 mL, 0.65 mmol) and HATU (149 mg, 0.39 mmol) in DMF (2.0 mL) was stirred overnight at room temperature. To the reaction mixture were added water and ethyl acetate, and the organic layer was separated. The organic layer was dried over magnesium sulfate, and the solvent was evaporated under reduced pressure. The obtained residue was purified by silica gel column chromatography (solvent gradient; 0→50% ethyl acetate/hexane), and crystallized from ethyl acetate/hexane to give the title compound (5.6 mg, 0.012 mmol, 3.64%) as a white solid.

MS(API): Calculated 471.6, Found 470.0 (M−H).

$^1$H NMR (300 MHz, CDCl$_3$): δ0.28 (9H, s), 3.08 (3H, s), 3.83 (3H, s), 6.26 (1H, s), 6.47 (1H, s), 6.91-6.98 (2H, m), 7.09 (1H, dd, J=7.9, 1.9 Hz), 7.28-7.46 (4H, m), 7.68 (1H, brs).

Example 16

2-(4-methoxyphenyl)-2-(((6-oxo-1,6-dihydropyridin-3-yl)acetyl)amino)-N-(4-(trimethylsilyl)phenyl)acetamide (Step 1)

A solution of 2-amino-2-(4-methoxyphenyl)-N-(4-(trimethylsilyl)phenyl)acetamide (200 mg, 0.61 mmol), 2-(6-methoxypyridin-3-yl)acetic acid (112 mg, 0.67 mmol), DIEA (0.213 mL, 1.22 mmol) and HATU (278 mg, 0.73 mmol) in DMF (2.0 mL) was stirred overnight at room temperature. To the reaction mixture were added water and ethyl acetate, and the organic layer was separated. The organic layer was dried over magnesium sulfate, and the solvent was evaporated under reduced pressure to give 2-(4-methoxyphenyl)-2-(2-(6-methoxypyridin-3-yl)acetamide)-N-(4-(trimethylsilyl)phenyl)acetamide (226.2 mg, 0.474 mmol, 78%) as a white solid.

$^1$H NMR (300 MHz, DMSO-$d_6$): δ0.20 (9H, s), 3.51 (2H, s), 3.73 (3H, s), 3.81 (3H, s), 5.55 (1H, d, J=7.2 Hz), 6.75 (1H, d, J=8.7 Hz), 6.93 (2H, d, J=8.3 Hz), 7.34-7.47 (4H, m), 7.51-7.65 (3H, m), 8.02 (1H, s), 8.84 (1H, d, J=7.6 Hz), 10.28 (1H, s).

(Step 2)

A solution of 2-(4-methoxyphenyl)-2-(2-(6-methoxypyridin-3-yl)acetamide)-N-(4-(trimethylsilyl)phenyl)acetamide (220 mg, 0.46 mmol), sodium iodide (207 mg, 1.38 mmol) and TMSCl (0.177 mL, 1.38 mmol) in acetonitrile (6.0 mL) was stirred at 70° C. for 2 hr. To the reaction mixture were added water and ethyl acetate, and the organic layer was separated. The organic layer was dried over magnesium sulfate, and the solvent was evaporated under reduced pressure. The obtained residue was purified by silica gel column chromatography (solvent; ethyl acetate), and crystallized from ethyl acetate/hexane to give the title compound (30.2 mg, 0.065 mmol, 14.14%) as white crystals.

MS(API): Calculated 463.6, Found 464.2 (M+H).

$^1$H NMR (300 MHz, DMSO-$d_6$): δ3.30 (2H, brs), 3.73 (3H, s), 5.54 (1H, d, J=7.6 Hz), 6.26 (1H, d, J=9.1 Hz), 6.92 (2H, d, J=8.7 Hz), 7.21 (1H, s), 7.28-7.46 (5H, m), 7.55 (2H, d, J=8.3 Hz), 8.73 (1H, d, J=7.6 Hz), 10.28 (1H, s), 11.39 (1H, brs).

Example 17

N-(2-((3,5-difluoro-4-(trimethylsilyl)phenyl)amino)-1-(4-methoxyphenyl)-2-oxoethyl)-3-hydroxy-N-methyl-1,2-oxazole-5-carboxamide (Step 1)

To a solution of 2-(allyl(methyl)amino)-2-(4-methoxyphenyl)acetic acid (5.0 g, 21.25 mmol) in a mixed solvent of MeOH (50 mL) and toluene (100 mL) was added 0.6M trimethylsilyldiazomethane hexane solution (49.6 mL, 29.75 mmol) at room temperature, and the mixture was stirred for 1 hr. The reaction mixture was concentrated under reduced pressure, and the obtained residue was purified by silica gel column chromatography (solvent; ethyl acetate/hexane) to give methyl 2-(allyl(methyl)amino)-2-(4-methoxyphenyl)acetate (4.48 g, 17.97 mmol, 85%) as a colorless oil.

MS(API): Calculated 249.3, Found 250.2 (M+H).

(Step 2)

To a solution of methyl 2-(allyl(methyl)amino)-2-(4-methoxyphenyl)acetate (4.48 g, 17.97 mmol) and 1,3-dimethylbarbituric acid (3.09 g, 19.77 mmol) in THF (70 mL) was added Pd(PPh$_3$)$_4$ (0.415 g, 0.36 mmol), and the mixture was stirred at room temperature for 3 hr under nitrogen atmosphere. The reaction mixture was concentrated under reduced pressure, and the obtained residue was purified by silica gel column chromatography (NH, solvent gradient; 5→25% ethyl acetate/hexane) to give methyl 2-(4-methoxyphenyl)-2-(methylamino)acetate (3.74 g, 17.87 mmol, 99%) as a colorless oil.

(Step 3)

A solution of methyl 2-(4-methoxyphenyl)-2-(methylamino)acetate (3.74 g, 17.87 mmol), 3-hydroxy-1,2-oxazole-5-carboxylic acid (2.54 g, 19.66 mmol), DIEA (6.24 mL, 35.75 mmol) and HATU (8.16 g, 21.45 mmol) in DMF (100 mL) was stirred overnight at room temperature. To the reaction mixture were added water and ethyl acetate, and the organic layer was separated. The organic layer was dried over magnesium sulfate, and the solvent was evaporated under reduced pressure. The obtained residue was purified by silica gel column chromatography (solvent gradient; 0→50% ethyl acetate/hexane) to give methyl 2-(3-hydroxy-N-methyl-1,2-oxazole-5-carboxamide)-2-(4-methoxyphenyl)acetate (2.41 g, 7.52 mmol, 42.1%) as a white solid.

$^1$H NMR (300 MHz, CDCl$_3$): δ2.90 (3H, s), 2.98 (3H, s), 3.83 (3H, s), 6.29 (1H, s), 6.47 (1H, s), 6.88-6.96 (2H, m), 7.17-7.25 (2H, m), 8.04 (1H, s).

(Step 4)

To a solution of methyl 2-(3-hydroxy-N-methyl-1,2-oxazole-5-carboxamide)-2-(4-methoxyphenyl)acetate (2.41 g, 7.52 mmol) in a mixed solvent of MeOH (24 mL) and THF (24.00 mL) was added 1N aqueous sodium hydroxide solution (15.05 mL, 15.05 mmol), and the mixture was stirred overnight at room temperature. To the reaction mixture was added water, and the pH of the mixture was adjusted to 2-3 with 1N hydrochloric acid. The mixture was extracted with ethyl acetate, and the organic layer was dried over magnesium sulfate, and the solvent was evaporated under reduced pressure to give 2-(3-hydroxy-N-methyl-1,2-oxazole-5-carboxamide)-2-(4-methoxyphenyl)acetic acid (2.15 g, 7.02 mmol, 93%) as a white solid.

$^1$H NMR (300 MHz, DMSO-$d_6$): δ2.64-2.94 (3H, m), 3.77 (3H, s), 5.64-6.01 (1H, m), 6.42-6.58 (1H, m), 6.91-7.05 (2H, m), 7.17-7.34 (2H, m), 11.74 (1H, brs), 13.22 (1H, brs).

(Step 5)

A solution of 2-(3-hydroxy-N-methyl-1,2-oxazole-5-carboxamide)-2-(4-methoxyphenyl)acetic acid (100 mg, 0.33 mmol), 3,5-difluoro-4-(trimethylsilyl)aniline (79 mg, 0.39 mmol), DIEA (0.285 mL, 1.63 mmol) and T3P (0.408 mL, 0.65 mmol) in DMF (2.0 mL) was stirred at 80° C. for 3 hr. To the reaction mixture were added water and ethyl acetate, and the organic layer was separated. The organic layer was dried over magnesium sulfate, and the solvent was evaporated under reduced pressure. The obtained residue was purified by silica gel column chromatography (solvent gradient; 0→50% ethyl acetate/hexane) to give the title compound (15.4 mg, 0.031 mmol, 9.63%) as a white solid.

MS(API): Calculated 489.5, Found 490.1 (M+H).

$^1$H NMR (300 MHz, DMSO-$d_6$): δ0.32 (9H, s), 2.74-2.94 (3H, m), 3.77 (3H, s), 5.72-6.15 (1H, m), 6.39-6.59 (1H, m), 7.01 (2H, d, J=8.7 Hz), 7.16-7.34 (4H, m), 10.55-10.79 (1H, m), 11.80 (1H, brs).

Example 18

2-(4-methoxyphenyl)-2-(((3-methyl-1,2-oxazol-5-yl)acetyl)amino)-N-(4-(trimethylsilyl)phenyl)acetamide A solution of 2-amino-2-(4-methoxyphenyl)-N-(4-(trimethylsilyl)phenyl)acetamide (100 mg, 0.30 mmol), 2-(3-methyl-1,2-oxazol-5-yl)acetic acid (51.6 mg, 0.37 mmol), HATU (150 mg, 0.40 mmol) and DIEA (0.106 mL, 0.61 mmol) in DMF (3 mL) was stirred at room temperature for 10 hr. To the reaction mixture were added water and ethyl acetate, and the organic layer was separated. The organic layer was dried over magnesium sulfate, and the solvent was evaporated under reduced pressure. The obtained residue was purified by silica gel column chromatography (solvent gradient; 20-50% ethyl acetate/hexane), and crystallized from ethyl acetate/hexane to give the title compound (113 mg, 0.250 mmol, 82%) as white crystals.

MS(API): Calculated 451.6, Found 452.2 (M+H).

Example 19

2-(4-methoxyphenyl)-2-(((1-methyl-1H-pyrazol-3-yl)acetyl)amino)-N-(4-(trimethylsilyl)phenyl)acetamide A solution of 2-amino-2-(4-methoxyphenyl)-N-(4-(trimethylsilyl)phenyl)acetamide (100 mg, 0.30 mmol), 2-(1-methyl-1H-pyrazol-3-yl)acetic acid (51.2 mg, 0.37 mmol), HATU (150 mg, 0.40 mmol) and DIEA (0.106 mL, 0.61 mmol) in DMF (1.5 mL) was stirred at room temperature for 10 hr. To the reaction mixture were added water and ethyl acetate, and the organic layer was separated. The organic layer was dried over magnesium sulfate, and the solvent was evaporated under reduced pressure, and crystallized from ethyl acetate to give the title compound (99 mg, 0.219 mmol, 71.9%) as white crystals.

MS(API): Calculated 450.6, Found 451.1 (M+H).

$^1$H NMR (300 MHz, DMSO-$d_6$): δ0.20 (9H, s), 3.51 (2H, s), 3.73 (3H, s), 3.76 (3H, s), 5.56 (1H, d, J=7.6 Hz), 6.08 (1H, d, J=1.9 Hz), 6.92 (2H, d, J=8.7 Hz), 7.35-7.47 (4H, m), 7.51-7.60 (3H, m), 8.67 (1H, d, J=7.6 Hz), 10.28 (1H, s).

Example 20

2-(4-methoxyphenyl)-2-(((1-methyl-1H-pyrazol-4-yl)acetyl)amino)-N-(4-(trimethylsilyl)phenyl)acetamide A solution of 2-amino-2-(4-methoxyphenyl)-N-(4-(trimethylsilyl)phenyl)acetamide (100 mg, 0.30 mmol), 2-(1-methyl-1H-pyrazol-4-yl)acetic acid (51.2 mg, 0.37 mmol), HATU (150 mg, 0.40 mmol) and DIEA (0.106 mL, 0.61 mmol) in DMF (3 mL) was stirred at room temperature for 10 hr. To the reaction mixture were added water and ethyl acetate, and the organic layer was separated. The organic layer was dried over magnesium sulfate, and the solvent was evaporated under reduced pressure. The obtained residue was purified by silica gel column chromatography (solvent gradient; 75→99% ethyl acetate/hexane) to give the title compound (83 mg, 0.183 mmol, 60.2%) as white crystals.

MS(API): Calculated 450.6, Found 451.1 (M+H).

$^1$H NMR (300 MHz, DMSO-$d_6$): δ0.20 (9H, s), 3.36 (2H, s), 3.72 (3H, s), 3.76 (3H, s), 5.55 (1H, d, J=7.9 Hz), 6.92 (2H, d, J=8.7 Hz), 7.25 (1H, s), 7.34-7.60 (7H, m), 8.63 (1H, d, J=7.6 Hz), 10.28 (1H, s).

Example 21

N-(2-((2,5-difluoro-4-(trimethylsilyl)phenyl)amino)-1-(4-methoxyphenyl)-2-oxoethyl)-3-hydroxy-N-methyl-1,2-oxazole-5-carboxamide (Step 1)

A solution of 1-bromo-2,5-difluoro-4-nitrobenzene (3.0 g, 12.61 mmol), HMDS (3.10 mL, 15.13 mmol), Pd$_2$(dba)$_3$ (0.173 g, 0.19 mmol), 2'-(di-tert-butylphosphino)-N,N-dimethyl-[1,1'-biphenyl]-2-amine (0.387 g, 1.13 mmol), water (0.454 g, 25.21 mmol) and lithium acetate (4.16 g, 63.03 mmol) in DMF (60 mL) was stirred at 100° C. for 24 hr under argon gas atmosphere. To the reaction mixture were added water and ethyl acetate, and the organic layer was separated. The organic layer was dried over magnesium sulfate, and the solvent was evaporated under reduced pressure. The obtained residue was purified by silica gel column chromatography (solvent gradient; 0→5% ethyl acetate/hexane) to give (2,5-difluoro-4-nitrophenyl)trimethylsilane (745.9 mg, 3.23 mmol, 25.61%) as a yellow oil.

$^1$H NMR (300 MHz, CDCl$_3$): δ0.36 (9H, d, J=0.8 Hz), 7.27-7.33 (1H, m), 7.64-7.72 (1H, m).

(Step 2)

A solution of (2,5-difluoro-4-nitrophenyl)trimethylsilane (740 mg, 3.20 mmol) and 10% palladium on carbon (74 mg, 0.70 mmol) in MeOH (15 mL) was stirred at room temperature for 5 hr under hydrogen atmosphere (1 atm). The catalyst was removed by filtration, and the filtrate was concentrated under reduced pressure to give 2,5-difluoro-4-(trimethylsilyl)aniline as an oil. This compound was directly used in the next step.

(Step 3)

A solution of 2-(3-hydroxy-N-methyl-1,2-oxazole-5-carboxamide)-2-(4-methoxyphenyl)acetic acid (200 mg, 0.65 mmol), 2,5-difluoro-4-(trimethylsilyl)aniline (158 mg, 0.78 mmol), DIEA (0.570 mL, 3.27 mmol) and T3P (0.816 mL, 1.31 mmol) in DMF (2.0 ML) was stirred at 80° C. for 5 hr. To the reaction mixture were added water and ethyl acetate, and the organic layer was separated. The organic layer was dried over magnesium sulfate, and the solvent was evaporated under reduced pressure. The obtained residue was purified by silica gel column chromatography (solvent gradient; 0→5% ethyl acetate/hexane) to give the title compound (11.3 mg, 0.023 mmol, 3.53%) as a pale yellow solid.

MS(API): Calculated 489.5, Found 488.0 (M−H).

$^1$H NMR (300 MHz, CDCl$_3$): δ0.28 (9H, s), 3.07 (3H, brs), 3.83 (3H, s), 6.30 (1H, brs), 6.48 (1H, s), 6.87-7.09 (3H, m), 7.36 (2H, d, J=7.9 Hz), 7.77 (1H, brs), 8.07 (1H, dd, J=9.3, 5.9 Hz).

Example 22

2-(4-(methoxymethyl)phenyl)-2-(((1-methyl-1H-pyrazol-4-yl)acetyl)amino)-N-(4-(trimethylsilyl)phenyl)acetamide (Step 1)

A solution of (4-(methoxymethyl)phenyl)boronic acid (999 mg, 6.02 mmol), glyoxylic acid monohydrate (554 mg, 6.02 mmol) and diallylamine (0.741 mL, 6.02 mmol) in acetonitrile (12 mL) was stirred at 60° C. for 5 hr. The reaction mixture was concentrated under reduced pressure. The obtained residue was purified by silica gel column chromatography (Diol, solvent; ethyl acetate), and crystallized from ethyl acetate to give 2-(diallylamino)-2-(4-(methoxymethyl)phenyl)acetic acid (200 mg, 0.726 mmol, 12.07%) as white crystals.

$^1$H NMR (300 MHz, DMSO-$d_6$): δ3.04-3.46 (7H, m), 4.39 (2H, s), 4.43 (1H, s), 5.04-5.23 (4H, m), 5.78 (2H, ddt, J=16.9, 10.5, 6.3 Hz), 7.23-7.40 (4H, m).

(Step 2)

A solution of 2-(diallylamino)-2-(4-(methoxymethyl)phenyl)acetic acid (200 mg, 0.73 mmol), 4-(trimethylsilyl)aniline (132 mg, 0.80 mmol), HATU (331 mg, 0.87 mmol) and DIEA (0.254 mL, 1.45 mmol) in DMF (3 mL) was stirred at room temperature for 1 hr. To the reaction mixture were added water and ethyl acetate, and the organic layer was separated. The organic layer was dried over magnesium sulfate, and the solvent was evaporated under reduced pressure. The obtained residue was purified by silica gel column chromatography (solvent gradient; 1→25% ethyl acetate/hexane) to give 2-(diallylamino)-2-(4-(methoxymethyl)phenyl)-N-(4-(trimethylsilyl)phenyl)acetamide (150 mg, 0.355 mmol, 48.9%) as a yellow oil.

¹H NMR (300 MHz, DMSO-d$_6$): δ0.16-0.25 (9H, m), 3.04-3.14 (2H, m), 3.18-3.29 (5H, m), 4.39 (2H, s), 4.52 (1H, s), 5.07-5.22 (4H, m), 5.85 (2H, ddt, J=16.8, 10.4, 6.2 Hz), 7.30 (2H, d, J=7.9 Hz), 7.43 (4H, d, J=7.9 Hz), 7.61 (2H, d, J=8.7 Hz), 10.07 (1H, s).
(Step 3)

To a solution of 2-(diallylamino)-2-(4-(methoxymethyl)phenyl)-N-(4-(trimethylsilyl)phenyl)acetamide (150 mg, 0.35 mmol) and 1,3-dimethylbarbituric acid (122 mg, 0.78 mmol) in THF (3 mL) was added Pd(PPh$_3$)$_4$(16.41 mg, 0.01 mmol) at room temperature under argon gas atmosphere, and the mixture was stirred for 6 hr. The reaction mixture was concentrated under reduced pressure, and the obtained residue was purified by silica gel column chromatography (solvent gradient; 40-80% MeOH/ethyl acetate) to give 2-amino-2-(4-(methoxymethyl)phenyl)-N-(4-(trimethylsilyl)phenyl)acetamide (104 mg, 0.304 mmol, 865) as a yellow oil.

¹H NMR (300 MHz, DMSO-d$_6$): δ0.15-0.24 (9H, m), 3.26 (3H, s), 4.37 (2H, s), 4.52 (1H, s), 7.26 (2H, d, J=8.3 Hz), 7.35-7.47 (4H, m), 7.57-7.64 (2H, m), 10.06 (1H, brs).
(Step 4)

A solution of 2-amino-2-(4-(methoxymethyl)phenyl)-N-(4-(trimethylsilyl)phenyl)acetamide (104 mg, 0.30 mmol), 2-(1-methyl-1H-pyrazol-4-yl)acetic acid (51.1 mg, 0.36 mmol), HATU (150 mg, 0.39 mmol) and DIEA (0.106 mL, 0.61 mmol) in DMF (1.5 mL) was stirred at room temperature for 10 hr. To the reaction mixture were added water and ethyl acetate, and the organic layer was separated. The organic layer was dried over magnesium sulfate, and the solvent was evaporated under reduced pressure. The obtained residue was purified by silica gel column chromatography (solvent gradient; 40→80% ethyl acetate/hexane), and crystallized from ethyl acetate/hexane to give the title compound (45.0 mg, 0.097 mmol, 31.9%) as white crystals.

MS(API): Calculated 464.6, Found 465.1 (M+H).

¹H NMR (300 MHz, DMSO-d$_6$): δ0.17-0.22 (9H, m), 3.31 (3H, s), 3.38 (2H, s), 3.76 (3H, s), 4.37 (2H, s), 5.63 (1H, d, J=7.9 Hz), 7.24-7.34 (3H, m), 7.39-7.60 (7H, m), 8.71 (1H, d, J=7.9 Hz), 10.35 (1H, s).

Example 23

N-((1R)-2-((3,5-difluoro-4-(trimethylsilyl)phenyl)amino)-1-(4-methoxyphenyl)-2-oxoethyl)-3-hydroxy-N-methyl-1,2-oxazole-5-carboxamide N-(2-((3,5-Difluoro-4-(trimethylsilyl)phenyl)amino)-1-(4-methoxyphenyl)-2-oxoethyl)-3-hydroxy-N-methyl-1,2-oxazole-5-carboxamide (750.5 mg) was subjected to optical resolution using chiral column chromatography. The preparative fraction having a shorter retention time was concentrated to give the title compound (292.2 mg, >99.9% ee) as a white solid.

MS(API): Calculated 489.5, Found 488.0 (M−H).

¹H NMR (300 MHz, DMSO-d$_6$): δ0.32 (9H, s), 2.75-2.91 (3H, m), 3.77 (3H, s), 5.72-6.16 (1H, m), 6.39-6.59 (1H, m), 7.01 (2H, d, J=8.7 Hz), 7.14-7.32 (4H, m), 10.55-10.80 (1H, m), 11.79 (1H, brs).
purification condition using chiral column chromatography
column: CHIRALPAK IA(NL001)50 mmID×500 mmL
solvent: hexane/EtOH/acetic acid=500/500/1
flow rate: 60 mL/min
temperature: 30° C.
detection method: UV 220 nm
$[\alpha]_D^{25}$ −132.7 (c 0.2345, MeOH)

Example 24

N-((1R)-2-((3-fluoro-4-(trimethylsilyl)phenyl)amino)-1-(4-methoxyphenyl)-2-oxoethyl)-3-hydroxy-N-methyl-1,2-oxazole-5-carboxamide N-(2-((3-Fluoro-4-(trimethylsilyl)phenyl)amino)-1-(4-methoxyphenyl)-2-oxoethyl)-3-hydroxy-N-methyl-1,2-oxazole-5-carboxamide (80 mg) was subjected to optical resolution using chiral column chromatography. The preparative fraction having a shorter retention time was concentrated to give the title compound (32.2 mg, >99.9% ee) as a white solid.

MS(API): Calculated 471.6, Found 470.0 (M−H).
purification condition using chiral column chromatography
column: CHIRAPAK AD(NL001)50 mmID×500 mmL
solvent: hexane/EtOH/acetic acid 300/700/1
flow rate: 60 mL/min
temperature: 30° C.
detection method: UV 220 nm
$[\alpha]_D^{25}$ 179.8 (c 0.2250, MeOH)

Example 25

N-((1R)-2-((2,5-difluoro-4-(trimethylsilyl)phenyl)amino)-1-(4-methoxyphenyl)-2-oxoethyl)-3-hydroxy-N-methyl-1,2-oxazole-5-carboxamide N-(2-((2,5-Difluoro-4-(trimethylsilyl)phenyl)amino)-1-(4-methoxyphenyl)-2-oxoethyl)-3-hydroxy-N-methyl-1,2-oxazole-5-carboxamide (120 mg) was subjected to optical resolution using chiral column chromatography. The preparative fraction having a shorter retention time was concentrated to give the title compound (38.9 mg, >99.9% ee) as a white solid.

MS(API): Calculated 489.5, Found 488.0 (M−H).
purification condition using chiral column chromatography
column: CHIRALPAK IA(NL001) 50 mmID×500 mmL
solvent: hexane/EtOH/acetic acid 300/700/1
flow rate: 60 mL/min
temperature: 30° C.
detection method: UV 220 nm
$[\alpha]_D^{25}$ −162.4 (c 0.1960, MeOH)

Example 26

N-(2-((3-cyano-4-(trimethylsilyl)phenyl)amino)-1-(4-(methoxymethyl)phenyl)-2-oxoethyl)-5-oxopyrrolidine-3-carboxamide (Mixture of Four Optical Isomers)

(Step 1)

A solution of 2-chloro-5-nitrobenzonitrile (19.5 g, 106.81 mmol), HMDS (43.7 mL, 213.62 mmol), Pd$_2$(dba)$_3$ (2.93 g, 3.20 mmol), 2'-(di-tert-butylphosphino)-N,N-dimethyl-[1,1'-biphenyl]-2-amine (3.28 g, 9.61 mmol), water (3.85 g, 213.62 mmol) and lithium acetate (35.2 g, 534.06 mmol) in DMF (400 mL) was stirred at 100° C. for 5 hr under argon gas atmosphere. To the reaction mixture were added water and ethyl acetate, and the organic layer was separated. The organic layer was dried over magnesium sulfate, and the solvent was evaporated under reduced pressure. The obtained residue was purified by silica gel column chromatography (solvent gradient; 0→5% ethyl acetate/hexane) to give 5-nitro-2-(trimethylsilyl)benzonitrile (13.2 g, 59.9 mmol, 56.1%) as a white solid.
(Step 2)
A solution of 5-nitro-2-(trimethylsilyl)benzonitrile and 10% palladium-carbon (1.32 g, 0.62 mmol, 50% wet) in MeOH (260 mL) was stirred at room temperature for 5 hr under hydrogen atmosphere (1 atm). The catalyst was removed by filtration, and the filtrate was concentrated under reduced pressure. The obtained residue was purified by silica gel column chromatography (solvent gradient; 10→20% ethyl acetate/hexane) to give 5-amino-2-(trimethylsilyl)benzonitrile (9.56 g, 50.2 mmol, 84%) as a white solid.
(Step 3)
A solution of 2-(diallylamino)-2-(4-(methoxymethyl)phenyl)acetic acid (1186 mg, 4.31 mmol), 5-amino-2-(trimethylsilyl)benzonitrile (820 mg, 4.31 mmol), T3P (3.80 mL, 6.46 mmol), DIEA (3.84 mL, 21.54 mmol) and DMAP (526 mg, 4.31 mmol) in ethyl acetate (20 mL) was stirred overnight at 80° C. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 10→100% ethyl acetate/hexane) to give N-(3-cyano-4-(trimethylsilyl)phenyl)-2-(diallylamino)-2-(4-(methoxymethyl)phenyl)acetamide (2890 mg, 6.46 mmol, 150%) as a pale yellow oil.

$^1$H NMR (300 MHz, CDCl$_3$): δ0.32-0.50 (9H, m), 2.89 (2H, dd, J=14.7, 7.2 Hz), 3.25-3.39 (2H, m), 3.38-3.51 (3H, m), 4.36-4.64 (3H, m), 5.18-5.41 (4H, m), 5.65-6.04 (2H, m), 7.27-7.38 (4H, m), 7.54 (1H, d, J=8.3 Hz), 7.78 (1H, dd, J=8.3, 2.3 Hz), 7.91 (1H, d, J=2.3 Hz), 9.57 (1H, s).
(Step 4)
A solution of N-(3-cyano-4-(trimethylsilyl)phenyl)-2-(diallylamino)-2-(4-(methoxymethyl)phenyl)acetamide (2.89 g, 6.46 mmol), 1,3-dimethylbarbituric acid (2.218 g, 14.20 mmol) and Pd(PPh$_3$)$_4$(0.298 g, 0.26 mmol) in THF (40 mL) was stirred overnight at room temperature under nitrogen atmosphere. The reaction mixture was concentrated under reduced pressure, and the obtained residue was purified by silica gel column chromatography (NH, solvent gradient; 10→100% ethyl acetate/hexane) to give 2-amino-N-(3-cyano-4-(trimethylsilyl)phenyl)-2-(4-(methoxymethyl)phenyl)acetamide (2.180 g, 5.93 mmol, 92%) as a brown oil.

$^1$H NMR (300 MHz, DMSO-d$_6$): δ0.35 (9H, s), 3.26 (3H, s), 4.37 (2H, s), 7.22-7.36 (2H, m), 7.44 (2H, d, J=8.3 Hz), 7.50-7.67 (5H, m), 7.85 (1H, dd, J=8.3, 1.9 Hz), 8.15 (1H, d, J=1.9 Hz).
(Step 5)
A solution of 2-amino-N-(3-cyano-4-(trimethylsilyl)phenyl)-2-(4-(methoxymethyl)phenyl)acetamide (290 mg, 0.79 mmol), 5-oxopyrrolidine-3-carboxylic acid (112 mg, 0.87 mmol), HATU (330 mg, 0.87 mmol) and DIEA (0.152 mL, 0.87 mmol) in DMF (5 mL) was stirred overnight at room temperature. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 10→100% ethyl acetate/hexane, 1→15% MeOH/ethyl acetate) to give the title compound (50.0 mg, 0.104 mmol, 13.24%) as a white solid.

MS(API): Calculated 478.6, Found 479.2 (M+H).

$^1$H NMR (300 MHz, DMSO-d$_6$): δ0.34 (9H, d, J=1.5 Hz), 2.26 (2H, d, J=7.6 Hz), 3.27 (4H, d, J=1.9 Hz), 3.36-3.55 (2H, m), 4.38 (2H, s), 5.58 (1H, d, J=7.2 Hz), 7.32 (2H, d, J=7.6 Hz), 7.38-7.66 (4H, m), 7.67-7.83 (1H, m), 8.10 (1H, s), 8.81 (1H, d, J=7.2 Hz), 10.70 (1H, s).

Example 27

N-(2-((3-cyano-4-(trimethylsilyl)phenyl)amino)-1-(4-methoxyphenyl)-2-oxoethyl)-5-oxopyrrolidine-3-carboxamide (Mixture of Four Optical Isomers)

(Step 1)
A solution of 2-(diallylamino)-2-(4-methoxyphenyl)acetic acid (2.060 g, 7.88 mmol), 5-amino-2-(trimethylsilyl)benzonitrile (1.5 g, 7.88 mmol), T3P (7.39 mL, 11.82 mmol), DIEA (6.88 mL, 39.41 mmol) and DMAP (1.059 g, 8.67 mmol) in ethyl acetate (20 mL) was stirred overnight at 80° C. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 10→100% ethyl acetate/hexane) to give N-(3-cyano-4-(trimethylsilyl)phenyl)-2-(diallylamino)-2-(4-methoxyphenyl)acetamide (2.000 g, 4.61 mmol, 58.5%) as a yellow oil.

(Step 2)
A solution of N-(3-cyano-4-(trimethylsilyl)phenyl)-2-(diallylamino)-2-(4-methoxyphenyl)acetamide (3 g, 6.92 mmol), 1,3-dimethylbarbituric acid (2.377 g, 15.22 mmol) and Pd(PPh$_3$)$_4$ (0.320 g, 0.28 mmol) in THF (50 mL) was stirred overnight at room temperature under nitrogen atmosphere. The reaction mixture was concentrated under reduced pressure, and the obtained residue was purified by silica gel column chromatography (NH, solvent gradient; 10→100% ethyl acetate/hexane) to give 2-amino-N-(3-cyano-4-(trimethylsilyl)phenyl)-2-(4-methoxyphenyl)acetamide (2.000 g, 5.66 mmol, 82%) as a pale yellow oil.

$^1$H NMR (300 MHz, DMSO-d$_6$): δ0.35 (9H, s), 3.72 (3H, s), 4.44-4.60 (1H, m), 6.89 (2H, d, J=8.7 Hz), 7.24-7.44 (2H, m), 7.49-7.71 (2H, m), 7.85 (1H, dd, J=8.3, 1.9 Hz), 8.16 (1H, d, J=2.3 Hz) (NH$_2$ D peak was not observed.).
(Step 3)
A solution of 2-amino-N-(3-cyano-4-(trimethylsilyl)phenyl)-2-(4-methoxyphenyl)acetamide (400 mg, 1.13 mmol), 5-oxopyrrolidine-3-carboxylic acid (146 mg, 1.13 mmol), HATU (430 mg, 1.13 mmol) and DMAP (0.198 mL, 1.13 mmol) in DMF (5 mL) was stirred overnight at room temperature. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 10→100% ethyl acetate/hexane, 1→10% MeOH/ethyl acetate) to give the title compound (452 mg, 0.973 mmol, 86%) as a white solid.

MS(API): Calculated 464.6, Found 463.0 (M−H).

$^1$H NMR (300 MHz, DMSO-d$_6$): δ0.24-0.53 (9H, m), 2.29 (2H, dd, J=14.5, 8.5 Hz), 3.13-3.30 (1H, m), 3.37-3.50 (2H, m), 3.74 (3H, s), 5.51 (1H, t, J=6.8 Hz), 6.95 (2H, dd, J=8.7, 1.1 Hz), 7.39 (2H, d, J=9.1 Hz), 7.50-7.66 (2H, m), 7.74 (1H, ddd, J=8.3, 3.8, 2.3 Hz), 8.10 (1H, t, J=2.3 Hz), 8.76 (1H, t, J=7.6 Hz), 10.64 (1H, d, J=3.4 Hz).

Example 28

N-(2-((3-fluoro-4-(trimethylsilyl)phenyl)amino)-1-(4-methoxyphenyl)-2-oxoethyl)-5-oxopyrrolidine-3-carboxamide (Mixture of Four Optical Isomers)

(Step 1)
To a solution of 3-fluoro-4-(trimethylsilyl)aniline (500 mg, 2.73 mmol), 2-(diallylamino)-2-(4-methoxyphenyl)acetic acid (784 mg, 3.00 mmol), DMAP (367 mg, 3.00 mmol) and DIEA (2.382 mL, 13.64 mmol) in ethyl acetate (15 mL) was added T3P (2.407 mL, 4.09 mmol), and the mixture was stirred at 80° C. for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 5→50% ethyl acetate/hexane) to give 2-(diallylamino)-N-(3-fluoro-4-(trimethylsilyl)phenyl)-2-(4-methoxyphenyl)acetamide (935 mg, 2.192 mmol, 80%) as a colorless oil.
$^1$H NMR (300 MHz, CDCl$_3$): δ0.13-0.47 (9H, m), 2.89 (2H, dd, J=14.7, 7.2 Hz), 3.32 (2H, dd, J=14.7, 5.3 Hz), 3.80 (3H, s), 4.49 (1H, s), 5.12-5.35 (4H, m), 5.73-6.00 (2H, m), 6.81-6.98 (2H, m), 7.13-7.37 (4H, m), 7.45 (1H, dd, J=10.6, 1.9 Hz), 9.49 (1H, s).
(Step 2)
A solution of 2-(diallylamino)-N-(3-fluoro-4-(trimethylsilyl)phenyl)-2-(4-methoxyphenyl)acetamide (900 mg, 2.11 mmol), 1,3-dimethylbarbituric acid (692 mg, 4.43 mmol) and Pd(PPh$_3$)$_4$ (98 mg, 0.08 mmol) in THF (8 mL) was stirred at room temperature for 3 days under nitrogen atmosphere. The reaction mixture was concentrated under reduced pressure, and the obtained residue was purified by silica gel column chromatography (NH, solvent gradient; 5→75% ethyl acetate/hexane) to give 2-amino-N-(3-fluoro-4-(trimethylsilyl)phenyl)-2-(4-methoxyphenyl)acetamide (679 mg, 1.959 mmol, 93%) as a white oil.
$^1$H NMR (300 MHz, CDCl$_3$): δ0.28 (9H, s), 1.88 (2H, brs), 3.79 (3H, s), 4.59 (1H, s), 6.79-6.97 (2H, m), 7.14-7.38 (4H, m), 7.38-7.51 (1H, m), 9.45 (1H, brs).
(Step 3)
A solution of 2-amino-N-(3-fluoro-4-(trimethylsilyl)phenyl)-2-(4-methoxyphenyl)acetamide (350 mg, 1.01 mmol), 5-oxopyrrolidine-3-carboxylic acid (150 mg, 1.16 mmol), HOBt (77 mg, 0.51 mmol), TEA (0.422 mL, 3.03 mmol) and WSC (235 mg, 1.52 mmol) in DMF (4 mL) was stirred overnight at room temperature. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 10→100% ethyl acetate/hexane) to give the title compound (392 mg, 0.856 mmol, 85%) as a white solid.
MS(API): Calculated 457.6, Found 456.0 (M+H).
$^1$H NMR (300 MHz, DMSO-d$_6$): δ0.22-0.40 (9H, m), 2.16-2.40 (2H, m), 3.08-3.28 (1H, m), 3.33-3.55 (2H, m), 3.73 (3H, s), 5.52 (1H, t, J=6.8 Hz), 6.94 (2H, dd, J=8.7, 1.1 Hz), 7.19-7.44 (4H, m), 7.44-7.61 (2H, m), 8.75 (1H, t, J=7.6 Hz), 10.51 (1H, d, J=3.8 Hz).

Example 29

N-(2-((3-fluoro-4-(trimethylsilyl)phenyl)amino)-1-(4-methoxyphenyl)-2-oxoethyl)-3-hydroxypyrrolidine-1-carboxamide (Mixture of Four Optical Isomers)

(Step 1)
To a solution of 2-amino-N-(3-fluoro-4-(trimethylsilyl)phenyl)-2-(4-methoxyphenyl)acetamide (350 mg, 1.01 mmol) in THF (6 mL) were added p-nitrophenyl chloroformate (234 mg, 1.16 mmol) and pyridine (0.094 mL, 1.16 mmol), and the mixture was stirred at room temperature for 1 hr. To the reaction mixture were added water and ethyl acetate, and the organic layer was separated. The organic layer was washed with water, and dried over magnesium sulfate, and the solvent was evaporated under reduced pressure to give 4-nitrophenyl (2-((3-fluoro-4-(trimethylsilyl)phenyl)amino)-1-(4-methoxyphenyl)-2-oxoethyl)carbamate (560 mg, 1.095 mmol, 1081) as a pale yellow solid.
(Step 2)
A solution of DL-3-pyrrolidinol (0.128 mL, 1.58 mmol) and DIEA (0.553 mL, 3.17 mmol) in DMF (2 mL) was added to a solution of 4-nitrophenyl (2-((3-fluoro-4-(trimethylsilyl)phenyl)amino)-1-(4-methoxyphenyl)-2-oxoethyl)carbamate (270 mg, 0.53 mmol) in DMF (2.000 mL), and the mixture was stirred overnight at room temperature. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 10→100% ethyl acetate/hexane, 0→15% MeOH/ethyl acetate) to give the title compound (18.80 mg, 0.041 mmol, 7.753) as a pale yellow solid.
MS(API): Calculated 459.6, Found 460.3 (M+H).
$^1$H NMR (300 MHz, CDCl$_3$): δ0.13-0.38 (9H, m), 1.64-1.88 (2H, m), 1.88-2.12 (2H, m), 3.38-3.53 (3H, m), 3.69-3.88 (3H, m), 4.29-4.55 (1H, m), 5.50-5.76 (2H, m), 6.70-6.90 (2H, m), 7.06-7.46 (5H, m), 9.23 (1H, d, J=8.3 Hz).

Example 30

N-(2-((3-fluoro-4-(trimethylsilyl)phenyl)amino)-1-(4-methoxyphenyl)-2-oxoethyl)-3-hydroxyazetidine-1-carboxamide A solution of azetidin-3-ol hydrochloride (289 mg, 2.64 mmol) and DIEA (1.383 mL, 7.92 mmol) in DMF (2 mL) was added to a solution of 4-nitrophenyl (2-((3-fluoro-4-(trimethylsilyl)phenyl)amino)-1-(4-methoxyphenyl)-2-oxoethyl)carbamate (270 mg, 0.53 mmol) in DMF (2.000 mL), and the mixture was stirred overnight at room temperature. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 10→100% ethyl acetate/hexane, 0→15% MeOH/ethyl acetate) to give the title compound (55.8 mg, 0.125 mmol, 23.733) as a white solid.
MS(API): Calculated 445.6, Found 446.2 (M+H).
$^1$H NMR (300 MHz, DMSO-d$_6$): δ0.10-0.28 (9H, m), 3.51-3.68 (2H, m), 3.73 (3H, s), 3.93-4.15 (2H, m), 4.27-4.49 (1H, m), 5.39 (1H, d, J=7.9 Hz), 5.56 (1H, d, J=6.4 Hz), 6.75 (1H, d, J=7.9 Hz), 6.91 (2H, d, J=8.7 Hz), 7.21-7.45 (4H, m), 7.45-7.60 (1H, m), 10.40 (1H, s).

Example 31

N-(2-((3-fluoro-4-(trimethylsilyl)phenyl)amino)-1-(4-(methoxymethyl)phenyl)-2-oxoethyl)-3-hydroxy-N-methyl-1,2-oxazole-5-carboxamide (Step 1)

A solution of (4-(methoxymethyl)phenyl)boronic acid (11.67 g, 70.30 mmol), glyoxylic acid monohydrate (6.47 g, 70.30 mmol) and N-methyl-2-propen-1-amine (6.75 mL, 70.30 mmol) in acetonitrile (150 mL) was stirred overnight at 50° C. The reaction mixture was concentrated under reduced pressure. The obtained residue was purified by silica gel column chromatography (Diol, solvent gradient; 5→100% ethyl acetate/hexane) to give 2-(allyl(methyl) amino)-2-(4-(methoxymethyl)phenyl)acetic acid (7.20 g, 28.9 mmol, 41.1%) as a pale yellow oil.

$^1$H NMR (300 MHz, DMSO-$d_6$): δ2.22 (3H, s), 3.13 (2H, t, J=5.7 Hz), 3.29 (3H, s), 4.19 (1H, s), 4.40 (2H, s), 5.04-5.40 (2H, m), 5.65-6.12 (1H, m), 7.23-7.34 (2H, m), 7.34-7.43 (2H, m). (COOH D peak was not observed.)

(Step 2)

To a solution of 3-fluoro-4-(trimethylsilyl)aniline (1.0 g, 5.46 mmol), 2-(allyl(methyl)amino)-2-(4-(methoxymethyl) phenyl)acetic acid (1.496 g, 6.00 mmol), DMAP (0.733 g, 6.00 mmol) and DIEA (4.76 mL, 27.28 mmol) in ethyl acetate (30 mL) was added T3P (4.81 mL, 8.18 mmol), and the mixture was stirred at 80° C. for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 5-50% ethyl acetate/hexane) to give 2-(allyl(methyl)amino)-N-(3-fluoro-4-(trimethylsilyl)phenyl)-2-(4-(methoxymethyl)phenyl)acetamide (2.140 g, 5.16 mmol, 95%) as a pale yellow oil.

$^1$H NMR (300 MHz, CDCl$_3$): δ0.17-0.32 (9H, m), 2.21 (3H, s), 2.90-3.20 (2H, m), 3.32-3.42 (3H, m), 4.13-4.24 (1H, m), 4.44 (2H, s), 5.17-5.32 (2H, m), 5.75-6.00 (1H, m), 7.13-7.39 (6H, m), 7.44 (1H, dd, J=10.4, 1.7 Hz), 9.32 (1H, s).

(Step 3)

A solution of 2-(allyl(methyl)amino)-N-(3-fluoro-4-(trimethylsilyl)phenyl)-2-(4-(methoxymethyl)phenyl)acetamide (2.05 g, 4.94 mmol), 1,3-dimethylbarbituric acid (1.158 g, 7.42 mmol) and Pd(PPh$_3$)$_4$ (0.114 g, 0.10 mmol) in THF (18 mL) was stirred overnight at room temperature under nitrogen atmosphere. The reaction mixture was concentrated under reduced pressure, and the obtained residue was purified by silica gel column chromatography (NH, solvent gradient; 5→75% ethyl acetate/hexane) to give N-(3-fluoro-4-(trimethylsilyl)phenyl)-2-(4-(methoxymethyl)phenyl)-2-(methylamino)acetamide (1.828 g, 4.88 mmol, 99%) as a white solid.

$^1$H NMR (300 MHz, CDCl$_3$): δ0.28 (9H, s), 2.53 (3H, s), 3.36 (3H, s), 4.10-4.20 (1H, m), 4.43 (2H, s), 7.15-7.41 (6H, m), 7.46 (1H, dd, J=10.4, 1.7 Hz), 9.39 (1H, s) (The peak of NH was not observed.).

(Step 4)

To a solution of N-(3-fluoro-4-(trimethylsilyl)phenyl)-2-(4-(methoxymethyl)phenyl)-2-(methylamino)acetamide (620 mg, 1.66 mmol), 3-hydroxy-1,2-oxazole-5-carboxylic acid (246 mg, 1.90 mmol), HOBt (127 mg, 0.83 mmol), DMAP (20.22 mg, 0.17 mmol) and TEA (0.692 mL, 4.97 mmol) in DMF (10 mL) was added WSC (476 mg, 2.48 mmol), and the mixture was stirred at 80° C. for 1.5 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 10→100% ethyl acetate/hexane, 0→15% MeOH/ethyl acetate) to give the title compound (527 mg, 1.086 mmol, 65.6%) as a white solid.

MS(API): Calculated 485.6, Found 484.1 (M−H).

$^1$H NMR (300 MHz, DMSO-$d_6$): δ0.11-0.30 (9H, m), 2.67-2.86 (1H, m), 2.89 (3H, s), 3.36-3.45 (2H, m), 4.31-4.56 (2H, m), 5.79-6.30 (1H, m), 6.37-6.63 (1H, m), 7.15-7.48 (6H, m), 7.56 (1H, d, J=11.3 Hz), 10.45-10.75 (1H, m).

Example 32

N-(2-((3-fluoro-4-(trimethylsilyl)phenyl)amino)-1-(4-(methoxymethyl)phenyl)-2-oxoethyl)-5-oxopyrrolidine-3-carboxamide (Mixture of Four Optical Isomers)

(Step 1)

To a solution of 3-fluoro-4-(trimethylsilyl)aniline (1.0 g, 5.46 mmol), 2-(diallylamino)-2-(4-(methoxymethyl)phenyl) acetic acid (1.652 g, 6.00 mmol), DMAP (0.733 g, 6.00 mmol) and DIEA (4.76 mL, 27.28 mmol) in ethyl acetate (30 mL) was added T3P (4.81 mL, 8.18 mmol), and the mixture was stirred at 80° C. for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 5→35% ethyl acetate/hexane) to give 2-(diallylamino)-N-(3-fluoro-4-(trimethylsilyl)phenyl)-2-(4-(methoxymethyl)phenyl)acetamide (1.890 g, 4.29 mmol, 79%) as a pale yellow oil.

$^1$H NMR (300 MHz, CDCl$_3$): δ0.20-0.36 (9H, m), 2.88 (2H, dd, J=14.7, 7.2 Hz), 3.25-3.46 (5H, m), 4.41-4.50 (2H, m), 4.55 (1H, s), 5.16-5.35 (4H, m), 5.74-5.97 (2H, m), 7.12-7.38 (6H, m), 7.44 (1H, dd, J=10.4, 1.7 Hz), 9.48 (1H, s).

(Step 2)

A solution of 2-(diallylamino)-N-(3-fluoro-4-(trimethylsilyl)phenyl)-2-(4-(methoxymethyl)phenyl)acetamide (1.80 g, 4.09 mmol), 1,3-dimethylbarbituric acid (1.339 g, 8.58 mmol) and Pd(PPh$_3$)$_4$ (0.189 g, 0.16 mmol) in THF (18 mL) was stirred overnight at room temperature under nitrogen atmosphere. The reaction mixture was concentrated under reduced pressure, and the obtained residue was purified by silica gel column chromatography (NH, solvent gradient; 5-75% ethyl acetate/hexane) to give 2-amino-N-(3-fluoro-4-(trimethylsilyl)phenyl)-2-(4-(methoxymethyl)phenyl)acetamide (1.085 g, 3.01 mmol, 73.7%) as a colorless oil.

$^1$H NMR (300 MHz, CDCl$_3$): δ0.25-0.43 (9H, m), 1.88 (2H, brs), 3.37 (3H, s), 4.43 (2H, s), 4.63 (1H, s), 7.15-7.36 (4H, m), 7.36-7.51 (3H, m), 9.48 (1H, brs).

(Step 3)

A solution of 2-amino-N-(3-fluoro-4-(trimethylsilyl)phenyl)-2-(4-(methoxymethyl)phenyl)acetamide (220 mg, 0.61 mmol), 5-oxopyrrolidine-3-carboxylic acid (91 mg, 0.70 mmol), HOBt (46.7 mg, 0.31 mmol), TEA (0.255 mL, 1.83 mmol) and WSC (142 mg, 0.92 mmol) in DMF (4 mL) was stirred overnight at room temperature. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 10→100% ethyl acetate/hexane, 0→15% MeOH/ethyl acetate) to give the title compound (198 mg, 0.420 mmol, 68.8%) as a white solid.

MS(API): Calculated 471.6, Found 470.2 (M+H).

$^1$H NMR (300 MHz, DMSO-$d_6$): δ0.25 (9H, s), 2.12-2.40 (2H, m), 3.10-3.30 (4H, m), 3.33-3.55 (2H, m), 4.38 (2H, s), 5.60 (1H, t, J=6.8 Hz), 7.18-7.39 (4H, m), 7.39-7.65 (4H, m), 8.83 (1H, t, J=7.7 Hz), 10.58 (1H, d, J=4.2 Hz).

Example 33

N-(2-((3-fluoro-4-(trimethylsilyl)phenyl)amino)-1-(4-(methoxymethyl)phenyl)-2-oxoethyl)-3-hydroxy-pyrrolidine-1-carboxamide (Mixture of Four Optical Isomers)

(Step 1)

To a solution of 2-amino-N-(3-fluoro-4-(trimethylsilyl)phenyl)-2-(4-(methoxymethyl)phenyl)acetamide (390 mg, 1.08 mmol) in THF (6 mL) were added p-nitrophenyl chloroformate (251 mg, 1.24 mmol) and pyridine (0.100 mL, 1.24 mmol), and the mixture was stirred at room temperature for 1 hr. To the reaction mixture were added water and ethyl acetate, and the organic layer was separated. The organic layer was washed with water, and dried over magnesium sulfate, and the solvent was evaporated under reduced pressure to give 4-nitrophenyl (2-((3-fluoro-4-(trimethylsilyl)phenyl)amino)-1-(4-(methoxymethyl)phenyl)-2-oxoethyl)carbamate (476 mg, 0.906 mmol, 84%) as a pale yellow solid.

(Step 2)

A solution of DL-3-pyrrolidinol (0.106 mL, 1.31 mmol) and DIEA (0.459 mL, 2.63 mmol) in DMF (2 mL) was added to a solution of 4-nitrophenyl (2-((3-fluoro-4-(trimethylsilyl)phenyl)amino)-1-(4-(methoxymethyl)phenyl)-2-oxoethyl)carbamate (230 mg, 0.44 mmol) in DMF (2.000 mL), and the mixture was stirred overnight at room temperature. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 10→100% ethyl acetate/hexane, 0→15% MeOH/ethyl acetate) to give the title compound (17.30 mg, 0.037 mmol, 8.35%) as a pale yellow solid.

MS(API): Calculated 473.6, Found 474.2 (M+H).

$^1$H NMR (300 MHz, CDCl$_3$): δ0.22-0.42 (9H, m), 1.70-2.10 (3H, m), 3.28-3.64 (7H, m), 4.23-4.52 (3H, m), 5.56-5.86 (2H, m), 7.07-7.38 (5H, m), 7.44 (2H, d, J=7.9 Hz), 9.34 (1H, brs).

Example 34

N-(2-((3-fluoro-4-(trimethylsilyl)phenyl)amino)-1-(4-(methoxymethyl)phenyl)-2-oxoethyl)-3-hydroxyazetidine-1-carboxamide A solution of azetidin-3-ol hydrochloride (240 mg, 2.19 mmol) and DIEA (1.146 mL, 6.56 mmol) in DMF (2 mL) was added to a solution of 4-nitrophenyl ((2-((3-fluoro-4-(trimethylsilyl)phenyl)amino)-1-(4-(methoxymethyl)phenyl)-2-oxoethyl)carbamate (230 mg, 0.44 mmol) in DMF (2.000 mL), and the mixture was stirred overnight at room temperature. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 10→100% ethyl acetate/hexane, 0→15% MeOH/ethyl acetate) to give the title compound (60.8 mg, 0.132 mmol, 30.2%) as a white solid.

MS(API): Calculated 459.6, Found 460.3 (M+H).

$^1$H NMR (300 MHz, DMSO-$d_6$): δ0.11-0.41 (9H, m), 3.28 (3H, s), 3.53-3.75 (2H, m), 3.95-4.13 (2H, m), 4.29-4.49 (3H, m), 5.47 (1H, d, J=8.3 Hz), 5.56 (1H, d, J=6.0 Hz), 6.84 (1H, d, J=8.3 Hz), 7.19-7.38 (4H, m), 7.38-7.60 (3H, m), 10.47 (1H, s).

Example 35

N-(3-fluoro-4-(trimethylsilyl)phenyl)-2-(4-(methoxymethyl)phenyl)-2-(((5-methyl-1,3,4-oxadiazol-2-yl)acetyl)amino)acetamide To a solution of 2-amino-N-(3-fluoro-4-(trimethylsilyl)phenyl)-2-(4-(methoxymethyl)phenyl)acetamide (145 mg, 0.40 mmol), 2-(5-methyl-1,3,4-oxadiazol-2-yl)acetic acid (65.7 mg, 0.46 mmol), HOBt (30.8 mg, 0.20 mmol) and TEA (0.168 mL, 1.21 mmol) in DMF (4 mL) was added WSC (94 mg, 0.60 mmol), and the mixture was stirred overnight at room temperature. To the reaction mixture were added water and ethyl acetate, and the organic layer was separated. The organic layer was dried over magnesium sulfate, and the solvent was evaporated under reduced pressure. The obtained residue was purified by silica gel column chromatography (solvent gradient; 10→100% ethyl acetate/hexane) to give the title compound (159 mg, 0.329 mmol, 82%) as white crystals.

MS(API): Calculated 484.6, Found 485.2 (M+H).

$^1$H NMR (300 MHz, DMSO-$d_6$): δ0.14-0.48 (9H, m), 2.48 (3H, s), 3.18-3.31 (3H, m), 3.89-4.17 (2H, m), 4.29-4.52 (2H, m), 5.52-5.78 (1H, m), 7.21-7.42 (4H, m), 7.42-7.58 (3H, m), 9.05-9.33 (1H, m), 10.64 (1H, brs).

Example 36

N-(3-fluoro-4-(trimethylsilyl)phenyl)-2-(4-(methoxymethyl)phenyl)-2-(((6-oxopyrimidin-1(6H)-yl)acetyl)amino)acetamide To a solution of 2-amino-N-(3-fluoro-4-(trimethylsilyl)phenyl)-2-(4-(methoxymethyl)phenyl)acetamide (150 mg, 0.42 mmol), 2-(6-oxopyrimidin-1(6H)-yl)acetic acid (73.7 mg, 0.48 mmol), HOBt (31.9 mg, 0.21 mmol) and TEA (0.174 mL, 1.25 mmol) in DMF (4 mL) was added WSC (97 mg, 0.62 mmol), and the mixture was stirred overnight at room temperature. To the reaction mixture were added water and ethyl acetate, and the organic layer was separated. The organic layer was dried over magnesium sulfate, and the solvent was evaporated under reduced pressure. The obtained residue was purified by silica gel column chromatography (solvent gradient; 10→100% ethyl acetate/hexane, 0→15% MeOH/ethyl acetate) to give the title compound (128 mg, 0.258 mmol, 62.0%) as white crystals.

MS(API): Calculated 496.6, Found 497.2 (M+H).

$^1$H NMR (300 MHz, DMSO-$d_6$): δ0.25 (9H, s), 3.26 (3H, s), 4.39 (2H, s), 4.72 (2H, s), 5.65 (1H, d, J=7.6 Hz), 6.38

(1H, d, J=6.4 Hz), 7.21-7.41 (4H, m), 7.41-7.59 (3H, m), 7.91 (1H, d, J=6.4 Hz), 8.37 (1H, s), 9.26 (1H, d, J=7.9 Hz), 10.61 (1H, s).

Example 37

N-(2-((3,5-difluoro-4-(trimethylsilyl)phenyl)amino)-1-(4-methoxyphenyl)-2-oxoethyl)-5-oxopyrrolidine-3-carboxamide (Mixture of Four Optical Isomers)

(Step 1)

To a solution of 3,5-difluoro-4-(trimethylsilyl)aniline (1.0 g, 4.97 mmol), 2-(diallylamino)-2-(4-methoxyphenyl)acetic acid (1.428 g, 5.46 mmol), DMAP (0.668 g, 5.46 mmol) and DIEA (4.34 mL, 24.84 mmol) in ethyl acetate (30 mL) was added T3P (4.38 mL, 7.45 mmol), and the mixture was stirred at 80° C. for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 5→20% ethyl acetate/hexane) to give 2-(diallylamino)-N-(3,5-difluoro-4-(trimethylsilyl)phenyl)-2-(4-methoxyphenyl)acetamide (1.450 g, 3.26 mmol, 65.6%) as a white solid.

$^1$H NMR (300 MHz, CDCl$_3$): δ0.34 (9H, t, J=1.5 Hz), 2.88 (2H, dd, J=14.5, 7.0 Hz), 3.23-3.39 (2H, m), 3.81 (3H, s), 4.49 (1H, s), 5.22 (2H, dd, J=6.6, 0.9 Hz), 5.27 (2H, s), 5.73-5.95 (2H, m), 6.85-6.95 (2H, m), 7.04-7.15 (2H, m), 7.15-7.24 (2H, m), 9.53 (1H, s).

(Step 2)

A solution of 2-(diallylamino)-N-(3,5-difluoro-4-(trimethylsilyl)phenyl)-2-(4-methoxyphenyl)acetamide (1.45 g, 3.26 mmol), 1,3-dimethylbarbituric acid (1.069 g, 6.85 mmol) and Pd(PPh$_3$)$_4$ (0.151 g, 0.13 mmol) in THF (15 mL) was stirred overnight at room temperature under nitrogen atmosphere. The reaction mixture was concentrated under reduced pressure, and the obtained residue was purified by silica gel column chromatography (NH, solvent gradient; 5→75% ethyl acetate/hexane) to give 2-amino-N-(3,5-difluoro-4-(trimethylsilyl)phenyl)-2-(4-methoxyphenyl)acetamide (0.621 g, 1.703 mmol, 52.2%) as a pale yellow oil.

$^1$H NMR (300 MHz, CDCl$_3$): δ0.33 (9H, t, J=1.3 Hz), 1.61 (2H, brs), 3.79 (3H, s), 4.59 (1H, s), 6.83-6.93 (2H, m), 7.07-7.18 (2H, m), 7.28-7.37 (2H, m), 9.53 (1H, brs).

(Step 3)

5-Oxopyrrolidine-3-carboxylic acid (53.1 mg, 0.41 mmol), HATU (188 mg, 0.49 mmol) and DIEA (0.144 mL, 0.82 mmol) were added to a solution of 2-amino-N-(3,5-difluoro-4-(trimethylsilyl)phenyl)-2-(4-methoxyphenyl)acetamide (150 mg, 0.41 mmol) in DMF (4 mL), and the mixture was stirred overnight at room temperature. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→5% MeOH/ethyl acetate) to give the title compound (125 mg, 0.263 mmol, 63.9%) as a white solid.

MS(API): Calculated 475.6, Found 474.1 (M−H).

$^1$H NMR (300 MHz, DMSO-d$_6$): δ0.30 (9H, s), 2.20-2.38 (2H, m), 3.09-3.29 (1H, m), 3.34-3.51 (2H, m), 3.74 (3H, s), 5.47 (1H, t, J=6.8 Hz), 6.94 (2H, dd, J=8.7, 1.1 Hz), 7.20 (2H, d, J=9.4 Hz), 7.37 (2H, d, J=9.1 Hz), 7.54 (1H, d, J=3.4 Hz), 8.76 (1H, t, J=7.6 Hz), 10.65 (1H, d, J=3.8 Hz).

Example 38

N-(2-((3,5-difluoro-4-(trimethylsilyl)phenyl)amino)-1-(4-(methoxymethyl)phenyl)-2-oxoethyl)-3-hydroxy-N-methyl-1,2-oxazole-5-carboxamide (Step 1)

To a solution of 3,5-difluoro-4-(trimethylsilyl)aniline (2.136 g, 10.61 mmol), 2-(allyl(methyl)amino)-2-(4-(methoxymethyl)phenyl)acetic acid (2.91 g, 11.67 mmol), DMAP (1.426 g, 11.67 mmol) and DIEA (9.27 mL, 53.06 mmol) in ethyl acetate (60 mL) was added T3P (9.36 mL, 15.92 mmol), and the mixture was stirred at 80° C. for 4 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 5→35% ethyl acetate/hexane) to give 2-(allyl(methyl)amino)-N-(3,5-difluoro-4-(trimethylsilyl)phenyl)-2-(4-(methoxymethyl)phenyl)acetamide (3.71 g, 8.58 mmol, 81%) as a pale yellow oil.

$^1$H NMR (300 MHz, CDCl$_3$): δ0.33 (9H, t, J=1.5 Hz), 2.20 (3H, s), 2.88-3.15 (2H, m), 3.39 (3H, s), 4.18 (1H, s), 4.45 (2H, s), 5.15-5.33 (2H, m), 5.78-5.96 (1H, m), 7.04-7.16 (2H, m), 7.31 (4H, q, J=8.3 Hz), 9.37 (1H, s).

(Step 2)

A solution of 2-(allyl(methyl)amino)-N-(3,5-difluoro-4-(trimethylsilyl)phenyl)-2-(4-(methoxymethyl)phenyl)acetamide (3.71 g, 8.58 mmol), 1,3-dimethylbarbituric acid (1.473 g, 9.43 mmol) and Pd(PPh$_3$)$_4$ (0.297 g, 0.26 mmol) in THF (40 mL) was stirred overnight at room temperature under nitrogen atmosphere. The reaction mixture was concentrated under reduced pressure, and the obtained residue was purified by silica gel column chromatography (NH, solvent gradient; 10-60% ethyl acetate/hexane) to give N-(3,5-difluoro-4-(trimethylsilyl)phenyl)-2-(4-(methoxymethyl)phenyl)-2-(methylamino)acetamide (3.16 g, 8.05 mmol, 94%) as a colorless oil.

$^1$H NMR (300 MHz, CDCl$_3$): δ0.33 (9H, t, J=1.3 Hz), 1.62 (1H, brs), 2.53 (3H, s), 3.37 (3H, s), 4.13 (1H, s), 4.43 (2H, s), 7.03-7.18 (2H, m), 7.28-7.41 (4H, m), 9.44 (1H, s).

(Step 3)

3-Hydroxy-1,2-oxazole-5-carboxylic acid (1.091 g, 8.45 mmol), HATU (3.67 g, 9.66 mmol) and DIEA (2.81 mL, 16.10 mmol) were added to a solution of N-(3,5-difluoro-4-(trimethylsilyl)phenyl)-2-(4-(methoxymethyl)phenyl)-2-(methylamino)acetamide (3.16 g, 8.05 mmol) in DMF (50 mL), and the mixture was stirred overnight at 80° C. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 30-100% ethyl acetate/hexane) to give the title compound (2.96 g, 5.88 mmol, 73.0%) as a white solid.

MS(API): Calculated 503.6, Found 502.1 (M−H).

$^1$H NMR (300 MHz, DMSO-d$_6$): δ0.32 (9H, s), 2.70-2.97 (3H, m), 3.30 (3H, s), 4.43 (2H, s), 6.19 (1H, s), 6.57 (1H, s), 7.13-7.36 (4H, m), 7.36-7.47 (2H, m), 10.80 (1H, s), 11.77 (1H, brs).

Example 39

N-(3,5-difluoro-4-(trimethylsilyl)phenyl)-2-(((3-hydroxy-1,2-oxazol-5-yl)acetyl)amino)-2-(4-(methoxymethyl)phenyl)acetamide (Step 1)

n-BuLi (5.27 mL, 8.43 mmol) was added to a solution of diisopropylamine (1.301 mL, 9.20 mmol) in THF (40 mL) at −78° C. under argon gas atmosphere, and the mixture was stirred for 20 min. Then, a solution of 3-(benzyloxy)-5-methyl-1,2-oxazole (1450 mg, 7.66 mmol) in THF (10.0 mL) was added thereto at −78° C., and the mixture was stirred for 50 min. Then, a solution of chloroethyl formate (0.875 mL, 9.20 mmol) in THF (5.0 mL) was added thereto at −78° C., and the mixture was stirred for 2 hr. To the reaction mixture was added aqueous ammonium chloride solution, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 5→20% ethyl acetate/hexane) to give diethyl 2-(3-(benzyloxy)-1,2-oxazol-5-yl)malonate (391 mg, 1.173 mmol, 15.31%) as a colorless oil.

$^1$H NMR (300 MHz, CDCl$_3$): δ1.23-1.37 (6H, m), 4.19-4.33 (4H, m), 4.77 (1H, s), 5.27 (2H, s), 6.14 (1H, s), 7.29-7.50 (5H, m).

(Step 2)

2N Aqueous sodium hydroxide solution (3.52 mL, 7.04 mmol) was added to a solution of diethyl 2-(3-(benzyloxy)-1,2-oxazol-5-yl)malonate (391 mg, 1.17 mmol) in EtOH (3.5 mL), and the mixture was stirred at room temperature for 3 hr. THF (1.50 mL) was added thereto, and the mixture was stirred at room temperature for 1 hr, and then overnight at 50° C. The reaction mixture was neutralized with 1N hydrochloric acid, and extracted with ethyl acetate. The organic layer was washed with brine, and dried over magnesium sulfate, and the solvent was evaporated under reduced pressure. The residue was crystallized from hexane/IPE to give 2-(3-(benzyloxy)-1,2-oxazol-5-yl)acetic acid (154 mg, 0.660 mmol, 56.3%) as a white solid.

$^1$H NMR (300 MHz, CDCl$_3$): δ3.79 (2H, s), 5.26 (2H, s), 5.97 (1H, s), 7.30-7.50 (5H, m) (COOH D peak was not observed.).

(Step 3)

2-(3-(Benzyloxy)-1,2-oxazol-5-yl)acetic acid (154 mg, 0.66 mmol), HATU (301 mg, 0.79 mmol) and DIEA (0.231 mL, 1.32 mmol) were added to a solution of 2-amino-N-(3,5-difluoro-4-(trimethylsilyl)phenyl)-2-(4-(methoxymethyl)phenyl)acetamide (275 mg, 0.73 mmol) in DMF (5 mL), and the mixture was stirred overnight at room temperature. To the reaction mixture were added water and ethyl acetate, and the organic layer was separated. The organic layer was washed with brine, and dried over sodium sulfate, and the solvent was evaporated under reduced pressure. The obtained residue was purified by silica gel column chromatography (solvent gradient; 10→50% ethyl acetate/hexane) to give 2-(2-(3-(benzyloxy)-1,2-oxazol-5-yl)acetamide)-N-(3,5-difluoro-4-(trimethylsilyl)phenyl)-2-(4-(methoxymethyl)phenyl)acetamide (318 mg, 0.536 mmol, 81%) as a white solid.

$^1$H NMR (300 MHz, CDCl$_3$): δ0.31 (9H, s), 3.36 (3H, s), 3.72 (2H, s), 4.40 (2H, s), 5.24 (2H, s), 5.68 (1H, d, J=6.0 Hz), 5.91 (1H, s), 6.85-7.00 (2H, m), 7.17 (1H, brs), 7.28-7.47 (9H, m), 8.19 (1H, brs).

(Step 4)

A solution of 2-(2-(3-(benzyloxy)-1,2-oxazol-5-yl)acetamide)-N-(3,5-difluoro-4-(trimethylsilyl)phenyl)-2-(4-(methoxymethyl)phenyl)acetamide (300 mg, 0.51 mmol) and 10-palladium-barium sulfate (53.8 mg, 0.051 mmol) in MeOH (5 mL) was stirred at room temperature for 5 hr under hydrogen atmosphere (1 atm). The catalyst was removed by filtration, and the filtrate was concentrated under reduced pressure. The obtained residue was purified by silica gel column chromatography (solvent gradient; 50→100% ethyl acetate/hexane) to give the title compound (197 mg, 0.391 mmol, 77%) as a white solid.

MS(API): Calculated 503.6, Found 504.2 (M+H).

$^1$H NMR (300 MHz, DMSO-d$_6$): δ0.30 (9H, s), 3.28 (3H, s), 3.71 (2H, s), 4.39 (2H, s), 5.57 (1H, d, J=7.2 Hz), 5.84 (1H, s), 7.14-7.28 (2H, m), 7.28-7.39 (2H, m), 7.40-7.51 (2H, m), 9.05 (1H, d, J=7.6 Hz), 10.75 (1H, s), 11.13 (1H, brs).

Example 40

N-(3,5-difluoro-4-(trimethylsilyl)phenyl)-2-(4-(methoxymethyl)phenyl)-2-(((6-oxopyrimidin-1(6H)-yl)acetyl)amino)acetamide 2-(6-Oxopyrimidin-1(6H)-yl)acetic acid (55.0 mg, 0.36 mmol), HATU (163 mg, 0.43 mmol) and DIEA (0.125 mL, 0.71 mmol) were added to a solution of 2-amino-N-(3,5-difluoro-4-(trimethylsilyl)phenyl)-2-(4-(methoxymethyl)phenyl)acetamide (135 mg, 0.36 mmol) in DMF (4 mL), and the mixture was stirred overnight at room temperature. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→51% MeOH/ethyl acetate) to give the title compound (100 mg, 0.194 mmol, 54.5%) as a white solid.

MS(API): Calculated 514.6, Found 513.1 (M−H).

$^1$H NMR (300 MHz, DMSO-d$_6$): δ0.30 (9H, s), 3.25-3.30 (3H, m), 4.40 (2H, s), 4.72 (2H, s), 5.55-5.66 (1H, m), 6.38 (1H, d, J=6.4 Hz), 7.13-7.27 (2H, m), 7.29-7.39 (2H, m), 7.41-7.53 (2H, m), 7.91 (1H, d, J=6.4 Hz), 8.37 (1H, s), 9.27 (1H, d, J=7.6 Hz), 10.75 (1H, s).

Example 41

N-(2-((3,5-difluoro-4-(trimethylsilyl)phenyl)amino)-1-(4-methoxyphenyl)-2-oxoethyl)-3-hydroxyazetidine-1-carboxamide A solution of pyridine (0.048 mL, 0.59 mmol) and 2-amino-N-(3,5-difluoro-4-(trimethylsilyl)phenyl)-2-(4-methoxyphenyl)acetamide (108 mg, 0.30 mmol) in THF (2 mL) was added to a solution of bis(trichloromethyl) carbonate (34.3 mg, 0.12 mmol) in THF (2 mL) at 0° C., and the mixture was stirred at 0° C. for 15 min. Then, a solution of azetidin-3-ol hydrochloride (97 mg, 0.89 mmol) and DIEA (0.155 mL, 0.89 mmol) in DMF (1 mL) was added thereto at 0° C., and the mixture was stirred overnight at room temperature. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 30-100% ethyl acetate/hexane) to give the title compound (16.30 mg, 0.035 mmol, 11.87%) as a white solid.

MS(API): Calculated 463.6, Found 464.1 (M+H).

$^1$H NMR (300 MHz, CDCl$_3$): δ0.30 (9H, s), 2.88 (1H, brs), 3.73 (3H, s), 3.90 (2H, td, J=9.3, 4.2 Hz), 4.24 (2H, q, J=6.9 Hz), 4.63 (1H, brs), 5.49 (1H, d, J=7.2 Hz), 5.66 (1H, d, J=7.6 Hz), 6.79 (2H, d, J=8.3 Hz), 6.99 (2H, d, J=9.1 Hz), 7.33 (2H, d, J=8.3 Hz), 9.45 (1H, brs).

Example 42

N-(2-((2,5-difluoro-4-(trimethylsilyl)phenyl)amino)-1-(4-methoxyphenyl)-2-oxoethyl)-5-oxopyrrolidine-3-carboxamide (Mixture of Four Optical Isomers)

(Step 1)

To a solution of 2-(diallylamino)-2-(4-methoxyphenyl)acetic acid (4.70 g, 18.00 mmol), 2,5-difluoro-4-(trimethylsilyl)aniline (3.019 g, 15.00 mmol), DIEA (13.06 mL, 74.99 mmol) and DMAP (2.016 g, 16.50 mmol) in ethyl acetate (100 mL) was added T3P (13.38 mL, 22.50 mmol), and the mixture was stirred at 70° C. for 15 hr. To the reaction mixture were added aqueous sodium hydrogencarbonate solution and ethyl acetate, and the organic layer was separated. The organic layer was washed with brine, and dried over magnesium sulfate, and the solvent was evaporated under reduced pressure. The obtained residue was purified by silica gel column chromatography (NH, solvent gradient; 2→5% ethyl acetate/hexane) to give 2-(diallylamino)-N-(2,5-difluoro-4-(trimethylsilyl)phenyl)-2-(4-methoxyphenyl)acetamide (3.09 g) as a pale yellow oil.

(Step 2)

A solution of 2-(diallylamino)-N-(2,5-difluoro-4-(trimethylsilyl)phenyl)-2-(4-methoxyphenyl)acetamide (3.09 g), Pd(PPh$_3$)$_4$ (321 mg, 0.28 mmol) and 1,3-dimethylbarbituric acid (2.39 g, 15.31 mmol) in THF (65 mL) was stirred at room temperature for 15 hr under argon gas atmosphere, and the mixture was concentrated under reduced pressure. The obtained residue was purified by silica gel column chromatography (NH, solvent gradient; 5→50% ethyl acetate/hexane) to give 2-amino-N-(2,5-difluoro-4-(trimethylsilyl)phenyl)-2-(4-methoxyphenyl)acetamide (1.02 g, 2.80 mmol, 18.66%) as a colorless oil.

$^1$H NMR (300 MHz, CDCl$_3$): δ0.28 (9H, s), 1.95 (2H, s), 3.79 (3H, s), 4.63 (1H, s), 6.89 (2H, d, J=9.1 Hz), 7.05 (1H, dd, J=10.6, 4.5 Hz), 7.35 (2H, d, J=8.7 Hz), 8.10 (1H, dd, J=9.6, 5.9 Hz), 9.80 (1H, brs).

(Step 3)

To a solution of 2-amino-N-(2,5-difluoro-4-(trimethylsilyl)phenyl)-2-(4-methoxyphenyl)acetamide (200 mg, 0.55 mmol), 5-oxopyrrolidine-3-carboxylic acid (78 mg, 0.60 mmol) and DIEA (191 μL, 1.10 mmol) in DMF (3 mL) was added HATU (250 mg, 0.66 mmol), and the mixture was stirred at room temperature for 15 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→5% MeOH/ethyl acetate) to give the title compound (187.8 mg, 0.395 mmol, 72.0%) as a white solid.

MS(API): Calculated 475.6, Found 474.1 (M−H).

$^1$H NMR (300 MHz, CDCl$_3$): δ0.27 (9H, d, J=0.8 Hz), 2.44-2.75 (2H, m), 3.23-3.35 (1H, m), 3.52-3.57 (1H, m), 3.60-3.67 (1H, m), 3.76-3.82 (3H, m), 5.59-5.66 (2H, m), 6.85-7.03 (4H, m), 7.34 (2H, d, J=8.7 Hz), 7.71 (1H, brs), 7.95 (1H, dd, J=9.4, 6.0 Hz).

Example 43

N-(2-((2,5-difluoro-4-(trimethylsilyl)phenyl)amino)-1-(4-(methoxymethyl)phenyl)-2-oxoethyl)-3-hydroxy-N-methyl-1,2-oxazole-5-carboxamide (Step 1)

To a solution of 2-(allyl(methyl)amino)-2-(4-(methoxymethyl)phenyl)acetic acid (2.112 g, 8.47 mmol), 2,5-difluoro-4-(trimethylsilyl)aniline (1.55 g, 7.70 mmol), DIEA (6.71 mL, 38.50 mmol) and DMAP (1.035 g, 8.47 mmol) in ethyl acetate (50 mL) was added T3P (6.87 mL, 11.55 mmol), and the mixture was stirred at 70° C. for 15 hr. To the reaction mixture were added aqueous sodium hydrogencarbonate solution and ethyl acetate, and the organic layer was separated. The organic layer was washed with brine, and dried over magnesium sulfate, and the solvent was evaporated under reduced pressure. The obtained residue was purified by silica gel column chromatography (NH, solvent gradient; 2-5% ethyl acetate/hexane) to give 2-(allyl(methyl)amino)-N-(2,5-difluoro-4-(trimethylsilyl)phenyl)-2-(4-(methoxymethyl)phenyl)acetamide (2.36 g) as a pale yellow oil.

(Step 2)

A solution of 2-(allyl(methyl)amino)-N-(2,5-difluoro-4-(trimethylsilyl)phenyl)-2-(4-(methoxymethyl)phenyl)acetamide (2.36 g), Pd(PPh$_3$)$_4$(126 mg, 0.11 mmol) and 1,3-dimethylbarbituric acid (937 mg, 6.00 mmol) in THF (26 mL) was stirred at room temperature for 15 hr under argon gas atmosphere, and the mixture was concentrated under reduced pressure. The obtained residue was purified by silica gel column chromatography (NH, solvent gradient; 3→30% ethyl acetate/hexane) to give N-(2,5-difluoro-4-(trimethylsilyl)phenyl)-2-(4-(methoxymethyl)phenyl)-2-(methylamino)acetamide (1.89 g, 4.82 mmol, 62.5%) as a colorless oil.

$^1$H NMR (300 MHz, CDCl$_3$): δ0.28 (9H, d, J=0.8 Hz), 1.75 (1H, s), 2.55 (3H, s), 3.37 (3H, s), 4.17 (1H, s), 4.43 (2H, s), 7.0 (1H, dd, J=10.2, 4.5 Hz), 7.32 (2H, d), 7.40 (2H, d), 8.07 (1H, dd, J=9.6, 5.9 Hz), 9.73 (1H, brs).

(Step 3)

To a solution of N-(2,5-difluoro-4-(trimethylsilyl)phenyl)-2-(4-(methoxymethyl)phenyl)-2-(methylamino)acetamide (300 mg, 0.76 mmol), 3-hydroxy-1,2-oxazole-5-carboxylic acid (109 mg, 0.84 mmol) and DIEA (266 μL, 1.53 mmol) in DMF (4 mL) was added HATU (349 mg, 0.92 mmol), and the mixture was stirred at room temperature for 15 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 30→100% ethyl acetate/hexane), and crystallized from hexane/IPE to give the title compound (170.6 mg, 0.339 mmol, 44.3%) as a white solid.

MS(API): Calculated 503.6, Found 502.2 (M−H).

$^1$H NMR (300 MHz, CDCl$_3$): δ0.29 (9H, d, J=0.8 Hz), 1.65 (1H, brs), 3.09 (3H, s), 3.43 (3H, s), 4.49 (2H, s), 6.35 (1H, s), 6.47 (1H, s), 7.02 (1H, dd, J=10.6, 4.5 Hz), 7.42 (4H, s), 7.77 (1H, brs), 8.08 (1H, dd, J=9.4, 6.0 Hz).

Example 44

N-(2,5-difluoro-4-(trimethylsilyl)phenyl)-2-(4-(methoxymethyl)phenyl)-2-(((5-methyl-1,3,4-oxadiazol-2-yl)acetyl)amino)acetamide (Step 1)
To a solution of 2-(diallylamino)-2-(4-(methoxymethyl)phenyl)acetic acid (4.96 g, 18.00 mmol), 2,5-difluoro-4-(trimethylsilyl)aniline (3.02 g, 15 mmol), DIEA (13.06 mL, 75.00 mmol) and DMAP (2.016 g, 16.50 mmol) in ethyl acetate (100 mL) was added T3P (13.38 mL, 22.50 mmol), and the mixture was stirred at 70° C. for 15 hr. To the reaction mixture were added aqueous sodium hydrogencarbonate solution and ethyl acetate, and the organic layer was separated. The organic layer was washed with brine, and dried over magnesium sulfate, and the solvent was evaporated under reduced pressure. The obtained residue was purified by silica gel column chromatography (NH, solvent gradient; 2→5% ethyl acetate/hexane) to give 2-(diallylamino)-N-(2,5-difluoro-4-(trimethylsilyl)phenyl)-2-(4-methoxymethylphenyl)acetamide (3.13 g) as a pale yellow oil.

(Step 2)
A solution of 2-(diallylamino)-N-(2,5-difluoro-4-(trimethylsilyl)phenyl)-2-(4-methoxymethylphenyl)acetamide (3.13 g), Pd(PPh$_3$)$_4$(315 mg, 0.27 mmol) and 1,3-dimethylbarbituric acid (2.34 g, 14.99 mmol) in THF (65 mL) was stirred at room temperature for 15 hr under argon gas atmosphere, and the mixture was concentrated under reduced pressure. The obtained residue was purified by silica gel column chromatography (NH, solvent gradient; 5→50% ethyl acetate/hexane) to give 2-amino-N-(2,5-difluoro-4-(trimethylsilyl)phenyl)-2-(4-(methoxymethyl)phenyl)acetamide (1.08 g, 2.85 mmol, 19.02%) as a colorless oil.

$^1$H NMR (300 MHz, CDCl$_3$): δ0.28 (9H, d, J=0.8 Hz), 1.98 (2H, s), 3.37 (3H, s), 4.44 (2H, s), 4.68 (1H, s), 7.05 (1H, dd, J=1.6, 4.5 Hz), 7.34 (2H, d), 7.42 (2H, d), 8.09 (1H, dd, J=9.6, 5.9 Hz), 9.83 (1H, brs).

(Step 3)
To a solution of 2-amino-N-(2,5-difluoro-4-(trimethylsilyl)phenyl)-2-(4-(methoxymethyl)phenyl)acetamide (221 mg, 0.58 mmol), 2-(5-methyl-1,3,4-oxadiazol-2-yl)acetic acid (87 mg, 0.61 mmol) and DIEA (203 µL, 1.17 mmol) in DMF (3 mL) was added HATU (266 mg, 0.70 mmol), and the mixture was stirred at room temperature for 15 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 30→100% ethyl acetate/hexane) to give the title compound (175.7 mg, 0.350 mmol, 59.9%) as a white solid.

MS(API): Calculated 502.6, Found 503.2 (M+H).
$^1$H NMR (300 MHz, CDCl$_3$): δ0.27 (9H, d, J=0.8 Hz), 2.52 (3H, s), 3.38 (3H, s), 3.90 (2H, s), 4.44 (2H, s), 5.67 (1H, d, J=6.4 Hz), 6.99 (1H, dd, J=10.2, 4.5 Hz), 7.35 (2H, d), 7.43 (2H, d), 7.79 (1H, brs), 7.94-8.04 (2H, m).

Example 45

N-(2,5-difluoro-4-(trimethylsilyl)phenyl)-2-(4-(methoxymethyl)phenyl)-2-(((6-oxopyrimidin-1(6H)-yl)acetyl)amino)acetamide To a solution of 2-amino-N-(2,5-difluoro-4-(trimethylsilyl)phenyl)-2-(4-(methoxymethyl)phenyl)acetamide (200 mg, 0.53 mmol), 2-(6-oxopyrimidin-1(6H)-yl)acetic acid (86 mg, 0.55 mmol) and DIEA (184 µL, 1.06 mmol) in DMF (2.6 mL) was added HATU (241 mg, 0.63 mmol), and the mixture was stirred at room temperature for 15 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 30→100% ethyl acetate/hexane), and crystallized from IPE/hexane to give the title compound (178.6 mg, 0.347 mmol, 65.7%) as a white solid.

MS(API): Calculated 514.6, Found 515.2 (M+H).
$^1$H NMR (300 MHz, CDCl$_3$): δ0.27 (9H, d, J=0.8 Hz), 3.38 (3H, s), 4.42 (2H, s), 4.56 (1H, d), 4.70 (1H, d), 5.61 (1H, d, J=6.8 Hz), 6.50 (1H, dd, J=6.4, 0.8 Hz), 6.98 (1H, dd, J=10.2, 4.5 Hz), 7.33 (2H, d), 7.38 (2H, d), 7.70 (1H, d, J=6.4 Hz), 7.82 (1H, brs), 7.90-7.97 (2H, m), 8.13 (1H, s).

Example 46

N-(2,5-difluoro-4-(trimethylsilyl)phenyl)-2-((1H-indazol-1-ylacetyl)amino)-2-(4-methoxyphenyl)acetamide To a solution of 2-amino-N-(2,5-difluoro-4-(trimethylsilyl)phenyl)-2-(4-methoxyphenyl)acetamide (173 mg, 0.47 mmol), 2-(1H-indazol-1-yl)acetic acid (92 mg, 0.52 mmol) and DIEA (165 µL, 0.95 mmol) in DMF (2.4 mL) was added HATU (217 mg, 0.57 mmol), and the mixture was stirred at room temperature for 15 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 8→50% ethyl acetate/hexane), and crystallized from IPE/hexane to give the title compound (146.4 mg, 0.280 mmol, 59.0%) as a white solid.

MS(API): Calculated 522.6, Found 523.2 (M+H).
$^1$H NMR (300 MHz, CDCl$_3$): δ0.25 (9H, d, J=0.8 Hz), 3.77 (3H, s), 5.03-5.17 (2H, m), 5.58 (1H, d, J=6.8 Hz), 6.82 (2H, d, J=8.7 Hz), 6.96 (1H, dd, J=10.2, 4.5 Hz), 7.18 (2H, d, J=8.7 Hz), 7.21-7.30 (2H, m), 7.36-7.47 (2H, m), 7.74 (1H, brs), 7.79 (1H, d, J=7.9 Hz), 7.90 (1H, dd, J=9.6, 5.9 Hz), 8.18 (1H, d, J=0.8 Hz).

Example 47

N-(2,5-difluoro-4-(trimethylsilyl)phenyl)-2-((1H-indazol-1-ylacetyl)amino)-2-(4-(methoxymethyl)phenyl)acetamide To a solution of 2-amino-N-(2,5-difluoro-4-(trimethylsilyl)phenyl)-2-(4-(methoxymethyl)phenyl)acetamide (180 mg, 0.48 mmol), 2-(1H-indazol-1-yl)acetic acid (92 mg, 0.52 mmol) and DIEA (166 µL, 0.95 mmol) in DMF (2.4 mL) was added HATU (217 mg, 0.57 mmol), and the mixture was stirred at room temperature for 15 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent; ethyl acetate), and crystallized from IPE/hexane to give the title compound (220.6 mg, 0.411 mmol, 86%) as a white solid.

MS(API): Calculated 536.6, Found 537.2 (M+H).

¹H NMR (300 MHz, CDCl₃): δ0.25 (9H, s), 3.36 (3H, s), 4.41 (2H, s), 5.04-5.18 (2H, m), 5.59 (1H, d, J=6.4 Hz), 6.96 (1H, dd, J=10.2, 4.5 Hz), 7.19-7.47 (8H, m), 7.67 (1H, brs), 7.79 (1H, d, J=8.3 Hz), 7.89 (1H, dd, J=9.4, 5.7 Hz), 8.19 (1H, s).

Example 48

N-(2-((3-chloro-4-(trimethylsilyl)phenyl)amino)-1-(4-methoxyphenyl)-2-oxoethyl)-3-hydroxy-N-methyl-1,2-oxazole-5-carboxamide (Step 1)
Microflow system consisting of two T-type micromixers (M1, M2), two microtube reactors (R1, R2) and three tube precooling units (P1 (inner diameter φ=1 mm, length L=100 cm), P2 (φ=1 mm, L=50 cm) and P3 (φ=1 mm, L=100 cm)) was cooled to −20° C. A solution (flow rate: 6.0 mL/min) of 2-chloro-1-iodo-4-nitrobenzene (2835 mg, 10 mmol) in THF (100 mL) and 0.4M phenyllithium in dibutyl ether and THF mixed solution (100 mL, 40.00 mmol) (flow rate: 2.25 mL/min) were introduced into M1 (φ=0.5 mm) using syringe pump. The reaction solution was passed through R1 (φ=1 mm, L=25 cm), and 0.6M chlorotrimethylsilane THF solution (100 mL, 60.00 mmol) (flow rate: 3.0 mL/min) was mixed in M2 (φ=1 mm). The reaction solution was passed through R2 (φ=1 nm, L=100 cm). After the reaction reached the static state, the solution containing a product was poured into water. The mixture was extracted with ethyl acetate, the organic layer was dried over magnesium sulfate, and the solvent was evaporated under reduced pressure. The obtained residue was purified by silica gel column chromatography (solvent gradient; 0→5% ethyl acetate/hexane) to give (2-chloro-4-nitrophenyl)trimethylsilane (780 mg, 3.40 mmol, 34.0%) as a white solid.
¹H NMR (300 MHz, DMSO-d₆): δ0.40 (9H, s), 7.78 (1H, d, J=8.3 Hz), 8.13-8.17 (1H, m), 8.20 (1H, d, J=2.3 Hz).
(Step 2)
A solution of (2-chloro-4-nitrophenyl)trimethylsilane (0.30 g, 1.31 mmol), calcium chloride (0.072 g, 0.65 mmol) and iron (0.365 g, 6.53 mmol) in a mixed solvent of EtOH (10.88 mL) and water (2.176 mL) was stirred at 100° C. for 2 hr. The insoluble substance was removed by filtration, and the filtrate was concentrated under reduced pressure. The obtained residue was purified by silica gel column chromatography (solvent gradient; 0→15% ethyl acetate/hexane) to give 3-chloro-4-(trimethylsilyl)aniline (0.150 g, 0.751 mmol, 57.5-) as a pale yellow oil.
¹H NMR (300 MHz, DMSO-d₆) δ: 0.25 (9H, s), 5.51 (2H, s), 6.48 (1H, dd, J=8.1, 2.1 Hz), 6.58 (1H, d, J=2.3 Hz), 7.07 (1H, d, J=7.9 Hz).
(Step 3)
To a solution of 3-chloro-4-(trimethylsilyl)aniline (0.15 g, 0.75 mmol), 2-(3-hydroxy-N-methyl-1,2-oxazole-5-carboxamide)-2-(4-methoxyphenyl)acetic acid (0.253 g, 0.83 mmol), DMAP (0.101 g, 0.83 mmol) and DIEA (0.654 mL, 3.75 mmol) in ethyl acetate (4.13 mL) was added T3P (0.663 mL, 1.13 mmol), and the mixture was stirred at 80° C. for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→10% MeOH/ethyl acetate), and then preparative HPLC (C18, mobile phase: water/acetonitrile (containing 0.1, TFA)) to give the title compound (0.050 g, 0.102 mmol, 13.64%) as a pale yellow solid.
MS(API): Calculated 488.0, Found 486.1 (M−H).

Example 49

(3S)—N-((1R)-2-((3-fluoro-4-(trimethylsilyl)phenyl)amino)-1-(4-(methoxymethyl)phenyl)-2-oxoethyl)-5-oxopyrrolidine-3-carboxamide (Step 1)
To a solution of 2-amino-N-(3-fluoro-4-(trimethylsilyl)phenyl)-2-(4-(methoxymethyl)phenyl)acetamide (6.62 g, 18.36 mmol) and DIEA (9.62 mL, 55.09 mmol) in THF (130 mL) was added allyl chloroformate (2.338 mL, 22.04 mmol), and the mixture was stirred at room temperature for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→-10% ethyl acetate/hexane) to give allyl (2-((3-fluoro-4-(trimethylsilyl)phenyl)amino)-1-(4-(methoxymethyl)phenyl)-2-oxoethyl)carbamate (5.08 g, 11.43 mmol, 62.2%) as a white solid.
(Step 2)
Allyl (2-((3-fluoro-4-(trimethylsilyl)phenyl)amino)-1-(4-(methoxymethyl)phenyl)-2-oxoethyl)carbamate (6.955 g) was subjected to optical resolution using chiral column chromatography. The preparative fraction having a shorter retention time was concentrated to give allyl ((1R)-2-((3-fluoro-4-(trimethylsilyl)phenyl)amino)-1-(4-(methoxymethyl)phenyl)-2-oxoethyl)carbamate (2.16 g, >99.9% ee) as a white solid.
purification condition using chiral column chromatography
column: CHIRALCEL OD-H(OF002)30 mmID×250 mmL
solvent: CO₂/MeOH=860/140
back pressure: 100 bar
temperature: 35° C.
detection method: UV 220 nm
(Step 3)
A solution of allyl ((1R)-2-((3-fluoro-4-(trimethylsilyl)phenyl)amino)-1-(4-(methoxymethyl)phenyl)-2-oxoethyl)carbamate (340 mg, 0.76 mmol), 1,3-dimethylbarbituric acid (251 mg, 1.61 mmol) and Pd(PPh₃)₄(35.4 mg, 0.03 mmol) in THF (6.0 mL) was stirred at room temperature for 2 hr under argon gas atmosphere. The reaction mixture was concentrated under reduced pressure, and the obtained residue was purified by silica gel column chromatography (NH, solvent gradient; 5→50% ethyl acetate/hexane) to give (R)-2-amino-N-(3-fluoro-4-(trimethylsilyl)phenyl)-2-(4-(methoxymethyl)phenyl)acetamide (253.3 mg, 0.703 mmol, 92%) as a pale yellow oil.
(Step 4)
A solution of (R)-2-amino-N-(3-fluoro-4-(trimethylsilyl)phenyl)-2-(4-(methoxymethyl)phenyl)acetamide (120 mg, 0.33 mmol), (S)-5-oxopyrrolidine-3-carboxylic acid (47.3 mg, 0.37 mmol), DIEA (0.116 mL, 0.67 mmol) and HATU (152 mg, 0.40 mmol) in DMF (2.0 mL) was stirred at room temperature for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent; ethyl acetate), and crystallized from ethyl acetate/hexane to give the title compound (85.2 mg, 0.181 mmol, 54.3%) as white crystals.

MS(API): Calculated 471.6, Found 470.2 (M−H).

$^1$H NMR (300 MHz, DMSO-d$_6$): δ0.20-0.32 (9H, m), 2.23-2.37 (2H, m), 3.11-3.21 (1H, m), 3.27 (3H, s), 3.35-3.47 (2H, m), 4.38 (2H, s), 5.61 (1H, d, J=7.6 Hz), 7.23-7.39 (4H, m), 7.40-7.57 (4H, m), 8.83 (1H, d, J=7.6 Hz), 10.58 (1H, s).

$[α]_D^{25}$−119.3 (c 0.1965, MeOH)

Example 50

(3S)—N-((1R)-2-((3-fluoro-4-(trimethylsilyl)phenyl)amino)-1-(4-methoxyphenyl)-2-oxoethyl)-5-oxopyrrolidine-3-carboxamide (Step 1)

To a solution of 2-amino-N-(3-fluoro-4-(trimethylsilyl)phenyl)-2-(4-methoxyphenyl)acetamide (7.78 g, 22.45 mmol) and DIEA (11.77 mL, 67.36 mmol) in THF (100 mL) was added allyl chloroformate (2.86 mL, 26.95 mmol) at 0° C., and the mixture was stirred for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 5→75% ethyl acetate/hexane), and crystallized from IPE/hexane to give allyl (2-((3-fluoro-4-(trimethylsilyl)phenyl)amino)-1-(4-methoxyphenyl)-2-oxoethyl)carbamate (7.0 g, 16.26 mmol, 72.4%) as a white solid.

(Step 2)

Allyl (2-((3-fluoro-4-(trimethylsilyl)phenyl)amino)-1-(4-methoxyphenyl)-2-oxoethyl)carbamate (7.0 g) was subjected to optical resolution using chiral column chromatography. The preparative fraction having a shorter retention time was concentrated to give allyl ((1R)-2-((3-fluoro-4-(trimethylsilyl)phenyl)amino)-1-(4-(methoxymethyl)phenyl)-2-oxoethyl)carbamate (3.383 g, >99.9% ee) as a white solid.

purification condition using chiral column chromatography
column: CHIRALPAK AD(NF001) 50 mmID×500 mmL
solvent: hexane/2-propanol=800/200
flow rate: 80 mL/min
temperature: 30° C.
detection method: UV 220 nm (Step 3)

A solution of allyl ((1R)-2-((3-fluoro-4-(trimethylsilyl)phenyl)amino)-1-(4-(methoxymethyl)phenyl)-2-oxoethyl)carbamate (165 mg, 0.38 mmol), 1,3-dimethylbarbituric acid (132 mg, 0.84 mmol) and Pd(PPh$_3$)$_4$ (17.71 mg, 0.02 mmol) in THF (2.55 mL) was stirred at room temperature for 6 hr under argon gas atmosphere. The reaction mixture was concentrated under reduced pressure, and the obtained residue was purified by silica gel column chromatography (NH, solvent gradient; 40→80% ethyl acetate/hexane) to give (R)-2-amino-N-(3-fluoro-4-(trimethylsilyl)phenyl)-2-(4-methoxyphenyl)acetamide (178 mg, 0.514 mmol, 134%) as a yellow oil.

(Step 4)

A solution of (R)-2-amino-N-(3-fluoro-4-(trimethylsilyl)phenyl)-2-(4-methoxyphenyl)acetamide (178 mg, 0.51 mmol), (S)-5-oxopyrrolidine-3-carboxylic acid (86 mg, 0.67 mmol), HATU (293 mg, 0.77 mmol) and DIEA (0.269 mL, 1.54 mmol) in DMF (0.5 mL) was stirred at room temperature for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→7% MeOH/ethyl acetate) to give the title compound (137 mg, 0.299 mmol, 58.3%) as a white solid.

MS(API): Calculated 457.6, Found 458.2 (M+H).

$^1$H NMR (300 MHz, DMSO-d$_6$): δ0.25 (9H, s), 2.31 (2H, d, J=7.9 Hz), 3.17 (1H, d, J=4.9 Hz), 3.33-3.44 (2H, m), 3.73 (3H, s), 5.53 (1H, d, J=7.6 Hz), 6.94 (2H, d, J=8.7 Hz), 7.22-7.60 (6H, m), 8.76 (1H, d, J=7.2 Hz), 10.51 (1H, s).

$[α]_D^{25}$−107.9 (c 0.119, MeOH)

Example 51

(3S)—N-((1R)-2-((2,5-difluoro-4-(trimethylsilyl)phenyl)amino)-1-(4-(methoxymethyl)phenyl)-2-oxoethyl)-5-oxopyrrolidine-3-carboxamide (Step 1)

To a solution of 2-amino-N-(2,5-difluoro-4-(trimethylsilyl)phenyl)-2-(4-(methoxymethyl)phenyl)acetamide (1.57 g, 4.15 mmol) and DIEA (2.173 mL, 12.44 mmol) in THF (30 mL) was added allyl chloroformate (0.528 mL, 4.98 mmol), and the mixture was stirred at room temperature for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→10% ethyl acetate/hexane) to give allyl (2-((2,5-difluoro-4-(trimethylsilyl)phenyl)amino)-1-(4-(methoxymethyl)phenyl)-2-oxoethyl)carbamate (2.59 g, 5.60 mmol, 135%) as a white solid.

$^1$H NMR (300 MHz, CDCl$_3$): δ0.27 (9H, d, J=0.8 Hz), 3.38 (3H, s), 4.45 (2H, s), 4.54-4.61 (2H, m), 5.15-5.44 (3H, m), 5.80-6.03 (2H, m), 7.00 (1H, dd, J=10.2, 4.5 Hz), 7.31-7.46 (4H, m), 7.69 (1H, brs), 7.99 (1H, dd, J=9.4, 5.7 Hz).

(Step 2)

Allyl (2-((2,5-difluoro-4-(trimethylsilyl)phenyl)amino)-1-(4-(methoxymethyl)phenyl)-2-oxoethyl)carbamate (1.37 g) was subjected to optical resolution using chiral column chromatography. The preparative fraction having a shorter retention time was concentrated to give allyl ((1R)2-((2,5-difluoro-4-(trimethylsilyl)phenyl)amino)-1-(4-(methoxymethyl)phenyl)-2-oxoethyl) carbamate (600.7 mg, >99.9% ee) as a white solid.

purification condition using chiral column chromatography
column: CHIRALPAK AD(LF001)50 mmID×500 mmL
solvent: hexane/EtOH=500/500
flow rate: 80 mL/min
temperature: 30° C.
detection method: UV 220 nm (Step 3)

A solution of allyl ((1R)2-((2,5-difluoro-4-(trimethylsilyl)phenyl)amino)-1-(4-(methoxymethyl)phenyl)-2-oxoethyl) carbamate (600 mg, 1.30 mmol), 1,3-dimethylbarbituric acid (425 mg, 2.72 mmol) and Pd(PPh$_3$)$_4$ (60.0 mg, 0.05 mmol) in THF (12 mL) was stirred at room temperature for 1 hr under argon gas atmosphere. The reaction mixture was concentrated under reduced pressure, and the obtained residue was purified by silica gel column chromatography (NH, solvent gradient; 5→50% ethyl acetate/hexane) to give (R)-2-amino-N-(2,5-difluoro-4-(trimethylsilyl)phenyl)-2-(4-(methoxymethyl)phenyl)acetamide (524.8 mg, 1.387 mmol, 107%) as a yellow oil.

(Step 4)

A solution of (R)-2-amino-N-(2,5-difluoro-4-(trimethylsilyl)phenyl)-2-(4-(methoxymethyl)phenyl)acetamide (100 mg, 0.26 mmol), (S)-5-oxopyrrolidine-3-carboxylic acid (37.5 mg, 0.29 mmol), DIEA (0.092 mL, 0.53 mmol) and HATU (121 mg, 0.32 mmol) in DMF (2.0 mL) was stirred at room temperature for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent; ethyl acetate), and crystallized from ethyl acetate/hexane to give the title compound (66.3 mg, 0.135 mmol, 51.3%) as white crystals.

MS(API): Calculated 489.6, Found 490.2 (M+H).

$^1$H NMR (300 MHz, DMSO-$d_6$): δ0.27 (9H, d, J=0.8 Hz), 2.26-2.35 (2H, m), 3.10-3.23 (1H, m), 3.27 (3H, s), 3.36-3.45 (2H, m), 4.39 (2H, s), 5.85 (1H, d, J=7.6 Hz), 7.20 (1H, dd, J=10.4, 4.7 Hz), 7.32 (2H, d, J=8.3 Hz), 7.46 (2H, d, J=8.3 Hz), 7.53 (1H, s), 7.76 (1H, dd, J=10.4, 5.9 Hz), 8.79 (1H, d, J=7.6 Hz), 10.36 (1H, s).

$[\alpha]_D^{25}$ −112.6 (c 0.251, MeOH)

Example 52

(3S)—N-((1R)-2-((3,5-difluoro-4-(trimethylsilyl)phenyl)amino)-1-(4-(methoxymethyl)phenyl)-2-oxoethyl)-5-oxopyrrolidine-3-carboxamide (Step 1)

To a solution of 3,5-difluoro-4-(trimethylsilyl)aniline (6.69 g, 33.25 mmol), 2-(diallylamino)-2-(4-(methoxymethyl)phenyl)acetic acid (11.9 g, 43.22 mmol), DMAP (4.47 g, 36.57 mmol) and DIEA (29.0 mL, 166.23 mmol) in ethyl acetate (200 mL) was added T3P (29.3 mL, 49.87 mmol), and the mixture was stirred at 80° C. for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 3→35% ethyl acetate/hexane) to give 2-(diallylamino)-N-(3,5-difluoro-4-(trimethylsilyl)phenyl)-2-(4-(methoxymethyl)phenyl)acetamide (9.00 g, 19.62 mmol, 59.0%) as a pale yellow oil.

(Step 2)

A solution of 2-(diallylamino)-N-(3,5-difluoro-4-(trimethylsilyl)phenyl)-2-(4-(methoxymethyl)phenyl)acetamide (1.64 g, 3.58 mmol), 1,3-dimethylbarbituric acid (1.173 g, 7.51 mmol) and Pd(PPh$_3$)$_4$ (0.165 g, 0.14 mmol) in THF (15 mL) was stirred overnight at room temperature under argon gas atmosphere. The obtained residue was purified by silica gel column chromatography (NH, solvent gradient; 5→75% ethyl acetate/hexane) to give 2-amino-N-(3,5-difluoro-4-(trimethylsilyl)phenyl)-2-(4-(methoxymethyl)phenyl)acetamide (470.5 mg, 1.243 mmol, 34.8%) as a pale yellow oil.

(Step 3)

To a solution of 2-amino-N-(3,5-difluoro-4-(trimethylsilyl)phenyl)-2-(4-(methoxymethyl)phenyl)acetamide (470 mg, 1.24 mmol) and DIEA (0.651 mL, 3.73 mmol) in THF (10 mL) was added allyl chloroformate (0.158 mL, 1.49 mmol) at 0° C., and the mixture was stirred for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→10% ethyl acetate/hexane) to give allyl (2-((3,5-difluoro-4-(trimethylsilyl)phenyl)amino)-1-(4-(methoxymethyl)phenyl)-2-oxoethyl)carbamate (297 mg, 0.641 mmol, 51.7%) as a white solid.

(Step 4)

Allyl (2-((3,5-difluoro-4-(trimethylsilyl)phenyl)amino)-1-(4-(methoxymethyl)phenyl)-2-oxoethyl)carbamate (296 mg) was subjected to optical resolution using chiral column chromatography. The preparative fraction having a shorter retention time was concentrated to give allyl (R)-(2-((3,5-difluoro-4-(trimethylsilyl)phenyl)amino)-1-(4-(methoxymethyl)phenyl)-2-oxoethyl)carbamate (108.5 mg, >99.9% ee) as a white solid.

purification condition using chiral column chromatography
column: CHIRALPAK AD(NF001) 50 mmID×500 mmL
solvent: hexane/EtOH=600/400
flow rate: 80 mL/min
temperature: 30° C.
detection method: UV 220 nm (Step 5)

A solution of allyl (R)-(2-((3,5-difluoro-4-(trimethylsilyl)phenyl)amino)-1-(4-(methoxymethyl)phenyl)-2-oxoethyl)carbamate (109 mg, 0.24 mmol), 1,3-dimethylbarbituric acid (81 mg, 0.52 mmol) and Pd(PPh$_3$)$_4$ (10.89 mg, 9.43 μmol) in THF (1571 μL) was stirred at room temperature for 6 hr under argon gas atmosphere. The reaction solution was concentrated under reduced pressure, and the obtained residue was purified by silica gel column chromatography (NH, solvent gradient; 40→80% ethyl acetate/hexane) to give (R)-2-amino-N-(3,5-difluoro-4-(trimethylsilyl)phenyl)-2-(4-(methoxymethyl)phenyl)acetamide (100 mg, 0.263 mmol, 112) as a yellow oil.

(Step 6)

A solution of (R)-2-amino-N-(3,5-difluoro-4-(trimethylsilyl)phenyl)-2-(4-(methoxymethyl)phenyl)acetamide (99.7 mg, 0.26 mmol), (S)-5-oxopyrrolidine-3-carboxylic acid (44.2 mg, 0.34 mmol), HATU (150 mg, 0.40 mmol) and DIEA (0.138 mL, 0.79 mmol) in DMF (2 mL) was stirred at room temperature for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 1→7% MeOH/ethyl acetate) to give (3S)—N-((1R)-2-((3,5-difluoro-4-(trimethylsilyl)phenyl)amino)-1-(4-(methoxymethyl)phenyl)-2-oxoethyl)-5-oxopyrrolidine-3-carboxamide (103 mg, 0.210 mmol, 80) as a white solid.

MS(API): Calculated 489.6, Found 488.2 (M−H).

$^1$H NMR (300 MHz, DMSO-$d_6$): δ0.30 (9H, s), 2.26-2.34 (2H, m), 3.08-3.47 (6H, m), 4.39 (2H, s), 5.57 (1H, d, J=7.6 Hz), 7.14-7.26 (2H, m), 7.29-7.37 (2H, m), 7.39-7.47 (2H, m), 7.54 (1H, s), 8.85 (1H, d, J=7.2 Hz), 10.73 (1H, s).

$[\alpha]_D^{25}$ −103.2 (c 0.262, MeOH)

Example 53

(2R)—N-(3-fluoro-4-(trimethylsilyl)phenyl)-2-(4-(methoxymethyl)phenyl)-2-(((6-oxopyrimidin-1(6H)-yl)acetyl)amino)acetamide A solution of (R)-2-amino-N-(3-fluoro-4-(trimethylsilyl)phenyl)-2-(4-(methoxymethyl)phenyl)acetamide (100 mg, 0.28 mmol), 2-(6-oxopyrimidin-1(6H)-yl)acetic acid (47.0 mg, 0.31 mmol), HATU (148 mg, 0.39 mmol) and DIEA (0.097 mL, 0.55 mmol) in DMF (2 mL) was stirred at room temperature for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 1→7% MeOH/ethyl acetate), and crystallized from ethyl acetate/hexane to give the title compound (68.1 mg, 0.137 mmol, 49.4) as a white solid.

MS(API): Calculated 496.6, Found 497.2 (M+H).

$^1$H NMR (300 MHz, DMSO-$d_6$): δ0.17-0.33 (9H, m), 3.27 (3H, s), 4.39 (2H, s), 4.72 (2H, s), 5.65 (1H, d, J=7.6 Hz), 6.38 (1H, dd, J=6.8, 0.8 Hz), 7.24-7.40 (4H, m), 7.43-7.54 (3H, m), 7.91 (1H, d, J=6.8 Hz), 8.37 (1H, s), 9.26 (1H, d, J=7.9 Hz), 10.62 (1H, s).

$[α]_D^{25}$ −49.8 (c 0.2515, MeOH)

Example 54

(3R)—N-((1R)-2-((3-fluoro-4-(trimethylsilyl)phenyl)amino)-1-(4-(methoxymethyl)phenyl)-2-oxoethyl)-5-oxopyrrolidine-3-carboxamide (Step 1)

2-Methylenesuccinic acid (11.74 g, 90.24 mmol) and (R)-1-phenylethanamine (10.94 g, 90.24 mmol) were stirred at 160° C. for 4 hr. The reaction mixture was crystallized from EtOH (50 mL)/water (50 mL), and the obtained crystals were recrystallized from EtOH (70 mL)/water (100 mL) to give (3R)-5-oxo-1-((1R)-1-phenylethyl)pyrrolidine-3-carboxylic acid (5.55 g, 23.79 mmol, 52.9%) as pale orange crystals.

(Step 2)

A solution of (3R)-5-oxo-1-((1R)-1-phenylethyl)pyrrolidine-3-carboxylic acid (5.55 g, 23.79 mmol) in TFA (10 mL) was stirred under microwave irradiation at 160° C. for 1.5 hr. Then, TEA (2 mL) was added thereto, and the mixture was stirred under microwave irradiation at 160° C. for 0.5 hr. The reaction mixture was concentrated under reduced pressure, and the residue was crystallized from ethyl acetate to give (R)-5-oxopyrrolidine-3-carboxylic acid (2.1 g, 16.26 mmol, 68.4%) as white crystals.

(Step 3)

A solution of (R)-2-amino-N-(3-fluoro-4-(trimethylsilyl)phenyl)-2-(4-(methoxymethyl)phenyl)acetamide (100 mg, 0.28 mmol), (R)-5-oxopyrrolidine-3-carboxylic acid (39.4 mg, 0.31 mmol), HATU (148 mg, 0.39 mmol) and DIEA (0.097 mL, 0.55 mmol) in DMF (2 mL) was stirred at room temperature for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 1-7% MeOH/ethyl acetate), and crystallized from ethyl acetate/hexane to give the title compound (102 mg, 0.216 mmol, 78%) as a white solid.

MS(API): Calculated 471.6, Found 470.1 (M−H).

$^1$H NMR (300 MHz, DMSO-$d_6$): δ0.25 (9H, s), 2.22-2.30 (2H, m), 3.13-3.52 (6H, m), 4.38 (2H, s), 5.59 (1H, d, J=7.6 Hz), 7.23-7.62 (8H, m), 8.80 (1H, d, J=7.6 Hz), 10.57 (1H, s).

$[α]_D^{25}$ −85.0 (c 0.2595, MeOH)

Example 55

(3R)—N-((1R)-2-((2,5-difluoro-4-(trimethylsilyl)phenyl)amino)-1-(4-(methoxymethyl)phenyl)-2-oxoethyl)-5-oxopyrrolidine-3-carboxamide A solution of (R)-2-amino-N-(2,5-difluoro-4-(trimethylsilyl)phenyl)-2-(4-(methoxymethyl)phenyl)acetamide (100 mg, 0.26 mmol), (R)-5-oxopyrrolidine-3-carboxylic acid (37.5 mg, 0.29 mmol), DIEA (0.092 mL, 0.53 mmol) and HATU (121 mg, 0.32 mmol) in DMF (2.0 mL) was stirred at room temperature for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent; ethyl acetate), and crystallized from ethyl acetate/hexane to give the title compound (62.9 mg, 0.128 mmol, 48.6%) as white crystals.

MS(API): Calculated 489.6, Found 488.1 (M−H).

$^1$H NMR (300 MHz, DMSO-$d_6$): δ0.26 (9H, d, J=0.8 Hz), 2.21-2.30 (2H, m), 3.21-3.28 (4H, m), 3.37-3.49 (2H, m), 4.39 (2H, s), 5.83 (1H, d, J=7.2 Hz), 7.20 (1H, dd, J=10.6, 4.9 Hz), 7.32 (2H, d, J=7.9 Hz), 7.46 (2H, d, J=7.9 Hz), 7.55 (1H, s), 7.77 (1H, dd, J=10.6, 5.7 Hz), 8.76 (1H, d, J=7.2 Hz), 10.35 (1H, s).

Example 56

(2R)—N-(2,5-difluoro-4-(trimethylsilyl)phenyl)-2-(4-(methoxymethyl)phenyl)-2-(((5-methyl-1,3,4-oxadiazol-2-yl)acetyl)amino)acetamide A solution of (R)-2-amino-N-(2,5-difluoro-4-(trimethylsilyl)phenyl)-2-(4-(methoxymethyl)phenyl)acetamide (200 mg, 0.53 mmol), 2-(5-methyl-1,3,4-oxadiazol-2-yl)acetic acid (83 mg, 0.58 mmol), DIEA (0.185 mL, 1.06 mmol) and HATU (241 mg, 0.63 mmol) in DMF (2.0 mL) was stirred at room temperature for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→50% ethyl acetate/hexane), and crystallized from ethyl acetate/hexane to give the title compound (110.2 mg, 0.219 mmol, 41.5%) as white crystals.

MS(API): Calculated 502.6, Found 503.2 (M−H).

$^1$H NMR (300 MHz, DMSO-$d_6$): δ0.27 (9H, d, J=0.8 Hz), 2.46 (3H, s), 3.28 (3H, s), 3.98 (2H, s), 4.40 (2H, s), 5.87 (1H, d, J=7.2 Hz), 7.20 (1H, dd, J=10.4, 4.7 Hz), 7.33 (2H, d, J=8.3 Hz), 7.49 (2H, d, J=8.3 Hz), 7.76 (1H, dd, J=10.4, 5.9 Hz), 9.14 (1H, d, J=7.2 Hz), 10.42 (1H, s).

Example 57

(2R)—N-(2,5-difluoro-4-(trimethylsilyl)phenyl)-2-(4-(methoxymethyl)phenyl)-2-(((6-oxopyrimidin-1(6H)-yl)acetyl)amino)acetamide A solution of (R)-2-amino-N-(2,5-difluoro-4-(trimethylsilyl)phenyl)-2-(4-(methoxymethyl)phenyl)acetamide (150 mg, 0.40 mmol), 2-(6-oxopyrimidin-1(6H)-yl)acetic acid (61.1 mg, 0.40 mmol), DIEA (0.138 mL, 0.79 mmol) and HATU (181 mg, 0.48 mmol) in DMF (2.0 ML) was stirred at room temperature for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→50% ethyl acetate/hexane), and crystallized from ethyl acetate/hexane to give the title compound (102.5 mg, 0.199 mmol, 50.3%) as white crystals.

MS(API): Calculated 514.6, Found 515.2 (M+H).

$^1$H NMR (300 MHz, DMSO-d$_6$): δ0.27 (9H, d, J=0.8 Hz), 3.28 (3H, s), 4.40 (2H, s), 4.71 (2H, s), 5.91 (1H, d, J=7.6 Hz), 6.38 (1H, dd, J=6.4, 0.8 Hz), 7.20 (1H, dd, J=10.6, 4.9 Hz), 7.33 (2H, d, J=8.3 Hz), 7.49 (2H, d, J=8.3 Hz), 7.77 (1H, dd, J=10.6, 5.9 Hz), 7.91 (1H, d, J=6.4 Hz), 8.37 (1H, s), 9.21 (1H, d, J=7.6 Hz), 10.43 (1H, s).

Example 58

(2R)—N-(3,5-difluoro-4-(trimethylsilyl)phenyl)-2-(4-(methoxymethyl)phenyl)-2-(((6-oxopyrimidin-1(6H)-yl)acetyl)amino)acetamide A solution of (R)-2-amino-N-(3,5-difluoro-4-(trimethylsilyl)phenyl)-2-(4-(methoxymethyl)phenyl)acetamide (100 mg, 0.26 mmol), 2-(6-oxopyrimidin-1(6H)-yl)acetic acid (44.8 mg, 0.29 mmol), HATU (111 mg, 0.29 mmol) and DIEA (0.051 mL, 0.29 mmol) in DMF (2 mL) was stirred at room temperature for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 20→100% ethyl acetate/hexane), and crystallized from acetone/water to give the title compound (80 mg, 0.155 mmol, 58.8%) as white crystals.

MS(API): Calculated 514.6, Found 513.1 (M−H). 1H NMR (300 MHz, DMSO-d$_6$): δ0.30 (9H, s), 3.28 (3H, s), 4.40 (2H, s), 4.72 (2H, s), 5.61 (1H, d, J=7.2 Hz), 6.39 (1H, d, J=7.2 Hz), 7.21 (2H, d, J=9.4 Hz), 7.29-7.38 (2H, m), 7.41-7.52 (2H, m), 7.91 (1H, d, J=6.4 Hz), 8.37 (1H, s), 9.27 (1H, d, J=7.6 Hz), 10.75 (1H, s).

[α]$_D^{25}$−48.5 (c 0.2600, MeOH)

Example 59

(2R)-2-(((2,4-dioxo-3,4-dihydropyrimidin-1(2H)-yl)acetyl)amino)-N-(3-fluoro-4-(trimethylsilyl)phenyl)-2-(4-(methoxymethyl)phenyl)acetamide A solution of (R)-2-amino-N-(3-fluoro-4-(trimethylsilyl)phenyl)-2-(4-(methoxymethyl)phenyl)acetamide (100 mg, 0.28 mmol), 2-(2,4-dioxo-3,4-dihydropyrimidin-1(2H)-yl)acetic acid (51.9 mg, 0.31 mmol), DIEA (0.097 mL, 0.55 mmol) and HATU (127 mg, 0.33 mmol) in DMF (2.0 mL) was stirred at room temperature for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 20→100% ethyl acetate/hexane), and crystallized from ethyl acetate/hexane to give the title compound (77.0 mg, 0.150 mmol, 54.2%) as a white solid.
MS(API): Calculated 512.6, Found 513.1 (M+H).

$^1$H NMR (300 MHz, DMSO-d$_6$): δ0.25 (9H, s), 3.27 (3H, s), 4.39 (2H, s), 4.48 (2H, s), 5.54 (1H, d, J=7.9 Hz), 5.65 (1H, d, J=7.9 Hz), 7.24-7.39 (4H, m), 7.42-7.59 (4H, m), 9.11 (1H, d, J=7.9 Hz), 10.61 (1H, s), 11.26 (1H, s).

[α]$_D^{25}$−57.2 (c 0.2515, MeOH)

Example 60

(2R)-2-(((2,6-dioxo-3,6-dihydropyrimidin-1(2H)-yl)acetyl)amino)-N-(3-fluoro-4-(trimethylsilyl)phenyl)-2-(4-(methoxymethyl)phenyl)acetamide A solution of (R)-2-amino-N-(3-fluoro-4-(trimethylsilyl)phenyl)-2-(4-(methoxymethyl)phenyl)acetamide (100 mg, 0.28 mmol), 2-(2,6-dioxo-2,3-dihydropyrimidin-1(6H)-yl)acetic acid (51.9 mg, 0.31 mmol), DIEA (0.097 mL, 0.55 mmol) and HATU (127 mg, 0.33 mmol) in DMF (2.0 mL) was stirred at room temperature for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent; ethyl acetate), and crystallized from ethyl acetate/hexane to give the title compound (24.8 mg, 0.048 mmol, 17.44%) as a white solid.

MS(API): Calculated 512.6, Found 513.1 (M+H).

$^1$H NMR (300 MHz, DMSO-d$_6$): δ0.25 (9H, s), 3.27 (3H, s), 4.39 (2H, s), 4.48 (2H, s), 5.54 (1H, d, J=7.9 Hz), 5.62-5.67 (1H, m), 7.25-7.36 (4H, m), 7.41-7.59 (4H, m), 9.11 (1H, d, J=7.9 Hz), 10.61 (1H, s), 11.25 (1H, brs).

[α]$_D^{25}$−55.6 (c 0.2505, MeOH)

Example 61

(2R)—N-(3,5-difluoro-4-(trimethylsilyl)phenyl)-2-(4-(methoxymethyl)phenyl)-2-(((3-methyl-6-oxopyridazin-1(6H)-yl)acetyl)amino)acetamide A solution of (R)-2-amino-N-(3,5-difluoro-4-(trimethylsilyl)phenyl)-2-(4-(methoxymethyl)phenyl)acetamide (60 mg, 0.16 mmol), 2-(3-methyl-6-oxopyridazin-1(6H)-yl)acetic acid (29.3 mg, 0.17 mmol), DIEA (0.055 mL, 0.32 mmol) and HATU (72.3 mg, 0.19 mmol) in DMF (2.0 mL) was stirred at room temperature for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→50% ethyl acetate/hexane), and crystallized from ethyl acetate/hexane to give the title compound (56.7 mg, 0.107 mmol, 67.7%) as a white solid.

MS(API): Calculated 512.6, Found 529.2 (M+H).

$^1$H NMR (300 MHz, DMSO-d$_6$): δ0.28-0.33 (9H, m), 2.24 (3H, s), 3.28 (3H, s), 4.40 (2H, s), 4.76 (2H, s), 5.57 (1H, d, J=7.2 Hz), 6.88 (1H, d, J=9.8 Hz), 7.23 (2H, d, J=9.8 Hz), 7.31-7.38 (3H, m), 7.42-7.49 (2H, m), 9.08 (1H, d, J=7.2 Hz), 10.72 (1H, s).

[α]$_D^{25}$−546.8 (c 0.2495, MeOH)

Example 62

(2R)-2-(((2,5-dioxoimidazolidin-1-yl) acetyl)amino)-N-(3-fluoro-4-(trimethylsilyl)phenyl)-2-(4-(methoxymethyl)phenyl)acetamide A solution of (R)-2-amino-N-(3-fluoro-4-(trimethylsilyl)phenyl)-2-(4-(methoxymethyl)phenyl)acetamide (100 mg, 0.28 mmol), 2-(2,5-dioxoimidazolidin-1-yl)acetic acid (48.2 mg, 0.31 mmol), DIEA (0.097 mL, 0.55 mmol) and HATU (127 mg, 0.33 mmol) in DMF (2.0 mL) was stirred at room temperature for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent; ethyl acetate), and crystallized from ethyl acetate/hexane to give the title compound (72.3 mg, 0.144 mmol, 52.1%) as a white solid.

MS(API): Calculated 500.6, Found 501.2 (M+H).

$^1$H NMR (300 MHz, DMSO-d$_6$): δ0.25 (9H, d, J=0.8 Hz), 3.27 (3H, s), 3.95 (2H, s), 4.10 (2H, d, J=1.9 Hz), 4.39 (2H, s), 5.61 (1H, d, J=7.6 Hz), 7.26-7.38 (4H, m), 7.42-7.53 (3H, m), 8.09 (1H, s), 9.04 (1H, d, J=7.6 Hz), 10.59 (1H, s).

$[α]_D^{25}$ −79.3 (c 0.2570, MeOH)

Example 63

(2R)—N-(3-fluoro-4-(trimethylsilyl)phenyl)-2-(4-(methoxymethyl)phenyl)-2-(((4-oxopyridazin-1(4H)-yl)acetyl)amino)acetamide A solution of (R)-2-amino-N-(3-fluoro-4-(trimethylsilyl)phenyl)-2-(4-(methoxymethyl)phenyl)acetamide (140 mg, 0.39 mmol), 2-(4-oxopyridazin-1(4H)-yl)acetic acid (65.8 mg, 0.43 mmol), HATU (207 mg, 0.54 mmol) and DIEA (0.136 mL, 0.78 mmol) in DMF (2 mL) was stirred at room temperature for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 1→7% MeOH/ethyl acetate), and crystallized from EtOH/hexane to give the title compound (48.0 mg, 0.097 mmol, 24.89%) as white crystals.

MS(API): Calculated 496.6, Found 495.1 (M−H).

$^1$H NMR (300 MHz, DMSO-d$_6$): δ0.25 (9H, d, J=0.8 Hz), 3.31 (3H, s), 4.39 (2H, s), 4.92 (2H, s), 5.59-5.71 (1H, m), 6.33 (1H, dd, J=7.7, 3.2 Hz), 7.22-7.54 (7H, m), 7.72 (1H, d, J=3.0 Hz), 8.17 (1H, d, J=7.6 Hz), 9.23 (1H, d, J=7.9 Hz), 10.64 (1H, s).

$[α]_D^{25}$ −97.4 (c 0.2455, MeOH)

Example 64

(3S)—N-((1R)-2-((3-fluoro-4-(trimethylsilyl)phenyl)amino)-1-(4-methoxyphenyl)-2-oxoethyl)-3-hydroxypyrrolidine-1-carboxamide A solution of bis(trichloromethyl) carbonate (100 mg, 0.34 mmol) in THF (6 mL) was added to a solution of pyridine (0.140 mL, 1.73 mmol) and (R)-2-amino-N-(3-fluoro-4-(trimethylsilyl)phenyl)-2-(4-methoxyphenyl)acetamide (300 mg, 0.87 mmol) in THF (6 mL) at 0° C., and the mixture was stirred for 10 min. To the reaction mixture was added a solution of (S)-(−)-3-hydroxypyrrolidine (0.180 mL, 2.16 mmol) in DMF (6 mL) at 0° C., and the mixture was stirred at room temperature for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 50→100% ethyl acetate/hexane, 0→10% MeOH/ethyl acetate), and crystallized from ethyl acetate/hexane to give the title compound (26.6 mg, 0.058 mmol, 6.683) as white crystals.

MS(API): Calculated 459.6, Found 460.3 (M+H).

$^1$H NMR (300 MHz, DMSO-d$_6$): δ0.25 (9H, s), 1.64-1.96 (2H, m), 3.16-3.26 (1H, m), 3.33-3.45 (3H, m), 3.73 (3H, s), 4.24 (1H, brs), 4.89 (1H, d, J=3.4 Hz), 5.37-5.48 (1H, m), 6.31 (1H, d, J=7.9 Hz), 6.85-6.96 (2H, m), 7.24-7.43 (4H, m), 7.51 (1H, dd, J=11.3, 1.5 Hz), 10.40 (1H, s).

Example 65

(3S)—N-((1R)-2-((3-fluoro-4-(trimethylsilyl)phenyl)amino)-1-(4-(methoxymethyl)phenyl)-2-oxoethyl)-3-hydroxypyrrolidine-1-carboxamide A solution of bis(trichloromethyl) carbonate (96 mg, 0.32 mmol) in THF (2 mL) was added to a solution of pyridine (0.135 mL, 1.66 mmol) and (R)-2-amino-N-(3-fluoro-4-(trimethylsilyl)phenyl)-2-(4-(methoxymethyl)phenyl)acetamide (300 mg, 0.83 mmol) in THF (3 mL) at 0° C., and the mixture was stirred for 10 min. To the reaction mixture was added a solution of (S)-(−)-3-hydroxypyrrolidine (0.173 mL, 2.08 mmol) in DMF (5 mL) at 0° C., and the mixture was stirred at room temperature for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→10% MeOH/ethyl acetate), and crystallized from ethyl acetate/hexane to give the title compound (246 mg, 0.519 mmol, 62.4%) as white crystals.

MS(API): Calculated 473.6, Found 474.2 (M+H).

$^1$H NMR (300 MHz, DMSO-d$_6$): δ0.25 (9H, s), 1.68-1.94 (2H, m), 3.18-3.42 (7H, m), 4.19-4.30 (1H, m), 4.38 (2H, s), 4.89 (1H, d, J=3.4 Hz), 5.50 (1H, d, J=7.9 Hz), 6.41 (1H, d, J=7.9 Hz), 7.22-7.59 (7H, m), 10.46 (1H, s).

Example 66

(3R)—N-((1R)-2-((3-fluoro-4-(trimethylsilyl)phenyl)amino)-1-(4-(methoxymethyl)phenyl)-2-oxoethyl)-3-hydroxypyrrolidine-1-carboxamide A solution of bis(trichloromethyl) carbonate (96 mg, 0.32 mmol) in THE (2 mL) was added to a solution of pyridine (0.135 mL, 1.66 mmol) and (R)-2-amino-N-(3-fluoro-4-(trimethylsilyl)phenyl)-2-(4-(methoxymethyl)phenyl)acetamide (300 mg, 0.83 mmol) in THF (3 mL) at 0° C., and the mixture was stirred for 10 min. To the reaction mixture was added a solution of (R)-pyrrolidin-3-ol (0.173 mL, 2.08 mmol) in DMF (5 mL) at 0° C., and the mixture was stirred at room temperature for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→10% MeOH/ethyl acetate), and crystallized from ethyl acetate/hexane to give the title compound (246 mg, 0.519 mmol, 62.4%) as white crystals.

MS(API): Calculated 473.6, Found 474.2 (M+H).

$^1$H NMR (300 MHz, DMSO-d$_6$): δ0.21-0.29 (9H, m), 1.68-1.95 (2H, m), 3.14-3.45 (7H, m), 4.25 (1H, brs), 4.38

(2H, s), 4.89 (1H, d, J=3.4 Hz), 5.46-5.54 (1H, m), 6.41 (1H, d, J=8.3 Hz), 7.24-7.56 (7H, m), 10.47 (1H, s).

Example 67

(2R)—N-(3-fluoro-4-(trimethylsilyl)phenyl)-2-(4-(methoxymethyl)phenyl)-2-(((5-methyl-1,3,4-oxadiazol-2-yl)acetyl)amino)acetamide A solution of (R)-2-amino-N-(3-fluoro-4-(trimethylsilyl)phenyl)-2-(4-(methoxymethyl)phenyl)acetamide (100 mg, 0.28 mmol), 2-(5-methyl-1,3,4-oxadiazol-2-yl)acetic acid (43.4 mg, 0.31 mmol), HATU (148 mg, 0.39 mmol) and DIEA (0.097 mL, 0.55 mmol) in DMF (2 mL) was stirred at room temperature for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 1→7% MeOH/ethyl acetate), and crystallized from EtOH/water to give the title compound (68.2 mg, 0.141 mmol, 50.7%) as white crystals.

MS(API): Calculated 484.6, Found 483.2 (M−H).
$^1$H NMR (300 MHz, DMSO-$d_6$): δ0.25 (9H, s), 2.46 (3H, s), 3.27 (3H, s), 3.99 (2H, s), 4.39 (2H, s), 5.56-5.69 (1H, m), 7.23-7.54 (7H, m), 9.19 (1H, d, J=7.6 Hz), 10.62 (1H, s).

Example 68

(3R)—N-((1R)-2-((3,5-difluoro-4-(trimethylsilyl)phenyl)amino)-1-(4-(methoxymethyl)phenyl)-2-oxoethyl)-5-oxopyrrolidine-3-carboxamide A solution of (R)-2-amino-N-(3,5-difluoro-4-(trimethylsilyl)phenyl)-2-(4-(methoxymethyl)phenyl)acetamide (100 mg, 0.26 mmol), (R)-5-oxopyrrolidine-3-carboxylic acid (37.5 mg, 0.29 mmol), HATU (111 mg, 0.29 mmol) and DIEA (37.6 mg, 0.29 mmol) in DMF (5 mL) was stirred at room temperature for 3 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 10→100% ethyl acetate/hexane), and crystallized from acetone/water to give the title compound (45.0 mg, 0.092 mmol, 34.83) as white crystals.

MS(API): Calculated 489.6, Found 488.2 (M−H).
$^1$H NMR (300 MHz, DMSO-$d_6$): δ0.30 (9H, s), 1.04 (2H, d, J=6.0 Hz), 2.18-2.35 (2H, m), 3.23-3.30 (4H, m), 4.39 (2H, s), 5.54 (1H, d, J=7.2 Hz), 7.21 (2H, d, J=9.8 Hz), 7.28-7.38 (2H, m), 7.39-7.47 (2H, m), 7.55 (1H, s), 8.82 (1H, d, J=7.6 Hz), 10.71 (1H, s).

Example 69

N-((1R)-2-((3-fluoro-4-(trimethylsilyl)phenyl)amino)-1-(4-(methoxymethyl)phenyl)-2-oxoethyl)-3-hydroxyazetidine-1-carboxamide A solution of bis(trichloromethyl) carbonate (96 mg, 0.32 mmol) in THF (2 mL) was added to pyridine (0.135 mL, 1.66 mmol) and (R)-2-amino-N-(3-fluoro-4-(trimethylsilyl)phenyl)-2-(4-(methoxymethyl)phenyl)acetamide (300 mg, 0.83 mmol) in THF (3 mL) at 0° C., and the mixture was stirred for 10 min. To the reaction mixture was added a solution of azetidin-3-ol hydrochloride (228 mg, 2.08 mmol) in DMF (5 mL) at 0° C., and the mixture was stirred at room temperature for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→10% MeOH/ethyl acetate), and crystallized from ethyl acetate/hexane to give the title compound (8.8 mg, 0.019 mmol, 2.301%) as white crystals.

MS(API): Calculated 459.6, Found 460.3 (M−H).
$^1$H NMR (300 MHz, DMSO-$d_6$): δ0.25 (9H, d, J=0.8 Hz), 3.26 (3H, s), 3.57-3.66 (2H, m), 3.99-4.09 (2H, m), 4.37 (3H, s), 5.43-5.49 (1H, m), 5.56 (1H, d, J=6.0 Hz), 6.84 (1H, d, J=7.9 Hz), 7.25-7.37 (4H, m), 7.41-7.54 (3H, m), 10.47 (1H, s).

Example 70

(3R)—N-((1R)-2-((3-fluoro-4-(trimethylsilyl)phenyl)amino)-1-(4-methoxyphenyl)-2-oxoethyl)-5-oxopyrrolidine-3-carboxamide A solution of (R)-2-amino-N-(3-fluoro-4-(trimethylsilyl)phenyl)-2-(4-methoxyphenyl)acetamide (120 mg, 0.35 mmol), (R)-5-oxopyrrolidine-3-carboxylic acid (49.2 mg, 0.38 mmol), DIEA (0.121 mL, 0.69 mmol) and HATU (158 mg, 0.42 mmol) in DMF (2.0 mL) was stirred at room temperature for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent; ethyl acetate), and crystallized from ethyl acetate/hexane to give the title compound (82.6 mg, 0.181 mmol, 52.1%) as a white solid.

MS(API): Calculated 457.6, Found 458.2 (M+H).
$^1$H NMR (300 MHz, DMSO-$d_6$): δ0.25 (9H, d, J=0.8 Hz), 2.20-2.32 (2H, m), 3.21-3.28 (1H, m), 3.34-3.50 (2H, m), 3.73 (3H, s), 5.51 (1H, d, J=7.2 Hz), 6.90-6.98 (2H, m), 7.23-7.42 (4H, m), 7.45-7.58 (2H, m), 8.73 (1H, d, J=7.2 Hz), 10.50 (1H, s).

Example 71

(3R)—N-((1R)-2-((3-fluoro-4-(trimethylsilyl)phenyl)amino)-1-(4-methoxyphenyl)-2-oxoethyl)-3-hydroxypyrrolidine-1-carboxamide A solution of bis(trichloromethyl) carbonate (100 mg, 0.34 mmol) in THF (2.0 mL) was added to a solution of pyridine (0.140 mL, 1.73 mmol) and (R)-2-amino-N-(3-fluoro-4-(trimethylsilyl)phenyl)-2-(4-methoxyphenyl)acetamide (300 mg, 0.87 mmol) in THF (3.0 mL) at 0° C., and the mixture was stirred for 10 min. To the reaction mixture was added a solution of (R)-(+)-3-hydroxypyrrolidine (0.180 mL, 2.16 mmol) in DMF (5.0 mL) at 0° C., and the mixture was stirred at room temperature for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 50→100% ethyl acetate/hexane, 0→10% MeOH/ethyl acetate), and crystallized from ethyl acetate/hexane to give the title compound (25.4 mg, 0.055 mmol, 6.38%) as white crystals.

MS(API): Calculated 459.6, Found 460.3 (M+H).

$^1$H NMR (300 MHz, DMSO-d$_6$): δ0.25 (9H, s), 1.68-1.96 (2H, m), 3.12-3.25 (1H, m), 3.34-3.42 (3H, m), 3.73 (3H, s), 4.25 (1H, brs), 4.88 (1H, d, J=3.4 Hz), 5.42 (1H, d, J=7.9 Hz), 6.32 (1H, d, J=7.9 Hz), 6.86-6.94 (2H, m), 7.24-7.43 (4H, m), 7.51 (1H, dd, J=11.3, 1.5 Hz), 10.40 (1H, s).

Example 72

N-((1R)-2-((3,5-difluoro-4-(trimethylsilyl)phenyl)amino)-1-(4-(methoxymethyl)phenyl)-2-oxoethyl)-3-hydroxypropanamide A solution of (R)-2-amino-N-(3,5-difluoro-4-(trimethylsilyl)phenyl)-2-(4-(methoxymethyl)phenyl)acetamide (100 mg, 0.26 mmol), 3-hydroxypropanoic acid (26.2 mg, 0.29 mmol), DIEA (0.092 mL, 0.53 mmol) and HATU (121 mg, 0.32 mmol) in DMF (2.0 mL) was stirred at room temperature for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→50% ethyl acetate/hexane), and crystallized from ethyl acetate/hexane to give the title compound (24.3 mg, 0.054 mmol, 20.41%) as a white solid.

MS(API): Calculated 450.6, Found 451.2 (M+H).

$^1$H NMR (300 MHz, DMSO-d$_6$): δ0.30 (9H, s), 2.33-2.43 (2H, m), 3.27 (3H, s), 3.56-3.67 (2H, m), 4.38 (2H, s), 4.62 (1H, t, J=4.9 Hz), 5.58 (1H, d, J=7.6 Hz), 7.16-7.26 (2H, m), 7.28-7.35 (2H, m), 7.39-7.48 (2H, m), 8.66 (1H, d, J=7.6 Hz), 10.69 (1H, s).

$[α]_D^{25}$ −109.1 (c 0.1755, MeOH)

Example 73

3-cyano-N-((1R)-2-((3,5-difluoro-4-(trimethylsilyl)phenyl)amino)-1-(4-(methoxymethyl)phenyl)-2-oxoethyl)propanamide A solution of (R)-2-amino-N-(3,5-difluoro-4-(trimethylsilyl)phenyl)-2-(4-(methoxymethyl)phenyl)acetamide (100 mg, 0.26 mmol), 3-cyanopropanoic acid (28.8 mg, 0.29 mmol), DIEA (0.092 mL, 0.53 mmol) and HATU (121 mg, 0.32 mmol) in DMF (2.0 mL) was stirred at room temperature for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→50% ethyl acetate/hexane) to give the title compound (49.1 mg, 0.107 mmol, 40.4%) as a white solid.

MS(API): Calculated 459.6, Found 458.1 (M−H).

$^1$H NMR (300 MHz, DMSO-d$_6$): δ0.30 (9H, s), 2.57-2.69 (4H, m), 3.27 (3H, s), 4.39 (2H, s), 5.50-5.65 (1H, m), 7.17-7.25 (2H, m), 7.28-7.36 (2H, m), 7.40-7.48 (2H, m), 8.89 (1H, d, J=7.6 Hz), 10.74 (1H, s).

Example 74

(2R)—N-(3,5-difluoro-4-(trimethylsilyl)phenyl)-2-(4-(methoxymethyl)phenyl)-2-(((5-methyl-1,3,4-oxadiazol-2-yl)acetyl)amino)acetamide A solution of (R)-2-amino-N-(3,5-difluoro-4-(trimethylsilyl)phenyl)-2-(4-(methoxymethyl)phenyl)acetamide (200 mg, 0.53 mmol), 2-(5-methyl-1,3,4-oxadiazol-2-yl)acetic acid (83 mg, 0.58 mmol), HATU (221 mg, 0.58 mmol) and DIEA (0.102 mL, 0.58 mmol) in DMF (5 mL) was stirred at room temperature for 3 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 10→90% ethyl acetate/hexane) to give the title compound (107 mg, 0.213 mmol, 40.3% s) as a white solid.

MS(API): Calculated 502.6, Found 501.2 (M−H).

$^1$H NMR (300 MHz, DMSO-d$_6$): δ0.30 (9H, s), 2.46 (3H, s), 3.19-3.30 (3H, m), 3.98 (2H, s), 4.39 (2H, s), 5.57 (1H, d, J=7.2 Hz), 7.21 (2H, d, J=9.8 Hz), 7.28-7.40 (2H, m), 7.41-7.54 (2H, m), 9.20 (1H, d, J=7.2 Hz), 10.76 (1H, s).

$[α]_D^{25}$ −106.3 (c 0.2430, MeOH)

Example 75

(2R)—N-(3-fluoro-4-(trimethylsilyl)phenyl)-2-(((3-hydroxy-1,2-oxazol-5-yl)acetyl)amino)-2-(4-(methoxymethyl)phenyl)acetamide (Step 1)

A solution of (R)-2-amino-N-(3-fluoro-4-(trimethylsilyl)phenyl)-2-(4-(methoxymethyl)phenyl)acetamide (100 mg, 0.28 mmol), 2-(3-(benzyloxy)-1,2-oxazol-5-yl)acetic acid (71.2 mg, 0.31 mmol), DIEA (0.097 mL, 0.55 mmol) and HATU (127 mg, 0.33 mmol) in DMF (2.0 mL) was stirred at room temperature for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→50% ethyl acetate/hexane) to give (R)-2-(2-(3-(benzyloxy)-1,2-oxazol-5-yl)acetamide)-N-(3-fluoro-4-(trimethylsilyl)phenyl)-2-(4-(methoxymethyl)phenyl)acetamide (110.2 mg, 0.191 mmol, 69.0%) as a colorless oil.

$^1$H NMR (300 MHz, CDCl$_3$): δ0.22-0.29 (9H, m), 3.38 (3H, s), 3.70 (2H, s), 4.42 (2H, s), 5.24 (2H, s), 5.65 (1H, d, J=6.8 Hz), 5.91 (1H, s), 7.03 (1H, dd, J=8.1, 1.7 Hz), 7.17-7.25 (1H, m), 7.27-7.46 (11H, m), 7.92 (1H, s).

(Step 2)

A solution of (R)-2-(2-(3-(benzyloxy)-1,2-oxazol-5-yl)acetamide)-N-(3-fluoro-4-(trimethylsilyl)phenyl)-2-(4-(methoxymethyl)phenyl)acetamide (110 mg, 0.19 mmol) and 10% palladium-barium sulfate (50 mg, 0.046 mmol) in MeOH (3.0 mL) was stirred at room temperature for 5 hr under hydrogen atmosphere (1 atm). The catalyst was removed by filtration, and the filtrate was concentrated under reduced pressure. The obtained residue was purified by silica gel column chromatography (solvent gradient; 0→50% ethyl acetate/hexane), and crystallized from ethyl acetate/hexane to give the title compound (47.3 mg, 0.097 mmol, 51.0%) as a white solid.

MS(API): Calculated 485.6, actual measured value 486.2 (M−H).

$^1$H NMR (300 MHz, DMSO-d$_6$): δ0.25 (9H, s), 3.27 (3H, s), 3.72 (2H, s), 4.39 (2H, s), 5.61 (1H, d, J=7.2 Hz), 5.84 (1H, s), 7.24-7.39 (4H, m), 7.42-7.53 (3H, m), 9.03 (1H, d, J=7.2 Hz), 10.60 (1H, s), 11.12 (1H, brs).

$[α]_D^{25}$ −108.8 (c 0.2530, MeOH)

Example 76

(2R)—N-(3,5-difluoro-4-(trimethylsilyl)phenyl)-2-(((3-hydroxy-1,2-oxazol-5-yl)acetyl)amino)-2-(4-(methoxymethyl)phenyl)acetamide (Step 1)
A solution of (R)-2-amino-N-(3,5-difluoro-4-(trimethylsilyl)phenyl)-2-(4-(methoxymethyl)phenyl)acetamide (115 mg, 0.30 mmol), 2-(3-(benzyloxy)-1,2-oxazol-5-yl)acetic acid (78 mg, 0.33 mmol), DIEA (43.2 mg, 0.33 mmol) and HATU (127 mg, 0.33 mmol) in DMF (2 mL) was stirred at room temperature for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 10→60% ethyl acetate/hexane) to give (R)-2-(2-(3-(benzyloxy)-1,2-oxazol-5-yl)acetamide)-N-(3,5-difluoro-4-(trimethylsilyl)phenyl)-2-(4-(methoxymethyl)phenyl)acetamide as an oil. The total amount of this compound was used for the reaction in Step 2, without purification.

(Step 2)
A solution of (R)-2-(2-(3-(benzyloxy)-1,2-oxazol-5-yl)acetamide)-N-(3,5-difluoro-4-(trimethylsilyl)phenyl)-2-(4-(methoxymethyl)phenyl)acetamide obtained in Step 1 and 10% palladium-barium sulfate (32.3 mg, 0.030 mmol) in EtOH (4 mL) was stirred at room temperature for 5 hr under hydrogen atmosphere (1 atm). The catalyst was removed by filtration, and the filtrate was concentrated under reduced pressure. The obtained residue was purified by silica gel column chromatography (solvent gradient; 20→100% ethyl acetate/hexane) to give the title compound (45.0 mg, 0.089 mmol, 29.4%) as a white solid.

MS(API): Calculated 503.6, actual measured value 502.1 (M−H).

$^1$H NMR (300 MHz, DMSO-$d_6$): δ0.30 (9H, s), 3.27 (3H, s), 3.71 (2H, s), 4.39 (2H, s), 5.56 (1H, d, J=7.2 Hz), 5.84 (1H, s), 7.21 (2H, d, J=9.8 Hz), 7.28-7.38 (2H, m), 7.39-7.50 (2H, m), 9.05 (1H, d, J=7.6 Hz), 10.75 (1H, s) (The free 1H was not observed.).

Example 77

N-((1R)-2-((3,5-difluoro-4-(trimethylsilyl)phenyl)amino)-1-(4-(methoxymethyl)phenyl)-2-oxoethyl)-3-hydroxy-N-methyl-1,2-oxazole-5-carboxamide N-(2-((3,5-Difluoro-4-(trimethylsilyl)phenyl)amino)-1-(4-(methoxymethyl)phenyl)-2-oxoethyl)-3-hydroxy-N-methyl-1,2-oxazole-5-carboxamide (2.9 g) was subjected to optical resolution using chiral column chromatography. The preparative fraction having a shorter retention time was concentrated to give the title compound (1.58 g, >99.9% ee) as a white solid.
purification condition using chiral column chromatography
column: CHIRALPAK IA(NL001)50 mmID×500 mmL
solvent: hexane/EtOH/acetic acid=500/500/1
flow rate: 60 mL/min
temperature: room temperature
detection method: UJV 220 nm
$[\alpha]_D^{25}$−165.0 (c 0.2445, MeOH)
MS(API): Calculated 503.6, Found 502.1 (M−H).

Example 78

(2R)—N-(3-fluoro-4-(trimethylsilyl)phenyl)-2-(4-(methoxymethyl)phenyl)-2-(((4-oxopyridin-1(4H)-yl)acetyl)amino)acetamide A solution of (R)-2-amino-N-(3-fluoro-4-(trimethylsilyl)phenyl)-2-(4-(methoxymethyl)phenyl)acetamide (140 mg, 0.39 mmol), 2-(4-oxopyridin-1(4H)-yl)acetic acid (65.4 mg, 0.43 mmol), HATU (207 mg, 0.54 mmol) and DIEA (0.136 mL, 0.78 mmol) in DMF (2 mL) was stirred at room temperature for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 3→25% MeOH/ethyl acetate) to give the title compound (70.9 mg, 0.143 mmol, 36.8%) as white crystals.

MS(API): Calculated 495.6, Found 496.2 (M+H).

$^1$H NMR (300 MHz, DMSO-$d_6$): δ0.25 (9H, s), 3.27 (3H, s), 4.39 (2H, s), 4.69 (2H, s), 5.64 (1H, d, J=7.6 Hz), 6.03 (2H, d, J=7.6 Hz), 7.22-7.39 (4H, m), 7.42-7.59 (5H, m), 9.15 (1H, d, J=7.6 Hz), 10.63 (1H, s).

Example 79

N-((1R)-2-((3-fluoro-4-(trimethylsilyl)phenyl)amino)-1-(4-(methoxymethyl)phenyl)-2-oxoethyl)propanamide A solution of (R)-2-amino-N-(3-fluoro-4-(trimethylsilyl)phenyl)-2-(4-(methoxymethyl)phenyl)acetamide (80 mg, 0.22 mmol), propionic acid (18.08 mg, 0.24 mmol), DIEA (0.078 mL, 0.44 mmol) and HATU (101 mg, 0.27 mmol) in DMF (2.0 mL) was stirred at room temperature for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→50% ethyl acetate/hexane) to give the title compound (24.3 mg, 0.058 mmol, 26.3%) as white crystals.

MS(API): Calculated 416.6, Found 417.2 (M+H).

$^1$H NMR (300 MHz, DMSO-$d_6$): δ0.25 (9H, s), 0.99 (3H, t, J=7.6 Hz), 2.23 (2H, q, J=7.6 Hz), 3.27 (3H, s), 4.38 (2H, s), 5.61 (1H, d, J=7.6 Hz), 7.24-7.38 (4H, m), 7.40-7.55 (3H, m), 8.58 (1H, d, J=7.6 Hz), 10.56 (1H, s).

Example 80

N-((1R)-2-((3-fluoro-4-(trimethylsilyl)phenyl)amino)-1-(4-(methoxymethyl)phenyl)-2-oxoethyl)-3-(methylsulfonyl)propanamide A solution of (R)-2-amino-N-(3-fluoro-4-(trimethylsilyl)phenyl)-2-(4-(methoxymethyl)phenyl)acetamide (100 mg, 0.28 mmol), 3-(methylsulfonyl)propanoic acid (46.4 mg, 0.31 mmol), DIEA (0.097 mL, 0.55 mmol) and HATU (127 mg, 0.33 mmol) in DMF (2.0 mL) was stirred at room temperature for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→50% ethyl acetate/hexane), and crystallized from ethyl acetate/hexane to give the title compound (24.3 mg, 0.049 mmol, 17.71%) as white crystals.

MS(API): Calculated 494.7, Found 495.2 (M+H).

$^1$H NMR (300 MHz, DMSO-d$_6$): δ0.25 (9H, s), 2.67-2.79 (2H, m), 2.97 (3H, s), 3.27 (3H, s), 3.29-3.38 (2H, m), 4.38 (2H, s), 5.61 (1H, d, J=7.2 Hz), 7.23-7.39 (4H, m), 7.41-7.55 (3H, m), 8.93 (1H, d, J=7.2 Hz), 10.56 (1H, s).

Example 81

(2R)—N-(3-fluoro-4-(trimethylsilyl)phenyl)-2-(4-(methoxymethyl)phenyl)-2-(((methylsulfonyl)acetyl)amino)acetamide A solution of (R)-2-amino-N-(3-fluoro-4-(trimethylsilyl)phenyl)-2-(4-(methoxymethyl)phenyl)acetamide (100 mg, 0.28 mmol), 2-(methylsulfonyl)acetic acid (42.2 mg, 0.31 mmol), HATU (148 mg, 0.39 mmol) and DIEA (0.097 mL, 0.55 mmol) in DMF (2 mL) was stirred at room temperature for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 1→73% MeOH/ethyl acetate), and crystallized from EtOH/water to give the title compound (76 mg, 0.158 mmol, 57.0%) as white crystals.

MS(API): Calculated 480.6, Found 481.2 (M+H).

$^1$H NMR (300 MHz, DMSO-d$_6$): δ0.25 (9H, s), 3.10 (3H, s), 3.27 (3H, s), 4.20-4.35 (2H, m), 4.39 (2H, s), 5.58-5.69 (1H, m), 7.24-7.54 (7H, m), 9.20 (1H, d, J=7.6 Hz), 10.63 (1H, s).

$[\alpha]_D^{25}$ −93.8 (c 0.2490, MeOH)

Example 82

N-((1R)-2-((3,5-difluoro-4-(trimethylsilyl)phenyl)amino)-1-(4-(methoxymethyl)phenyl)-2-oxoethyl)-3-hydroxy-1,2-oxazole-5-carboxamide A solution of (R)-2-amino-N-(3,5-difluoro-4-(trimethylsilyl)phenyl)-2-(4-(methoxymethyl)phenyl)acetamide (800 mg, 2.11 mmol), 3-hydroxy-1,2-oxazole-5-carboxylic acid (327 mg, 2.54 mmol), DIEA (0.723 mL, 4.23 mmol) and HATU (1086 mg, 2.54 mmol) in DMF (15 mL) was stirred at room temperature for 5 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→50% ethyl acetate/hexane), and crystallized from ethyl acetate/hexane to give the title compound (649.0 mg, 1.326 mmol, 62.7%) as white crystals.

MS(API): Calculated 489.5, Found 490.1 (M+H).

$^1$H NMR (300 MHz, DMSO-d$_6$): δ0.30 (9H, s), 3.28 (3H, s), 4.40 (2H, s), 5.71 (1H, d, J=7.2 Hz), 6.79-6.83 (1H, m), 7.21 (1H, s), 7.24 (1H, s), 7.34 (2H, d, J=8.3 Hz), 7.47 (2H, d, J=8.3 Hz), 9.41 (1H, d, J=7.2 Hz), 10.75 (1H, s), 11.69 (1H, s).

$[\alpha]_D^{25}$ −126.8 (c 0.2020, MeOH)

Example 83

N-((1R)-2-((3-fluoro-4-(trimethylsilyl)phenyl)amino)-1-(4-methoxyphenyl)-2-oxoethyl)-3-hydroxy-1,2-oxazole-5-carboxamide To a solution of (R)-2-amino-N-(3-fluoro-4-(trimethylsilyl)phenyl)-2-(4-methoxyphenyl)acetamide (1.25 g, 3.61 mmol), DIEA (1.234 mL, 7.22 mmol) and 3-hydroxy-1,2-oxazole-5-carboxylic acid (0.559 g, 4.33 mmol) in DMF (25 mL) was added HATU (1.854 g, 4.33 mmol), and the mixture was stirred at room temperature for 5 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 10→50% ethyl acetate/hexane), and crystallized from ethyl acetate/hexane to give the title compound (1.01 g, 2.208 mmol, 61.2%) as white crystals.

MS(API): Calculated 457.5, Found 458.1 (M+H).

$^1$H NMR (300 MHz, DMSO-d$_6$): δ0.25 (9H, s), 3.74 (3H, s), 5.67 (1H, d, J=7.2 Hz), 6.81 (1H, s), 6.91-7.00 (2H, m), 7.24-7.38 (2H, m), 7.39-7.55 (3H, m), 9.28 (1H, d, J=7.2 Hz), 10.55 (1H, s), 11.68 (1H, s).

$[\alpha]_D^{25}$ −150.4 (c 0.1890, MeOH)

Example 84

2,2-difluoro-N-((1R)-2-((3-fluoro-4-(trimethylsilyl)phenyl)amino)-1-(4-(methoxymethyl)phenyl)-2-oxoethyl)cyclopropanecarboxamide (Mixture of Two Diastereomers)

A solution of (R)-2-amino-N-(3-fluoro-4-(trimethylsilyl)phenyl)-2-(4-(methoxymethyl)phenyl)acetamide (90 mg, 0.25 mmol), 2,2-difluorocyclopropanecarboxylic acid (33.5 mg, 0.27 mmol), HATU (104 mg, 0.27 mmol) and DIEA (0.048 mL, 0.27 mmol) in DMF (3 mL) was stirred overnight at room temperature. To the reaction mixture was added water, and the precipitate was collected by filtration to give the title compound (111 mg, 0.239 mmol, 96%) as white crystals.

MS(API): Calculated 464.6, Found 465.1 (M+H).

$^1$H NMR (300 MHz, DMSO-d$_6$): δ0.19-0.30 (9H, m), 1.79-1.98 (2H, m), 2.77-2.95 (1H, m), 3.25-3.29 (3H, m), 4.39 (2H, s), 5.53-5.75 (1H, m), 7.24-7.38 (4H, m), 7.41-7.55 (3H, m), 9.14-9.28 (1H, m), 10.58-10.68 (1H, m).

Example 85

(2R)—N-(3-fluoro-4-(trimethylsilyl)phenyl)-2-(glycoloylamino)-2-(4-(methoxymethyl)phenyl)acetamide A solution of (R)-2-amino-N-(3-fluoro-4-(trimethylsilyl)phenyl)-2-(4-(methoxymethyl)phenyl)acetamide (80 mg, 0.22 mmol), 2-hydroxyacetic acid (18.56 mg, 0.24 mmol), DIEA (0.078 mL, 0.44 mmol) and HATU (101 mg, 0.27 mmol) in DMF (2.0 mL) was stirred at room temperature for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→50% ethyl acetate/hexane) to give the title compound (34.5 mg, 0.082 mmol, 37.1%) as a white solid.
MS(API): Calculated 418.5, Found 419.1 (M+H).
$^1$H NMR (300 MHz, DMSO-$d_6$): δ0.25 (9H, s), 3.27 (3H, s), 3.90 (2H, d, J=6.0 Hz), 4.38 (2H, s), 5.59-5.70 (2H, m), 7.25-7.53 (7H, m), 8.15 (1H, d, J=7.9 Hz), 10.66 (1H, s).

Example 86

$N^2$-acetyl-N-((1R)-2-((3-fluoro-4-(trimethylsilyl) phenyl)amino)-1-(4-(methoxymethyl)phenyl)-2-oxoethyl)glycinamide A solution of (R)-2-amino-N-(3-fluoro-4-(trimethylsilyl) phenyl)-2-(4-(methoxymethyl)phenyl)acetamide (100 mg, 0.28 mmol), 2-acetamidoacetic acid (35.7 mg, 0.31 mmol), DIEA (0.097 mL, 0.55 mmol) and HATU (127 mg, 0.33 mmol) in DMF (2.0 mL) was stirred at room temperature for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 50→100% ethyl acetate/hexane), and crystallized from ethyl acetate/hexane to give the title compound (73.4 mg, 0.160 mmol, 57.6%) as white crystals.
MS(API): Calculated 459.6, Found 460.3 (M+H).
$^1$H NMR (300 MHz, DMSO-$d_6$): δ0.25 (9H, d, J=0.8 Hz), 1.85 (3H, s), 3.27 (3H, s), 3.77-3.84 (2H, m), 4.38 (2H, s), 5.57-5.65 (1H, m), 7.26-7.38 (4H, m), 7.41-7.53 (3H, m), 8.11 (1H, t, J=5.7 Hz), 8.68 (1H, d, J=7.6 Hz), 10.56 (1H, s).

Example 87

1-acetyl-N-((1R)-2-((3-fluoro-4-(trimethylsilyl)phenyl)amino)-1-(4-(methoxymethyl)phenyl)-2-oxoethyl)piperidine-4-carboxamide A solution of (R)-2-amino-N-(3-fluoro-4-(trimethylsilyl) phenyl)-2-(4-(methoxymethyl)phenyl)acetamide (100 mg, 0.28 mmol), 1-acetylpiperidine-4-carboxylic acid (52.2 mg, 0.31 mmol), DIEA (0.097 mL, 0.55 mmol) and HATU (127 mg, 0.33 mmol) in DMF (2.0 mL) was stirred at room temperature for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 50→100% ethyl acetate/hexane) to give the title compound (67.1 mg, 0.131 mmol, 47.1%) as a white solid.
MS(API): Calculated 513.7, Found 512.2 (M+H).
$^1$H NMR (300 MHz, DMSO-$d_6$): δ0.25 (9H, s), 1.21-1.57 (3H, m), 1.61-1.79 (2H, m), 1.95-2.00 (3H, m), 2.56-2.67 (1H, m), 2.91-3.08 (1H, m), 3.27 (3H, s), 3.81 (1H, brs), 4.38 (3H, s), 5.60 (1H, dd, J=7.4, 2.5 Hz), 7.24-7.37 (4H, m), 7.40-7.53 (3H, m), 8.60-8.68 (1H, m), 10.56 (1H, s).

Example 88

N-((1R)-2-((3-fluoro-4-(trimethylsilyl)phenyl) amino)-1-(4-(methoxymethyl)phenyl)-2-oxoethyl) tetrahydro-2H-pyran-4-carboxamide A solution of (R)-2-amino-N-(3-fluoro-4-(trimethylsilyl) phenyl)-2-(4-(methoxymethyl)phenyl)acetamide (100 mg, 0.28 mmol), tetrahydro-2H-pyran-4-carboxylic acid (39.7 mg, 0.31 mmol), DIEA (0.097 mL, 0.55 mmol) and HATU (127 mg, 0.33 mmol) in DMF (2.0 mL) was stirred at room temperature for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→50% ethyl acetate/hexane), and crystallized from ethyl acetate/hexane to give the title compound (68.3 mg, 0.145 mmol, 52.1%) as white crystals.
MS(API): Calculated 472.6, Found 473.2 (M+H).
$^1$H NMR (300 MHz, DMSO-$d_6$): δ0.25 (9H, s), 1.48-1.67 (4H, m), 2.55-2.69 (1H, m), 3.21-3.32 (5H, m), 3.78-3.91 (2H, m), 4.38 (2H, s), 5.55-5.64 (1H, m), 7.23-7.38 (4H, m), 7.41-7.53 (3H, m), 8.61 (1H, d, J=7.9 Hz), 10.56 (1H, s).

Example 89

(2R)—N-(3-fluoro-4-(trimethylsilyl)phenyl)-2-(4-(methoxymethyl)phenyl)-2-((tetrahydro-2H-pyran-4-ylacetyl)amino)acetamide A solution of (R)-2-amino-N-(3-fluoro-4-(trimethylsilyl) phenyl)-2-(4-(methoxymethyl)phenyl)acetamide (100 mg, 0.28 mmol), 2-(tetrahydro-2H-pyran-4-yl)acetic acid (44.0 mg, 0.31 mmol), DIEA (0.097 mL, 0.55 mmol) and HATU (127 mg, 0.33 mmol) in DMF (2.0 mL) was stirred at room temperature for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→50% ethyl acetate/hexane), and crystallized from ethyl acetate/hexane to give the title compound (39.8 mg, 0.082 mmol, 29.5%) as white crystals.
MS(API): Calculated 486.7, Found 487.2 (M+H).
$^1$H NMR (300 MHz, DMSO-$d_6$): δ0.25 (9H, s), 1.05-1.30 (2H, m), 1.43-1.61 (2H, m), 1.80-2.02 (1H, m), 2.11-2.21 (2H, m), 3.19-3.30 (5H, m), 3.73-3.85 (2H, m), 4.38 (2H, s), 5.55-5.64 (1H, m), 7.23-7.37 (4H, m), 7.40-7.53 (3H, m), 8.64 (1H, d, J=7.6 Hz), 10.55 (1H, s).

Example 90

(2R)-2-((ethylcarbamoyl)amino)-N-(3-fluoro-4-(trimethylsilyl)phenyl)-2-(4-(methoxymethyl)phenyl)acetamide To a solution of (R)-2-amino-N-(3-fluoro-4-(trimethylsilyl)phenyl)-2-(4-(methoxymethyl)phenyl)acetamide (100 mg, 0.28 mmol) and TEA (0.046 mL, 0.33 mmol) in THF (2.0 mL) was added ethyl isocyanate (0.024 mL, 0.31 mmol), and the mixture was stirred at room temperature for 2 hr. The reaction mixture was concentrated under reduced pressure, and the residue was crystallized from ethyl acetate/hexane to give the title compound (95.5 mg, 0.221 mmol, 80-) as white crystals.
MS(API): Calculated 431.6, Found 432.1 (M+H).
$^1$H NMR (300 MHz, DMSO-$d_6$): δ0.25 (9H, d, J=0.8 Hz), 0.98 (3H, t, J=7.2 Hz), 2.92-3.09 (2H, m), 3.26 (3H, s), 4.37 (2H, s), 5.43-5.52 (1H, m), 6.14 (1H, t, J=5.3 Hz), 6.74 (1H, d, J=8.3 Hz), 7.26-7.43 (6H, m), 7.49 (1H, dd, J=11.1, 1.3 Hz), 10.58 (1H, s).

Example 91

3,3-difluoro-N-((1R)-2-((3-fluoro-4-(trimethylsilyl)phenyl)amino)-1-(4-(methoxymethyl)phenyl)-2-oxoethyl)cyclobutanecarboxamide A solution of (R)-2-amino-N-(3-fluoro-4-(trimethylsilyl)phenyl)-2-(4-(methoxymethyl)phenyl)acetamide (113 mg, 0.31 mmol), 3,3-difluorocyclobutanecarboxylic acid (46.9 mg, 0.34 mmol), HATU (131 mg, 0.34 mmol) and DIEA (0.060 mL, 0.34 mmol) in DMF (3 mL) was stirred at room temperature for 2 hr. To the reaction mixture was added water, and the precipitate was collected by filtration, and washed with water to give the title compound (133 mg, 0.278 mmol, 89%) as white crystals.

MS(API): Calculated 478.6, Found 479.2 (M+H).

$^1$H NMR (300 MHz, DMSO-$d_6$): δ0.25 (9H, s), 2.58-2.79 (4H, m), 3.13 (1H, td, J=8.4, 4.0 Hz), 3.27 (3H, s), 4.38 (2H, s), 5.54-5.65 (1H, m), 7.22-7.37 (4H, m), 7.39-7.54 (3H, m), 8.88 (1H, d, J=7.6 Hz), 10.59 (1H, s).

Example 92

4,4-difluoro-N-((1R)-2-((3-fluoro-4-(trimethylsilyl)phenyl)amino)-1-(4-(methoxymethyl)phenyl)-2-oxoethyl)butanamide A solution of (R)-2-amino-N-(3-fluoro-4-(trimethylsilyl)phenyl)-2-(4-(methoxymethyl)phenyl)acetamide (100 mg, 0.28 mmol), 4,4-difluorobutanoic acid (37.9 mg, 0.31 mmol), HATU (116 mg, 0.31 mmol) and DIEA (0.053 mL, 0.31 mmol) in DMF (3 mL) was stirred overnight at room temperature. To the reaction mixture was added water, and the precipitate was collected by filtration. The obtained precipitate was purified by silica gel column chromatography (solvent; ethyl acetate), and crystallized from ethyl acetate/hexane to give the title compound (107 mg, 0.229 mmol, 83%) as white crystals.

MS(API): Calculated 466.6, Found 467.2 (M+H).

$^1$H NMR (300 MHz, DMSO-$d_6$): δ0.25 (9H, s), 1.91-2.17 (2H, m), 2.37-2.43 (2H, m), 3.27 (3H, s), 4.38 (2H, s), 5.56-5.64 (1H, m), 6.08 (1H, tt, J=57.0, 4.3 Hz), 7.24-7.38 (4H, m), 7.40-7.55 (3H, m), 8.80 (1H, d, J=7.6 Hz), 10.57 (1H, s).

Example 93

3,3,3-trifluoro-N-((1R)-2-((3-fluoro-4-(trimethylsilyl)phenyl)amino)-1-(4-(methoxymethyl)phenyl)-2-oxoethyl)propanamide A solution of (R)-2-amino-N-(3-fluoro-4-(trimethylsilyl)phenyl)-2-(4-(methoxymethyl)phenyl)acetamide (100 mg, 0.28 mmol), 3,3,3-trifluoropropanoic acid (0.027 mL, 0.31 mmol), HATU (116 mg, 0.31 mmol) and DIEA (0.053 mL, 0.31 mmol) in DMF (3 mL) was stirred at room temperature for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent; 50% ethyl acetate/hexane), and crystallized from acetone/water to give the title compound (36 mg, 0.077 mmol, 27.6%) as white crystals.

MS(API): Calculated 470.5, Found 471.1 (M+H).

$^1$H NMR (300 MHz, CDCl$_3$): δ0.27 (9H, d, J=0.8 Hz), 3.14 (2H, q, J=10.6 Hz), 3.40 (3H, s), 4.45 (2H, s), 5.57 (1H, d, J=6.4 Hz), 7.02 (1H, dd, J=7.9, 1.9 Hz), 7.20 (1H, s), 7.27-7.31 (2H, m), 7.31-7.45 (5H, m).

Example 94

4,4,4-trifluoro-N-((1R)-2-((3-fluoro-4-(trimethylsilyl)phenyl)amino)-1-(4-(methoxymethyl)phenyl)-2-oxoethyl)butanamide A solution of (R)-2-amino-N-(3-fluoro-4-(trimethylsilyl)phenyl)-2-(4-(methoxymethyl)phenyl)acetamide (100 mg, 0.28 mmol), 4,4,4-trifluorobutanoic acid (43.4 mg, 0.31 mmol), HATU (116 mg, 0.31 mmol) and DIEA (0.053 mL, 0.31 mmol) in DMF (3 mL) was stirred at room temperature for 4 hr. To the reaction mixture was added water, and the precipitate was collected by filtration. The obtained precipitate was washed with water to give the title compound (115 mg, 0.237 mmol, 86%) as white crystals.

MS(API): Calculated 484.6, Found 485.2 (M+H).

$^1$H NMR (300 MHz, CDCl$_3$): δ 0.27 (9H, d, J=0.8 Hz), 2.36-2.61 (4H, m), 3.40 (3H, s), 4.45 (2H, s), 5.55 (1H, d, J=6.8 Hz), 6.87 (1H, d, J=6.4 Hz), 7.02 (1H, dd, J=7.9, 1.9 Hz), 7.20-7.31 (2H, m), 7.33-7.45 (5H, m).

Example 95

(3R)-3-fluoro-N-((1R)-2-((3-fluoro-4-(trimethylsilyl)phenyl)amino)-1-(4-(methoxymethyl)phenyl)-2-oxoethyl)pyrrolidine-1-carboxamide (Step 1)

To a solution of (R)-2-amino-N-(3-fluoro-4-(trimethylsilyl)phenyl)-2-(4-(methoxymethyl)phenyl)acetamide (270 mg, 0.75 mmol) in THF (6 mL) were added p-nitrophenyl chloroformate (174 mg, 0.86 mmol) and pyridine (0.069 mL, 0.86 mmol), and the mixture was stirred at room temperature for 1 hr. The precipitate was collected by filtration. The obtained precipitate was washed successively with water and hexane to give 4-nitrophenyl ((1R)-2-((3-fluoro-4-(trimethylsilyl)phenyl)amino)-1-(4-(methoxymethyl)phenyl)-2-oxoethyl)carbamate (320 mg, 0.609 mmol, 81%) as a white solid.

(Step 2)

To a solution of (R)-3-fluoropyrrolidine hydrochloride (203 mg, 1.62 mmol) and DIEA (0.847 mL, 4.85 mmol) in DMF (5 mL) was added dropwise a solution of 4-nitrophenyl ((1R)-2-((3-fluoro-4-(trimethylsilyl)phenyl)amino)-1-(4-(methoxymethyl)phenyl)-2-oxoethyl)carbamate (170 mg, 0.32 mmol) in DMF (2 mL) at 0° C., and the mixture was stirred at 0° C. for 30 min. To the reaction mixture were added water and ethyl acetate, and the organic layer was separated. The organic layer was washed with water and brine, and dried over magnesium sulfate, and the solvent was evaporated under reduced pressure. The obtained residue was purified by silica gel column chromatography (solvent gradient; 30→100% ethyl acetate/hexane, 0→10% MeOH/ethyl acetate) to give the title compound (28 mg, 0.059 mmol, 18.20%) as a white solid.

MS(API): Calculated 475.6, Found 476.2 (M+H).

$^1$H NMR (300 MHz, DMSO-$d_6$): δ0.25 (9H, s), 1.90-2.18 (2H, m), 3.27 (3H, s), 3.30-3.65 (4H, m), 4.38 (2H, s), 5.18-5.44 (1H, m), 5.78 (1H, dd, J=339.9, 7.5 Hz), 5.50 (1H, s), 7.24-7.39 (4H, m), 7.42-7.57 (3H, m), 10.48 (1H, s).

Example 96

(3S)-3-fluoro-N-((1R)-2-((3-fluoro-4-(trimethylsilyl) phenyl)amino)-1-(4-(methoxymethyl)phenyl)-2-oxoethyl)pyrrolidine-1-carboxamide To a solution of (S)-3-fluoropyrrolidine hydrochloride (196 mg, 1.56 mmol) and DIEA (0.822 mL, 4.71 mmol) in DMF (5 mL) was added a solution of 4-nitrophenyl ((1R)-2-((3-fluoro-4-(trimethylsilyl)phenyl)amino)-1-(4-(methoxymethyl)phenyl)-2-oxoethyl)carbamate (165 mg, 0.31 mmol) in DMF (2 mL) at 0° C., and the mixture was stirred at 0° C. for 1 hr. To the reaction mixture were added water and ethyl acetate, and the organic layer was separated. The organic layer was washed with water and brine, and dried over magnesium sulfate, and the solvent was evaporated under reduced pressure to give the title compound (56 mg, 0.118 mmol, 37.5%) as a white solid.

MS(API): Calculated 475.6, Found 476.3 (M+H).

$^1$H NMR (300 MHz, DMSO-$d_6$): δ0.25 (9H, d, J=0.8 Hz), 1.91-2.21 (2H, m), 3.27 (3H, s), 3.28-3.72 (4H, m), 4.38 (2H, s), 5.18-5.43 (1H, m), 5.95 (1H, dd, J=342.9, 7.9 Hz), 5.49 (1H, s), 7.22-7.40 (4H, m), 7.42-7.59 (3H, m), 10.47 (1H, s).

Example 97

(2R)—N-(3-fluoro-4-(trimethylsilyl)phenyl)-2-(4-(methoxymethyl)phenyl)-2-((morpholin-4-ylacetyl) amino)acetamide hydrochloride A solution of (R)-2-amino-N-(3-fluoro-4-(trimethylsilyl) phenyl)-2-(4-(methoxymethyl)phenyl)acetamide (156 mg, 0.43 mmol), 2-morpholinoacetic acid (62.7 mg, 0.43 mmol), DIEA (0.085 mL, 0.48 mmol) and HATU (181 mg, 0.48 mmol) in DMF (2 mL) was stirred at room temperature for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by preparative HPLC (C18, mobile phase: water/acetonitrile (containing 0.1% TFA)), treated with 1 mol equivalent of hydrogen chloride/ethyl acetate, and crystallized from to give the title compound (80 mg, 0.153 mmol, 35.3%) as a white solid.

MS(API): Calculated 524.1, Found 488.2 (M−HCl+H).

$^1$H NMR (300 MHz, DMSO-$d_6$): δ0.25 (9H, s), 1.04 (1H, d, J=6.0 Hz), 3.11-3.30 (6H, m), 3.65-4.19 (6H, m), 4.39 (2H, s), 5.68 (1H, d, J=7.2 Hz), 7.24-7.41 (4H, m), 7.42-7.59 (3H, m), 9.48 (1H, brs), 10.41-11.02 (2H, m).

Example 98

N-((1R)-2-((2,5-difluoro-4-(trimethylsilyl)phenyl) amino)-1-(4-(methoxymethyl)phenyl)-2-oxoethyl)-3-hydroxy-1,2-oxazole-5-carboxamide A solution of (R)-2-amino-N-(2,5-difluoro-4-(trimethylsilyl)phenyl)-2-(4-(methoxymethyl)phenyl)acetamide (161 mg, 0.43 mmol), 3-hydroxy-1,2-oxazole-5-carboxylic acid (60.4 mg, 0.47 mmol), HATU (178 mg, 0.47 mmol) and DIEA (0.082 mL, 0.47 mmol) in DMF (5 mL) was stirred at room temperature for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 10→100% ethyl acetate/hexane) to give the title compound (40.0 mg, 0.082 mmol, 19.21%) as a white solid.

MS(API): Calculated 489.5, Found 490.1 (M+H).

Example 99

N-((1R)-2-((3,5-difluoro-4-(trimethylsilyl)phenyl) amino)-1-(4-methoxyphenyl)-2-oxoethyl)-3-hydroxy-1,2-oxazole-5-carboxamide (Step 1)

A solution of 2-amino-N-(3,5-difluoro-4-(trimethylsilyl) phenyl)-2-(4-methoxyphenyl)acetamide (0.853 g, 2.34 mmol), HATU (0.979 g, 2.57 mmol), DIEA (0.450 mL, 2.57 mmol) and 3-hydroxy-1,2-oxazole-5-carboxylic acid (0.332 g, 2.57 mmol) in DMF (2 mL) was stirred at room temperature for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent; ethyl acetate/hexane, MeOH/ethyl acetate) to give N-(2-((3,5-difluoro-4-(trimethylsilyl)phenyl)amino)-1-(4-methoxyphenyl)-2-oxoethyl)-3-hydroxy-1,2-oxazole-5-carboxamide (835 mg, 1.756 mmol, 75.0%) as a white solid.

(Step 2)

N-(2-((3,5-Difluoro-4-(trimethylsilyl)phenyl)amino)-1-(4-methoxyphenyl)-2-oxoethyl)-3-hydroxy-1,2-oxazole-5-carboxamide (2.72 g) was subjected to optical resolution using chiral column chromatography. The preparative fraction having a longer retention time was concentrated to give the title compound (680.0 mg, >99.9% ee) as a white solid.

MS(API): Calculated 475.5, Found 476.2 (M+H).

purification condition using chiral column chromatography column: CHIRALPAK AD-H(PF001)30 mmID×250 mmL solvent: $CO_2$/EtOH=660/340 back pressure: 100 bar temperature: 35° C.

detection method: UV 220 nm $[α]_D^{25}$−134.1 (c 0.1440, MeOH)

Example 100

(2R)—N-(4-tert-butyl-3-fluorophenyl)-2-(4-(methoxymethyl)phenyl)-2-(((6-oxopyrimidin-1(6H)-yl)acetyl)amino)acetamide (Step 1)

2-(tert-Butyl)aniline (10 g, 67.01 mmol) was slowly added dropwise to sulfuric acid (63.8 mL, 670.09 mmol) while the mixture was kept at 10° C. or lower. Then, potassium nitrate (6.77 g, 67.01 mmol) was slowly added thereto while the mixture was kept at 10° C. or lower. The reaction mixture was stirred at 5° C. for 30 min, and then at room temperature for 1 hr. The reaction mixture was poured into ice (ca, 500 g), and the mixture was extracted with diethyl ether. The organic layer was washed with brine, and dried over magnesium sulfate, and the solvent was evaporated under reduced pressure. The obtained residue was purified by silica gel column chromatography (solvent; 20% ethyl acetate/hexane), and crystallized from hexane to give 2-(tert-butyl)-5-nitroaniline (12.26 g, 63.1 mmol, 94-) as a pale yellow solid.

¹H NMR (300 MHz, CDCl₃): δ1.44 (9H, s), 3.81-4.32 (2H, m), 7.34 (1H, d, J=8.7 Hz), 7.46 (1H, d, J=2.3 Hz), 7.49-7.59 (1H, m).

(Step 2)

A solution of 2-(tert-butyl)-5-nitroaniline (2054 mg, 10.58 mmol) and nitrosonium tetrafluoroborate (0.920 mL, 17.21 mmol) in o-dichlorobenzene (20 mL) was stirred at 0° C. for 1 hr. The reaction mixture was stirred at 110° C. for 1 hr, cooled, and poured into water. The mixture was extracted with ethyl acetate. The organic layer was washed with brine, and dried over magnesium sulfate, and the solvent was evaporated under reduced pressure. The obtained residue was purified by silica gel column chromatography (solvent gradient; 0-10% ethyl acetate/hexane) to give 1-(tert-butyl)-2-fluoro-4-nitrobenzene (1600 mg, 8.11 mmol, 60.4%) as a brown oil.

¹H NMR (300 MHz, CDCl₃): δ1.42 (9H, d, J=1.1 Hz), 7.48 (1H, t, J=8.3 Hz), 7.87 (1H, dd, J=11.9, 2.5 Hz), 7.96 (1H, dd, J=8.7, 2.3 Hz).

(Step 3)

A solution of 1-(tert-butyl)-2-fluoro-4-nitrobenzene (1.6 g, 8.11 mmol) and 10% palladium-carbon (0.432 g, 0.20 mmol, 50% wet) in EtOH (20 mL) was stirred at room temperature for 5 hr under hydrogen atmosphere (1 atm). The catalyst was removed by filtration, and the filtrate was concentrated under reduced pressure. The obtained residue was purified by silica gel column chromatography (solvent gradient; 0→20% ethyl acetate/hexane) to give 4-(tert-butyl)-3-fluoroaniline (1.310 g, 7.83 mmol, 97%) as a brown oil.

¹H NMR (300 MHz, CDCl₃): δ1.32 (9H, d, J=1.1 Hz), 3.61 (2H, brs), 6.26-6.46 (2H, m), 6.95-7.12 (1H, m).

(Step 4)

A solution of 2-(diallylamino)-2-(4-(methoxymethyl)phenyl)acetic acid (1.811 g, 6.58 mmol), T3P (4.22 mL, 7.18 mmol), DMAP (0.731 g, 5.98 mmol), DIEA (2.089 mL, 11.96 mmol) and 4-(tert-butyl)-3-fluoroaniline (1 g, 5.98 mmol) in ethyl acetate (20 mL) was stirred overnight at 60° C. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 10→50% ethyl acetate/hexane) to give N-(4-(tert-butyl)-3-fluorophenyl)-2-(diallylamino)-2-(4-(methoxymethyl)phenyl)acetamide (1.450 g, 3.42 mmol, 57.1%) as a brown oil.

¹H NMR (300 MHz, CDCl₃): δ1.36 (9H, s), 2.88 (2H, dd, J=14.7, 7.2 Hz), 3.33 (2H, dd, J=14.7, 5.3 Hz), 3.40 (3H, s), 4.34-4.63 (3H, m), 5.13-5.38 (4H, m), 5.85 (2H, dddd, J=17.4, 9.9, 7.1, 5.3 Hz), 7.06-7.24 (2H, m), 7.27-7.53 (5H, m), 9.41 (1H, s).

(Step 5)

A solution of N-(4-(tert-butyl)-3-fluorophenyl)-2-(diallylamino)-2-(4-(methoxymethyl)phenyl)acetamide (1.45 g, 3.42 mmol), 1,3-dimethylbarbituric acid (1.173 g, 7.51 mmol) and Pd(PPh₃)₄ (0.158 g, 0.14 mmol) in THF (20 mL) was stirred overnight at room temperature. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (NH, solvent gradient; 2-100% ethyl acetate/hexane) to give 2-amino-N-(4-(tert-butyl)-3-fluorophenyl)-2-(4-(methoxymethyl)phenyl)acetamide (0.891 g, 2.59 mmol, 76%) as a brown oil.

¹H NMR (300 MHz, CDCl₃): δ1.34 (9H, s), 3.37 (3H, s), 4.44 (2H, s), 4.64 (1H, s), 7.10-7.25 (2H, m), 7.28-7.75 (7H, m), 9.38 (1H, brs).

(Step 6)

A solution of 2-amino-N-(4-(tert-butyl)-3-fluorophenyl)-2-(4-(methoxymethyl)phenyl)acetamide (890 mg, 2.58 mmol), allyl chloroformate (0.288 ML, 2.71 mmol) and DIEA (0.677 mL, 3.88 mmol) in THF (10 mL) was stirred at 0° C. for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 10→50% ethyl acetate/hexane) to give allyl (2-((4-(tert-butyl)-3-fluorophenyl)amino)-1-(4-(methoxymethyl)phenyl)-2-oxoethyl)carbamate (774 mg, 1.806 mmol, 69.9) as a white solid.

¹H NMR (300 MHz, CDCl₃): δ1.33 (9H, d, J=0.8 Hz), 3.38 (3H, s), 4.44 (2H, s), 4.57 (2H, ddd, J=4.2, 2.9, 1.5 Hz), 5.08-5.41 (3H, m), 5.60-6.37 (2H, m), 6.71-7.22 (2H, m), 7.28-7.76 (6H, m).

(Step 7)

Allyl (2-((4-(tert-butyl)-3-fluorophenyl)amino)-1-(4-(methoxymethyl)phenyl)-2-oxoethyl)carbamate (350 mg) was subjected to optical resolution using chiral column chromatography. The preparative fraction having a longer retention time was concentrated to give allyl (R)-(2-((4-(tert-butyl)-3-fluorophenyl)amino)-1-(4-(methoxymethyl)phenyl)-2-oxoethyl)carbamate (345.3 mg, >99.9% ee) as a white solid.

purification condition using chiral column chromatography
column: CHIRALPAK AD(NF001)50 mmID×500 mmL
solvent: hexane/EtOH=800/200
flow rate: 80 mL/min
temperature: 30° C.
detection method: UJV 220 nm (Step 8)

A solution of allyl (R)-(2-((4-(tert-butyl)-3-fluorophenyl)amino)-1-(4-(methoxymethyl)phenyl)-2-oxoethyl)carbamate (339.2 mg, 0.79 mmol), Pd(PPh₃)₄ (27.4 mg, 0.02 mmol) and 1,3-dimethylbarbituric acid (247 mg, 1.58 mmol) in acetonitrile (10 mL) was stirred overnight at room temperature. The reaction mixture was concentrated under reduced pressure, and the obtained residue was purified by silica gel column chromatography (solvent gradient; 10→100% ethyl acetate/hexane) to give (R)-2-amino-N-(4-(tert-butyl)-3-fluorophenyl)-2-(4-(methoxymethyl)phenyl)acetamide (190 mg, 0.552 mmol, 69.7%) as a brown oil.

(Step 9)

A solution of (R)-2-amino-N-(4-(tert-butyl)-3-fluorophenyl)-2-(4-(methoxymethyl)phenyl)acetamide (90 mg, 0.26 mmol), 2-(6-oxopyrimidin-1(6H)-yl)acetic acid (44.3 mg, 0.29 mmol), HATU (109 mg, 0.29 mmol) and DIEA (0.052 mL, 0.29 mmol) in DMF (5 mL) was stirred at room temperature for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 10→100% ethyl acetate/hexane), and crystallized from ethyl acetate/hexane to give the title compound (90 mg, 0.187 mmol, 71.7%) as white crystals.

MS(API): Calculated 480.5, Found 481.2 (M−H).

Example 101

(3S)—N-((1R)-2-((4-tert-butyl-3-fluorophenyl)amino)-1-(4-(methoxymethyl)phenyl)-2-oxoethyl)-5-oxopyrrolidine-3-carboxamide A solution of (R)-2-amino-N-(4-(tert-butyl)-3-fluorophenyl)-2-(4-(methoxymethyl)phenyl)acetamide (50 mg, 0.15 mmol), (S)-5-oxopyrrolidine-3-carboxylic acid (18.74 mg, 0.15 mmol), HATU (60.7 mg, 0.16 mmol) and DIEA (0.029 mL, 0.16 mmol) in DMF (5 mL) was stirred at room temperature for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 20→100% ethyl acetate/hexane, 1→15% MeOH/ethyl acetate), and crystallized from ethyl acetate/hexane to give the title compound (12.00 mg, 0.026 mmol, 18.15%) as white crystals.

MS(API): Calculated 455.5, Found 454.1 (M−H).

$^1$H NMR (300 MHz, DMSO-$d_6$): δ1.29 (9H, s), 2.16-2.40 (2H, m), 3.27 (5H, s), 4.38 (2H, s), 5.60 (1H, d, J=7.6 Hz), 7.14-7.37 (4H, m), 7.38-7.61 (4H, m), 8.83 (1H, d, J=7.9 Hz), 10.50 (1H, s) (The free 1H was not observed.).

$[\alpha]_D^{25}$ −116.8 (c 0.2065, MeOH)

Example 102

(3R)—N-((1R)-2-((4-tert-butyl-3-fluorophenyl)amino)-1-(4-(methoxymethyl)phenyl)-2-oxoethyl)-5-oxopyrrolidine-3-carboxamide A solution of (R)-2-amino-N-(4-(tert-butyl)-3-fluorophenyl)-2-(4-(methoxymethyl)phenyl)acetamide (50 mg, 0.15 mmol), (R)-5-oxopyrrolidine-3-carboxylic acid (20.62 mg, 0.16 mmol), HATU (60.7 mg, 0.16 mmol) and DIEA (0.029 mL, 0.16 mmol) in DMF (5 mL) was stirred at room temperature for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 10→100% ethyl acetate/hexane, 1→15% MeOH/ethyl acetate) to give the title compound (10.00 mg, 0.022 mmol, 15.12%) as white crystals.

MS(API): Calculated 455.5, Found 454.1 (M−H).

$^1$H NMR (300 MHz, DMSO-$d_6$): δ1.29 (9H, s), 2.26 (2H, dd, J=7.9, 2.6 Hz), 3.27 (5H, s), 4.38 (2H, s), 5.58 (1H, d, J=7.6 Hz), 7.11-7.37 (4H, m), 7.37-7.63 (4H, m), 8.81 (1H, d, J=7.6 Hz), 10.48 (1H, s) (The free 1H was not observed.).

Example 103

4-(((1R)-2-((3,5-difluoro-4-(trimethylsilyl)phenyl)amino)-1-(4-(methoxymethyl)phenyl)-2-oxoethyl)amino)-2,2-dimethyl-4-oxobutanoic acid A solution of (R)-2-amino-N-(3,5-difluoro-4-(trimethylsilyl)phenyl)-2-(4-(methoxymethyl)phenyl)acetamide (100 mg, 0.26 mmol) and 3,3-dimethyldihydrofuran-2,5-dione (35.5 mg, 0.28 mmol) in THF (2.0 mL) was stirred at room temperature for 3 hr. The reaction mixture was concentrated under reduced pressure, and the obtained residue was purified by silica gel column chromatography (solvent gradient; 0→15% ethyl acetate/hexane), and then preparative HPLC (C18, mobile phase: water/acetonitrile (containing 0.1% TFA)) to give the title compound (42.2 mg, 0.083 mmol, 31.5%) as a white solid.

MS(API): Calculated 506.6, Found 507.2 (M+H).

$^1$H NMR (300 MHz, DMSO-$d_F$): δ0.30 (9H, s), 1.12 (3H, s), 1.12 (3H, s), 3.27 (3H, s), 3.30 (2H, s), 4.38 (2H, s), 5.52 (1H, d, J=7.6 Hz), 7.21 (2H, d, J=9.8 Hz), 7.28-7.35 (2H, m), 7.39-7.45 (2H, m), 8.61 (1H, d, J=7.6 Hz), 10.68 (1H, s), 11.92 (1H, brs).

Example 104

(3S)—N-(2-((4-tert-butyl-3-chlorophenyl)amino)-1-(4-(methoxymethyl)phenyl)-2-oxoethyl)-5-oxopyrrolidine-3-carboxamide (Mixture of Two Diastereomers)

(Step 1)

A solution of 2-(tert-butyl)-5-nitroaniline (4 g, 20.59 mmol), pentyl nitrite (3.62 g, 30.89 mmol) and copper(I) chloride (2.039 g, 20.59 mmol) in acetonitrile (100 mL) was stirred at 50° C. for 2 hr. To the reaction mixture was added 1N hydrochloric acid at room temperature, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 0→5% ethyl acetate/hexane) to give 1-(tert-butyl)-2-chloro-4-nitrobenzene (1.760 g, 8.24 mmol, 40.0%) as a white solid.

$^1$H NMR (300 MHz, CDCl$_3$): δ1.52 (9H, s), 7.60 (1H, d, J=9.1 Hz), 8.04 (1H, dd, J=8.9, 2.5 Hz), 8.22 (1H, d, J=2.6 Hz).

(Step 2)

A solution of 1-(tert-butyl)-2-chloro-4-nitrobenzene (1.76 g, 8.24 mmol), ferric chloride hexahydrate (0.045 g, 0.16 mmol) and activated carbon (300 mg) in a mixed solvent of THF (10 mL) and MeOH (10 mL) was heated with reflux for 15 min. Then, a solution of hydrazine monohydrate (2.474 g, 49.42 mmol) in MeOH (5 mL) was added thereto, and the mixture was heated with reflux for 40 min. The reaction mixture was cooled, and the insoluble substance was removed by filtration. To the filtrate were added water and ethyl acetate, and the organic layer was separated. The organic layer was washed with brine, and dried over sodium sulfate, and the solvent was evaporated under reduced pressure to give 4-(tert-butyl)-3-chloroaniline (1.420 g, 7.73 mmol, 94%) as a colorless oil.

$^1$H NMR (300 MHz, CDCl$_3$): δ1.43 (9H, s), 3.58 (2H, brs), 6.51 (1H, dd, J=8.5, 2.5 Hz), 6.70 (1H, d, J=2.6 Hz), 7.18 (1H, d, J=8.3 Hz).

(Step 3)

A solution of 4-(tert-butyl)-3-chloroaniline (1.42 g, 7.73 mmol), 2-(diallylamino)-2-(4-(methoxymethyl)phenyl)acetic acid (2.342 g, 8.50 mmol), T3P (5.00 mL, 8.50 mmol), DMAP (1.039 g, 8.50 mmol) and DIEA (1.527 mL, 8.50 mmol) in ethyl acetate (20 mL) was stirred overnight at 70° C. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 10→100% ethyl acetate/hexane) to give N-(4-(tert-butyl)-3-chlorophenyl)-2-

(diallylamino)-2-(4-(methoxymethyl)phenyl)acetamide (2.210 g, 5.01 mmol, 64.8%) as a brownish-red oil.

$^1$H NMR (300 MHz, CDCl$_3$): δ1.35-1.51 (9H, m), 2.88 (2H, dd, J=14.7, 7.2 Hz), 3.22-3.42 (5H, m), 4.46 (2H, s), 4.54 (1H, s), 5.12-5.37 (4H, m), 5.73-6.00 (2H, m), 7.27-7.46 (6H, m), 7.60 (1H, d, J=2.3 Hz), 9.37 (1H, s).

(Step 4)

A solution of N-(4-(tert-butyl)-3-chlorophenyl)-2-(diallylamino)-2-(4-(methoxymethyl)phenyl)acetamide (2.21 g, 5.01 mmol), 1,3-dimethylbarbituric acid (1.721 g, 11.02 mmol) and Pd(PPh$_3$)$_4$ (0.174 g, 0.15 mmol) in THF (20 mL) was stirred overnight at room temperature. The reaction mixture was concentrated under reduced pressure. The obtained residue was purified by silica gel column chromatography (NH, solvent gradient; 10→100% ethyl acetate/hexane) to give 2-amino-N-(4-(tert-butyl)-3-chlorophenyl)-2-(4-(methoxymethyl)phenyl)acetamide (1.300 g, 3.60 mmol, 71.9%) as a pale yellow oil.

(Step 5)

A solution of 2-amino-N-(4-(tert-butyl)-3-chlorophenyl)-2-(4-(methoxymethyl)phenyl)acetamide (111 mg, 0.31 mmol), (S)-5-oxopyrrolidine-3-carboxylic acid (43.7 mg, 0.34 mmol), HATU (129 mg, 0.34 mmol) and DIEA (0.061 mL, 0.34 mmol) in DMF (5 mL) was stirred at room temperature for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 10→100% ethyl acetate/hexane, 0→15% MeOH/ethyl acetate) to give the title compound (90 mg, 0.191 mmol, 62.0%) as a white solid.

MS(API): Calculated 472.0, Found 470.1 (M−H).

$^1$H NMR (300 MHz, DMSO-d$_6$): δ1.39 (9H, brs), 2.30 (2H, brs), 3.27 (5H, brs), 4.38 (2H, brs), 5.57 (1H, brs), 7.17-7.64 (8H, m), 7.74 (1H, brs), 8.81 (1H, brs), 10.47 (1H, brs).

Example 105

(2R)—N-(4-tert-butyl-3-fluorophenyl)-2-(4-(methoxymethyl)phenyl)-2-(((5-methyl-1,3,4-oxadiazol-2-yl)acetyl)amino)acetamide A solution of (R)-2-amino-N-(4-(tert-butyl)-3-fluorophenyl)-2-(4-(methoxymethyl)phenyl)acetamide (45 mg, 0.13 mmol), lithium 2-(5-methyl-1,3,4-oxadiazol-2-yl)acetate (29.0 mg, 0.20 mmol), HATU (54.6 mg, 0.14 mmol) and DIEA (0.00 mmol) in DMF (5 mL) was stirred at room temperature for 3 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 10→100% ethyl acetate/hexane) to give the title compound (40.0 mg, 0.085 mmol, 65.3%) as a yellow oil.

MS(API): Calculated 468.5, Found 469.2 (M+H).

$^1$H NMR (300 MHz, CDCl$_3$): δ1.30 (9H, s), 2.40 (3H, d, J=1.1 Hz), 3.35 (3H, s), 3.91 (2H, d, J=4.5 Hz), 4.38 (2H, s), 5.78 (1H, d, J=7.2 Hz), 6.95-7.17 (2H, m), 7.23 (2H, d, J=7.9 Hz), 7.28-7.45 (3H, m), 8.24 (1H, d, J=7.2 Hz), 8.93 (1H, s).

Example 106

(2R)—N-(4-tert-butyl-3-fluorophenyl)-2-(((3-hydroxy-1,2-oxazol-5-yl)acetyl)amino)-2-(4-(methoxymethyl)phenyl)acetamide (Step 1)

A solution of (R)-2-amino-N-(4-(tert-butyl)-3-fluorophenyl)-2-(4-(methoxymethyl)phenyl) acetamide (88 mg, 0.26 mmol), 2-(3-(benzyloxy)-1,2-oxazol-5-yl)acetic acid (65.5 mg, 0.28 mmol), HATU (107 mg, 0.28 mmol) and DIEA (0.049 mL, 0.28 mmol) in DMF (5 mL) was stirred at room temperature for 3 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 10→50% ethyl acetate/hexane) to give (R)-2-(2-(3-(benzyloxy)-1,2-oxazol-5-yl)acetamide)-N-(4-(tert-butyl)-3-fluorophenyl)-2-(4-(methoxymethyl)phenyl)acetamide (146 mg, 0.261 mmol, 102%) as a white solid.

$^1$H NMR (300 MHz, CDCl$_3$): δ1.32 (9H, d, J=0.8 Hz), 2.84-3.03 (3H, m), 3.38 (3H, s), 3.56-3.81 (2H, m), 4.33-4.55 (1H, m), 5.16-5.34 (2H, m), 5.63 (1H, d, J=6.8 Hz), 5.84-6.04 (1H, m), 6.83-7.21 (2H, m), 7.30-7.57 (8H, m), 7.72-8.11 (1H, m).

(Step 2)

A solution of (R)-2-(2-(3-(benzyloxy)-1,2-oxazol-5-yl)acetamide)-N-(4-(tert-butyl)-3-fluorophenyl)-2-(4-(methoxymethyl)phenyl)acetamide (146 mg, 0.26 mmol) and 5% palladium-barium sulfate (100 mg, 0.05 mmol) in EtOH (5 mL) was stirred at room temperature for 5 hr. The catalyst was removed by filtration, and the filtrate was concentrated under reduced pressure. The obtained residue was purified by silica gel column chromatography (solvent gradient; 50→100% ethyl acetate/hexane, 0→20% MeOH/ethyl acetate) to give the title compound (50.0 mg, 0.106 mmol, 40.8%) as a white solid.

MS(API): Calculated 469.5, Found 470.2 (M+H).

$^1$H NMR (300 MHz, DMSO-d$_6$): δ1.29 (9H, s), 3.27 (3H, s), 3.72 (2H, s), 4.39 (2H, s), 5.60 (1H, d, J=7.6 Hz), 5.84 (1H, s), 7.16-7.38 (4H, m), 7.39-7.57 (3H, m), 9.03 (1H, d, J=7.9 Hz), 10.52 (1H, s), 11.09 (1H, s).

Example 107

5-(((1R)-2-((3,5-difluoro-4-(trimethylsilyl)phenyl)amino)-1-(4-(methoxymethyl)phenyl)-2-oxoethyl)amino)-5-oxopentanoic acid A solution of (R)-2-amino-N-(3,5-difluoro-4-(trimethylsilyl)phenyl)-2-(4-(methoxymethyl)phenyl)acetamide (90 mg, 0.24 mmol), dihydro-2H-pyran-2,6(3H)-dione (28.5 mg, 0.25 mmol) and TEA (0.036 mL, 0.26 mmol) in THF (2.0 mL) was stirred at room temperature for 3 hr. The reaction mixture was concentrated under reduced pressure, and the obtained residue was purified by silica gel column chromatography (solvent gradient; 0→50% ethyl acetate/hexane). The obtained residue was purified by preparative HPLC (C18, mobile phase: water/acetonitrile (containing 0.1% TFA)) to give the title compound (45.1 mg, 0.092 mmol, 38.5%) as a white solid.

MS(API): Calculated 492.6, Found 493.2 (M+H).

$^1$H NMR (300 MHz, DMSO-d$_6$): δ0.30 (9H, s), 1.71 (2H, quin, J=7.3 Hz), 2.16-2.31 (4H, m), 3.27 (3H, s), 4.38 (2H, s), 5.51-5.58 (1H, m), 7.21 (2H, d, J=9.4 Hz), 7.28-7.35 (2H, m), 7.40-7.47 (2H, m), 8.66 (1H, d, J=7.2 Hz), 10.70 (1H, s), 11.99 (1H, brs).

Example 108

4-(((1R)-2-((3,5-difluoro-4-(trimethylsilyl)phenyl) amino)-1-(4-(methoxymethyl)phenyl)-2-oxoethyl) amino)-4-oxobutanoic acid A solution of (R)-2-amino-N-(3,5-difluoro-4-(trimethylsilyl)phenyl)-2-(4-(methoxymethyl)phenyl)acetamide (80 mg, 0.21 mmol), dihydrofuran-2,5-dione (22.21 mg, 0.22 mmol) and TEA (0.032 mL, 0.23 mmol) in THF (2.0 mL) was stirred at room temperature for 3 hr. The reaction mixture was concentrated under reduced pressure, and the obtained residue was purified by silica gel column chromatography (solvent gradient; 0→50% ethyl acetate/hexane). The obtained residue was purified by preparative HPLC (C18, mobile phase: water/acetonitrile (containing 0.1% TFA)) to give the title compound (34.5 mg, 0.072 mmol, 34.1%) as a white solid.

MS(API): Calculated 478.6, Found 477.1 (M−H).

$^1$H NMR (300 MHz, DMSO-$d_6$): δ0.30 (9H, s), 2.38-2.48 (4H, m), 3.27 (3H, s), 4.38 (2H, s), 5.56 (1H, d, J=7.6 Hz), 7.22 (2H, d, J=9.4 Hz), 7.28-7.34 (2H, m), 7.40-7.47 (2H, m), 8.72 (1H, d, J=7.6 Hz), 10.68 (1H, s), 12.06 (1H, brs).

Example 109

(3S)—N-(2-((3-fluoro-4-(trimethylsilyl)phenyl) amino)-1-(1-methyl-1H-indazol-5-yl)-2-oxoethyl)-5-oxopyrrolidine-3-carboxamide (Mixture of Two Diastereomers)

(Step 1)

A solution of (1-methyl-1H-indazol-5-yl)boronic acid (1.0 g, 5.68 mmol), glyoxylic acid monohydrate (0.523 g, 5.68 mmol) and diallylamine (0.699 mL, 5.68 mmol) in acetonitrile (15 mL) was stirred overnight at 60° C. The precipitate was collected by filtration, and washed with ethyl acetate to give 2-(diallylamino)-2-(1-methyl-1H-indazol-5-yl)acetic acid (1.41 g, 4.94 mmol, 87%) as a white solid.

$^1$H NMR (300 MHz, DMSO-$d_6$): δ3.04-3.28 (4H, m), 4.03 (3H, s), 4.53 (1H, s), 5.07-5.21 (4H, m), 5.70-5.93 (2H, m), 7.45 (1H, dd, J=8.9, 1.3 Hz), 7.62 (1H, d, J=8.7 Hz), 7.70 (1H, s), 8.04 (1H, d, J=0.8 Hz), 12.53 (1H, brs).

(Step 2)

To a solution of 3-fluoro-4-(trimethylsilyl)aniline (300 mg, 1.64 mmol), 2-(diallylamino)-2-(1-methyl-1H-indazol-5-yl)acetic acid (514 mg, 1.80 mmol), DMAP (220 mg, 1.80 mmol) and DIEA (1.429 mL, 8.18 mmol) in ethyl acetate (10 mL) was added T3P (1.926 mL, 3.27 mmol), and the mixture was stirred at 80° C. for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→10% ethyl acetate/hexane) to give 2-(diallylamino)-N-(3-fluoro-4-(trimethylsilyl)phenyl)-2-(1-methyl-1H-indazol-5-yl)acetamide (454.4 mg, 1.008 mmol, 61.6%) as a pale yellow oil.

$^1$H NMR (300 MHz, CDCl$_3$): δ0.29 (9H, d, J=0.8 Hz), 2.91 (2H, dd, J=14.5, 7.0 Hz), 3.37 (2H, dd, J=14.5, 5.5 Hz), 4.07 (3H, s), 4.67 (1H, s), 5.19-5.33 (4H, m), 5.77-5.97 (2H, m), 7.19-7.25 (1H, m), 7.29-7.49 (4H, m), 7.65 (1H, s), 7.97 (1H, d, J=0.8 Hz), 9.55 (1H, s).

(Step 3)

To a solution of 2-(diallylamino)-N-(3-fluoro-4-(trimethylsilyl)phenyl)-2-(1-methyl-1H-indazol-5-yl)acetamide (450 mg, 1.00 mmol) and 1,3-dimethylbarbituric acid (327 mg, 2.10 mmol) in THF (10 mL) was added Pd(PPh$_3$)$_4$ (46.2 mg, 0.04 mmol), and the mixture was stirred overnight at room temperature under argon gas atmosphere. The reaction mixture was concentrated under reduced pressure, and the obtained residue was purified by silica gel column chromatography (NH, solvent gradient; 50→100% ethyl acetate/hexane) to give 2-amino-N-(3-fluoro-4-(trimethylsilyl)phenyl)-2-(1-methyl-1H-indazol-5-yl)acetamide (313.3 mg, 0.846 mmol, 85%) as a yellow oil.

(Step 4)

To a solution of 2-amino-N-(3-fluoro-4-(trimethylsilyl)phenyl)-2-(1-methyl-1H-indazol-5-yl)acetamide (100 mg, 0.27 mmol), DIEA (0.092 mL, 0.54 mmol) and (S)-5-oxopyrrolidine-3-carboxylic acid (38.3 mg, 0.30 mmol) in DMF (10 mL) was added COMU (127 mg, 0.30 mmol) at 0° C., and the mixture was stirred at room temperature for 5 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→5% MeOH/ethyl acetate), and crystallized from ethyl acetate/hexane to give the title compound (52.5 mg, 0.109 mmol, 40.4%) as white crystals.

MS(API): Calculated 481.6, Found 480.1 (M−H).

$^1$H NMR (300 MHz, DMSO-$d_6$): δ0.24 (9H, s), 2.29 (2H, dd, J=18.7, 8.5 Hz), 3.12-3.53 (3H, m), 4.02 (3H, s), 5.69 (1H, t, J=6.8 Hz), 7.22-7.37 (2H, m), 7.44-7.59 (3H, m), 7.65 (1H, d, J=8.7 Hz), 7.82 (1H, s), 8.08 (1H, s), 8.85 (1H, t, J=7.7 Hz), 10.57 (1H, d, J=3.8 Hz).

Example 110

(3S)—N-(2-((4-(2,2-dimethylpropyl)-3-fluorophenyl)amino)-1-(4-(methoxymethyl)phenyl)-2-oxoethyl)-5-oxopyrrolidine-3-carboxamide (Mixture of Two Diastereomers)

(Step 1)

To a solution of lithium chloride (0.81 g, 19.11 mmol) in THF (10 mL) was added 1.8M tert-butylmagnesium chloride/THF solution (10.61 mL, 19.11 mmol), and the mixture was stirred for 15 min under ice-cooling. Then, a solution of lithium chloride (1.785 g, 42.11 mmol) and coprous cyanide (0.646 mL, 21.05 mmol) in THF (20 mL) was added thereto, and the mixture was stirred for 10 min under ice-cooling. Then, 4-bromo-2-fluorobenzoyl chloride (4.89 g, 20.59 mmol) was added thereto, and the mixture was stirred overnight at room temperature. To the reaction mixture were added aqueous ammonium chloride solution/281 aqueous ammonia solution (9:1.50 mL), and the precipitate was removed by filtration. To the filtrate was added ethyl acetate, and the organic layer was separated. The organic layer was washed with brine, and dried over magnesium sulfate, and the solvent was evaporated under reduced pressure. The obtained residue was purified by silica gel column chromatography (solvent gradient; 3→50% ethyl acetate/hexane) to give 1-(4-bromo-2-fluorophenyl)-2,2-dimethylpropan-1-one (3.54 g, 13.66 mmol, 78%) as a yellow oil.

$^1$H NMR (300 MHz, CDCl$_3$): δ1.24 (9H, d, J=0.8 Hz), 7.07 (1H, dd, J=8.3, 6.8 Hz), 7.27-7.36 (2H, m).

(Step 2)

To a solution of 1-(4-bromo-2-fluorophenyl)-2,2-dimethylpropan-1-one (3.54 g, 13.66 mmol) in TFA (15 mL) was added triethylsilane (5.46 mL, 34.15 mmol) at room temperature, and the mixture was stirred for 3 days. TFA was evaporated under reduced pressure, and the residue were added water and ethyl acetate, and the organic layer was separated. The organic layer was washed with brine, and dried over magnesium sulfate, and the solvent was evaporated under reduced pressure. The obtained residue was purified by silica gel column chromatography (NH, solvent gradient; 0→30% ethyl acetate/hexane) to give 4-bromo-2-fluoro-1-neopentylbenzene (2.54 g, 10.36 mmol, 76%) as a colorless oil.

$^1$H NMR (300 MHz, CDCl$_3$): δ0.91 (9H, d, J=1.1 Hz), 2.49 (2H, d, J=1.5 Hz), 6.93-7.10 (1H, m), 7.13-7.24 (2H, m).

(Step 3)

A solution of 4-bromo-2-fluoro-1-neopentylbenzene (2.54 g, 10.36 mmol), diphenylmethanimine (2.253 g, 12.43 mmol), Pd$_2$(dba)$_3$ (0.047 g, 0.05 mmol), BINAP (0.097 g, 0.16 mmol) and sodium t-butoxide (1.394 g, 14.51 mmol) in toluene (20 mL) was stirred at 80° C. for 18 hr. To the reaction mixture was added ethyl acetate, and the insoluble substance was removed by filtration. The filtrate was concentrated under reduced pressure, and the obtained residue was purified by silica gel column chromatography (solvent gradient; 1→30% ethyl acetate/hexane) to give a pale orange oil. To this oil were added MeOH (30 mL), hydroxylamine hydrochloride (1.296 g, 18.65 mmol) and sodium acetate (2.040 g, 24.87 mmol), and the mixture was stirred at room temperature for 1 hr. 0.1M Aqueous sodium hydroxide solution was added thereto, and the mixture was extracted with ethyl acetate. The organic layer was washed with brine, and dried over magnesium sulfate, and the solvent was evaporated under reduced pressure. The obtained residue was purified by silica gel column chromatography (NH, solvent gradient; 3→97% ethyl acetate/hexane), and then preparative HPLC (C18, mobile phase: water/acetonitrile (containing 0.1% TFA)) to give 3-fluoro-4-neopentylaniline (1.28 g, 7.06 mmol, 68%) as an oil.

$^1$H NMR (300 MHz, CDCl$_3$): δ0.89 (9H, d, J=0.8 Hz), 2.41 (2H, d, J=1.5 Hz), 3.64 (2H, brs), 6.25-6.46 (2H, m), 6.80-6.94 (1H, m).

(Step 4)

To a solution of 3-fluoro-4-neopentylaniline (200 mg, 1.10 mmol), 2-(diallylamino)-2-(4-(methoxymethyl)phenyl)acetic acid (304 mg, 1.10 mmol), DMAP (148 mg, 1.21 mmol) and DIEA (0.964 mL, 5.52 mmol) in ethyl acetate (30 mL) was added T3P (0.974 mL, 1.66 mmol), and the mixture was stirred at 70° C. for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→35% ethyl acetate/hexane) to give 2-(diallylamino)-N-(3-fluoro-4-neopentylphenyl)-2-(4-(methoxymethyl)phenyl)acetamide (307 mg, 0.700 mmol, 63.4%) as a yellow oil.

$^1$H NMR (300 MHz, CDCl$_3$): δ0.91 (9H, s), 2.49 (2H, s), 2.87 (2H, dd, J=14.7, 7.2 Hz), 3.34 (2H, dd, J=14.7, 5.3 Hz), 3.40 (3H, s), 4.46 (2H, s), 4.56 (1H, s), 5.17-5.32 (4H, m), 5.75-5.96 (2H, m), 6.98-7.10 (1H, m), 7.10-7.18 (1H, m), 7.26-7.30 (2H, m), 7.31-7.37 (2H, m), 7.46 (1H, dd, J=11.7, 1.9 Hz), 9.44 (1H, s).

(Step 5)

A solution of 2-(diallylamino)-N-(3-fluoro-4-neopentylphenyl)-2-(4-(methoxymethyl)phenyl)acetamide (307 mg, 0.70 mmol), Pd(PPh$_3$)$_4$ (16.18 mg, 0.01 mmol) and 1,3-dimethylbarbituric acid (230 mg, 1.47 mmol) in THF (5 mL) was stirred at room temperature for 2 days. The reaction mixture was concentrated under reduced pressure. The obtained residue was purified by silica gel column chromatography (NH, solvent gradient; 40-100% ethyl acetate/hexane), and the obtained crystals were washed with ethyl acetate to give 2-amino-N-(3-fluoro-4-neopentylphenyl)-2-(4-(methoxymethyl)phenyl)acetamide (160 mg, 0.446 mmol, 63.8%) as a yellow solid.

$^1$H NMR (300 MHz, CDCl$_3$): δ0.90 (9H, s), 1.94 (2H, brs), 2.49 (2H, s), 3.37 (3H, s), 4.44 (2H, s), 4.65 (1H, s), 7.01-7.10 (1H, m), 7.13-7.21 (1H, m), 7.29-7.36 (2H, m), 7.39-7.45 (2H, m), 7.49 (1H, dd, J=11.7, 1.9 Hz), 9.40 (1H, brs).

(Step 6)

A solution of 2-amino-N-(3-fluoro-4-neopentylphenyl)-2-(4-(methoxymethyl)phenyl)acetamide (79 mg, 0.22 mmol), DIEA (0.042 mL, 0.24 mmol), (S)-5-oxopyrrolidine-3-carboxylic acid (31.3 mg, 0.24 mmol) and HATU (92 mg, 0.24 mmol) in DMF (2 mL) was stirred overnight at room temperature. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 50→100% ethyl acetate/hexane, 0→15% MeOH/ethyl acetate), and triturated with ethyl acetate/hexane to give the title compound (110 mg, 0.234 mmol, 106%) as a white powder.

MS(API): Calculated 469.5, Found 468.2 (M−H).

$^1$H NMR (300 MHz, DMSO-d$_6$): δ0.85 (9H, s), 2.20-2.35 (2H, m), 2.43 (2H, s), 3.12-3.51 (6H, m), 4.38 (2H, s), 5.53-5.64 (1H, m), 7.06-7.17 (1H, m), 7.18-7.25 (1H, m), 7.32 (2H, d, J=7.2 Hz), 7.42-7.59 (4H, m), 8.76-8.87 (1H, m), 10.44-10.56 (1H, m).

Example 111

(3S)—N-((1R)-2-((4-tert-butyl-3-fluorophenyl)amino)-1-(2,3-dihydro-1-benzofuran-5-yl)-2-oxoethyl)-5-oxopyrrolidine-3-carboxamide (Step 1)

A solution of (2,3-dihydrobenzofuran-5-yl)boronic acid (680 mg, 4.15 mmol), glyoxylic acid monohydrate (382 mg, 4.15 mmol) and diallylamine (0.510 mL, 4.15 mmol) in acetonitrile (15 mL) was stirred overnight at 60° C. The reaction mixture was concentrated under reduced pressure. The obtained residue was purified by silica gel column chromatography (Diol, solvent gradient; 0→10% MeOH/ethyl acetate) to give 2-(diallylamino)-2-(2,3-dihydrobenzofuran-5-yl)acetic acid (1.02 g, 3.73 mmol, 90%) as a colorless oil.

$^1$H NMR (300 MHz, DMSO-d$_6$): δ3.06-3.25 (6H, m), 4.33 (1H, s), 4.44-4.60 (2H, m), 5.05-5.24 (4H, m), 5.79 (2H, ddt, J=16.8, 10.4, 6.2 Hz), 6.72 (1H, d, J=7.9 Hz), 7.00-7.13 (1H, m), 7.22 (1H, s), 12.37 (1H, brs).

(Step 2)

To a solution of 4-(tert-butyl)-3-fluoroaniline (300 mg, 1.79 mmol), 2-(diallylamino)-2-(2,3-dihydrobenzofuran-5-yl)acetic acid (539 mg, 1.97 mmol), DMAP (241 mg, 1.97 mmol) and DIEA (1.567 mL, 8.97 mmol) in ethyl acetate (10 mL) was added T3P (2.111 mL, 3.59 mmol), and the mixture was stirred at 80° C. for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→20% ethyl acetate/hexane) to give N-(4-(tert-butyl)-3-fluorophenyl)-2-(diallylamino)-2-(2,3-dihydrobenzofuran-5-yl)acetamide (558.7 mg, 1.322 mmol, 73.7%) as a yellow oil.
(Step 3)
A solution of N-(4-(tert-butyl)-3-fluorophenyl)-2-(diallylamino)-2-(2,3-dihydrobenzofuran-5-yl)acetamide (550 mg, 1.30 mmol), 1,3-dimethylbarbituric acid (427 mg, 2.73 mmol) and Pd(PPh$_3$)$_4$ (60.2 mg, 0.05 mmol) in THF (10 mL) was stirred overnight at room temperature under argon gas atmosphere. The reaction mixture was concentrated under reduced pressure. The obtained residue was purified by silica gel column chromatography (NH, solvent gradient; 50→100% ethyl acetate/hexane) to give 2-amino-N-(4-(tert-butyl)-3-fluorophenyl)-2-(2,3-dihydrobenzofuran-5-yl)acetamide (352.6 mg, 1.030 mmol, 79%) as a yellow oil.
(Step 4)
To a solution of 2-amino-N-(4-(tert-butyl)-3-fluorophenyl)-2-(2,3-dihydrobenzofuran-5-yl)acetamide (100 mg, 0.29 mmol), DIEA (0.100 mL, 0.58 mmol) and (S)-5-oxopyrrolidine-3-carboxylic acid (41.5 mg, 0.32 mmol) in DMF (10 mL) was added COMU (138 mg, 0.32 mmol) at 0° C., and the mixture was stirred at room temperature for 5 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0-5% MeOH/ethyl acetate), and crystallized from ethyl acetate/hexane to give (3S)—N-(2-((4-(tert-butyl)-3-fluorophenyl)amino)-1-(2,3-dihydrobenzofuran-5-yl)-2-oxoethyl)-5-oxopyrrolidine-3-carboxamide (mixture of two diastereomers) (51.2 mg, 0.113 mmol, 38.7%) as white crystals.
$^1$H NMR (300 MHz, DMSO-d$_6$): δ1.29 (9H, s), 2.27 (2H, dd, J=14.2, 8.1 Hz), 3.16 (2H, t, J=8.5 Hz), 3.22-3.48 (3H, m), 4.50 (2H, t, J=8.7 Hz), 5.42-5.51 (1H, m), 6.75 (1H, d, J=8.3 Hz), 7.13-7.35 (4H, m), 7.44-7.59 (2H, m), 8.69 (1H, t, J=7.6 Hz), 10.39 (1H, d, J=3.8 Hz).
(Step 5)
(3S)—N-(2-((4-(tert-Butyl)-3-fluorophenyl)amino)-1-(2,3-dihydrobenzofuran-5-yl)-2-oxoethyl)-5-oxopyrrolidine-3-carboxamide (mixture of two diastereomers) (45 mg) was subjected to optical resolution using preparative HPLC (C18, mobile phase: water/acetonitrile (containing 0.1% TEA)). The preparative fraction having a longer retention time was concentrated to give the title compound (13.2 mg) as white crystals.
MS(API): Calculated 453.5, Found 452.1 (M−H).

Example 112

(3S)—N-((1R)-2-((3-fluoro-4-(trimethylsilyl)phenyl)amino)-1-(1-methyl-1H-indazol-5-yl)-2-oxoethyl)-5-oxopyrrolidine-3-carboxamide (3S)—N-(2-((3-Fluoro-4-(trimethylsilyl)phenyl)amino)-1-(1-methyl-1H-indazol-5-yl)-2-oxoethyl)-5-oxopyrrolidine-3-carboxamide (diastereomer mixture) (45 mg) was subjected to optical resolution using preparative HPLC (C18, mobile phase: water/acetonitrile (containing 0.1% TEA)). The preparative fraction having a longer retention time was concentrated, and crystallized from ethyl acetate/hexane to give the title compound (8.7 mg) as white crystals.
MS(API): Calculated 481.6, Found 482.2 (M+H).

Example 113

(3R)—N-((1R)-2-((4-tert-butyl-3,5-difluorophenyl)amino)-1-(4-(methoxymethyl)phenyl)-2-oxoethyl)-5-oxopyrrolidine-3-carboxamide (Step 1)
To a solution of 3,5-difluorophenol (17.0 g, 130.68 mmol) in 2-methoxy-2-methylpropane (34 mL, 285.43 mmol) was slowly added zirconium(IV) chloride (15.23 g, 65.34 mmol) while the mixture was kept at 30 to 40° C. The mixture was stirred at room temperature for 2 hr, and then, zirconium(IV) chloride (15.23 g, 65.34 mmol) was slowly added thereto. The mixture was stirred at room temperature for 2 hr, and poured into ice and 8N aqueous sodium hydroxide solution (90 mL). Diethyl ether (about 400 mL) was added thereto, and the insoluble substance was removed by filtration. The filtrate was washed with brine, and dried over magnesium sulfate, and the solvent was evaporated under reduced pressure. The obtained residue was purified by silica gel column chromatography (solvent gradient; 0→10% ethyl acetate/hexane) to give 4-(tert-butyl)-3,5-difluorophenol (16.80 g, 90 mmol, 69.0%) as a brown oil.
$^1$H NMR (300 MHz, CDCl$_3$): δ1.42 (9H, t, J=2.3 Hz), 5.07-5.26 (1H, m), 6.24-6.42 (2H, m)
(Step 2)
To a solution of 4-(tert-butyl)-3,5-difluorophenol (16.8 g, 90.23 mmol) in THF (168 mL) was added sodium hydride (60% in oil, 4.33 g, 108.27 mmol) at 0° C., and then, 1,1,1-trifluoro-N-phenyl-N-((trifluoromethyl)sulfonyl)methanesulfonamide (35.5 g, 99.25 mmol) was added thereto. The reaction mixture was stirred at room temperature for 2 hr, and poured into aqueous ammonium chloride solution. The mixture was extracted with ethyl acetate, and the organic layer was washed with aqueous sodium hydrogencarbonate solution, and dried over magnesium sulfate, and the solvent was evaporated under reduced pressure. The obtained residue was purified by silica gel column chromatography (solvent; hexane) to give 4-(tert-butyl)-3,5-difluorophenyl trifluoromethanesulfonate (8.14 g, 25.6 mmol, 28.3%) as a pale yellow oil.
$^1$H NMR (300 MHz, CDCl$_3$): δ1.46 (9H, t, J=2.3 Hz), 6.80 (2H, d, J=10.2 Hz)
(Step 3)
A solution of XANTPHOS (1.407 g, 2.43 mmol), diphenylmethanimine (4.06 mL, 24.32 mmol), cesium carbonate (15.85 g, 48.64 mmol), 4-(tert-butyl)-3,5-difluorophenyl trifluoromethanesulfonate (5.16 g, 16.21 mmol) and Pd$_2$(dba)$_3$ (0.742 g, 0.81 mmol) in THF (50 mL) was heated with reflux overnight. The reaction mixture was neutralized with aqueous sodium hydrogencarbonate solution. To the reaction mixture was added ethyl acetate, and the organic layer was separated. The organic layer was washed with brine, and dried over magnesium sulfate, and the solvent was evaporated under reduced pressure. To the obtained residue were added THF (50.00 mL) and 6N hydrochloric acid (5 mL, 30 mmol), and the mixture was stirred at room temperature for 2 hr. The reaction mixture was neutralized with aqueous sodium hydrogencarbonate solution, and extracted with ethyl acetate. The organic layer was washed with brine, and dried over magnesium sulfate, and the solvent was evaporated under reduced pressure. The obtained residue was purified by silica gel column chromatography (solvent gradient; 5→15% ethyl acetate/hexane) to give 4-(tert-butyl)-3,5-difluoroaniline (2.100 g, 11.34 mmol, 69.9-) as a pale yellow oil.

$^1$H NMR (300 MHz, DMSO-$d_6$): δ1.33 (9H, t, J=2.1 Hz), 5.46 (2H, s), 6.02-6.18 (2H, m).

(Step 4)

T3P (10.11 mL, 17.01 mmol) was added to a solution of 2-(diallylamino)-2-(4-methoxyphenyl)acetic acid (3.12 g, 11.34 mmol), 4-(tert-butyl)-3,5-difluoroaniline (2.1 g, 11.34 mmol), DIEA (9.90 mL, 56.69 mmol) and DMAP (1.524 g, 12.47 mmol) in ethyl acetate (100 mL) at room temperature, and the mixture was stirred at 70° C. for 15 hr. To the reaction mixture were added water and ethyl acetate, and the organic layer was separated. The organic layer was washed with aqueous sodium hydrogencarbonate solution and brine, and dried over magnesium sulfate, and the solvent was evaporated under reduced pressure. The obtained residue was purified by silica gel column chromatography (solvent gradient; 0→30% ethyl acetate/hexane) to give N-(4-(tert-butyl)-3,5-difluorophenyl)-2-(diallylamino)-2-(4-(methoxymethyl)phenyl)acetamide (3.16 g, 7.14 mmol, 63.0%) as a pale yellow oil.

$^1$H NMR (300 MHz, DMSO-$d_6$): δ1.39 (9H, t, J=1.9 Hz), 3.02-3.26 (4H, m), 3.28 (3H, s), 4.39 (2H, s), 4.47 (1H, s), 5.12 (2H, s), 5.17 (2H, d, J=4.9 Hz), 5.73-5.95 (2H, m), 7.22-7.35 (4H, m), 7.37-7.45 (2H, m), 10.32 (1H, s).

(Step 5)

To a solution of N-(4-(tert-butyl)-3,5-difluorophenyl)-2-(diallylamino)-2-(4-(methoxymethyl)phenyl)acetamide (3.16 g, 7.14 mmol) and 1,3-dimethylbarbituric acid (2.341 g, 15.00 mmol) in THF (15 mL) was added Pd(PPh$_3$)$_4$(0.330 g, 0.29 mmol), and the mixture was stirred overnight at room temperature. The reaction mixture was concentrated under reduced pressure, and the obtained residue was purified by silica gel column chromatography (NH, solvent gradient; 10→100% ethyl acetate/hexane) to give 2-amino-N-(4-(tert-butyl)-3,5-difluorophenyl)-2-(4-(methoxymethyl)phenyl)acetamide (2.000 g, 5.52 mmol, 77%) as a pale yellow oil.

$^1$H NMR (300 MHz, DMSO-$d_6$): δ1.38 (9H, t, J=2.1 Hz), 3.26 (3H, s), 4.37 (2H, s), 4.49 (1H, s), 7.23-7.36 (4H, m), 7.42 (2H, d, J=7.9 Hz) (The free 3H was not observed.).

(Step 6)

To a solution of 2-amino-N-(4-(tert-butyl)-3,5-difluorophenyl)-2-(4-(methoxymethyl)phenyl)acetamide (2 g, 5.52 mmol) and TEA (1.538 mL, 11.04 mmol) in THF (50 mL) was added Boc$_2$O (1.538 mL, 6.62 mmol) at 0° C., and the mixture was stirred for 1 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent gradient; 0→30% ethyl acetate/hexane) to give tert-butyl (2-((4-(tert-butyl)-3,5-difluorophenyl)amino)-1-(4-(methoxymethyl)phenyl)-2-oxoethyl)carbamate (2.180 g, 4.71 mmol, 85%) as white crystals.

$^1$H NMR (300 MHz, DMSO-$d_6$): δ1.38 (18H, d, J=2.3 Hz), 3.27 (3H, s), 4.38 (2H, s), 5.27 (1H, d, J=6.8 Hz), 7.11-7.25 (2H, m), 7.29 (2H, d, J=7.9 Hz), 7.43 (2H, d, J=7.9 Hz), 7.59 (1H, d, J=7.9 Hz), 10.49 (1H, s).

(Step 7)

tert-Butyl (2-((4-(tert-butyl)-3,5-difluorophenyl)amino)-1-(4-(methoxymethyl)phenyl)-2-oxoethyl)carbamate (2.18 g) was subjected to optical resolution using chiral column chromatography. The preparative fraction having a shorter retention time was concentrated to give tert-butyl (R)-(2-((4-(tert-butyl)-3,5-difluorophenyl)amino)-1-(4-(methoxymethyl)phenyl)-2-oxoethyl)carbamate (1.02 g, >99.9% ee) as a white solid.

purification condition using chiral column chromatography column: CHIRALPAK AD(AF001)50 mmID×500 mmL solvent: hexane/EtOH=850/150 flow rate: 80 mL/min temperature: 30° C.

detection method: UV 220 nm (Step 8)

tert-Butyl (R)-(2-((4-(tert-butyl)-3,5-difluorophenyl)amino)-1-(4-(methoxymethyl)phenyl)-2-oxoethyl)carbamate (1.02 g, 2.21 mmol) was dissolved in TFA (3 mL, 38.94 mmol), and the solution was stirred at room temperature for 1 hr. The reaction mixture was neutralized with aqueous sodium hydrogencarbonate solution, and extracted with ethyl acetate. The organic layer was washed with brine, and dried over magnesium sulfate, and the solvent was evaporated under reduced pressure to give (R)-2-amino-N-(4-(tert-butyl)-3,5-difluorophenyl)-2-(4-(methoxymethyl)phenyl)acetamide (0.840 g, 2.318 mmol, 105%) as a colorless oil.

$^1$H NMR (300 MHz, DMSO-$d_6$): δ1.38 (9H, t, J=1.9 Hz), 3.27 (3H, s), 3.29-3.31 (1H, m), 4.38 (2H, s), 4.62 (1H, s), 7.22-7.34 (4H, m), 7.44 (2H, d, J=7.9 Hz) (The free 2H was not observed.).

(Step 9)

HATU (126 mg, 0.33 mmol) was added to a solution of (R)-5-oxopyrrolidine-3-carboxylic acid (35.6 mg, 0.28 mmol), DIEA (0.145 mL, 0.83 mmol) and (R)-2-amino-N-(4-(tert-butyl)-3,5-difluorophenyl)-2-(4-(methoxymethyl)phenyl)acetamide (100 mg, 0.28 mmol) in DMF (4 mL) at room temperature, and the mixture was stirred for 3 hr. The reaction mixture was neutralized with aqueous sodium hydrogencarbonate solution, and extracted with ethyl acetate. The organic layer was washed with brine, and dried over magnesium sulfate, and the solvent was evaporated under reduced pressure. The obtained residue was purified by silica gel column chromatography (solvent gradient; 0→20% MeOH/ethyl acetate), and crystallized from ethyl acetate/hexane to give the title compound (75 mg, 0.158 mmol, 57.4%) as white crystals.

MS(API): Calculated 473.5, Found 472.1 (M–H).

$^1$H NMR (300 MHz, DMSO-$d_6$): δ1.38 (9H, s), 2.21-2.31 (2H, m), 3.20-3.30 (4H, m), 3.38-3.52 (2H, m), 4.39 (2H, s), 5.53 (1H, d, J=7.2 Hz), 7.13-7.26 (2H, m), 7.28-7.35 (2H, m), 7.39-7.49 (2H, m), 7.57 (1H, s), 8.83 (1H, d, J=7.2 Hz), 10.62 (1H, s).

Example 114

(2R)—N-(4-tert-butyl-3,5-difluorophenyl)-2-(((3-hydroxy-1,2-oxazol-5-yl)acetyl)amino)-2-(4-(methoxymethyl)phenyl)acetamide (Step 1)

n-BuLi (15.96 mL, 25.53 mmol) was added to diisopropylamine (3.90 mL, 27.85 mmol) at −10 to at 0° C., and the mixture was stirred at the same temperature for 30 min. Then, a solution of 5-methyl-1,2-oxazol-3-ol (1.15 g, 11.61 mmol) in THF (20 mL) was slowly added thereto while the mixture was kept at 0° C., and the mixture was stirred at the same temperature for 1 hr. The reaction mixture was cooled to −78° C., and excess amount of crushed dry ice was added thereto. The reaction mixture was stirred at room temperature for 2 hr, and 6N hydrochloric acid was added thereto. The mixture was extracted with ethyl acetate (×2). The organic layer was washed with brine, and dried over magnesium sulfate, and the solvent was evaporated under reduced pressure, and the precipitate was washed with ethyl acetate/hexane to give 2-(3-hydroxy-1,2-oxazol-5-yl)acetic acid (0.630 g, 4.40 mmol, 37.9%) as a pale yellow solid.

$^1$H NMR (300 MHz, DMSO-d$_6$): δ3.73 (2H, s), 5.91 (1H, s), 11.14 (1H, brs), 12.76 (1H, brs).

(Step 2)

HATU (99 mg, 0.26 mmol) was added to a solution of DIEA (0.070 mL, 0.40 mmol), 2-(3-hydroxy-1,2-oxazol-5-yl)acetic acid (31.5 mg, 0.22 mmol) and (R)-2-amino-N-(4-(tert-butyl)-3,5-difluorophenyl)-2-(4-(methoxymethyl)phenyl)acetamide (72.5 mg, 0.2 mmol) in DMF (5 mL) at room temperature, and the mixture was stirred for 5 hr. The reaction mixture was neutralized with aqueous sodium hydrogencarbonate solution, and extracted with ethyl acetate. The organic layer was washed with brine, and dried over magnesium sulfate, and the solvent was evaporated under reduced pressure. The obtained residue was purified by silica gel column chromatography (solvent gradient; 0→15% MeOH/ethyl acetate), and crystallized from ethyl acetate/hexane to give the title compound (40.0 mg, 0.082 mmol, 41.0%) as a white solid.

MS(API): Calculated 487.5, Found 486.0 (M−H).

$^1$H NMR (300 MHz, DMSO-d$_6$): δ1.38 (9H, s), 3.27 (3H, s), 3.71 (2H, s), 4.39 (2H, s), 5.55 (1H, d, J=7.2 Hz), 5.84 (1H, s), 7.10-7.26 (2H, m), 7.28-7.37 (2H, m), 7.41-7.48 (2H, m), 9.05 (1H, d, J=7.6 Hz), 10.64 (1H, s), 11.11 (1H, brs).

Example 116

(2R)—N-(4-tert-butyl-3-fluorophenyl)-2-(((2,4-dioxo-3,4-dihydropyrimidin-1(2H)-yl)acetyl)amino)-2-(4-(methoxymethyl)phenyl)acetamide To a solution of (R)-2-amino-N-(4-(tert-butyl)-3-fluorophenyl)-2-(4-(methoxymethyl)phenyl)acetamide (30 mg, 0.09 mmol), DIEA (0.030 mL, 0.17 mmol) and 2-(2,4-dioxo-3,4-dihydropyrimidin-1(2H)-yl)acetic acid (16.30 mg, 0.10 mmol) in DMF (2.0 mL) was added HATU (39.7 mg, 0.10 mmol) at room temperature, and the mixture was stirred for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent; ethyl acetate/hexane), and crystallized from ethyl acetate/hexane to give the title compound (23.2 mg, 0.047 mmol, 53.6%) as white crystals.

MS(API): Calculated 496.5, Found 497.1 (M+H).

$^1$H NMR (300 MHz, DMSO-d$_6$): δ1.29 (9H, s), 3.27 (3H, s), 4.39 (2H, s), 4.48 (2H, s), 5.54 (1H, d, J=7.9 Hz), 5.61-5.67 (1H, m), 7.15-7.36 (4H, m), 7.42-7.61 (4H, m), 9.11 (1H, d, J=7.6 Hz), 10.52 (1H, s), 11.27 (1H, s).

Example 117

(2R)—N-(4-tert-butyl-3-fluorophenyl)-2-(((2,6-dioxopiperidin-4-yl)acetyl)amino)-2-(4-(methoxymethyl)phenyl)acetamide To a solution of (R)-2-amino-N-(4-(tert-butyl)-3-fluorophenyl)-2-(4-(methoxymethyl)phenyl)acetamide (50 mg, 0.15 mmol), DIEA (0.050 mL, 0.29 mmol) and 2-(2,6-dioxopiperidin-4-yl)acetic acid (27.3 mg, 0.16 mmol) in DMF (2.0 mL) was added HATU (66.2 mg, 0.17 mmol) at room temperature, and the mixture was stirred for 2 hr. To the reaction mixture were added water and ethyl acetate, and the organic layer was separated. The organic layer was washed with brine, and dried over magnesium sulfate, and the solvent was evaporated under reduced pressure. The obtained residue was purified by silica gel column chromatography (solvent; ethyl acetate/hexane), and crystallized from ethyl acetate/hexane to give the title compound (21.9 mg, 0.044 mmol, 30.3%) as white crystals.

MS(API): Calculated 497.6, Found 498.2 (M+H).

$^1$H NMR (300 MHz, DMSO-d$_6$): δ1.29 (9H, s), 2.20-2.40 (5H, m), 3.27 (3H, s), 3.30 (2H, s), 4.38 (2H, s), 5.57 (1H, d, J=7.2 Hz), 7.16-7.35 (4H, m), 7.40-7.54 (3H, m), 8.75 (1H, d, J=7.2 Hz), 10.46 (1H, s), 10.71 (1H, s).

The compounds of Examples 115, 118 to 126, 128 to 154, 156 to 214, 216 to 253, 255 to 382, 384 to 402, 406, 407 and 409 to 418 were synthesized in the same manner as in Examples 1 to 117.

Example 419

(2R)—N-(4-tert-butyl-3,5-difluorophenyl)-2-(((3-hydroxy-1,2-oxazol-5-yl)acetyl)amino)-2-(1-methyl-1H-indazol-5-yl)acetamide (Step 1)

T3P (6.35 ml, 10.80 mmol) was added to a solution of 4-(tert-butyl)-3,5-difluoroaniline (1.0 g, 5.40 mmol), 2-(diallylamino)-2-(1-methyl-1H-indazol-5-yl)acetic acid (1.695 g, 5.94 mmol), DMAP (0.726 g, 5.94 mmol) and DIEA (4.71 ml 27.0 mmol) in ethyl acetate (30 ml), and the mixture was stirred at 80° C. for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent; ethyl acetate/hexane) to give N-(4-(tert-butyl)-3,5-difluorophenyl)-2-(diallylamino)-2-(1-methyl-1H-indazol-5-yl)acetamide (1.37 g, 3.03 mmol, 56.1%) as a grayish white solid.

MS(API): Calculated 452.5, Found 453.2 (M+H).

(Step 2)

A solution of N-(4-(tert-butyl)-3,5-difluorophenyl)-2-(diallylamino)-2-(1-methyl-1H-indazol-5-yl)acetamide (1.37 g, 3.03 mmol) and 1,3-dimethylbarbituric acid (0.993 g, 6.36 mmol) in THF (25 ml) was degassed, and Pd(PPh$_3$)$_4$ (0.140 g, 0.12 mmol) was added thereto. The mixture was stirred overnight at room temperature under argon gas atmosphere. The reaction mixture was concentrated under reduced pressure, and the obtained residue was purified by silica gel column chromatography (NH, solvent gradient; 50→100% ethyl acetate/hexane) to give crude 2-amino-N-(4-(tert-butyl)-3,5-difluorophenyl)-2-(1-methyl-1H-indazol-5-yl) acetamide (1.15 g, 3.09 mmol, 102%) as a pale yellow oil.

MS(API): Calculated 372.4, Found 371.2 (M−H).

(Step 3)

To a solution of the crude 2-amino-N-(4-(tert-butyl)-3,5-difluorophenyl)-2-(1-methyl-1H-indazol-5-yl)acetamide (1.05 g, 2.82 mmol) and TEA (0.786 ml, 5.64 mmol) in THF (20 ml) was added Boc$_2$O (0.786 ml, 3.38 mmol) at room temperature, and the mixture was stirred at room temperature for 2 hr. To the reaction mixture were added water and ethyl acetate, and the organic layer was separated. The organic layer was dried over magnesium sulfate, and the solvent was evaporated under reduced pressure. The obtained residue was purified by silica gel column chromatography (solvent; ethyl acetate/hexane) to give tert-butyl (2-((4-(tert-butyl)-3,5-difluorophenyl)amino)-1-(1-methyl-1H-indazol-5-yl)-2-oxoethyl)carbamate (1.36 g, 2.88 mmol, 102%) as a white solid.

MS(API): Calculated 472.5, Found 471.3 (M−H).

(Step 4)

tert-Butyl (2-((4-(tert-butyl)-3,5-difluorophenyl)amino)-1-(1-methyl-1H-indazol-5-yl)-2-oxoethyl)carbamate was subjected to optical resolution using chiral column chromatography. The preparative fraction having a shorter retention time was concentrated to give tert-butyl (S)-2-((4-(tert-butyl)-3,5-difluorophenyl)amino)-1-(1-methyl-1H-indazol-5-yl)-2-oxoethyl)carbamate (0.43 g, >99% ee), and the preparative fraction having a longer retention time was concentrated to give tert-butyl (R)-2-((4-(tert-butyl)-3,5-difluorophenyl)amino)-1-(1-methyl-1H-indazol-5-yl)-2-oxoethyl)carbamate (0.43 g, >99% ee).

purification condition using chiral column chromatography
column: CHIRALCEL IA(QK001)50 mmID×500 mmL
solvent: hexane/2-propanol=600/400
flow rate: 80 mL/min
temperature: 30° C.
detection method: UJV 220 nm (Step 5)

4N Hydrogen chloride/ethyl acetate (4.5 ml, 18.0 mmol) was added to a solution of tert-butyl (R)-(2-((4-(tert-butyl)-3,5-difluorophenyl)amino)-1-(1-methyl-1H-indazol-5-yl)-2-oxoethyl)carbamate (430 mg, 0.91 mmol) in ethyl acetate (6.0 ml), and the mixture was stirred at room temperature for 5 hr. The precipitate was collected by filtration with ethyl acetate to give (R)-2-amino-N-(4-(tert-butyl)-3,5-difluorophenyl)-2-(1-methyl-1H-indazol-5-yl)acetamide hydrochloride (381.0 mg, 0.932 mmol, 102%) as a white solid.

$^1$H NMR (300 MHz, DMSO-d$_6$): δ1.37 (9H, t, J=1.9 Hz), 4.05 (3H, s), 5.40 (1H, d, J=4.9 Hz), 7.22-7.35 (2H, m), 7.62-7.69 (1H, m), 7.70-7.77 (1H, m), 8.04 (1H, s), 8.16 (1H, s), 8.92 (3H, d, J=2.6 Hz), 11.57 (1H, s).

(Step 6)

HATU (112 mg, 0.29 mmol) was added to a solution of (R)-2-amino-N-(4-(tert-butyl)-3,5-difluorophenyl)-2-(1-methyl-1H-indazol-5-yl)acetamide hydrochloride (100 mg, 0.24 mmol), DIEA (0.084 ml, 0.49 mmol) and 2-(3-hydroxy-1,2-oxazol-5-yl)acetic acid (42.0 mg, 0.29 mmol) in DMF (2.0 ml) at room temperature, and the mixture was stirred at room temperature for 2 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent gradient; 5→50% ethyl acetate/hexane) to give the title compound (19.2 mg, 0.039 mmol, 15.81) as a pale yellow solid.

$^1$H NMR (300 MHz, DMSO-d$_6$): δ1.37 (9H, s), 3.71 (2H, s), 4.03 (3H, s), 5.64 (1H, d, J=7.6 Hz), 5.85 (1H, s), 7.20 (2H, d, J=12.5 Hz), 7.48 (1H, d, J=8.7 Hz), 7.66 (1H, d, J=8.7 Hz), 7.82 (1H, s), 8.08 (1H, s), 9.06 (1H, d, J=7.6 Hz), 10.62 (1H, s), 11.08 (1H, brs).

The compounds described in Examples 1 to 126, 128 to 154, 156 to 214, 216 to 253, 255 to 382, 384 to 402, 406, 407 and 409 to 419 are as follows (Table 1-1 to Table 1-42).

TABLE 1-1

| Ex. No. | IUPAC NAME | Structure | Salt | MS (Found) |
|---|---|---|---|---|
| 1 | N-(3,5-difluoro-4-(trimethylsilyl)phenyl)-2-(((6-oxopyrimidin-1(6H)-yl)acetyl)amino)-2-(tetrahydro-2H-pyran-4-yl)acetamide | 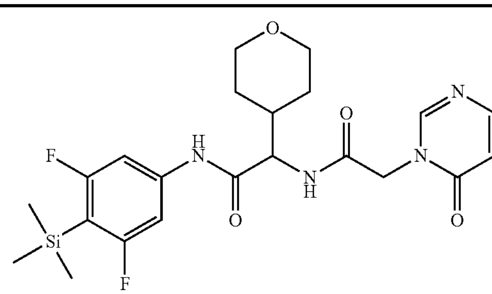 | | 477.1 (M − H) |
| 2 | N-(3,5-difluoro-4-(trimethylsilyl)phenyl)-2-(((5-methyl-(1,3,4-oxadiazol-2-yl)acetyl)amino)-2-(tetrahydro-2H-pyran-4-yl)acetamide | 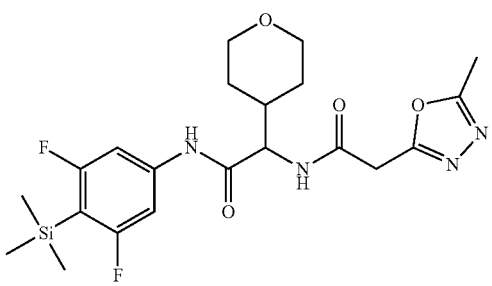 [SMILES: Cc1nnc(CC(=O)NC(C(=O)Nc2cc(F)c([Si](C)(C)C)c(F)c2)C2CCOCC2)o1] | | 465.1 (M − H) |

TABLE 1-1-continued

| Ex. No. | IUPAC NAME | Structure | Salt | MS (Found) |
|---|---|---|---|---|
| 3 | N-((1R)-2-((3,5-difluoro-4-(trimethylsilyl)phenyl)amino)-2-oxo-1-(tetrahydro-2H-pyran-4-yl)ethyl)-3-hydroxy-1,2-oxazole-5-carboxamide | 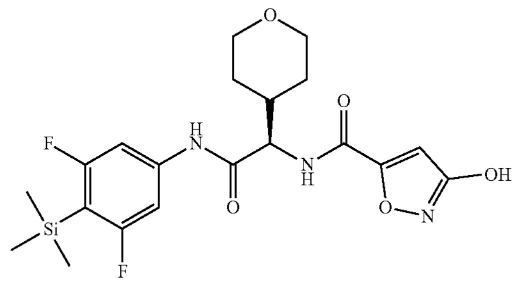 [SMILES: C[Si](C)(C)c1c(F)cc(NC(=O)[C@H](NC(=O)c2cc(O)no2)C2CCOCC2)cc1F] | | 451.9 (M − H) |
| 4 | N-(1-(4,4-difluorocyclohexyl)-2-((3-fluoro-4-(trimethylsilyl)phenyl)amino)-2-oxoethyl)-3-hydroxy-1,2-oxazole-5-carboxamide | 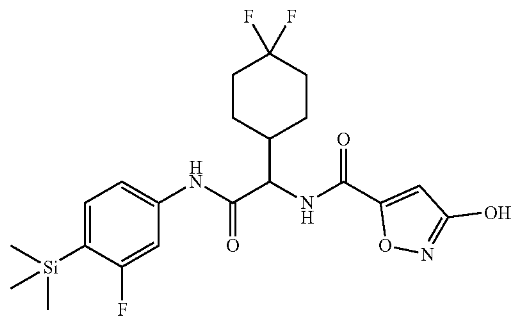 [SMILES: C[Si](C)(C)c1ccc(NC(=O)C(NC(=O)c2cc(O)no2)C2CCC(F)(F)CC2)cc1F] | | 468.1 (M − H) |
| 5 | (3S)-N-(1-(4,4-difluorocyclohexyl)-2-((3-fluoro-4-(trimethylsilyl)phenyl)amino)-2-oxoethyl)-5-oxopyrrolidine-3-carboxamide | 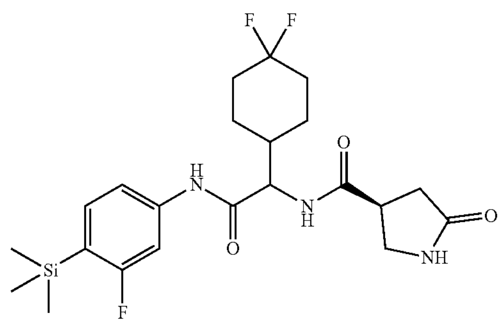 [SMILES: C[Si](C)(C)c1ccc(NC(=O)C(NC(=O)[C@@H]2CNC(=O)C2)C2CCC(F)(F)CC2)cc1F] | | 468.1 (M − H) |
| 6 | N-(2-((3,5-difluoro-4-(trimethylsilyl)phenyl)amino)-2-oxo-1-(tetrahydro-2H-pyran-4-yl)ethyl)-3-hydroxy-N-methyl-1,2-oxazole-5-carboxamide | 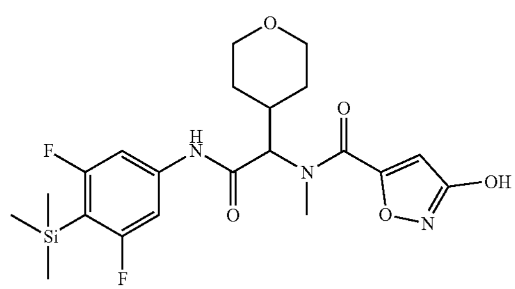 [SMILES: CN(C(=O)c1cc(O)no1)C(C(=O)Nc1cc(F)c([Si](C)(C)C)c(F)c1)C1CCOCC1] | | 466.0 (M − H) |
| 7 | (3S)-N-((1R)-2-((4-tert-butyl-3-fluorophenyl)amino)-1-(4,4-difluorocyclohexyl)-2-oxoethyl)-5-oxopyrrolidine-3-carboxamide | 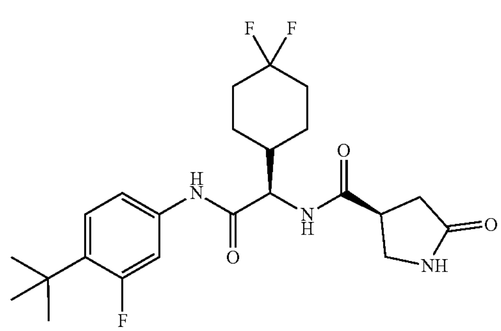 [SMILES: CC(C)(C)c1ccc(NC(=O)[C@H](NC(=O)[C@@H]2CNC(=O)C2)C2CCC(F)(F)CC2)cc1F] | | 452.1 (M − H) |

TABLE 1-1-continued

| Ex. No. | IUPAC NAME | Structure | Salt | MS (Found) |
|---|---|---|---|---|
| 8 | N-(2-((4-tert-butyl-3-fluorophenyl)amino)-1-(4,4-difluorocyclohexyl)-2-oxoethyl)-2-oxo-1,3-oxazolidine-5-carboxamide (mixture of two diastereomers) | 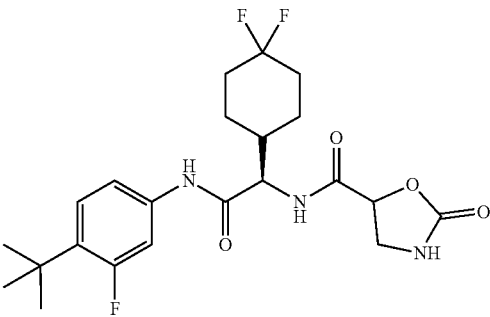 [SMILES: CC(C)(C)c1ccc(NC(=O)[C@H](NC(=O)C2CNC(=O)O2)C2CCC(F)(F)CC2)cc1F] | | 454.1 (M − H) |
| 9 | N-((1R)-2-((4-tert-butyl-3-chlorophenyl)amino)-2-oxo-1-(tetrahydro-2H-pyran-4-yl)ethyl)-3,3,3-trifluoropropanamide | 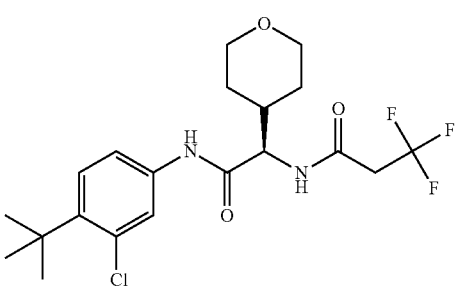 [SMILES: CC(C)(C)c1ccc(NC(=O)[C@H](NC(=O)CC(F)(F)F)C2CCOCC2)cc1Cl] | | 433.0 (M − H) |
| 10 | N-((1R)-2-((4-tert-butyl-3-chlorophenyl)amino)-2-oxo-1-(tetrahydro-2H-pyran-4-yl)ethyl)-3,3,3-trifluoro-2-hydroxypropanamide (single optical isomer) | 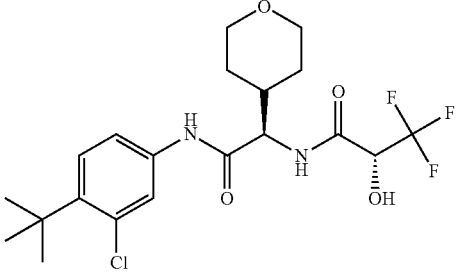 [SMILES: CC(C)(C)c1ccc(NC(=O)[C@H](NC(=O)[C@@H](O)C(F)(F)F)C2CCOCC2)cc1Cl] | | 448.9 (M − H) |

TABLE 1-2

| Ex. No | IUPAC NAME | Structure | Salt | MS (Found) |
|---|---|---|---|---|
| 11 | N-((1R)-2-((4-tert-butyl-3-chlorophenyl)amino)-2-oxo-1-(tetrahydro-2H-pyran-4-yl)ethyl)-3,3,3-trifluoro-2-hydroxypropanamide (single optical isomer) | 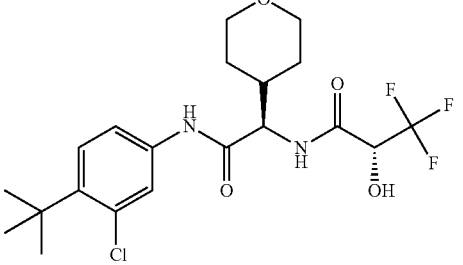 | | 448.9 (M − H) |

TABLE 1-2-continued

| Ex. No | IUPAC NAME | Structure | Salt | MS (Found) |
|---|---|---|---|---|
| 12 | 3-hydroxy-N-(1-(4-methoxyphenyl)-2-oxo-2-((4-(trimethylsilyl)phenyl)amino)ethyl)-N-methyl-1,2-oxazole-5-carboxamide | 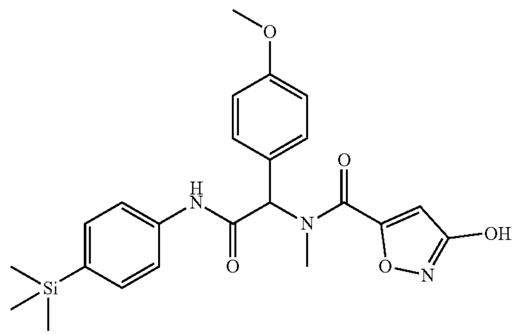 [SMILES: COc1ccc(C(C(=O)Nc2ccc([Si](C)(C)C)cc2)N(C)C(=O)c2cc(O)no2)cc1] | | 452.0 (M − H) |
| 13 | N-(1-(4-methoxyphenyl)-2-oxo-2-((4-(trimethylsilyl)phenyl)amino)ethyl)-5-oxopyrrolidine-3-carboxamide (mixture of four optical isomers) | 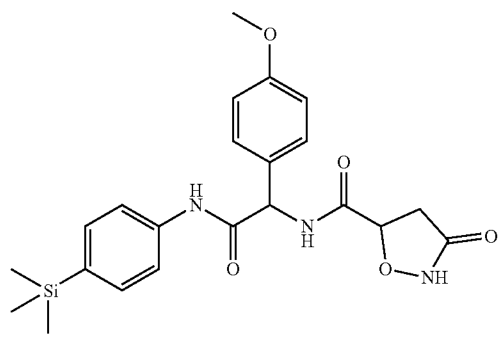 | | 438.2 (M − H) |
| 14 | 3-hydroxy-N-((1R)-1-(4-methoxyphenyl)-2-oxo-2-((4-(trimethylsilyl)phenyl)amino)ethyl)-N-methyl-1,2-oxazole-5-carboxamide | 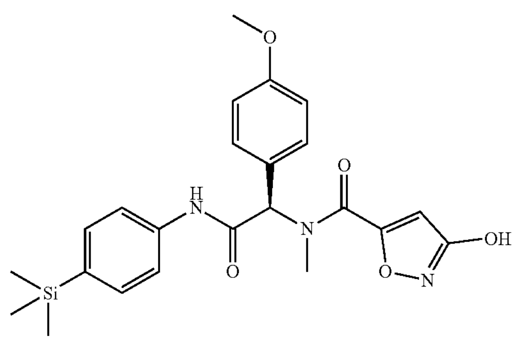 [SMILES: COc1ccc([C@H](C(=O)Nc2ccc([Si](C)(C)C)cc2)N(C)C(=O)c2cc(O)no2)cc1] | | 452.0 (M − H) |
| 15 | N-(2-((3-fluoro-4-(trimethylsilyl)phenyl)amino)-1-(4-methoxyphenyl)-2-oxoethyl)-3-hydroxy-N-methyl-1,2-oxazole-5-carboxamide | 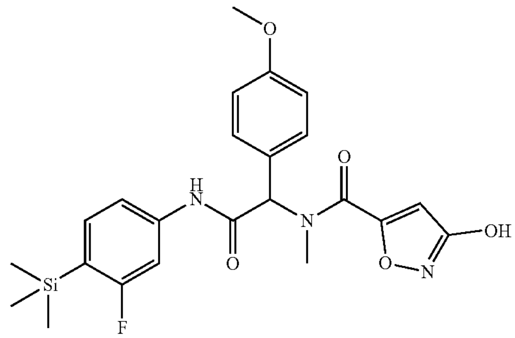 [SMILES: COc1ccc(C(C(=O)Nc2ccc([Si](C)(C)C)c(F)c2)N(C)C(=O)c2cc(O)no2)cc1] | | 470.0 (M − H) |

TABLE 1-2-continued

| Ex. No | IUPAC NAME | Structure | Salt | MS (Found) |
|---|---|---|---|---|
| 16 | 2-(4-methoxyphenyl)-2-(((6-oxo-1,6-dihydropyridin-3-yl)acetyl)amino)-N-(4-(trimethylsilyl)phenyl)acetamide | 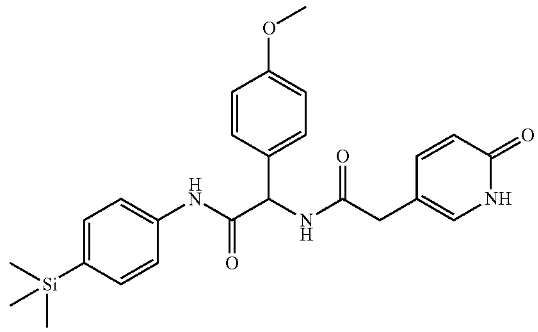 [SMILES: COc1ccc(C(NC(=O)Cc2ccc(=O)[nH]c2)C(=O)Nc2ccc([Si](C)(C)C)cc2)cc1] | | 464.2 (M + H) |
| 17 | N-(2-((3,5-difluoro-4-(trimethylsilyl)phenyl)amino)-1-(4-methoxyphenyl)-2-oxoethyl)-3-hydroxy-N-methyl-1,2-oxazole-5-carboxamide | 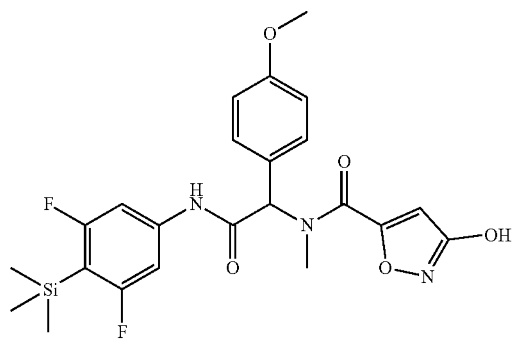 [SMILES: COc1ccc(C(C(=O)Nc2cc(F)c([Si](C)(C)C)c(F)c2)N(C)C(=O)c2cc(O)no2)cc1] | | 490.1 (M + H) |
| 18 | 2-(4-methoxyphenyl)-2-(((3-methyl-1,2-oxazol-5-yl)acetyl)amino)-N-(4-(trimethylsilyl)phenyl)acetamide | 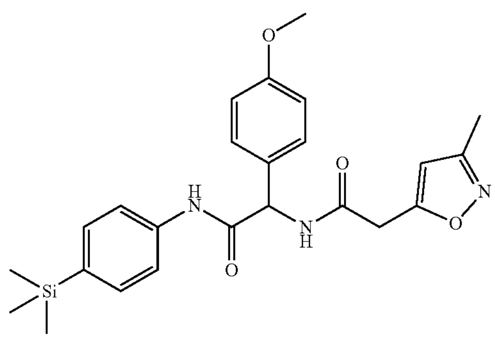 [SMILES: COc1ccc(C(NC(=O)Cc2cc(C)no2)C(=O)Nc2ccc([Si](C)(C)C)cc2)cc1] | | 452.2 (M + H) |
| 19 | 2-(4-methoxyphenyl)-2-(((1-methyl-1H-pyrazol-3-yl)acetyl)amino)-N-(4-(trimethylsilyl)phenyl)acetamide | 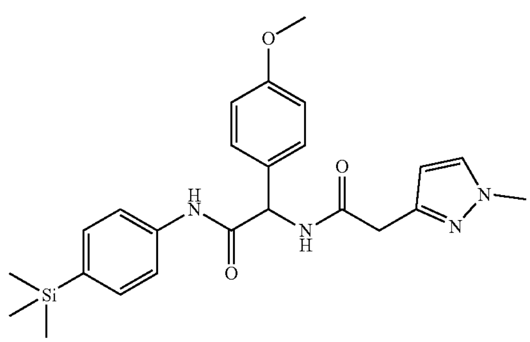 | | 451.1 (M + H) |

TABLE 1-2-continued

| Ex. No | IUPAC NAME | Structure | Salt | MS (Found) |
|---|---|---|---|---|
| 20 | 2-(4-methoxyphenyl)-2-(((1-methyl-1H-pyrazol-4-yl)acetyl)amino)-N-(4-(trimethylsilyl)phenyl)acetamide | 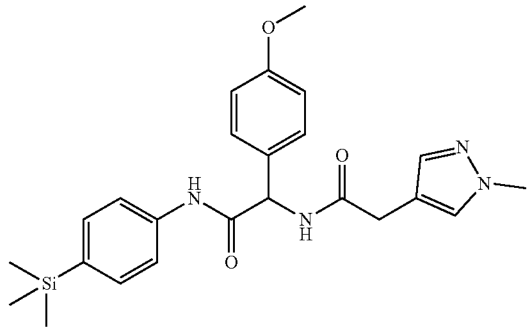 | | 451.1 (M + H) |

TABLE 1-3

| Ex. No. | IUPAC NAME | Structure | Salt | MS (Found) |
|---|---|---|---|---|
| 21 | N-(2-((2,5-diflouro-4-(trimethylsilyl)phenyl)amino)-1-(4-methoxyphenyl)-2-oxoethyl)-3-hydroxy-N-methyl-1,2-oxazole-5-carboxamide | 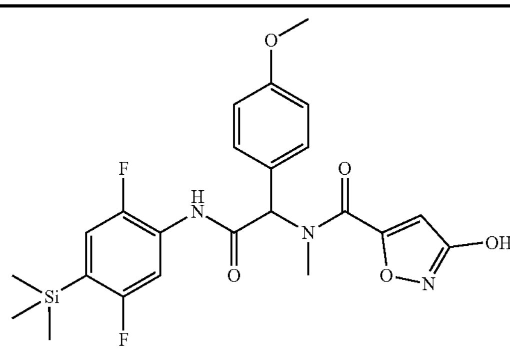 | | 488.0 (M − H) |
| 22 | 2-(4-(methoxymethyl)phenyl)-2-(((1-methyl-1H-pyrazol-4-yl)acetyl)amino)-N-(4-(trimethylsilyl)phenyl)acetamide | 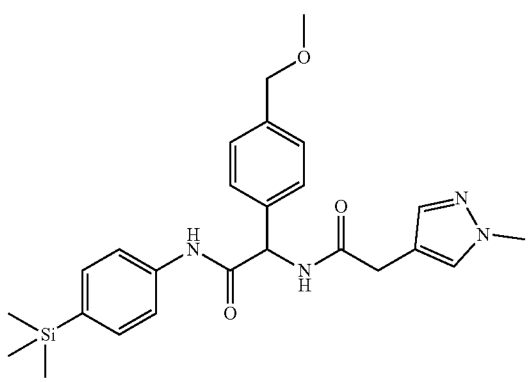 | | 465.1 (M + H) |
| 23 | N-((1R)-2-((3,5-difluoro-4-(trimethylsilyl)phenyl)amino)-1-(4-methoxyphenyl)-2-oxoethyl)-3-hydroxy-N-methyl-1,2-oxazole-5-carboxamide | 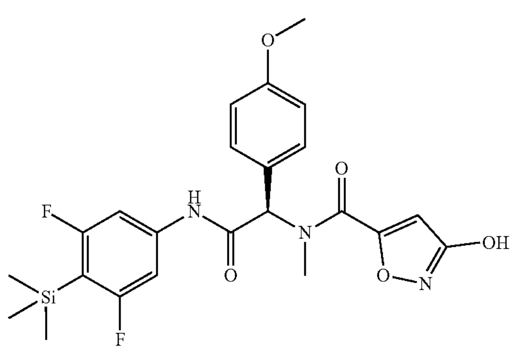 [SMILES: COc1ccc([C@H](C(=O)Nc2cc(F)c([Si](C)(C)C)c(F)c2)N(C)C(=O)c2cc(O)no2)cc1] | | 488.0 (M − H) |

TABLE 1-3-continued

| Ex. No. | IUPAC NAME | Structure | Salt | MS (Found) |
|---|---|---|---|---|
| 24 | N-((1R)-2-((3-fluoro-4-(trimethylsilyl)phenyl)amino)-1-(4-methoxyphenyl)-2-oxoethyl)-3-hydroxy-N-methyl-1,2-oxazole-5-carboxamide | 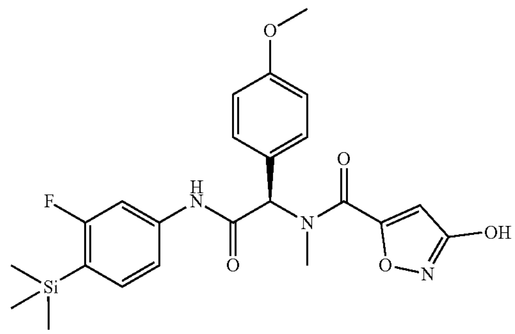 [SMILES: COc1ccc([C@H](C(=O)Nc2ccc([Si](C)(C)C)c(F)c2)N(C)C(=O)c2cc(O)no2)cc1] | | 470.0 (M − H) |
| 25 | N-((1R)-2-((2,5-difluoro-4-(trimethylsilyl)phenyl)amino)-1-(4-methoxyphenyl)-2-oxoethyl)-3-hydroxy-N-methyl-1,2-oxazole-5-carboxamide | 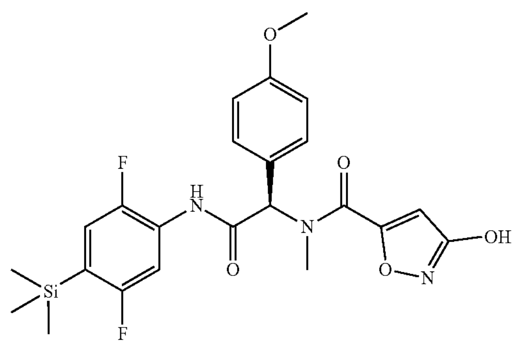 [SMILES: COc1ccc([C@H](C(=O)Nc2cc(F)c([Si](C)(C)C)cc2F)N(C)C(=O)c2cc(O)no2)cc1] | | 488.0 (M − H) |
| 26 | N-(2-((3-cyano-4-(trimethylsilyl)phenyl)amino)-1-(4-(methoxymethyl)phenyl)-2-oxoethyl)-5-oxopyrrolidine-3-carboxamide (mixture of four optical isomers) | 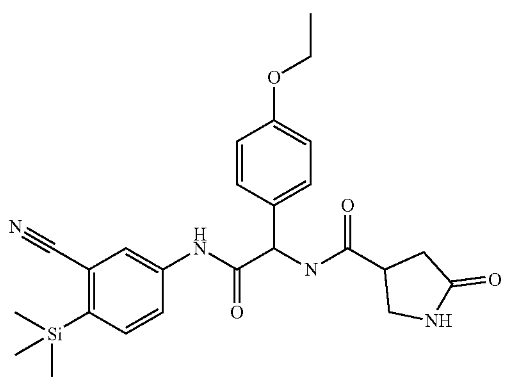 [SMILES: CCOc1ccc(C(NC(=O)C2CNC(=O)C2)C(=O)Nc2ccc([Si](C)(C)C)c(C#N)c2)cc1] | | 479.2 (M + H) |
| 27 | N-(2-((3-cyano-4-(trimethylsilyl)phenyl)amino)-1-(4-methoxyphenyl)-2-oxoethyl)-5-oxopyrrolidine-3-carboxamide (mixture of four optical isomers) | 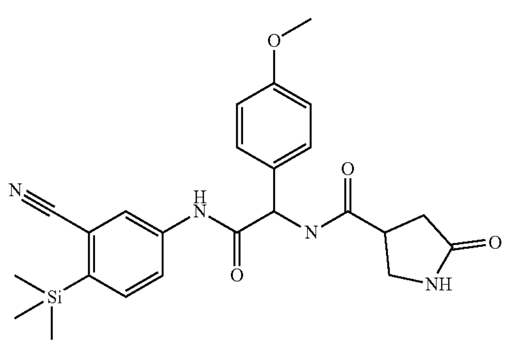 [SMILES: COc1ccc(C(NC(=O)C2CNC(=O)C2)C(=O)Nc2ccc([Si](C)(C)C)c(C#N)c2)cc1] | | 463.0 (M − H) |

TABLE 1-3-continued

| Ex. No. | IUPAC NAME | Structure | Salt | MS (Found) |
|---|---|---|---|---|
| 28 | N-(2-((3-fluoro-4-(trimethylsilyl)phenyl)amino)-1-(4-methoxyphenyl)-2-oxoethyl)-5-oxopyrrolidine-3-carboxamide (mixture of four optical isomers) | 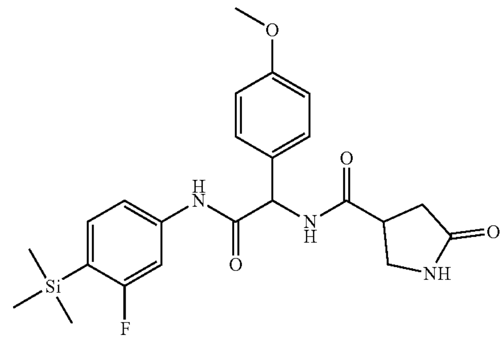 [SMILES: COc1ccc(C(NC(=O)C2CNC(=O)C2)C(=O)Nc2ccc([Si](C)(C)C)c(F)c2)cc1] | | 456.0 (M − H) |
| 29 | N-(2-((3-fluoro-4-(trimethylsilyl)phenyl)amino)-1-(4-methoxyphenyl)-2-oxoethyl)-3-hydroxypyrrolidine-1-carboxamide (mixture of four optical isomers) | 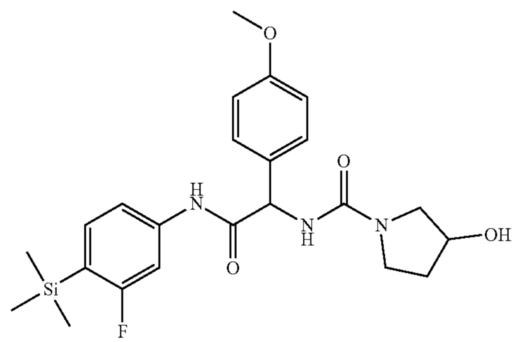 [SMILES: COc1ccc(C(NC(=O)N2CCC(O)C2)C(=O)Nc2ccc([Si](C)(C)C)c(F)c2)cc1] | | 460.3 (M + H) |
| 30 | N-(2-((3-fluoro-4-(trimethylsilyl)phenyl)amino)-1-(4-(methoxyphenyl)-2-oxoethyl)-3-hydroxyazetidine-1-carboxamide | 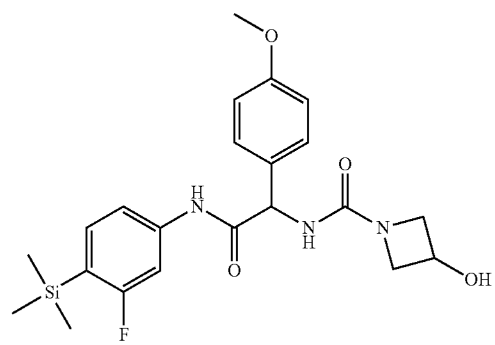 [SMILES: COc1ccc(C(NC(=O)N2CC(O)C2)C(=O)Nc2ccc([Si](C)(C)C)c(F)c2)cc1] | | 446.2 (M + H) |

TABLE 1-4

| Ex. No. | IUPAC NAME | Structure | Salt | MS (Found) |
|---|---|---|---|---|
| 31 | N-(2-((3-fluoro-4-(trimethylsilyl)phenyl)amino)-1-(4-(methoxymethyl)phenyl)-2-oxoethyl)-3-hydroxy-N-methyl-1,2-oxazole-5-carboxamide | 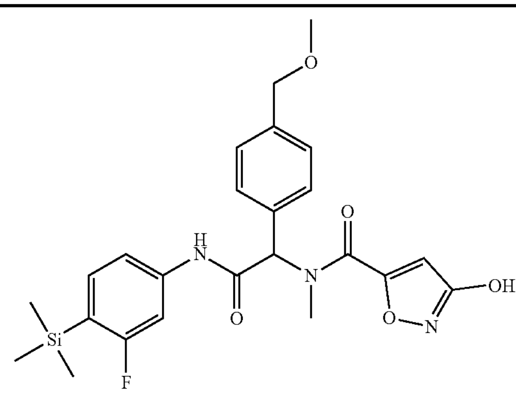 | | 484.1 (M − H) |

TABLE 1-4-continued

| Ex. No. | IUPAC NAME | Structure | Salt | MS (Found) |
|---|---|---|---|---|
| 32 | N-(2-((3-fluoro-4-(trimethylsilyl)phenyl)amino)-1-(4-(methoxymethyl)phenyl)-2-oxoethyl)-5-oxopyrrolidine-3-carboxamide (mixture of four optical isomers) | 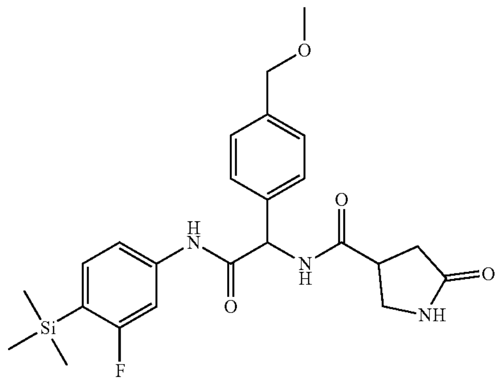 [SMILES: COCc1ccc(C(NC(=O)C2CNC(=O)C2)C(=O)Nc2ccc([Si](C)(C)C)c(F)c2)cc1] | | 470.2 (M − H) |
| 33 | N-(2-((3-fluoro-4-(trimethylsilyl)phenyl)amino)-1-(4-(methoxymethyl) phenyl)-2-oxoethyl)-3-hydroxypyrrolidine-1-carboxamide (mixture of four optical isomers) | 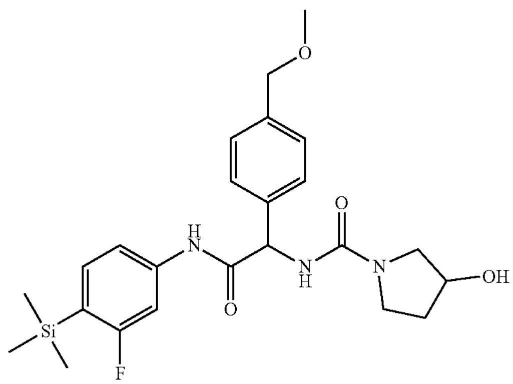 [SMILES: COCc1ccc(C(NC(=O)N2CCC(O)C2)C(=O)Nc2ccc([Si](C)(C)C)c(F)c2)cc1] | | 474.2 (M + H) |
| 34 | N-(2-((3-fluoro-4-(trimethylsilyl)phenyl)amino)-1-(4-(methoxymethyl) phenyl)-2-oxoethyl)-3-hydroxyazetidine-1-carboxamide | 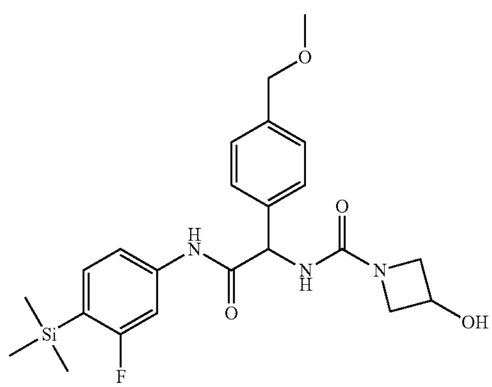 [SMILES: COCc1ccc(C(NC(=O)N2CC(O)C2)C(=O)Nc2ccc([Si](C)(C)C)c(F)c2)cc1] | | 460.3 (M + H) |
| 35 | N-(3-fluoro-4-(trimethylsilyl)phenyl)-2-(4-(methoxymethyl)phenyl)-2-(((5-methyl-1,3,4-oxadiazol-2-yl)acetyl)amino)acetamide | 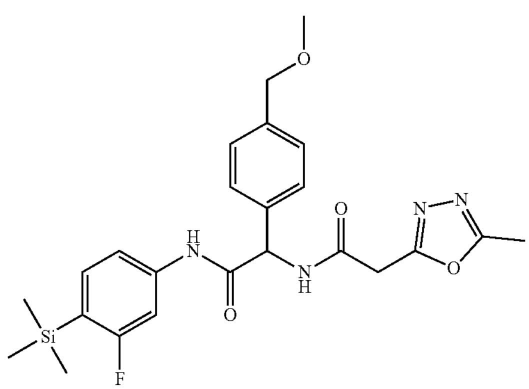 | | 485.2 (M + H) |

TABLE 1-4-continued

| Ex. No. | IUPAC NAME | Structure | Salt | MS (Found) |
|---|---|---|---|---|
| 36 | N-(3-fluoro-4-(trimethylsilyl)phenyl)-2-(4-(methoxymethyl)phenyl)-2-(((6-oxopyrimidin-1(6H)-yl)acetyl)amino)acetamide | 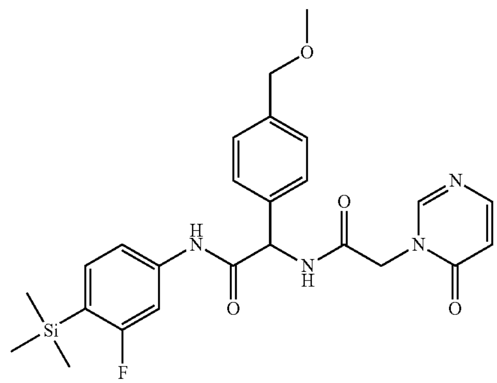 [SMILES: COCc1ccc(C(NC(=O)Cn2cnccc2=O)C(=O)Nc2ccc([Si](C)(C)C)c(F)c2)cc1] | | 497.2 (M + H) |
| 37 | N-(2-((3,5-difluoro-4-(trimethylsilyl)phenyl)amino)-1-(4-methoxyphenyl)-2-oxoethyl)-5-oxopyrrolidine-3-carboxamide | 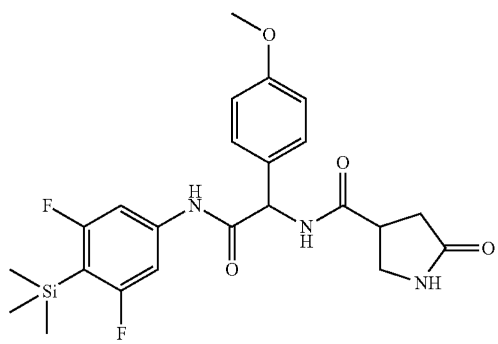 [SMILES: COc1ccc(C(NC(=O)C2CNC(=O)C2)C(=O)Nc2cc(F)c([Si](C)(C)C)c(F)c2)cc1] | | 474.1 (M − H) |
| 38 | N-(2-((3,5-difluoro-4-(trimethylsilyl)phenyl)amino)-1-(4-(methoxymethyl)phenyl)-2-oxoethyl)-3-hydroxy-N-methyl-1,2-oxazole-5-carboxamide | 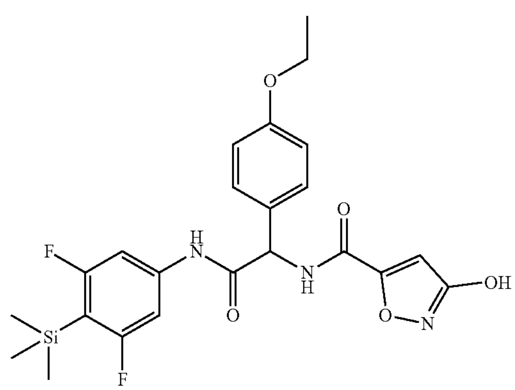 [SMILES: CCOc1ccc(C(NC(=O)c2cc(O)no2)C(=O)Nc2cc(F)c([Si](C)(C)C)c(F)c2)cc1] | | 502.1 (M − H) |
| 39 | N-(3,5-difluoro-4-(trimethylsilyl)phenyl)-2-(((3-hydroxy-1,2-oxazol-5-yl)acetyl)amino)-2-(4-(methoxymethyl)phenyl)acetamide | 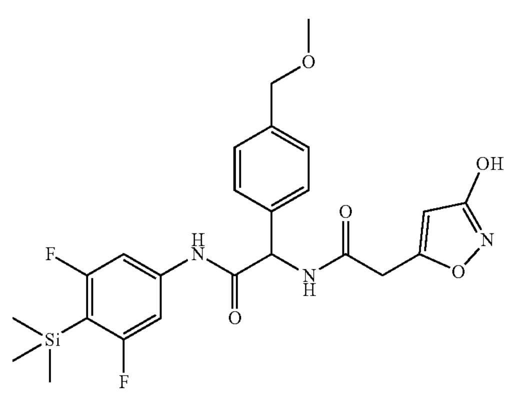 [SMILES: COCc1ccc(C(NC(=O)Cc2cc(O)no2)C(=O)Nc2cc(F)c([Si](C)(C)C)c(F)c2)cc1] | | 504.2 (M + H) |

TABLE 1-4-continued

| Ex. No. | IUPAC NAME | Structure | Salt | MS (Found) |
|---|---|---|---|---|
| 40 | N-(3,5-difluoro-4-(trimethylsilyl)phenyl)-2-(4-(methoxymethyl)phenyl)-2-(((6-oxopyrimidin-1(6H)-yl)acetyl)amino)acetamide | 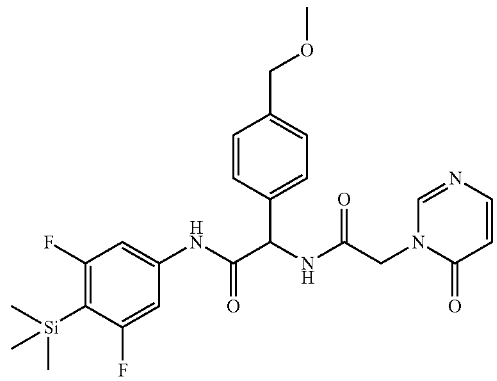 [SMILES: COCc1ccc(C(NC(=O)Cn2cnccc2=O)C(=O)Nc2cc(F)c([Si](C)(C)C)c(F)c2)cc1] | | 513.1 (M − H) |

TABLE 1-5

| Ex. No | IUPAC NAME | Structure | Salt | MS (Found) |
|---|---|---|---|---|
| 41 | N-(2-((3,5-difluoro-4-(trimethylsilyl)phenyl)amino)-1-(4-methoxyphenyl)-2-oxoethyl)-3-hydroxyazetidine-1-carboxamide | 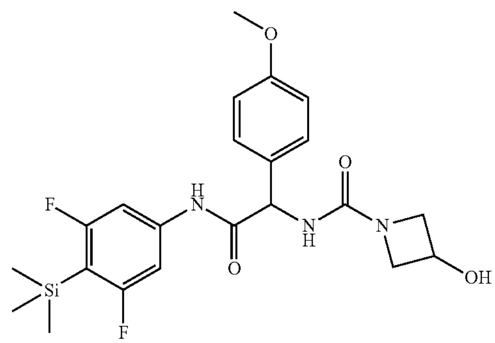 [SMILES: COc1ccc(C(NC(=O)N2CC(O)C2)C(=O)Nc2cc(F)c([Si](C)(C)C)c(F)c2)cc1] | | 464.1 (M + H) |
| 42 | N-(2-((2,5-difluoro-4-(trimethylsilyl)phenyl)amino)-1-(4-methoxyphenyl)-2-oxoethyl)-5-oxopyrrolidine-3-carboxamide (mixture of four optical isomers) | 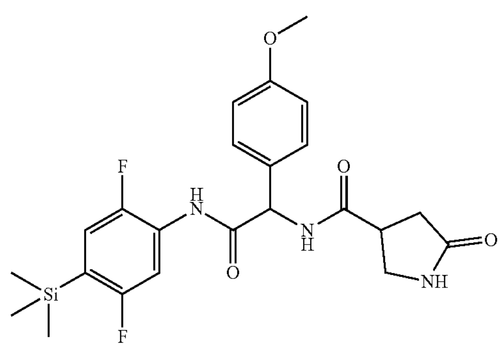 [SMILES: COc1ccc(C(NC(=O)C2CNC(=O)C2)C(=O)Nc2cc(F)c([Si](C)(C)C)cc2F)cc1] | | 474.1 (M − H) |
| 43 | N-(2-((2,5-difluoro-4-(trimethylsilyl)phenyl)amino)-1-(4-(methoxymethyl)phenyl)-2-oxoethyl)-3-hydroxy-N-methyl-1,2-oxazole-5-carboxamide | 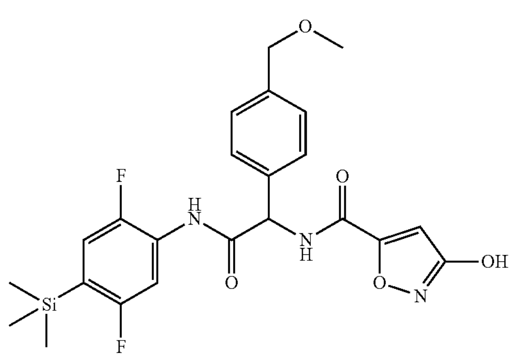 [SMILES: COCc1ccc(C(NC(=O)c2cc(O)no2)C(=O)Nc2cc(F)c([Si](C)(C)C)cc2F)cc1] | | 502.2 (M − H) |

TABLE 1-5-continued

| Ex. No | IUPAC NAME | Structure | Salt | MS (Found) |
|---|---|---|---|---|
| 44 | N-(2,5-difluoro-4-(trimethylsilyl)phenyl)-2-(4-(methoxymethyl)phenyl)-2-(((5-methyl-1,3,4-oxadiazol-2-yl)acetyl)amino)acetamide | 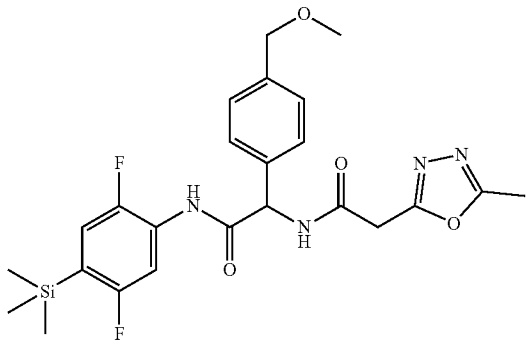 | | 503.2 (M + H) |
| 45 | N-(2,5-difluoro-4-(trimethylsilyl)phenyl)-2-(4-(methoxymethyl)phenyl)-2-(((6-oxopyrimidin-1(6H)-yl)acetyl)amino)acetamide | 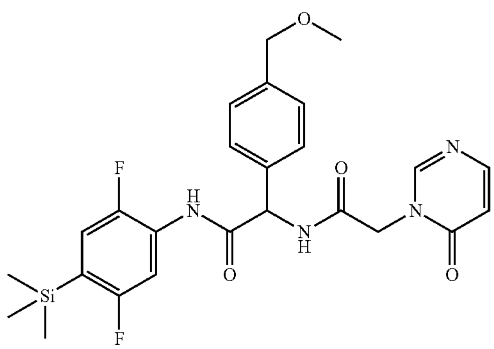 [SMILES: COCc1ccc(C(NC(=O)Cn2cnccc2=O)C(=O)Nc2cc(F)c([Si](C)(C)C)cc2F)cc1] | | 515.2 (M + H) |
| 46 | N-(2,5-difluoro-4-(trimethylsilyl)phenyl)-2-((1H-indazol-1-yl)acetyl)amino)-2-(4-methoxyphenyl)acetamide | 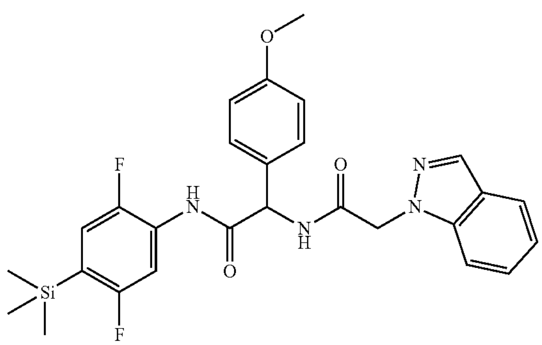 [SMILES: COc1ccc(C(NC(=O)Cn2ncc3ccccc32)C(=O)Nc2cc(F)c([Si](C)(C)C)cc2F)cc1] | | 523.2 (M + H) |
| 47 | N-(2,5-difluoro-4-(trimethylsilyl)phenyl)-2-((1H-indazol-1-yl)acetyl)amino)-2-(4-(methoxymethyl)phenyl)acetamide | 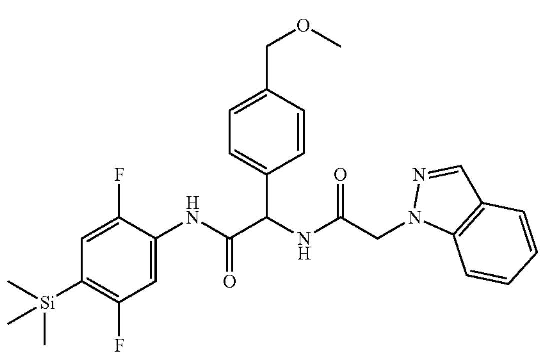 [SMILES: COCc1ccc(C(NC(=O)Cn2ncc3ccccc32)C(=O)Nc2cc(F)c([Si](C)(C)C)cc2F)cc1] | | 537.2 (M + H) |

TABLE 1-5-continued

| Ex. No | IUPAC NAME | Structure | Salt | MS (Found) |
|---|---|---|---|---|
| 48 | N-(2-((3-chloro-4-(trimethylsilyl)phenyl)amino)-1-(4-methoxyphenyl)-2-oxoethyl)-3-hydroxy-N-methyl-1,2-oxazole-5-carboxamide | 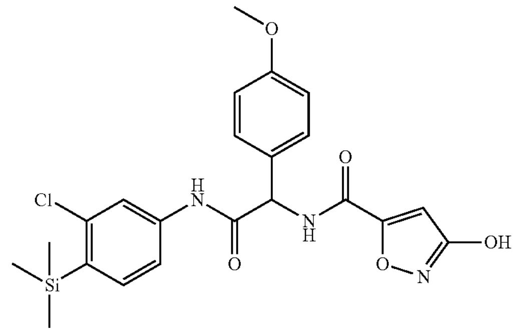 [SMILES: COc1ccc(C(NC(=O)c2cc(O)no2)C(=O)Nc2ccc([Si](C)(C)C)c(Cl)c2)cc1] | | 486.1 (M − H) |
| 49 | (3S)-N-(1R)-2-((3-fluoro-4-(trimethylsilyl)phenyl)amino)-1-(4-(methoxymethyl)phenyl)-2-oxoethyl)-5-oxopyrrolidine-3-carboxamide | 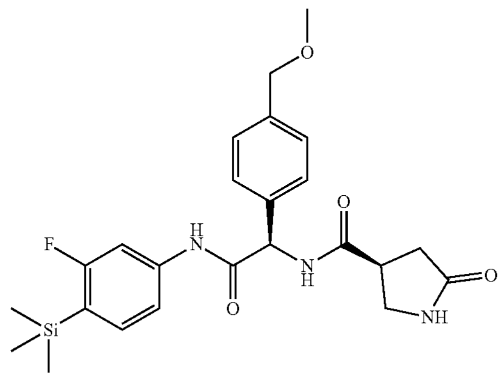 [SMILES: COCc1ccc([C@@H](NC(=O)[C@@H]2CNC(=O)C2)C(=O)Nc2ccc([Si](C)(C)C)c(F)c2)cc1] | | 470.2 (M − H) |
| 50 | (3S)-N-((1R)-2-((3-fluoro-4-(trimethylsilyl)phenyl)amino)-1-(4-methoxyphenyl)-2-oxoethyl)-5-oxopyrrolidine-3-carboxamnide | 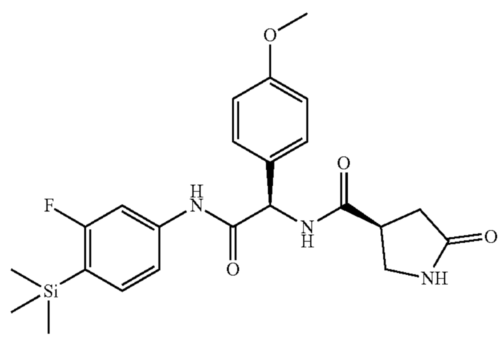 [SMILES: COc1ccc([C@@H](NC(=O)[C@@H]2CNC(=O)C2)C(=O)Nc2ccc([Si](C)(C)C)c(F)c2)cc1] | | 458.2 (M + H) |

TABLE 1-6

| Ex. No. | IUPAC NAME | Structure | Salt | MS (Found) |
|---|---|---|---|---|
| 51 | (3S)-N-((1R)-2-((2,5-difluoro-4-(trimethylsilyl)phenyl)amino)-1-(4-(methoxymethyl)phenyl)-2-oxoethyl)-5-oxopyrrolidine-3-carboxamide | 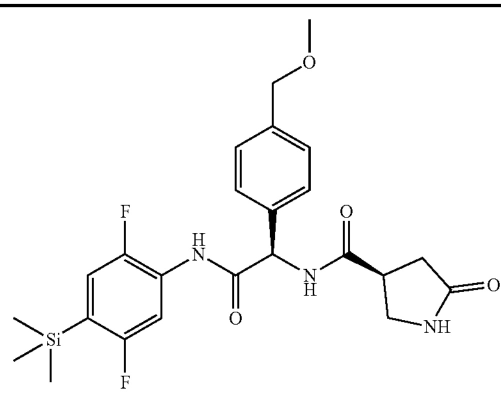 | | 490.2 (M + H) |

TABLE 1-6-continued

| Ex. No. | IUPAC NAME | Structure | Salt | MS (Found) |
|---|---|---|---|---|
| 52 | (3S)-N-((1R)-2-((3,5-difluoro-4-(trimethylsilyl)phenyl)amino)-1-(4-(methoxymethyl)phenyl)-2-oxoethyl)-5-oxopyrrolidine-3-carboxamide | 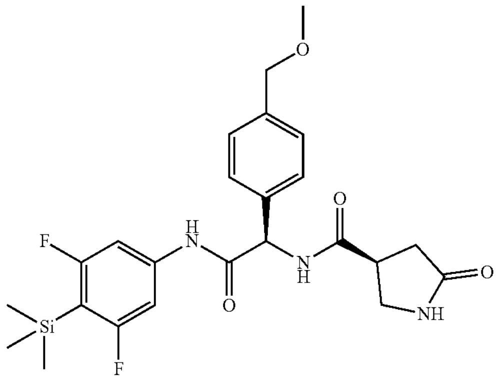 [SMILES: COCc1ccc([C@@H](NC(=O)[C@@H]2CNC(=O)C2)C(=O)Nc2cc(F)c([Si](C)(C)C)c(F)c2)cc1] | | 488.2 (M − H) |
| 53 | (2R)-N-(3-fluoro-4-(trimethylsilyl)phenyl)-2-(4-(methoxymethyl)phenyl)-2-(((6-oxopyrimidin-1(6H)-yl)acetyl)amino)acetamide | 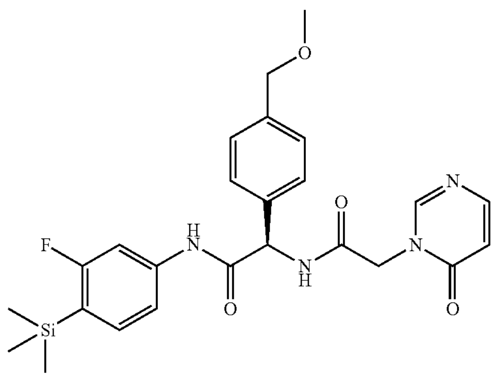 [SMILES: COCc1ccc([C@@H](NC(=O)Cn2cnccc2=O)C(=O)Nc2ccc([Si](C)(C)C)c(F)c2)cc1] | | 497.2 (M + H) |
| 54 | (3R)-N-((1R)-2-((3-fluoro-4-(trimethylsilyl)phenyl)amino)-1-(4-(methoxymethyl)phenyl)-2-oxoethyl)-5-oxopyrrolidine-3-carboxamide | 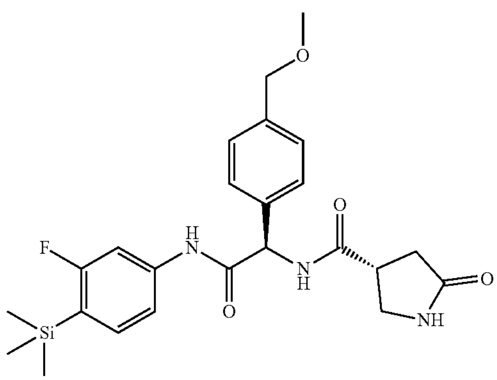 [SMILES: COCc1ccc([C@@H](NC(=O)[C@H]2CNC(=O)C2)C(=O)Nc2ccc([Si](C)(C)C)c(F)c2)cc1] | | 470.1 (M − H) |
| 55 | (3R)-N-((1R)-2-((2,5-difluoro-4-(trimethylsilyl)phenyl)amino)-1-(4-((methoxymethyl)phenyl)-2-oxoethyl)-5-oxopyrrolidine-3-carboxamide | 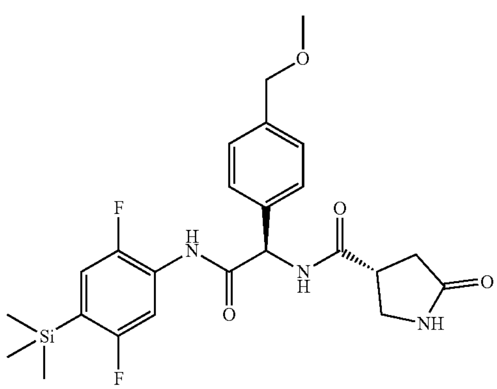 [SMILES: COCc1ccc([C@@H](NC(=O)[C@H]2CNC(=O)C2)C(=O)Nc2cc(F)c([Si](C)(C)C)cc2F)cc1] | | 488.1 (M − H) |

TABLE 1-6-continued

| Ex. No. | IUPAC NAME | Structure | Salt | MS (Found) |
|---|---|---|---|---|
| 56 | (2R)-N-(2,5-difluoro-4-(trimethylsilyl)phenyl)-2-(4-(methoxymethyl)phenyl)-2-(((5-methyl-1,3,4-oxadiazoi-2-yl)acetyl)amino)acetamide | 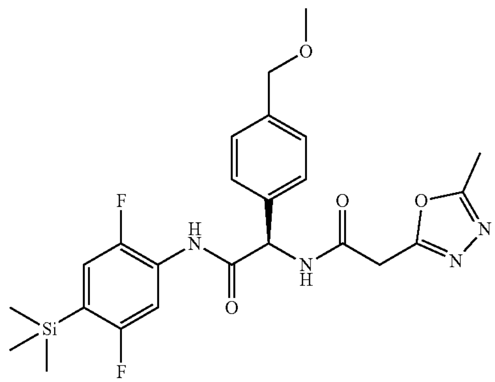 [SMILES: COCc1ccc([C@@H](NC(=O)Cc2nnc(C)o2)C(=O)Nc2cc(F)c([Si](C)(C)C)cc2F)cc1] | | 503.2 (M + H) |
| 57 | (2R)-N-(2,5-difluoro-4-(trimethylsilyl)phenyl)-2-(4-(methoxymethyl)phenyl)-2-(((6-oxopyrimidin-1(6H)-yl)acetyl)amino)acetamide | 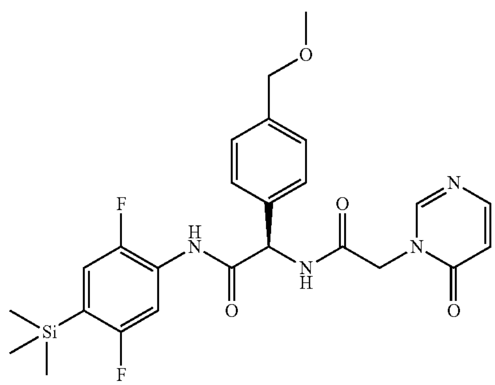 [SMILES: COCc1ccc([C@@H](NC(=O)Cn2cnccc2=O)C(=O)Nc2cc(F)c([Si](C)(C)C)cc2F)cc1] | | 515.2 (M + H) |
| 58 | (2R)-N-(3,5-difluoro-4-(trimethylsilyl)phenyl)-2-(4-(methoxymethyl)phenyl)-2-(((6-oxopyrimidin-1(6H)-yl)acetyl)amino)acetamide | 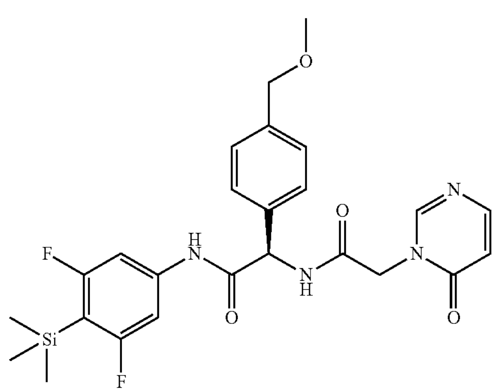 [SMILES: COCc1ccc([C@@H](NC(=O)Cn2cnccc2=O)C(=O)Nc2cc(F)c([Si](C)(C)C)c(F)c2)cc1] | | 513.1 (M − H) |
| 59 | ((2R)-2-(((2,4-dioxo-3,4-dihydropyrimidin-1(2H)-yl)acetyl)amino)-N-(3-fluoro-4-(trimethylsilyl)phenyl)-2-(4-(methoxymethyl)phenyl)acetamide | 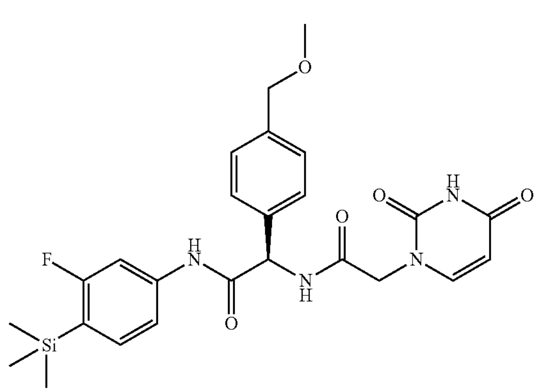 [SMILES: COCc1ccc([C@@H](NC(=O)Cn2ccc(=O)[nH]c2=O)C(=O)Nc2ccc([Si](C)(C)C)c(F)c2)cc1] | | 513.1 (M + H) |

TABLE 1-6-continued

| Ex. No. | IUPAC NAME | Structure | Salt | MS (Found) |
|---|---|---|---|---|
| 60 | (2R)-2-(((2,6-dioxo-3,6-dihydropyrimidin-1(2H)-yl)acetyl)amino)-N-(3-fluoro-4-(trimethylsilyl)phenyl)-2-(4-(methoxymethyl)phenyl)acetamide | 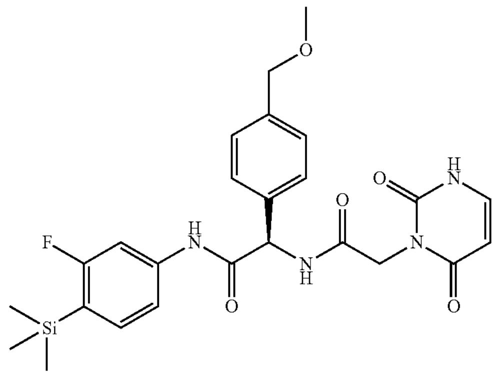 [SMILES: COCc1ccc([C@@H](NC(=O)Cn2c(=O)cc[nH]c2=O)C(=O)Nc2ccc([Si](C)(C)C)c(F)c2)cc1] | | 513.1 (M + H) |

TABLE 1-7

| Ex. No. | IUPAC NAME | Structure | Salt | MS (Found) |
|---|---|---|---|---|
| 61 | (2R)-N-(3,5-difluoro-4-(trimethylsilyl)phenyl)-2-(4-(methoxymethyl)phenyl)-2-(((3-methyl-6-oxopyridazin-1(6H)-yl)acetyl)amino)acetamide | 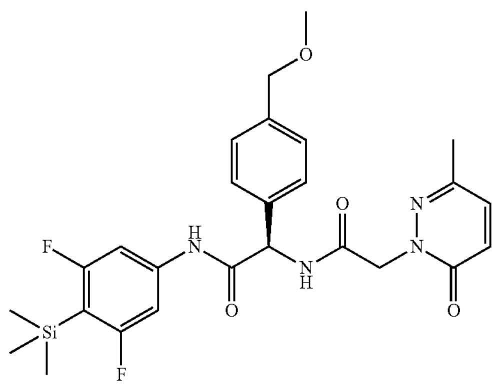 [SMILES: COCc1ccc([C@@H](NC(=O)Cn2nc(C)ccc2=O)C(=O)Nc2cc(F)c([Si](C)(C)C)c(F)c2)cc1] | | 529.2 (M + H) |
| 62 | (2R)-2-(((2,5-dioxoimidazolidin-1-yl)acetyl)amino)-N-(3-fluoro-4-(trimethylsilyl)phenyl)-2-(4-(methoxymethyl)phenyl)acetamide | 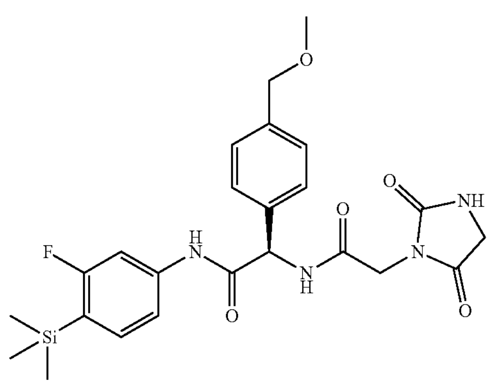 [SMILES: COCc1ccc([C@@H](NC(=O)CN2C(=O)CNC2=O)C(=O)Nc2ccc([Si](C)(C)C)c(F)c2)cc1] | | 501.2 (M + H) |

TABLE 1-7-continued

| Ex. No. | IUPAC NAME | Structure | Salt | MS (Found) |
|---|---|---|---|---|
| 63 | (2R)-N-(3-fluoro-4-(trimethylsilyl)phenyl)-2-(4-(methoxymethyl)phenyl)-2-(((4-oxopyridazin-1(4H)-yl)acetyl)amino)acetamide | 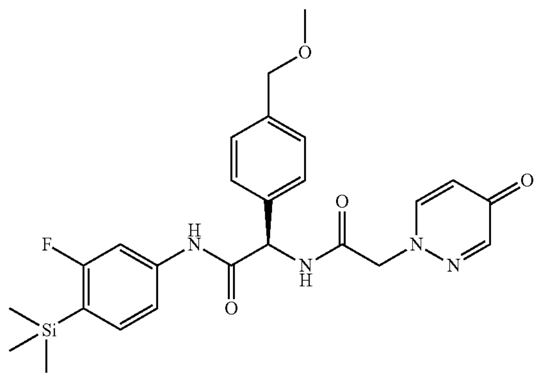 [SMILES: COCc1ccc([C@@H](NC(=O)Cn2ccc(=O)cn2)C(=O)Nc2ccc([Si](C)(C)C)c(F)c2)cc1] | | 495.1 (M − H) |
| 64 | ((3S)-N-(1R)-2-(3-fluoro-4-(trimethylsilyl)phenyl)amino)-1-(4-methoxyphenyl)-2-oxoethyl)-3-hydroxypyrrolidine-1-carboxamide | 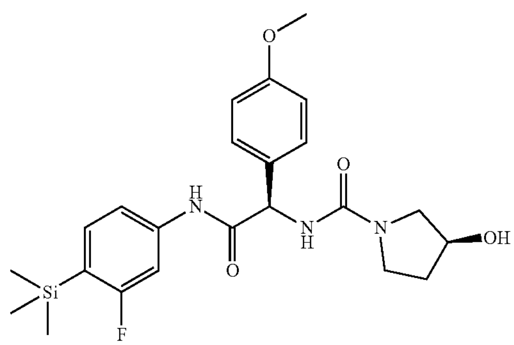 [SMILES: COc1ccc([C@@H](NC(=O)N2CC[C@H](O)C2)C(=O)Nc2ccc([Si](C)(C)C)c(F)c2)cc1] | | 460.3 (M + H) |
| 65 | (3S)-N-((1R)-2-((3-fluoro-4-(trimethylsilyl)phenyl)amino)-1-(4-(methoxymethyl)phenyl)-2-oxoethyl)-3-hydroxypyrrolidine-1-carboxamide | 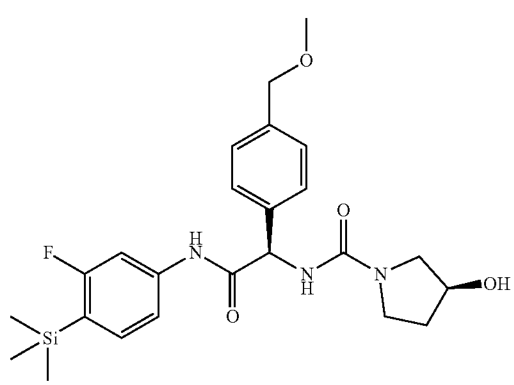 [SMILES: COCc1ccc([C@@H](NC(=O)N2CC[C@H](O)C2)C(=O)Nc2ccc([Si](C)(C)C)c(F)c2)cc1] | | 474.2 (M + H) |
| 66 | (3R)-N-((1R)-2-((3-fluoro-4-(trimethylsilyl)phenyl)amino)-1-(4-(methoxymethyl)phenyl)-2-oxoethyl)-3-hydroxypyrrolidine-1-carboxamide | 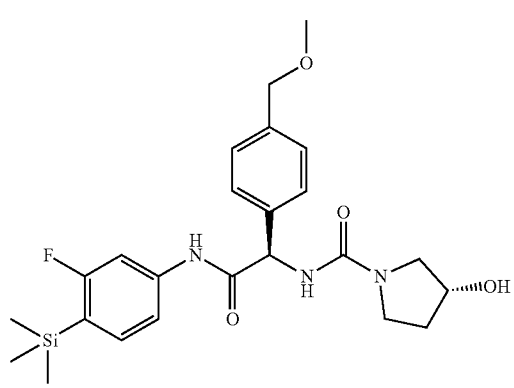 [SMILES: COCc1ccc([C@@H](NC(=O)N2CC[C@@H](O)C2)C(=O)Nc2ccc([Si](C)(C)C)c(F)c2)cc1] | | 474.2 (M + H) |

TABLE 1-7-continued

| Ex. No. | IUPAC NAME | Structure | Salt | MS (Found) |
|---|---|---|---|---|
| 67 | (2R)-N-(3-fluoro-4-(trimethylsilyl)phenyl)-2-(4-(methoxymethyl)phenyl)-2-(((5-methyl-1,3,4-oxadiazol-(2-yl)acetyl)amino)acetamide | 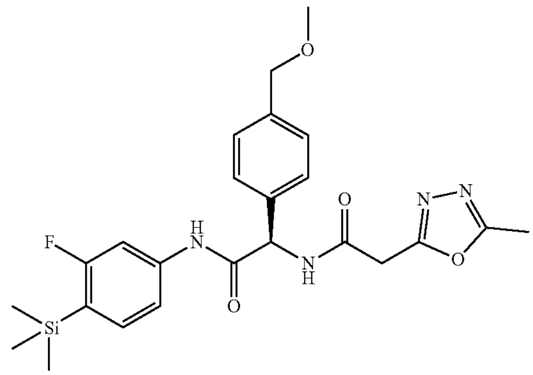 | | 483.2 (M − H) |
| 68 | (3R)-N-((1R)-2-((3,5-difluoro-4-(trimethylsilyl)phenyl)amino)-1-(4-(methoxymethyl)phenyl)-2-oxoethyl)-5-oxopyrrolidine-3-carboxamide | 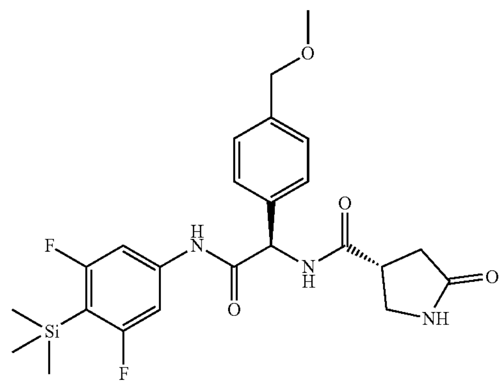 [SMILES: COCc1ccc([C@@H](NC(=O)[C@H]2CNC(=O)C2)C(=O)Nc2cc(F)c([Si](C)(C)C)c(F)c2)cc1] | | 488.2 (M − H) |
| 69 | N-((1R)-2-((3-fluoro-4-(trimethylsilyl)phenyl)amino)-1-(4-(methoxymethyl)phenyl)-2-oxoethyl)-3-hydroxyazetidine-1-carboxamide | 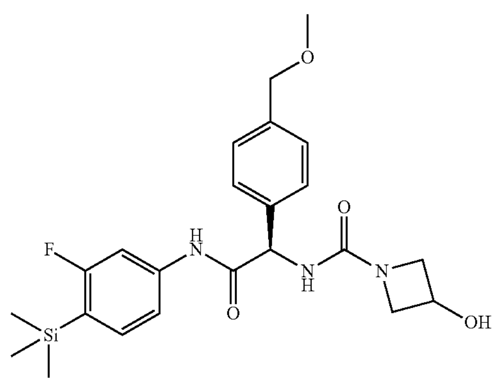 [SMILES: COCc1ccc([C@@H](NC(=O)N2CC(O)C2)C(=O)Nc2ccc([Si](C)(C)C)c(F)c2)cc1] | | 460.3 (M + H) |
| 70 | (3R)-N-((1R)-2-((3-fluoro-4-(trimethylsilyl)phenyl)amino)-1-(4-methoxyphenyl)-2-oxoethyl)-5-oxopyrrolidine-3-carboxamnide | 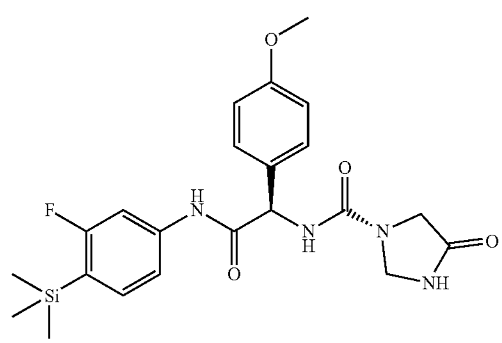 | | 458.2 (M + H) |

TABLE 1-8

| Ex. No. | IUPAC NAME | Structure | Salt | MS (Found) |
|---|---|---|---|---|
| 71 | (3R)-N-((1R)-2-((3-fluoro-4-(trimethylsilyl)phenyl)amino)-1-(4-methoxyphenyl)-2-oxoethyl)-3-hydroxypyrrolidine-1-carboxamide | 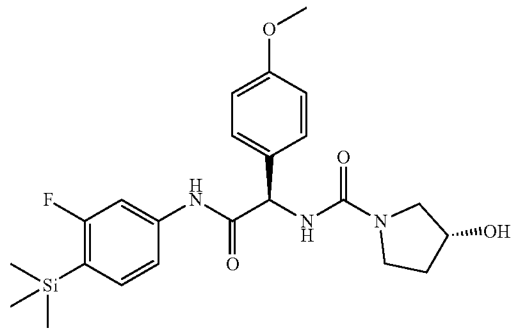 [SMILES: COc1ccc([C@@H](NC(=O)N2CC[C@@H](O)C2)C(=O)Nc2ccc([Si](C)(C)C)c(F)c2)cc1] | | 460.3 (M + H) |
| 72 | N-((1R)-2-((3,5-difluoro-4-(trimethylsilyl)phenyl)amino)-1-(4-(methoxymethyl)phenyl)-2-oxoethyl)-3-hydroxypropanamide | 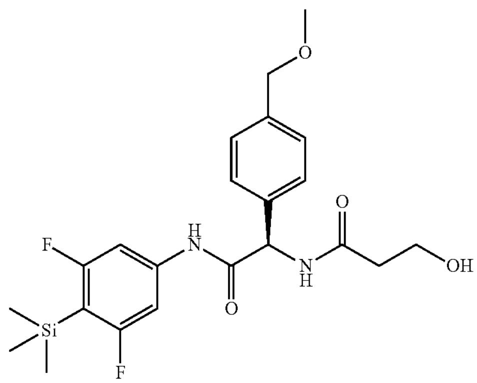 [SMILES: COCc1ccc([C@@H](NC(=O)CCO)C(=O)Nc2cc(F)c([Si](C)(C)C)c(F)c2)cc1] | | 451.2 (M + H) |
| 73 | 3-cyano-N-((1R)-2-((3,5-difluoro-4-(trimethylsilyl)phenyl)amino)-1-(4-(methoxymethyl)phenyl)-2-oxoethyl)propanamide | 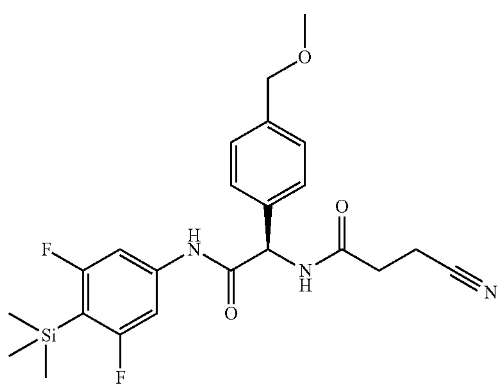 [SMILES: COCc1ccc([C@@H](NC(=O)CCC#N)C(=O)Nc2cc(F)c([Si](C)(C)C)c(F)c2)cc1] | | 458.1 (M − H) |
| 74 | (2R)-N-(3,5-difluoro-4-(trimethylsilyl)phenyl)-2-(4-(methoxymethyl)phenyl)-2-(((5-methyl-1,3,4-oxadiazol-2-yl)acetyl)amino)acetamide | 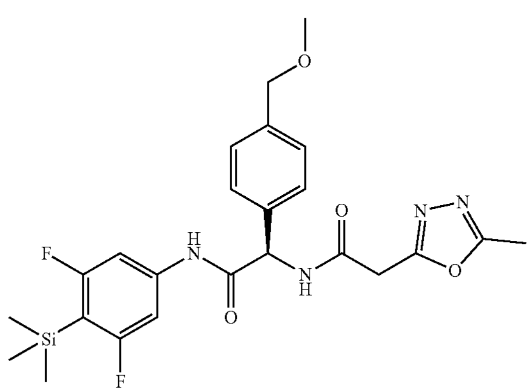 | | 501.2 (M − H) |

TABLE 1-8-continued

| Ex. No. | IUPAC NAME | Structure | Salt | MS (Found) |
|---|---|---|---|---|
| 75 | (2R)-N-(3-fluoro-4-(trimethylsilyl)phenyl)-2-(((3-hydroxy-1,2-oxazol-5-yl)acetyl)amino)-2-(4-(methoxymethyl)phenyl)acetamide | 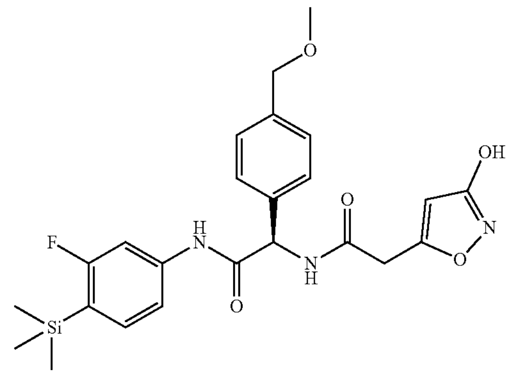 [SMILES: COCc1ccc([C@@H](NC(=O)Cc2cc(O)no2)C(=O)Nc2ccc([Si](C)(C)C)c(F)c2)cc1] | | 486.2 (M + H) |
| 76 | (2R)-N-(3,5-difluoro-4-(trimethylsilyl)phenyl)-2-(((3-(hydroxy-1,2-oxazol-5-yl)acetyl)amino)-2-(4-(methoxymethyl)phenyl)acetamide | 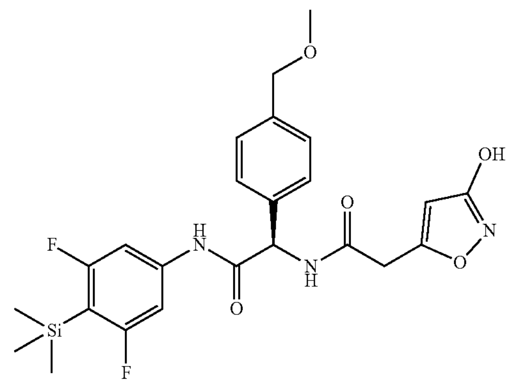 [SMILES: COCc1ccc([C@@H](NC(=O)Cc2cc(O)no2)C(=O)Nc2cc(F)c([Si](C)(C)C)c(F)c2)cc1] | | 502.1 (M − H) |
| 77 | N-((1R)-2-((3,5-difluoro-4-(trimethylsilyl)phenyl)amino)-1-(4-(methoxymethyl)phenyl)-2-oxoethyl)-3-hydroxy-N-methyl-1,2-oxazole-5-carboxamide | 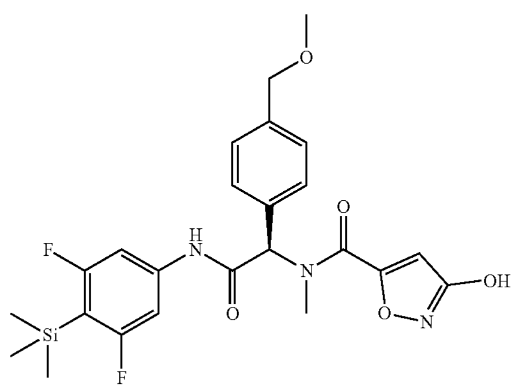 [SMILES: COCc1ccc([C@H](C(=O)Nc2cc(F)c([Si](C)(C)C)c(F)c2)N(C)C(=O)c2cc(O)no2)cc1] | | 502.1 (M − H) |
| 78 | (2R)-N-(3-fluoro-4-(trimethylsilyl)phenyl)-2-(4-(methoxymethyl)phenyl)-2-(((4-oxopyridin-1(4H)-yl)acetyl)amino)acetamide | 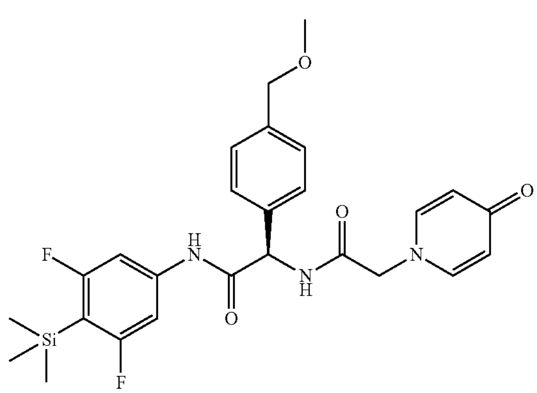 [SMILES: COCc1ccc([C@@H](NC(=O)Cn2ccc(=O)cc2)C(=O)Nc2cc(F)c([Si](C)(C)C)c(F)c2)cc1] | | 496.2 (M + H) |

TABLE 1-8-continued

| Ex. No. | IUPAC NAME | Structure | Salt | MS (Found) |
|---|---|---|---|---|
| 79 | N-((1R)-2-((3-fluoro-4-(trimethylsilyl)phenyl)amino)-1-(4-(methoxymethyl)phenyl)-2-oxoethyl)propanamide | 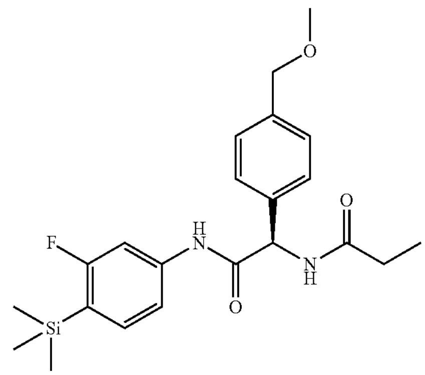 [SMILES: CCC(=O)N[C@@H](C(=O)Nc1ccc([Si](C)(C)C)c(F)c1)c1ccc(COC)cc1] | | 417.2 (M + H) |
| 80 | N-((1R)-2-((3-fluoro-4-(trimethylsilyl)phenyl)amino)-1-(4-(methoxymethyl)phenyl)-2-oxoethyl)-3-(methylsulfonyl)propanamide | 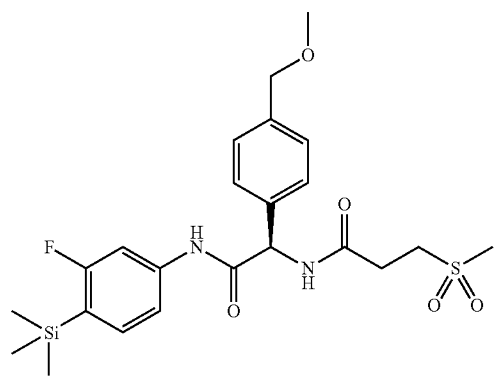 | | 495.2 (M + H) |

TABLE 1-9

| Ex. No | IUPAC NAME | Structure | Salt | MS (Found) |
|---|---|---|---|---|
| 81 | (2R)-N-(3-fluoro-4-(trimethylsilyl)phenyl)-2-(4-(methoxymethyl)phenyl)-2-(((methylsulfonyl)acetyl)amino)acetamide | 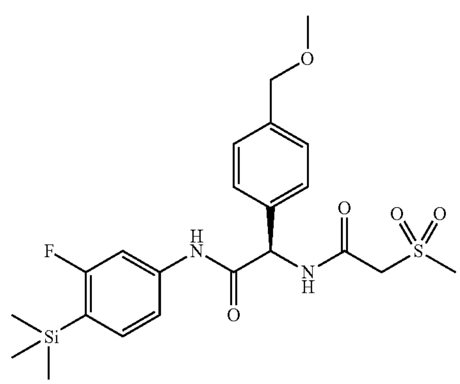 | | 481.2 (M + H) |

TABLE 1-9-continued

| Ex. No | IUPAC NAME | Structure | Salt | MS (Found) |
|---|---|---|---|---|
| 82 | N-((1R)-2-((3,5-difluoro-4-(trimethylsilyl)phenyl)amino)-1-(4-(methoxymethyl)phenyl)-2-oxoethyl)-3-hydroxy-1,2-oxazole-5-carboxamide | 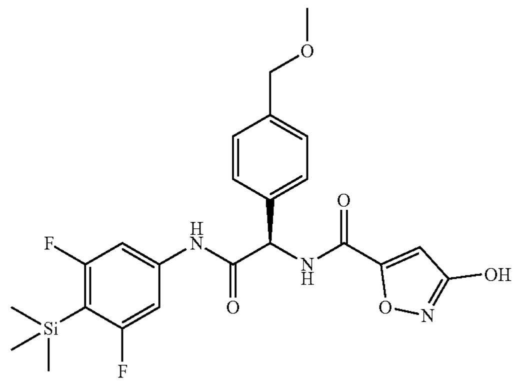 [SMILES: COCc1ccc([C@@H](NC(=O)c2cc(O)no2)C(=O)Nc2cc(F)c([Si](C)(C)C)c(F)c2)cc1] | | 490.1 (M + H) |
| 83 | N-((1R)-2-((3-fluoro-4-(trimethylsilyl)phenyl)amino)-1-(4-methoxyphenyl)-2-oxoethyl)-3-hydroxy-1,2-oxazole-5-carboxamide | 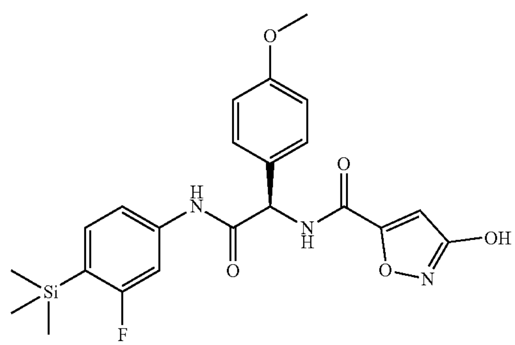 [SMILES: COc1ccc([C@@H](NC(=O)c2cc(O)no2)C(=O)Nc2ccc([Si](C)(C)C)c(F)c2)cc1] | | 458.1 (M + H) |
| 84 | 2,2-difluoro-N-((1R)-2-((3-fluoro-4-(trimethylsilyl)phenyl)amino)-1-(4-(methoxymethyl)phenyl)-2-oxoethyl)cyclopropanecarboxamide (mixture of two diastereomers) | 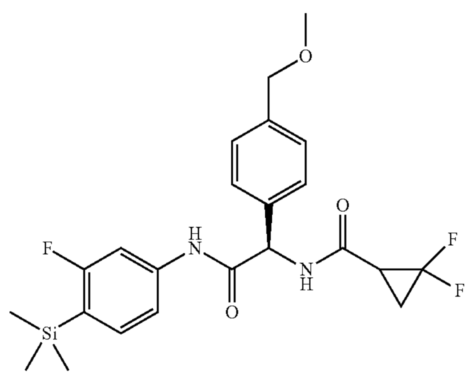 [SMILES: COCc1ccc([C@@H](NC(=O)C2CC2(F)F)C(=O)Nc2ccc([Si](C)(C)C)c(F)c2)cc1] | | 465.1 (M + H) |
| 85 | (2R)-N-(3-fluoro-4-(trimethylsilyl)phenyl)-2-(glycoloylamino)-2-(4-(methoxymethyl)phenyl)acetamide | 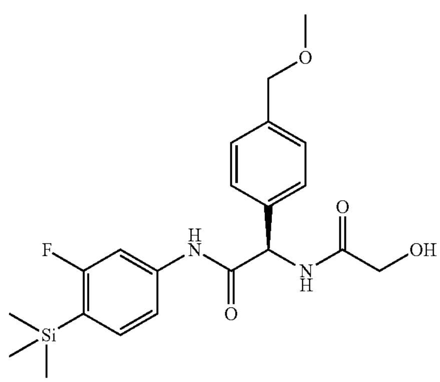 [SMILES: COCc1ccc([C@@H](NC(=O)CO)C(=O)Nc2ccc([Si](C)(C)C)c(F)c2)cc1] | | 419.1 (M + H) |

TABLE 1-9-continued

| Ex. No | IUPAC NAME | Structure | Salt | MS (Found) |
|---|---|---|---|---|
| 86 | N2-acetyl-N-((1R)-2-((3-fluoro-4-(trimethylsilyl)phenyl)amino)-1-(4-(methoxymethyl)phenyl)-2-oxoethyl)glycinamide | 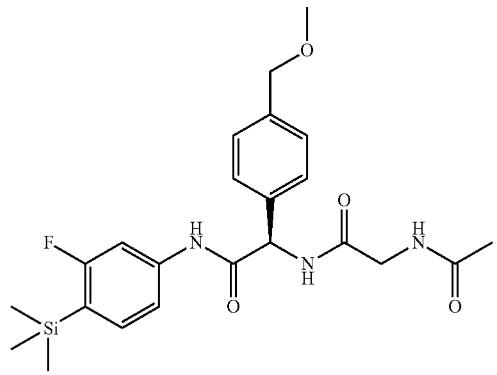 [SMILES: COCc1ccc([C@@H](NC(=O)CNC(C)=O)C(=O)Nc2ccc([Si](C)(C)C)c(F)c2)cc1] | | 460.3 (M + H) |
| 87 | 1-acetyl-N-((1R)-2-((3-fluoro-4-(trimethylsilyl)phenyl)amino)-1-(4-(methoxymethyl)phenyl)-2-oxoethyl)piperidine-4-carboxamide | 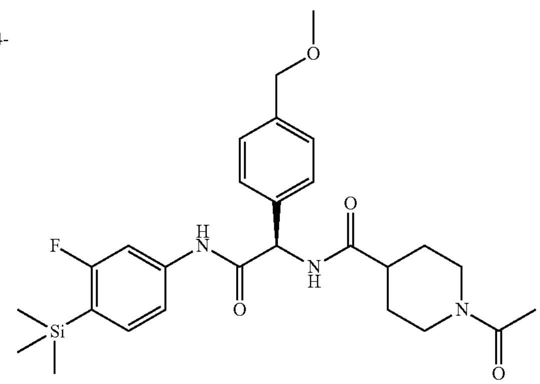 | | 512.2 (M − H) |
| 88 | N-((1R)-2-((3-fluoro-4-(trimethylsilyl)phenyl)amino)-1-(4-(methoxymethyl)phenyl)-2-oxoethyl)tetrahydro-2H-pyran-4-carboxamide | 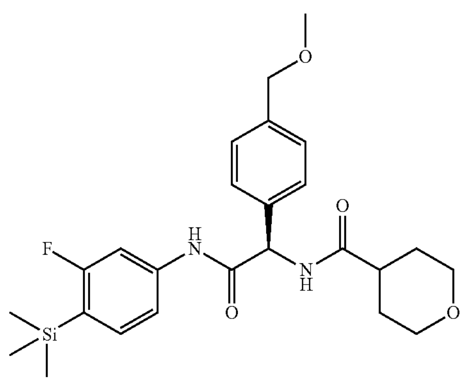 [SMILES: COCc1ccc([C@@H](NC(=O)C2CCOCC2)C(=O)Nc2ccc([Si](C)(C)C)c(F)c2)cc1] | | 473.2 (M + H) |
| 89 | (2R)-N-(3-fluoro-4-(trimethylsilyl)phenyl)-2-(4-(methoxymethyl)phenyl)-2-((tetrahydro-2H-pyran-4-yl)acetyl)amino)acetamide | 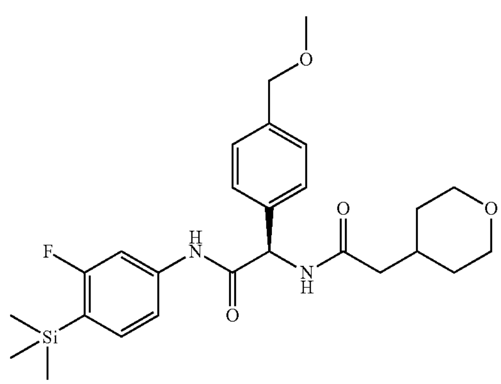 [SMILES: COCc1ccc([C@@H](NC(=O)CC2CCOCC2)C(=O)Nc2ccc([Si](C)(C)C)c(F)c2)cc1] | | 487.2 (M + H) |

TABLE 1-9-continued

| Ex. No | IUPAC NAME | Structure | Salt | MS (Found) |
|---|---|---|---|---|
| 90 | (2R)-2-((ethylcarbamoyl)amino)-N-(3-fluoro-4-(trimethylsilyl)phenyl)-2-(4-(methoxymethyl)phenyl)acetamide | 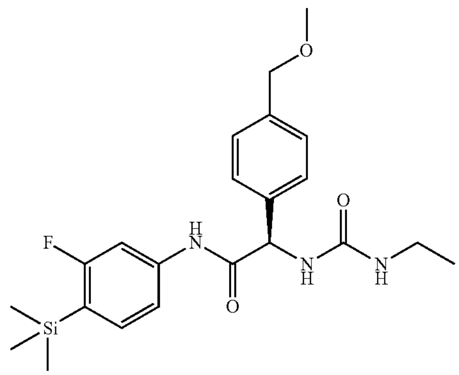 [SMILES: CCNC(=O)N[C@@H](C(=O)Nc1ccc([Si](C)(C)C)c(F)c1)c1ccc(COC)cc1] | | 432.1 (M + H) |

TABLE 1-10

| Ex. No | IUPAC NAME | Structure | Salt | MS (Found) |
|---|---|---|---|---|
| 91 | 3,3-difluoro-N-((1R)-2-((3-fluoro-4-(trimethylsilyl)phenyl)amino)-1-(4-(methoxymethyl)phenyl)-2-oxoethyl)cyclobutanecarboxamide | 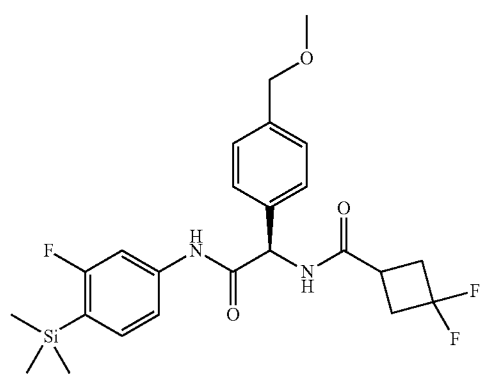 [SMILES: COCc1ccc([C@@H](NC(=O)C2CC(F)(F)C2)C(=O)Nc2ccc([Si](C)(C)C)c(F)c2)cc1] | | 479.2 (M + H) |
| 92 | 4,4-difluoro-N-((1R)-2-((3-fluoro-4-(trimethylsilyl)phenyl)amino)-1-(4-(methoxymethyl)phenyl)-2-oxoethyl)propanamide | 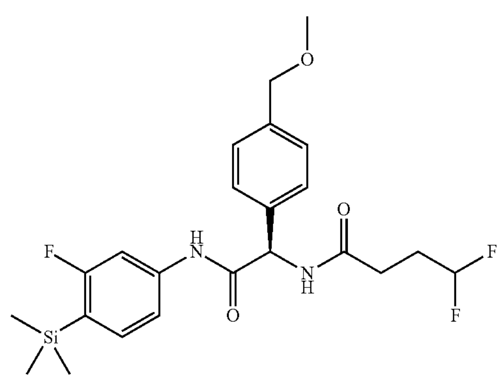 [SMILES: COCc1ccc([C@@H](NC(=O)CCC(F)F)C(=O)Nc2ccc([Si](C)(C)C)c(F)c2)cc1] | | 467.2 (M + H) |

TABLE 1-10-continued

| Ex. No | IUPAC NAME | Structure | Salt | MS (Found) |
|---|---|---|---|---|
| 93 | 3,3,3-trifluoro-N-((1R)-2-((3-fluoro-4-(trimethylsilyl)phenyl)amino)-1-(4-(methoxymethyl)phenyl)-2-oxoethyl)propanamide | 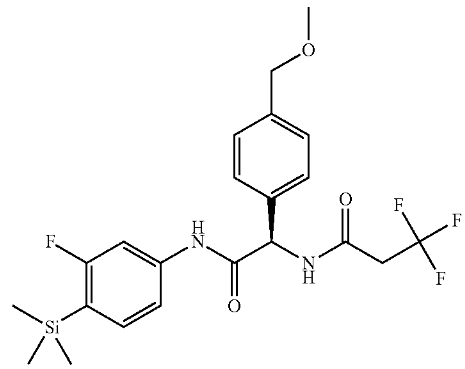 [SMILES: COCc1ccc([C@@H](NC(=O)CC(F)(F)F)C(=O)Nc2ccc([Si](C)(C)C)c(F)c2)cc1] | | 471.1 (M + H) |
| 94 | 4,4,4-trifluoro-N-((1R)-2-((3-fluoro-4-(trimethylsilyl)phenyl)amino)-1-(4-(methoxymethyl)phenyl)-2-oxoethyl)butanamide | 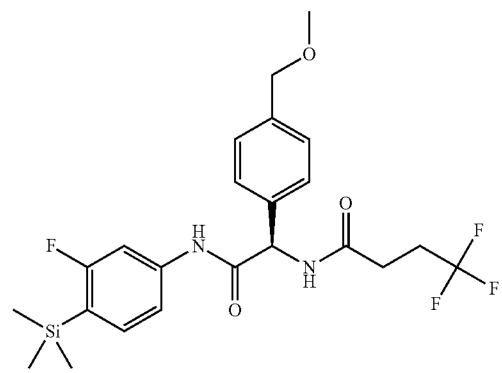 [SMILES: COCc1ccc([C@@H](NC(=O)CCC(F)(F)F)C(=O)Nc2ccc([Si](C)(C)C)c(F)c2)cc1] | | 485.2 (M + H) |
| 95 | (3R)-3-fluoro-N-((1R)-2-((3-fluoro-4-(trimethylsilyl)phenyl)amino)-1-(4-(methoxymethyl)phenyl)-2-oxoethyl)pyrrolidine-1-carboxamide | 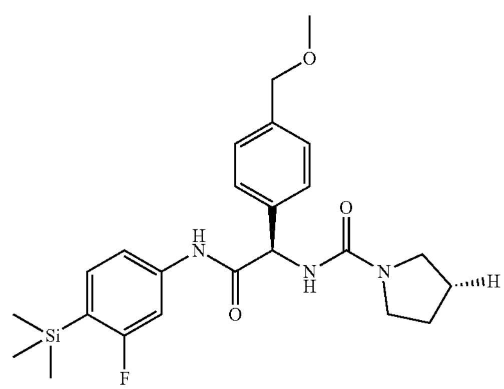 | | 476.2 (M + H) |
| 96 | (3S)-3-fluoro-N-((1R)-2-((3-fluoro-4-(trimethylsilyl)phenyl)amino)-1-(4-(methoxymethyl)phenyl)-2-oxoethyl)pyrrolidine-1-carboxamide | 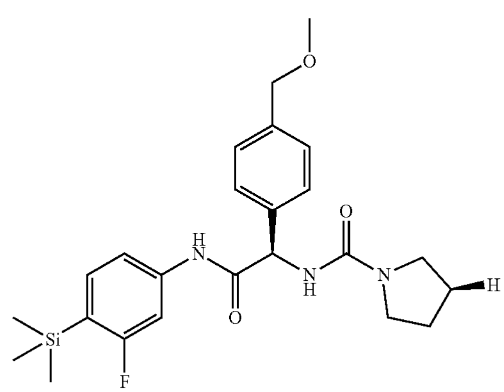 | | 476.3 (M + H) |

TABLE 1-10-continued

| Ex. No | IUPAC NAME | Structure | Salt | MS (Found) |
|---|---|---|---|---|
| 97 | (2R)-N-(3-fluoro-4-(trimethylsilyl)phenyl)-2-(4-(methoxymethyl)phenyl)-2-((morpholin-4-ylacetyl)amino)acetamide | 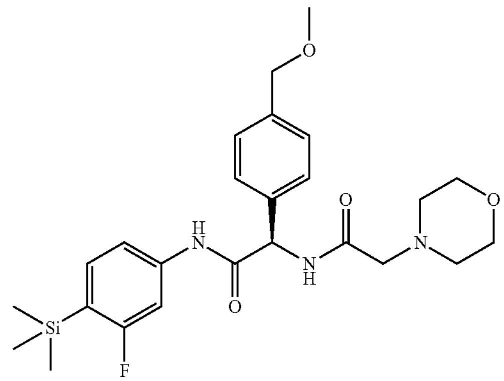 [SMILES: COCc1ccc([C@@H](NC(=O)CN2CCOCC2)C(=O)Nc2ccc([Si](C)(C)C)c(F)c2)cc1] | HCl | 488.2 (M − HCl + H) |
| 98 | N-((1R)-2-((2,5-difluoro-4-(trimethylsilyl)phenyl)amino)-1-(4-(methoxymethyl)phenyl)-2-oxoethyl)-3-hydroxy-1,2-oxazole-5-carboxamide | 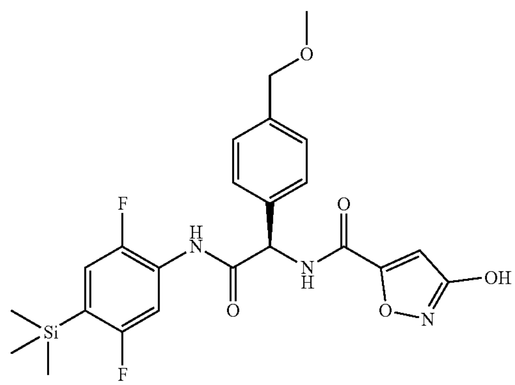 [SMILES: COCc1ccc([C@@H](NC(=O)c2cc(O)no2)C(=O)Nc2cc(F)c([Si](C)(C)C)cc2F)cc1] | | 490.1 (M + H) |
| 99 | N-(2-((3,5-difluoro-4-(trimethylsilyl)phenyl)amino)-1-(4-methoxyphenyl)-2-oxoethyl)-3-hydroxy-1,2-oxazole-5-carboxamide | 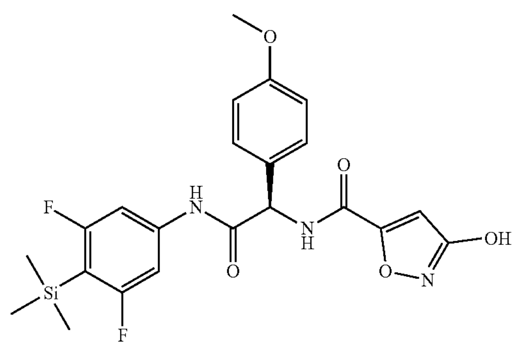 [SMILES: COc1ccc([C@@H](NC(=O)c2cc(O)no2)C(=O)Nc2cc(F)c([Si](C)(C)C)c(F)c2)cc1] | | 476.2 (M + H) |
| 100 | (2R)-N-(4-tert-butyl-3-fluorophenyl)-2-(4-(methoxymethyl)phenyl)-2-(((6-oxopyrimidin-1(6H)-yl)acetyl)amino)acetamide | 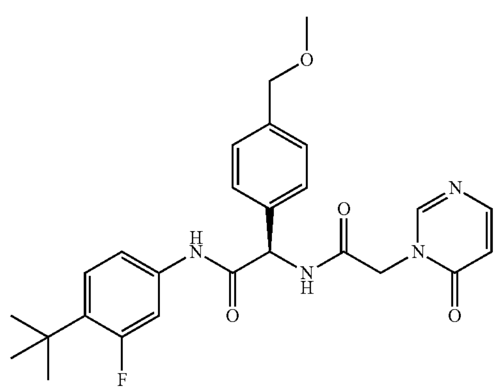 [SMILES: COCc1ccc([C@@H](NC(=O)Cn2cnccc2=O)C(=O)Nc2ccc(C(C)(C)C)c(F)c2)cc1] | | 481.2 (M + H) |

TABLE 1-11

| Ex. No. | IUPAC NAME | Structure | Salt | MS (Found) |
|---|---|---|---|---|
| 101 | (3S)-N-((1R)-2-((4-tert-butyl-3-fluorophenyl)amino)-1-(4-(methoxymethyl)phenyl)-2-oxoethyl)-5-oxopyrrolidine-3-carboxamide | 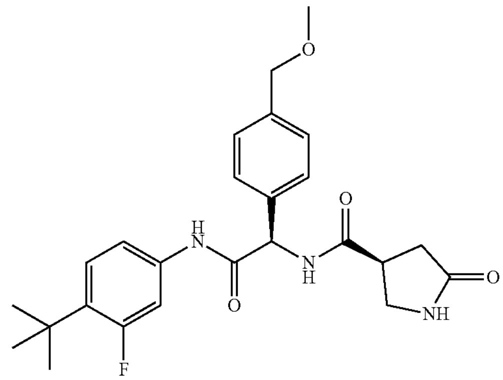 [SMILES: COCc1ccc([C@@H](NC(=O)[C@@H]2CNC(=O)C2)C(=O)Nc2ccc(C(C)(C)C)c(F)c2)cc1] | | 454.1 (M − H) |
| 102 | (3R)-N-((1R)-2-((4-tert-butyl-3-fluorophenyl)amino)-1-(4-(methoxymethyl)phenyl)-2-oxoethyl)-5-oxopyrrolidine-3-carboxamide | 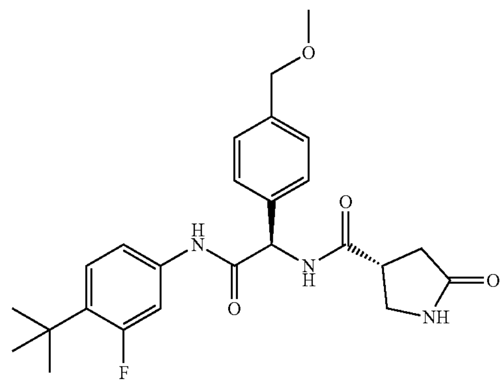 [SMILES: COCc1ccc([C@@H](NC(=O)[C@H]2CNC(=O)C2)C(=O)Nc2ccc(C(C)(C)C)c(F)c2)cc1] | | 454.1 (M − H) |
| 103 | 4-(((1R)-2-((3,5-difluoro-4-(trimethylsilyl)phenyl)amino)-1-(4-(methoxymethyl)phenyl)-2-oxoethyl)amino)-2,2-dimethyl-4-oxobutanoic acid | 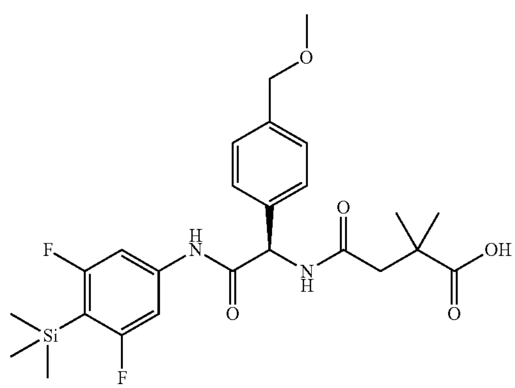 [SMILES: COCc1ccc([C@@H](NC(=O)CC(C)(C)C(=O)O)C(=O)Nc2cc(F)c([Si](C)(C)C)c(F)c2)cc1] | | 507.2 (M + H) |
| 104 | (3S)-N-(2-((4-tert-butyl-3-chlorophenyl)amino)-1-(4-(methoxymethyl)phenyl)-2-oxoethyl)-5-oxopyrrolidine-3-carboxamide | 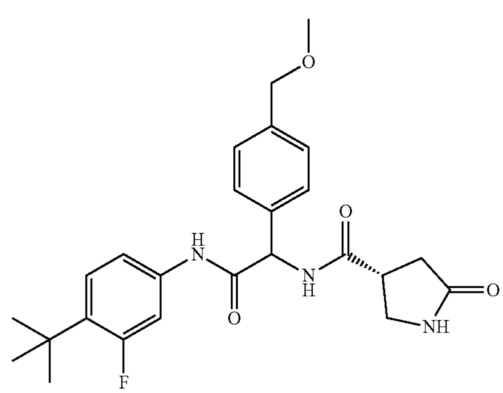 [SMILES: COCc1ccc(C(NC(=O)[C@H]2CNC(=O)C2)C(=O)Nc2ccc(C(C)(C)C)c(F)c2)cc1] | | 470.1 (M − H) |

TABLE 1-11-continued

| Ex. No. | IUPAC NAME | Structure | Salt | MS (Found) |
|---|---|---|---|---|
| 105 | (2R)-N-(4-tert-butyl-3-fluorophenyl)-2-(4-(methoxymethyl)phenyl)-2-(((5-methyl-1,3,4-oxadiazol-2-yl)acetyl)amino)acetamide | 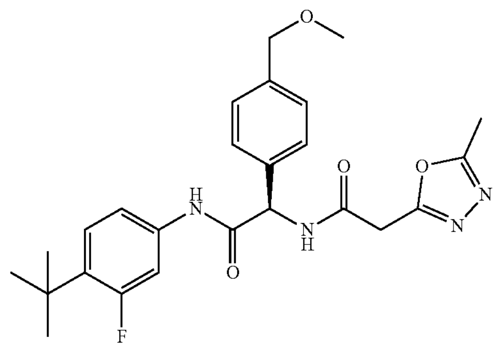 [SMILES: COCc1ccc([C@@H](NC(=O)Cc2nnc(C)o2)C(=O)Nc2ccc(C(C)(C)C)c(F)c2)cc1] | | 469.2 (M + H) |
| 106 | (2R)-N-(4-tert-butyl-3-fluorophenyl)-2-(((3-hydroxy-1,2-oxazol-5-yl)acetyl)amino)-2-(4-(methoxymethyl)phenyl)acetamide | 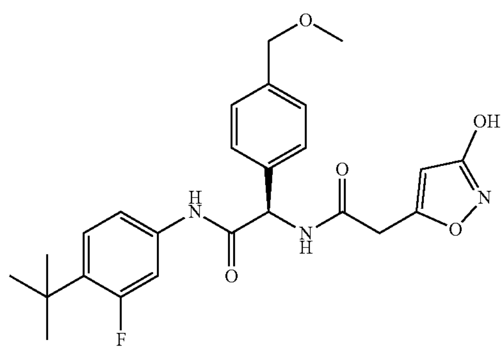 [SMILES: COCc1ccc([C@@H](NC(=O)Cc2cc(O)no2)C(=O)Nc2ccc(C(C)(C)C)c(F)c2)cc1] | | 470.2 |
| 107 | 5-(((1R)-2-((3,5-difluoro-4-(trimethylsilyl)phenyl)amino)-1-(4-(methoxymethyl)phenyl)-2-oxoethyl)amino)-5-oxopentanoic acid | 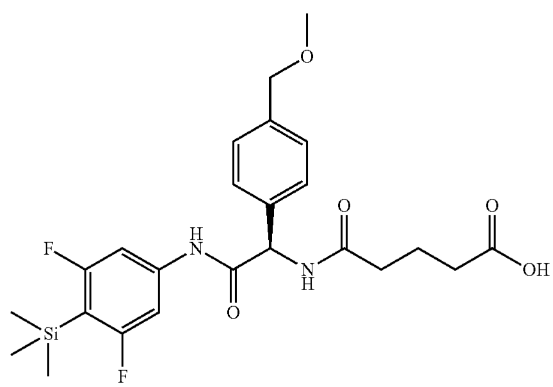 [SMILES: COCc1ccc([C@@H](NC(=O)CCCC(=O)O)C(=O)Nc2cc(F)c([Si](C)(C)C)c(F)c2)cc1] | | 493.2 (M + H) |
| 108 | 4-(((1R)-2-((3,5-difluoro-4-(trimethylsilyl)phenyl)amino)-1-(4-(methoxymethyl)phenyl)-2-oxoethyl)amino)-4-oxobutanoic acid | 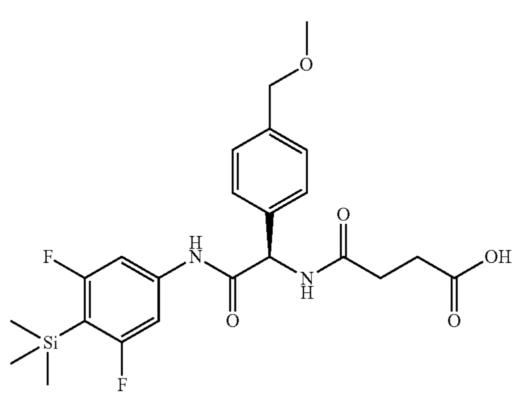 [SMILES: COCc1ccc([C@@H](NC(=O)CCC(=O)O)C(=O)Nc2cc(F)c([Si](C)(C)C)c(F)c2)cc1] | | 477.1 (M − H) |

TABLE 1-11-continued

| Ex. No. | IUPAC NAME | Structure | Salt | MS (Found) |
|---|---|---|---|---|
| 109 | (3S)-N-(2-((3-fluoro-4-(trimethylsilyl)phenyl)amino)-1-(1-methyl-1H-indazol-5-yl)-2-oxoethyl)-5-oxopyrrolidine-3-carboxamide (mixture of two diastereomers) | 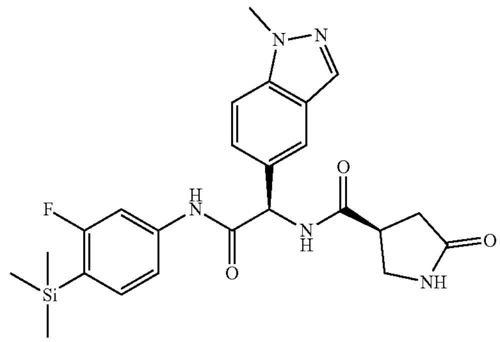 [SMILES: Cn1ncc2cc([C@@H](NC(=O)[C@@H]3CNC(=O)C3)C(=O)Nc3ccc([Si](C)(C)C)c(F)c3)ccc21] | | 480.1 (M − H) |
| 110 | (3S)-N-(2-((4-(2,2-dimethylpropyl)-3-fluorophenyl)amino)-1-(4-(methoxymethyl)phenyl)-2-oxoethyl)-5-oxopyrrolidine-3-carboxamide (mixture of two diastereomers) | 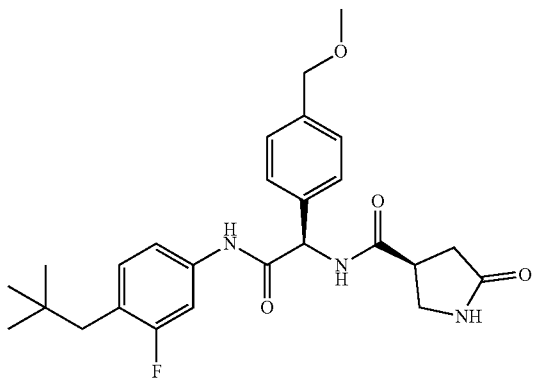 [SMILES: COCc1ccc([C@@H](NC(=O)[C@@H]2CNC(=O)C2)C(=O)Nc2ccc(CC(C)(C)C)c(F)c2)cc1] | | 468.2 (M − H) |

TABLE 1-12

| Ex. No. | IUPAC NAME | Structure | Salt | MS (Found) |
|---|---|---|---|---|
| 111 | (3S)-N-(2-((4-tert-butyl-3-fluorophenyl)amino)-1-(2,3-dihydro-1-benzofuran-5-yl)-2-oxoethyl)-5-oxopyrrolidine-3-carboxamide | 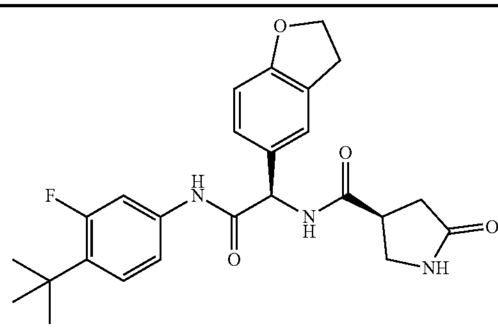 | | 452.1 (M − H) |
| 112 | (3S)-N-(2-((3-fluoro-4-(trimethylsilyl)phenyl)amino)-1-(1-methyl-1H-indazol-5-yl)-2-oxoethyl)-5-oxopyrrolidine-3-carboxamide | 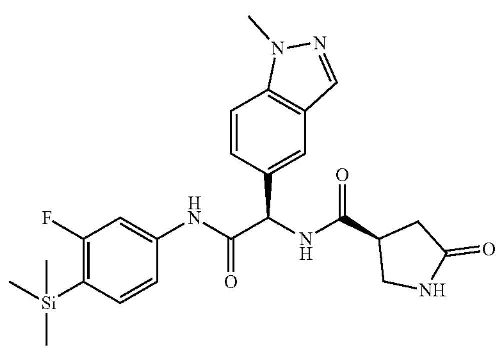 [SMILES: Cn1ncc2cc([C@@H](NC(=O)[C@@H]3CNC(=O)C3)C(=O)Nc3ccc([Si](C)(C)C)c(F)c3)ccc21] | | 482.2 (M + H) |

TABLE 1-12-continued

| Ex. No. | IUPAC NAME | Structure | Salt | MS (Found) |
|---|---|---|---|---|
| 113 | (3R)-N-((1R)-2-((4-tert-butyl-3,5-difluorophenyl)amino)-1-(4-(methoxymethyl)phenyl)-2-oxoethyl)-5-oxopyrrolidine-3-carboxamide | 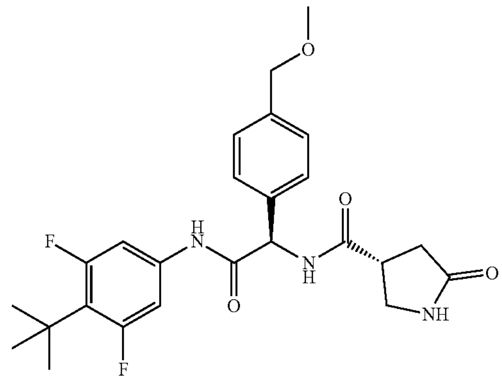 [SMILES: COCc1ccc([C@@H](NC(=O)[C@H]2CNC(=O)C2)C(=O)Nc2cc(F)c(C(C)(C)C)c(F)c2)cc1] | | 472.1 (M − H) |
| 114 | (2R)-N-(4-tert-butyl-3,5-difluorophenyl)-2-(((3-hydroxy-1,2-oxazol-5-yl)acetyl)amino)-2-(4-(methoxymethyl)phenyl)acetamide | 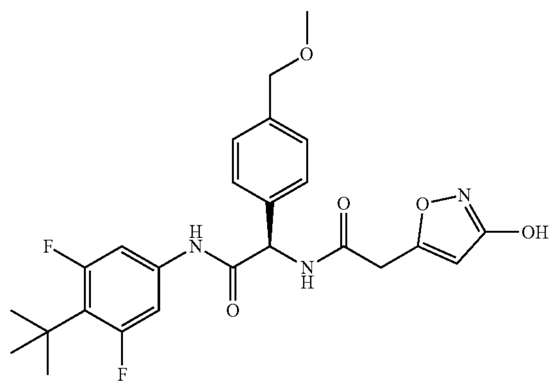 [SMILES: COCc1ccc([C@@H](NC(=O)Cc2cc(O)no2)C(=O)Nc2cc(F)c(C(C)(C)C)c(F)c2)cc1] | | 486.0 (M − H) |
| 115 | (3S)-N-((1R)-2-((4-(2,2-dimethylpropyl)-3-fluorophenyl)amino)-1-(4-(methoxymethyl)phenyl)-2-oxoethyl)-5-oxopyrrolidine-3-carboxamide | 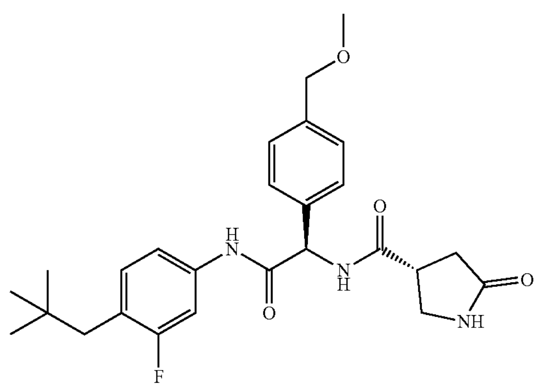 [SMILES: COCc1ccc([C@@H](NC(=O)[C@H]2CNC(=O)C2)C(=O)Nc2ccc(CC(C)(C)C)c(F)c2)cc1] | | 468.1 (M − H) |
| 116 | (2R)-N-(4-tert-butyl-3-fluorophenyl)-2-(((2,4-dioxo-3,4-dihydropyrimidin-1(2H)-yl)acetyl)amino)-2-(4-(methoxymethyl)phenyl)acetamide | 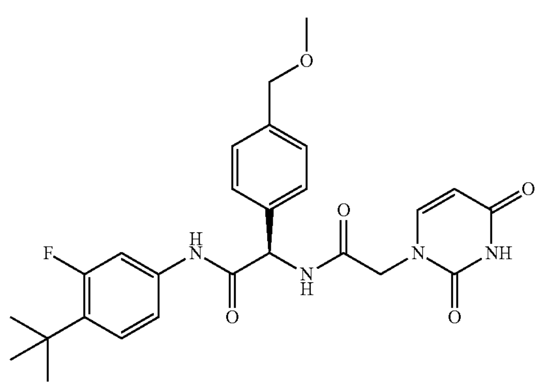 [SMILES: COCc1ccc([C@@H](NC(=O)Cn2ccc(=O)[nH]c2=O)C(=O)Nc2ccc(C(C)(C)C)c(F)c2)cc1] | | 497.1 (M + H) |

TABLE 1-12-continued

| Ex. No. | IUPAC NAME | Structure | Salt | MS (Found) |
|---|---|---|---|---|
| 117 | (2R)-N-(4-tert-butyl-3-fluorophenyl)-2-(((2,6-dioxopiperidin-4-yl)acetyl)amino)-2-(4-(methoxymethyl)phenyl)acetamide | 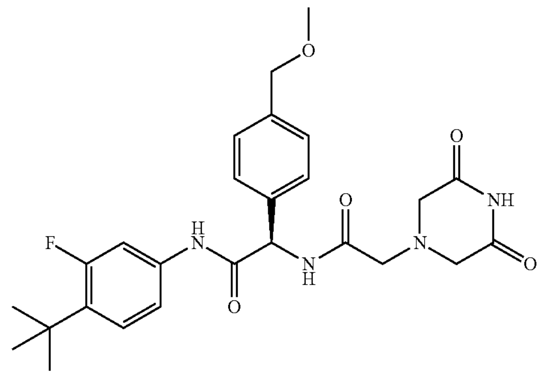 [SMILES: COCc1ccc([C@@H](NC(=O)CN2CC(=O)NC(=O)C2)C(=O)Nc2ccc(C(C)(C)C)c(F)c2)cc1] | | 498.2 (M + H) |
| 118 | 3-cyano-N-(2-oxo-1-(tetrahydro-2H-pyran-4-yl)-2-((4-(trimethylsilyl)phenyl)amino)ethyl)propanamide | 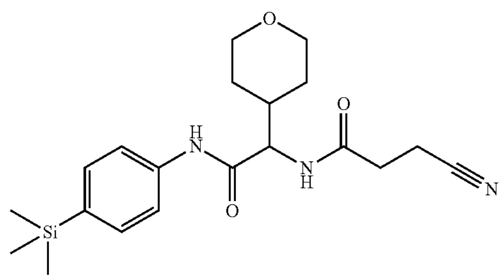 [SMILES: C[Si](C)(C)c1ccc(NC(=O)C(NC(=O)CCC#N)C2CCOCC2)cc1] | | 386.1 (M − H) |
| 119 | N-(2-((3,5-diflouro-4-(trimethylsilyl)phenyl)amino)-2-oxo-1-(tetrahydro-2H-pyran-4-yl)ethyl)-3-hydroxy-1,2-oxazole-5-carboxamide | 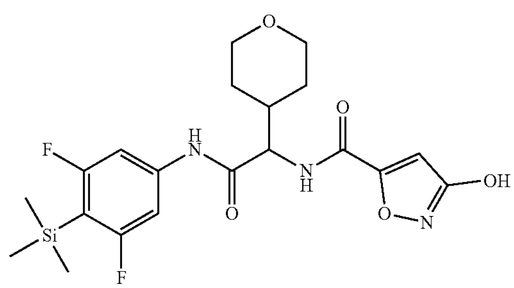 [SMILES: C[Si](C)(C)c1c(F)cc(NC(=O)C(NC(=O)c2cc(O)no2)C2CCOCC2)cc1F] | | 452.0 (M − H) |
| 120 | (3S)-N-((1S)-2-((4-tert-butyl-3-fluorophenyl)amino)-1-(4,4-difluorocyclohexyl)-2-oxoethyl)-5-oxopyrrolidine-3-carboxamide | 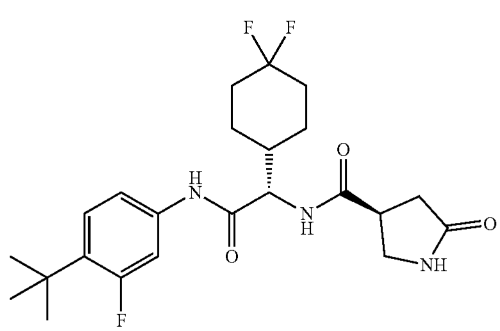 [SMILES: CC(C)(C)c1ccc(NC(=O)[C@@H](NC(=O)[C@@H]2CNC(=O)C2)C2CCC(F)(F)CC2)cc1F] | | 452.1 (M − H) |

TABLE 1-13

| Ex. No. | IUPAC NAME | Structure | Salt | MS (Found) |
|---|---|---|---|---|
| 121 | 5-(((1R)-2-((4-tert-butyl-3-fluorophenyl)amino)-1-(4,4-difluorocyclohexyl)-2-oxoethyl)amino)-5-oxopentanoic acid | 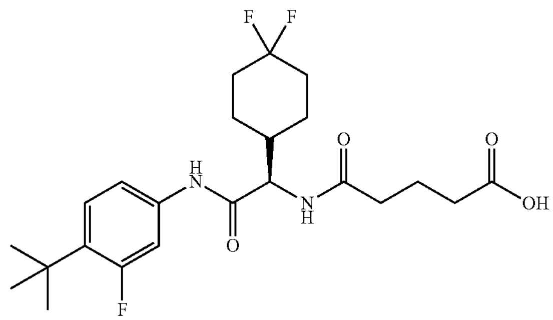 [SMILES: CC(C)(C)c1ccc(NC(=O)[C@H](NC(=O)CCCC(=O)O)C2CCC(F)(F)CC2)cc1F] | | 455.1 (M − H) |
| 122 | (3S)-N-(1S)-2-(4-tert-butyl-3-chlorophenyl)amino)-(2-oxo-1-(tetrahydro-2H-pyran-4-yl)ethyl)-5-oxopyrrolidine-3-carboxamide | 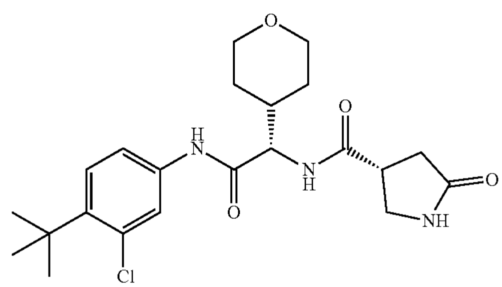 [SMILES: CC(C)(C)c1ccc(NC(=O)[C@@H](NC(=O)[C@H]2CNC(=O)C2)C2CCOCC2)cc1Cl] | | 434.0 (M − H) |
| 123 | (3S)-N-(1R)-2-(4-tert-butyl-3-chlorophenyl)amino)-2-oxo-1-(tetrahydro-2H-pyran-4-yl)ethyl)-5-oxopyrrolidine-3-carboxamnide | 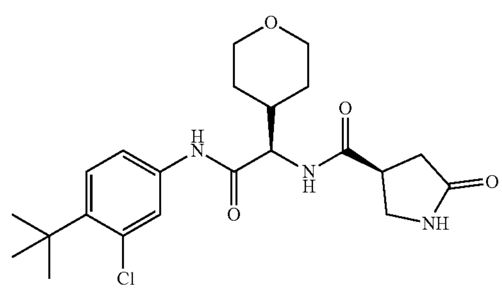 [SMILES: CC(C)(C)c1ccc(NC(=O)[C@H](NC(=O)[C@@H]2CNC(=O)C2)C2CCOCC2)cc1Cl] | | 434.1 (M − H) |
| 124 | (2Z)-N"5"-((1R)-2-((4-tert-butyl-3-fluorophenyl)amino)-1-(4,4-difluorocyclohexyl)-2-foxoethyl)-3-hydroxypent-2-enediamide | 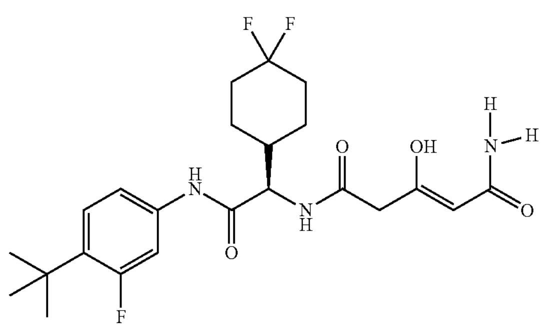 [SMILES: CC(C)(C)c1ccc(NC(=O)[C@H](NC(=O)C/C(O)=C/C(N)=O)C2CCC(F)(F)CC2)cc1F] | | 470.4 (M + H) |
| 125 | (2R)-N-(4-tert-butyl-3-fluorophenyl)-2-(4,4-difluorocyclohexyl)-2-(((3-hydroxy-1,2-oxazol-5-yl)acetyl)amino)acetamide | 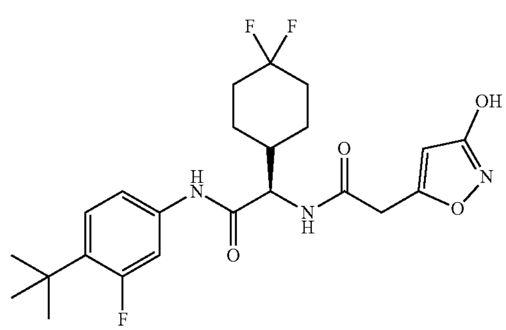 [SMILES: CC(C)(C)c1ccc(NC(=O)[C@H](NC(=O)Cc2cc(O)no2)C2CCC(F)(F)CC2)cc1F] | | 466.0 (M − H) |

TABLE 1-13-continued

| Ex. No. | IUPAC NAME | Structure | Salt | MS (Found) |
|---|---|---|---|---|
| 126 | (3S)-N-(2-((4-tert-butyl-3-fluorophenyl)amino)-2-oxo-1-(1-(2,2,2-trifluoroethyl)piperidin-4-yl)ethyl)-5-oxopyrrolidine-3-carboxamide | 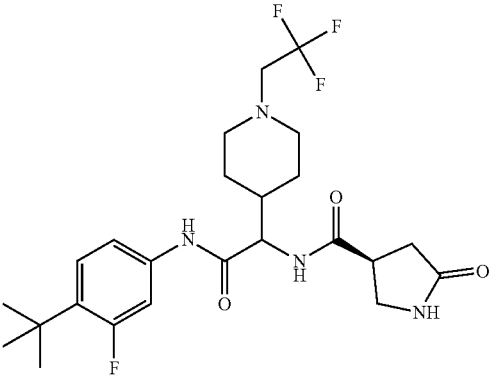 [SMILES: CC(C)(C)c1ccc(NC(=O)C(NC(=O)[C@@H]2CNC(=O)C2)C2CCN(CC(F)(F)F)CC2)cc1F] | | 501.2 (M + H) |
| 128 | (2R)-N-(4-tert-butyl-3-chlorophenyl)-2-(((3-hydroxy-1,2-oxazol-5-yl)acetyl)amino)-2-(tetrahydro-2H-pyran-4-yl)acetamide | 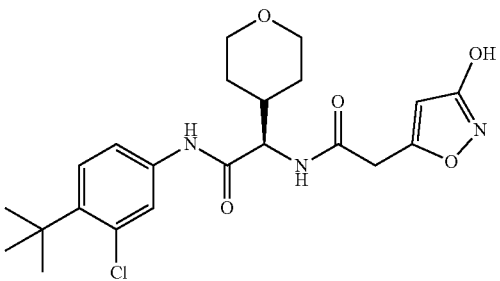 [SMILES: CC(C)(C)c1ccc(NC(=O)[C@H](NC(=O)Cc2cc(O)no2)C2CCOCC2)cc1Cl] | | 448.0 (M − H) |
| 129 | (3S)-N-((1R)-2-((4-tert-butyl-3-fluorophenyl)amino)-1-(4,4-difluorocyclohexyl)-2-oxoethyl)-3-hydroxypyrrolidine-1-carboxamide | 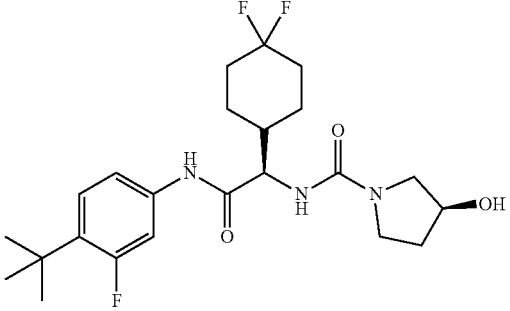 [SMILES: CC(C)(C)c1ccc(NC(=O)[C@H](NC(=O)N2CC[C@H](O)C2)C2CCC(F)(F)CC2)cc1F] | | 454.1 (M − H) |
| 130 | (3S)-N-((1R)-2-((4-tert-butyl-3-chlorophenyl)amino)-2-oxo-1-(tetrahydro-2H-pyran-4-yl)ethyl)-3-hydroxypyrrolidine-1-carboxamide | 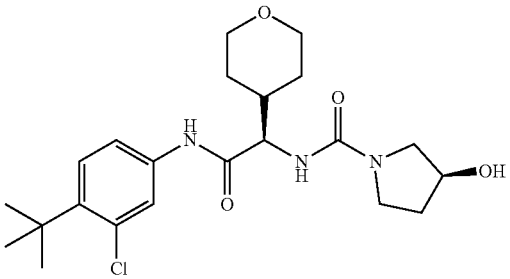 [SMILES: CC(C)(C)c1ccc(NC(=O)[C@H](NC(=O)N2CC[C@H](O)C2)C2CCOCC2)cc1Cl] | | 436.1 (M − H) |

TABLE 1-14

| Ex. No. | IUPAC NAME | Structure | Salt | MS (Found) |
|---|---|---|---|---|
| 131 | N-(2-((4-tert-butyl-3-fluorophenyl)amino)-1-(1,1-dioxidotetrahydro-2H-thiopyran-4-yl)-2-oxoethyl)-3-hydroxy-1,2-oxazole-5-carboxamide | 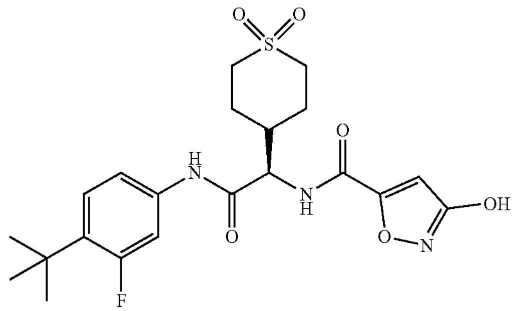 [SMILES: CC(C)(C)c1ccc(NC(=O)[C@H](NC(=O)c2cc(O)no2)C2CCS(=O)(=O)CC2)cc1F] | | 465.9 (M − H) |
| 132 | (3S)-N-(2-((4-tert-butyl-3-fluorophenyl)amino)-1-(4,4-difluoro-1-hydroxycyclohexyl)-2-oxoethyl)-5-oxopyrrolidine-3-carboxamide (mixture of two diastereomers) | 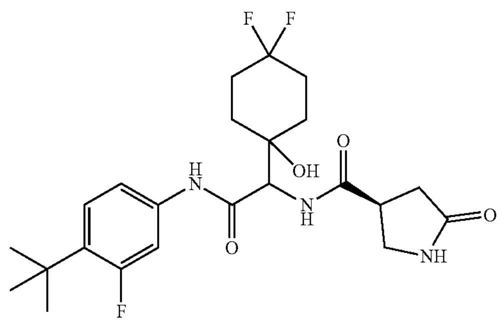 [SMILES: CC(C)(C)c1ccc(NC(=O)C(NC(=O)[C@@H]2CNC(=O)C2)C2(O)CCC(F)(F)CC2)cc1F] | | 468.0 (M − H) |
| 133 | N-(4-tert-butyl-3-fluorophenyl)-2-(1,1-dioxidotetrahydro-2H-thiopyran-4-yl)-2-((1H-indazol-1-ylacetyl)amino)acetamide | 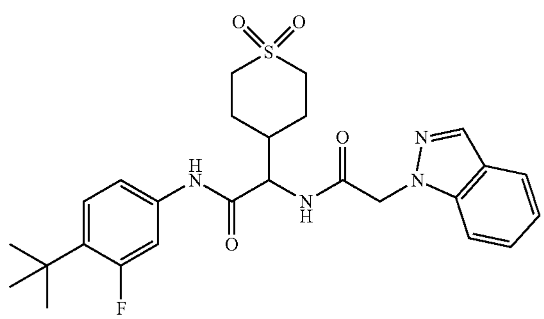 [SMILES: CC(C)(C)c1ccc(NC(=O)C(NC(=O)Cn2ncc3ccccc32)C2CCS(=O)(=O)CC2)cc1F] | | 515.1 (M + H) |
| 134 | N-(4-tert-butyl-3-fluorophenyl)-2-(((3-hydroxy-1,2-oxazol-5-yl)acetyl)amino)-2-(1-(2,2,2-trifluoroethyl)piperidin-4-yl)acetamide | 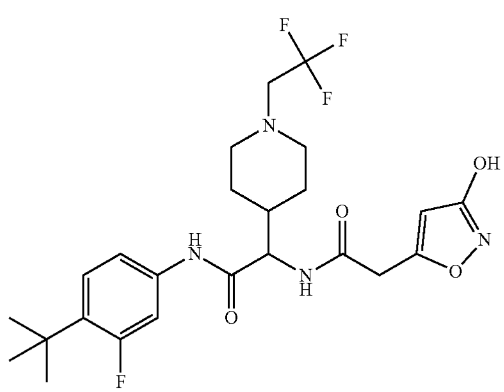 [SMILES: CC(C)(C)c1ccc(NC(=O)C(NC(=O)Cc2cc(O)no2)C2CCN(CC(F)(F)F)CC2)cc1F] | | 515.2 (M + H) |

TABLE 1-14-continued

| Ex. No. | IUPAC NAME | Structure | Salt | MS (Found) |
|---|---|---|---|---|
| 135 | N-((1R)-2-((4-tert-butyl-3-chlorophenyl)amino)-2-oxo-1-(tetrahydro-2H-pyran-4-yl)ethyl)-3,3,3-trifluoro-2-hydroxy-2-(trifluoromethyl)propanamide | 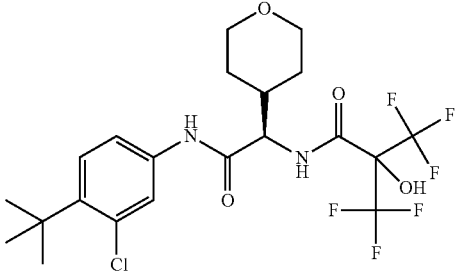 [SMILES: CC(C)(C)c1ccc(NC(=O)[C@H](NC(=O)C(O)(C(F)(F)F)C(F)(F)F)C2CCOCC2)cc1Cl] | | 517.0 (M − H) |
| 136 | N-((1R)-2-((4-tert-butyl-3-fluorophenyl)amino)-1-(4,4-difluorocyclohexyl)-2-oxoethyl)-1-hydroxycyclopropanecarboxamide | 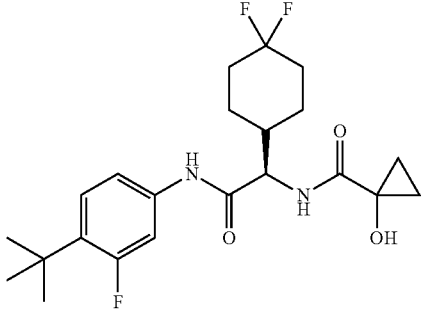 [SMILES: CC(C)(C)c1ccc(NC(=O)[C@H](NC(=O)C2(O)CC2)C2CCC(F)(F)CC2)cc1F] | | 425.1 (M − H) |
| 137 | (2S)-N-((1R)-2-((4-tert-butyl-3-chlorophenyl)amino)-2-oxo-1-(tetrahydro-2H-pyran-4-yl)ethyl)-2-hydroxypropanamide | 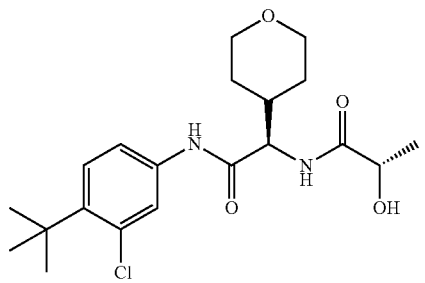 [SMILES: C[C@H](O)C(=O)N[C@@H](C(=O)Nc1ccc(C(C)(C)C)c(Cl)c1)C1CCOCC1] | | 397.1 (M + H) |
| 138 | (2S)-N-((1R)-2-((4-tert-butyl-3-fluorophenyl)amino)-1-(4,4-difluorocyclohexyl)-2-oxoethyl)-2-hydroxypropanamide | 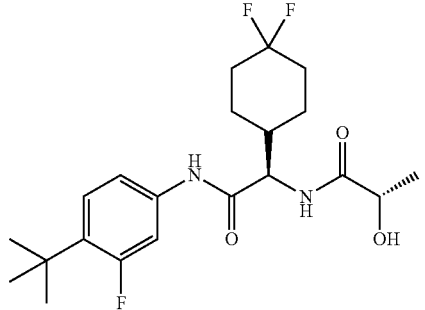 [SMILES: C[C@H](O)C(=O)N[C@@H](C(=O)Nc1ccc(C(C)(C)C)c(F)c1)C1CCC(F)(F)CC1] | | 413.1 (M − H) |
| 139 | (2S)-N-((1R)-2-((4-tert-butyl-3,5-difluorophenyl)amino)-2-oxo-1-(tetrahydro-2H-pyran-4-yl)ethyl)-2-hydroxypropanamide | 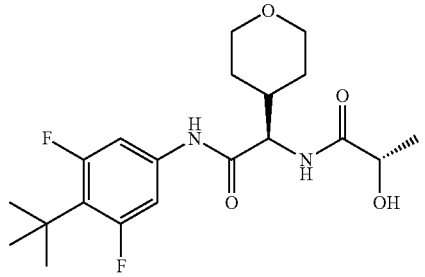 [SMILES: C[C@H](O)C(=O)N[C@@H](C(=O)Nc1cc(F)c(C(C)(C)C)c(F)c1)C1CCOCC1] | | 397.1 (M − H) |

TABLE 1-14-continued

| Ex. No. | IUPAC NAME | Structure | Salt | MS (Found) |
|---|---|---|---|---|
| 140 | N-(2-((4-tert-butylphenyl)amino)-1-(4-methoxyphenyl)-2-oxoethyl)-N-methyl-2-furamide | 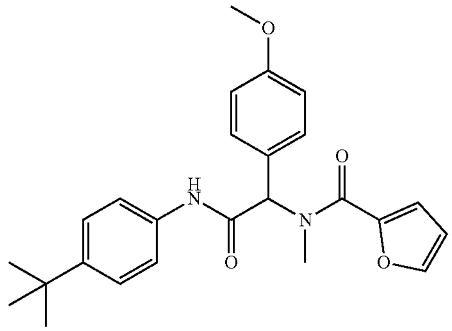 [SMILES: COc1ccc(C(C(=O)Nc2ccc(C(C)(C)C)cc2)N(C)C(=O)c2ccco2)cc1] | | 419.2 (M − H) |

TABLE 1-15

| Ex. No. | IUPAC NAME | Structure | Salt | MS (Found) |
|---|---|---|---|---|
| 141 | N-(2-((4-tert-butylphenyl)amino)-1-(4-(methoxyphenyl)-2-oxoethyl)-N-methyl-1,2-oxazole-5-carboxamide | 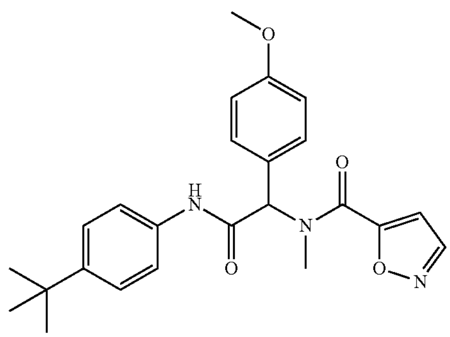 [SMILES: COc1ccc(C(C(=O)Nc2ccc(C(C)(C)C)cc2)N(C)C(=O)c2ccno2)cc1] | | 420.1 (M − H) |
| 142 | 6-acetamido-N-(2-((4-tert-butylphenyl)amino)-1-(4-methoxyphenyl)-2-oxoethyl)-N-methylnicotinamide | 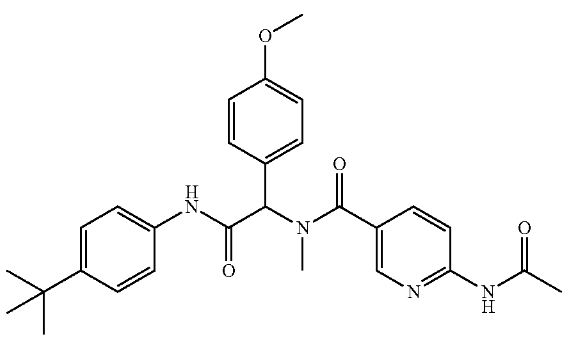 [SMILES: COc1ccc(C(C(=O)Nc2ccc(C(C)(C)C)cc2)N(C)C(=O)c2ccc(NC(C)=O)nc2)cc1] | | 489.1 (M + H) |
| 143 | (N-(2-((4-tert-butylphenyl)amino)-1-(4-methoxyphenyl)-2-oxoethyl)-6-cyano-N-methylnicotinamide | 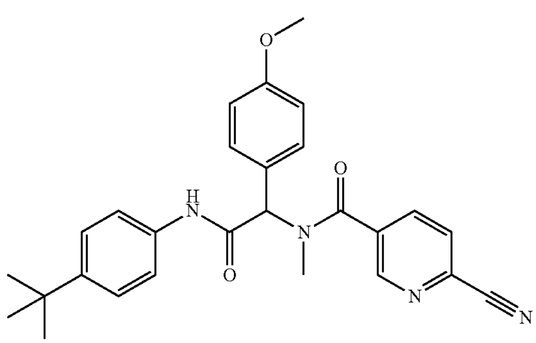 [SMILES: COc1ccc(C(C(=O)Nc2ccc(C(C)(C)C)cc2)N(C)C(=O)c2ccc(C#N)nc2)cc1] | | 455.1 (M − H) |

TABLE 1-15-continued

| Ex. No. | IUPAC NAME | Structure | Salt | MS (Found) |
|---|---|---|---|---|
| 144 | N-(2-((4-tert-butylphenyl)amino)-1-(4-methoxyphenyl)-2-oxoethyl)-3-hydroxy-N-methyl-1,2-oxazole-5-carboxamide | 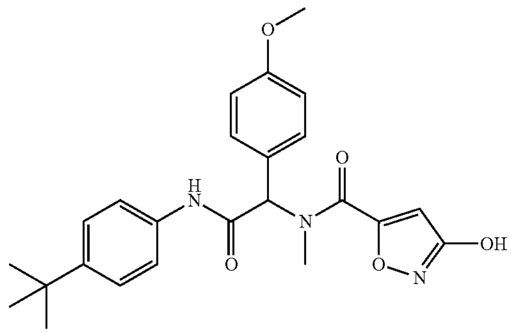 | | 438.1 (M + H) |
| 145 | N-(2-((4-tert-butylphenyl)amino)-1-(4-(methoxyphenyl)-2-oxoethyl)-N-methyl-1H-imidazole-4-carboxamide | 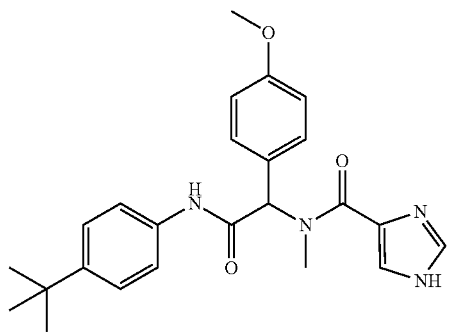 [SMILES: COc1ccc(C(C(=O)Nc2ccc(C(C)(C)C)cc2)N(C)C(=O)c2c[nH]cn2)cc1] | | 421.1 (M + H) |
| 146 | N-(2-((4-tert-butylphenyl)amino)-1-(4-methoxyphenyl)-2-oxoethyl)-N-methyl-5-oxopyrrolidine-3-carboxamide (mixture of four optical isomers) | 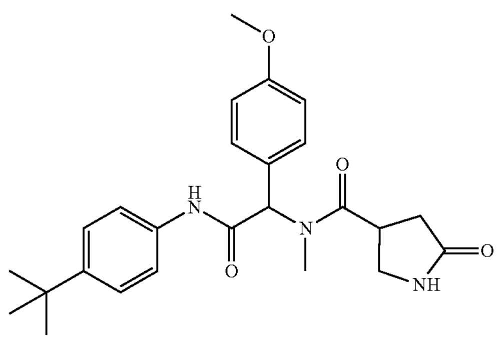 [SMILES: COc1ccc(C(C(=O)Nc2ccc(C(C)(C)C)cc2)N(C)C(=O)C2CNC(=O)C2)cc1] | | 436.1 (M − H) |
| 147 | N-(2-((4-tert-butylphenyl)amino)-1-(4-(methoxyphenyl)-2-oxoethyl)-4-hydroxy-N-methylbenzamide | 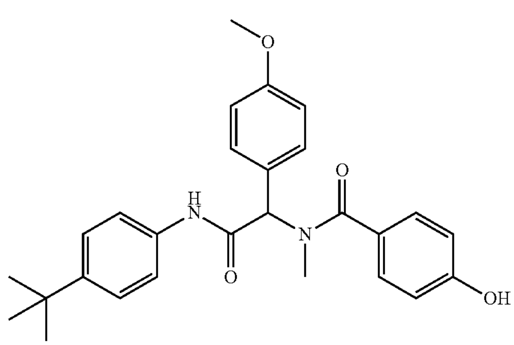 [SMILES: COc1ccc(C(C(=O)Nc2ccc(C(C)(C)C)cc2)N(C)C(=O)c2ccc(O)cc2)cc1] | | 445.1 (M − H) |

TABLE 1-15-continued

| Ex. No. | IUPAC NAME | Structure | Salt | MS (Found) |
|---|---|---|---|---|
| 148 | N-(2-((4-tert-butylphenyl)amino)-1-(4-(methoxyphenyl)-2-oxoethyl)-N-methyl-6-oxopiperidine-3-carboxamide (mixture of four optical isomers) | 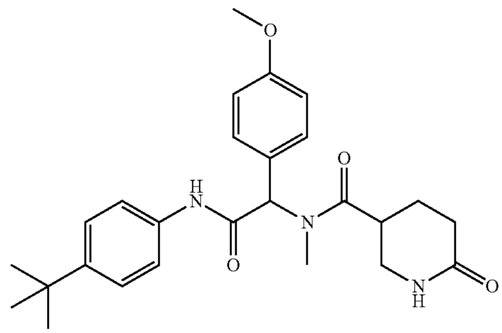 [SMILES: COc1ccc(C(C(=O)Nc2ccc(C(C)(C)C)cc2)N(C)C(=O)C2CCC(=O)NC2)cc1] | | 452.1 (M + H) |
| 149 | N-(2-((4-tert-butyl-phenyl)amino)-1-(4-methoxyphenyl)-2-oxoethyl)-3-hydroxy-1,2-oxazole-5-carboxamide | 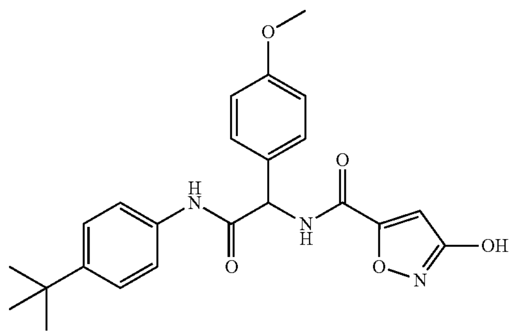 [SMILES: COc1ccc(C(NC(=O)c2cc(O)no2)C(=O)Nc2ccc(C(C)(C)C)cc2)cc1] | | 424.1 (M + H) |
| 150 | N-(2-((4-tert-butylphenyl)amino)-1-(4-(methoxyphenyl)-2-oxoethyl)-N-methyl-4-oxocyclohexanecarboxamide | 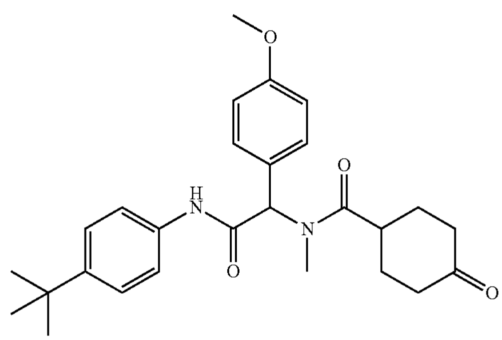 [SMILES: COc1ccc(C(C(=O)Nc2ccc(C(C)(C)C)cc2)N(C)C(=O)C2CCC(=O)CC2)cc1] | | 451.2 (M + H) |

TABLE 1-16

| Ex. No. | IUPAC NAME | Structure | Salt | MS (Found) |
|---|---|---|---|---|
| 151 | N-(2-((4-tert-butylphenyl)amino)-1-(4-methoxyphenyl)-2-oxoethyl)-N-methyltetrahydro-2H-thiopyran-4-carboxamide | 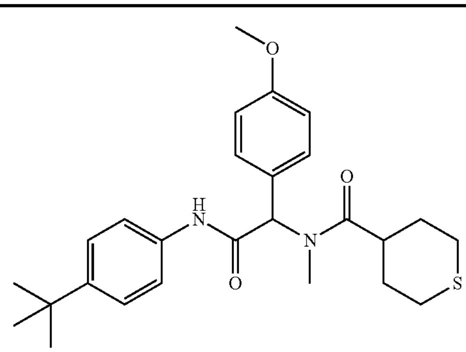 | | 453.2 (M − H) |

TABLE 1-16-continued

| Ex. No. | IUPAC NAME | Structure | Salt | MS (Found) |
|---|---|---|---|---|
| 152 | N-(2-((4-tert-butylphenyl)amino)-1-(4-methoxyphenyl)-2-oxoethyl)-N-methyltetrahydro-2H-thiopyran-4-carboxamide 1,1-dioxide | 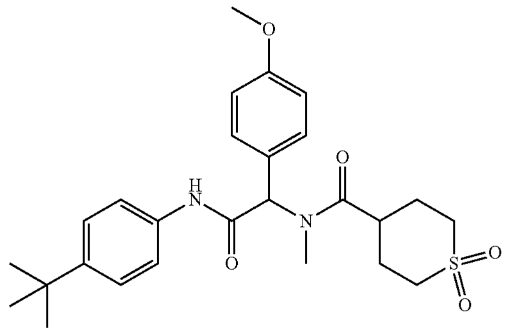 [SMILES: COc1ccc(C(C(=O)Nc2ccc(C(C)(C)C)cc2)N(C)C(=O)C2CCS(=O)(=O)CC2)cc1] | | 485.2 (M − H) |
| 153 | N-(2-((4-tert-butylphenyl)amino)-1-(4-methoxyphenyl)-2-oxoethyl)-N-methyltetrahydro-2H-thiopyran-4-carboxamide 1-oxide | 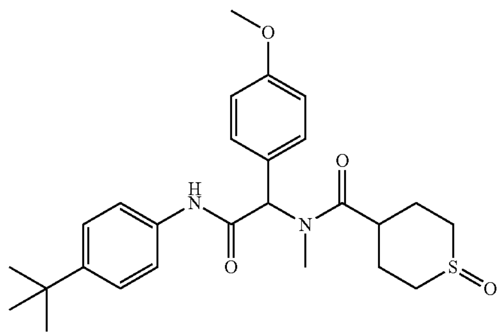 [SMILES: COc1ccc(C(C(=O)Nc2ccc(C(C)(C)C)cc2)N(C)C(=O)C2CCS(=O)CC2)cc1] | | 471.2 (M + H) |
| 154 | N-(2-((4-tert-butylphenyl)amino)-1-(4-methoxyphenyl)-2-oxoethyl)-5-methoxy-N-methyl-1H-pyrazole-3-carboxamide | 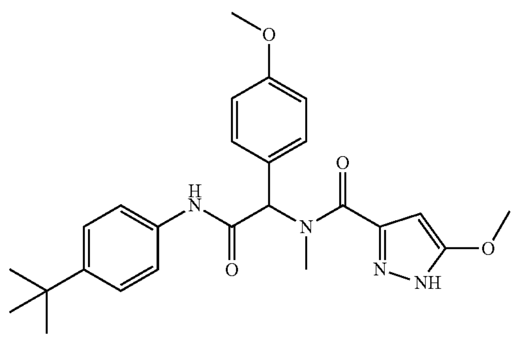 [SMILES: COc1ccc(C(C(=O)Nc2ccc(C(C)(C)C)cc2)N(C)C(=O)c2cc(OC)[nH]n2)cc1] | | 451.1 (M + H) |
| 156 | N-(2-((4-(1,1,1,3,3,3-hexafluoro-2-hydroxypropan-2-yl)phenyl)amino)-1-(4-methoxyphenyl)-2-oxoethyl)-N-methyl-5-oxopyrrolidine-3-carboxamide (mixture of four optical isomers) | 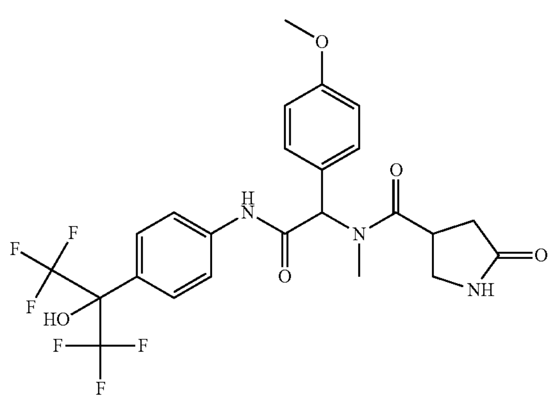 [SMILES: COc1ccc(C(C(=O)Nc2ccc(C(O)(C(F)(F)F)C(F)(F)F)cc2)N(C)C(=O)C2CNC(=O)C2)cc1] | | 546.0 (M − H) |

TABLE 1-16-continued

| Ex. No. | IUPAC NAME | Structure | Salt | MS (Found) |
|---|---|---|---|---|
| 157 | N-(2-((4-(2,2-dimethylpropyl)phenyl)amino)-1-(4-methoxyphenyl)-2-oxoethyl)-N-methyl-5-oxopyrrolidine-3-carboxamide (mixture of four optical fisomers) | 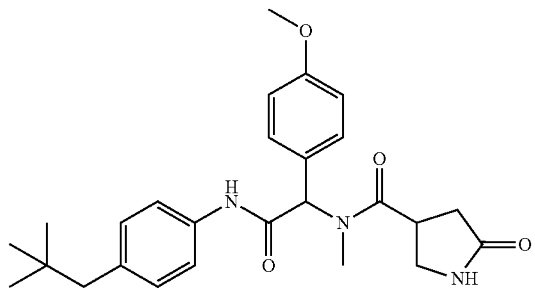 [SMILES: COc1ccc(C(C(=O)Nc2ccc(CC(C)(C)C)cc2)N(C)C(=O)C2CNC(=O)C2)cc1] | | 452.2 (M + H) |
| 158 | N-(2-((4-tert-butylphenyl)amino)-1-(4-methoxyphenyl)-2-oxoethyl)-5-oxopyrrolidine-3-carboxamide (mixture of four optical isomers) | 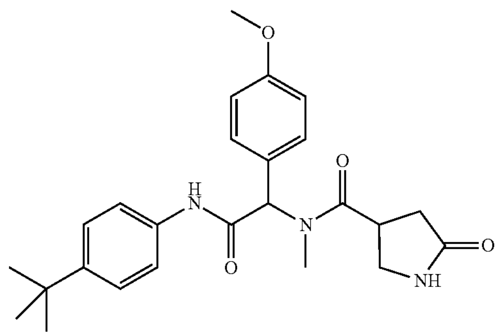 | | 424.2 (M + H) |
| 159 | 4-hydroxy-N-(1-(4-methoxyphenyl)-2-oxo-2-((4-(trimethylsilyl)phenyl)amino)ethyl)-N-methylthiophene-2-carboxamide | 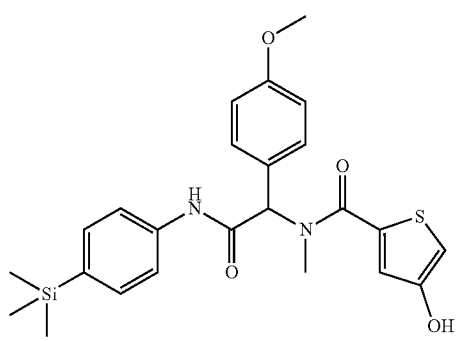 [SMILES: COc1ccc(C(C(=O)Nc2ccc([Si](C)(C)C)cc2)N(C)C(=O)c2cc(O)cs2)cc1] | | 467.2 (M − H) |
| 160 | 2-hydroxy-N-(1-(4-methoxyphenyl)-2-oxo-2-((4-(trimethylsilyl)phenyl)amino)ethyl)-N-methyl-1H-imidazole-4-carboxamide | 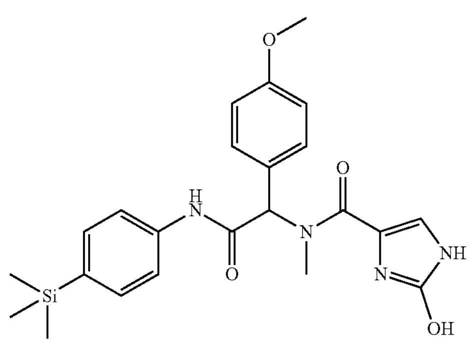 [SMILES: COc1ccc(C(C(=O)Nc2ccc([Si](C)(C)C)cc2)N(C)C(=O)c2c[nH]c(O)n2)cc1] | | 451.2 (M − H) |

TABLE 1-16-continued

| Ex. No. | IUPAC NAME | Structure | Salt | MS (Found) |
|---|---|---|---|---|
| 161 | N-(1-(4-methoxyphenyl)-2-oxo-2-((4-(trimethylsilyl)phenyl)amino)ethyl)-N-methyl-2-oxoimidazolidine-4-carboxamide (mixture of four optical isomers) | 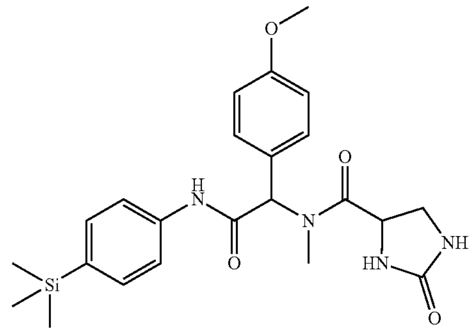 [SMILES: COc1ccc(C(C(=O)Nc2ccc([Si](C)(C)C)cc2)N(C)C(=O)C2CNC(=O)N2)cc1] | | 453.2 (M − H) |

TABLE 1-17

| Ex. No. | IUPAC NAME | Structure | Salt | MS (Found) |
|---|---|---|---|---|
| 162 | 3-hydroxy-N-(1-(4-methoxyphenyl)-2-oxo-2-((4-(trimethylsilyl)phenyl)amino)ethyl)-N-methyl-1H-1,2,4-triazole-5-carboxamide | 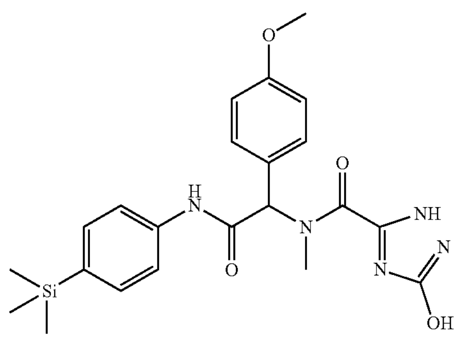 [SMILES: COc1ccc(C(C(=O)Nc2ccc([Si](C)(C)C)cc2)N(C)C(=O)/C(N)=N/C(=N)O)cc1] | | 452.2 (M − H) |
| 163 | 2-hydroxy-N-(1-(4-methoxyphenyl)-2-oxo-2-((4-(trimethylsilyl)phenyl)amino)ethyl)-N,5-dimethyl-1,3-oxazole-4-carboxamide | 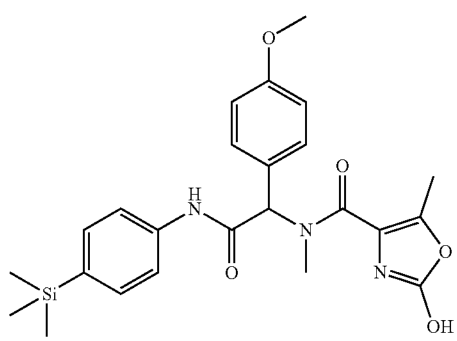 [SMILES: COc1ccc(C(C(=O)Nc2ccc([Si](C)(C)C)cc2)N(C)C(=O)c2nc(O)oc2C)cc1] | | 466.2 (M − H) |
| 164 | 2-hydroxy-N-(1-(4-methoxyphenyl)-2-oxo-2-((4-(trimethylsilyl)phenyl)amino)ethyl)-N,4-dimethyl-1,3-thiazole-5-carboxamide | 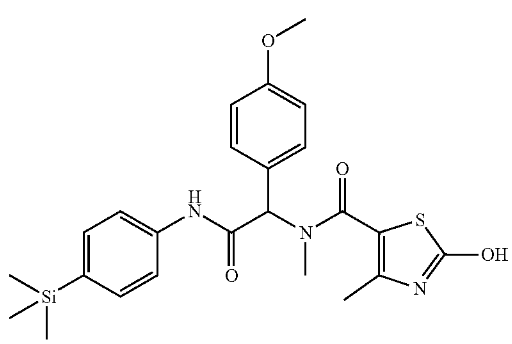 [SMILES: COc1ccc(C(C(=O)Nc2ccc([Si](C)(C)C)cc2)N(C)C(=O)c2sc(O)nc2C)cc1] | | 482.2 (M − H) |

TABLE 1-17-continued

| Ex. No. | IUPAC NAME | Structure | Salt | MS (Found) |
|---|---|---|---|---|
| 165 | 6-fluoro-N-(1-(4-methoxyphenyl)-2-oxo-2-((4-(trimethylsilyl)phenyl)amino)ethyl)-N-methylnicotinamide | 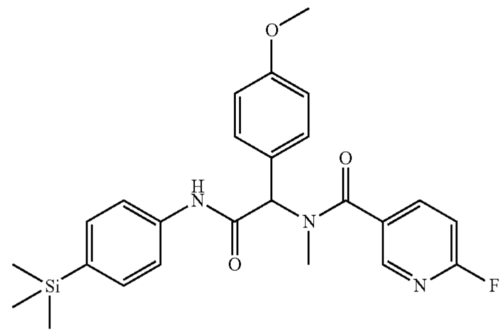 [SMILES: COc1ccc(C(C(=O)Nc2ccc([Si](C)(C)C)cc2)N(C)C(=O)c2ccc(F)nc2)cc1] | | 464.2 (M − H) |
| 166 | 6-amino-N-(1-(4-methoxyphenyl)-2-oxo-2-((4-(trimethylsilyl)phenyl)amino)ethyl)-N-methylnicotinamide | 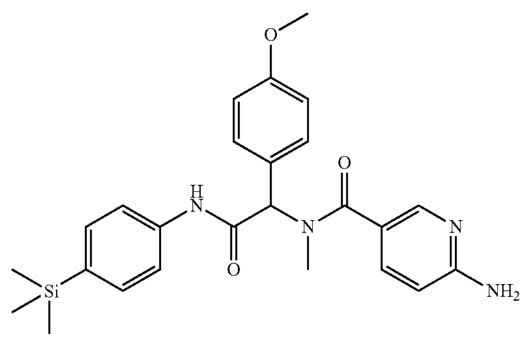 [SMILES: COc1ccc(C(C(=O)Nc2ccc([Si](C)(C)C)cc2)N(C)C(=O)c2ccc(N)nc2)cc1] | | 461.3 (M − H) |
| 167 | N-(1-(4-methoxyphenyl)-2-oxo-2-((4-(trimethylsilyl)phenyl)amino)ethyl)-N-methyl-2-oxoindoline-5-carboxamide | 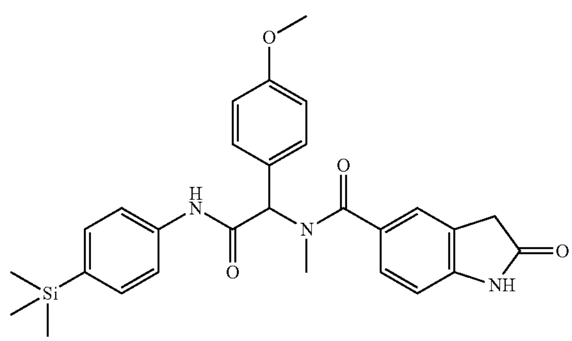 [SMILES: COc1ccc(C(C(=O)Nc2ccc([Si](C)(C)C)cc2)N(C)C(=O)c2ccc3c(c2)CC(=O)N3)cc1] | | 500.3 (M − H) |
| 168 | N-(1-(4-methoxyphenyl)-2-oxo-2-((4-(trimethylsilyl)phenyl)amino)ethyl)-N-methyl-2-oxoindoline-6-carboxamide | 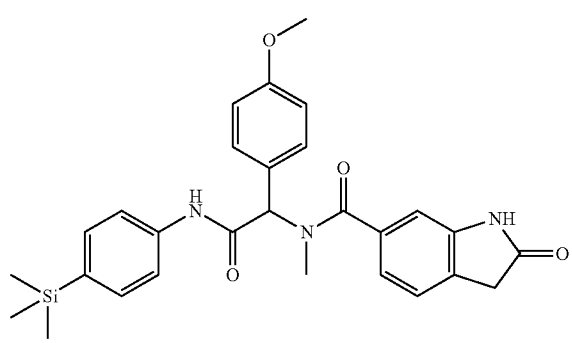 [SMILES: COc1ccc(C(C(=O)Nc2ccc([Si](C)(C)C)cc2)N(C)C(=O)c2ccc3c(c2)NC(=O)C3)cc1] | | 500.3 (M − H) |

TABLE 1-17-continued

| Ex. No. | IUPAC NAME | Structure | Salt | MS (Found) |
| --- | --- | --- | --- | --- |
| 169 | N-(1-(4-methoxyphenyl)-2-oxo-2-((4-(trimethylsilyl)phenyl)amino)ethyl)-N-methyl-3-oxo-3,4-dihydro-2H-1,4-benzoxazine-7-carboxamide | 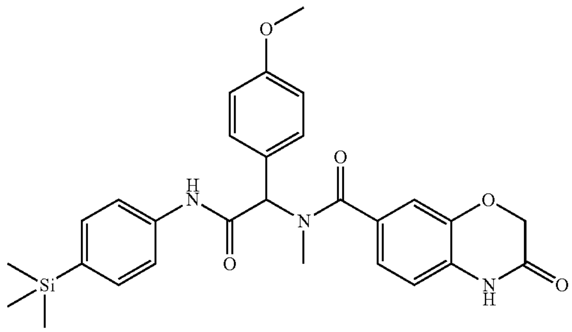 [SMILES: COc1ccc(C(C(=O)Nc2ccc([Si](C)(C)C)cc2)N(C)C(=O)c2ccc3c(c2)OCC(=O)N3)cc1] | | 516.3 (M − H) |
| 170 | N-(1-(4-methoxyphenyl)-2-oxo-2-((4-(trimethylsilyl)phenyl)amino)ethyl)-N-methyl-1H-pyrrolo[2,3-b]pyridine-5-carboxamide | 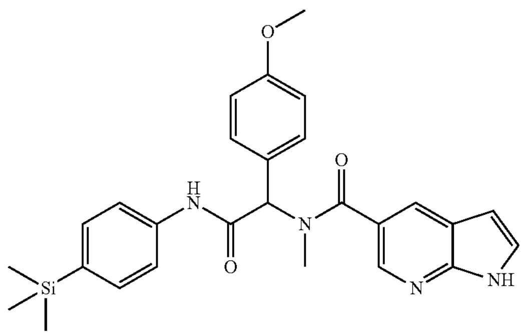 [SMILES: COc1ccc(C(C(=O)Nc2ccc([Si](C)(C)C)cc2)N(C)C(=O)c2cnc3[nH]ccc3c2)cc1] | | 485.3 (M − H) |
| 171 | N-(1-(4-methoxyphenyl)-2-oxo-2-((4-(trimethylsilyl)phenyl)amino)ethyl)-N-methyl-1H-pyrazolo[3,4-b]pyridine-3-carboxamide | 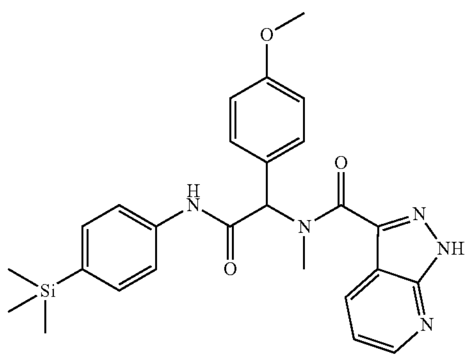 [SMILES: COc1ccc(C(C(=O)Nc2ccc([Si](C)(C)C)cc2)N(C)C(=O)c2n[nH]c3ncccc23)cc1] | | 486.3 (M − H) |

TABLE 1-18

| Ex. No. | IUPAC NAME | Structure | Salt | MS (Found) |
| --- | --- | --- | --- | --- |
| 172 | N-(1-(4-methoxyphenyl)-2-oxo-2-((4-(trimethylsilyl)phenyl)amino)ethyl)-N-methyl-1H-pyrrolo[2,3-b]pyridine-3-carboxamide | 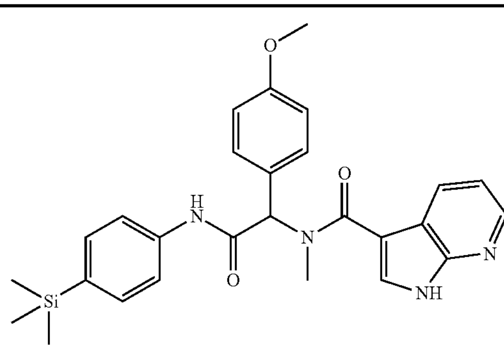 | | 485.3 (M − H) |

TABLE 1-18-continued

| Ex. No. | IUPAC NAME | Structure | Salt | MS (Found) |
|---|---|---|---|---|
| 173 | N-(1-(4-methoxyphenyl)-2-oxo-2-((4-(trimethylsilyl)phenyl)amino)ethyl)-N-methyltetrahydrofuran-2-carboxamide (mixture of four optical isomers) | 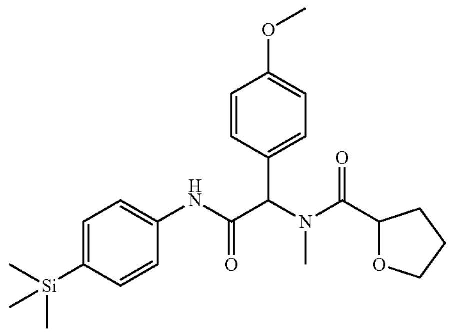 [SMILES: COc1ccc(C(C(=O)Nc2ccc([Si](C)(C)C)cc2)N(C)C(=O)C2CCCO2)cc1] | | 439.2 (M − H) |
| 174 | N-(1-(4-methoxyphenyl)-2-oxo-2-((4-(trimethylsilyl)phenyl)amino)ethyl)-N-methyl-2-furamide | 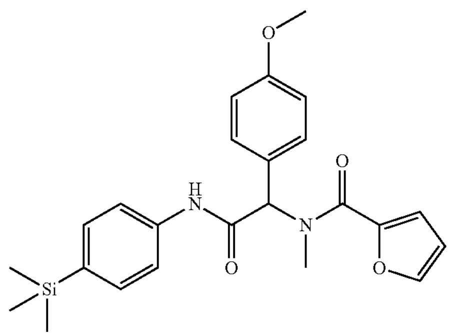 [SMILES: COc1ccc(C(C(=O)Nc2ccc([Si](C)(C)C)cc2)N(C)C(=O)c2ccco2)cc1] | | 435.2 (M − H) |
| 175 | N-(1-(4-methoxyphenyl)-2-oxo-2-((4-(trimethylsilyl)phenyl)amino)ethyl)-N-methyl-1,2-oxazole-5-carboxamide | 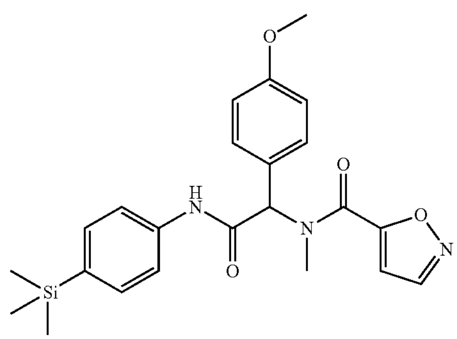 [SMILES: COc1ccc(C(C(=O)Nc2ccc([Si](C)(C)C)cc2)N(C)C(=O)c2ccno2)cc1] | | 436.2 (M − H) |
| 176 | N-(1-(4-methoxyphenyl)-2-oxo-2-((4-(trimethylsilyl)phenyl)amino)ethyl)-N-methyl-2-(pyridin-2-yl)acetamide | 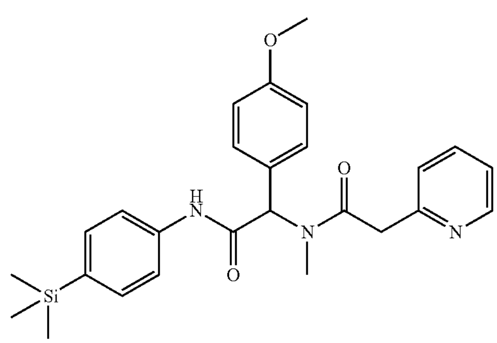 [SMILES: COc1ccc(C(C(=O)Nc2ccc([Si](C)(C)C)cc2)N(C)C(=O)Cc2ccccn2)cc1] | | 460.2 (M − H) |

TABLE 1-18-continued

| Ex. No. | IUPAC NAME | Structure | Salt | MS (Found) |
|---|---|---|---|---|
| 177 | N-(1-(4-methoxyphenyl)-2-oxo-2-((4-(trimethylsilyl)phenyl)amino)ethyl)-N-methyl-2-(pyridin-3-yl)acetamide | 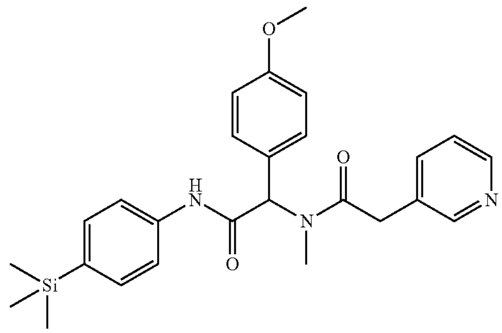 [SMILES: COc1ccc(C(C(=O)Nc2ccc([Si](C)(C)C)cc2)N(C)C(=O)Cc2cccnc2)cc1] | | 460.3 (M − H) |
| 178 | N-(1-(4-methoxyphenyl)-2-oxo-2-((4-(trimethylsilyl)phenyl)amino)ethyl)-N-methyltetrahydrothiophene-3-carboxamide 1,1-dioxide (mixture of four optical isomers) | 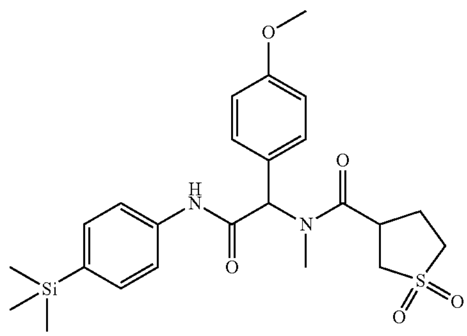 [SMILES: COc1ccc(C(C(=O)Nc2ccc([Si](C)(C)C)cc2)N(C)C(=O)C2CCS(=O)(=O)C2)cc1] | | 487.2 (M − H) |
| 179 | N-(1-(4-methoxyphenyl)-2-oxo-2-((4-(trimethylsilyl)phenyl)amino)ethyl)-N-methyl-5-oxopyrrolidine-3-carboxamide (mixture of four optical isomers) | 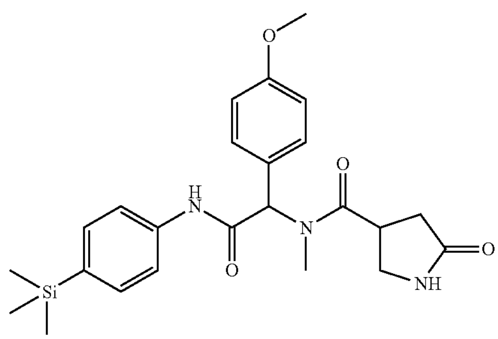 [SMILES: COc1ccc(C(C(=O)Nc2ccc([Si](C)(C)C)cc2)N(C)C(=O)C2CNC(=O)C2)cc1] | | 452.3 (M − H) |
| 180 | N-(1-(4-methoxyphenyl)-2-oxo-2-((4-(trimethylsilyl)phenyl)amino)ethyl)-N-methyl-2-oxo-1,2,3,4-tetrahydroquinoline-6-carboxamide | 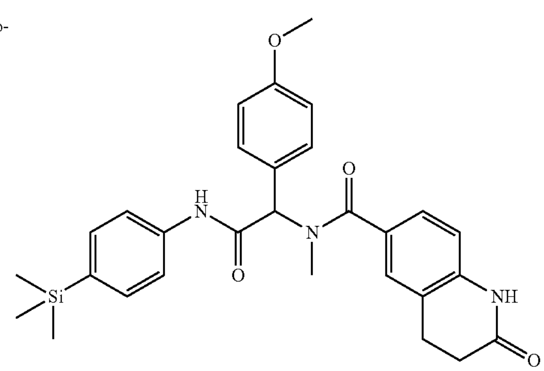 | | 514.3 (M − H) |

TABLE 1-18-continued

| Ex. No. | IUPAC NAME | Structure | Salt | MS (Found) |
|---|---|---|---|---|
| 181 | N-(2-((4-tert-butylphenyl)amino)-1-(4-methoxyphenyl)-2-oxoethyl)-4-hydroxycyclohexanecarboxamide (mixture of four optical isomers) | 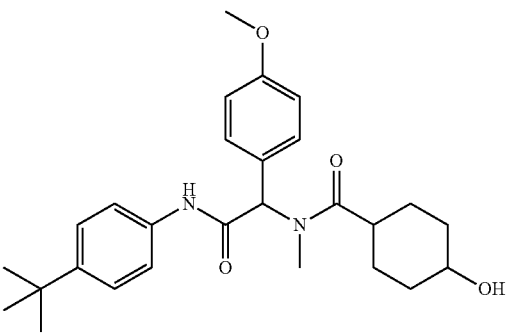 | | 439.2 (M + H) |

TABLE 1-19

| Ex. No. | IUPAC NAME | Structure | Salt | MS (Found) |
|---|---|---|---|---|
| 182 | N-(2-((4-tert-butylphenyl)amino)-1-(4-ethylphenyl)-2-oxoethyl)-3-hydroxy-N-methyl-1,2-oxazole-5-carboxamide | 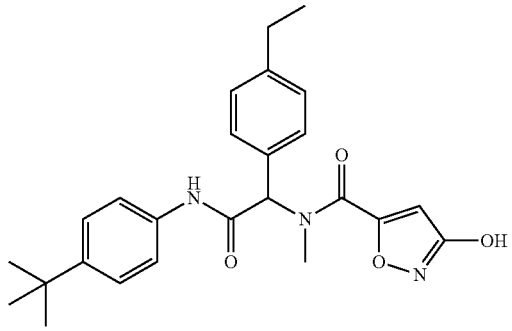 | | 434.1 (M − H) |
| 183 | N-(2-((4-tert-butylphenyl)amino)-1-(4-ethoxyphenyl)-2-oxoethyl)-3-hydroxy-N-methyl-1,2-oxazole-5-carboxamide | 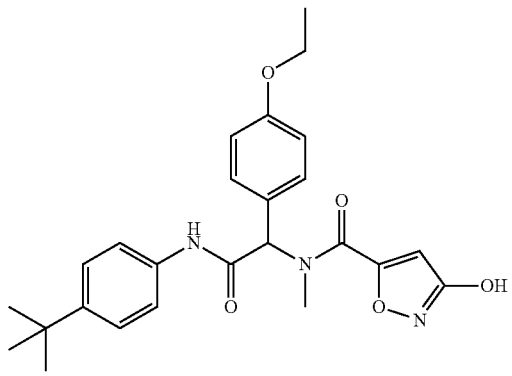 [SMILES: CCOc1ccc(C(C(=O)Nc2ccc(C(C)(C)C)cc2)N(C)C(=O)c2cc(O)no2)cc1] | | 450.0 (M − H) |
| 184 | N-(2-((4-tert-butylphenyl)amino)-1-(4-isopropylphenyl)-2-oxoethyl)-3-hydroxy-N-methyl-1,2-oxazole-5-carboxamide | 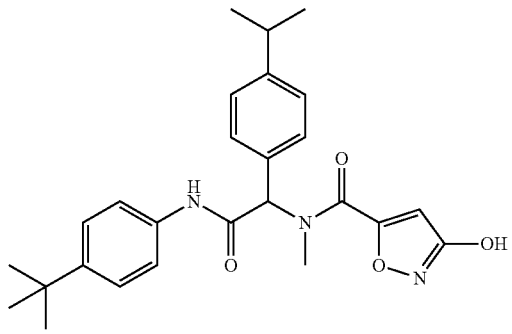 [SMILES: CC(C)c1ccc(C(C(=O)Nc2ccc(C(C)(C)C)cc2)N(C)C(=O)c2cc(O)no2)cc1] | | 448.1 (M − H) |

TABLE 1-19-continued

| Ex. No. | IUPAC NAME | Structure | Salt | MS (Found) |
|---|---|---|---|---|
| 185 | N-(2-((4-tert-butylphenyl)amino)-1-(4-methoxyphenyl)-2-oxoethyl)tetrahydrothiophene-3-carboxamide 1,1-dioxide (mixture of four optical isomers) | 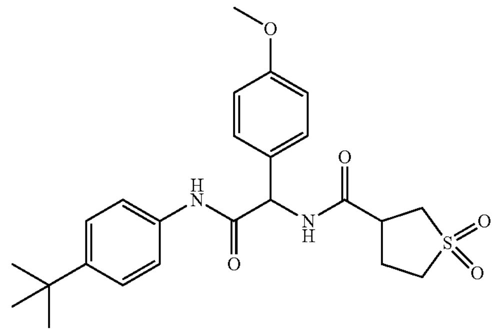 [SMILES: COc1ccc(C(NC(=O)C2CCS(=O)(=O)C2)C(=O)Nc2ccc(C(C)(C)C)cc2)cc1] | | 459.2 (M + H) |
| 186 | N-(2-((4-tert-butylphenyl)amino)-1-(4-methoxyphenyl)-2-oxoethyl)-5-oxoprolinamide (mixture of four optical isomers) | 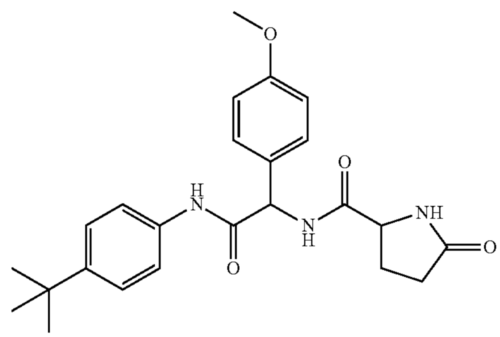 [SMILES: COc1ccc(C(NC(=O)C2CCC(=O)N2)C(=O)Nc2ccc(C(C)(C)C)cc2)cc1] | | 424.1 (M + H) |
| 187 | N-(2-((4-tert-butylphenyl)amino)-1-(4-methoxyphenyl)-2-oxoethyl)-2-oxoimidazolidine-4-carboxamide (mixture of four optical isomers) | 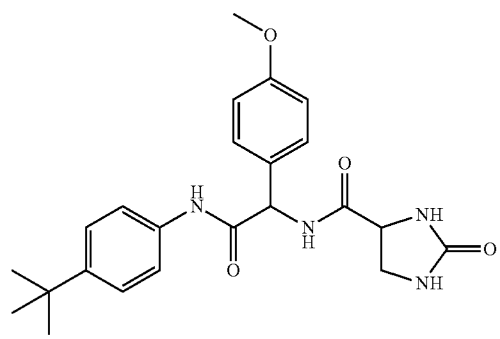 [SMILES: COc1ccc(C(NC(=O)C2CNC(=O)N2)C(=O)Nc2ccc(C(C)(C)C)cc2)cc1] | | 423.1 (M − H) |
| 188 | 3-hydroxy-N-(1-(4-methoxyphenyl)-2-oxo-2-((4-(trimethylsilyl)phenyl)amino)ethyl)-1,2-oxazole-5-carboxamide | 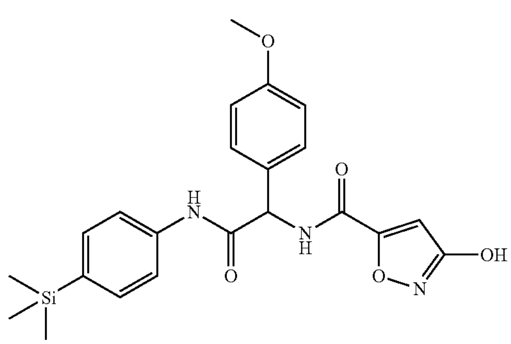 [SMILES: COc1ccc(C(NC(=O)c2cc(O)no2)C(=O)Nc2ccc([Si](C)(C)C)cc2)cc1] | | 440.1 (M + H) |

TABLE 1-19-continued

| Ex. No. | IUPAC NAME | Structure | Salt | MS (Found) |
|---|---|---|---|---|
| 189 | N-(2-((4-(dimethyl (phenyl)amino)-1-(4-methoxyphenyl)-2-oxoethyl)-3-hydroxy-N-methyl-1,2-oxazole-5-carboxamide | 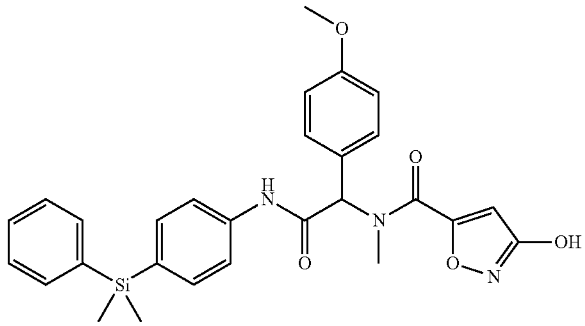 [SMILES: COc1ccc(C(C(=O)Nc2ccc([Si](C)(C)c3ccccc3)cc2)N(C)C(=O)c2cc(O)no2)cc1] | | 514.1 (M − H) |
| 190 | ethyl ((1-(4-methoxyphenyl)-2-oxo-2-((4-(trimethylsilyl)phenyl) amino)ethyl)(methyl) amino)(oxo)acetate | 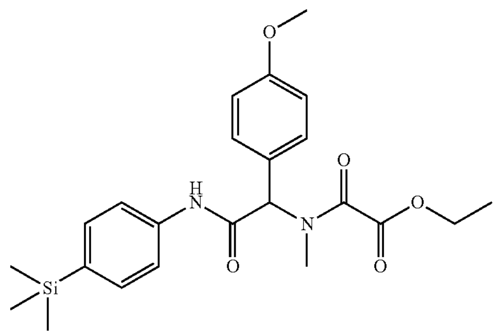 [SMILES: CCOC(=O)C(=O)N(C)C(C(=O)Nc1ccc([Si](C)(C)C)cc1)c1ccc(OC)cc1] | | 441.1 (M − H) |
| 191 | 5-hydroxy-N-(1-(4-methoxyphenyl)-2-oxo-2-((4-(trimethylsilyl)phenyl) amino)ethyl)-N-methyl-1,3,4-oxadiazole-2-carboxamide | 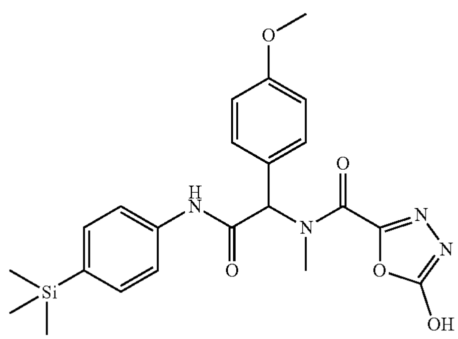 [SMILES: COc1ccc(C(C(=O)Nc2ccc([Si](C)(C)C)cc2)N(C)C(=O)c2nnc(O)o2)cc1] | | 455.1 (M + H) |

TABLE 1-20

| Ex. No | IUPAC NAME | Structure | Salt | MS (Found) |
|---|---|---|---|---|
| 192 | N-(2-((4-tert-butylphenyl) amino)-1-(4-methoxyphenyl)-2-oxoethyl)morpholine-4-carboxamide | 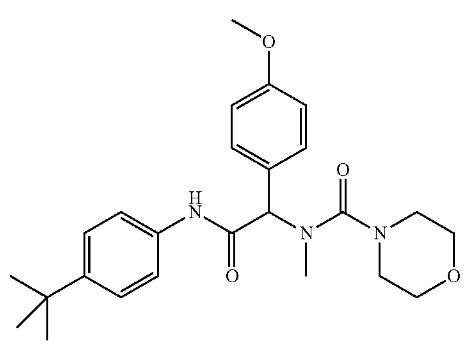 | | 426.2 (M + H) |

TABLE 1-20-continued

| Ex. No | IUPAC NAME | Structure | Salt | MS (Found) |
|---|---|---|---|---|
| 193 | N-(2-((4-tert-butylphenyl)amino)-1-(4-(methoxyphenyl)-2-oxoethyl)-N-methylmorpholine-4-carboxamide | 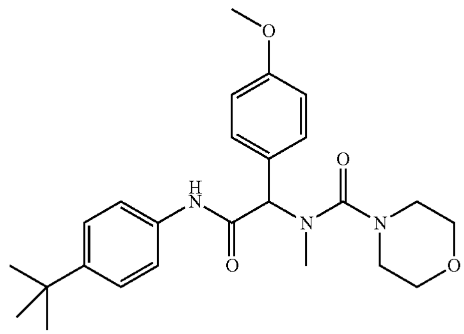 [SMILES: COc1ccc(C(C(=O)Nc2ccc(C(C)(C)C)cc2)N(C)C(=O)N2CCOCC2)cc1] | | 440.2 (M + H) |
| 194 | N-(1-(2,3-dihydro-1-benzofuran-5-yl)-2-oxo-2-((4-(trimethylsilyl)phenyl)amino)ethyl)-3-hydroxy-N-methyl-1,2-oxazole-5-carboxamide | 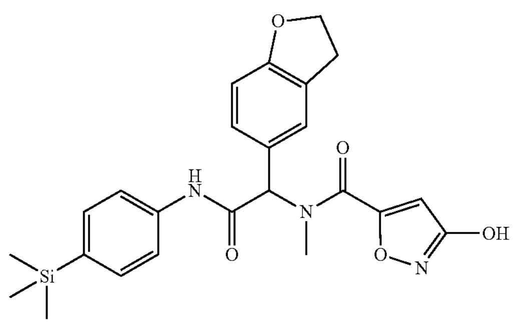 [SMILES: CN(C(=O)c1cc(O)no1)C(C(=O)Nc1ccc([Si](C)(C)C)cc1)c1ccc2c(c1)CCO2] | | 464.0 (M − H) |
| 195 | N-(2-((4-tert-butylphenyl)amino)-1-(4-methoxyphenyl)-2-oxoethyl)-2-oxopiperidine-4-carboxamide (mixture of four optical isomers) | 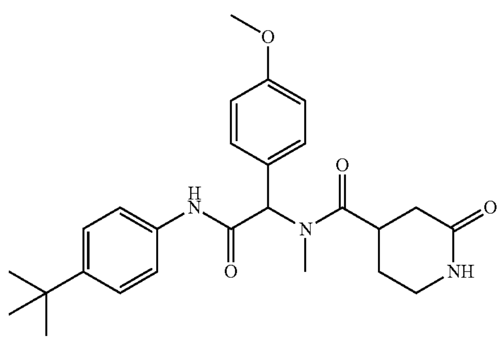 | | 438.2 (M + H) |
| 196 | N-(2-((4-(2,2-dimethylpropyl)phenyo)amino)-1-(4-(methoxyphenyl)-2-oxoethyl)-3-hydroxy-N-methyl-1,2-oxazole-5-carboxamide | 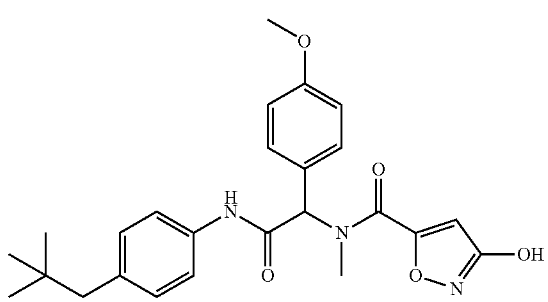 [SMILES: COc1ccc(C(C(=O)Nc2ccc(CC(C)(C)C)cc2)N(C)C(=O)c2cc(O)no2)cc1] | | 450.1 (M − H) |

TABLE 1-20-continued

| Ex. No | IUPAC NAME | Structure | Salt | MS (Found) |
|---|---|---|---|---|
| 197 | (3S)-N-((1R)-2-((4-tert-butylphenyl)amino)-1-(4-methoxyphenyl)-2-oxoethyl)-5-oxopyrrolidine-3-carboxamide | 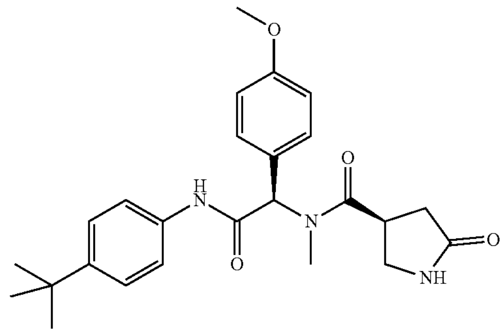 | | 424.2 (M + H) |
| 198 | (3R)-N-((1R)-2-((4-tert-butylphenyl)amino)-1-(4-methoxyphenyl)-2-oxoethyl)-5-oxopyrrolidine-3-carboxamide | 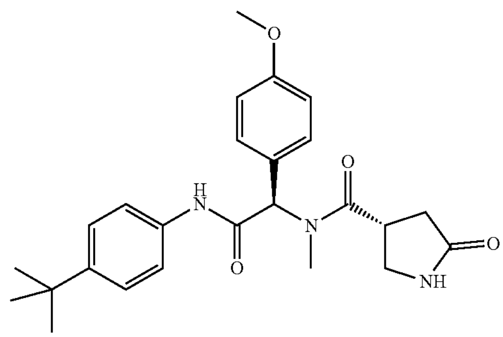 | | 424.2 (M + H) |
| 199 | 3-hydroxy-N-(1-(4-methoxyphenyl)-2-oxo-2-((4-((trimethylsilyl)methyl)phenyl)amino)ethyl)-N-methyl-1,2-oxazole-5-carboxamide | 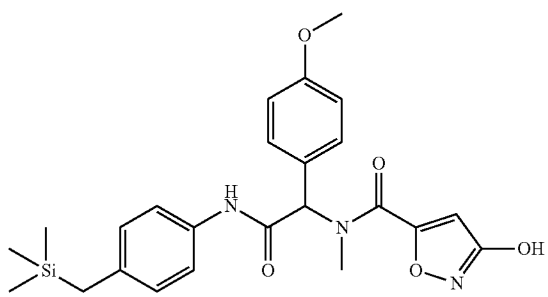 [SMILES: COc1ccc(C(C(=O)Nc2ccc(C[Si](C)(C)C)cc2)N(C)C(=O)c2cc(O)no2)cc1] | | 466.0 (M − H) |
| 200 | N-(2-((4-tert-butylphenyl)amino)-1-(4-(methoxyphenyl)-2-oxoethyl)-N-methyl-2-(6-oxo-1,6-dihydropyridin-2-yl)acetamide | 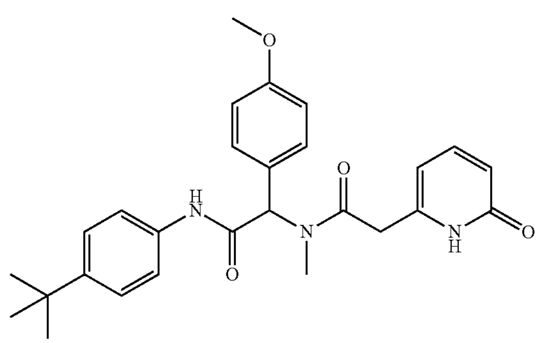 [SMILES: COc1ccc(C(C(=O)Nc2ccc(C(C)(C)C)cc2)N(C)C(=O)Cc2cccc(=O)[nH]2)cc1] | | 462.2 (M + H) |

TABLE 1-20-continued

| Ex. No | IUPAC NAME | Structure | Salt | MS (Found) |
|---|---|---|---|---|
| 201 | N-(4-tert-butylphenyl)-2-(4-methoxyphenyl)-2-(((6-oxo-1,6-dihydropyridin-2-yl)acetyl)amino)acetamide | 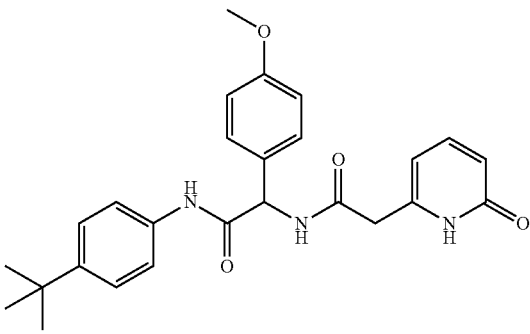 [SMILES: COc1ccc(C(NC(=O)Cc2cccc(=O)[nH]2)C(=O)Nc2ccc(C(C)(C)C)cc2)cc1] | | 448.2 (M + H) |

TABLE 1-21

| Ex. No. | IUPAC NAME | Structure | Salt | MS (Found) |
|---|---|---|---|---|
| 202 | N-(1-(4-methoxyphenyl)-2-oxo-2-((4-(trimethylsilyl)phenyl)amino)ethyl)-N-methyl-2-oxo-2,3-dihydro-1,3-oxazole-5-carboxamide | 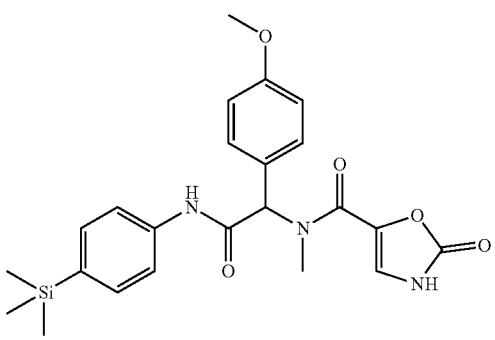 [SMILES: COc1ccc(C(C(=O)Nc2ccc([Si](C)(C)C)cc2)N(C)C(=O)c2c[nH]c(=O)o2)cc1] | | 452.0 (M − H) |
| 203 | 2-bromo-N-(2-((4-tert-butylphenyl)amino)-1-(4-methoxyphenyl)-2-oxoethyl)-N-methyl-1,3-thiazole-5-carboxamide | 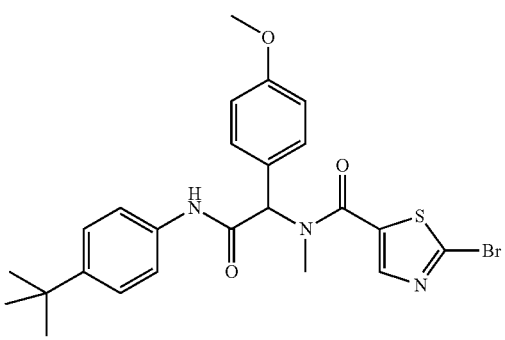 [SMILES: COc1ccc(C(C(=O)Nc2ccc(C(C)(C)C)cc2)N(C)C(=O)c2cnc(Br)s2)cc1] | | 513.8 (M − H) |
| 204 | N-(2-((4-tert-butylphenyl)amino)-1-(4-methoxyphenyl)-2-oxoethyl)-N-methyl-2-oxo-2,3-dihydro-1,3-thiazole-5-carboxamide | 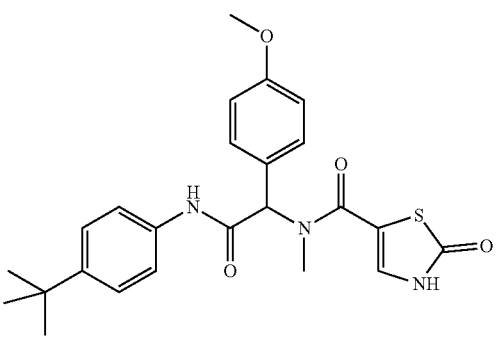 [SMILES: COc1ccc(C(C(=O)Nc2ccc(C(C)(C)C)cc2)N(C)C(=O)c2c[nH]c(=O)s2)cc1] | | 454.1 (M + H) |

TABLE 1-21-continued

| Ex. No. | IUPAC NAME | Structure | Salt | MS (Found) |
|---|---|---|---|---|
| 205 | N-(1-(4-methoxyphenyl)-2-oxo-2-((4-(trimethylsilyl)phenyl)amino)ethyl)-N-methyl-2-oxo-2,3-dihydro-1,3-oxazole-4-carboxamide | 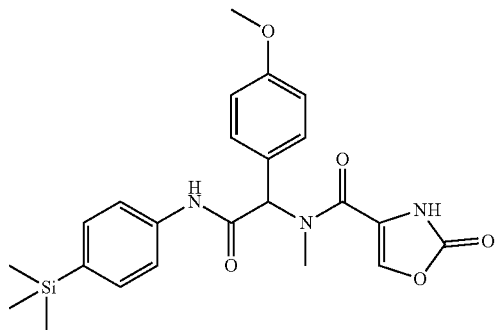 [SMILES: COc1ccc(C(C(=O)Nc2ccc([Si](C)(C)C)cc2)N(C)C(=O)c2coc(=O)[nH]2)cc1] | | 451.9 (M − H) |
| 206 | 3-hydroxy-N-(1-(4-methoxyphenyl)-2-oxo-2-((4-(trimethylgermyl)phenyl)amino)ethyl)-N-methyl-1,2-oxazole-5-carboxamide | 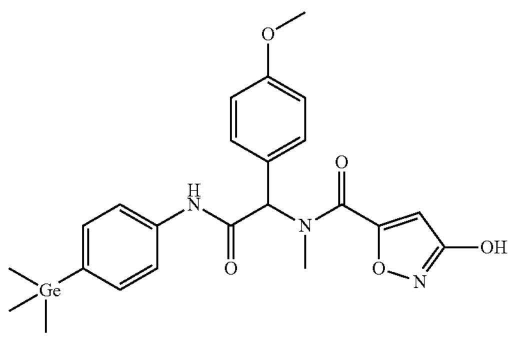 | | 497.9 (M − H) |
| 207 | N-(2-((4-(cyclopropyl(dimethyl)silyl)phenyl)amino)-1-(4-methoxyphenyl)-2-oxoethyl)-3-hydroxy-N-methyl-1,2-oxazole-5-carboxamide | 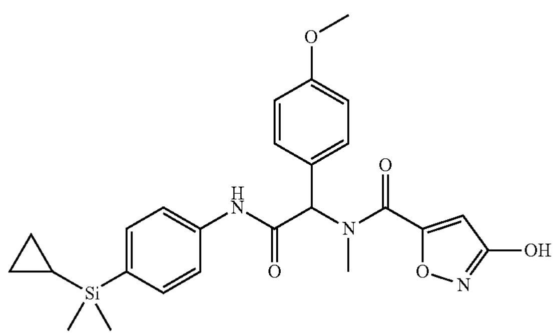 | | 478.0 (M − H) |
| 208 | N-(1-(4-ethoxyphenyl)-2-oxo-2-((4-(trimethylsilyl)phenyl)amino)ethyl)-5-oxopyrrolidine-3-carboxamide (mixture of four optical isomers) | 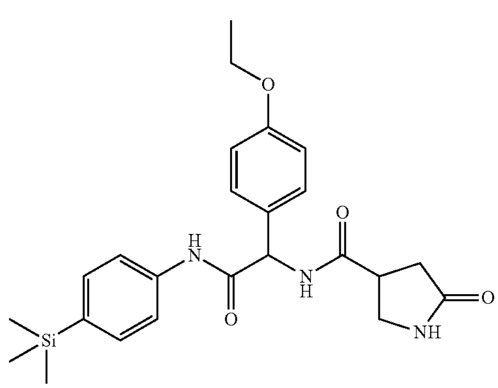 [SMILES: CCOc1ccc(C(NC(=O)C2CNC(=O)C2)C(=O)Nc2ccc([Si](C)(C)C)cc2)cc1] | | 452.0 (M − H) |

TABLE 1-21-continued

| Ex. No. | IUPAC NAME | Structure | Salt | MS (Found) |
|---|---|---|---|---|
| 209 | N-(2-((4-(cyclopropyl (dimethyl)germyl) phenyl)amino)-1- (4-methoxyphenyl)-2-oxoethyl)- 3-hydroxy-N-methyl- 1,2-oxazole-5-carboxamide | 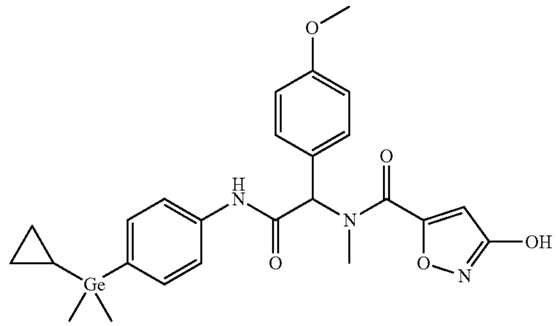 | | 524.0 (M − H) |
| 210 | N-(4-tert-butylphenyl)-2- (4-methoxyphenyl)-2-(((6- oxo-1,6-dihydropyridin-3- yl)acetyl)amino)acetamide | 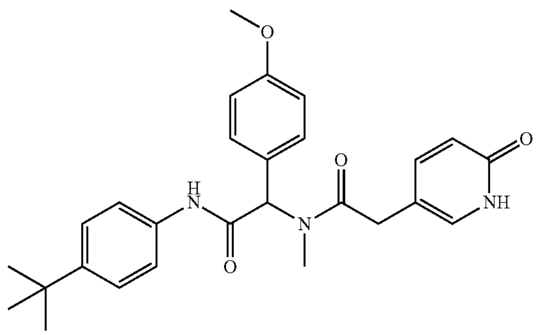 | | 448.1 (M + H) |

TABLE 1-22

| Ex. No. | IUPAC NAME | Structure | Salt | MS (Found) |
|---|---|---|---|---|
| 211 | 5-(hydroxymethyl)-N- (1-(4-methoxyphenyl)-2-oxo-2- ((4-(trimethylsilyl)phenyl) amino)ethyl)-N-methyl-1,2- oxazole-3-carboxamide | 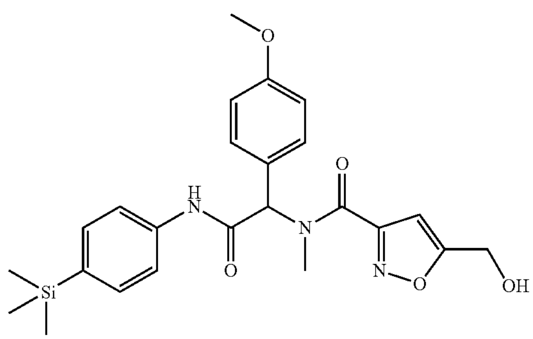 [SMILES: COc1ccc(C(C(=O)Nc2ccc([Si](C)(C)C)cc2)N(C)C(=O)c2cc(CO)on2)cc1] | | 466.0 (M − H) |
| 212 | N-(2-((4-(ethyl(dimethyl) silyl)phenyl)amino)-1-(4- methoxyphenyl)-2-oxoethyl)- 3-hydroxy-N-methyl-1,2- oxazole-5-carboxamide | 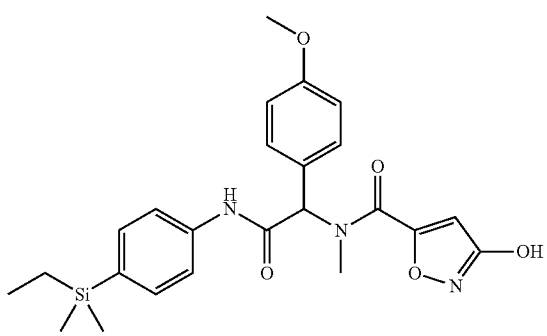 [SMILES: CC[Si](C)(C)c1ccc(NC(=O)C(c2ccc(OC)cc2)N(C)C(=O)c2cc(O)no2)cc1] | | 468.2 (M + H) |

TABLE 1-22-continued

| Ex. No. | IUPAC NAME | Structure | Salt | MS (Found) |
|---|---|---|---|---|
| 213 | N-ethyl-3-hydroxy-N-(1-(4-methoxyphenyl)-2-oxo-2-((4-(trimethylsilyl)phenyl)amino)ethyl)-1,2-oxazole-5-carboxamide | 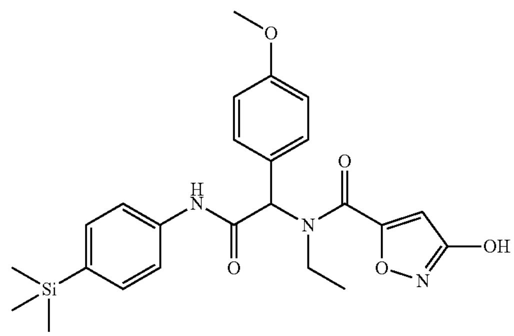 [SMILES: CCN(C(=O)c1cc(O)no1)C(C(=O)Nc1ccc([Si](C)(C)C)cc1)c1ccc(OC)cc1] | | 466.0 (M − H) |
| 214 | N-(4-tert-butylphenyl)-2-(1,8-dioxo-2,7-diazaspiro[4.4]non-2-yl)-2-(4-methoxyphenyl)acetamide (mixture of four optical isomers) | 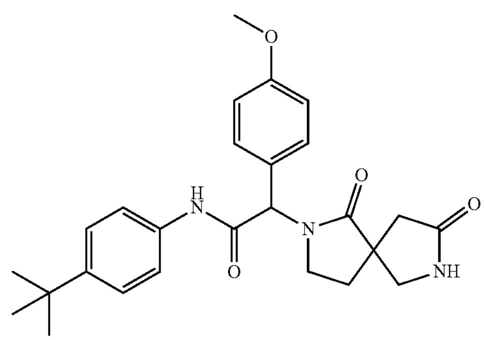 [SMILES: COc1ccc(C(C(=O)Nc2ccc(C(C)(C)C)cc2)N2CCC3(CNC(=O)C3)C2=O)cc1] | | 450.2 (M + H) |
| 216 | N-(2-((4-ethyl(dimethyl)silyl)phenyl)amino)-1-(4-(methoxyphenyl)-2-oxoethyl)-5-oxopyrrolidine-3-carboxamide (mixture of four optical isomers) | 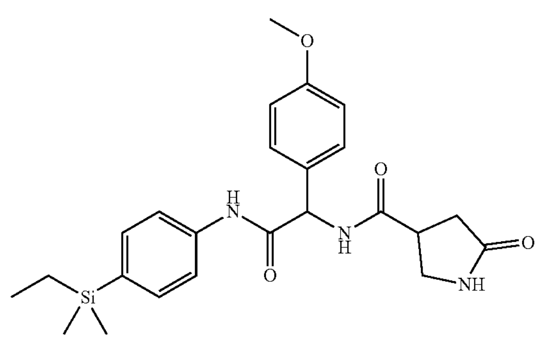 [SMILES: CC[Si](C)(C)c1ccc(NC(=O)C(NC(=O)C2CNC(=O)C2)c2ccc(OC)cc2)cc1] | | 454.2 (M + H) |
| 217 | N-(2-((4-ethyl(dimethyl)silyl)phenyl)amino)-1-(4-methoxyphenyl)-2-oxoethyl)-2-oxopiperidine-4-carboxamide (mixture of four optical isomers) | 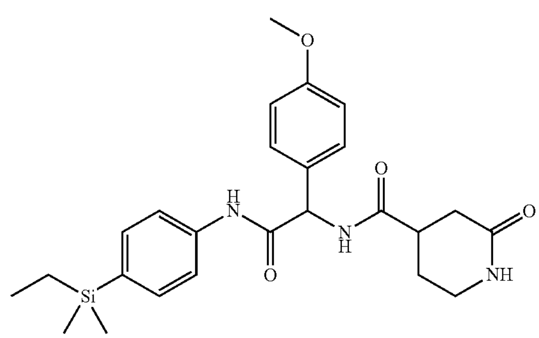 [SMILES: CC[Si](C)(C)c1ccc(NC(=O)C(NC(=O)C2CCNC(=O)C2)c2ccc(OC)cc2)cc1] | | 468.2 (M + H) |

TABLE 1-22-continued

| Ex. No. | IUPAC NAME | Structure | Salt | MS (Found) |
|---|---|---|---|---|
| 218 | N-(2-((2-fluoro-4-(trimethylsilyl)phenyl)amino)-1-(4-methoxyphenyl)-2-oxoethyl)-5-oxopyrrolidine-3-carboxamide (mixture of four optical isomers) | 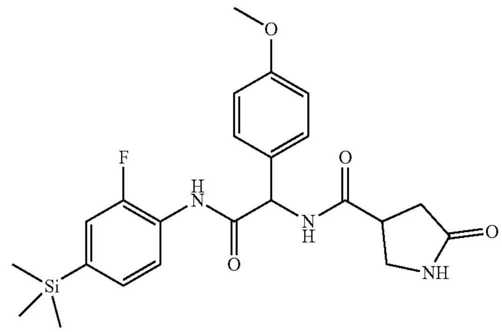 [SMILES: COc1ccc(C(NC(=O)C2CNC(=O)C2)C(=O)Nc2ccc([Si](C)(C)C)cc2F)cc1] | | 458.2 (M + H) |
| 219 | N-(2-((2-fluoro-4-(trimethylsilyl)phenyl)amino)-1-(4-methoxyphenyl)-2-oxoethyl)-3-hydroxy-N-methyl-1,2-oxazole-5-carboxamide | 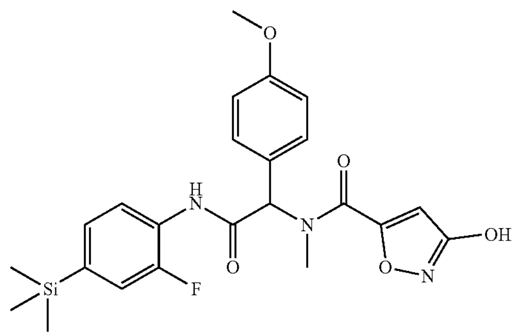 [SMILES: COc1ccc(C(C(=O)Nc2ccc([Si](C)(C)C)cc2F)N(C)C(=O)c2cc(O)no2)cc1] | | 470.0 (M − H) |
| 220 | N-(2-((4-tert-butylphenyl)amino)-1-(4-methoxyphenyl)-2-oxoethyl)-4-oxoimidazolidine-1-carboxamide | 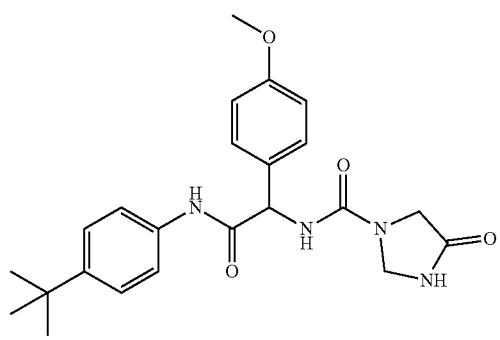 [SMILES: COc1ccc(C(NC(=O)N2CNC(=O)C2)C(=O)Nc2ccc(C(C)(C)C)cc2)cc1] | | 425.2 (M + H) |
| 221 | N-(2-((4-tert-butylphenyl)amino)-1-(4-methoxyphenyl)-2-oxoethyl)-3-methyl-5-oxopyrrolidine-3-carboxamide (mixture of four optical isomers) | 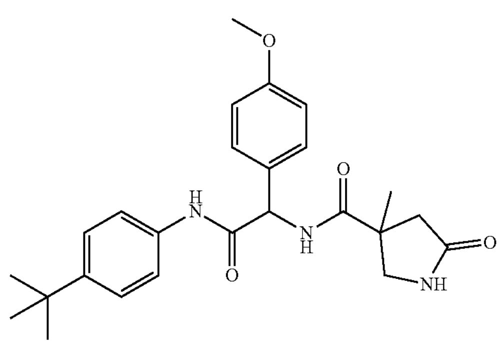 [SMILES: COc1ccc(C(NC(=O)C2(C)CNC(=O)C2)C(=O)Nc2ccc(C(C)(C)C)cc2)cc1] | | 438.2 (M + H) |

TABLE 1-23

| Ex. No. | IUPAC NAME | Structure | Salt | MS (Found) |
|---|---|---|---|---|
| 222 | N-(1-(4-methoxyphenyl)-2-oxo-2-((4-(trimethylsilyl)phenyl)amino)ethyl)-4-oxoimidazolidine-1-carboxamide | 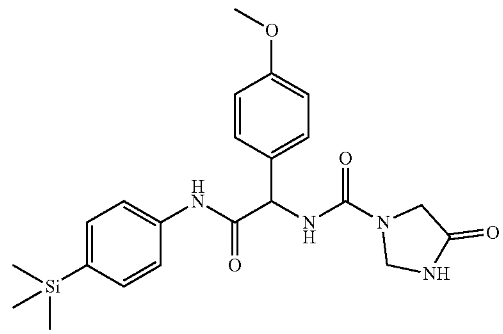 [SMILES: COc1ccc(C(NC(=O)N2CNC(=O)C2)C(=O)Nc2ccc([Si](C)(C)C)cc2)cc1] | | 441.2 (M + H) |
| 223 | N-(2-((4-(2,2-dimethylpropyl)phenyl)amino)-1-(4-(methoxyphenyl)-2-oxoethyl)-2-oxopiperidine-4-carboxamide (mixture of four optical isomers) | 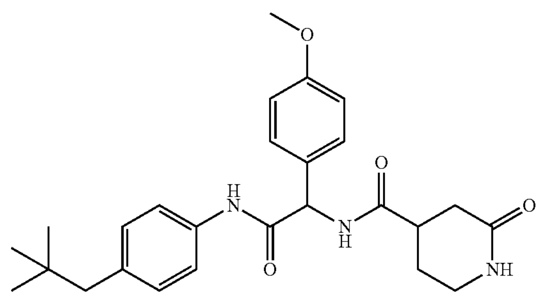 [SMILES: COc1ccc(C(NC(=O)C2CCNC(=O)C2)C(=O)Nc2ccc(CC(C)(C)C)cc2)cc1] | | 452.2 (M + H) |
| 224 | N-(1-(4-methoxyphenyl)-2-oxo-2-((4-(trimethylsilyl)phenyl)amino)ethyl)-2-oxopiperidine-4-carboxamide (mixture of four optical isomers) | 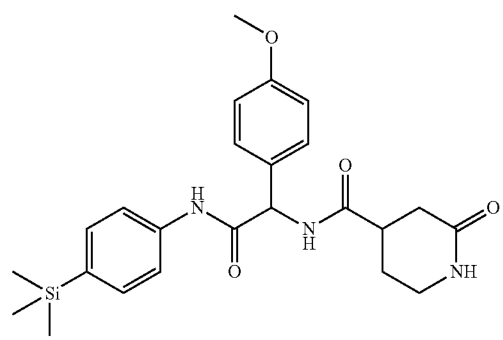 [SMILES: COc1ccc(C(NC(=O)C2CCNC(=O)C2)C(=O)Nc2ccc([Si](C)(C)C)cc2)cc1] | | 454.2 (M + H) |
| 225 | 3-hydroxy-N-(1-(4-(methoxymethyl)phenyl)-2-oxo-2-(((4-(trimethylsilyl)phenyl)amino)ethyl)-N-methyl-1,2-oxazole-5-carboxamide | 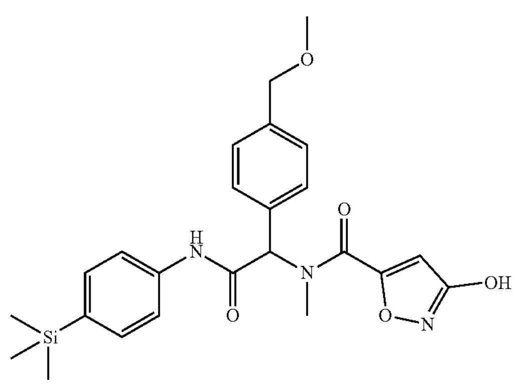 [SMILES: COCc1ccc(C(C(=O)Nc2ccc([Si](C)(C)C)cc2)N(C)C(=O)c2cc(O)no2)cc1] | | 466.0 (M − H) |

TABLE 1-23-continued

| Ex. No. | IUPAC NAME | Structure | Salt | MS (Found) |
|---|---|---|---|---|
| 226 | N-(1-(4-methoxyphenyl)-2-oxo-2-((4-(trimethylsilyl)phenyl)amino)ethyl)tetrahydrofuran-2-carboxamide | 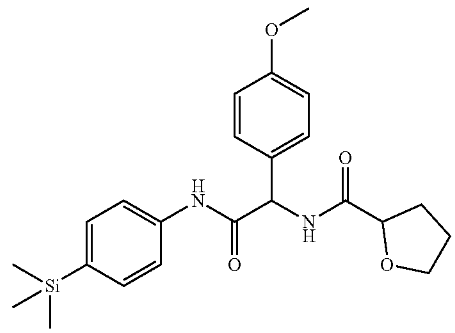 [SMILES: COc1ccc(C(NC(=O)C2CCCO2)C(=O)Nc2ccc([Si](C)(C)C)cc2)cc1] | | 427.2 (M + H) |
| 227 | N-(1-(4-methoxyphenyl)-2-oxo-2-((4-(trimethylsilyl)phenyl)amino)ethyl)-2-oxoimidazolidine-4-carboxamide | 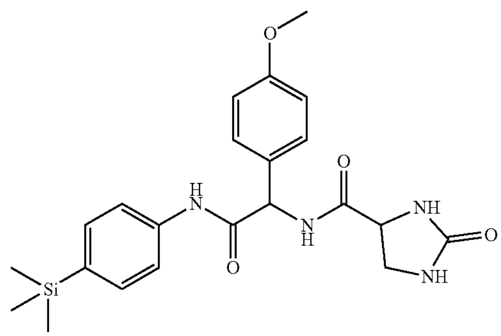 [SMILES: COc1ccc(C(NC(=O)C2CNC(=O)N2)C(=O)Nc2ccc([Si](C)(C)C)cc2)cc1] | | 439.0 (M − H) |
| 228 | N-(1-(4-methoxyphenyl)-2-oxo-2-((4-(trimethylsilyl)phenyl)amino)ethyl)tetrahydrofuran-3-carboxamide | 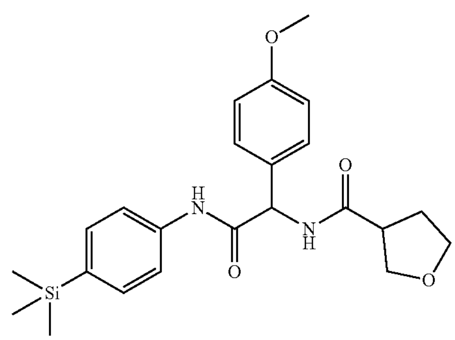 [SMILES: COc1ccc(C(NC(=O)C2CCOC2)C(=O)Nc2ccc([Si](C)(C)C)cc2)cc1] | | 427.2 (M + H) |
| 229 | 5-hydroxy-N-(1-(4-methoxyphenyl)-2-oxo-2-((4-(trimethylsilyl)phenyl)amino)ethyl)pyridine-2-carboxamide | 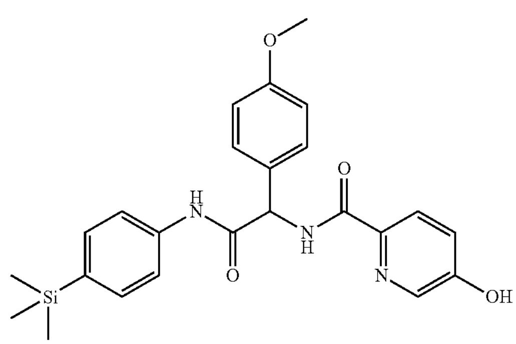 [SMILES: COc1ccc(C(NC(=O)c2ccc(O)cn2)C(=O)Nc2ccc([Si](C)(C)C)cc2)cc1] | | 450.1 (M + H) |

TABLE 1-23-continued

| Ex. No. | IUPAC NAME | Structure | Salt | MS (Found) |
|---|---|---|---|---|
| 230 | 6-acetamido-N-(1-(4-methoxyphenyl)-2-oxo-2-((4-(trimethylsilyl)phenyl)amino)ethyl)nicotinamide | 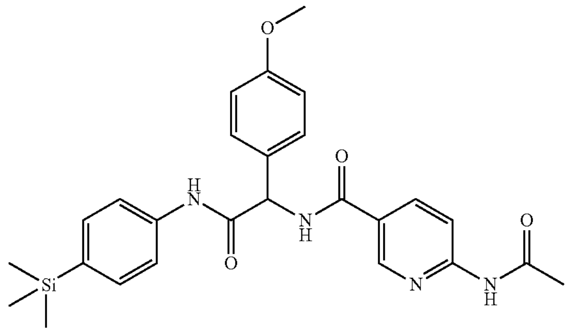 | | 491.3 (M + H) |
| 231 | 2-((1H-imidazol-4-ylacetyl)amino)-2-(4-methoxyphenyl)-N-(4-(trimethylsilyl)phenyl)acetamide | 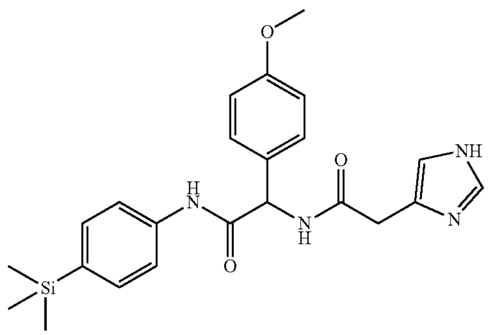 [SMILES: COc1ccc(C(NC(=O)Cc2c[nH]cn2)C(=O)Nc2ccc([Si](C)(C)C)cc2)cc1] | | 437.2 (M + H) |

TABLE 1-24

| Ex. No. | UPAC NAME | Structure | Salt | MS (Found) |
|---|---|---|---|---|
| 232 | methyl 5-((1-(4-methoxyphenyl)-2-oxo-2-((4-(trimethylsilyl)phenyl)amino)ethyl)(methyl)carbomoyl)pyridine-2-carboxylate | 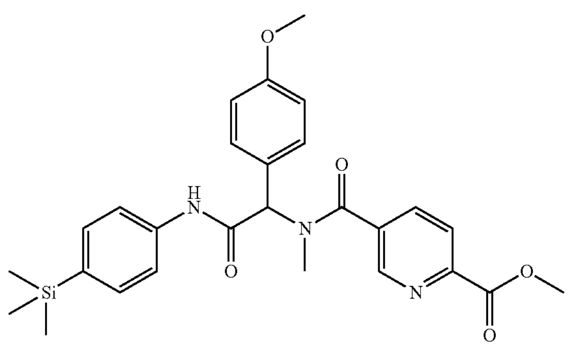 | | 506.2 (M + H) |
| 233 | 5-((1-(4-methoxyphenyl)-2-oxo-2-((4-(trimethylsilyl)phenyl)amino)ethyl)(methyl)carbomoyl)pyridine-2-carboxylic acid | 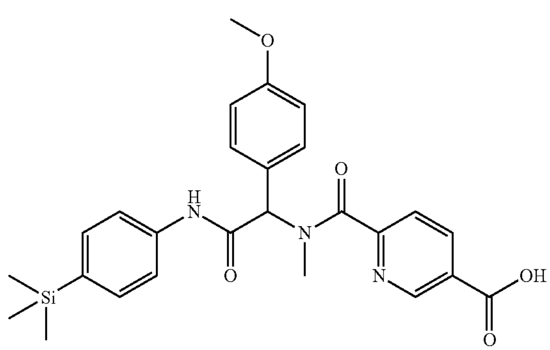 [SMILES: COc1ccc(C(C(=O)Nc2ccc([Si](C)(C)C)cc2)N(C)C(=O)c2ccc(C(=O)O)cn2)cc1] | | 492.2 (M + H) |

TABLE 1-24-continued

| Ex. No. | UPAC NAME | Structure | Salt | MS (Found) |
|---|---|---|---|---|
| 234 | 6-(hydroxymethyl)-N-(1-(4-methoxyphenyl)-2-oxo-2-((4-(trimethylsilyl)phenyl)amino)ethyl)-N-methylnicotinamide | 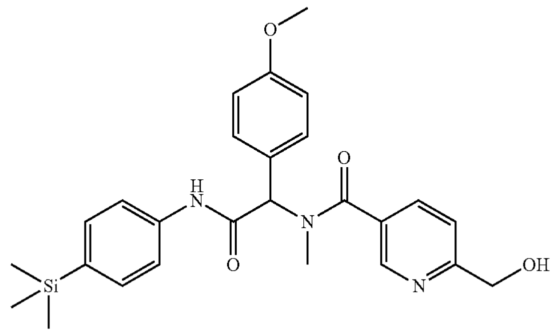 [SMILES: COc1ccc(C(C(=O)Nc2ccc([Si](C)(C)C)cc2)N(C)C(=O)c2ccc(CO)nc2)cc1] | | 478.2 (M + H) |
| 235 | 1-hydroxy-N-(1-(4-methoxyphenyl)-2-oxo-2-((4-(trimethylsilyl)phenyl)amino)ethyl)-5-oxopyrrolidine-3-carboxamide (mixture of four optical isomers) | 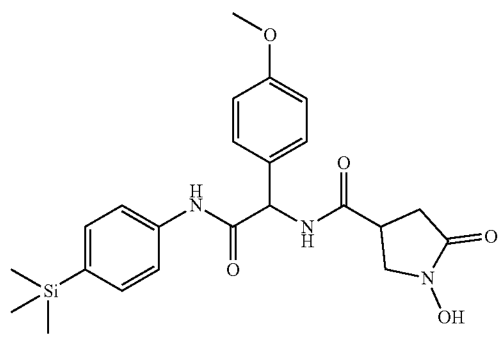 [SMILES: COc1ccc(C(NC(=O)C2CC(=O)N(O)C2)C(=O)Nc2ccc([Si](C)(C)C)cc2)cc1] | | 456.1 (M + H) |
| 236 | 3-hydroxy-N-(1-(4-methoxy-3-methylphenyl)-2-oxo-2-((4-(trimethylsilyl)phenyl)amino)ethyl)-N-methyl-1,2-oxazole-5-carboxamide | 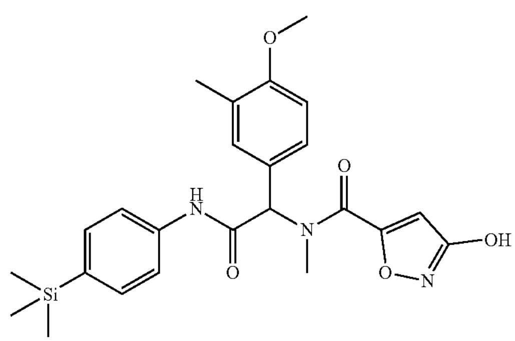 [SMILES: COc1ccc(C(C(=O)Nc2ccc([Si](C)(C)C)cc2)N(C)C(=O)c2cc(O)no2)cc1C] | | 466.0 (M − H) |
| 237 | 2-((cyanoacetyl)amino)-2-(4-methoxyphenyl)-N-(4-(trimethylsilyl)phenyl)acetamide | 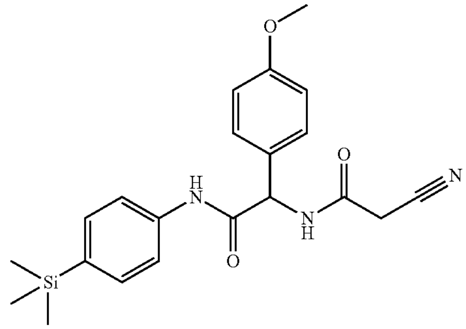 [SMILES: COc1ccc(C(NC(=O)CC#N)C(=O)Nc2ccc([Si](C)(C)C)cc2)cc1] | | 396.2 (M + H) |

TABLE 1-24-continued

| Ex. No. | UPAC NAME | Structure | Salt | MS (Found) |
|---|---|---|---|---|
| 238 | (3Z)-3-amino-3-(hydroxylmino)-N-(1-(4-methoxyphenyl)-2-oxo-2-((4-(trimethylsilyl)phenyl)amino)ethyl)propanamide | 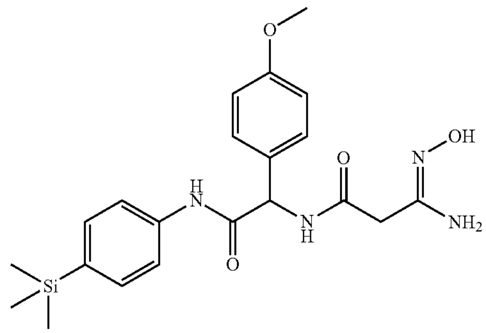 [SMILES: COc1ccc(C(NC(=O)C/C(N)=N/O)C(=O)Nc2ccc([Si](C)(C)C)cc2)cc1] | | 429.2 (M + H) |
| 239 | 2-(4-methoxyphenyl)-2-(((5-oxo-4,5-dihydro-1,2,4-oxadiazol-3-yl)acetyl)amino)-N-(4-(trimethylsilyl)phenyl)acetamide | 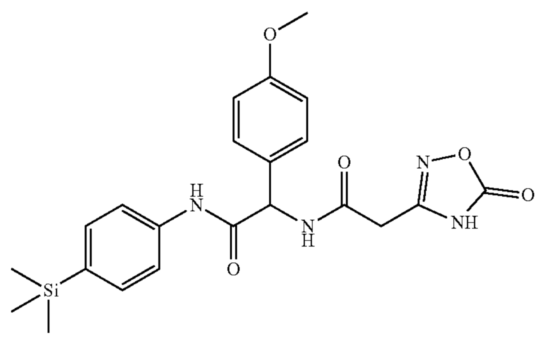 [SMILES: COc1ccc(C(NC(=O)Cc2noc(=O)[nH]2)C(=O)Nc2ccc([Si](C)(C)C)cc2)cc1] | | 453.0 (M − H) |
| 240 | 1-cyano-N-(1-(4-methoxyphenyl)-2-oxo-2-((4-(trimethylsilyl)phenyl)amino)ethyl)cyclopropane-carboxamide | 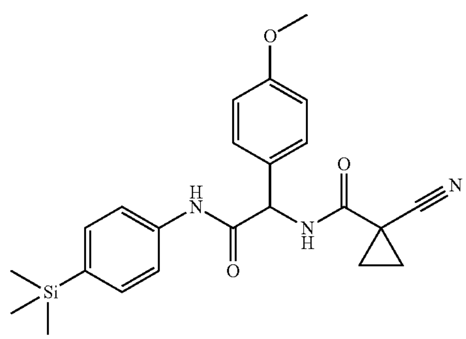 [SMILES: COc1ccc(C(NC(=O)C2(C#N)CC2)C(=O)Nc2ccc([Si](C)(C)C)cc2)cc1] | | 422.2 (M + H) |
| 241 | 1-cyano-N-(1-(4-methoxyphenyl)-2-oxo-2-((4-(trimethylsilyl)phenyl)amino)ethyl)-N-methylcyclopropane-carboxamide | 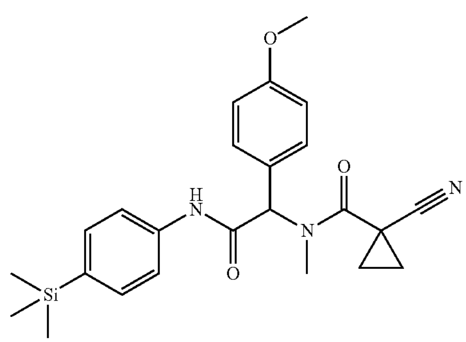 [SMILES: COc1ccc(C(C(=O)Nc2ccc([Si](C)(C)C)cc2)N(C)C(=O)C2(C#N)CC2)cc1] | | 434.0 (M − H) |

TABLE 1-25

| Ex. No | IUPAC NAME | Structure | Salt | MS (Found) |
|---|---|---|---|---|
| 242 | N-(2-((4-tert-butyl-3-chlorophenyl)amino)-1-(4-methoxyphenyl)-2-oxoethyl)-3-hydroxy-N-methyl-1,2-oxazole-5-carboxamide | 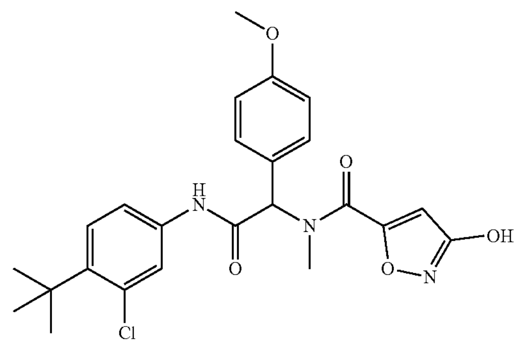 [SMILES: COc1ccc(C(C(=O)Nc2ccc(C(C)(C)C)c(Cl)c2)N(C)C(=O)c2cc(O)no2)cc1] | | 470.0 (M − H) |
| 243 | N-(2-cyanoethyl)-3-hydroxy-N-(1-(4-methoxyphenyl)-2-oxo-2-((4-(trimethylsilyl)phenyl)amino)ethyl)-1,2-oxazole-5-carboxamide | 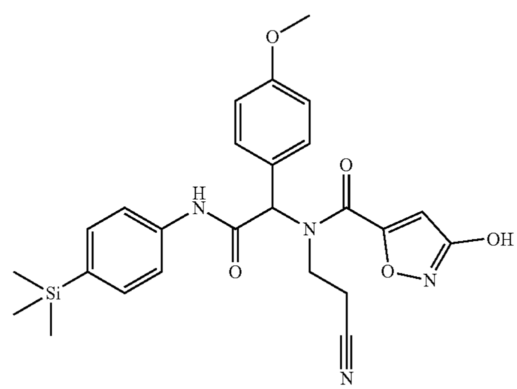 [SMILES: COc1ccc(C(C(=O)Nc2ccc([Si](C)(C)C)cc2)N(CCC#N)C(=O)c2cc(O)no2)cc1] | | 491.1 (M − H) |
| 244 | 3-(benzyloxy)-N-(1-(4-methoxyphenyl)-2-oxo-2-((4-(trimethylsilyl)phenyl)amino)ethyl)pyrrolidine-1-carboxamide (mixture of four optical isomers) | 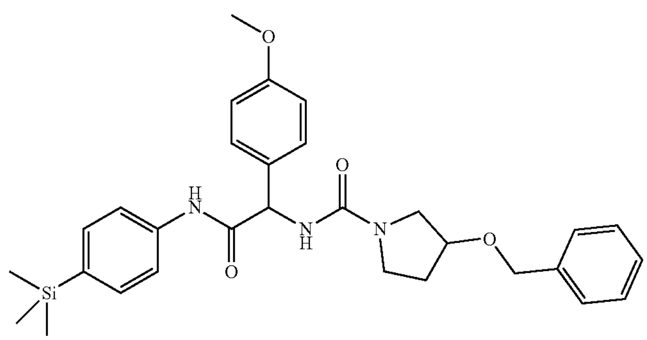 [SMILES: COc1ccc(C(NC(=O)N2CCC(OCc3ccccc3)C2)C(=O)Nc2ccc([Si](C)(C)C)cc2)cc1] | | 532.2 (M + H) |
| 245 | N-(1-(4-methoxyphenyl)-2-oxo-2-((4-(trimethylsilyl)phenyl)amino)ethyl)-3-oxopiperazine-1-carboxamide | 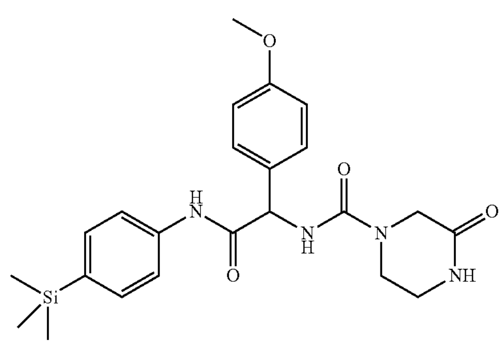 [SMILES: COc1ccc(C(NC(=O)N2CCNC(=O)C2)C(=O)Nc2ccc([Si](C)(C)C)cc2)cc1] | | 455.2 (M + H) |

TABLE 1-25-continued

| Ex. No | IUPAC NAME | Structure | Salt | MS (Found) |
|---|---|---|---|---|
| 246 | N-(1-(4-methoxyphenyl)-2-oxo-2-((4-(trimethylsilyl)phenyl)amino)ethyl)-2-oxa-6-azaspiro[3.5]nonane-6-carboxamide | 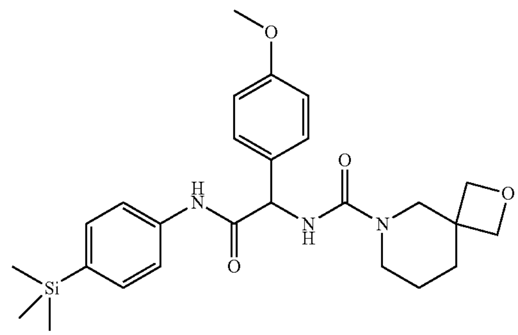 [SMILES: COc1ccc(C(NC(=O)N2CCCC3(COC3)C2)C(=O)Nc2ccc([Si](C)(C)C)cc2)cc1] | | 482.2 (M + H) |
| 247 | 3-hydroxy-N-(1-(4-methoxyphenyl)-2-oxo-2-((4-(trimethylsilyl)phenyl)amino)ethyl)pyrrolidine-1-carboxamide (mixture of four optical isomers) | 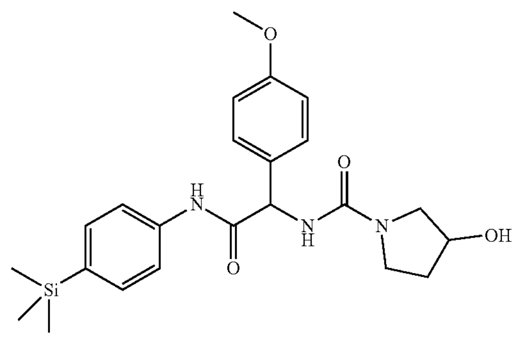 [SMILES: COc1ccc(C(NC(=O)N2CCC(O)C2)C(=O)Nc2ccc([Si](C)(C)C)cc2)cc1] | | 442.2 (M + H) |
| 248 | N-(1-(4-methoxyphenyl)-2-oxo-2-((4-(trimethylsilyl)phenyl)amino)ethyl)-2-oxa-6-azaspiro[3.4]octane-6-carboxamide | 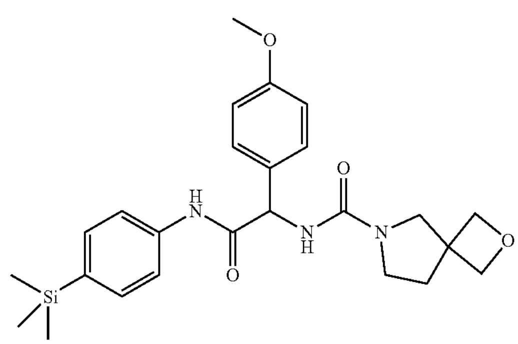 [SMILES: COc1ccc(C(NC(=O)N2CCC3(COC3)C2)C(=O)Nc2ccc([Si](C)(C)C)cc2)cc1] | | 468.1 (M + H) |
| 249 | oxetan-3-yl (1-(4-methoxyphenyl)-2-oxo-2-((4-(trimethylsilyl)phenyl)amino)ethyl)carbamate | 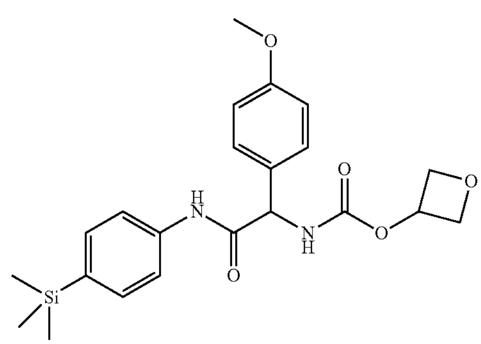 [SMILES: COc1ccc(C(NC(=O)OC2COC2)C(=O)Nc2ccc([Si](C)(C)C)cc2)cc1] | | 429.2 (M + H) |

TABLE 1-25-continued

| Ex. No | IUPAC NAME | Structure | Salt | MS (Found) |
|---|---|---|---|---|
| 250 | 2-(4-ethoxyphenyl)-2-(((1-methyl-1H-pyrazol-4-yl)acetyl)amino)-N-(4-(trimethylsilyl)phenyl)acetamide | 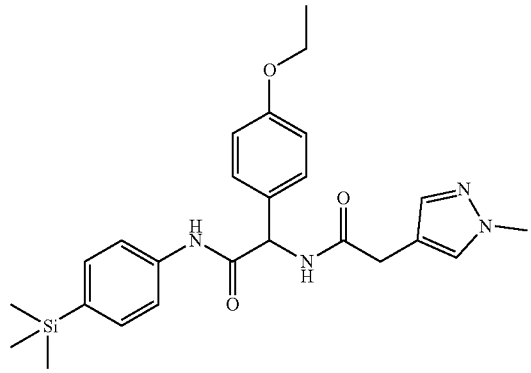 | | 465.1 (M + H) |
| 251 | 2-(4-ethoxyphenyl)-2-(((1-methyl-1H-pyrazol-4-yl)acetyl)amino)-N-(4-(trimethylgermyl)phenyl)acetamide | 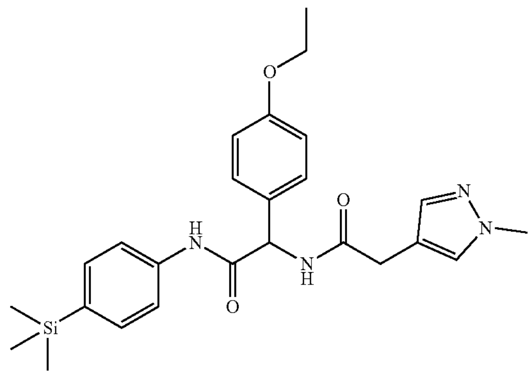 | | 511.2 (M + H) |

TABLE 1-26

| Ex. No. | IUPAC NAME | Structure | Salt | MS (Found) |
|---|---|---|---|---|
| 252 | 2-(2,3-dihydro-1-benzofuran-5-yl)-2-(((1-methyl-1H-pyrazol-4-yl)acetyl)amino)-N-(4-(trimethylsilyl)phenyl)acetamide | 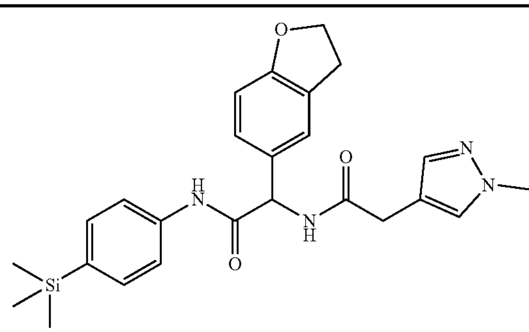 | | 463.2 (M + H) |
| 253 | 2-(4-methoxyphenyl)-2-((1H-pyrazol-1-yl)acetyl)amino)-N-(4-(trimethylsilyl)phenyl)acetamide | 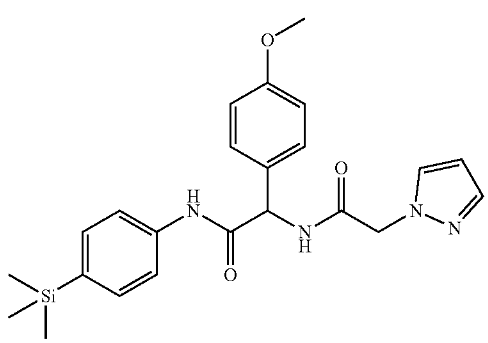 [SMILES: COc1ccc(C(NC(=O)Cn2cccn2)C(=O)Nc2ccc([Si](C)(C)C)cc2)cc1] | | 437.2 (M + H) |

TABLE 1-26-continued

| Ex. No. | IUPAC NAME | Structure | Salt | MS (Found) |
|---|---|---|---|---|
| 255 | 3-cyano-N-(1-(4-methoxyphenyl)-2-oxo-2-((4-(trimethylsilyl)phenyl)amino)ethyl)azetidine-1-carboxamide | 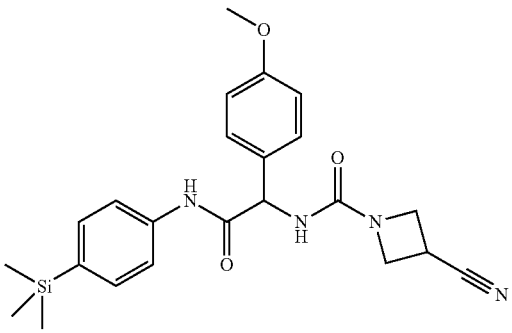 [SMILES: COc1ccc(C(NC(=O)N2CC(C#N)C2)C(=O)Nc2ccc([Si](C)(C)C)cc2)cc1] | | 437.2 (M + H) |
| 256 | N-(2-((4-tert-butyl-3-cyanophenyl)amino)-1-(4-methoxyphenyl)-2-oxoethyl)-5-oxopyrrolidine-3-carboxamide (mixture of four optical isomers) | 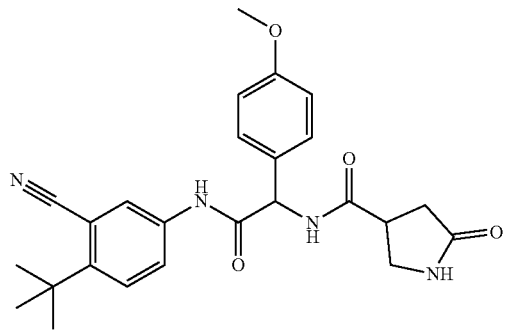 [SMILES: COc1ccc(C(NC(=O)C2CNC(=O)C2)C(=O)Nc2ccc(C(C)(C)C)c(C#N)c2)cc1] | | 449.2 (M + H) |
| 257 | 2-(4-methoxyphenyl)-2-((((1-methyl-1H-pyrazol-3-yl)oxy)acetyl)amino)-N-(4-(trimethylsilyl)phenyl)acetamide | 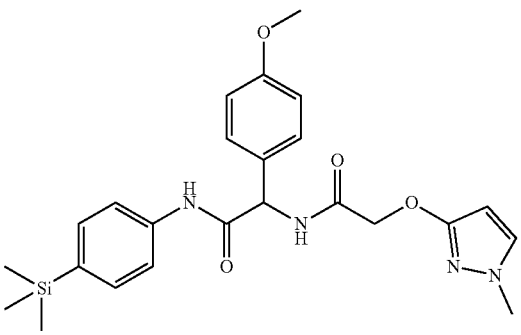 [SMILES: COc1ccc(C(NC(=O)COc2ccn(C)n2)C(=O)Nc2ccc([Si](C)(C)C)cc2)cc1] | | 467.2 (M + H) |
| 258 | 3-hydroxy-N-(1-(4-methoxyphenyl)-2-oxo-2-((4-(trimethylsilyl)phenyl)amino)ethyl)piperidine-1-carboxamide (mixture of four optical isomers) | 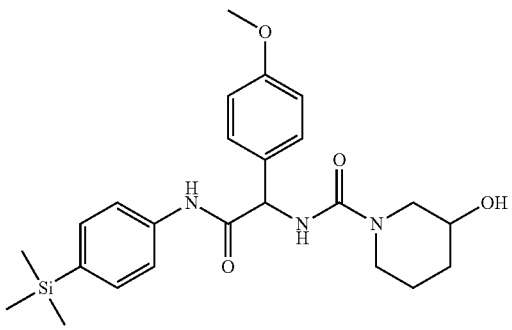 [SMILES: COc1ccc(C(NC(=O)N2CCCC(O)C2)C(=O)Nc2ccc([Si](C)(C)C)cc2)cc1] | | 456.1 (M + H) |

TABLE 1-26-continued

| Ex. No. | IUPAC NAME | Structure | Salt | MS (Found) |
|---|---|---|---|---|
| 259 | 2-(hydroxymethyl)-N-(1-(4-methoxyphenyl)-2-oxo-2-((4-(trimethylsilyl)phenyl)amino)ethyl)pyrrolidine-1-carboxamide (mixture of four optical isomers) | 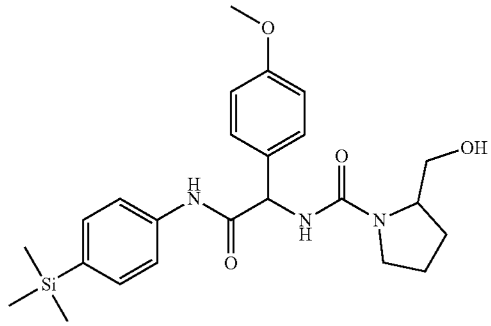 [SMILES: COc1ccc(C(NC(=O)N2CCCC2CO)C(=O)Nc2ccc([Si](C)(C)C)cc2)cc1] | | 456.2 (M + H) |
| 260 | 2-(hydroxymethyl)-N-(1-(4-methoxyphenyl)-2-oxo-2-((4-(trimethylsilyl)phenyl)amino)ethyl)piperidine-1-carboxamide (mixture of four optical isomers) | 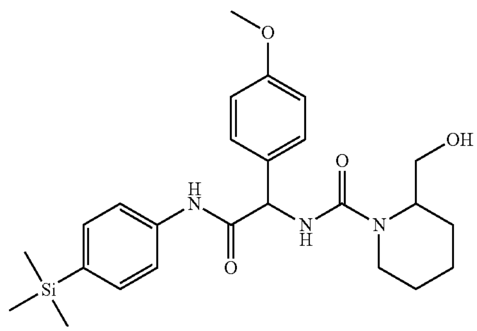 [SMILES: COc1ccc(C(NC(=O)N2CCCCC2CO)C(=O)Nc2ccc([Si](C)(C)C)cc2)cc1] | | 470.2 (M + H) |
| 261 | (1S,2R)-2-((1-(4-methoxyphenyl)-2-oxo-2-((4-(trimethylsilyl)phenyl)amino)ethyl)carbamoyl)cyclopentanecarboxylic acid (mixture of four optical isomers) | 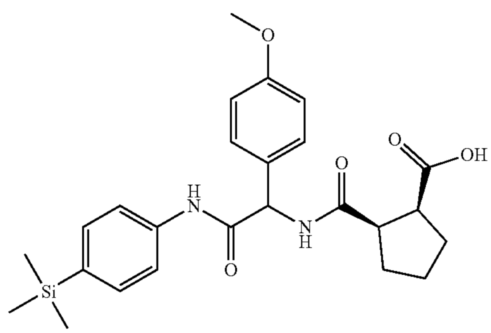 [SMILES: COc1ccc(C(NC(=O)[C@@H]2CCC[C@@H]2C(=O)O)C(=O)Nc2ccc([Si](C)(C)C)cc2)cc1] | | 469.2 (M + H) |

TABLE 1-27

| Ex. No. | IUPAC NAME | Structure | Salt | MS (Found) |
|---|---|---|---|---|
| 262 | 2,3-dihydroxy-N-(1-(4-methoxyphenyl)-2-oxo-2-((4-(trimethylsilyl)phenyl)amino)ethyl)propanamide (mixture of four optical isomers) | 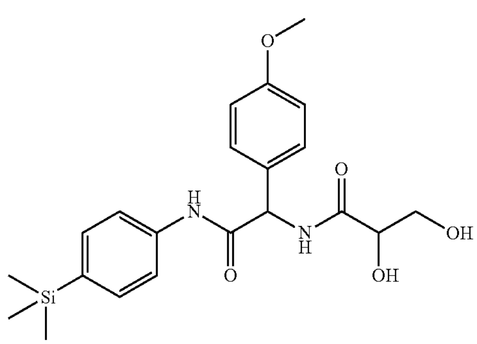 [SMILES: COc1ccc(C(NC(=O)C(O)CO)C(=O)Nc2ccc([Si](C)(C)C)cc2)cc1] | | 417.2 (M + H) |

TABLE 1-27-continued

| Ex. No. | IUPAC NAME | Structure | Salt | MS (Found) |
|---|---|---|---|---|
| 263 | 3-hydroxy-N-(1-(4-methoxyphenyl)-2-oxo-2-((4-(trimethylsilyl)phenyl)amino)ethyl)azetidine-1-carboxamide | 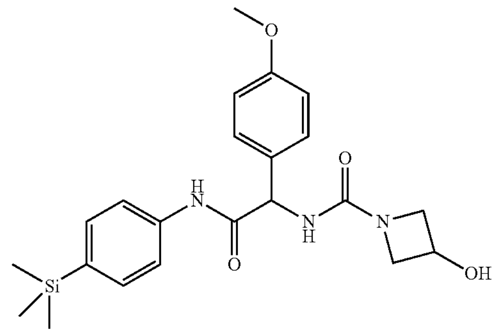 [SMILES: COc1ccc(C(NC(=O)N2CC(O)C2)C(=O)Nc2ccc([Si](C)(C)C)cc2)cc1] | | 428.2 (M + H) |
| 264 | 2-(4-methoxyphenyl)-2-(((4-oxopyridin-1(4H)-yl)acetyl)amino)-N-(4-(trimethylsilyl)phenyl)acetamide | 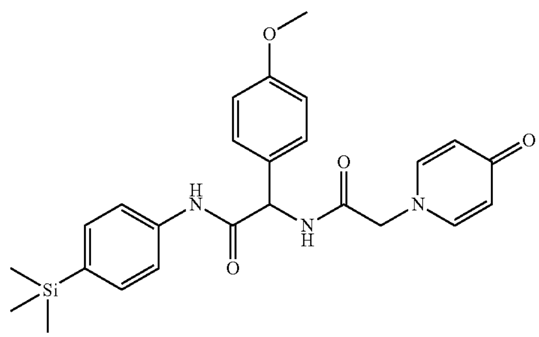 [SMILES: COc1ccc(C(NC(=O)Cn2ccc(=O)cc2)C(=O)Nc2ccc([Si](C)(C)C)cc2)cc1] | | 464.2 (M + H) |
| 265 | 2-(4-methoxyphenyl)-2-((tetrahydro-2H-pyran-4-ylacetyl)amino)-N-(4-(trimethylsilyl)phenyl)acetamide | 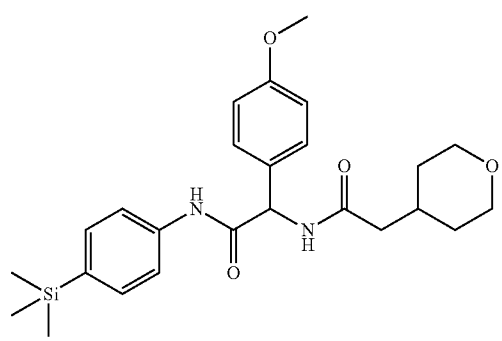 [SMILES: COc1ccc(C(NC(=O)CC2CCOCC2)C(=O)Nc2ccc([Si](C)(C)C)cc2)cc1] | | 455.2 (M + H) |
| 266 | 2-(4-methoxyphenyl)-2-((piperidin-1-ylacetyl)amino)-N-(4-(trimethylsilyl)phenyl)acetamide | 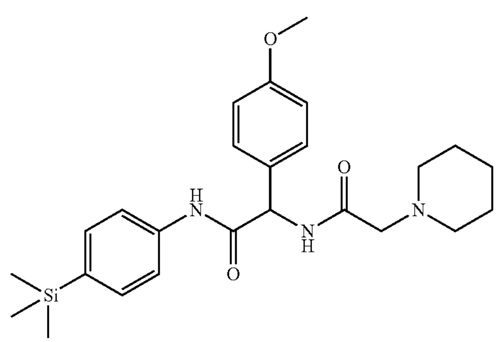 [SMILES: COc1ccc(C(NC(=O)CN2CCCCC2)C(=O)Nc2ccc([Si](C)(C)C)cc2)cc1] | | 454.2 (M + H) |

TABLE 1-27-continued

| Ex. No. | IUPAC NAME | Structure | Salt | MS (Found) |
|---|---|---|---|---|
| 267 | 2-(4-methoxyphenyl)-2-(((2-oxopyrrolidin-1-yl)acetyl)amino)-N-(4-(trimethylsilyl)phenyl)acetamide | 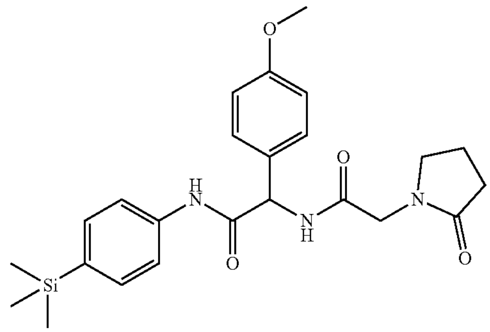 [SMILES: COc1ccc(C(NC(=O)CN2CCCC2=O)C(=O)Nc2ccc([Si](C)(C)C)cc2)cc1] | | 454.2 (M + H) |
| 268 | N-(1-(4-methoxyphenyl)-2-oxo-2-((4-(trimethylsilyl)phenyl)amino)ethyl)-2-(2-oxopyrrolidin-1-yl)propanamide (mixture of four optical isomers) | 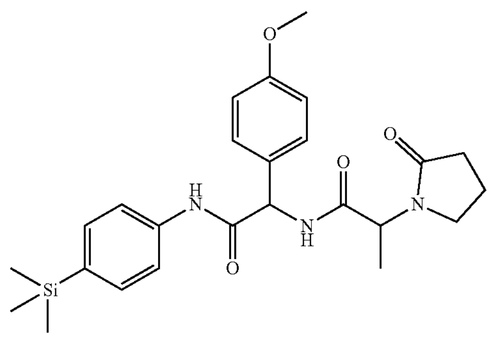 [SMILES: COc1ccc(C(NC(=O)C(C)N2CCCC2=O)C(=O)Nc2ccc([Si](C)(C)C)cc2)cc1] | | 468.2 (M + H) |
| 269 | 2-(4-methoxyphenyl)-2-((tetrahydrofuran-2-yl)acetyl)amino)-N-(4-(trimethylsilyl)phenyl)acetamide (mixture of four optical isomers) | 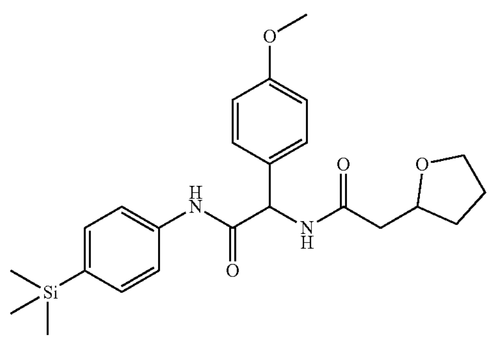 [SMILES: COc1ccc(C(NC(=O)CC2CCCO2)C(=O)Nc2ccc([Si](C)(C)C)cc2)cc1] | | 441.2 (M + H) |
| 270 | 2-(4-methoxyphenyl)-2-((tetrahydrofuran-3-yl)acetyl)amino)-N-(4-(trimethylsilyl)phenyl)acetamide (mixture of four optical isomers) | 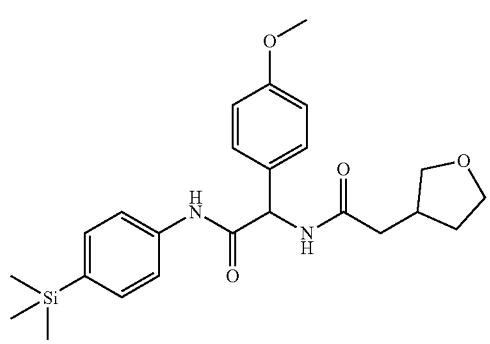 [SMILES: COc1ccc(C(NC(=O)CC2CCOC2)C(=O)Nc2ccc([Si](C)(C)C)cc2)cc1] | | 441.2 (M + H) |

TABLE 1-27-continued

| Ex. No. | IUPAC NAME | Structure | Salt | MS (Found) |
|---|---|---|---|---|
| 271 | 2-(((2,5-dioxoimidazolidin-4-yl)acetyl)amino)-2-(4-(methoxyphenyl)-N-(4-(trimethylsilyl)phenyl)acetamide (mixture of four optical isomers) | 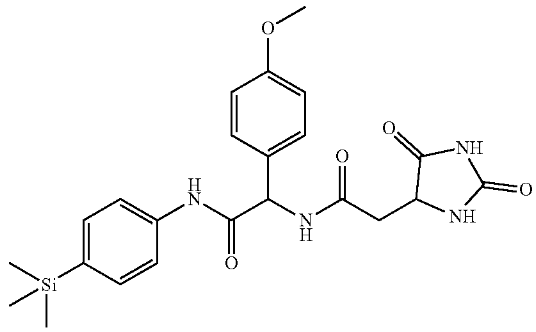 [SMILES: COc1ccc(C(NC(=O)CC2NC(=O)NC2=O)C(=O)Nc2ccc([Si](C)(C)C)cc2)cc1] | | 469.2 (M + H) |

TABLE 1-28

| Ex. NO. | IUPAC NAME | Structure | Salt | MS (Found) |
|---|---|---|---|---|
| 272 | 2-(4-methoxyphenyl)-2-((2-thienyl)acetyl)amino)-N-(4-(trimethylsilyl)phenyl)acetamide | 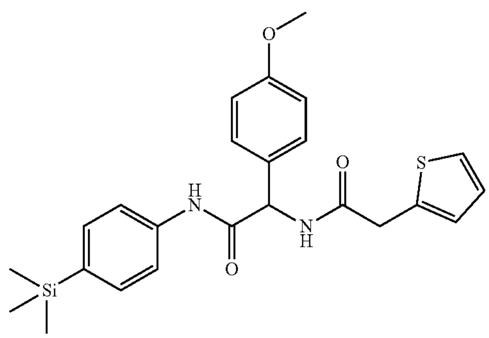 [SMILES: COc1ccc(C(NC(=O)Cc2cccs2)C(=O)Nc2ccc([Si](C)(C)C)cc2)cc1] | | 453.2 (M + H) |
| 273 | 2-(4-methoxyphenyl)-2-((3-thienylacetyl)amino)-N-(4-(trimethylsilyl)phenyl)acetamide | 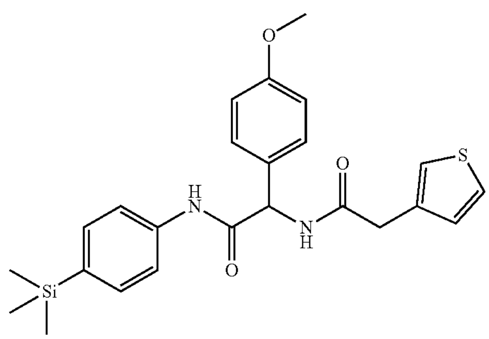 [SMILES: COc1ccc(C(NC(=O)Cc2ccsc2)C(=O)Nc2ccc([Si](C)(C)C)cc2)cc1] | | 453.2 (M + H) |
| 274 | 2-((1H-imidazol-1-ylacetyl)amino)-2-(4-methoxyphenyl)-N-(4-(trimethylsilyl)phenyl)acetamide | 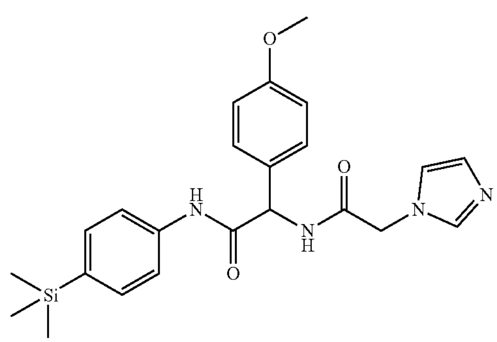 [SMILES: COc1ccc(C(NC(=O)Cn2ccnc2)C(=O)Nc2ccc([Si](C)(C)C)cc2)cc1] | | 437.2 (M + H) |

TABLE 1-28-continued

| Ex. NO. | IUPAC NAME | Structure | Salt | MS (Found) |
|---|---|---|---|---|
| 275 | 2-(4-methoxyphenyl)-2-((1H-tetrazol-1-ylacetyl)amino)-N-(4-(trimethylsilyl)phenyl)acetamide | 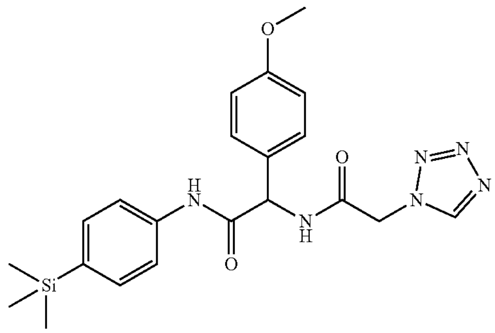 [SMILES: COc1ccc(C(NC(=O)Cn2cnnn2)C(=O)Nc2ccc([Si](C)(C)C)cc2)cc1] | | 437.1 (M − H) |
| 276 | 2-(4-methoxyphenyl)-2-((1H-tetrazol-5-ylacetyl)amino)-N-(4-(trimethylsilyl)phenyl)acetamide | 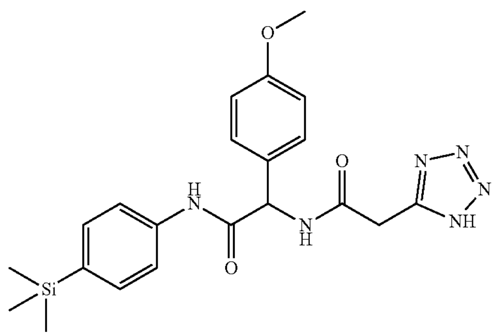 [SMILES: COc1ccc(C(NC(=O)Cc2nnn[nH]2)C(=O)Nc2ccc([Si](C)(C)C)cc2)cc1] | | 439.2 (M + H) |
| 277 | 2-((1,2-benzoxazol-3-ylacetyl)amino)-2-(4-methoxyphenyl)-N-(4-(trimethylsilyl)phenyl)acetamide | 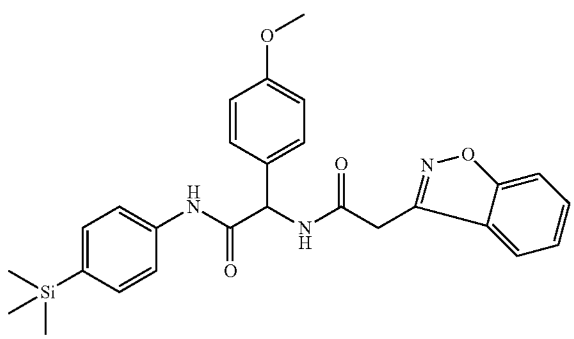 [SMILES: COc1ccc(C(NC(=O)Cc2noc3ccccc23)C(=O)Nc2ccc([Si](C)(C)C)cc2)cc1] | | 488.3 (M + H) |
| 278 | 2-(4-methoxyphenyl)-2-((pyridin-3-ylacetyl)amino)-N-(4-(trimethylsilyl)phenyl)acetamide | 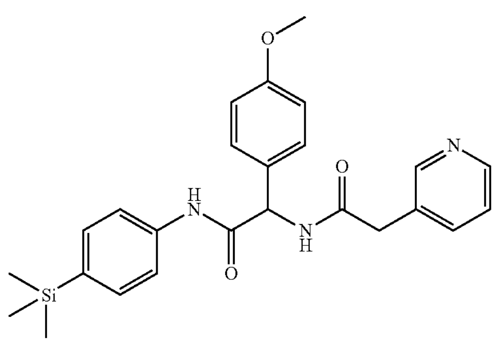 [SMILES: COc1ccc(C(NC(=O)Cc2cccnc2)C(=O)Nc2ccc([Si](C)(C)C)cc2)cc1] | | 448.2 (M + H) |

TABLE 1-28-continued

| Ex. NO. | IUPAC NAME | Structure | Salt | MS (Found) |
|---|---|---|---|---|
| 279 | N-(1-(4-methoxyphenyl)-2-oxo-2-((4-(trimethylsilyl)phenyl)amino)ethyl)-3-(pyridin-3-yl)propanamide | 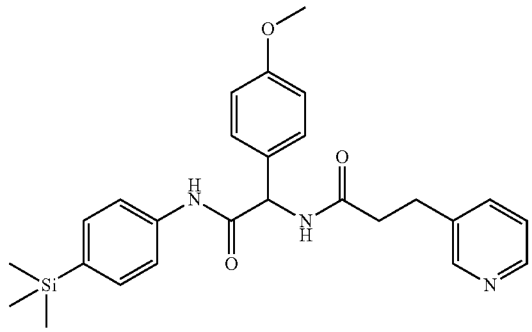 [SMILES: COc1ccc(C(NC(=O)CCc2cccnc2)C(=O)Nc2ccc([Si](C)(C)C)cc2)cc1] | | 462.2 (M + H) |
| 280 | 2-(glycoloylamino)-2-(4-methoxyphenyl)-N-(4-(trimethylsilyl)phenyl)acetamide | 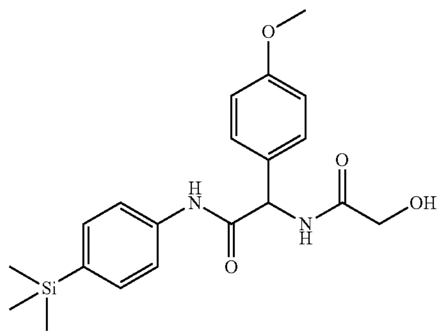 [SMILES: COc1ccc(C(NC(=O)CO)C(=O)Nc2ccc([Si](C)(C)C)cc2)cc1] | | 387.2 (M + H) |
| 281 | 3-hydroxy-N-(1-(4-methoxyphenyl)-2-oxo-2-((4-(trimethylsilyl)phenyl)amino)ethyl)propanamide | 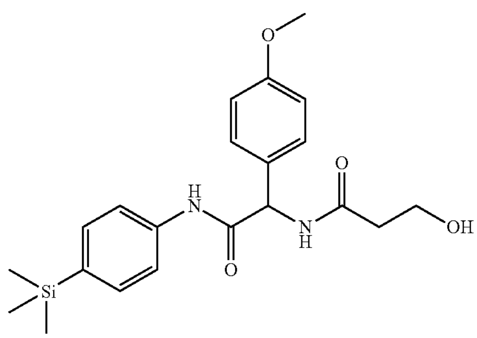 [SMILES: COc1ccc(C(NC(=O)CCO)C(=O)Nc2ccc([Si](C)(C)C)cc2)cc1] | | 401.2 (M + H) |

TABLE 1-29

| Ex. No. | IUPAC NAME | Structure | Salt | MS (Found) |
|---|---|---|---|---|
| 282 | 3-hydroxy-N-(1-(4-methoxyphenyl)-2-oxo-2-((4-(trimethylsilyl)phenyl)amino)ethyl)butanamide (mixture of four optical isomers) | 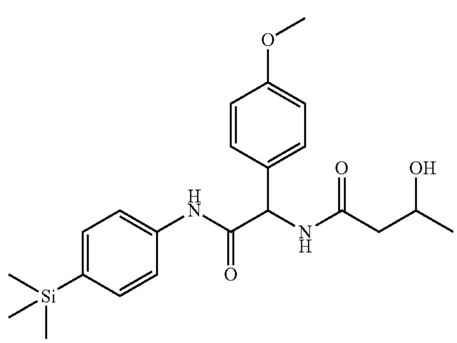 [SMILES: COc1ccc(C(NC(=O)CC(C)O)C(=O)Nc2ccc([Si](C)(C)C)cc2)cc1] | | 415.2 (M + H) |

TABLE 1-29-continued

| Ex. No. | IUPAC NAME | Structure | Salt | MS (Found) |
|---|---|---|---|---|
| 283 | 3-hydroxy-N-(1-(4-methoxyphenyl)-2-oxo-2-((4-(trimethylsilyl)phenyl)amino)ethyl)-3-methylbutanamide | 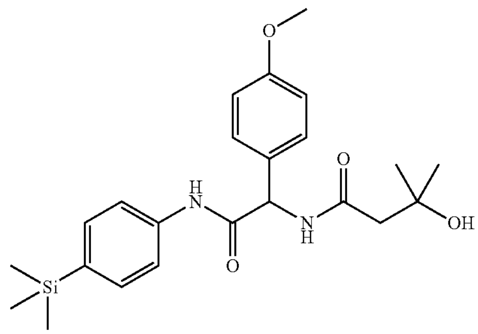 [SMILES: COc1ccc(C(NC(=O)CC(C)(C)O)C(=O)Nc2ccc([Si](C)(C)C)cc2)cc1] | | 429.2 (M + H) |
| 284 | (3-cyano-N-(1-(4-methoxyphenyl)-2-oxo-2-((4-(trimethylsilyl)phenyl)amino)ethyl) propanamide | 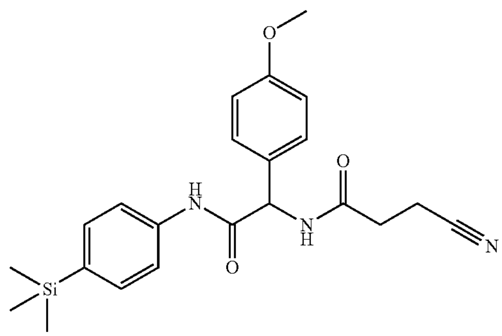 [SMILES: COc1ccc(C(NC(=O)CCC#N)C(=O)Nc2ccc([Si](C)(C)C)cc2)cc1] | | 410.2 (M + H) |
| 285 | N-(1-(4-methoxyphenyl)-2-oxo-2-((4-(trimethylsilyl)phenyl)amino)ethyl) succinamide | 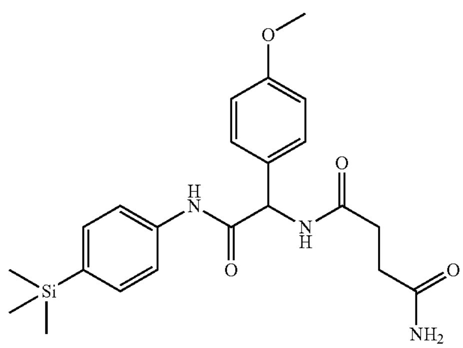 [SMILES: COc1ccc(C(NC(=O)CCC(N)=O)C(=O)Nc2ccc([Si](C)(C)C)cc2)cc1] | | 428.3 (M + H) |
| 286 | N-(1-(4-methoxyphenyl)-2-oxo-2-((4-(trimethylsilyl)phenyl)amino)ethyl)-3-(methylsulfonyl) propanamide | 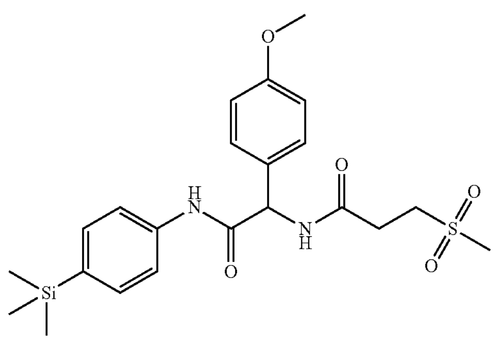 | | 463.1 (M + H) |

TABLE 1-29-continued

| Ex. No. | IUPAC NAME | Structure | Salt | MS (Found) |
|---|---|---|---|---|
| 287 | N-(1-(4-methoxyphenyl)-2-oxo-2-((4-(trimethylsilyl)phenyl)amino)ethyl)-N2,N2-dimethylglycinamide | 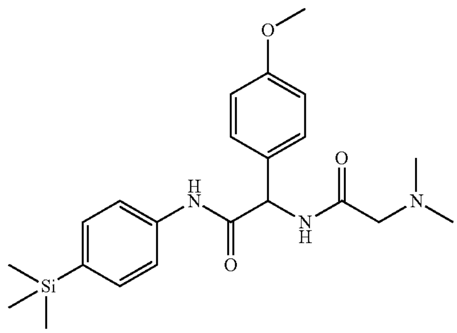 | | 414.2 (M + H) |
| 288 | N-(1-(4-methoxyphenyl)-2-oxo-2-((4-pyrazol-1-yl)propanamide (mixture of four optical isomers) | 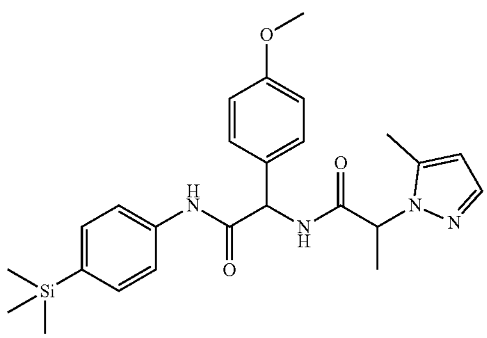 [SMILES: COc1ccc(C(NC(=O)C(C)n2nccc2C)C(=O)Nc2ccc([Si](C)(C)C)cc2)cc1] | | 465.1 (M + H) |
| 289 | 2-((1H-benzimidazol-1-ylacetyl)amino)-2-(4-methoxyphenyl)-N-(4-(trimethylsilyl)phenyl)acetamide | 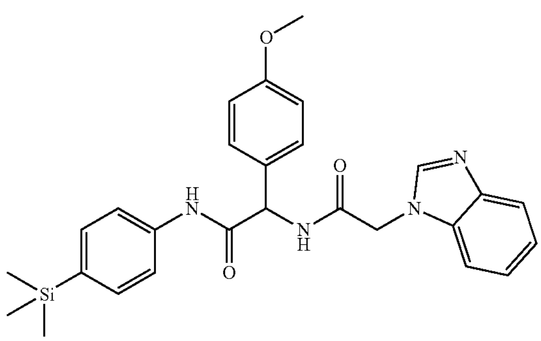 [SMILES: COc1ccc(C(NC(=O)Cn2cnc3ccccc32)C(=O)Nc2ccc([Si](C)(C)C)cc2)cc1] | | 487.2 (M + H) |
| 290 | 2-(4-methoxyphenyl)-2-(((4-methylpiperazin-1-yl)acetyl)amino)-N-(4-(trimethylsilyl)phenyl)acetamide | 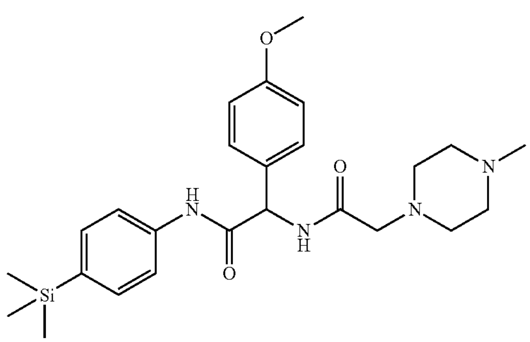 | | 469.3 (M + H) |

TABLE 1-29-continued

| Ex. No. | IUPAC NAME | Structure | Salt | MS (Found) |
|---|---|---|---|---|
| 291 | 2-(4-methoxyphenyl)-2-(((2-oxopyridin-1(2H)-yl)acetyl)amino)-N-(4-(trimethylsilyl)phenyl)acetamide | 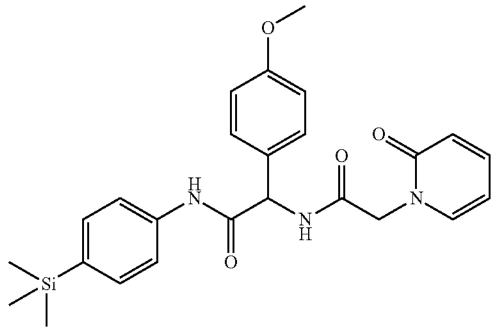 [SMILES: COc1ccc(C(NC(=O)Cn2ccccc2=O)C(=O)Nc2ccc([Si](C)(C)C)cc2)cc1] | | 464.2 (M + H) |

TABLE 1-30

| Ex. No. | IUPAC NAME | Structure | Salt | MS (Found) |
|---|---|---|---|---|
| 292 | 2-(4-methoxyphenyl)-2-(((2-oxo-1,3-benzoxazol-3(2H)-yl)acetyl)amino)-N-(4-(trimethylsilyl)phenyl)acetamide | 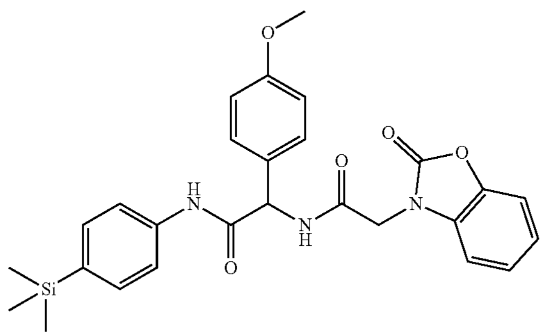 [SMILES: COc1ccc(C(NC(=O)Cn2c(=O)oc3ccccc32)C(=O)Nc2ccc([Si](C)(C)C)cc2)cc1] | | 504.2 (M + H) |
| 293 | 2-(((2,4-dioxo-1,3-thiazolidin-3-yl)acetyl)amino)-2-(4-methoxyphenyl)-N-(4-(trimethylsilyl)phenyl)acetamide | 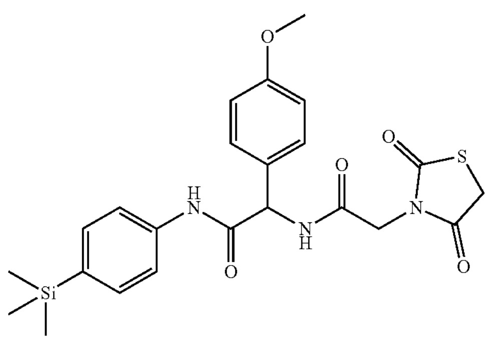 [SMILES: COc1ccc(C(NC(=O)CN2C(=O)CSC2=O)C(=O)Nc2ccc([Si](C)(C)C)cc2)cc1] | | 486.2 (M + H) |
| 294 | 2-(((2,5-dioxopyrrolidin-1-yl)acetyl)amino)-2-(4-methoxyphenyl)-N-(4-(trimethylsilyl)phenyl)acetamide | 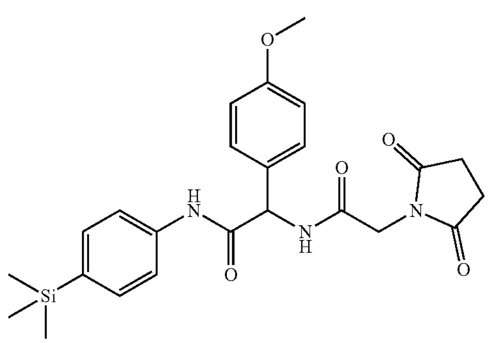 [SMILES: COc1ccc(C(NC(=O)CN2C(=O)CCC2=O)C(=O)Nc2ccc([Si](C)(C)C)cc2)cc1] | | 468.2 (M + H) |

TABLE 1-30-continued

| Ex. No. | IUPAC NAME | Structure | Salt | MS (Found) |
|---|---|---|---|---|
| 295 | 2-(((2,5-dioxoimidazolidin-1-yl)acetyl)amino)-2-(4-methoxyphenyl)-N-(4-(trimethylsilyl)phenyl)acetamide | 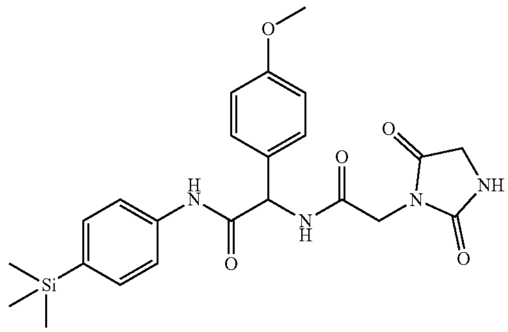 [SMILES: COc1ccc(C(NC(=O)CN2C(=O)CNC2=O)C(=O)Nc2ccc([Si](C)(C)C)cc2)cc1] | | 469.2 (M + H) |
| 296 | 2-(4-methoxyphenyl)-2-(((2-oxopiperidin-1-yl)acetyl)amino)-N-(4-(trimethylsilyl)phenyl)acetamide | 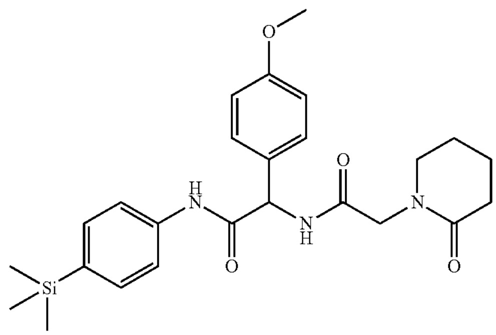 [SMILES: COc1ccc(C(NC(=O)CN2CCCCC2=O)C(=O)Nc2ccc([Si](C)(C)C)cc2)cc1] | | 468.2 (M + H) |
| 297 | 2-(4-methoxyphenyl)-2-(((2-oxo-1,3-oxazolidin-3-yl)acetyl)amino)-N-(4-(trimethylsilyl)phenyl)acetamide | 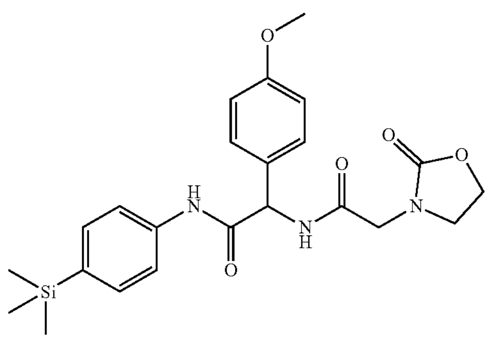 [SMILES: COc1ccc(C(NC(=O)CN2CCOC2=O)C(=O)Nc2ccc([Si](C)(C)C)cc2)cc1] | | 456.1 (M + H) |
| 298 | 2-(4-methoxyphenyl)-2-(((2-oxoimidazolidin-1-yl)acetyl)amino)-N-(4-(trimethylsilyl)phenyl)acetamide | 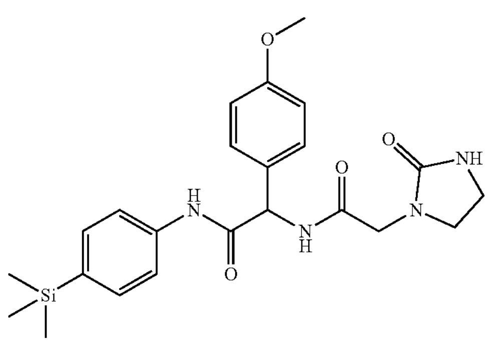 [SMILES: COc1ccc(C(NC(=O)CN2CCNC2=O)C(=O)Nc2ccc([Si](C)(C)C)cc2)cc1] | | 455.2 (M + H) |

TABLE 1-30-continued

| Ex. No. | IUPAC NAME | Structure | Salt | MS (Found) |
|---|---|---|---|---|
| 299 | 2-(4-methoxyphenyl)-2-(((3-methyl-2,5-dioxoimidazolidin-1-yl)acetyl)amino)-N-(4-(trimethylsilyl)phenyl)acetamide | 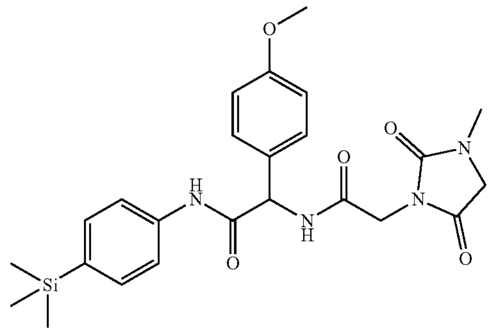 [SMILES: COc1ccc(C(NC(=O)CN2C(=O)CN(C)C2=O)C(=O)Nc2ccc([Si](C)(C)C)cc2)cc1] | | 483.2 (M + H) |
| 300 | 2-(4-methoxyphenyl)-2-((morpholin-4-ylacetyl)amino)-N-(4-(trimethylsilyl)phenyl)acetamide | 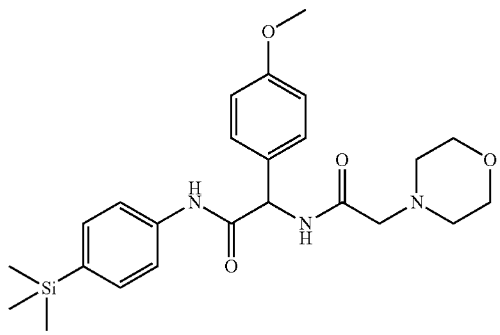 | | 456.1 (M + H) |
| 301 | 2-(((2,4-dioxo-3,4-dihydropyrimidin-1(2H)-yl)acetyl)amino)-2-(4-methoxyphenyl)-N-(4-(trimethylsilyl)phenyl)acetamide | 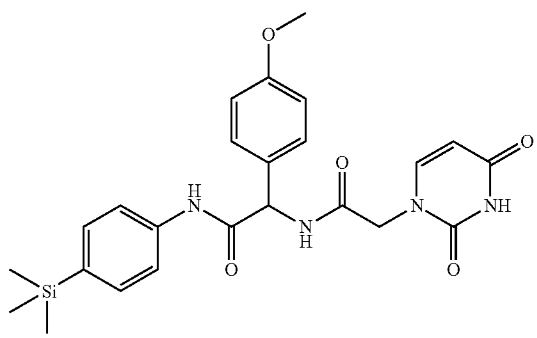 [SMILES: COc1ccc(C(NC(=O)Cn2ccc(=O)[nH]c2=O)C(=O)Nc2ccc([Si](C)(C)C)cc2)cc1] | | 481.2 (M + H) |

TABLE 1-31

| Ex. No. | IUPAC NAME | Structure | Salt | MS (Found) |
|---|---|---|---|---|
| 302 | 2-(((2,4-dioxo-1,3-oxazolidin-3-yl)acetyl)amino)-2-(4-methoxyphenyl)-N-(4-(trimethylsilyl)phenyl)acetamide | 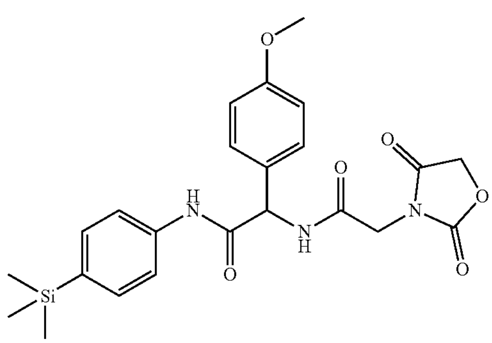 [SMILES: COc1ccc(C(NC(=O)CN2C(=O)COC2=O)C(=O)Nc2ccc([Si](C)(C)C)cc2)cc1] | | 470.1 (M + H) |

TABLE 1-31-continued

| Ex. No. | IUPAC NAME | Structure | Salt | MS (Found) |
|---|---|---|---|---|
| 303 | 2-(((3-(difluoromethyl)-5-methyl-1H-pyrazol-1-yl)acetyl)amino)-2-(4-methoxyphenyl)-N-(4-(trimethylsilyl)phenyl)acetamide | 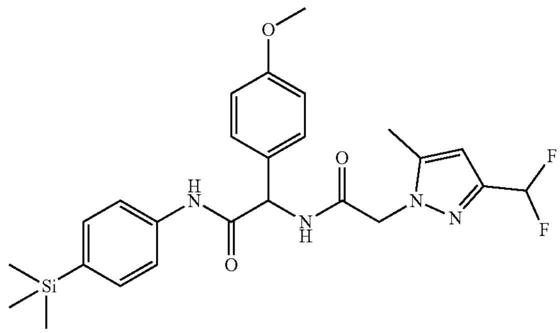 [SMILES: COc1ccc(C(NC(=O)Cn2nc(C(F)F)cc2C)C(=O)Nc2ccc([Si](C)(C)C)cc2)cc1] | | 501.2 (M + H) |
| 304 | 2-(4-methoxyphenyl)-2-(((4-oxopiperidin-1-yl)acetyl)amino)-N-(4-(trimethylsilyl)phenyl)acetamide | 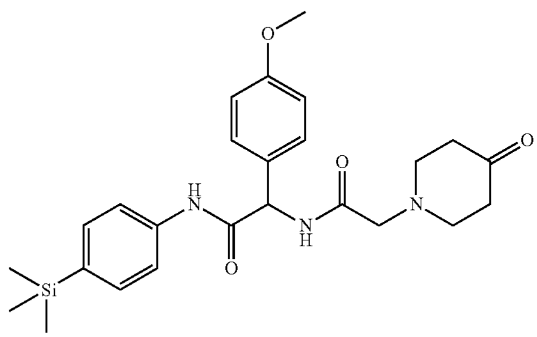 [SMILES: COc1ccc(C(NC(=O)CN2CCC(=O)CC2)C(=O)Nc2ccc([Si](C)(C)C)cc2)cc1] | | 468.3 (M + H) |
| 305 | 2-(((3,5-dioxomorpholin-4-yl)acetyl)amino)-2-(4-methoxyphenyl)-N-(4-(trimethylsilyl)phenyl)acetamide | 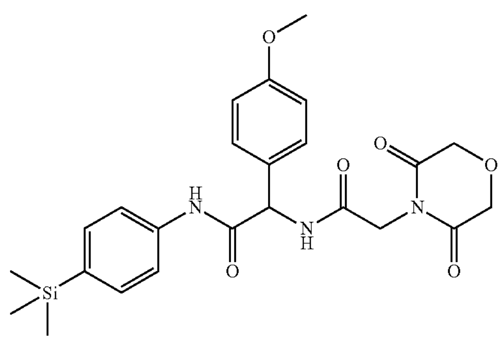 [SMILES: COc1ccc(C(NC(=O)CN2C(=O)COCC2=O)C(=O)Nc2ccc([Si](C)(C)C)cc2)cc1] | | 484.2 (M + H) |
| 306 | 2-(((2-ethyl-1H-imidazol-1-yl)acetyl)amino)-2-(4-methoxyphenyl)-N-(4-(trimethylsilyl)phenyl)acetamide | 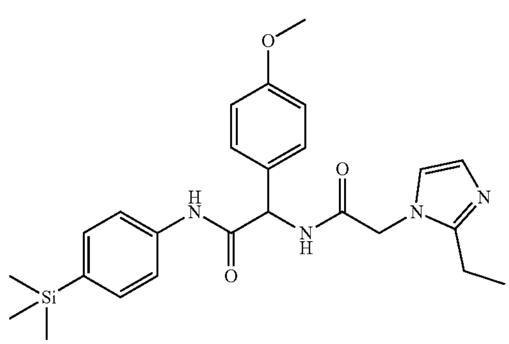 [SMILES: CCc1nccn1CC(=O)NC(C(=O)Nc1ccc([Si](C)(C)C)cc1)c1ccc(OC)cc1] | | 465.1 (M + H) |

TABLE 1-31-continued

| Ex. No. | IUPAC NAME | Structure | Salt | MS (Found) |
|---|---|---|---|---|
| 307 | 2-(4-methoxyphenyl)-2-(((3-(trifluoromethyl)-1H-pyrazol-1-yl)acetyl)amino)-N-(4-(trimethylsilyl)phenyl)acetamide | 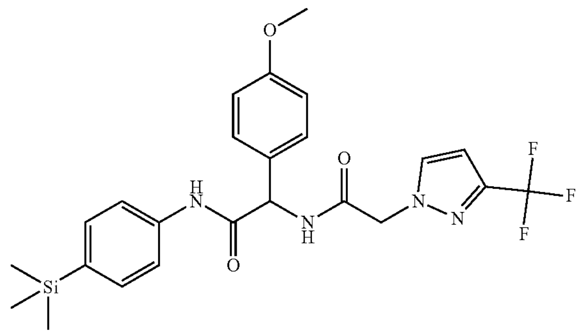 [SMILES: COc1ccc(C(NC(=O)Cn2ccc(C(F)(F)F)n2)C(=O)Nc2ccc([Si](C)(C)C)cc2)cc1] | | 505.2 (M + H) |
| 308 | N-(1-(4-methoxyphenyl)-2-oxo-2-((4-(trimethylsilyl)phenyl)amino)ethyl)-2-methyl-2-(1H-pyrazol-1-yl)propanamide | 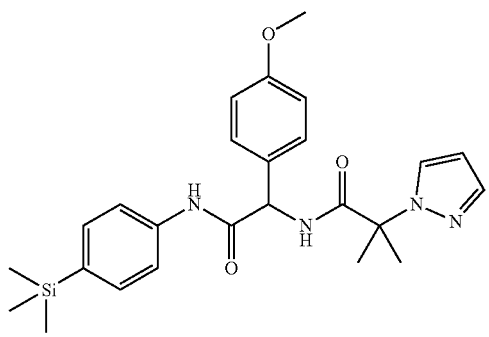 [SMILES: COc1ccc(C(NC(=O)C(C)(C)n2cccn2)C(=O)Nc2ccc([Si](C)(C)C)cc2)cc1] | | 465.1 (M + H) |
| 309 | 2-(((2,6-dioxo-3,6-dihydropyrimidin-1(2H)-yl)acetyl)amino)-2-(4-methoxyphenyl)-N-(4-(trimethylsilyl)phenyl)acetamide | 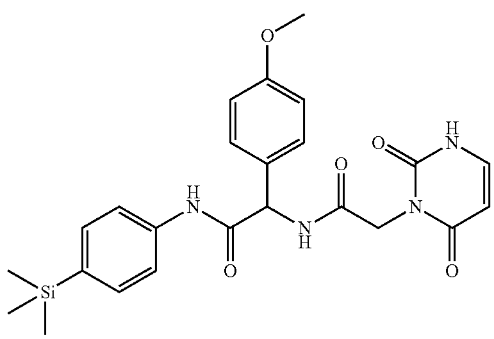 [SMILES: COc1ccc(C(NC(=O)Cn2c(=O)cc[nH]c2=O)C(=O)Nc2ccc([Si](C)(C)C)cc2)cc1] | | 481.2 (M + H) |
| 310 | 2-(((3-hydroxypyrrolidin-1-yl)acetyl)amino)-2-(4-methoxyphenyl)-N-(4-(trimethylsilyl)phenyl)acetamide (mixture of four optical isomers) | 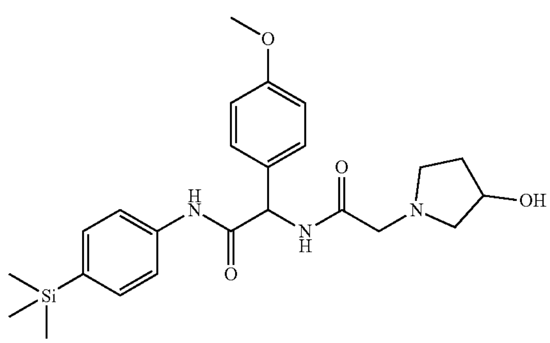 [SMILES: COc1ccc(C(NC(=O)CN2CCC(O)C2)C(=O)Nc2ccc([Si](C)(C)C)cc2)cc1] | | 456.1 (M + H) |

TABLE 1-31-continued

| Ex. No. | IUPAC NAME | Structure | Salt | MS (Found) |
|---|---|---|---|---|
| 311 | 2-(4-methoxyphenyl)-2-(((4-oxoimidazolidin-1-yl)acetyl)amino)-N-(4-(trimethylsilyl)phenyl)acetamide | 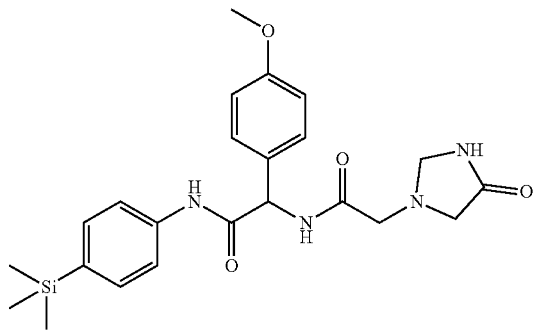 [SMILES: COc1ccc(C(NC(=O)CN2CNC(=O)C2)C(=O)Nc2ccc([Si](C)(C)C)cc2)cc1] | | 455.2 (M + H) |

TABLE 1-32

| Ex. No. | IUPAC NAME | Structure | Salt | MS (Found) |
|---|---|---|---|---|
| 312 | N-(1-(3,4-dimethoxyphenyl)-2-oxo-2-((4-(trimethylsilyl)phenyl)amino)ethyl)-3-hydroxy-N-methyl-1,2-oxazole-5-carboxamide | 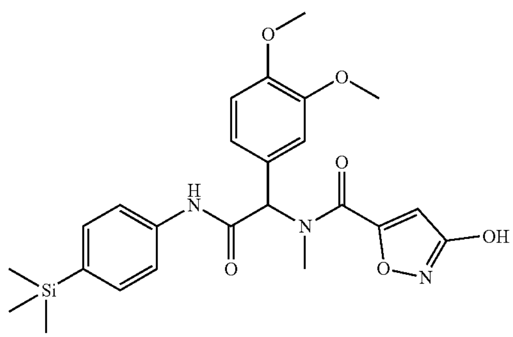 [SMILES: COc1ccc(C(C(=O)Nc2ccc([Si](C)(C)C)cc2)N(C)C(=O)c2cc(O)no2)cc1OC] | | 482.0 (M − H) |
| 313 | 3-hydroxy-N-(1-(4-(hydroxymethyl)phenyl)-2-oxo-2-((4-(trimethylsilyl)phenyl)amino)ethyl)-N-methyl-1,2-oxazole-5-carboxamide | 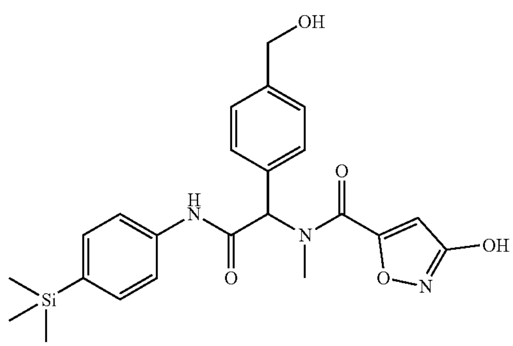 [SMILES: CN(C(=O)c1cc(O)no1)C(C(=O)Nc1ccc([Si](C)(C)C)cc1)c1ccc(CO)cc1] | | 452.0 (M − H) |
| 314 | N-(3-cyano-4-(trimethylsilyl)phenyl)-2-(4-methoxyphenyl)-2-(((4-oxopyridin-1(4H)-yl)acetyl)amino)acetamide | 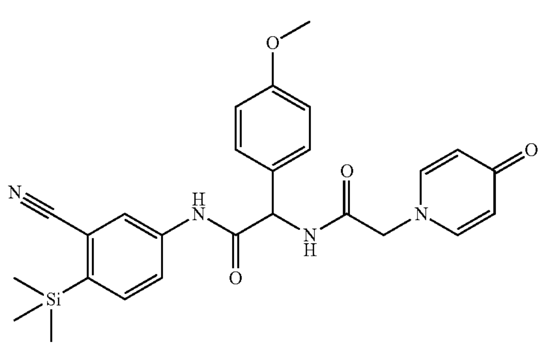 [SMILES: COc1ccc(C(NC(=O)Cn2ccc(=O)cc2)C(=O)Nc2ccc([Si](C)(C)C)c(C#N)c2)cc1] | | 489.2 (M + H) |

TABLE 1-32-continued

| Ex. No. | IUPAC NAME | Structure | Salt | MS (Found) |
|---|---|---|---|---|
| 315 | 2-(((3-hydroxypiperidin-1-yl)acetyl)amino)-2-(4-methoxyphenyl)-N-(4-(trimethylsilyl)phenyl)acetamide (mixture of four optical isomers) | 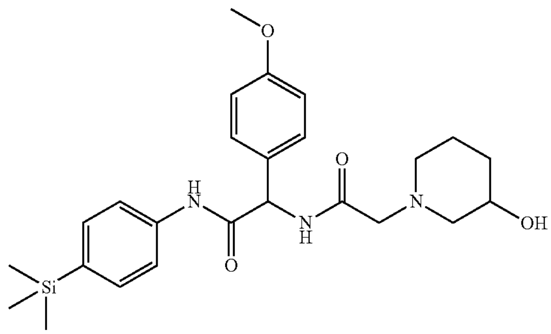 [SMILES: COc1ccc(C(NC(=O)CN2CCCC(O)C2)C(=O)Nc2ccc([Si](C)(C)C)cc2)cc1] | | 470.3 (M + H) |
| 316 | N-(1-(4-methoxyphenyl)-2-oxo-2-((4-(trimethylsilyl)phenyl)amino)ethyl)-3-oxocyclopentanecarboxamide (mixture of four optical isomers) | 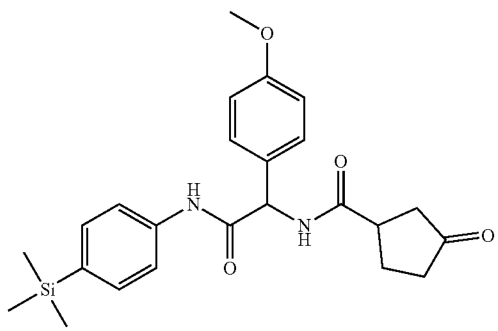 [SMILES: COc1ccc(C(NC(=O)C2CCC(=O)C2)C(=O)Nc2ccc([Si](C)(C)C)cc2)cc1] | | 439.2 (M + H) |
| 317 | (1R,2S)-2-(hydroxymethyl)-N-(1-(4-methoxyphenyl)-2-oxo-2-((4-(trimethylsilyl)phenyl)amino)ethyl)cyclopentanecarboxamide (mixture of four optical isomers) | 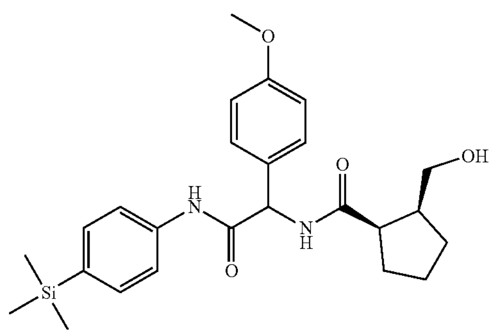 [SMILES: COc1ccc(C(NC(=O)[C@@H]2CCC[C@@H]2CO)C(=O)Nc2ccc([Si](C)(C)C)cc2)cc1] | | 453.1 (M − H) |
| 318 | 3-hydroxy-N-(1-(4-methoxyphenyl)-2-oxo-2-((4-(trimethylsilyl)phenyl)amino)ethyl)cyclopentanecarboxamide (mixture of four optical isomers) | 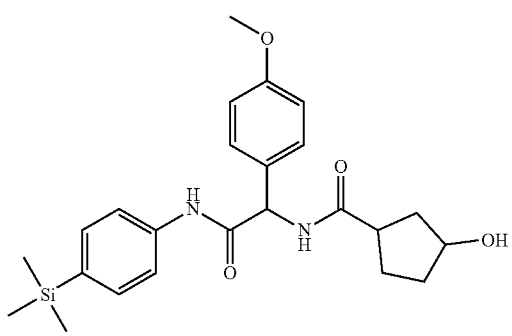 [SMILES: COc1ccc(C(NC(=O)C2CCC(O)C2)C(=O)Nc2ccc([Si](C)(C)C)cc2)cc1] | | 441.2 (M + H) |

TABLE 1-32-continued

| Ex. No. | IUPAC NAME | Structure | Salt | MS (Found) |
|---|---|---|---|---|
| 319 | 3-(hydroxymethyl)-N-(1-(4-methoxyphenyl)-2-oxo-2-((4-(trimethylsilyl)phenyl)amino)ethyl)piperidine-1-carboxamide (mixture of four optical isomers) | 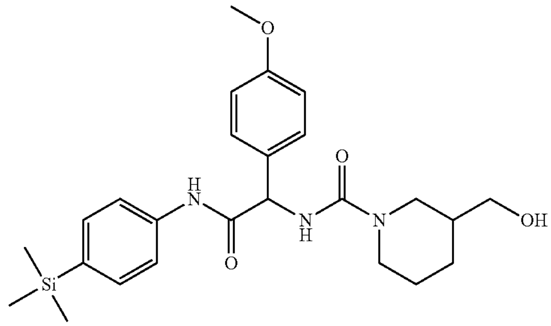 [SMILES: COc1ccc(C(NC(=O)N2CCCC(CO)C2)C(=O)Nc2ccc([Si](C)(C)C)cc2)cc1] | | 470.3 (M + H) |
| 320 | 2-(((3-hydroxyazetidin-1-yl)acetyl)amino)-2-(4-methoxyphenyl)-N-(4-(trimethylsilyl)phenyl)acetamide | 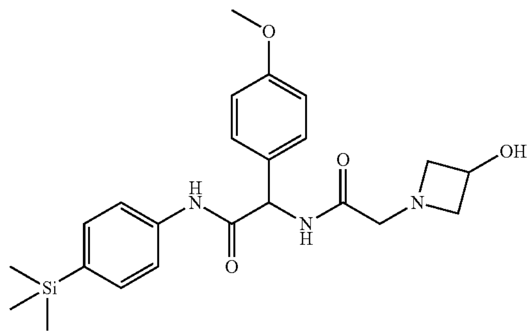 [SMILES: COc1ccc(C(NC(=O)CN2CC(O)C2)C(=O)Nc2ccc([Si](C)(C)C)cc2)cc1] | | 442.2 (M + H) |
| 321 | 2-(3-hydroxypyrrolidin-1-yl)-N-(1-(4-methoxyphenyl)-2-oxo-2-((4-(trimethylsilyl)phenyl)amino)ethyl)-2-methylpropanamide (mixture of four optical isomers) | 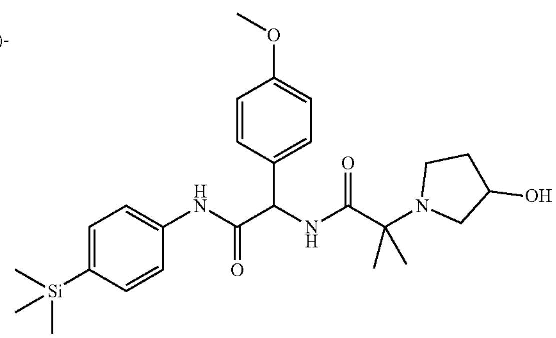 | | 484.3 (M + H) |

TABLE 1-33

| Ex. No. | IUPAC NAME | Structure | Salt | MS (Found) |
|---|---|---|---|---|
| 322 | 2-(((3-(benzyloxy)-1-ethyl-1H-pyrazol-4-yl)acetyl)amino)-2-(4-methoxyphenyl)-N-(4-(trimethylsilyl)phenyl)acetamide | 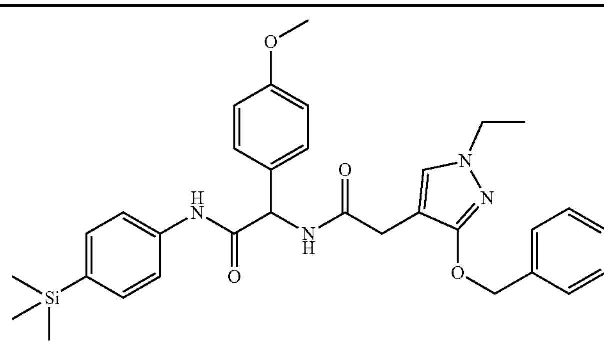 | | 571.3 (M + H) |

TABLE 1-33-continued

| Ex. No. | IUPAC NAME | Structure | Salt | MS (Found) |
|---|---|---|---|---|
| 323 | N-(1-(4-methoxyphenyl)-2-oxo-2-((4-(trimethylsilyl)phenyl)amino)ethyl)-3-oxocyclohexanecarboxamide (mixture of four optical isomers) | 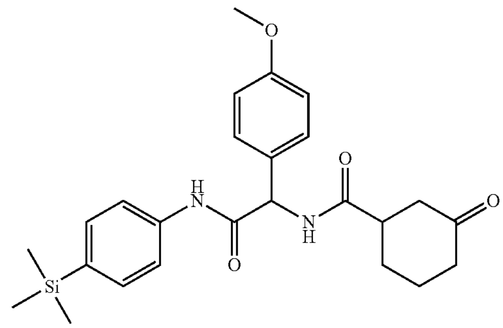 [SMILES: COc1ccc(C(NC(=O)C2CCCC(=O)C2)C(=O)Nc2ccc([Si](C)(C)C)cc2)cc1] | | 453.2 (M + H) |
| 324 | 2-(((3-cyanoazetidin-1-yl)acetyl)amino)-2-(4-(methoxyphenyl)-N-(4-(trimethylsilyl)phenyl)acetamide | 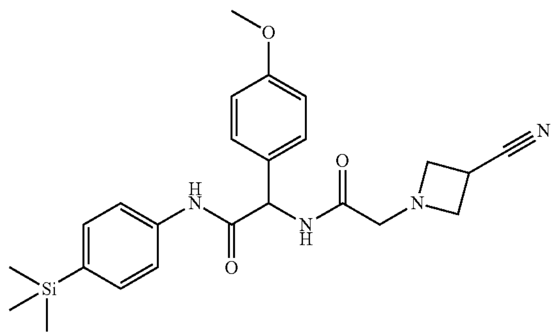 [SMILES: COc1ccc(C(NC(=O)CN2CC(C#N)C2)C(=O)Nc2ccc([Si](C)(C)C)cc2)cc1] | | 451.2 (M + H) |
| 325 | N-(1-(4-(ethoxymethyl)phenyl)-2-oxo-2-((4-(trimethylsilyl)phenyl)amino)ethyl)-3-hydroxy-N-methyl-1,2-oxazole-5-carboxamide | 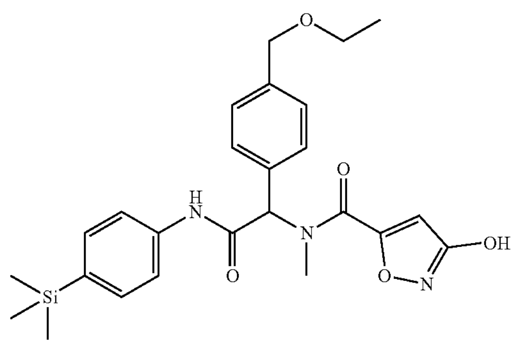 [SMILES: CCOCc1ccc(C(C(=O)Nc2ccc([Si](C)(C)C)cc2)N(C)C(=O)c2cc(O)no2)cc1] | | 480.1 (M − H) |
| 326 | N-(1-(4-((2,2-difluoroethoxy)methyl)phenyl)-2-oxo-2-((4-(trimethylsilyl)phenyl)amino)ethyl)-3-hydroxy-N-methyl-1,2-oxazole-5-carboxamide | 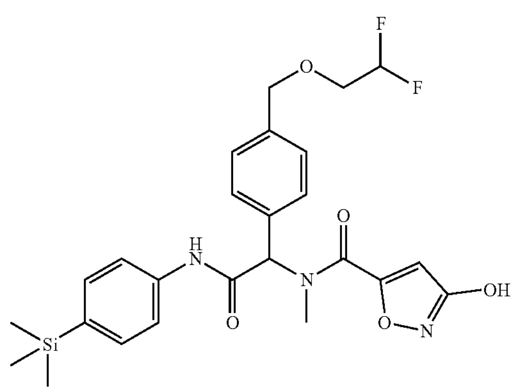 [SMILES: CN(C(=O)c1cc(O)no1)C(C(=O)Nc1ccc([Si](C)(C)C)cc1)c1ccc(COCC(F)F)cc1] | | 516.0 (M − H) |

TABLE 1-33-continued

| Ex. No. | IUPAC NAME | Structure | Salt | MS (Found) |
|---|---|---|---|---|
| 327 | 3-hydroxy-N-(1-(4-((2-methoxyethoxy)methyl)phenyl)-2-oxo-2-((4-(trimethylsilyl)phenyl)amino)ethyl)-N-methyl-1,2-oxazole-5-carboxamide | 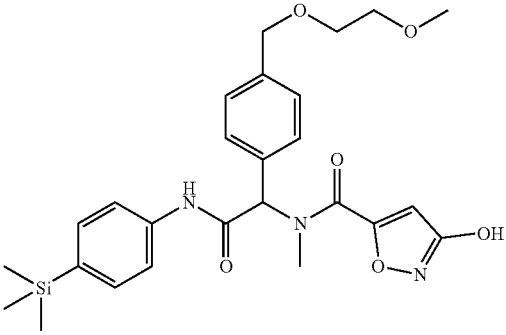 [SMILES: COCCOCc1ccc(C(C(=O)Nc2ccc([Si](C)(C)C)cc2)N(C)C(=O)c2cc(O)no2)cc1] | | 510.1 (M − H) |
| 328 | 3-hydroxy-N-(1-(4-((3-methoxypropoxy)methyl)phenyl)-2-oxo-2-((4-(trimethylsilyl)phenyl)amino)ethyl)-N-methyl-1,2-oxazole-5-carboxamide | 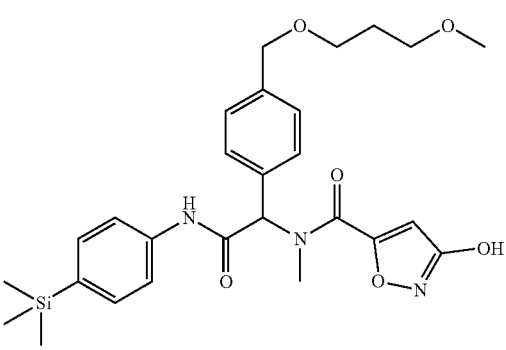 | | 526.3 (M + H) |
| 329 | 2-(((1-hydroxycyclopentyl)acetyl)amino)-2-(4-methoxyphenyl)-N-(4-(trimethylsilyl)phenyl)acetamide | 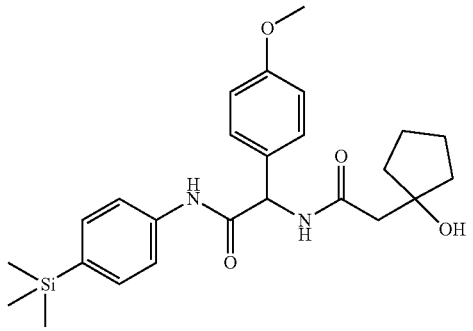 [SMILES: COc1ccc(C(NC(=O)CC2(O)CCCC2)C(=O)Nc2ccc([Si](C)(C)C)cc2)cc1] | | 455.2 (M + H) |
| 330 | N-(1-(4-methoxyphenyl)-2-oxo-2-((4-(trimethylsilyl)phenyl)amino)ethyl)-N,5-dimethyl-1,3,4-oxadiazole-2-carboxamide | 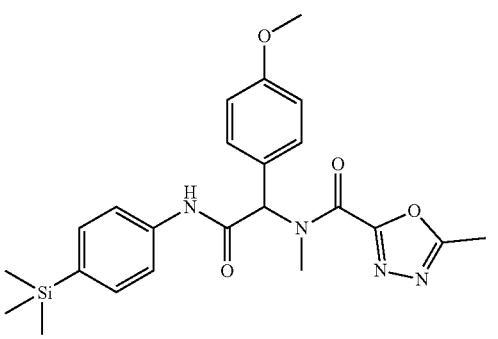 | | 453.2 (M + H) |

TABLE 1-33-continued

| Ex. No. | IUPAC NAME | Structure | Salt | MS (Found) |
|---|---|---|---|---|
| 331 | 2-(4-(methoxymethyl) phenyl)-2-(((4-oxopyridin-1(4H)-yl)acetyl)amino)-N-(4-(trimethylsilyl)phenyl) acetamide | 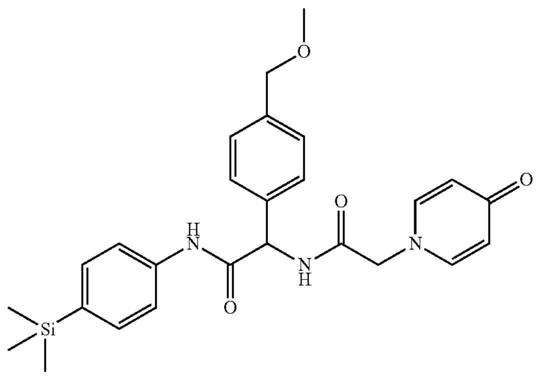 [SMILES: COCc1ccc(C(NC(=O)Cn2ccc(=O)cc2)C(=O)Nc2ccc([Si](C)(C)C)cc2)cc1] | | 478.2 (M + H) |

TABLE 1-34

| Ex. No. | IUPAC NAME | Structure | Salt | MS (Found) |
|---|---|---|---|---|
| 332 | 3-hydroxy-N-(1-(4-(2-methoxyethoxy)phenyl)-2-oxo-2-((4-(trimethylsilyl) phenyl)amino)ethyl)-N-methyl-1,2-oxazole-5-carboxamide | 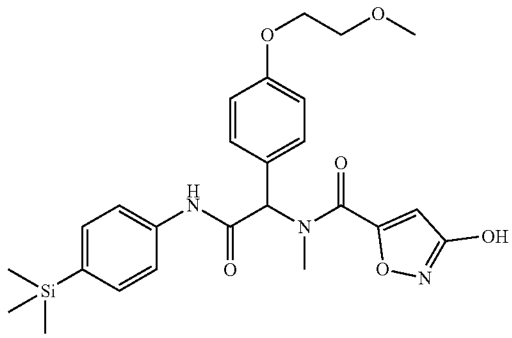 [SMILES: COCCOc1ccc(C(C(=O)Nc2ccc([Si](C)(C)C)cc2)N(C)C(=O)c2cc(O)no2)cc1] | | 496.1 (M − H) |
| 333 | 3-hydroxy-N-(1-(4-(3-methoxypropoxy)phenyl)-2-oxo-2-((4-(trimethylsilyl) phenyl)amino)ethyl)-N-methyl-1,2-oxazole-5-carboxamide | 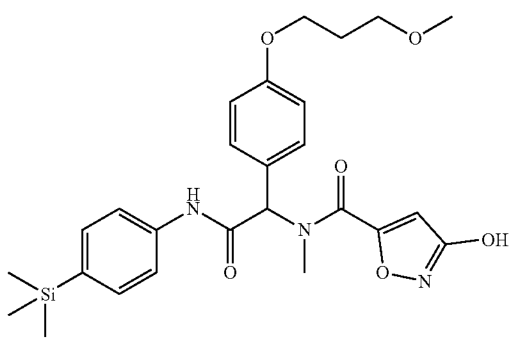 [SMILES: COCCCOc1ccc(C(C(=O)Nc2ccc([Si](C)(C)C)cc2)N(C)C(=O)c2cc(O)no2)cc1] | | 510.1 (M − H) |
| 334 | N-(1-(4-(methoxymethyl)phenyl)-2-oxo-2-((4-(trimethylsilyl)phenyl) amino)ethyl)-5-oxopyrrolidine-3-carboxamide (mixture of four optical isomers) | 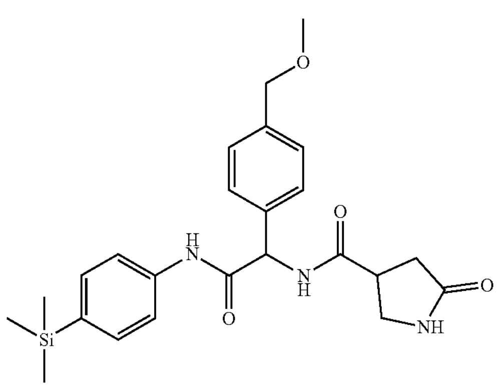 [SMILES: COCc1ccc(C(NC(=O)C2CNC(=O)C2)C(=O)Nc2ccc([Si](C)(C)C)cc2)cc1] | | 452.0 (M − H) |

TABLE 1-34-continued

| Ex. No. | IUPAC NAME | Structure | Salt | MS (Found) |
|---|---|---|---|---|
| 335 | 3-hydroxy-N-(1-(4-methoxyphenyl)-2-oxo-2-((4-(trimethylsilyl)phenyl)amino)ethyl)cyclohexanecarboxamide (mixture of four optical isomers) | 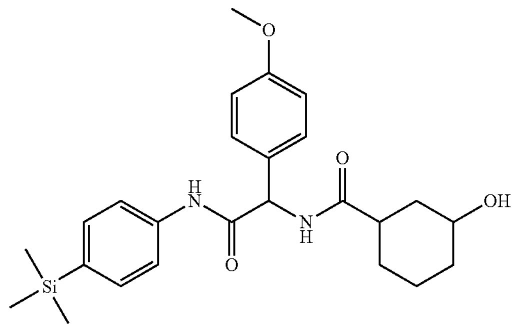 [SMILES: COc1ccc(C(NC(=O)C2CCCC(O)C2)C(=O)Nc2ccc([Si](C)(C)C)cc2)cc1] | | 455.2 (M + H) |
| 336 | 2-(((1-ethyl-5-hydroxy-1H-pyrazol-4-yl)acetyl)amino)-2-(4-methoxyphenyl)-N-(4-(trimethylsilyl)phenyl)acetamide | 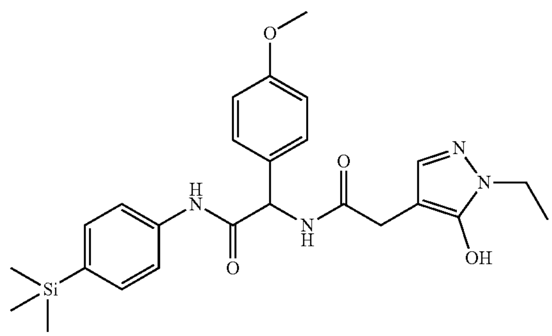 [SMILES: CCn1ncc(CC(=O)NC(C(=O)Nc2ccc([Si](C)(C)C)cc2)c2ccc(OC)cc2)c1O] | | 481.2 (M + H) |
| 337 | N-((1S)-2-((2,5-difluoro-4-(trimethylsilyl)phenyl)amino)-1-(4-methoxyphenyl)-2-oxoethyl)-3-hydroxy-N-methyl-1,2-oxazole-5-carboxamide | 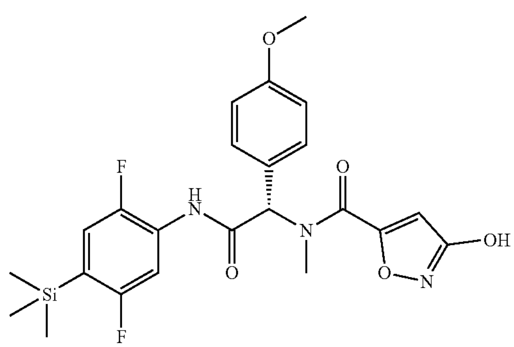 [SMILES: COc1ccc([C@@H](C(=O)Nc2cc(F)c([Si](C)(C)C)cc2F)N(C)C(=O)c2cc(O)no2)cc1] | | 488.0 (M − H) |
| 338 | N-(1-(4-methoxyphenyl)-2-oxo-2-((4-(trimethylsilyl)phenyl)amino)ethyl)-N-methyl-5-oxo-4,5-dihydro-1,2,4-oxadiazole-3-carboxamide | 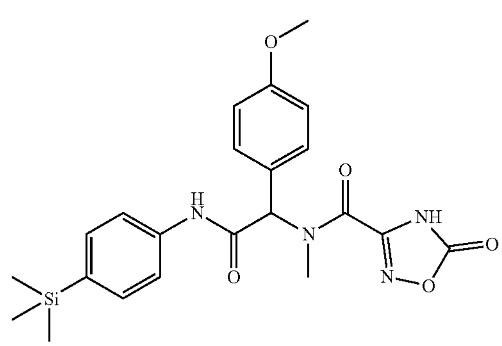 [SMILES: COc1ccc(C(C(=O)Nc2ccc([Si](C)(C)C)cc2)N(C)C(=O)c2noc(=O)[nH]2)cc1] | | 453.1 (M − H) |

TABLE 1-34-continued

| Ex. No. | IUPAC NAME | Structure | Salt | MS (Found) |
|---|---|---|---|---|
| 339 | 2-(((3-cyanopyrrolidin-1-yl)acetyl)amino)-2-(4-methoxyphenyl)-N-(4-(trimethylsilyl)phenyl)acetamide (mixture of four optical isomers) | 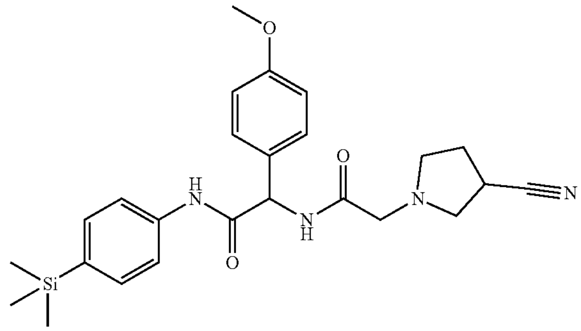 [SMILES: COc1ccc(C(NC(=O)CN2CCC(C#N)C2)C(=O)Nc2ccc([Si](C)(C)C)cc2)cc1] | | 465.1 (M + H) |
| 340 | N-(2-((3-cyano-4-(trimethylsilyl)phenyl)amino)-1-(4-methoxyphenyl)-2-oxoethyl)-3-hydroxy-N-methyl-1,2-oxazole-5-carboxamide | 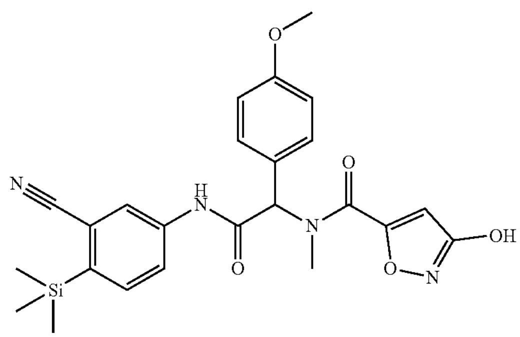 [SMILES: COc1ccc(C(C(=O)Nc2ccc([Si](C)(C)C)c(C#N)c2)N(C)C(=O)c2cc(O)no2)cc1] | | 477.1 (M − H) |
| 341 | 2-(((5-hydroxy-1-methyl-1H-pyrazol-3-yl)acetyl)amino)-2-(4-methoxyphenyl)-N-(4-(trimethylsilyl)phenyl)acetamide | 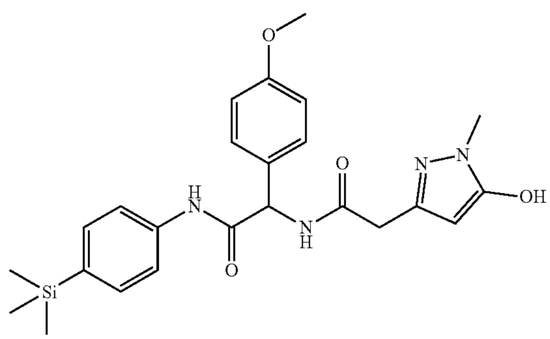 [SMILES: COc1ccc(C(NC(=O)Cc2cc(O)n(C)n2)C(=O)Nc2ccc([Si](C)(C)C)cc2)cc1] | | 467.2 (M + H) |

TABLE 1-35

| Ex. No. | IUPAC NAME | Structure | Salt | MS (Found) |
|---|---|---|---|---|
| 342 | 2-(((1-ethyl-3-hydroxy-1H-pyrazol-4-yl)acetyl)amino)-2-(4-methoxyphenyl)-N-(4-(trimethylsilyl)phenyl)acetamide | 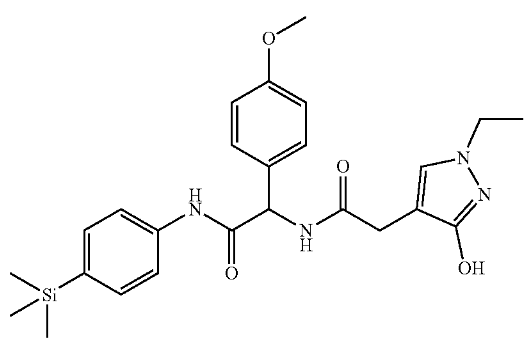 [SMILES: CCn1cc(CC(=O)NC(C(=O)Nc2ccc([Si](C)(C)C)cc2)c2ccc(OC)cc2)c(O)n1] | | 481.2 (M + H) |

TABLE 1-35-continued

| Ex. No. | IUPAC NAME | Structure | Salt | MS (Found) |
|---|---|---|---|---|
| 343 | 2-(((1-cyanocyclopentyl)acetyl)amino)-2-(4-methoxyphenyl)-N-(4-(trimethylsilyl)phenyl)acetamide | 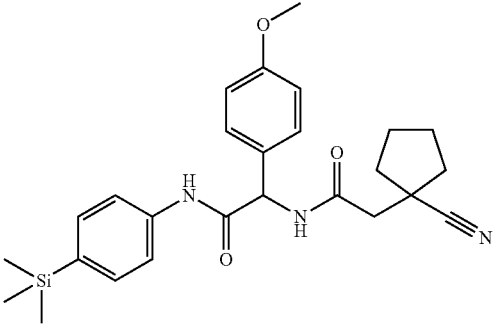 [SMILES: COc1ccc(C(NC(=O)CC2(C#N)CCCC2)C(=O)Nc2ccc([Si](C)(C)C)cc2)cc1] | | 464.2 (M + H) |
| 344 | 2-(4-(methoxymethyl)phenyl)-2-(((5-methyl-1,3,4-oxadiazol-2-yl)acetyl)amino)-N-(4-(trimethylsilyl)phenyl)acetamide | 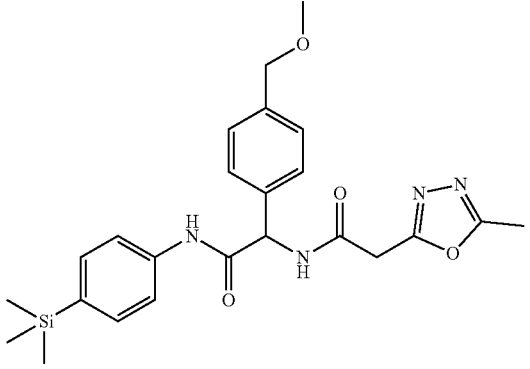 | | 467.2 (M + H) |
| 345 | N-(2-((3-chloro-4-(1-cyanocyclopentyl)phenyl)amino)-1-(4-methoxyphenyl)-2-oxoethyl)-5-oxopyrrolidine-3-carboxamide (mixture of four optical isomers) | 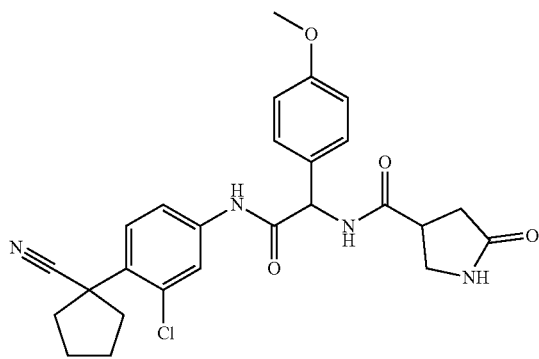 [SMILES: COc1ccc(C(NC(=O)C2CNC(=O)C2)C(=O)Nc2ccc(C3(C#N)CCCC3)c(Cl)c2)cc1] | | 495.2 (M + H) |
| 346 | 2-(4-methoxyphenyl)-2-(((5-oxopyrrolidin-3-yl)acetyl)amino)-N-(4-(trimethylsilyl)phenyl)acetamide (mixture of four optical isomers) | 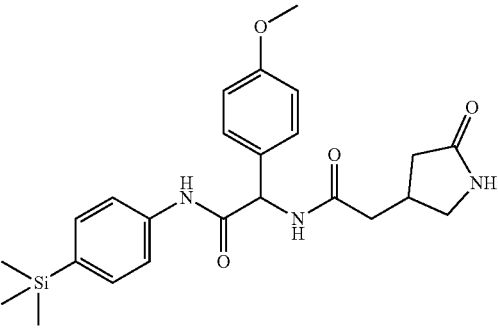 [SMILES: COc1ccc(C(NC(=O)CC2CNC(=O)C2)C(=O)Nc2ccc([Si](C)(C)C)cc2)cc1] | | 454.2 (M + H) |

TABLE 1-35-continued

| Ex. No. | IUPAC NAME | Structure | Salt | MS (Found) |
|---|---|---|---|---|
| 347 | 2-(((1-benzyl-3-hydroxy-1H-pyrazol-4-yl)acetyl)amino)-2-(4-methoxyphenyl)-N-(4-(trimethylsilyl)phenyl)acetamide | 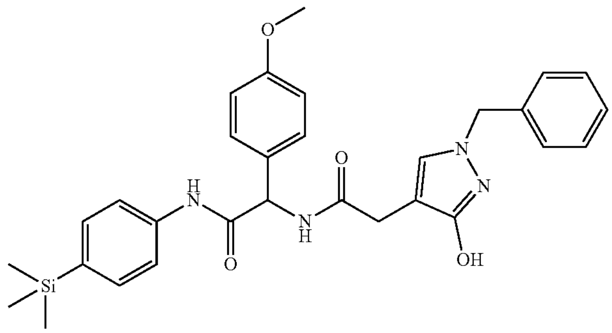 [SMILES: COc1ccc(C(NC(=O)Cc2cn(Cc3ccccc3)nc2O)C(=O)Nc2ccc([Si](C)(C)C)cc2)cc1] | | 543.2 (M + H) |
| 348 | 2-(3-hydroxyazetidin-1-yl)-N-(1-(4-methoxyphenyl)-2-oxo-2-((4-(trimethylsilyl)phenyl)amino)ethyl)-2-methylpropanamide | 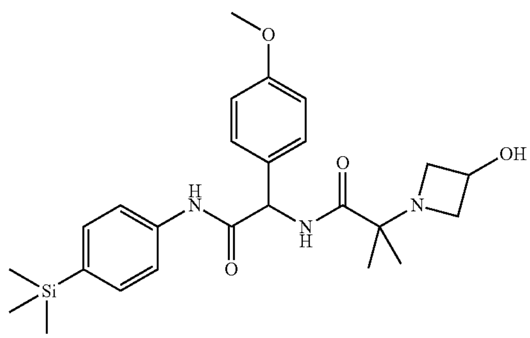 [SMILES: COc1ccc(C(NC(=O)C(C)(C)N2CC(O)C2)C(=O)Nc2ccc([Si](C)(C)C)cc2)cc1] | | 470.2 (M + H) |
| 349 | 2-(((3-hydroxy-1H-pyrazol-4-yl)acetyl)amino)-2-(4-(methoxyphenyl)-N-(4-(trimethylsilyl)phenyl)acetamide | 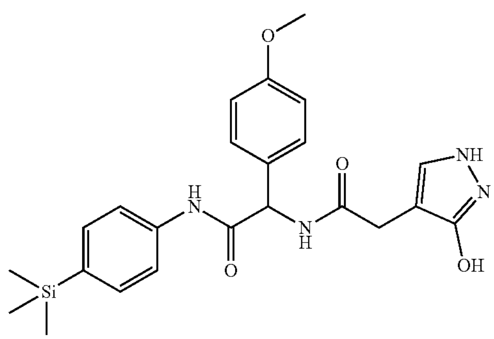 [SMILES: COc1ccc(C(NC(=O)Cc2c[nH]nc2O)C(=O)Nc2ccc([Si](C)(C)C)cc2)cc1] | | 453.2 (M + H) |
| 350 | 2-(4-methoxyphenyl)-2-(((5-methyl-1,3,4-oxadiazol-2-yl)acetyl)amino)-N-(4-(trimethylsilyl)phenyl)acetamide | 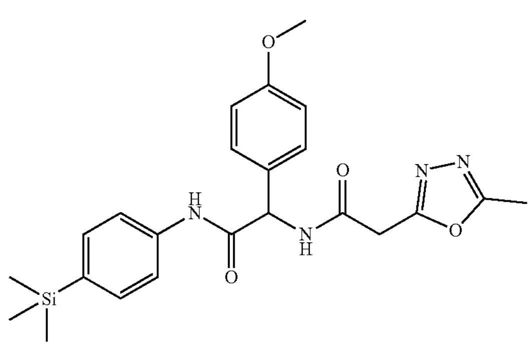 | | 453.2 (M + H) |

TABLE 1-35-continued

| Ex. No. | IUPAC NAME | Structure | Salt | MS (Found) |
|---|---|---|---|---|
| 351 | 3-hydroxy-N-(1-(4-(methoxymethyl)phenyl)-2-oxo-2-((4-(trimethylsilyl)phenyl)amino)ethyl)pyrrolidine-1-carboxamide (mixture of four optical isomers) | 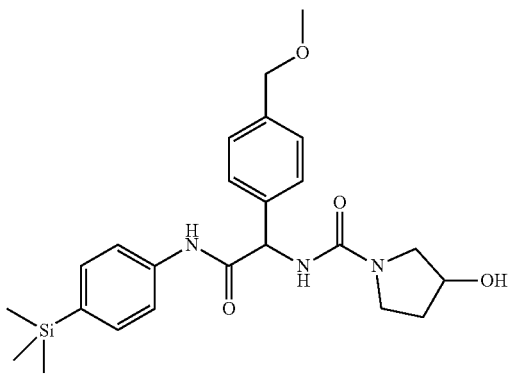 [SMILES: COCc1ccc(C(NC(=O)N2CCC(O)C2)C(=O)Nc2ccc([Si](C)(C)C)cc2)cc1] | | 456.2 (M + H) |

TABLE 1-36

| Ex. No. | IUPAC NAME | Structure | Salt | MS (Found) |
|---|---|---|---|---|
| 352 | N-(1-(4-methoxyphenyl)-2-oxo-2-((4-(trimethylsilyl)phenyl)amino)ethyl)-2-(1-methyl-1H-pyrazol-4-yl)propanamide | 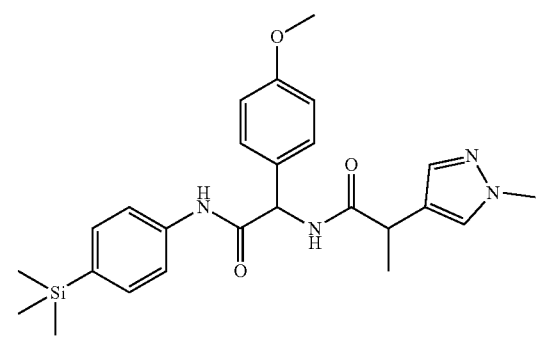 | | 465.2 (M + H) |
| 353 | 2-(((3-hydroxy-1-methyl-1H-pyrazol-5-yl)acetyl)amino)-2-(4-methoxyphenyl)-N-(4-(trimethylsilyl)phenyl)acetamide | 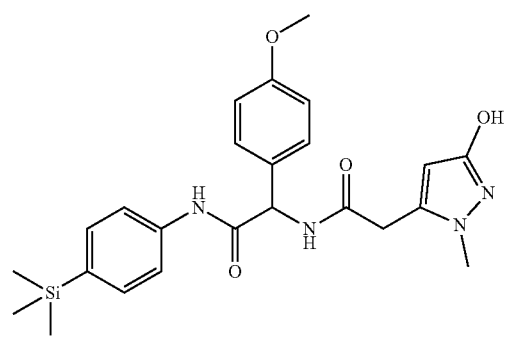 [SMILES: COc1ccc(C(NC(=O)Cc2cc(O)nn2C)C(=O)Nc2ccc([Si](C)(C)C)cc2)cc1] | | 467.2 (M + H) |
| 354 | N-(1-(4-(1-hydroxyethyl)phenyl)-2-oxo-2-((4-(trimethylsilyl)phenyl)amino)ethyl)-5-oxopyrrolidine-3-carboxamide (mixture of eight optical isomers) | 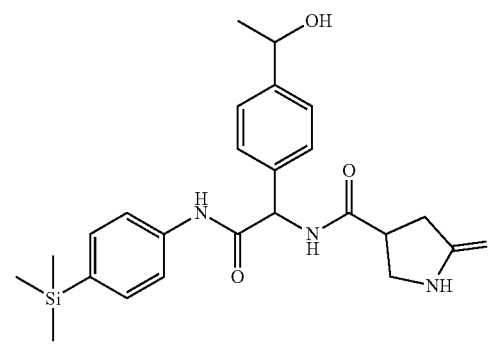 | | 452.0 (M − H) |

TABLE 1-36-continued

| Ex. No. | IUPAC NAME | Structure | Salt | MS (Found) |
|---|---|---|---|---|
| 355 | 2-(((2-hydroxy-2-methylpropyl)carbamoyl)amino)-2-(4-methoxyphenyl)-N-(4-(trimethylsilyl)phenyl)acetamide | 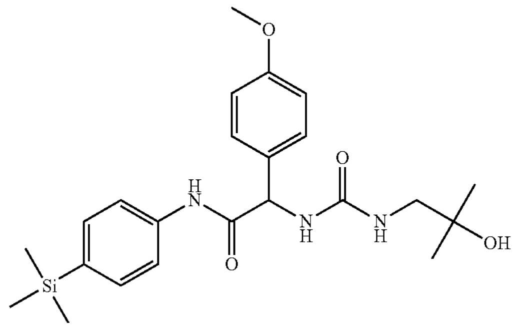 [SMILES: COc1ccc(C(NC(=O)NCC(C)(C)O)C(=O)Nc2ccc([Si](C)(C)C)cc2)cc1] | | 444.2 (M + H) |
| 356 | 2-(((3-(benzyloxy)-1,2-oxazol-5-yl)acetyl)amino)-2-(4-methoxyphenyl)-N-(4-(trimethylsilyl)phenyl)acetamide | 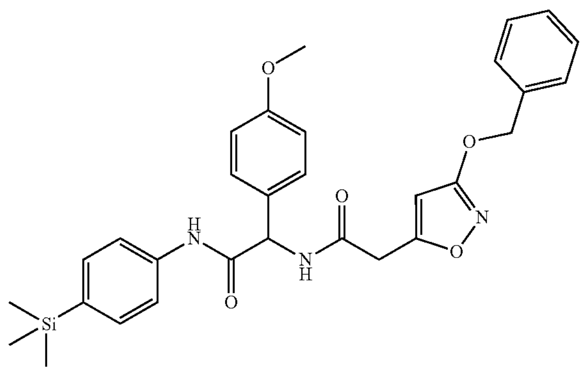 [SMILES: COc1ccc(C(NC(=O)Cc2cc(OCc3ccccc3)no2)C(=O)Nc2ccc([Si](C)(C)C)cc2)cc1] | | 544.3 (M + H) |
| 357 | 2-(((3-hydroxy-1,2-oxazol-5-yl)acetyl)amino)-2-(4-methoxyphenyl)-N-(4-(trimethylsilyl)phenyl)acetamide | 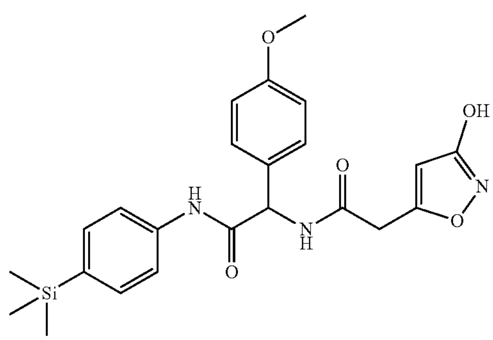 [SMILES: COc1ccc(C(NC(=O)Cc2cc(O)no2)C(=O)Nc2ccc([Si](C)(C)C)cc2)cc1] | | 454.2 (M + H) |
| 358 | ((3S)-3-hydroxy-N-((1R)-1-(4-methoxyphenyl)-2-oxo-2-((4-(trimethylsilyl)phenyl)amino)ethyl)pyrrolidine-1-carboxamide | 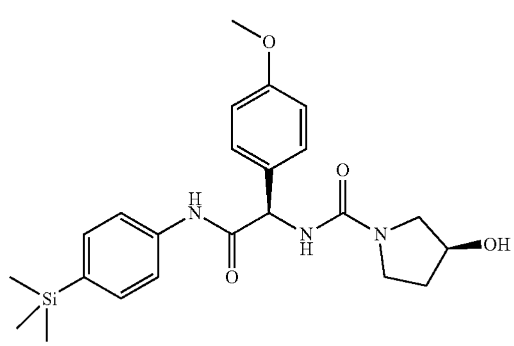 [SMILES: COc1ccc([C@@H](NC(=O)N2CC[C@H](O)C2)C(=O)Nc2ccc([Si](C)(C)C)cc2)cc1] | | 442.2 (M + H) |

TABLE 1-36-continued

| Ex. No. | IUPAC NAME | Structure | Salt | MS (Found) |
|---|---|---|---|---|
| 359 | (3R)-3-hydroxy-N-((1R)-1-(4-methoxyphenyl)-2-oxo-2-((4-(trimethylsilyl)phenyl)amino)ethyl)pyrrolidine-1-carboxamide | 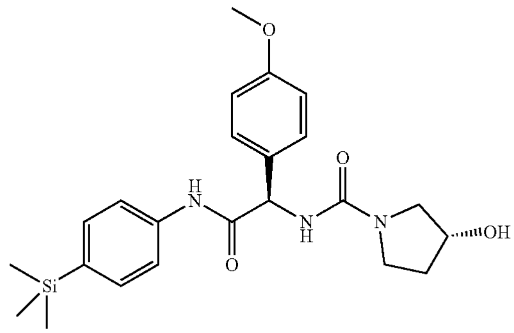 [SMILES: COc1ccc([C@@H](NC(=O)N2CC[C@@H](O)C2)C(=O)Nc2ccc([Si](C)(C)C)cc2)cc1] | | 442.2 (M + H) |
| 360 | N-(1-(4-((2,2-difluoroethoxy)methyl)phenyl)-2-((3-fluoro-4-(trimethylsilyl)phenyl)amino)-2-oxoethyl)-3-hydroxy-N-methyl-1,2-oxazole-5-carboxamide | 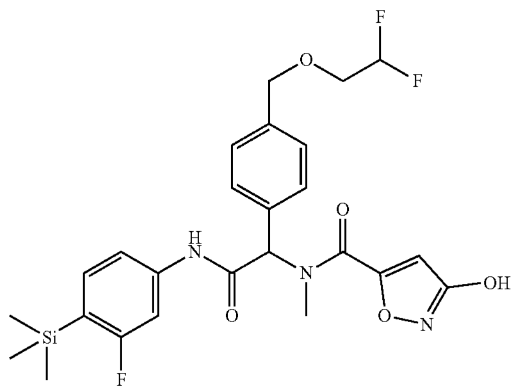 [SMILES: CN(C(=O)c1cc(O)no1)C(C(=O)Nc1ccc([Si](C)(C)C)c(F)c1)c1ccc(COCC(F)F)cc1] | | 534.2 (M − H) |
| 361 | N-(1-(4-((2,2-difluoroethoxy)methyl)phenyl)-2-((2-fluoro-4-(trimethylsilyl)phenyl)amino)-2-oxoethyl)-3-hydroxy-N-methyl-1,2-oxazole-5-carboxamide | 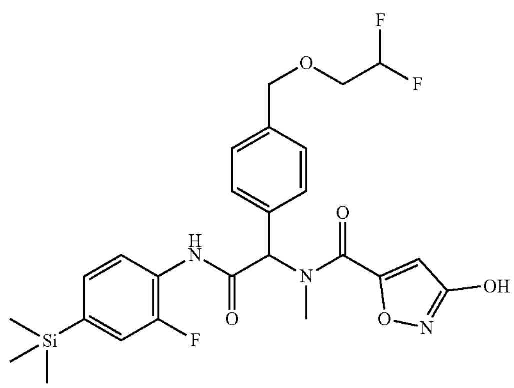 [SMILES: CN(C(=O)c1cc(O)no1)C(C(=O)Nc1ccc([Si](C)(C)C)cc1F)c1ccc(COCC(F)F)cc1] | | 534.2 (M − H) |

TABLE 1-37

| Ex. No. | IUPAC NAME | Structure | Salt | MS (Found) |
|---|---|---|---|---|
| 362 | 2-(4-methoxyphenyl)-2-(((6-oxopyrimidin-1(6H)-yl)acetyl)amino)-N-(4-(trimethylsilyl)phenyl)acetamide | 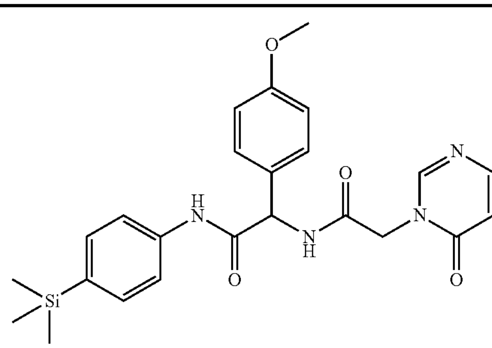 | | 465.2 (M + H) |

TABLE 1-37-continued

| Ex. No. | IUPAC NAME | Structure | Salt | MS (Found) |
|---|---|---|---|---|
| 363 | 2-(4-(methoxymethyl)phenyl)-2-(((6-oxopyrimidin-1(6H)-yl)acetyl)amino)-N-(4-(trimethylsilyl)phenyl)acetamide | 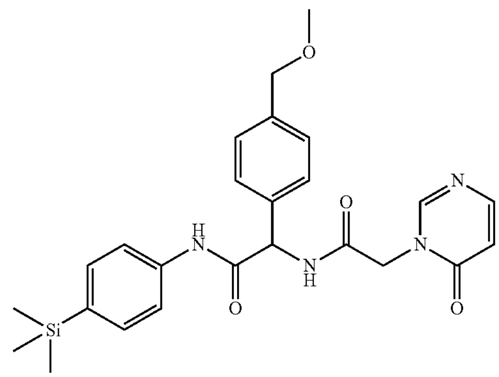 [SMILES: COCc1ccc(C(NC(=O)Cn2cnccc2=O)C(=O)Nc2ccc([Si](C)(C)C)cc2)cc1] | | 479.2 (M + H) |
| 364 | 3-hydroxy-N-(1-(4-(1-methoxyethyl)phenyl)-2-oxo-2-((4-(trimethylsilyl)phenyl)amino)ethyl)-N-methyl-1,2-oxazole-5-carboxamide (mixture of four optical isomers) | 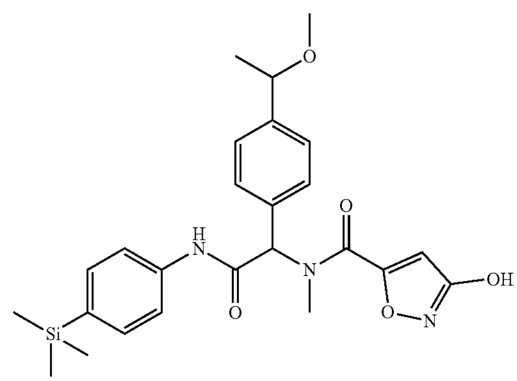 [SMILES: COC(C)c1ccc(C(C(=O)Nc2ccc([Si](C)(C)C)cc2)N(C)C(=O)c2cc(O)no2)cc1] | | 480.1 (M − H) |
| 365 | tert-butyl (2-hydroxy-4-((1-(4-methoxyphenyl)-2-oxo-2-((4-(trimethylsilyl)phenyl)amino)ethyl)amino)-4-oxobutyl)carbamate (mixture of four optical isomers) | 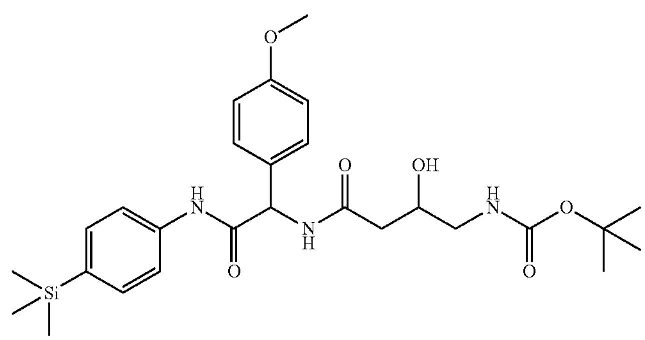 [SMILES: COc1ccc(C(NC(=O)CC(O)CNC(=O)OC(C)(C)C)C(=O)Nc2ccc([Si](C)(C)C)cc2)cc1] | | 528.2 (M − H) |
| 366 | 2-(((3-(benzyloxy)-1,2-oxazol-5-yl)acetyl)amino)-N-(3,5-difluoro-4-(trimethylsilyl)phenyl)-2-(4-(methoxymethyl)phenyl)acetamide | 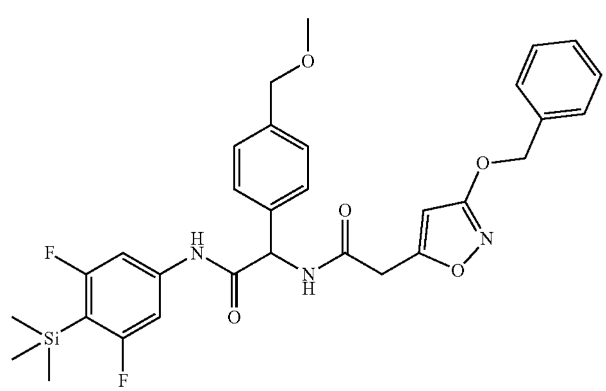 [SMILES: COCc1ccc(C(NC(=O)Cc2cc(OCc3ccccc3)no2)C(=O)Nc2cc(F)c([Si](C)(C)C)c(F)c2)cc1] | | 592.2 (M − H) |

TABLE 1-37-continued

| Ex. No. | IUPAC NAME | Structure | Salt | MS (Found) |
|---|---|---|---|---|
| 367 | N-(2-fluoro-4-(trimethylsilyl)phenyl)-2-(4-(methoxymethyl)phenyl)-2-(((6-oxopyrimidin-1(6H)-yl)acetyl)amino)acetamide | 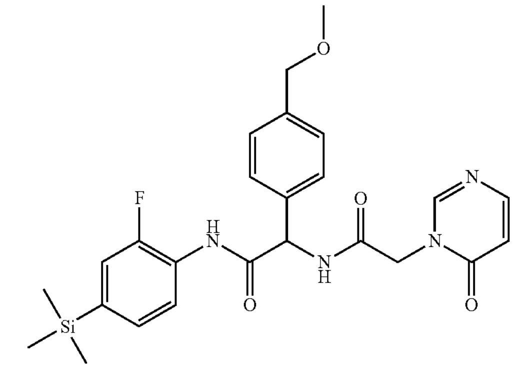 [SMILES: COCc1ccc(C(NC(=O)Cn2cnccc2=O)C(=O)Nc2ccc([Si](C)(C)C)cc2F)cc1] | | 497.2 (M + H) |
| 368 | N-(2-fluoro-4-(trimethylsilyl)phenyl)-2-(4-(methoxymethyl)phenyl)-2-(((5-methyl-1,3,4-oxadiazol-2-yl)acetyl)amino)acetamide | 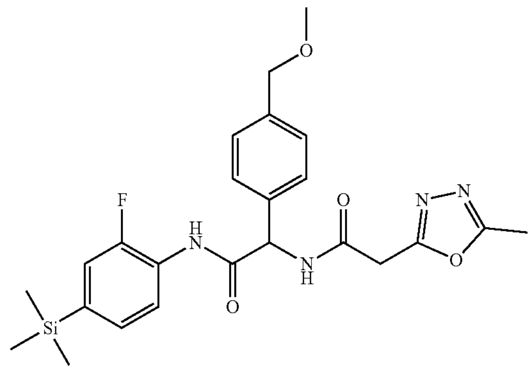 | | 485.2 (M + H) |
| 369 | 3-hydroxy-N-(1-(4-(1-hydroxyethyl)phenyl)-2-oxo-2-(4-(trimethylsilyl)phenyl)amino)ethyl)-N-methyl-1,2-oxazole-5-carboxamide (mixture of four optical isomers) | 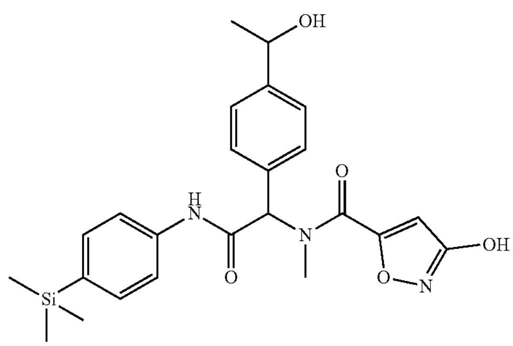 [SMILES: CC(O)c1ccc(C(C(=O)Nc2ccc([Si](C)(C)C)cc2)N(C)C(=O)c2cc(O)no2)cc1] | | 466.1 (M − H) |
| 370 | N-(2-((4-tert-butyl-3-cyanophenyl)amino)-1-(4-(methoxymethyl)phenyl)-2-oxoethyl)-3-hydroxypyrrolidine-1-carboxamide (mixture of four optical isomers) | 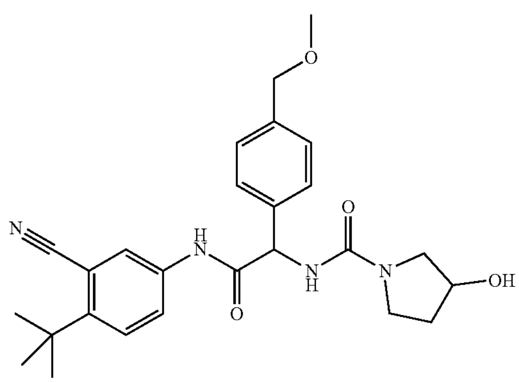 [SMILES: COCc1ccc(C(NC(=O)N2CCC(O)C2)C(=O)Nc2ccc(C(C)(C)C)c(C#N)c2)cc1] | | 465.2 (M + H) |

TABLE 1-37-continued

| Ex. No. | IUPAC NAME | Structure | Salt | MS (Found) |
|---|---|---|---|---|
| 371 | N-(2-((4-tert-butyl-3-cyanophenyl)amino)-1-(4-(methoxymethyl)phenyl)-2-oxoethyl)-3-hydroxyazetidine-1-carboxamide | 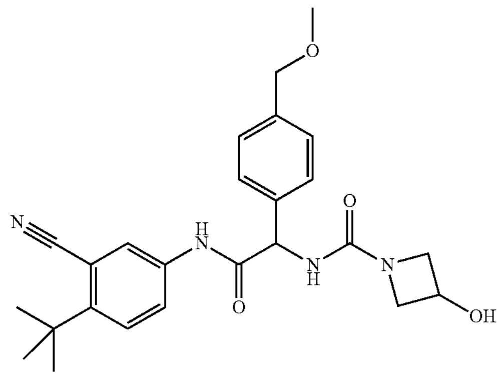 [SMILES: COCc1ccc(C(NC(=O)N2CC(O)C2)C(=O)Nc2ccc(C(C)(C)C)c(C#N)c2)cc1] | | 451.2 (M + H) |

TABLE 1-38

| Ex. No. | IUPAC NAME | Structure | Salt | MS (Found) |
|---|---|---|---|---|
| 372 | N-(2-((4-tert-butyl-3-cyanophenyl)amino)-1-(4-(methoxymethyl)phenyl)-2-oxoethyl)-5-oxopyrrolidine-3-carboxamide (mixture of four optical isomers) | 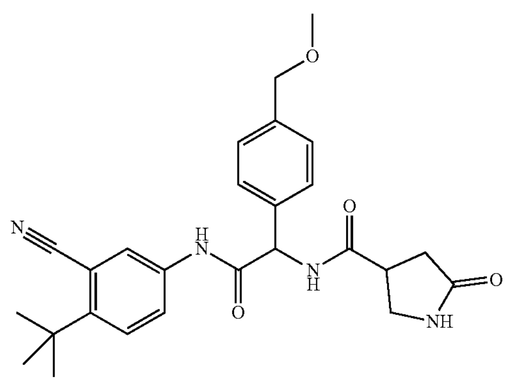 [SMILES: COCc1ccc(C(NC(=O)C2CNC(=O)C2)C(=O)Nc2ccc(C(C)(C)C)c(C#N)c2)cc1] | | 461.1 (M − H) |
| 373 | N-(2-((3-cyano-4-(trimethylsilyl)phenyl)amino)-1-(4-((methoxymethyl)phenyl)-2-oxoethyl)-3-hydroxy-N-methyl-1,2-oxazole-5-carboxamide | 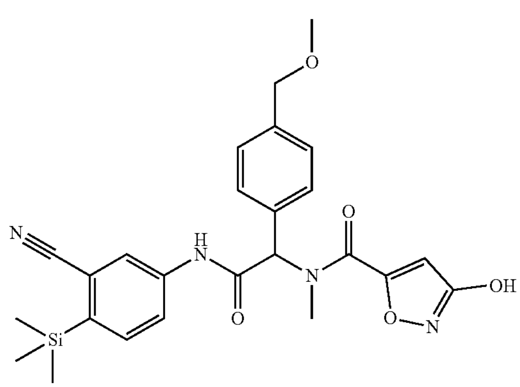 [SMILES: COCc1ccc(C(C(=O)Nc2ccc([Si](C)(C)C)c(C#N)c2)N(C)C(=O)c2cc(O)no2)cc1] | | 491.2 (M − H) |

TABLE 1-38-continued

| Ex. No. | IUPAC NAME | Structure | Salt | MS (Found) |
|---|---|---|---|---|
| 374 | N-(2-((3-cyano-4-(trimethylsilyl)phenyl)amino)-1-(4-methoxyphenyl)-2-oxoethyl)-3-hydroxyazetidine-1-carboxamide | 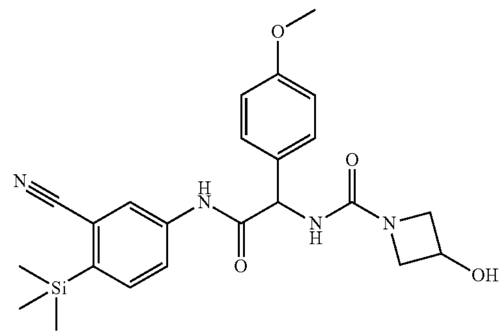 [SMILES: COc1ccc(C(NC(=O)N2CC(O)C2)C(=O)Nc2ccc([Si](C)(C)C)c(C#N)c2)cc1] | | 453.1 (M + H) |
| 375 | N-(2-((3-cyano-4-(trimethylsilyl)phenyl)amino)-1-(4-(methoxymethyl)phenyl)-2-oxoethyl)-3-hydroxyazetidine-1-carboxamide | 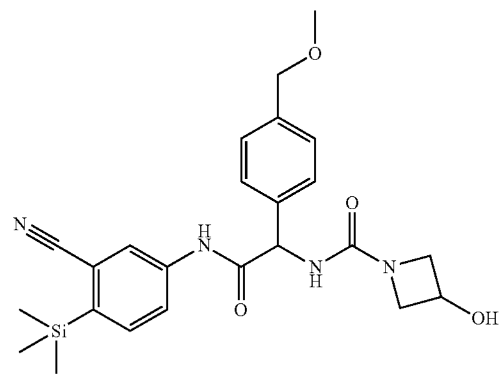 [SMILES: COCc1ccc(C(NC(=O)N2CC(O)C2)C(=O)Nc2ccc([Si](C)(C)C)c(C#N)c2)cc1] | | 465.1 (M − H) |
| 376 | N-(2-((4-tert-butyl-3-cyanophenyl)amino)-1-(4-methoxyphenyl)-2-oxoethyl)-3-hydroxypyrrolidine-1-carboxamide (mixture of four optical isomers) | 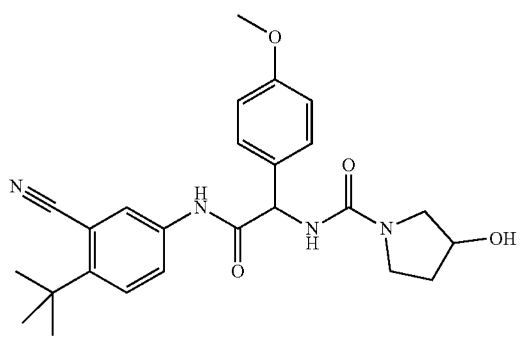 [SMILES: COc1ccc(C(NC(=O)N2CCC(O)C2)C(=O)Nc2ccc(C(C)(C)C)c(C#N)c2)cc1] | | 451.2 (M + H) |
| 377 | N-(2-((2,5-difluoro-4-(trimethylsilyl)phenyl)amino)-1-(4-methoxyphenyl)-2-oxoethyl)-3-hydroxyazetidine-1-carboxamide | 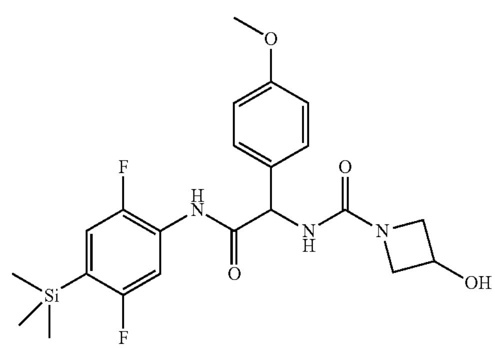 [SMILES: COc1ccc(C(NC(=O)N2CC(O)C2)C(=O)Nc2cc(F)c([Si](C)(C)C)cc2F)cc1] | | 464.2 (M + H) |

TABLE 1-38-continued

| Ex. No. | IUPAC NAME | Structure | Salt | MS (Found) |
|---|---|---|---|---|
| 378 | N-(2-((3-cyano-4-(trimethylsilyl)phenyl)amino)-1-(4-methoxyphenyl)-2-oxoethyl)-3-hydroxypyrrolidine-1-carboxamide (mixture of four optical isomers) | 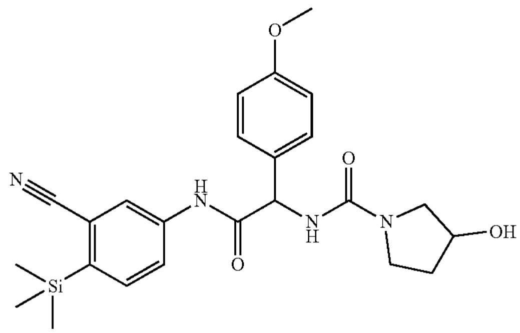 [SMILES: COc1ccc(C(NC(=O)N2CCC(O)C2)C(=O)Nc2ccc([Si](C)(C)C)c(C#N)c2)cc1] | | 467.2 (M + H) |
| 379 | 3-hydroxy-N-((1R)-1-(4-methoxyphenyl)-2-oxo-2-((4-(trimethylsilyl)phenyl)amino)ethyl)azetidine-1-carboxamide | 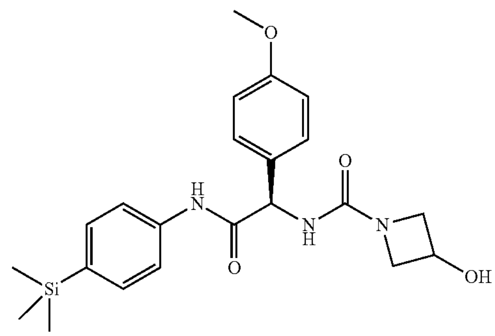 [SMILES: COc1ccc([C@@H](NC(=O)N2CC(O)C2)C(=O)Nc2ccc([Si](C)(C)C)cc2)cc1] | | 428.2 (M + H) |
| 380 | (3S)-N-(1S)-2-((3-fluoro-4-(trimethylsilyl)phenyl)amino)-1-(4-(methoxymethyl)phenyl)-2-oxoethyl)-5-oxopyrrolidine-3-carboxamide | 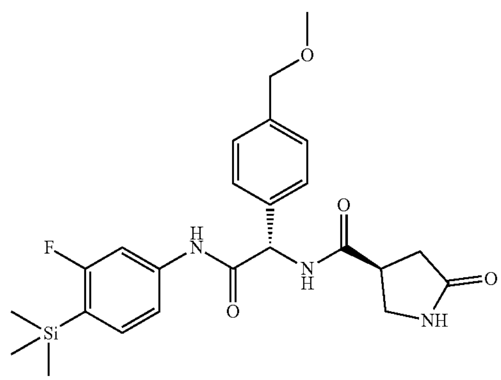 [SMILES: COCc1ccc([C@H](NC(=O)[C@@H]2CNC(=O)C2)C(=O)Nc2ccc([Si](C)(C)C)c(F)c2)cc1] | | 470.1 (M − H) |
| 381 | (3S)-N-((1S)-2-((3-fluoro-4-(trimethylsilyl)phenyl)amino)-1-(4-methoxyphenyl)-2-oxoethyl)-5-oxopyrrolidine-3-carboxamide | 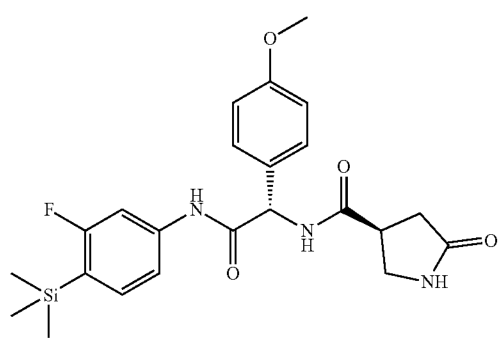 [SMILES: COc1ccc([C@H](NC(=O)[C@@H]2CNC(=O)C2)C(=O)Nc2ccc([Si](C)(C)C)c(F)c2)cc1] | | 458.2 (M + H) |

TABLE 1-39

| Ex. No. | IUPAC NAME | Structure | Salt | MS (Found) |
|---|---|---|---|---|
| 382 | 4-(((1R)-2-((3-fluoro-4-(trimethylsilyl)phenyl)amino)-1-(4-(methoxymethyl)phenyl)-2-oxoethyl)amino)-4-oxobutanoic acid | 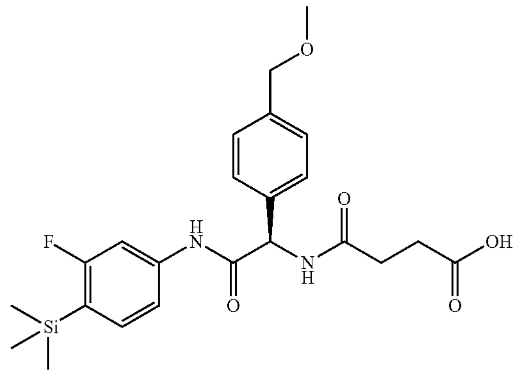 [SMILES: COCc1ccc([C@@H](NC(=O)CCC(=O)O)C(=O)Nc2ccc([Si](C)(C)C)c(F)c2)cc1] | | 459.1 (M − H) |
| 384 | N-((1R)-2-((3-fluoro-4-(trimethylsilyl)phenyl)amino)-1-(4-(methoxymethyl)phenyl)-2-oxoethyl)-3-hydroxy-1,2-oxazole-5-carboxamide | 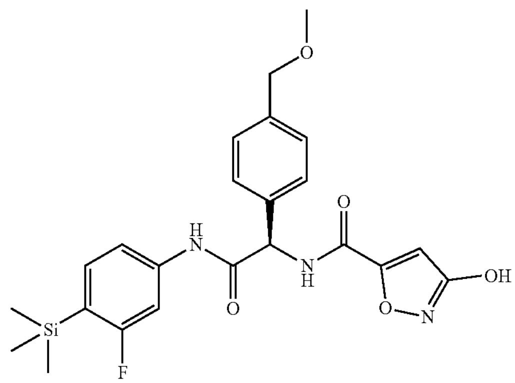 [SMILES: COCc1ccc([C@@H](NC(=O)c2cc(O)no2)C(=O)Nc2ccc([Si](C)(C)C)c(F)c2)cc1] | | 472.2 (M + H) |
| 385 | N-((1R)-2-((4-tert-butyl-3-flourophenyl)amino)-1-(4-(methoxymethyl)phenyl)-2-oxoethyl)-3-hydroxy-1,2-oxazole-5-carboxamide | 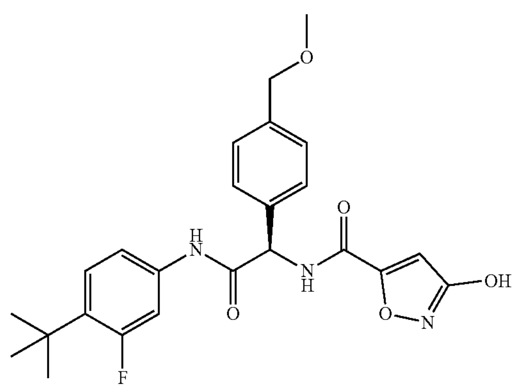 [SMILES: COCc1ccc([C@@H](NC(=O)c2cc(O)no2)C(=O)Nc2ccc(C(C)(C)C)c(F)c2)cc1] | | 456.1 (M + H) |
| 386 | 4-(((1R)-2-((3,5-difluoro-4-(trimethylsilyl)phenyl)amino)-1-(4-(methoxymethyl)phenyl)-2-oxoethyl)amino)-3,3-dimethyl-4-oxobutanoic acid | 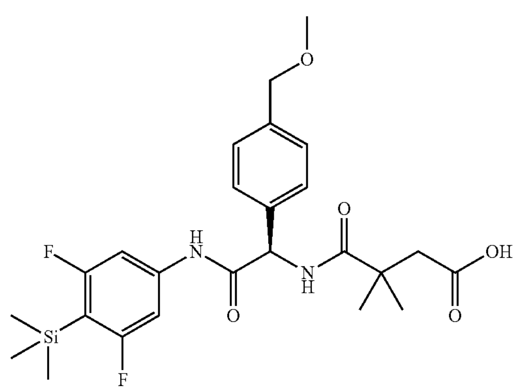 [SMILES: COCc1ccc([C@@H](NC(=O)C(C)(C)CC(=O)O)C(=O)Nc2cc(F)c([Si](C)(C)C)c(F)c2)cc1] | | 507.1 (M + H) |

TABLE 1-39-continued

| Ex. No. | IUPAC NAME | Structure | Salt | MS (Found) |
|---|---|---|---|---|
| 387 | N-(2-((4-tert-butyl-3-chlorophenyl)amino)-1-(4-(methoxymethyl)phenyl)-2-oxoethyl)-3-hydroxy-1,2-oxazole-5-carboxamide | 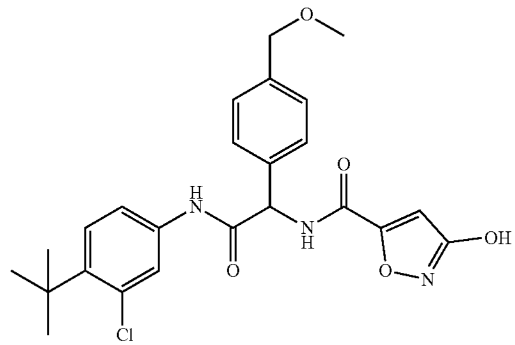 [SMILES: COCc1ccc(C(NC(=O)c2cc(O)no2)C(=O)Nc2ccc(C(C)(C)C)c(Cl)c2)cc1] | | 472.2 (M + H) |
| 388 | N-(4-tert-butyl-3-chlorophenyl)-2-(4-(methoxymethyl)phenyl)-2-(((6-oxopyrimidin-1(6H)-yl)acetyl)amino)acetamide | 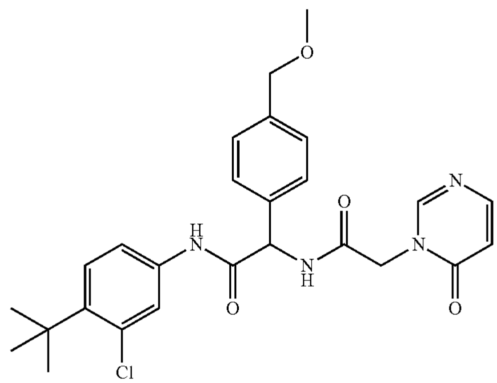 [SMILES: COCc1ccc(C(NC(=O)Cn2cnccc2=O)C(=O)Nc2ccc(C(C)(C)C)c(Cl)c2)cc1] | | 497.2 (M + H) |
| 389 | N-(3,5-difluoro-4-(trimethylsilyl)phenyl)-2-(4-(methoxymethyl)phenyl)-2-(2-oxopyrrolidin-1-yl)acetamide | 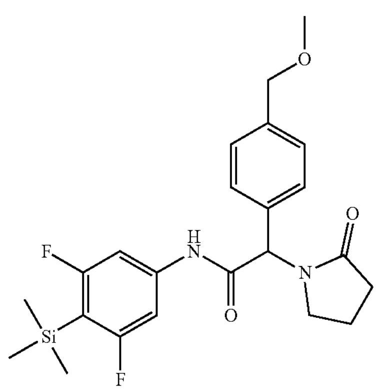 [SMILES: COCc1ccc(C(C(=O)Nc2cc(F)c([Si](C)(C)C)c(F)c2)N2CCCC2=O)cc1] | | 447.1 (M + H) |
| 390 | 6-(((1R)-2-((3,5-difluoro-4-(trimethylsilyl)phenyl)amino)-1-(4-(methoxymethyl)phenyl)-2-oxoethyl)amino)-6-oxohexanoic acid | 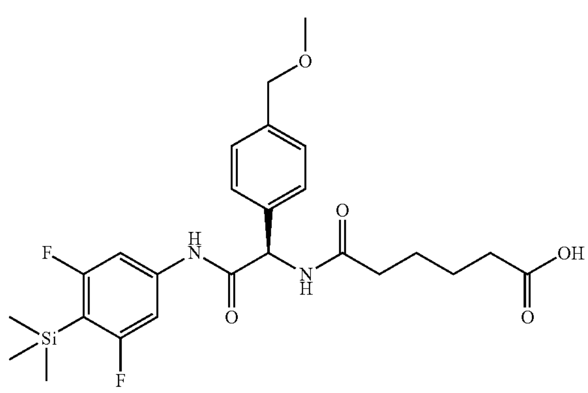 [SMILES: COCc1ccc([C@@H](NC(=O)CCCCC(=O)O)C(=O)Nc2cc(F)c([Si](C)(C)C)c(F)c2)cc1] | | 507.2 (M + H) |

TABLE 1-39-continued

| Ex. No. | IUPAC NAME | Structure | Salt | MS (Found) |
|---|---|---|---|---|
| 391 | (3S)-N-(2-((4-tert-butyl-3-fluorophenyl)amino)-1-(2,3-dihydro-1-benzofuran-5-yl)-2-oxoethyl)-5-oxopyrrolidine-3-carboxamide (mixture of two diastereomers) | 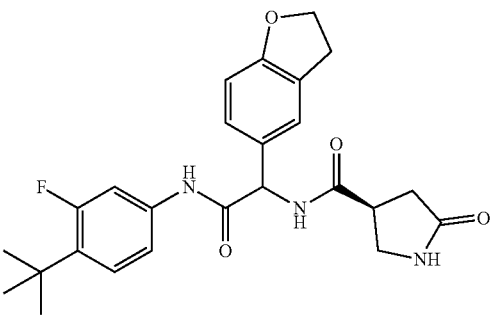 [SMILES: CC(C)(C)c1ccc(NC(=O)C(NC(=O)[C@@H]2CNC(=O)C2)c2ccc3c(c2)CCO3)cc1F] | | 452.2 (M − H) |

TABLE 1-40

| Ex. No. | UPAC NAME | Structure | Salt | MS (Found) |
|---|---|---|---|---|
| 392 | N-(2-((4-tert-butyl-3-fluorophenyl)amino)-1-(2,3-dihydro-1-benzofuran-5-yl)-2-oxoethyl)-3-hydroxy-1,2-oxazole-5-carboxamide | 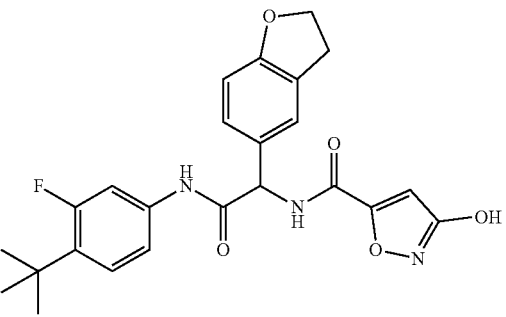 [SMILES: CC(C)(C)c1ccc(NC(=O)C(NC(=O)c2cc(O)no2)c2ccc3c(c2)CCO3)cc1F] | | 454.1 (M + H) |
| 393 | N-(2-((3-fluoro-4-(trimethylsilyl)phenyl)amino)-1-(1-methyl-1H-indazol-5-yl)-2-oxoethyl)-3-hydroxy-1,2-oxazole-5-carboxamide | 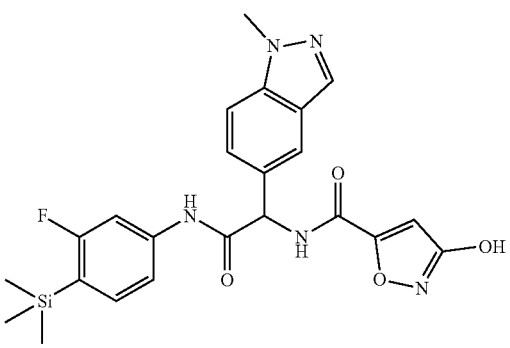 [SMILES: Cn1ncc2cc(C(NC(=O)c3cc(O)no3)C(=O)Nc3ccc([Si](C)(C)C)c(F)c3)ccc21] | | 480.1 (M − H) |
| 394 | (3S)-N-(2-((4-tert-butyl-3-fluorophenyl)amino)-1-(4-(2-hydroxypropan-2-yl)phenyl)-2-oxoethyl)-5-oxopyrrolidine-3-carboxamide (mixture of two diastereomers) | 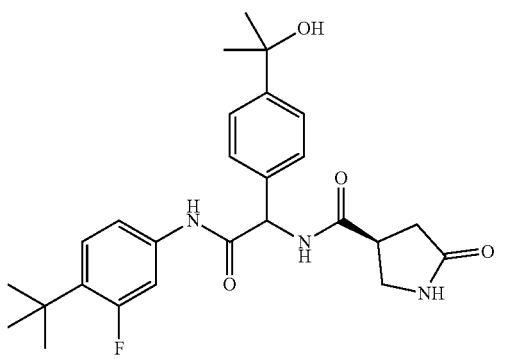 [SMILES: CC(C)(C)c1ccc(NC(=O)C(NC(=O)[C@@H]2CNC(=O)C2)c2ccc(C(C)(C)O)cc2)cc1F] | | 468.2 (M − H) |

TABLE 1-40-continued

| Ex. No. | UPAC NAME | Structure | Salt | MS (Found) |
|---|---|---|---|---|
| 395 | (3R)-N-(2-((4-tert-butyl-3-fluorophenyl)amino)-1-(4-(2-hydroxypropan-2-yl)phenyl)-2-oxoethyl)-5-oxopyrrolidine-3-carboxamide (mixture of two diastereomers) | 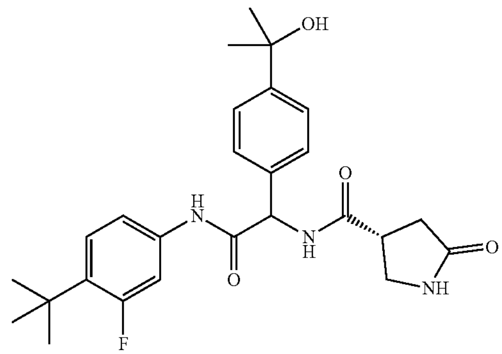 [SMILES: CC(C)(C)c1ccc(NC(=O)C(NC(=O)[C@H]2CNC(=O)C2)c2ccc(C(C)(C)O)cc2)cc1F] | | 468.2 (M − H) |
| 396 | ((3S)-N-(2-((4-(2,2-dimethylpropyl)-3-fluorophenyl)amino)-1-(4-(2-hydroxypropan-2-yl)phenyl)-2-oxoethyl)-5-oxopyrrolidine-3-carboxamnide (mixture of two diastereomers) | 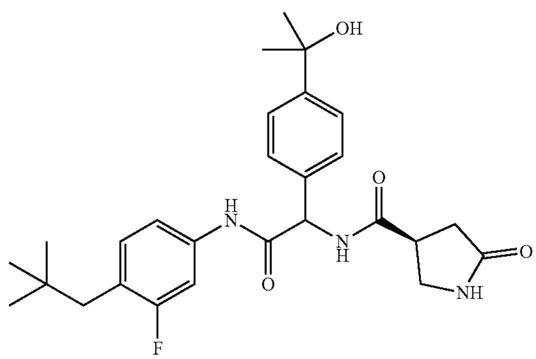 [SMILES: CC(C)(C)Cc1ccc(NC(=O)C(NC(=O)[C@@H]2CNC(=O)C2)c2ccc(C(C)(C)O)cc2)cc1F] | | 482.0 (M − H) |
| 397 | 5-((2-((4-(2,2-dimethylpropyl)-3-fluorophenyl)amino)-1-(4-(methoxymethyl)phenyl)-2-oxoethyl)amino)-5-oxopentanoic acid | 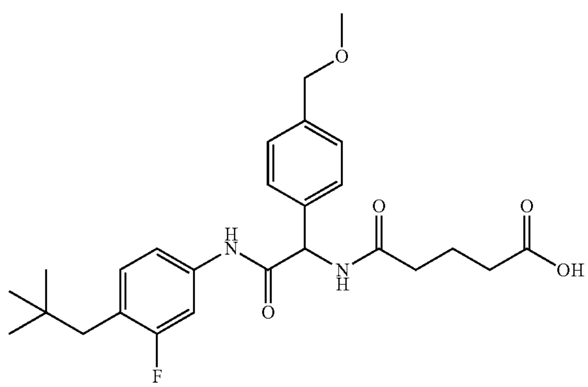 [SMILES: COCc1ccc(C(NC(=O)CCCC(=O)O)C(=O)Nc2ccc(CC(C)(C)C)c(F)c2)cc1] | | 473.2 (M + H) |
| 398 | (3S)-N-(2-((4-tert-butyl-3-fluorophenyl)amino)-1-(1-(methyl-1H-indol-5-yl)-2-oxoethyl)-5-oxopyrrolidine-3-carboxamide (mixture of two diastereomers) | 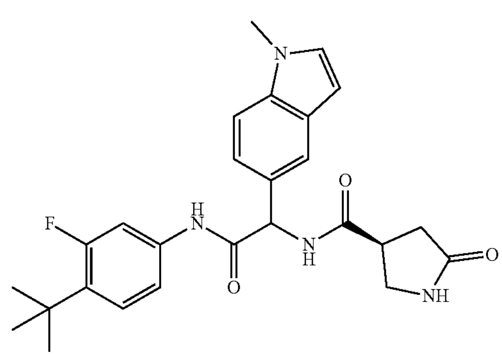 [SMILES: Cn1ccc2cc(C(NC(=O)[C@@H]3CNC(=O)C3)C(=O)Nc3ccc(C(C)(C)C)c(F)c3)ccc21] | | 463.0 (M − H) |

TABLE 1-40-continued

| Ex. No. | IUPAC NAME | Structure | Salt | MS (Found) |
|---|---|---|---|---|
| 399 | (3R)-N-(2-((4-tert-butyl-3-fluorophenyl)amino)-1-(1-methyl-1H-indol-5-yl)-2-oxoethyl)-5-oxopyrrolidine-3-carboxamide (mixture of two diastereomers) | 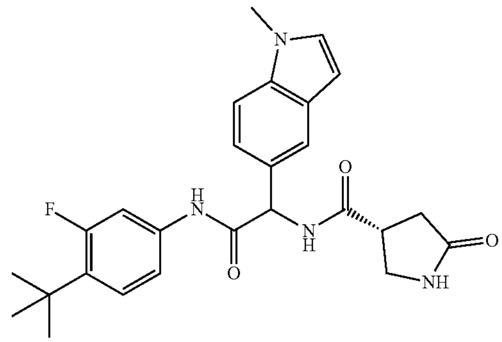 [SMILES: Cn1ccc2cc(C(NC(=O)[C@H]3CNC(=O)C3)C(=O)Nc3ccc(C(C)(C)C)c(F)c3)ccc21] | | 465.1 (M + H) |
| 400 | (3S)-N-(2-((4-tert-butyl-3-fluorophenyl)amino)-1-(1-(4-tert-butyl-3-fluorophenyl)amino)-1-(1-methyl-2,3-dihydro-1H-indol-5-yl)-2-oxoethyl)-5-oxopyrrolidine-3-carboxamide (mixture of two diastereomers) | 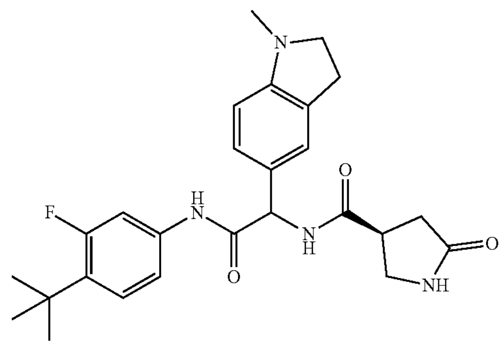 [SMILES: CN1CCc2cc(C(NC(=O)[C@@H]3CNC(=O)C3)C(=O)Nc3ccc(C(C)(C)C)c(F)c3)ccc21] | | 465.1 (M − H) |
| 401 | (3R)-N-(2-((4-tert-butyl-3-fluorophenyl)amino)-1-(1-(methyl-2,3-dihydro-1H-indol-5-yl)-2-oxoethyl)-5-oxopyrrolidine-3-carboxamide (mixture of two diastereomers) | 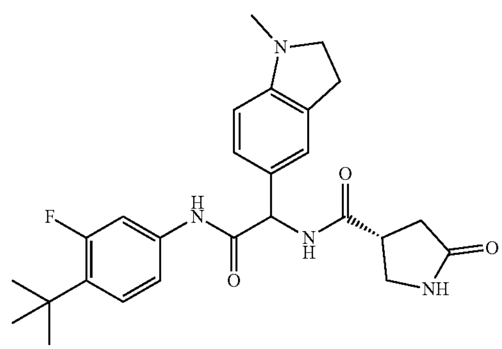 [SMILES: CN1CCc2cc(C(NC(=O)[C@H]3CNC(=O)C3)C(=O)Nc3ccc(C(C)(C)C)c(F)c3)ccc21] | | 465.1 (M − H) |

TABLE 1-41

| Ex. No. | IUPAC NAME | Structure | Salt | MS (Found) |
|---|---|---|---|---|
| 402 | (3S)-N-((1R)-2-((4-tert-butyl-3-fluorophenyl)amino)-1-(4-(2-hydroxypropan-2-yl)phenyl)-2-oxoethyl)-5-oxopyrrolidine-3-carboxamide | 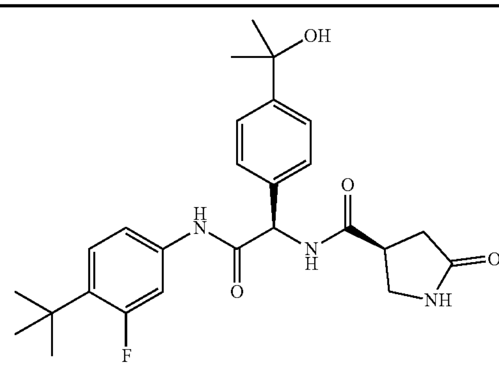 | | 468.2 (M − H) |

TABLE 1-41-continued

| Ex. No. | IUPAC NAME | Structure | Salt | MS (Found) |
|---|---|---|---|---|
| 406 | (3R)-N-(2-((4-tert-butyl-3-fluorophenyl)amino)-1-(4-(2-hydroxypropan-2-yl)phenyl)-2-oxoethyl)-5-oxopyrrolidine-3-carboxamide | 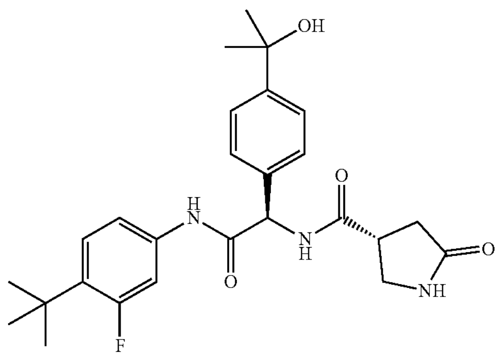 [SMILES: CC(C)(C)c1ccc(NC(=O)[C@H](NC(=O)[C@H]2CNC(=O)C2)c2ccc(C(C)(C)O)cc2)cc1F] | | 468.2 (M − H) |
| 407 | N-(2-((4-tert-butyl-3-fluorophenyl)amino)-1-(4-(2-hydroxypropan-2-yl)phenyl)-2-oxoethyl)tetrahydrothiophene-3-carboxamide 1,1-dioxide (mixture of four optical isomers) | 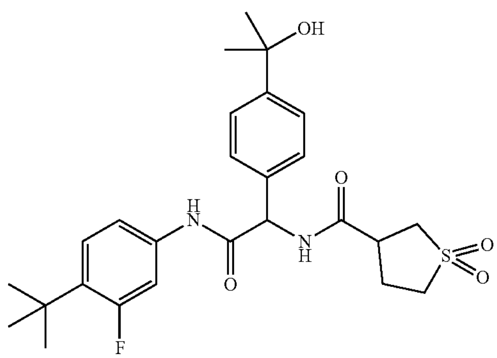 [SMILES: CC(C)(C)c1ccc(NC(=O)C(NC(=O)C2CCS(=O)(=O)C2)c2ccc(C(C)(C)O)cc2)cc1F] | | 505.2 (M + H) |
| 409 | (3R)-N-((1S)-2-((4-tert-butyl-3,5-(difluorophenyl)amino)-1-(4-(methoxymethyl)phenyl)-2-oxoethyl)-5-oxopyrrolidine-3-carboxamide | 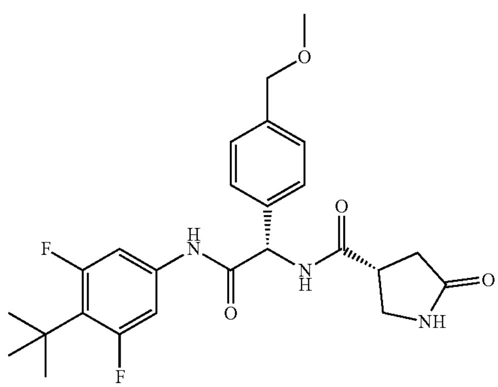 [SMILES: COCc1ccc([C@H](NC(=O)[C@H]2CNC(=O)C2)C(=O)Nc2cc(F)c(C(C)(C)C)c(F)c2)cc1] | | 472.1 (M − H) |
| 410 | (3S)-N-(2-((4-(2,2-dimethylpropyl)-3-fluorophenyl)amino)-1-(4-(methoxymethyl)phenyl)-2-oxoethyl)-5-oxopyrrolidine-3-carboxamide | 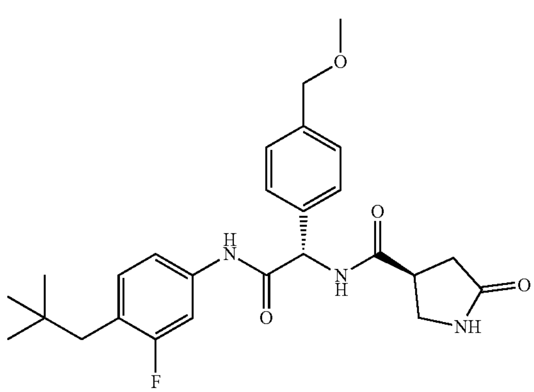 [SMILES: COCc1ccc([C@H](NC(=O)[C@@H]2CNC(=O)C2)C(=O)Nc2ccc(CC(C)(C)C)c(F)c2)cc1] | | 470.2 (M + H) |

TABLE 1-41-continued

| Ex. No. | IUPAC NAME | Structure | Salt | MS (Found) |
|---|---|---|---|---|
| 411 | (2R)-N-(4-tert-butyl-3-fluorophenyl)-2-(4-(methoxymethyl)phenyl)-2-(((2-oxoimidazolidin-1-yl)acetyl)amino)acetamide | 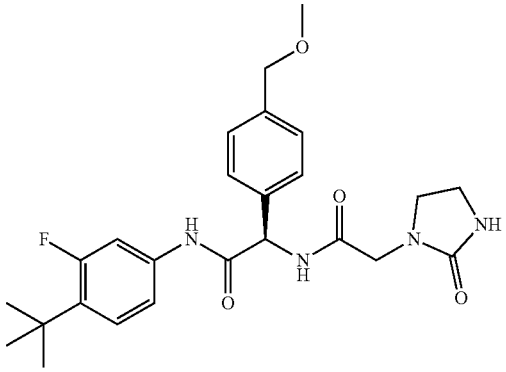 [SMILES: COCc1ccc([C@@H](NC(=O)CN2CCNC2=O)C(=O)Nc2ccc(C(C)(C)C)c(F)c2)cc1] | | 471.2 (M + H) |
| 412 | (2R)-N-(4-tert-butyl-3-fluorophenyl)-2-(4-(methoxymethyl)phenyl)-2-((pyridazin-3-yl)carbamoyl)amino) acetamide | 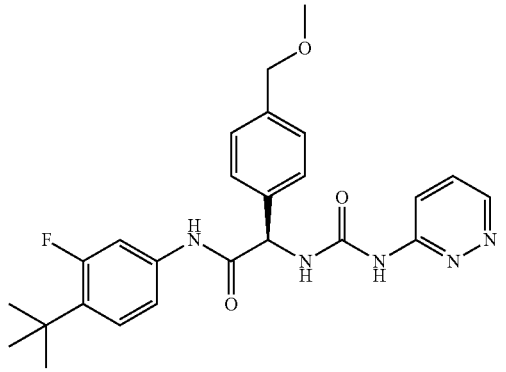 [SMILES: COCc1ccc([C@@H](NC(=O)Nc2cccnn2)C(=O)Nc2ccc(C(C)(C)C)c(F)c2)cc1] | | 466.1 (M + H) |
| 413 | N-(4-tert-butyl-3,5-difluorophenyl)-2-(((3-hydroxy-(1,2-oxazol-5-yl)acetyl)amino)-2-(1-methyl-1H-indazol-5-yl)acetamide | 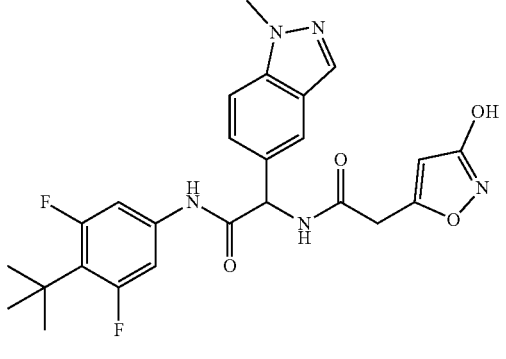 [SMILES: Cn1ncc2cc(C(NC(=O)Cc3cc(O)no3)C(=O)Nc3cc(F)c(C(C)(C)C)c(F)c3)ccc21] | | 498.1 (M + H) |
| 414 | N-(4-tert-butyl-3,5-difluorophenyl)-2-(((3-hydroxy-1,2-oxazol-5-yl)acetyl)amino)-2-(2-methyl-2H-indazol-5-yl)acetamide | 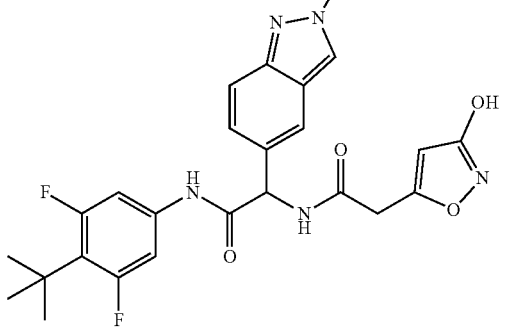 | | 498.1 (M + H) |

TABLE 1-41-continued

| Ex. No. | IUPAC NAME | Structure | Salt | MS (Found) |
|---|---|---|---|---|
| 415 | N-(3-fluoro-4-(trimethylsilyl)phenyl)-2-(((3-hydroxy-1,2-oxazol-5-yl)acetyl)amino)-2-(1-methyl-1H-indazol-5-yl)acetamide | 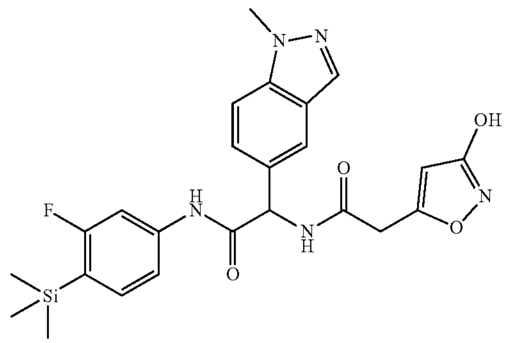 [SMILES: Cn1ncc2cc(C(NC(=O)Cc3cc(O)no3)C(=O)Nc3ccc([Si](C)(C)C)c(F)c3)ccc21] | | 496.1 (M + H) |

TABLE 1-42

| Ex. No. | IUPAC NAME | Structure | Salt | MS (Found) |
|---|---|---|---|---|
| 416 | N-(2-((4-(1-(cyclopropyl-amino)-2-methyl-1-oxopropan-2-yl)-3-fluorophenyl)amino)-1-(4-(methoxymethyl)phenyl)-2-oxoethyl)-3,3,3-trifluoropropanamide | 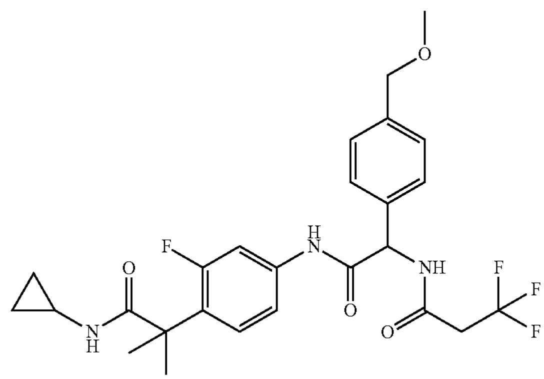 [SMILES: COCc1ccc(C(NC(=O)CC(F)(F)F)C(=O)Nc2ccc(C(C)(C)C(=O)NC3CC3)c(F)c2)cc1] | | 524.2 (M + H) |
| 417 | 3,3,3-triflouro-N-(2-((3-fluoro-4-(2-methyl-1-oxo-1-(pyrrolidin-1-yl)propan-2-yl)phenyl)amino)-1-(4-(methoxymethyl)phenyl)-2-oxoethyl)propanamide | 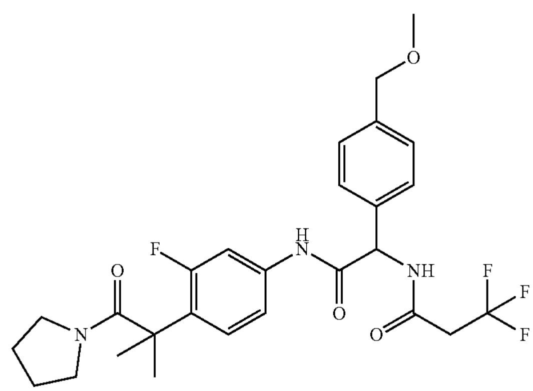 [SMILES: COCc1ccc(C(NC(=O)CC(F)(F)F)C(=O)Nc2ccc(C(C)(C)C(=O)N3CCCC3)c(F)c2)cc1] | | 538.2 (M + H) |
| 418 | (2S)-N-(4-tert-butyl-3,5-difluorophenyl)-2-(((3-hydroxy-1,2-oxazol-5-yl)acetyl)amino)-2-(1-methyl-1H-indazol-5-yl)acetamide | 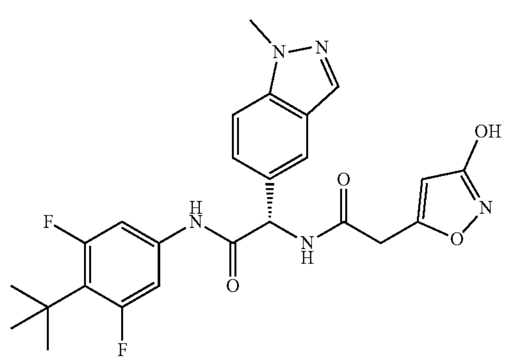 [SMILES: Cn1ncc2cc([C@H](NC(=O)Cc3cc(O)no3)C(=O)Nc3cc(F)c(C(C)(C)C)c(F)c3)ccc21] | | 498.1 (M + H) |

TABLE 1-42-continued

| Ex. No. | IUPAC NAME | Structure | Salt | MS (Found) |
|---------|------------|-----------|------|------------|
| 419 | (2R)-N-(4-tert-butyl-3,5-difluorophenyl)-2-(((3-hydroxy-1,2-oxazol-5-yl)acetyl)amino)-2-(1-methyl-1H-indazol-5-yl)acetamide | 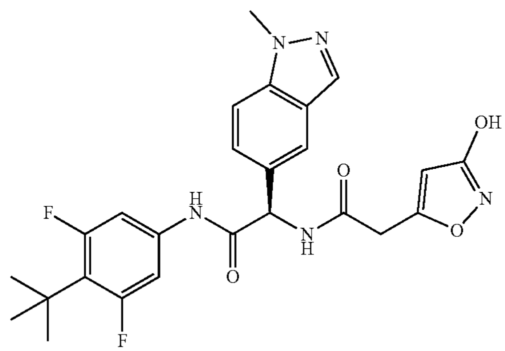 [SMILES: Cn1ncc2cc([C@@H](NC(=O)Cc3cc(O)no3)C(=O)Nc3cc(F)c(C(C)(C)C)c(F)c3)ccc21] | | 498.1 (M + H) |

The compounds of Examples 421 to 426 were synthesized in the same manner as in Examples 1 to 126, 128 to 154, 156 to 214, 216 to 253, 255 to 382, 384 to 402, 406, 407 and 409 to 419.

The compounds described in Examples 421 to 426 are as follows (Table 1-43).

TABLE 1-43

| Ex. No. | IUPAC NAME | Structure | Salt | MS (Found) |
|---------|------------|-----------|------|------------|
| 421 | N-(2-((3-fluoro-4-(1-methoxy-2-methylpropan-2-yl)phenyl)amino)-1-(4-(methoxymethyl)phenyl)-2-oxoethyl)-3-hydroxy-1,2-oxazole-5-carboxamide | 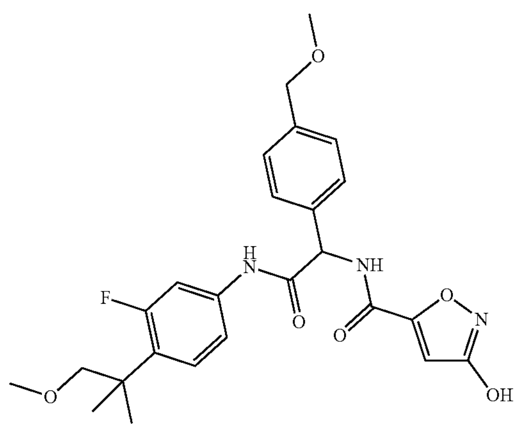 [SMILES: COCc1ccc(C(NC(=O)c2cc(O)no2)C(=O)Nc2ccc(C(C)(C)COC)c(F)c2)cc1] | | 486.1 (M + H) |
| 422 | N-(3-fluoro-4-(1-methoxy-2-methylpropan-2-yl)phenyl)-2-(((3-hydroxy-1,2-oxazol-5-yl)acetyl)amino)-2-(4-(methoxymethyl)phenyl)acetamide | 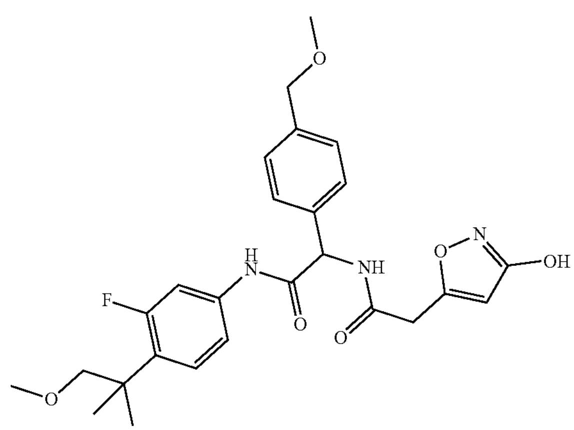 [SMILES: COCc1ccc(C(NC(=O)Cc2cc(O)no2)C(=O)Nc2ccc(C(C)(C)COC)c(F)c2)cc1] | | 500.2 (M + H) |

TABLE 1-43-continued

| Ex. No. | IUPAC NAME | Structure | Salt | MS (Found) |
|---|---|---|---|---|
| 423 | 5-((2-((3,5-difluoro-4-(trimethylsilyl)phenyl)amino)-2-oxo-1-(tetrahydro-2H-pyran-4-yl)ethyl)(methyl)amino)-5-oxopentanoic acid | 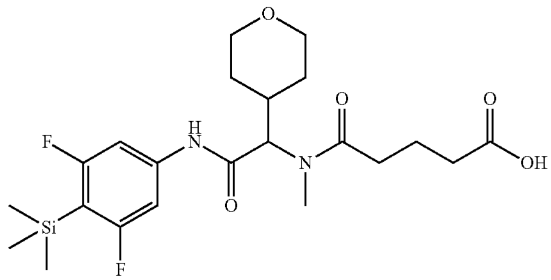 [SMILES: CN(C(=O)CCCC(=O)O)C(C(=O)Nc1cc(F)c([Si](C)(C)C)c(F)c1)C1CCOCC1] | | 469.1 (M − H) |
| 424 | N-(2-((3,5-difluoro-4-(trimethylsilyl)phenyl)amino)-2-oxo-1-(tetrahydro-2H-pyran-4-yl)ethyl)-2-(3-hydroxy-1,2-oxazol-5-yl)-N-methylacetamide | 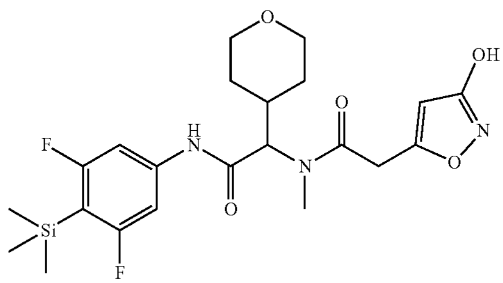 [SMILES: CN(C(=O)Cc1cc(O)no1)C(C(=O)Nc1cc(F)c([Si](C)(C)C)c(F)c1)C1CCOCC1] | | 479.9 (M − H) |
| 425 | N-((1R)-2-((3,5-difluoro-4-(trimethylsilyl)phenyl)amino)-2-oxo-1-(tetrahydro-2H-pyran-4-yl)ethyl)-3-hydroxy-N-methyl-1,2-oxazole-5-carboxamide | 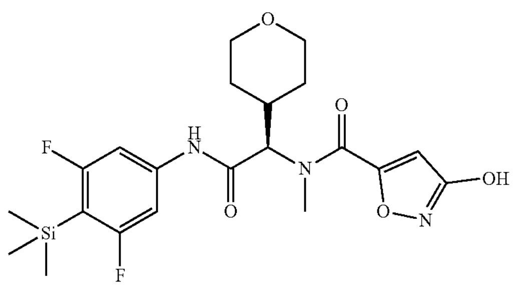 [SMILES: CN(C(=O)c1cc(O)no1)[C@@H](C(=O)Nc1cc(F)c([Si](C)(C)C)c(F)c1)C1CCOCC1] | | 466.0 (M − H) |
| 426 | N-((1R)-2-((4-tert-butyl-3-fluorophenyl)amino)-1-(4,4-difluorocyclohexyl)-2-oxoethyl)-3-hydroxy-N-methyl-1,2-oxazole-5-carboxamide | 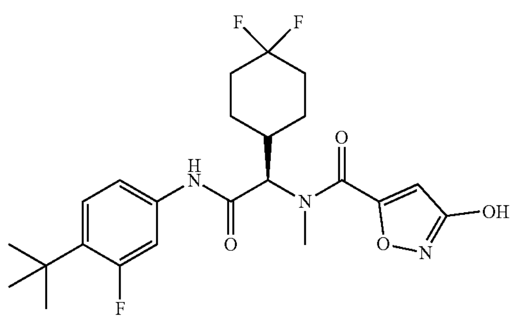 [SMILES: CN(C(=O)c1cc(O)no1)[C@@H](C(=O)Nc1ccc(C(C)(C)C)c(F)c1)C1CCC(F)(F)CC1] | | 466.0 (M − H) |

Example 427

5-((2Z)-2-((1-(difluoroboryl)-3,5-dimethyl-1H-pyrrol-2-yl)methylene)-2H-pyrrol-5-yl)-N-((1R)-2-((3,5-difluoro-4-(trimethylsilyl)phenyl)amino)-1-(4-(methoxymethyl)phenyl)-2-oxoethyl) pentanamide To a solution of (R)-2-amino-N-(3,5-difluoro-4-(trimethylsilyl)phenyl)-2-(4-(methoxymethyl)phenyl)acetamide (9.07 mg, 0.02 mmol) in DMF (0.5 ml) was added 1-((5-((2Z)-2-((1-(difluoroboryl)-3,5-dimethyl-1H-pyrrol-2-yl)methylene)-2H-pyrrol-5-yl)pentanoyl)oxy)pyrrolidine-2,5-dione (BODIPY (trade name) FL-C5 succinimidyl ester) (5.0 mg, 0.01 mmol) at room temperature, and the mixture was stirred at room temperature for 3 hr. To the reaction mixture was added water, and the mixture was extracted with ethyl acetate. The organic layer was washed with brine, and dried over magnesium sulfate, and the solvent was evaporated under reduced pressure. The obtained residue was purified by silica gel column chromatography (solvent; ethyl acetate/hexane), and then preparative HPLC (C18, mobile phase: water/acetonitrile (containing 0.1% TFA)) to give the title compound (3.8 mg, 5.58 μmol, 46.6%) as an orange solid.

$^1$H NMR (300 MHz, CDCl$_3$): δ0.31 (9H, t, J=1.3 Hz), 1.71-1.87 (4H, m), 2.25 (3H, s), 2.32-2.42 (2H, m), 2.53 (3H, s), 2.91-3.03 (2H, m), 3.35 (3H, s), 4.40 (2H, s), 5.71 (1H, d, J=7.2 Hz), 6.09 (1H, s), 6.23 (1H, d, J=4.2 Hz), 6.80-6.90 (2H, m), 6.90-6.99 (2H, m), 7.06 (1H, s), 7.23-7.31 (2H, m), 7.33-7.42 (2H, m), 8.63 (1H, s).

MS(API): Calculated 680.6, Found 679.3 (M−H).

The compound described in Example 427 is as follows (Table 1-44).

TABLE 1-44

| Ex. No. | IUPAC NAME | Structure | Salt | MS (Found) |
|---|---|---|---|---|
| 427 | 5-((2Z)-2-((1-(difluoroboryl)-3,5-dimethyl-1H-pyrrol-2-yl)methylene)-2H-pyrrol-5-yl)-N-((1R)-2-((3,5-difluoro-4-(trimethylsilyl)phenyl)amino)-1-(4-(methoxymethyl)phenyl)-2-oxoethyl)pentanamide | 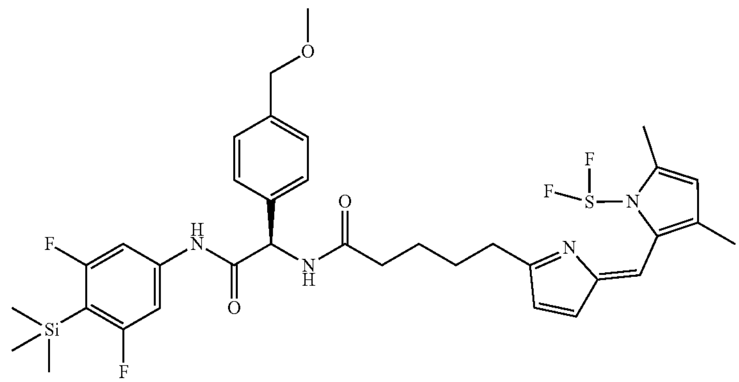 | | 679.3 (M − H) |

Experimental Example 1

RORγt Binding Test

The binding activity of the test compound to RORγt was measured by a time resolved fluorescence resonance energy transfer method (TR-FRET) utilizing histidine-tagged RORγt, fluorescent-labeled cholesterol (BODIPY-cholesterol, AVIVA), and terbium-labeled anti-histidine tag antibody (Invitrogen). First, a test compound diluted with an assay buffer (20 mM Tris-HCl (pH 7.5), 100 mM NaCl, 1 mM DTT, 0.1% BSA) was added to a 384 well plate by 3 µL. Then, RORγt diluted with an assay buffer to 240 nM was added by 3 µL, after which fluorescent-labeled cholesterol diluted with the assay buffer to 12 µM was added by 3 µL, and the mixture was stood at room temperature for 20 min. Thereafter, a terbium-labeled anti-histidine tag antibody diluted with the assay buffer to 8 nM was added by 3 µL. The mixture was stood at room temperature for 20 min, and fluorescence intensity (excitation wavelength 320 nm, fluorescence wavelength 520 nm, delay time 100 microseconds) was measured by Envision (PerkinElmer).

The results (binding inhibitory rate of fluorescent-labeled cholesterol to RORγt at test compound 1 µM) measured by the above-mentioned method are shown in Tables 2-1 to 2-5.

Experimental Example 2

Cofactor Recruitment Test

Cofactor recruitment test was performed by Alpha Screen (Histidine Detection Kit, PerkinElmer) method. First, a test compound was diluted with an assay buffer (50 mM Tris-HCl (pH 7.5), 50 mM KCl, 1 mM DTT, 0.1% BSA) and added to a 384 well plate by 5 µL. Then, RORγt diluted with an assay buffer to 125 nM was added by 10 µL each, after which solutions of 25 nM biotinylated SRC-1 peptide (biotin-CLTARHKILHRLLQEGSPSD), 12.5 µg/mL acceptor beads and 12.5 µg/mL donor beads prepared with the assay buffer were added by 10 µL each. The mixture was stood in a dark place for 1 hr, and the signal value was measured by Envision (PerkinElmer).

The results (signal value inhibitory rate at test compound 1 µM) measured by the above-mentioned method are shown in Tables 2-1 to 2-5.

Experimental Example 3

Jurkat Reporter Test

The Jurkat cells used for the reporter test were cultured in a culture medium (RPMI (Invitrogen), 10% FCS (AusGeneX), 100 U/mL penicillin, 100 µg/mL streptomycin). On the day of the test, $4 \times 10^7$ cells were recovered by a centrifugal operation (1000 rpm, 5 min.) and suspended in PBS (phosphate buffered saline) (Invitrogen). Thereafter, the cells were recovered again by a centrifugal operation, and suspended in 2 mL of R buffer (NEON transfection kit, Invitrogen). Then, a reporter vector 53 µg wherein a human IL-17 ROR response element was inserted into the upstream of luciferase of pGL 4.28 (Promega), and a vector (27 µg) wherein RORγt sequence was inserted into the downstream of CMV promoter were added to the cell suspension. Gene transfer was performed by Electroporation apparatus (NEON, Invitrogen) under the conditions of pulse voltage 1350 V, interval 10 milliseconds, number of times 3. The cells after gene transfer were suspended in 40 mL of a reaction medium (RPMI, 10% Lipid reduced FCS (HyClone), 10 mM HEPES (pH 7.5), 100 U/mL penicillin, 100 µg/mL streptomycin, 5 µM lovastatin), and plated in a 96 well plate by 90 µL. A test compound diluted with the reaction medium was added by 10 µL, and the cells were cultured overnight in an incubator. Bright-Glo (Promega) was added by 100 µL, and the mixture was stirred at room temperature for 10 min, and the luminescence level was measured by Envision (PerkinElmer).

The results (luminescence level inhibitory rate at test compound 3 µM) measured by the above-mentioned method are shown in Tables 2-1 to 2-5.

TABLE 2-1

| Ex. No. | Experimental Example 1 binding inhibitory rate (%) of fluorescent-labeled cholesterol to RORγt at test compound 1 μM | Experimental Example 2 signal value inhibitory rate (%) at test compound 1 μM | Experimental Example 3 luminescence level inhibitory rate (%) at test compound 3 μM |
|---|---|---|---|
| 1 | 100 | 72.7 | 97.3 |
| 2 | 102 | 78.0 | 98.1 |
| 3 | 100 | 72.3 | 98.4 |
| 4 | 100 | 78.8 | 97.0 |
| 5 | 100 | 84.8 | 98.0 |
| 6 | 102 | 99.4 | 101 |
| 7 | 102 | 56.9 | 97.0 |
| 8 | 102 | 49.1 | 93.4 |
| 9 | 100 | 29.7 | 97.6 |
| 10 | 102 | 2.04 | 95.3 |
| 11 | 102 | 32.0 | 97.5 |
| 12 | 101 | 89.0 | 116 |
| 13 | 101 | 51.1 | 92.6 |
| 14 | 103 | 85.5 | 119 |
| 15 | 109 | 91.6 | 99.4 |
| 16 | 102 | 81.9 | 93.2 |
| 17 | 102 | 94.6 | 98.8 |
| 18 | 101 | 60.3 | 90.9 |
| 19 | 101 | 50.7 | 84.7 |
| 20 | 101 | 73.0 | 91.8 |
| 21 | 101 | 93.1 | 98.3 |
| 22 | 101 | 90.6 | 97.2 |
| 23 | 102 | 96.5 | 101 |
| 24 | 102 | 95.3 | 100 |
| 25 | 102 | 95.7 | 100 |

TABLE 2-2

| Ex. No. | Experimental Example 1 binding inhibitory rate (%) of fluorescent-labeled cholesterol to RORγt at test compound 1 μM | Experimental Example 2 signal value inhibitory rate (%) at test compound 1 μM | Experimental Example 3 luminescence level inhibitory rate (%) at test compound 3 μM |
|---|---|---|---|
| 26 | 103 | 99.5 | 97.6 |
| 27 | 103 | 92.5 | 96.0 |
| 28 | 100 | 88.0 | 98.0 |
| 29 | 101 | 92.3 | 99.2 |
| 30 | 98.5 | 95.1 | 99.8 |
| 31 | 99.5 | 98.3 | 99.5 |
| 32 | 95.2 | 95.6 | 99.1 |
| 33 | 101 | 97.7 | 98.4 |
| 34 | 101 | 98.9 | 99.2 |
| 35 | 103 | 96.6 | 101 |
| 36 | 96.2 | 98.2 | 99.8 |
| 37 | 101 | 93.6 | 98.5 |
| 38 | 102 | 99.7 | 100 |
| 39 | 103 | 99.6 | 100 |
| 40 | 101 | 98.7 | 100 |
| 41 | 101 | 94.4 | 100 |
| 42 | 102 | 88.5 | 99.1 |
| 43 | 102 | 96.1 | 100 |
| 44 | 102 | 95.7 | 102 |
| 45 | 102 | 94.1 | 101 |
| 46 | 99.5 | 87.2 | 101 |
| 47 | 100 | 92.4 | 100 |
| 48 | 103 | 73.0 | 95.7 |
| 49 | 101 | 96.9 | 98.4 |
| 50 | 102 | 91.5 | 98.0 |

TABLE 2-3

| Ex. No. | Experimental Example 1 binding inhibitory rate (%) of fluorescent-labeled cholesterol to RORγt at test compound 1 μM | Experimental Example 2 signal value inhibitory rate (%) at test compound 1 μM | Experimental Example 3 luminescence level inhibitory rate (%) at test compound 3 μM |
|---|---|---|---|
| 51 | 102 | 97.3 | 98.0 |
| 52 | 102 | 98.7 | 100 |
| 53 | 102 | 97.8 | 98.4 |
| 54 | 102 | 95.6 | 99.0 |
| 55 | 102 | 95.8 | 98.6 |
| 56 | 102 | 97.7 | 100 |
| 57 | 103 | 97.3 | 98.9 |
| 58 | 102 | 97.1 | 98.4 |
| 59 | 102 | 96.0 | 99.2 |
| 60 | 102 | 96.6 | 99.7 |
| 61 | 102 | 97.0 | 100 |
| 62 | 99.9 | 96.3 | 97.8 |
| 63 | 103 | 95.1 | 99.7 |
| 64 | 102 | 90.1 | 98.7 |
| 65 | 102 | 94.3 | 98.5 |
| 66 | 103 | 94.6 | 98.5 |
| 67 | 103 | 96.0 | 98.5 |
| 68 | 101 | 96.2 | 98.7 |
| 69 | 103 | 96.8 | 98.4 |
| 70 | 101 | 82.8 | 96.5 |
| 71 | 101 | 89.9 | 99.0 |
| 72 | 102 | 96.7 | 99.2 |
| 73 | 103 | 96.7 | 97.9 |
| 74 | 101 | 97.6 | 99.4 |
| 75 | 102 | 95.8 | 99.7 |

TABLE 2-4

| Ex. No. | Experimental Example 1 binding inhibitory rate (%) of fluorescent-labeled cholesterol to RORγt at test compound 1 μM | Experimental Example 2 signal value inhibitory rate (%) at test compound 1 μM | Experimental Example 3 luminescence level inhibitory rate (%) at test compound 3 μM |
|---|---|---|---|
| 76 | 103 | 98.5 | 99.3 |
| 77 | 103 | 97.3 | 99.7 |
| 78 | 102 | 93.2 | 96.0 |
| 79 | 103 | 93.0 | 98.4 |
| 80 | 102 | 93.8 | 100 |
| 81 | 103 | 94.9 | 98.3 |
| 82 | 103 | 96.8 | 97.0 |
| 83 | 100 | 86.5 | 63.2 |
| 84 | 101 | 94.4 | 100 |
| 85 | 103 | 90.1 | 99.0 |
| 86 | 102 | 95.2 | 99.1 |
| 87 | 102 | 83.9 | 98.2 |
| 88 | 103 | 90.7 | 98.1 |
| 89 | 103 | 95.5 | 101 |
| 90 | 102 | 96.0 | 101 |
| 91 | 102 | 94.6 | 98.0 |
| 92 | 102 | 92.8 | 98.8 |
| 93 | 102 | 92.3 | 99.1 |
| 94 | 102 | 91.5 | 101 |
| 95 | 99.3 | 93.8 | 99.8 |
| 96 | 98.6 | 91.2 | 99.5 |
| 97 | 102 | 93.6 | 98.3 |
| 98 | 102 | 95.8 | 99.2 |
| 99 | 102 | 94.3 | 99.9 |
| 100 | 99.6 | 86.3 | 99.4 |

TABLE 2-5

| Ex. No. | Experimental Example 1 binding inhibitory rate (%) of fluorescent-labeled cholesterol to RORγt at test compound 1 µM | Experimental Example 2 signal value inhibitory rate (%) at test compound 1 µM | Experimental Example 3 luminescence level inhibitory rate (%) at test compound 3 µM |
|---|---|---|---|
| 101 | 101 | 87.6 | 99.5 |
| 102 | 100 | 83.8 | 97.8 |
| 103 | 102 | 96.2 | 100 |
| 104 | 101 | 74.9 | 96.1 |
| 105 | 101 | 85.5 | 100 |
| 106 | 103 | 88 | 99.8 |
| 107 | 103 | 95.7 | 100 |
| 108 | 100 | 95.3 | 99.7 |
| 109 | 100 | 87.6 | 100 |
| 110 | 99.6 | 71.1 | 95.4 |
| 111 | 100 | 53 | 97.4 |
| 112 | 103 | 83.2 | 100 |
| 113 | 102 | 83.9 | 99.7 |
| 114 | 101 | 90.1 | 102 |
| 115 | 102 | 71.6 | 97.3 |
| 116 | 103 | 76.6 | 99.8 |
| 117 | 103 | 78.4 | 98.5 |
| 289 | 99.6 | 87.2 | 100 |
| 419 | 103 | 87 | 101 |

Experimental Example 4

Effect on IL-23-Induced IL-17A Gene Expression in Mice

A mouse IL-23 solution (500 ng/10 µL, prepared by Takeda Pharmaceutical Company Limited) or PBS (10 µL, negative control group) was administered intradermally in the ear of Balb/c mice (Charles River Japan, male, 7 weeks old). Twenty-four hr after administration, the ear was resected under isoflurane anesthesia. The test compound was suspended in 0.5% methylcellulose and administered orally 30 min before and 8 hr after IL-23 administration.

RNA extraction from the ear tissue and quantitative PCR were performed as follows. Specifically, ear tissue 5 mm in diameter was punched from an area of the resected ear centering on the IL-23 injection site, and the tissue was immersed in RNAlater (QIAGEN) for at least 18 hr. The RNAlater-treated ear tissue was homogenized in 350 µL of RLT buffer (RNeasy mini kit, QIAGEN) and treated (55° C., 10 min) with Proteinase K (QIAGEN). Total RNA was then extracted according to the RNeasy mini kit protocol. The RNA thus obtained was then reverse transcribed into cDNA using the High-Capacity RNA-to-cDNA kit (Applied Biosystems), and the amount of each cytokine expressions was measured by real-time PCR (Viia7™, Applied Biosystems). The PCR buffer used was TaqMan Fast Advanced Master Mix (Applied Biosystems), and TaqMan Gene Expression Assays (Applied Biosystems) Mm00439618 m1 (IL-17A) and 4352341E (β-actin) were used for cytokine gene detection. The IL-17A gene expression level was normalized to the β-actin gene expression level, and the percent inhibition of IL-17A gene expression with the test compound was then calculated.

The results obtained with the above-described method (percent inhibition of IL-17A gene expression with oral administration of the test compound) are shown in Table 3.

TABLE 3

| Ex. No. | Dose (mg/kg) | percent inhibition of IL-17A gene expression * |
|---|---|---|
| 14 | 100 | 53% |
| 23 | 100 | 71% |
| 24 | 100 | 65% |
| 106 | 100 | 43% |

* versus the negative control group

The results above showed that oral administration of the example compounds inhibited IL-17A gene expression in vivo.

Experimental Example 5

Effect in a Mouse Model of IL-23-Induced Psoriasis

Mouse IL-23 (500 ng/15 µL, R&D) or PBS (15 µL, negative control group) was administered intradermally in the ear of Balb/c mice (Charles River Japan, male, 7 weeks old) 5 times every other days. Seven hr after IL-23 administration at 8 days after the initial administration (final administration), the mice were anesthetized with isoflurane, and ear thickness was measured with calipers. After the ear thickness was measured, the ear was resected, the tissue 8 mm in diameter was punched from an area centering on the IL-23 injection site, and the tissue was weighed. The test compound was suspended in 0.5% methylcellulose and administered orally twice daily on consecutive days from 30 min before the initial IL-23 administration to 30 min before the final IL-23 administration.

The change in ear thickness in this model was evaluated by calculating the difference in measured thickness between before IL-23 administration and 7 hr after the final IL-23 administration.

The amount of IL-17 in the ear tissue was performed as follows. The ear tissue 8 mm in diameter resected above was homogenized in 500 µL of Tissue extraction Reagent I (invitrogen) containing protease inhibitor (Roche Diagnostics). The homogenized solution was centrifuged, and the amount of IL-17 in the supernatant was measured using ELISA kit (R&D), and the amount of protein in the supernatant was measured using pierce BCA protein assay kit (Thermo scientific). The amount of IL-17 in each ear tissue was normalized to the amount of protein, and the percent inhibition of IL-17A production with the test compound was then calculated.

The measurement results obtained with the above-described method (percent inhibition of ear thickness, and percent inhibition of IL-17A production with oral administration of the test compound) are shown in Table 4.

TABLE 4

| Ex. No. | Dose (mg/kg) | percent inhibition of ear thickness* | percent inhibition of IL-17 production* |
|---|---|---|---|
| 24 | 100 | 76% | 96% |

*versus the negative control group

The results above showed that oral administration of the example compounds inhibited the increase in ear thickness, and IL-17A production in the mouse model of psoriasis.

| (1) the compound of Example 1 | 10.0 g |
|---|---|
| (2) lactose | 70.0 g |
| (3) cornstarch | 50.0 g |

| | |
|---|---|
| (4) soluble starch | 7.0 g |
| (5) magnesium stearate | 3.0 g |

The compound of Example 1 (10.0 g) and magnesium stearate (3.0 g) are granulated in aqueous solution (70 mL) of soluble starch (7.0 g as soluble starch) and then dried, the resulting mixture is mixed with lactose (70.0 g) and cornstarch (50.0 g) (lactose, cornstarch, soluble starch and magnesium stearate are all products in compliance with Japanese Pharmacopoeia 14$^{th}$ Edition). The mixture compressed to give tablets.

INDUSTRIAL APPLICABILITY

The compound of the present invention has a superior RORγt inhibitory action, and useful as an agent for the prophylaxis or treatment of psoriasis, inflammatory bowel disease (IBD), ulcerative colitis (UC), Crohn's disease (CD), rheumatoid arthritis, multiple sclerosis, uveitis, asthma, ankylopoietic spondylarthritis, systemic lupus erythematosus (SLE) and the like.

This application is based on patent application No. 2013-140213 filed on Jul. 3, 2013 in Japan, the contents of which are encompassed in full herein.

The invention claimed is:

1. A method for the treatment of inflammatory bowel disease (IBD), ulcerative colitis (UC), Crohn's disease (CD), rheumatoid arthritis, multiple sclerosis, uveitis, asthma, ankylosing spondylitis, or systemic lupus erythematosus (SLE), which comprises administering an effective amount of a compound represented by the following formula (I)

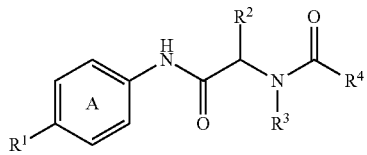

wherein
Ring A is a benzene ring optionally further substituted by 1 to 3 substituents selected from
  (1) a halogen atom, and
  (2) a cyano group;
$R_1$ is
  (1) a group represented by the formula: $-Q(R^{1a})(R^{1b})(R^{1c})$
    wherein
    Q is a carbon atom or a silicon atom, and
    $R^{1a}$, $R^{1b}$ and $R^{1c}$ are each independently a $C_{1-6}$ alkyl group, or
  (2) a neopentyl group;
$R^2$ is
  (1) a group represented by the formula:

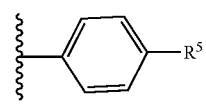

wherein
R⁵ is
(A) a C₁₋₆ alkyl group optionally substituted by 1 to 3 C₁₋₆ alkoxy groups, or
(B) a C₁₋₆ alkoxy group,
(2) a bicyclic fused heterocyclic group selected from dihydrobenzofuryl and indazolyl, each optionally substituted by 1 to 3 C₁₋₆ alkyl groups, or
(3) a group represented by the formula -L-Z¹:
wherein
L is a bond; and
Z¹ is
(A) a C₃₋₁₀ cycloalkyl group optionally substituted by 1 to 3 halogen atoms, or
(B) tetrahydropyranyl;
R³ is
(1) a hydrogen atom, or
(2) a C₁₋₆ alkyl group; and
R⁴ is
(1) a C₁₋₆ alkyl group optionally substituted by 1 to 7 substituents selected from (a) a 3- to 8-membered monocyclic non-aromatic heterocyclic group selected from dihydropyrimidinyl, dihydropyridyl, dihydropyridazinyl, imidazolidinyl, tetrahydropyranyl, morpholinyl, piperidyl and tetrahydropyrimidinyl, each optionally substituted by 1 to 3 substituents selected from
(i) an oxo group, and
(ii) a C₁₋₆ alkyl group,
(b) a 5- or 6-membered monocyclic aromatic heterocyclic group optionally substituted by 1 to 3 substituents selected from
(i) a C₁₋₆ alkyl group, and
(ii) a hydroxy group,
(c) a 8- to 14-membered fused bicyclic aromatic heterocyclic group selected from indazolyl and benzimidazolyl,
(d) a halogen atom,
(e) a hydroxy group,
(f) a cyano group,
(g) a carboxy group,
(h) a C₁₋₆ alkylsulfonyl group, and
(i) an amino group optionally mono- or di-substituted by C₁₋₆ alkyl-carbonyl group(s),
(2) a 3- to 8-membered monocyclic non-aromatic heterocyclic group selected from pyrrolidinyl, oxazolidinyl, azetidinyl, piperidyl and tetrahydropyranyl, each optionally substituted by 1 to 3 substituents selected from
(a) an oxo group,
(b) a hydroxy group,
(c) a halogen atom, and
(d) a C₁₋₆ alkyl-carbonyl group,
(3) a 5-membered monocyclic aromatic heterocyclic group optionally substituted by 1 to 3 hydroxy groups,
(4) a C₃₋₁₀ cycloalkyl group optionally substituted by 1 to 3 halogen atoms, or
(5) an amino group optionally mono- or di-substituted by C₁₋₆ alkyl group(s), provided that
α-(acetylamino)-N-[4-(1,1-dimethylethyl)phenyl]-cyclopentaneacetamide
is excluded,
or a salt thereof, to a mammal.

2. The method of claim 1, wherein the substituent that Ring A optionally further has is a fluorine atom or a chlorine atom.

3. The method of claim 1, wherein R¹ is a tert-butyl group, a neopentyl group or a trimethylsilyl group.

4. The method of claim 1, wherein R² is
(1) a group represented by the formula:

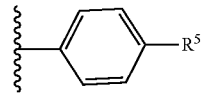

wherein R⁵ is an alkoxy group or an alkoxyalkyl group,
(2) a tetrahydro-2H-pyran-4-yl group,
(3) a 4,4-difluorocyclohexyl group,
(4) a 1-methyl-1H-indazol-5-yl group, or
(5) a 2,3-dihydro-1-benzofuran-5-yl group.

5. The method of claim 1, wherein R³ is a hydrogen atom or a methyl group.

6. The method of claim 1, wherein the compound is (3S)—N-((1R)-2-((4-tert-Butyl-3-fluoro phenyl)amino)-1-(4,4-difluorocyclohexyl)-2-oxoethyl)-5-oxopyrrolidine-3-carboxamide or a salt thereof.

7. The method of claim 1, wherein the compound is N-((1R)-2-((3,5-Difluoro-4-(trimethylsilyl)phenyl)amino)-1-(4-methoxyphenyl)-2-oxoethyl)-3-hydroxy-N-methyl-1,2-oxazole-5-carboxamide or a salt thereof.

8. The method of claim 1, wherein the compound is (2R)—N-(4-tert-Butyl-3,5-difluorophenyl)-2-(((3-hydroxy-1,2-oxazol-5-yl)acetyl)amino)-2-(1-methyl-1H-indazol-5-yl)acetamide or a salt thereof.

9. The method of claim 1, wherein the compound is (3R)—N-((1R)-2-((3-fluoro-4-(trimethylsilyl)phenyl)amino)-1-(4-(methoxymethyl)phenyl)-2-oxoethyl)-5-oxopyrrolidine-3-carboxamide or a salt thereof.

10. The method of claim 1, wherein the compound is selected from the group consisting of
(3S)—N-((1R)-2-((3-fluoro-4-(trimethylsilyl)phenyl)amino)-1-(4-(methoxymethyl)phenyl)-2-oxoethyl)-5-oxopyrrolidine-3-carboxamide,
N-((1R)-2-((3-fluoro-4-(trimethylsilyl)phenyl)amino)-1-(4-methoxyphenyl)-2-oxoethyl)-3-hydroxy-N-methyl-1,2-oxazole-5-carboxamide,
N-(2-((3-fluoro-4-(trimethylsilyl)phenyl)amino)-1-(4-(methoxymethyl)phenyl)-2-oxoethyl)-5-oxopyrrolidine-3-carboxamide,
(2R)-2-(((2,4-dioxo-3,4-dihydropyrimidin-1(2H)-yl)acetyl)amino)-N-(3-fluoro-4-(trimethylsilyl)phenyl)-2-(4-(methoxymethyl)phenyl)acetamide,
(2R)—N-(3-fluoro-4-(trimethylsilyl)phenyl)-2-(4-(methoxymethyl)phenyl)-2-(((4-oxopyridazin-1 (4H)-yl)acetyl)amino)acetamide,
1-acetyl-N-((1R)-2-((3-fluoro-4-(trimethylsilyl)phenyl)amino)-1-(4-(methoxymethyl)phenyl)-2-oxoethyl)piperidine-4-carboxamide,
(2R)—N-(3-fluoro-4-(trimethylsilyl)phenyl)-2-(((3-hydroxy-1,2-oxazol-5-yl)acetyl)amino)-2-(4-(methoxymethyl)phenyl)acetamide,
(2R)—N-(3-fluoro-4-(trimethylsilyl)phenyl)-2-(4-(methoxymethyl)phenyl)-2-(((4-oxopyridin-1 (4H)-yl)acetyl)amino)acetamide,
(2R)—N-(4-tert-butyl-3-fluorophenyl)-2-(4-(methoxymethyl)phenyl)-2-(((6-oxopyrimidin-1(6H)-yl)acetyl)amino)acetamide,
(3R)—N-((1R)-2-((4-tert-butyl-3-fluorophenyl)amino)-1-(4-(methoxymethyl)phenyl)-2-oxoethyl)-5-oxopyrrolidine-3-carboxamide, N-((1R)-2-((3,5-difluoro-4-(trimethylsilyl)phenyl)amino)-2-oxo-1-(tetrahydro-2H-pyran-4-yl)ethyl)-3-hydroxy-N-methyl-1,2-oxazole-5-carboxamide, N-((1R)-2-((4-tert-butyl-3-chlorophenyl)amino)-2-oxo-1-(tetrahydro-2H-pyran-4-yl)ethyl)-3,3,3-trifluoro-2-hydroxypropanamide, (2R)—N-(2,5-difluoro-4-(trimethylsilyl)phenyl)-2-(4-(methoxymethyl)phenyl)-2-(((5-methyl-1,3,4-oxadiazol-2-yl)acetyl)amino)acetamide, and (2R)—N-(4-tert-butyl-3-fluorophenyl)-2-(((2,4-dioxo-3,4-dihydropyrimidin-1(2H)-yl)acetyl)amino)-2-(4-(methoxymethyl)phenyl)acetamide, or a salt thereof.

11. The method of claim 1, wherein the compound is (3R)—N-((1R)-2-((4-tert-butyl-3-fluorophenyl)amino)-1-(4-(methoxymethyl)phenyl)-2-oxo ethyl)-5-oxopyrrolidine-3-carboxamide.

* * * * *